US011499150B2

(12) United States Patent
McCafferty et al.

(10) Patent No.: US 11,499,150 B2
(45) Date of Patent: Nov. 15, 2022

(54) SELECTING FOR DEVELOPABILITY OF POLYPEPTIDE DRUGS IN EUKARYOTIC CELL DISPLAY SYSTEMS

(71) Applicant: IONTAS LIMITED, Sawston (GB)

(72) Inventors: John McCafferty, Sawston (GB); Rajika Perera, Pasadena, CA (US); Michael Richard Dyson, Sawston (GB); Kothai Parthiban, Cambridge (GB); Johanna Liinamaria Syrjanen, New York, NY (US)

(73) Assignee: Iontas Limited, Sawston (GB)

( * ) Notice: Subject to any disclaimer, the term of this patent is extended or adjusted under 35 U.S.C. 154(b) by 0 days.

(21) Appl. No.: 16/767,727

(22) PCT Filed: Dec. 5, 2018

(86) PCT No.: PCT/EP2018/083698
§ 371 (c)(1),
(2) Date: May 28, 2020

(87) PCT Pub. No.: WO2019/110691
PCT Pub. Date: Jun. 13, 2019

(65) Prior Publication Data

US 2021/0163923 A1 Jun. 3, 2021

(30) Foreign Application Priority Data

Dec. 6, 2017 (GB) ...................................... 1720351

(51) Int. Cl.
*C12N 15/10* (2006.01)

(52) U.S. Cl.
CPC ....... *C12N 15/1037* (2013.01); *C12N 15/102* (2013.01)

(58) Field of Classification Search
None
See application file for complete search history.

(56) References Cited

U.S. PATENT DOCUMENTS

| | | | | |
|---|---|---|---|---|
| 6,300,065 | B1 * | 10/2001 | Kieke ................ | C12N 15/1037 435/6.14 |
| 8,697,359 | B1 | 4/2014 | Zhang | |
| 2002/0137897 | A1 | 9/2002 | Stevens et al. | |
| 2005/0048578 | A1 * | 3/2005 | Zhang ................ | G01N 33/6854 506/1 |
| 2012/0277120 | A1 | 11/2012 | Serber et al. | |
| 2017/0073664 | A1 | 3/2017 | McCafferty et al. | |
| 2020/0165595 | A1 | 5/2020 | McCafferty et al. | |
| 2020/0165596 | A1 | 5/2020 | McCafferty et al. | |
| 2020/0165597 | A1 | 5/2020 | McCafferty et al. | |

FOREIGN PATENT DOCUMENTS

WO WO-2013/092720 A1 6/2013

OTHER PUBLICATIONS

Dobson et al (Scientific Reports 6:38644 doi: 10.1038/srep38644 supplementary information) (Year: 2016).*
International Preliminary Report on Patentability for International Application No. PCT/EP2018/083698, dated Jun. 9, 2020 (7 pages).
Dobson, C, et al., "Engineering the surface properties of a human monoclonal antibody prevents self-association and rapid clearance in vivo", Sci Rep. 6, 38644; doi: 10.1038/srep38644 (2016).
Finch, D, et al., "Whole-Molecule Antibody Engineering: Generation of a High-Affinity Anti-IL-6 Antibody with Extended Pharmacokinetics", J Mol Biol 411, 791-807 (2011).
Geng, S, et al., "Measurements of Monoclonal Antibody Self-Association Are Correlated with Complex Biophysical Properties", Mol Pharmaceutics 13, 1636-1645 (2016).
Geoghegan, J, et al., "Mitigation of reversible self-association and viscosity in a human IgGI monoclonal antibody by rational, structure-guided Fv engineering", MABS 8(5), 941-950 (2016).
Jarasch, A, et al., "Developability Assessment During the Selection of Novel Therapeutic Antibodies", Journal of Pharmaceutical Sciences 104, 1885-1898 (2015).
Liu, Y, et al., "High-throughput screening for developability during early-stage antibody discovery using selfinteraction nanoparticle spectroscopy", MABS 6(2), 483-492 (2013).
Patent Cooperation Treaty, International Searching Authority, Search Report and Written Opinion for PCT/EP2018083698, 17 pages, Feb. 12, 2019.
Sormanni, P, et al., "Rapid and accurate in sHico solubility screening of a monoclonal antibody library", Scientific Reports 7, 8200, 9 pages (2017).
Doerner et al., "Therapeutic antibody engineering by high efficiency cell screening," FEBS Lett. 588(2):278-87 (2014).
Beerli et al., "Isolation of human monoclonal antibodies by mammalian cell display," Proc Natl Acad Sci U S A. 105(38):14336-41 (2008).
Cristea et al., "In vivo Cleavage of Transgene Donors Promotes Nuclease-Mediated Targeted Integration," Biotechnol Bioeng. 110(3):871-80 (2013).

(Continued)

*Primary Examiner* — Christopher M Gross
(74) *Attorney, Agent, or Firm* — Clark & Elbing LLP

(57) ABSTRACT

Use of the surface presentation level of binders (e.g., antibodies, receptors) on cultured higher eukaryotic cells in vitro as a predictive indicator of developability characteristics, e.g., solubility, of the binders. Display libraries of higher eukaryotic cells, e.g., mammalian cells, adapted for use in screening surface-displayed binders for developability and affinity of target binding. High-throughput screening of display libraries with in-built selection for developability including binder solubility, capability to be formulated at high concentrations, low propensity for non-specific binding, and half-life. Enrichment of populations of binders for developability characteristics and/or other qualities such as target binding and affinity, by controlling cell surface presentation of binders from an inducible promoter operably linked to binder-encoding DNA.

16 Claims, 95 Drawing Sheets

Specification includes a Sequence Listing.

(56) References Cited

OTHER PUBLICATIONS

Hockemeyer et al., "Genetic engineering of human ES and iPS cells using TALE nucleases," available in PMC Feb. 1, 2012, published in final edited form as: Nat Biotechnol. 29(8):731-4 (2011) (8 pages).

Lee et al., "Construction and characterization of a pseudo-immune human antibody library using yeast surface display," Biochem Biophys Res Commun. 346(3):896-903 (2006).

Li et al., "Identification of HBsAg-specific antibodies from a mammalian cell displayed full-length human antibody library of healthy immunized donor," Cel Mol Immunol. 9(2):184-90 (2012).

Marks et al., "By-passing Immunization: Human Antibodies from V-gene Libraries Displayed on Phage," J Mol Biol. 222:581-97 (1991).

Moehle et al., "Targeted gene addition into a specified location in the human genome using designed zinc finger nucleases," Proc Natl Acad Sci U S A. 104(9):3055-60 (2007) (7 pages).

Taube et al, "Lentivirus Display: Stable Expression of Human Antibodies on the Surface of Human Cells and Virus Particles," PLoS One. 3(9):e3181 (2008) (12 pages).

Xu et al., "The genomic sequence of the Chinese hamster ovary (CHO)-K1 cell line," Nat Biotechnol. 29(8):735-41 (2011) (8 pages).

Zhou et al., "Development of a novel mammalian cell surface antibody display platform," MAbs. 2(5):508-18(2010).

* cited by examiner

Figure 1b.

```
Sequence: pINT17-blasticidin_a Range: 1 to 10380

    >AAVS_-_Left_arm
             |
             |10         20         30         40         50         60
  GCG ATC GCT GCT TTC TCT GAC CTG CAT TCT CTC CCC TGG GCC TGT GCC GCT TTC TGT CTG
  CAG CTT GTG GCC TGG GTC ACC TCT ACG GCT GGC CCA GAT CCT TCC CTG CCG CCT CCT TCA
  GGT TCC GTC TTC CTC CAC TCC CTC TTC CCC TTG CTC TCT GCT GTG TTG CTG CCC AAG GAT
  GCT CTT TCC GGA GCA CTT CCT TCT CGG CGC TGC ACC ACG TGA TGT CCT CTG AGC GGA TCC
  TCC CCG TGT CTG GGT CCT CTC CGG GCA TCT CTC CTC CCT CAC CCA ACC CCA TGC CGT CTT
  CAC TCG CTG GGT TCC CTT TTC CTT CTC CTT CTG GGG CCT GTG CCA TCT CTC GTT TCT TAG
  GAT GGC CTT CTC CGA CGG ATG TCT CCC TTG CGT CCC GCC TCC CCT TCT TGT AGG CCT GCA
  TCA TCA CCG TTT TTC TGG ACA ACC CCA AAG TAC CCC GTC TCC CTG GCT TTA GCC ACC TCT
  CCA TCC TCT TGC TTT CTT TGC CTG GAC ACC CCG TTC TCC TGT GGA TTC GGG TCA CCT CTC
  ACT CCT TTC ATT TGG GCA GCT CCC CTA CCC CCC TTA CCT CTC TAG TCT GTG CAA GCT CTT
  CCA GCC CCC TGT CAT GGC ATC TTC CAG GGG TCC GAG AGC TCA GCT AGT CTT CTT CCT CCA
  ACC CGG GCC CCT ATG TCC ACT TCA GGA CAG CAT GTT TGC TGC CTC CAG GGA TCC TGT GTC
  CCC GAG CTG GGA CCA CCT TAT ATT CCC AGG GCC GGT TAA TGT GGC TCT GGT TCT GGG TAC
  TTT TAT CTG TCC CCT CCA CCC CAC AGT GGG GCA AGA TGC ATC TTC TGA CCT CTT CTC TTC

  >Splice_acceptor
            |
            | 850        860        870        880        890        900
  CTC CCA CAG GGC ATG GCA AAA CCT CTG AGC CAG GAA GAA AGC ACA CTG ATT GAA AGA GCA
                   M   A   K   P   L   S   Q   E   E   S   T   L   I   E   R   A>
                  ____a___a___a___a___a___a_BLASTICIDIN___a___a___a___a___a___a___>

             910        920        930        940        950        960
  ACC GCT ACT ATC AAC AGC ATC CCC ATC TCC GAA GAC TAT TCT GTG GCT AGT GCC GCT CTG
   T   A   T   I   N   S   I   P   I   S   E   D   Y   S   V   A   S   A   A   L>
  ____a___a___a___a___a___a___a___a_BLASTICIDIN___a___a___a___a___a___a___a___a___>

             970        980        990       1000       1010       1020
  TCC AGC GAC GGG AGA ATC TTC ACC GGT GTG AAC GTC TAC CAC TTT ACA GGC GGA CCA TGC
   S   S   D   G   R   I   F   T   G   V   N   V   Y   H   F   T   G   G   P   C>
  ____a___a___a___a___a___a___a___a_BLASTICIDIN___a___a___a___a___a___a___a___a___>

            1030       1040       1050       1060       1070       1080
  GCA GAG CTG GTG GTC CTG GGG ACT GCA GCC GCT GCA GCC GCT GGT AAT CTG ACC TGT ATC
   A   E   L   V   V   L   G   T   A   A   A   A   A   A   G   N   L   T   C   I>
  ____a___a___a___a___a___a___a___a_BLASTICIDIN___a___a___a___a___a___a___a___a___>

            1090       1100       1110       1120       1130       1140
  GTG GCC ATT GGC AAC GAA AAT AGG GGC ATC CTG TCC CCA TGC GGC AGG TGT CGG CAG GTG
   V   A   I   G   N   E   N   R   G   I   L   S   P   C   G   R   C   R   Q   V>
  ____a___a___a___a___a___a___a___a_BLASTICIDIN___a___a___a___a___a___a___a___a___>

            1150       1160       1170       1180       1190       1200
  CTG CTG GAT CTG CAT CCT GGC ATC AAG GCA ATT GTC AAA GAC TCT GAT GGA CAG CCT ACC
   L   L   D   L   H   P   G   I   K   A   I   V   K   D   S   D   G   Q   P   T>
  ____a___a___a___a___a___a___a___a_BLASTICIDIN___a___a___a___a___a___a___a___a___>

            1210       1220       1230       1240       1250       1260
  GCC GTC GGT ATC CGT GAA CTG CTG CCT AGC GGC TAT GTC TGG GAG GGA TAA TGA GCT TGG
   A   V   G   I   R   E   L   L   P   S   G   Y   V   W   E   G   *   *> (SEQ ID NO: 167)
  ____a___a___a___a___a___a___a_BLASTICIDIN___a___a___a___a___a___a___a___>

>SV40_poly_A
       |
>BstB1|
   |   |
   |   |    1270       1280       1290       1300       1310       1320
  CTT CGA AAT GAC CGA CCA AGC GAC GCC CAA CCT GCC ATC ACG AGA TTT CGA TTC CAC CGC
  CGC CTT CTA TGA AAG GTT GGG CTT CGG AAT CGT TTT CCG GGA CGC CGG CTG GAT GAT CCT
  CCA GCG CGG GGA TCT CAT GCT GGA GTT CTT CGC CCA CCC CAA CTT GTT TAT TGC AGC TTA
  TAA TGG TTA CAA ATA AAG CAA TAG CAT CAC AAA TTT CAC AAA TAA AGC ATT TTT TTC ACT
```

Figure 1b (cont)

```
                  >EF1_alpha_promoter
                                   |
        1510          1520         |     1530          1540          1550          1560
GCA TTC TAG TTG TGG AGA TCT CGT GAG GCT CCG GTG CCC GTC AGT GGG CAG AGC GCA CAT
CGC CCA CAG TCC CCG AGA AGT TGG GGG GAG GGG TCG GCA ATT GAA CCG GTG CCT AGA GAA
GGT GGC GCG GGG TAA ACT GGG AAA GTG ATG TCG TGT ACT GGC TCC GCC TTT TTC CCG AGG
GTG GGG GAG AAC CGT ATA TAA GTG CAC TAG TCG CCG TGA ACG TTC TTT TTC GCA ACG GGT
TTG CCG CCA GAA CAC AGG TAA GTG CCG TGT GTG GTT CCC GCG GGC CTG GCC TCT TTA CGG
GTT ATG GCC CTT GCG TGC CTT GAA TTA CTT CCA CCT GGC TGC AGT ACG TGA TTC TTG ATC
CCG AGC TTC GGG TTG GAA GTG GGT GGG AGA GTT CGT GGC CTT GCG CTT AAG GAG CCC CTT
CGC CTC GTG CTT GAG TTG TGG CCT GGC CTG GGC GCT GGG GCC GCC GCG TGC GAA TCT GGT
GGC ACC TTC GCG CCT GTC TCG CTG CTT TCG ATA AGT CTC TAG CCA TTT AAA ATT TTT GAT
GAC CTG CTG CGA CGC TTT TTT TCT GGC AAG ATA GTC TTG TAA ATG CGG GCC AAG ATC AGC
ACA CTG GTA TTT CGG TTT TTG GGG CCG CGG GCG GCG ACG GGG CCC GTG CGT CCC AGC GCA
CAT GTT CGG CGA GGC GGG GCC TGC GAG CGC GGC CAC CGA GAA TCG GAC GGG GGT AGT CTC
AAG CTG CCC GGC CTG CTC TGG TGC CTG GCC TCG CGC CGC CGT GTA TCG CCC CGC CCT GGG
CGG CAA GGC TGG CCC GGT CGG CAC CAG TTG CGT GAG CGG AAA GAT GGC CGC TTC CCG GCC
CTG CTG CAG GGA GCA CAA AAT GGA GGA CGC GGC GCT CGG GAG AGC GGG CGG GTG AGT CAC
CCA CAC AAA GGA AAA GGG CCT TTC CGT CCT CAG CCG TCG CTT CAT GTG ACT CCA CGG AGT
ACC GGG CGC CGT CCA GGC ACC TCG ATT AGT TCT CCA GCT TTT GGA GTA CGT CGT CTT TAG
GTT GGG GGG AGG GGT TTT ATG CGA TGG AGT TTC CCC ACA CTG AGT GGG TGG AGA CTG AAG
TTA GGC CAG CTT GGC ACT TGA TGT AAT TCT CCT TGG AAT TTG CCC TTT TTG AGT TTG GAT
CTT GGT TCA TTC TCA AGC CTC AGA CAG TGG TTC AAA GTT TTT TTC TTC CAT TTC AGG TGT

|
        2710          2720          2730          2740          2750          2760
CGT GAA AAC TAC CCC TAA AAG CCA AAA GAT CCG GAG TGG CCA CCA TGA GGG CCT GGA TCT
                                                             M   R   A   W   I>
                                                            _b___b__LEAD_b___b___>

                                                    NheI
                                                     |
        2770          2780          2790          2800          2810          2820
TCT TTC TCC TTT GCC TGG CCG GGA GGG CTC TGG CAG CTA GCG ACA TCC AGA TGA CCC AGA
F   F   L   L   C   L   A   G   R   A   L   A   A> (SEQ ID NO: 168)
____b___b___b___b___b___LEAD_____b___b___b___b___b___>
                                                 S   D   I   Q   M   T   Q>
                                                _c___c___c___VL__c___c___c___>

        2830          2840          2850          2860          2870          2880
GCC CAA GCA GCC TGA GCG CCA GCG TGG GTG ACA GAG TGA CCA TCA CCT GTA GAG CCA GCG
S   P   S   S   L   S   A   S   V   G   D   R   V   T   I   T   C   R   A   S>
____c___c___c___c___c___c___c___c___c__VL___c___c___c___c___c___c___c___c___c___>

        2890          2900          2910          2920          2930          2940
GTA ACA TCC ACA ACT ACC TGG CTT GGT ACC AGC AGA AGC CAG GTA AGG CTC CAA AGC TGC
G   N   I   H   N   Y   L   A   W   Y   Q   Q   K   P   G   K   A   P   K   L>
____c___c___c___c___c___c___c___c___c__VL___c___c___c___c___c___c___c___c___c___>

        2950          2960          2970          2980          2990          3000
TGA TCT ACT ACA CCA CCA CCC TGG CTG ACG GTG TGC CAA GCA GAT TCA GCG GTA GCG GTA
L   I   Y   Y   T   T   T   L   A   D   G   V   P   S   R   F   S   G   S   G>
____c___c___c___c___c___c___c___c___c__VL___c___c___c___c___c___c___c___c___c___>

        3010          3020          3030          3040          3050          3060
GCG GTA CCG ACT ACA CCT TCA CCA TCA GCA GCC TCC AGC CAG AGG ACA TCG CCA CCT ACT
S   G   T   D   Y   T   F   T   I   S   S   L   Q   P   E   D   I   A   T   Y>
____c___c___c___c___c___c___c___c___c__VL___c___c___c___c___c___c___c___c___c___>

        3070          3080          3090          3100          3110          3120
ACT GCC AGC ACT TCT GGA GCA CCC CAA GGA CGT TCG GCC AAG GGA CCA AGG TGG AAA TCA
Y   C   Q   H   F   W   S   T   P   R   T   F   G   Q   G   T   K   V   E   I>
____c___c___c___c___c___c___c___c___c__VL___c___c___c___c___c___c___c___c___c___>
```

Figure 1b (cont)

```
        >NotI
          |
          3130          3140          3150           3160          3170          3180
AAC GTA CCG CGG CCG CCC CTT CCG TGT TCA TCT TCC CTC CCT CCG ACG AGC AGC TGA AGT
K    R    T> (SEQ ID NO: 169)
___c___c___c_>
                        P   S   V   F   I   F   P   P   S   D   E   Q   L   K>
                       _d___d___d___d___d___d___d_CL____d___d___d___d___d___d___>

          3190          3200          3210           3220          3230          3240
CCG GCA CCG CCT CTG TGG TGT GCC TGC TGA ACA ACT TCT ACC CTC GGG AGG CCA AGG TGC
S   G   T   A   S   V   V   C   L   L   N   N   F   Y   P   R   E   A   K   V>
___d___d___d___d___d___d___d___d___d_CL___d___d___d___d___d___d___d___d___d___>

          3250          3260          3270           3280          3290          3300
AGT GGA AGG TGG ACA ACG CCC TGC AGT CCG GCA ACT CCC AGG AAT CCG TCA CCG AGC AGG
Q   W   K   V   D   N   A   L   Q   S   G   N   S   Q   E   S   V   T   E   Q>
___d___d___d___d___d___d___d___d___d_CL___d___d___d___d___d___d___d___d___d___>

          3310          3320          3330           3340          3350          3360
ACT CCA AGG ACT CTA CCT ACT CCC TGT CCT CCA CCC TGA CCC TGT CCA AGG CCG ACT ACG
D   S   K   D   S   T   Y   S   L   S   S   T   L   T   L   S   K   A   D   Y>
___d___d___d___d___d___d___d___d___d_CL___d___d___d___d___d___d___d___d___d___>

          3370          3380          3390           3400          3410          3420
AGA AGC ACA AGC TGT ACG CCT GCG AAG TGA CCC ACC AGG GCC TGT CCT CTC CCG TGA CCA
E   K   H   K   L   Y   A   C   E   V   T   H   Q   G   L   S   S   P   V   T>
___d___d___d___d___d___d___d___d___d_CL___d___d___d___d___d___d___d___d___d___>

                                                                >BGH_pA
                                                                   |
          3430          3440          3450           3460          3470          3480
AGT CCT TCA ACC GGG GCG AGT GCT AAT AAG GAT CCA CGA CGT GAT CAG CCT CGA CTG TGC
K   S   F   N   R   G   E   C> (SEQ ID NO: 170)
___d___d___d_CL____d___d___d__>

          3490          3500          3510           3520          3530          3540
CTT CTA GTT GCC AGC CAT CTG TTG TTT GCC CCT CCC CCG TGC CTT CCT TGA CCC TGG AAG
GTG CCA CTC CCA CTG TCC TTT CCT AAT AAA ATG AGG AAA TTG CAT CGC ATT GTC TGA GTA
GGT GTC ATT CTA TTC TGG GGG GTG GGG TGG GGC AGG ACA GCA AGG GGG AGG ATT GGG AAG

                                                    >CMV_promoter
                                                         |
          3670          3680          3690           3700|         3710          3720
ACA ATA GCA GGC ATG CTG GGG ACG ATC GTC AGC TGG ATC TAG TAA TCA ATT ACG GGG TCA
TTA GTT CAT AGC CCA TAT ATG GAG TTC CGC GTT ACA TAA CTT ACG GTA AAT GGC CCG CCT
GGC TGA CCG CCC AAC GAC CCC CGC CCA TTG ACG TCA ATA ATG ACG TAT GTT CCC ATA GTA
ACG CCA ATA GGG ACT TTC CAT TGA CGT CAA TGG GTG GAG TAT TTA CGG TAA ACT GCC CAC
TTG GCA GTA CAT CAA GTG TAT CAT ATG CCA AGT ACG CCC CCT ATT GAC GTC AAT GAC GGT
AAA TGG CCC GCC TGG CAT TAT GCC CAG TAC ATG ACC TTA TGG GAC TTT CCT ACT TGG CAG
TAC ATC TAC GTA TTA GTC ATC GCT ATT ACC ATG CTG ATG CGG TTT TGG CAG TAC ATC AAT
GGG CGT GGA TAG CGG TTT GAC TCA CGG GGA TTT CCA AGT CTC CAC CCC ATT GAC GTC AAT
GGG AGT TTG TTT TGG CAC CAA AAT CAA CGG GAC TTT CCA AAA TGT CGT AAC AAC TCC GCC
CCA TTG ACG CAA ATG GGC GGT AGG CGT GTA CGG TGG GAG GTC TAT ATA AGC AGA GCT GGT

                                    >Cla1
                                      |
          4270          4280          | 4290           4300          4310          4320
TTA GTG AAC CGT CAG ATC AGA TCC ATC GAT TGG CCA CCA TGA GTT GGA GCT GTA TCA TCC
                                                         M   S   W   S   C   I   I>
                                                       _e___e___e__LEAD_e___e___e___>
```

Figure 1b (cont)

```
                                   >intron
                                   |
       4330          4340          |  4350          4360          4370          4380
TCT TCT TGG TAG CAA CAG CTA CAG GTA AGG GGT TAA CAG TAG CAG GCT TGA GGT CTG GAC
 L   F   L   V   A   T   A   T> (SEQ ID NO: 171)
____e____e______LEAD____e____e____e__>
                                                                 >NcoI
                                                                   |
       4390          4400          4410          4420          4430          4440
ATA TAT ATG GGT GAC AAT GAC ATC CAC TTT GCC TTT CTC TCC ACA GGC GCC ATG GCC CAG
                                                                M   A   Q>
                                                           ____f____f____>

       4450          4460          4470          4480          4490          4500
GTC CAA CTG CAG GAG AGC GGT CCA GGT CTT GTG AGA CCT AGC CAG ACC CTG AGC CTG ACC
 V   Q   L   Q   E   S   G   P   G   L   V   R   P   S   Q   T   L   S   L   T>
____f____f____f____f____f____f____f____f____f__VH____f____f____f____f____f____f____f____f____f____>

       4510          4520          4530          4540          4550          4560
TGC ACC GTG TCT GGC AGC ACC TTC AGC GGC TAT GGT GTA AAC TGG GTG AGA CAG CCA CCT
 C   T   V   S   G   S   T   F   S   G   Y   G   V   N   W   V   R   Q   P   P>
____f____f____f____f____f____f____f____f____f__VH____f____f____f____f____f____f____f____f____f____>

       4570          4580          4590          4600          4610          4620
GGA CGA GGT CTT GAG TGG ATT GGA ATG ATT TGG GGT GAT GGA AAC ACA GAC TAT AAT TCA
 G   R   G   L   E   W   I   G   M   I   W   G   D   G   N   T   D   Y   N   S>
____f____f____f____f____f____f____f____f____f__VH____f____f____f____f____f____f____f____f____f____>

       4630          4640          4650          4660          4670          4680
GCT CTC AAA TCC AGA GTG ACA ATG CTG GTA GAC ACC AGC AAG AAC CAG TTC AGC CTG AGA
 A   L   K   S   R   V   T   M   L   V   D   T   S   K   N   Q   F   S   L   R>
____f____f____f____f____f____f____f____f____f__VH____f____f____f____f____f____f____f____f____f____>

       4690          4700          4710          4720          4730          4740
CTC AGC AGC GTG ACA GCC GCC GAC ACC GCG GTC TAT TAT TGT GCA AGA GAG AGA GAT TAT
 L   S   S   V   T   A   A   D   T   A   V   Y   Y   C   A   R   E   R   D   Y>
____f____f____f____f____f____f____f____f____f__VH____f____f____f____f____f____f____f____f____f____>

                                                      >XhoI
                                                        |
       4750          4760          4770          4780          4790          4800
AGG CTT GAC TAC TGG GGT CAA GGC AGC CTC GTC ACA GTC TCG AGT GCC TCC ACC AAG GGC
 R   L   D   Y   W   G   Q   G   S   L   V   T   V> (SEQ ID NO: 172)
____f____f____f____f____f_____VH_f____f____f____f____f____f____>
                                                    S   S   A   S   T   K   G>
                                                 ____g_____IGG1 CH1-3_g____g____>

       4810          4820          4830          4840          4850          4860
CCT AGC GTC TTT CCT CTG GCC CCT TCC TCC AAG TCT ACC TCT GGC GGC ACC GCT GCT CTG
 P   S   V   F   P   L   A   P   S   S   K   S   T   S   G   G   T   A   A   L>
____g____g____g____g____g____g____g____g___IGG1 CH1-3____g____g____g____g____g____g____g____g____>

       4870          4880          4890          4900          4910          4920
GGC TGC CTG GTG AAG GAC TAC TTC CCT GAG CCT GTG ACC GTG TCC TGG AAC TCT GGC GCC
 G   C   L   V   K   D   Y   F   P   E   P   V   T   V   S   W   N   S   G   A>
____g____g____g____g____g____g____g____g___IGG1 CH1-3____g____g____g____g____g____g____g____g____>

       4930          4940          4950          4960          4970          4980
CTG ACC TCC GGC GTG CAT ACC TTC CCT GCC GTC CTC CAG TCC TCC GGC CTG TAC TCC CTG
 L   T   S   G   V   H   T   F   P   A   V   L   Q   S   S   G   L   Y   S   L>
____g____g____g____g____g____g____g____g___IGG1 CH1-3____g____g____g____g____g____g____g____g____>

       4990          5000          5010          5020          5030          5040
TCC TCC GTG GTG ACC GTG CCT TCC TCC TCT CTG GGC ACC CAG ACC TAC ATC TGC AAC GTG
 S   S   V   V   T   V   P   S   S   S   L   G   T   Q   T   Y   I   C   N   V>
____g____g____g____g____g____g____g____g___IGG1 CH1-3____g____g____g____g____g____g____g____g____>
```

Figure 1b (cont)

```
            5050            5060            5070             5080            5090            5100
AAC CAC AAG CCT TCC AAC ACC AAG GTG GAC AAG AAG GTG GAG CCT AAG TCC TGC GAC AAG
 N   H   K   P   S   N   T   K   V   D   K   K   V   E   P   K   S   C   D   K>
____g____g____g____g____g____g____g____g___IGG1 CH1-3____g____g____g____g____g____g____g____g____>

            5110            5120            5130             5140            5150            5160
ACC CAC ACC TGC CCT CCA TGT CCT GCC CCT GAG CTG CTG GGC GGA CCC TCC GTG TTC CTG
 T   H   T   C   P   P   C   P   A   P   E   L   L   G   G   P   S   V   F   L>
____g____g____g____g____g____g____g____g___IGG1 CH1-3____g____g____g____g____g____g____g____g____>

            5170            5180            5190             5200            5210            5220
TTC CCT CCT AAG CCT AAG GAC ACC CTG ATG ATC TCC CGG ACC CCT GAA GTG ACC TGC GTG
 F   P   P   K   P   K   D   T   L   M   I   S   R   T   P   E   V   T   C   V>
____g____g____g____g____g____g____g____g___IGG1 CH1-3____g____g____g____g____g____g____g____g____>

            5230            5240            5250             5260            5270            5280
GTG GTG GAC GTG TCC CAC GAA GAT CCT GAA GTG AAG TTC AAT TGG TAC GTG GAC GGC GTG
 V   V   D   V   S   H   E   D   P   E   V   K   F   N   W   Y   V   D   G   V>
____g____g____g____g____g____g____g____g___IGG1 CH1-3____g____g____g____g____g____g____g____g____>

            5290            5300            5310             5320            5330            5340
GAG GTG CAC AAC GCC AAG ACC AAG CCT CGG GAG GAA CAG TAC AAC TCC ACC TAC CGG GTG
 E   V   H   N   A   K   T   K   P   R   E   E   Q   Y   N   S   T   Y   R   V>
____g____g____g____g____g____g____g____g___IGG1 CH1-3____g____g____g____g____g____g____g____g____>

            5350            5360            5370             5380            5390            5400
GTG TCT GTG CTG ACC GTG CTG CAC CAG GAC TGG CTG AAC GGC AAA GAA TAC AAG TGC AAG
 V   S   V   L   T   V   L   H   Q   D   W   L   N   G   K   E   Y   K   C   K>
____g____g____g____g____g____g____g____g___IGG1 CH1-3____g____g____g____g____g____g____g____g____>

            5410            5420            5430             5440            5450            5460
GTG TCC AAC AAG GCC CTG CCT GCC CCT ATC GAA AAG ACC ATC TCC AAG GCT AAG GGC CAG
 V   S   N   K   A   L   P   A   P   I   E   K   T   I   S   K   A   K   G   Q>
____g____g____g____g____g____g____g____g___IGG1 CH1-3____g____g____g____g____g____g____g____g____>

            5470            5480            5490             5500            5510            5520
CCA CGG GAA CCT CAG GTC TAC ACA CTG CCT CCT AGC CGG GAC GAG CTG ACC AAG AAC CAG
 P   R   E   P   Q   V   Y   T   L   P   P   S   R   D   E   L   T   K   N   Q>
____g____g____g____g____g____g____g____g___IGG1 CH1-3____g____g____g____g____g____g____g____g____>

            5530            5540            5550             5560            5570            5580
GTG TCC CTG ACC TGT CTG GTG AAG GGC TTC TAC CCT TCC GAT ATC GCC GTG GAG TGG GAG
 V   S   L   T   C   L   V   K   G   F   Y   P   S   D   I   A   V   E   W   E>
____g____g____g____g____g____g____g____g___IGG1 CH1-3____g____g____g____g____g____g____g____g____>

            5590            5600            5610             5620            5630            5640
TCT AAC GGC CAG CCT GAG AAC AAC TAC AAG ACC ACC CCT CCT GTG CTG GAC TCC GAC GGC
 S   N   G   Q   P   E   N   N   Y   K   T   T   P   P   V   L   D   S   D   G>
____g____g____g____g____g____g____g____g___IGG1 CH1-3____g____g____g____g____g____g____g____g____>

            5650            5660            5670             5680            5690            5700
TCC TTC TTC CTG TAC TCC AAG CTG ACC GTG GAC AAG TCC CGG TGG CAG CAG GGC AAC GTG
 S   F   F   L   Y   S   K   L   T   V   D   K   S   R   W   Q   Q   G   N   V>
____g____g____g____g____g____g____g____g___IGG1 CH1-3____g____g____g____g____g____g____g____g____>

            5710            5720            5730             5740            5750            5760
TTC TCC TGC TCC GTG ATG CAC GAG GCC CTG CAC AAC CAC TAC ACC CAG AAG TCC CTG TCC
 F   S   C   S   V   M   H   E   A   L   H   N   H   Y   T   Q   K   S   L   S>
____g____g____g____g____g____g____g____g___IGG1 CH1-3____g____g____g____g____g____g____g____g____>
```

Figure 1b (cont)

```
         5770         5780         5790          5800         5810          5820
CTG TCT CCT GGC AAG GAA CAA AAA CTC ATC TCA GAA GAG GAT CTG AAT GCT GTG GGC CAG
 L   S   P   G   K> (SEQ ID NO: 173)
____IGG1 CH1-3_g____>
                     E   Q   K   L   I   S   E   E   D   L> (SEQ ID NO: 174)
                    ___h___h___h_MYC-EPITOPE___h___h___h___>
                                                                 N   A   V   G   Q>
                                                                ___i____TM_i___i___>

         5830         5840         5850          5860         5870          5880
GAC ACG CAG GAG GTC ATC GTG GTG CCA CAC TCC TTG CCC TTT AAG GTG GTG GTG ATC TCA
 D   T   Q   E   V   I   V   V   P   H   S   L   P   F   K   V   V   V   I   S>
___i___i___i___i___i___i___i___i___i__TM___i___i___i___i___i___i___i___i___i___>

         5890         5900         5910          5920         5930          5940
GCC ATC CTG GCC CTG GTG GTG CTC ACC ATC ATC TCC CTT ATC ATC CTC ATC ATG CTT TGG
 A   I   L   A   L   V   V   L   T   I   I   S   L   I   I   L   I   M   L   W>
___i___i___i___i___i___i___i___i___i__TM___i___i___i___i___i___i___i___i___i___>

                         >HindIII                              >pre_polyA
                             |                                     |
         5950         5960   |     5970          5980              |5990          6000
CAG AAG AAG CCA CGT TAG TAA AAG CTT GTC ACT TGG AAA GTA ATA GTT TTT CCT GCA CGG
 Q   K   K   P   R   *   *> (SEQ ID NO: 175)
___i___i____TM_i___i___i___>

         >BGH_pA
            |
         6010|        6020         6030          6040         6050          6060
GTA GTA ATC AGC CTC GAC TGT GCC TTC TAG TTG CCA GCC ATC TGT TGT TTG CCC CTC CCC
CGT GCC TTC CTT GAC CCT GGA AGG TGC CAC TCC CAC TGT CCT TTC CTA ATA AAA TGA GGA
AAT TGC ATC GCA TTG TCT GAG TAG GTG TCA TTC TAT TCT GGG GGG TGG GGT GGG GCA GGA

                                                        <BGH_polyA          >loxP
                                                             |                 |
         6190         6200         6210          6220        |  6230          6240
CAG CAA GGG GGA GGA TTG GGA AGA CAA TAG CAG GCA TGC TGG GGA TGG CCC GGG CAT GAT

                                                         >AAVS_right_arm
                                                                 |
         6250         6260         6270          6280         6290          6300
AAC TTC GTA TAA TGT ATG CTA TAC GAA GTT ATG TAT ACG GCG CGC CCA CTA GGG ACA GGA
TTG GTG ACA GAA AAG CCC CAT CCT TAG GCC TCC TCC TTC CTA GTC TCC TGA TAT TGG GTC
TAA CCC CCA CCT CCT GTT AGG CAG ATT CCT TAT CTG GTG ACA CAC CCC CAT TTC CTG GAG
CCA TCT CTC TCC TTG CCA GAA CCT CTA AGG TTT GCT TAC GAT GGA GCC AGA GAG GAT CCT
GGG AGG GAG AGC TTG GCA GGG GGT GGG AGG GAA GGG GGG GAT GCG TGA CCT GCC CGG TTC
TCA GTG GCC ACC CTG CGC TAC CCT CTC CCA GAA CCT GAG CTG CTC TGA CGC GGC TGT CTG
GTG CGT TTC ACT GAT CCT GGT GCT GCA GCT TCC TTA CAC TTC CCA AGA GGA GAA GCA GTT
TGG AAA AAC AAA ATC AGA ATA AGT TGG TCC TGA GTT CTA ACT TTG GCT CTT CAC CTT TCT
AGT CCC CAA TTT ATA TTG TTC CTC CGT GCG TCA GTT TTA CCT GTG AGA TAA GGC CAG TAG
CCA GCC CCG TCC TGG CAG GGC TGT GGT GAG GAG GGG GGT GTC CGT GTG GAA AAC TCC CTT
TGT GAG AAT GGT GCG TCC TAG GTG TTC ACC AGG TCG TGG CCG CCT CTA CTC CCT TTC TCT
TTC TCC ATC CTT CTT TCC TTA AAG AGT CCC CAG TGC TAT CTG GGA CAT ATT CCT CCG CCC
AGA GCA GGG TCC CGC TTC CCT AAG GCC CTG CTC TGG GCT TCT GGG TTT GAG TCC TTG GCA
AGC CCA GGA GAG GCG CTC AGG CTT CCC TGT CCC CCT TCC TCG TCC ACC ATC TCA TGC CCC

                                                           >Sbf1
                                                             |
         7090         7100         7110          7120        |  7130          7140
TGG CTC TCC TGC CCC TTC CCT ACA GGG GTT CCT GGC TCT GCT CTC CTG CAG GCG ATC TCT

                    >beta_globin_insulator
                               |
         7150         7160     |   7170          7180         7190          7200
CGA TCT CTC GAT TTC GAT CAA GAC ATT CCT TTA ATG GTC TTT TCT GGA CAC CAC TAG GGG
TCA GAA GTA GTT CAT CAA ACT TTC TTC CCT CCC TAA TCT CAT TGG TTA CCT TGG GCT ATC
```

Figure 1b (cont)

```
                        >f1_origin
                                 |
        7270        7280         |      7290           7300         7310          7320
GAA ACT TAA TTA AGC CAC CTG ACG CGC CCT GTA GCG GCG CAT TAA GCG CGG CGG GTG TGG
TGG TTA CGC GCA GCG TGA CCG CTA CAC TTG CCA GCG CCC TAG CGC CCG CTC CTT TCG CTT
TCT TCC CTT CCT TTC TCG CCA CGT TCG CCG GCT TTC CCC GTC AAG CTC TAA ATC GGG GGC
TCC CTT TAG GGT TCC GAT TTA GTG CTT TAC GGC ACC TCG ACC CCA AAA AAC TTG ATT AGG
GTG ATG GTT CAC GTA GTG GGC CAT CGC CCT GAT AGA CGG TTT TTC GCC CTT TGA CGT TGG
AGT CCA CGT TCT TTA ATA GTG GAC TCT TGT TCC AAA CTG GAA CAA CAC TCA ACC CTA TCT
CGG TCT ATT CTT TTG ATT TAT AAG GGA TTT TGC CGA TTT CGG CCT ATT GGT TAA AAA ATG
AGC TGA TTT AAC AAA AAT TTA ACG CGA ATT TTA ACA AAA TAT TAA CGC TTA CAA TTT ACG
CGT TAA GAT ACA TTG ATG AGT TTG GAC AAA CCA CAA CTA GTT AAT TAA CCA GTC AAG TCA
GCT ACT TGG CGA GAT CGA CTT GTC TGG GTT TCG ACT ACG CTC AGA ATT GCG TCA GTC AAG

                                                                                     >pUC_origin
                                                                                       |
        7870        7880         7890           7900         7910                      | 7920
TTC GAT CTG GTC CTT GCT ATT GCA CCC GTT CTC CGA TTA CGA GTT TCA TTT AAA TCA TGT
GAG CAA AAG GCC AGC AAA AGG CCA GGA ACC GTA AAA AGG CCG CGT TGC TGG CGT TTT TCC
ATA GGC TCC GCC CCC CTG ACG AGC ATC ACA AAA ATC GAC GCT CAA GTC AGA GGT GGC GAA
ACC CGA CAG GAC TAT AAA GAT ACC AGG CGT TTC CCC CTG GAA GCT CCC TCG TGC GCT CTC
CTG TTC CGA CCC TGC CGC TTA CCG GAT ACC TGT CCG CCT TTC TCC CTT CGG GAA GCG TGG
CGC TTT CTC ATA GCT CAC GCT GTA GGT ATC TCA GTT CGG TGT AGG TCG TTC GCT CCA AGC
TGG GCT GTG TGC ACG AAC CCC CCG TTC AGC CCG ACC GCT GCG CCT TAT CCG GTA ACT ATC
GTC TTG AGT CCA ACC CGG TAA GAC ACG ACT TAT CGC CAC TGG CAG CAG CCA CTG GTA ACA
GGA TTA GCA GAG CGA GGT ATG TAG GCG GTG CTA CAG AGT TCT TGA AGT GGT GGC CTA ACT
ACG GCT ACA CTA GAA GAA CAG TAT TTG GTA TCT GCG CTC TGC TGA AGC CAG TTA CCT TCG
GAA AAA GAG TTG GTA GCT CTT GAT CCG GCA AAC AAA CCA CCG CTG GTA GCG GTG GTT TTT
TTG TTT GCA AGC AGC AGA TTA CGC GCA GAA AAA AAG GAT CTC AAG AAG ATC CTT TGA TCT
TTT CTA CGG GGT CTG ACG CTC AGT GGA ACG AAA ACT CAC GTT AAG GGA TTT TGG TCA TGA
GAT TAT CAA AAA GGA TCT TCA CCT AGA TCC TTT TAA ATT AAA AAT GAA GTT TTA AAT CAA
TCT AAA GTA TAT ATG AGT AAA CTT GGT CTG ACA GTT ACC AAT GCT TAA TCA GTG AGG CAC
CTA TCT CAG CGA TCT GTC TAT TTC GTT CAT CCA TAG TTG CAT TTA AAT TTC CGA ACT CTC
CAA GGC CCT CGT CGG AAA ATC TTC AAA CCT TTC GTC CGA TCC ATC TTG CAG GCT ACC TCT

                                      >Fse1
        8890        8900              | 8910           8920         8930          8940
CGA ACG AAC TAT CGC AAG TCT CTT GGC CGG CCT TGC GCC TTG GCT ATT GCT TGG CAG CGC
CTA TCG CCA GGT ATT ACT CCA ATC CCG AAT ATC CGA GAT CGG GAT CAC CCG AGA GAA GTT

                                                                                        >Asc1
        9010        9020         9030           9040         9050                      | 9060
CAA CCT ACA TCC TCA ATC CCG ATC TAT CCG AGA TCC GAG GAA TAT CGA AAT CGG GGC GCG
CCT GGT GTA CCG AGA ACG ATC CTC TCA GTG CGA GTC TCG ACG ATC CAT ATC GTT GCT TGG
CAG TCA GCC AGT CGG AAT CCA GCT TGG GAC CCA GGA AGT CCA ATC GTC AGA TAT TGT ACT
CAA GCC TGG TCA CGG CAG CGT ACC GAT CTG TTT AAA CCT AGA TAT TGA TAG TCT GAT CGG
TCA ACG TAT AAT CGA GTC CTA GCT TTT GCA AAC ATC TAT CAA GAG ACA GGA TCA GCA GGA

        >Kan-R
           |
        9310        9320         9330           9340         9350          9360
GGC TTT CGC ATG ATT GAA CAA GAT GGA TTG CAC GCA GGT TCT CCG GCG GCT TGG GTG GAG
             M   I   E   Q   D   G   L   H   A   G   S   P   A   A   W   V   E>
            ____j___j___j___j___j___j___j___KANR____j___j___j___j___j___j___j___>

        9370        9380         9390           9400         9410          9420
AGG CTA TTC GGC TAT GAC TGG GCA CAA CAG ACA ATC GGC TGC TCT GAT GCC GCC GTG TTC
 R   L   F   G   Y   D   W   A   Q   Q   T   I   G   C   S   D   A   A   V   F>
____j___j___j___j___j___j___j___j___j_KANR___j___j___j___j___j___j___j___j___j___>

        9430        9440         9450           9460         9470          9480
CGG CTG TCA GCG CAG GGG CGT CCG GTT CTT TTT GTC AAG ACC GAC CTG TCC GGT GCC CTG
 R   L   S   A   Q   G   R   P   V   L   F   V   K   T   D   L   S   G   A   L>
____j___j___j___j___j___j___j___j___j_KANR___j___j___j___j___j___j___j___j___j___>
```

Figure 1b (cont)

```
            9490        9500        9510         9520        9530        9540
AAT GAA CTG CAA GAC GAG GCA GCG CGG CTA TCG TGG CTG GCG ACG ACG GGC GTT CCT TGC
 N   E   L   Q   D   E   A   A   R   L   S   W   L   A   T   T   G   V   P   C>
____j____j____j____j____j____j____j____j____j_KANR___j____j____j____j____j____j____j____j____j____>

            9550        9560        9570         9580        9590        9600
GCG GCT GTG CTC GAC GTT GTC ACT GAA GCG GGA AGG GAC TGG CTG CTA TTG GGC GAA GTG
 A   A   V   L   D   V   V   T   E   A   G   R   D   W   L   L   L   G   E   V>
____j____j____j____j____j____j____j____j____j_KANR___j____j____j____j____j____j____j____j____j____>

            9610        9620        9630         9640        9650        9660
CCG GGG CAG GAT CTC CTG TCA TCT CAC CTT GCT CCT GCC GAG AAA GTA TCC ATC ATG GCT
 P   G   Q   D   L   L   S   S   H   L   A   P   A   E   K   V   S   I   M   A>
____j____j____j____j____j____j____j____j____j_KANR___j____j____j____j____j____j____j____j____j____>

            9670        9680        9690         9700        9710        9720
GAT GCA ATG CGG CGG CTG CAT ACG CTT GAT CCG GCT ACC TGC CCA TTC GAC CAC CAA GCG
 D   A   M   R   R   L   H   T   L   D   P   A   T   C   P   F   D   H   Q   A>
____j____j____j____j____j____j____j____j____j_KANR___j____j____j____j____j____j____j____j____j____>

            9730        9740        9750         9760        9770        9780
AAA CAT CGC ATC GAG CGA GCA CGT ACT CGG ATG GAA GCC GGT CTT GTC GAT CAG GAT GAT
 K   H   R   I   E   R   A   R   T   R   M   E   A   G   L   V   D   Q   D   D>
____j____j____j____j____j____j____j____j____j_KANR___j____j____j____j____j____j____j____j____j____>

            9790        9800        9810         9820        9830        9840
CTG GAC GAA GAG CAT CAG GGG CTC GCG CCA GCC GAA CTG TTC GCC AGG CTC AAG GCG TCT
 L   D   E   E   H   Q   G   L   A   P   A   E   L   F   A   R   L   K   A   S>
____j____j____j____j____j____j____j____j____j_KANR___j____j____j____j____j____j____j____j____j____>

            9850        9860        9870         9880        9890        9900
ATG CCC GAC GGC GAG GAT CTC GTC GTG ACC CAC GGC GAT GCC TGC TTG CCG AAT ATC ATG
 M   P   D   G   E   D   L   V   V   T   H   G   D   A   C   L   P   N   I   M>
____j____j____j____j____j____j____j____j____j_KANR___j____j____j____j____j____j____j____j____j____>

            9910        9920        9930         9940        9950        9960
GTG GAA AAT GGC CGC TTT TCT GGA TTC ATC GAC TGT GGC CGT CTG GGT GTG GCG GAC CGC
 V   E   N   G   R   F   S   G   F   I   D   C   G   R   L   G   V   A   D   R>
____j____j____j____j____j____j____j____j____j_KANR___j____j____j____j____j____j____j____j____j____>

            9970        9980        9990        10000       10010       10020
TAT CAG GAC ATA GCG TTG GCT ACC CGT GAT ATT GCT GAA GAG CTT GGC GGC GAA TGG GCT
 Y   Q   D   I   A   L   A   T   R   D   I   A   E   E   L   G   G   E   W   A>
____j____j____j____j____j____j____j____j____j_KANR___j____j____j____j____j____j____j____j____j____>

           10030       10040       10050        10060       10070       10080
GAC CGC TTC CTT GTG CTT TAC GGT ATC GCC GCG CCC GAT TCG CAG CGC ATC GCC TTC TAT
 D   R   F   L   V   L   Y   G   I   A   A   P   D   S   Q   R   I   A   F   Y>
____j____j____j____j____j____j____j____j____j_KANR___j____j____j____j____j____j____j____j____j____>

                                           >RgnG_terminator
                                                 |
           10090       10100       10110        10120       10130       10140
CGC CTT CTT GAC GAG TTC TTC TGA CCG ATT CTA GGT GCA TTG GCG CAG AAA AAA ATG CCT
 R   L   L   D   E   F   F   *> (SEQ ID NO: 176)
____j____j____j_KANR___j____j____j____>

           10150       10160       10170        10180       10190       10200
GAT GCG ACG CTG CGC GTC TTA TAC TCC CAC ATA TGC CAG ATT CAG CAA CGG ATA CGG CTT
CCC CAA CTT GCC CAC TTC CAT ACG TGT CCT CCT TAC CAG AAA TTT ATC CTT AAG GTC GTT
TAA ACT CGA CTC TGG CTC TAT CGA ATC TCC GTC GTT TCG AGC TTA CGC GAA CAG CCG TGG
CGC TCA TTT GCT CGT CGG GCA TCG AAT CTC GTC AGC TAT CGT CAG CTT ACC TTT TTG GCA
```
(SEQ ID NO: 166)

Figure 4

```
Sequence: VH-MEDI1912-geneblock-opt Range: 1 to 392

>MEDI1912-F3
 |         10         20         30         40         50         60
 CCA TGG CCC AGG TTC AGC TGG TTC AGT CTG GCG CCG AAG TGA AGA AAC CTG GCA GCA GCG
 GGT ACC GGG TCC AAG TCG ACC AAG TCA GAC CGC GGC TTC ACT TCT TTG GAC CGT CGT CGC
     M   A   Q   V   Q   L   V   Q   S   G   A   E   V   K   K   P   G   S   S>
   _b___b___b___b___b___b___b___b__VH-MEDI-1912_b___b___b___b___b___b___b___b___>
 ____a___a__>

                                          <MEDI-1912-3'    >MEDI-1912-F
                                                   |            |
            70         80         90         |  100 |         110         120
 TGA AGG TGT CCT GCA AAG CAA GCG GCG GCA CCT TTT GGT TCG GCG CCT TTA CAT GGG TCC
 ACT TCC ACA GGA CGT TTC GTT CGC CGC CGT GGA AAA CCA AGC CGC GGA AAT GTA CCC AGG
 V   K   V   S   C   K   A   S   G   G   T   F   W   F   G   A   F   T   W   V>
 ____b___b___b___b___b___b___b___b_VH-MEDI-1912__b___b___b___b___b___b___b___b___>
                                 G   G   T   F   W   F   G   A> (SEQ ID NO: 179)
                                _c___c___c___CDR1_____c___c___c__>

<MEDI1912_W30NNS_F31NNS-5'         >MEDI1912-L56NNS-3'
>MEDI_FWD2
       |                                     |                              |
       |   130        140        150        |   160        170            180
 GAC AGG CTC CAG GAC AGG GCC TTG AAT GGA TGG GCG GCA TCA TCC CTA TCT TCG GCC TGA
 CTG TCC GAG GTC CTG TCC CGG AAC TTA CCT ACC CGC CGT AGT AGG GAT AGA AGC CGG ACT
 R   Q   A   P   G   Q   G   L   E   W   M   G   G   I   I   P   I   F   G   L>
 ____b___b___b___b___b___b___b___b_VH-MEDI-1912__b___b___b___b___b___b___b___b___>
                                                     I   I   P   I   F   G   L>
                                                   _d___d___d__CDR2_d___d___d___>

                            <MEDI1912-L56NNS
                                    |
           190        200   |     210        220        230        240
 CCA ATC TGG CCC AGA ACT TCC AGG GCA GAG TGA CCA TCA CAG CCG ACG AGA GCA CCA GCA
 GGT TAG ACC GGG TCT TGA AGG TCC CGT CTC ACT GGT AGT GTC GGC TGC TCT CGT GGT CGT
 T   N   L   A   Q   N   F   Q   G   R   V   T   I   T   A   D   E   S   T   S>
 ____b___b___b___b___b___b___b___b_VH-MEDI-1912__b___b___b___b___b___b___b___b___>
 T> (SEQ ID NO: 180)
 __>

           250        260        270        280        290        300
 CCG TGT ACA TGG AAC TGA GCA GCC TGA GAA GCG AGG ACA CCG CCG TGT ACT ACT GTG CCA
 GGC ACA TGT ACC TTG ACT CGT CGG ACT CTT CGC TCC TGT GGC GGC ACA TGA TGA CAC GGT
 T   V   Y   M   E   L   S   S   L   R   S   E   D   T   A   V   Y   Y   C   A>
 ____b___b___b___b___b___b___b___b_VH-MEDI-1912__b___b___b___b___b___b___b___b___>
                                                                             A>
                                                                           _e___>

           310        320        330        340        350        360
 GAA GCA GCC GGA TCT ACG ATC TGA ACC CTA GCC TGA CCG CCT ACT ACG ACA TGG ATG TGT
 CTT CGT CGG CCT AGA TGC TAG ACT TGG GAT CGG ACT GGC GGA TGA TGC TGT ACC TAC ACA
 R   S   S   R   I   Y   D   L   N   P   S   L   T   A   Y   Y   D   M   D   V>
 ____b___b___b___b___b___b___b___b_VH-MEDI-1912__b___b___b___b___b___b___b___b___>
 R   S   S   R   I   Y   D   L   N   P   S   L   T   A   Y   Y   D   M   D   V> (SEQ ID NO: 181)
 ____e___e___e___e___e___e___e___e_____CDR3____e___e___e___e___e___e___e___e___e__>

                               >Fixed     <MEDI-1912-R
                                    |          |
           370        380       |   390     |
 GGG GCC AGG GCA CAA TGG TCA CCG TCT CGA GT (SEQ ID NO: 177)
 CCC CGG TCC CGT GTT ACC AGT GGC AGA GCT CA
 W   G   Q   G   T   M   V   T   V   S   S> (SEQ ID NO: 178)
 ____b___b___b__VH-MEDI-1912_b___b___b___b__>
```

Figure 5
a
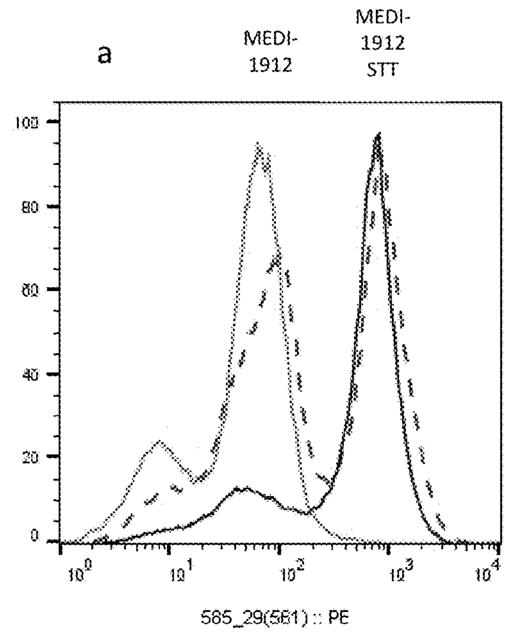
b
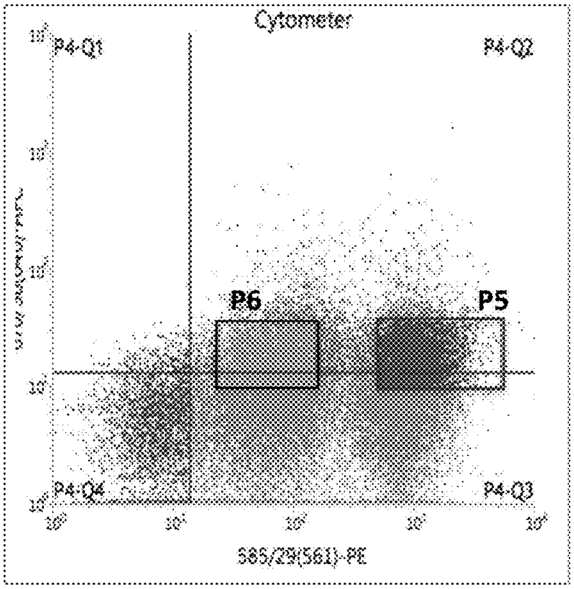

```
                                                  ____CDR1____               ______CDR2__
                            10             20             30             40             50             60
5A10 (mouse)        QVQLQQPGAELVKPG ASVKLSCKASGYTFT SYWMHWVKQRPGQGL EWIGEINPSNGRTNY (SEQ ID NO: 182)
5A10-i              ....V.S...VK... ....V.......... ..Y....R.A..... ..M......G..... (SEQ ID NO: 183)
Bococizumab         ....V.S...VK... ....V.......... ..Y....R.A..... ..M...S.FG..... (SEQ ID NO: 184)

                    _CDR2_                                    ____CDR3____
                            70             80             90            100            110
5A10 (mouse)        NEKFKSKATLTVDKS SSTAYMQLSSLTSED SAVYYCARERPLYAM DYWGQGTSVTVSS (SEQ ID NO: 182)
5A10-i              ......RV.M.R.T. T..V..E....R... T.............. .......T..... (SEQ ID NO: 183)
Bococizumab         ......RV.M.R.T. T..V..E....R... T............S. .L.....T..... (SEQ ID NO: 184)
```

B. 5A10 VL

```
                                                  ____CDR1____                  _CDR2_
                            10             20             30             40             50             60
5A10-VL (mouse)     DIVMTQSHKFMSTSV GDRVSITCKASQDVS TAVAWYQQKPGQSPK LLIYSASYRYTGVPD (SEQ ID NO: 182)
5A10-i-VL           ..Q....PSSL.A.. ....T.......... ...........KA.. ..............S (SEQ ID NO: 183)
Bococizumab_VL      ..Q....PSSL.A.. ....T...R...GI. S.L........KA.. ..............S (SEQ ID NO: 184)

                                                          ___CDR3___
                            70             80             90            100
5A10-VL (mouse)     RFTGSGSGTDFTFTI SSVQAEDLAVYYCQQ RYSTPRTFGGGTKLE IK (SEQ ID NO: 182)
5A10-i-VL           ..S............ ..L.P..I.T..... .........Q..... .. (SEQ ID NO: 183)
Bococizumab_VL      ..S............ ..L.P..I.T..... ...LN....Q..... .. (SEQ ID NO: 184)
```

Figure 11

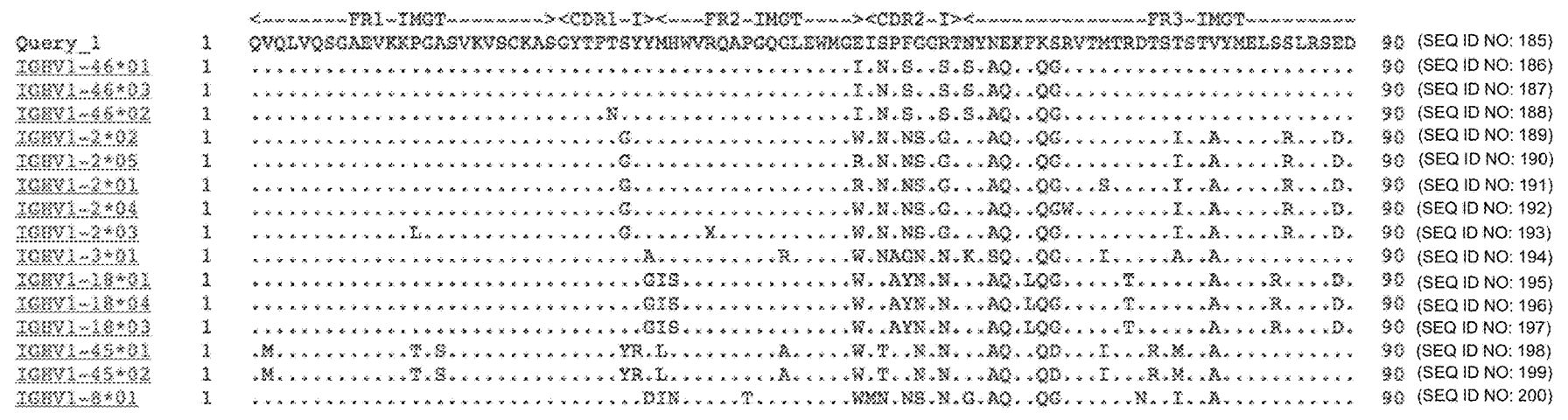

```
                      <~~~~~~~~FR1~IMGT~~~~~~~~><CDR1~I><~~~FR2~IMGT~~~~><CDR2~I><~~~~~~~~~~~~~~~FR3~IMGT~~~~~~~~~~
Query_1         1     QVQLVQSGAEVKKPGASVKVSCKASGYTFTSYYMHWVRQAPGQCLEWMGEISPFGGRTNYNEKFKSRVTMTRDTSTSTVYMELSSLRSED   90  (SEQ ID NO: 185)
IGHV1-46*01     1     .................................................I.N.S..S.S.AQ..QG........................   90  (SEQ ID NO: 186)
IGHV1-46*03     1     .................................................I.N.S..S.S.AQ..QG........................   90  (SEQ ID NO: 187)
IGHV1-46*02     1     .............................N...................I.N.S..S.S.AQ..QG........................   90  (SEQ ID NO: 188)
IGHV1-2*02      1     ..............................G..................W.N.NS.G...AQ..QG.........I..A.....R...D.   90  (SEQ ID NO: 189)
IGHV1-2*05      1     ..............................G..................R.N.NS.G...AQ..QG.........I..A.....R...D.   90  (SEQ ID NO: 190)
IGHV1-2*01      1     ..............................G..................R.N.NS.G...AQ..QG...S.....I..A.....R...D.   90  (SEQ ID NO: 191)
IGHV1-2*04      1     ..............................G..................W.N.NS.G...AQ..QGW........I..A.....R...D.   90  (SEQ ID NO: 192)
IGHV1-2*03      1     .............L................G......X...........W.N.NS.G...AQ..QG.........I..A.....R...D.   90  (SEQ ID NO: 193)
IGHV1-3*01      1     ................................A..........R.....W.NAGN.N.K.SQ..QG...I.....A..A...........   90  (SEQ ID NO: 194)
IGHV1-18*01     1     ................................GIS..............W..AYN.N...AQ.LQG.....T......A.....R...D.   90  (SEQ ID NO: 195)
IGHV1-18*04     1     ................................GIS..............W..AYN.N...AQ.LQG.....T......A.....R...D.   90  (SEQ ID NO: 196)
IGHV1-18*03     1     ................................GIS..............W..AYN.N...AQ.LQG.....T......A.....R...D.   90  (SEQ ID NO: 197)
IGHV1-45*01     1     .M...........T.S..............YR.L.........A.....W.T..N.N...AQ..QD...I...R.M..A...........   90  (SEQ ID NO: 198)
IGHV1-45*02     1     .M...........T.S..............YR.L.........A.....W.T..N.N...AQ..QD...I...R.M..A...........   90  (SEQ ID NO: 199)
IGHV1-8*01      1     ................................DIN.....T........WMN.NS.N.G.AQ..QG......N..I..A...........   90  (SEQ ID NO: 200)
```

Figure 12.

| VH | DNA Sequence |
|---|---|
| a.Y33A | TTTTTTGCCATGGCCCAGGTTCAGCTGGTTCAGTCTGGCGCCGAAGTGAAGAAACCT<br>GGCGCCTCTGTGAAGGTGTCCTGCAAGGCCAGCGGCTACACCTTTACCAGCTAC**GCT**<br>ATGCACTGGGTCCGACAGGCCCCTGGACAAGGACTTGAGTGGATGGGCGAGATCAGC<br>CCATTCGGCGGCAGGACCAACTACAACGAGAAGTTCAAGAGCCGCGTGACCATGACC<br>AGAGACACCAGCACCTCCACCGTGTACATGGAACTGAGCAGCCTGAGAAGCGAGGAC<br>ACCGCCGTGTACTACTGTGCCAGAGAGAGGCCACTGTACGCCTCTGATCTTTGGGGC<br>CAGGGCACCACCGTGACAGTCTCGAGTTTTTTT (SEQ ID NO: 201) |
| b.Y33D | TTTTTTGCCATGGCCCAGGTTCAGCTGGTTCAGTCTGGCGCCGAAGTGAAGAAACCT<br>GGCGCCTCTGTGAAGGTGTCCTGCAAGGCCAGCGGCTACACCTTTACCAGCTAC**GAT**<br>ATGCACTGGGTCCGACAGGCCCCTGGACAAGGACTTGAGTGGATGGGCGAGATCAGC<br>CCATTCGGCGGCAGGACCAACTACAACGAGAAGTTCAAGAGCCGCGTGACCATGACC<br>AGAGACACCAGCACCTCCACCGTGTACATGGAACTGAGCAGCCTGAGAAGCGAGGAC<br>ACCGCCGTGTACTACTGTGCCAGAGAGAGGCCACTGTACGCCTCTGATCTTTGGGGC<br>CAGGGCACCACCGTGACAGTCTCGAGTTTTTTT (SEQ ID NO: 202) |
| c.<br>S52N,<br>F54S,<br>R57S | TTTTTTGCCATGGCCCAGGTTCAGCTGGTTCAGTCTGGCGCCGAAGTGAAGAAACCT<br>GGCGCCTCTGTGAAGGTGTCCTGCAAGGCCAGCGGCTACACCTTTACCAGCTACTAC<br>ATGCACTGGGTCCGACAGGCCCCTGGACAAGGACTTGAGTGGATGGGCGAGATC**AAC**<br>CCA**TCT**GGCGGC**AGC**ACCAACTACAACGAGAAGTTCAAGAGCCGCGTGACCATGACC<br>AGAGACACCAGCACCTCCACCGTGTACATGGAACTGAGCAGCCTGAGAAGCGAGGAC<br>ACCGCCGTGTACTACTGTGCCAGAGAGAGGCCACTGTACGCCTCTGATCTTTGGGGC<br>CAGGGCACCACCGTGACAGTCTCGAGTTTTTTT (SEQ ID NO: 203) |
| d.<br>Y33A,<br>S52N,<br>F54S,<br>R57S | TTTTTTGCCATGGCCCAGGTTCAGCTGGTTCAGTCTGGCGCCGAAGTGAAGAAACCT<br>GGCGCCTCTGTGAAGGTGTCCTGCAAGGCCAGCGGCTACACCTTTACCAGCTAC**GCT**<br>ATGCACTGGGTCCGACAGGCCCCTGGACAAGGACTTGAGTGGATGGGCGAGATC**AAC**<br>CCA**TCT**GGCGGC**AGC**ACCAACTACAACGAGAAGTTCAAGAGCCGCGTGACCATGACC<br>AGAGACACCAGCACCTCCACCGTGTACATGGAACTGAGCAGCCTGAGAAGCGAGGAC<br>ACCGCCGTGTACTACTGTGCCAGAGAGAGGCCACTGTACGCCTCTGATCTTTGGGGC<br>CAGGGCACCACCGTGACAGTCTCGAGTTTTTTT (SEQ ID NO: 204) |
| e.<br>Y33D,<br>S52N,<br>F54S,<br>R57S | TTTTTTGCCATGGCCCAGGTTCAGCTGGTTCAGTCTGGCGCCGAAGTGAAGAAACCT<br>GGCGCCTCTGTGAAGGTGTCCTGCAAGGCCAGCGGCTACACCTTTACCAGCTAC**GAT**<br>ATGCACTGGGTCCGACAGGCCCCTGGACAAGGACTTGAGTGGATGGGCGAGATC**AAC**<br>CCA**TCT**GGCGGC**AGC**ACCAACTACAACGAGAAGTTCAAGAGCCGCGTGACCATGACC<br>AGAGACACCAGCACCTCCACCGTGTACATGGAACTGAGCAGCCTGAGAAGCGAGGAC<br>ACCGCCGTGTACTACTGTGCCAGAGAGAGGCCACTGTACGCCTCTGATCTTTGGGGC<br>CAGGGCACCACCGTGACAGTCTCGAGTTTTTTT (SEQ ID NO: 205) |
| f.<br>W.T. | TTTTTTGCCATGGCCCAGGTTCAGCTGGTTCAGTCTGGCGCCGAAGTGAAGAAACCT<br>GGCGCCTCTGTGAAGGTGTCCTGCAAGGCCAGCGGCTACACCTTTACCAGCTACTAC<br>ATGCACTGGGTCCGACAGGCCCCTGGACAAGGACTTGAGTGGATGGGCGAGATCAGC<br>CCATTCGGCGGCAGGACCAACTACAACGAGAAGTTCAAGAGCCGCGTGACCATGACC<br>AGAGACACCAGCACCTCCACCGTGTACATGGAACTGAGCAGCCTGAGAAGCGAGGAC<br>ACCGCCGTGTACTACTGTGCCAGAGAGAGGCCACTGTACGCCTCTGATCTTTGGGGC<br>CAGGGCACCACCGTGACAGTCTCGAGTTTTTTT (SEQ ID NO: 206) |
| Bococi<br>zumab<br>VL<br>plus<br>stop<br>codons | TTTTTTGCTAGCGACATCCAGATGACACAGAGCCCTAGCAGCCTGTCTGCCAGCGTG<br>GGAGACAGAGTGACCATCACCTGTAGAGCCAGCCAGGGCATCTCTTCTGCCCTGGCA<br>TGGTATCAGCAGAAGCCTGGCAAGGCCCCTAAGCTGCTGATCTACAGCGCCAGC**TAA**<br>AGATACACCGGCGTGCCCAGCAGATTTTCTGGCAGCGGCTCTGGCACCGACTTCACC<br>TTCACCATAAGCAGCCTGCAGCCTGAGGATATCGCCACCTACTACTGCCAGCAGCGG<br>TACTCT**TAGTAA**CGGACATTTGGCCAGGGCACCAAGCTGGAAATCAAGCGTACCGCG<br>GCCGCTTTTTT (SEQ ID NO: 207) |

Figure 14.
a. Antigen MACS input
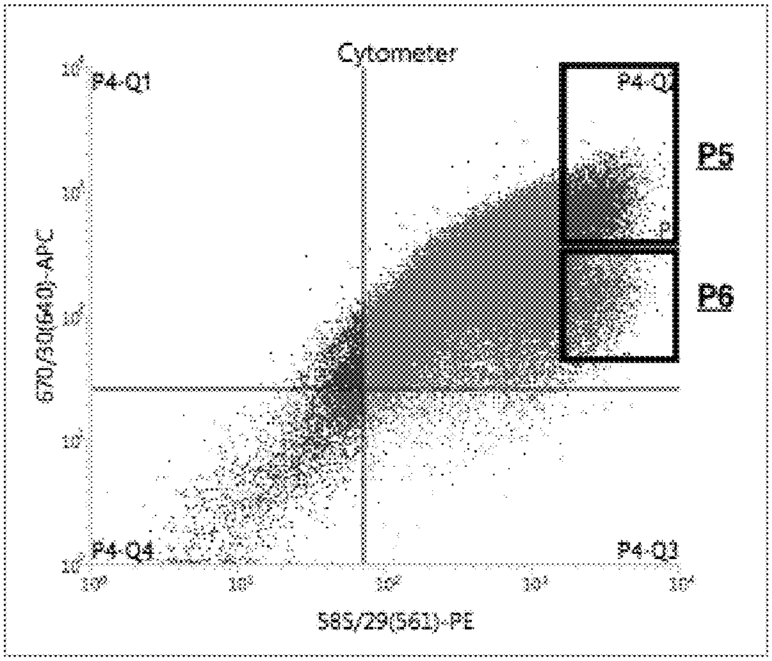
b. Anti-Fc MACS input
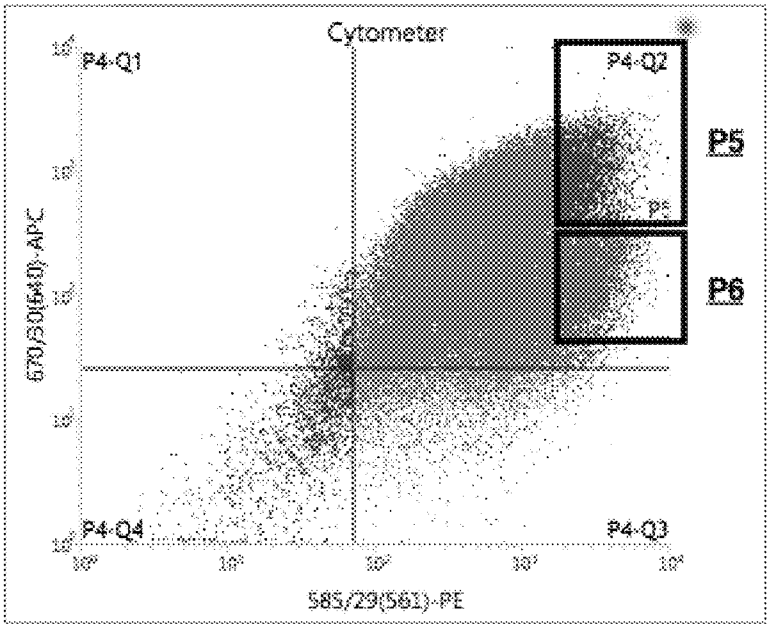

Figure 17

| Clone Name | Antigen binding (capture ELISA) | AC-SINS Δλ (nm) | VH CDR1 | VH CDR2 | VH | VL CDR2 | VL CDR3 |
|---|---|---|---|---|---|---|---|
| 884_01_A01 | 6174 | 12 | GYTFTSYY (SEQ ID NO:208) | INPSGGSTNYN (SEQ ID NO:213) | c | SLRYT (SEQ ID NO:217) | QQRYSLQRT (SEQ ID NO:231) |
| 884_01_A02 | 3570 | 10 | GYTFTSYY (SEQ ID NO:208) | INPSGGSTNYN (SEQ ID NO:213) | c | SERYT (SEQ ID NO:218) | QQRYSPWRT (SEQ ID NO:232) |
| 884_01_A03 | 3478 | 12 | GYTFTSYY (SEQ ID NO:208) | INPSGGSTNYN (SEQ ID NO:213) | c | SQRYT (SEQ ID NO:219) | QQRYSNSRT (SEQ ID NO:233) |
| 884_01_A04 | 5005 | 16 | GYTFTSYY (SEQ ID NO:208) | INPSGGSTNYN (SEQ ID NO:213) | c | SSRYT (SEQ ID NO:220) | QQRYSLKRT (SEQ ID NO:234) |
| 884_01_A05 | 1639 | 12 | GYTFTSYS (SEQ ID NO:209) | INPSGGRTNYN (SEQ ID NO:214) | | SQRYT (SEQ ID NO:219) | QQRYSSPRT (SEQ ID NO:235) |
| 884_01_A06 | 2912 | 10 | GYTFTSYY (SEQ ID NO:208) | INPSGGSTNYN (SEQ ID NO:213) | c | SARYT (SEQ ID NO:221) | QQRYSNNRT (SEQ ID NO:236) |
| 884_01_A07 | 189 | 12 | GYTFTSYD (SEQ ID NO:210) | INPSGGSTNYN (SEQ ID NO:213) | e | SPRYT (SEQ ID NO:222) | QQRYSSGRT (SEQ ID NO:237) |
| 884_01_A08 | 4338 | 10 | GYTFTSYY (SEQ ID NO:208) | INPSGGSTNYN (SEQ ID NO:213) | c | SERYT (SEQ ID NO:218) | QQRYSLART (SEQ ID NO:238) |
| 884_01_A09 | 1852 | 12 | GYTFTSYY (SEQ ID NO:208) | INPSGGSTNYN (SEQ ID NO:213) | c | SDRYT (SEQ ID NO:223) | QQRYSTLRT (SEQ ID NO:239) |
| 884_01_A10 | 124 | 12 | nd | nd | nd | nd | nd |
| 884_01_A11 | 2477 | 10 | GYTFTSYY (SEQ ID NO:208) | INPSGGSTNYN (SEQ ID NO:213) | c | STRYT (SEQ ID NO:224) | QQRYSLART (SEQ ID NO:240) |
| 884_01_A12 | 4703 | 10 | GYTFTSYY (SEQ ID NO:208) | INPSGGSTNYN (SEQ ID NO:213) | c | SLRYT (SEQ ID NO:217) | QQRYSSLRT (SEQ ID NO:241) |
| 884_01_B01 | 323 | 14 | GYTFTSYD (SEQ ID NO:210) | ISPFGGRTNYN (SEQ ID NO:215) | b | SQRYT (SEQ ID NO:219) | QQRYSTHRT (SEQ ID NO:242) |
| 884_01_B02 | 4756 | 12 | GYTFTSYY (SEQ ID NO:208) | INPSGGSTNYN (SEQ ID NO:213) | c | SMRYT (SEQ ID NO:225) | QQRYSFART (SEQ ID NO:243) |
| 884_01_B03 | 2180 | 12 | GYTFTSYY (SEQ ID NO:208) | INPSGGSTNYN (SEQ ID NO:213) | c | SDRYT (SEQ ID NO:223) | QQRYSIRRT (SEQ ID NO:244) |
| 884_01_B04 | 147 | 10 | GYTFTSYA (SEQ ID NO:211) | INPSGGSTNYN (SEQ ID NO:213) | d | STRYT (SEQ ID NO:224) | QQRYSVCRT (SEQ ID NO:245) |
| 884_01_B05 | 3038 | 10 | GYTFTSYY (SEQ ID NO:208) | INPSGGSTNYN (SEQ ID NO:213) | c | SARYT (SEQ ID NO:221) | QQRYSNNRT (SEQ ID NO:236) |
| 884_01_B06 | 449 | 24 | GYTFTSYD (SEQ ID NO:210) | ISPFGGRTNYN (SEQ ID NO:215) | b | SLRYT (SEQ ID NO:217) | QQRYSWART (SEQ ID NO:246) |
| 884_01_B07 | 2864 | 12 | GYTFTSYY (SEQ ID NO:208) | INPSGGSTNYN (SEQ ID NO:213) | c | SARYT (SEQ ID NO:221) | QQRYSTTRT (SEQ ID NO:247) |
| 884_01_B08 | 2576 | 10 | GYTFTSYY (SEQ ID NO:208) | INPSGGSTNYN (SEQ ID NO:213) | c | SERYT (SEQ ID NO:218) | QQRYSQMRT (SEQ ID NO:248) |
| 884_01_B09 | 926 | 10 | GYTFTSYY (SEQ ID NO:208) | INPSGGSTNYN (SEQ ID NO:213) | c | SVRYT (SEQ ID NO:226) | QQRYSTLRT (SEQ ID NO:239) |
| 884_01_B10 | 4752 | 10 | GYTFTSYY (SEQ ID NO:208) | INPSGGSTNYN (SEQ ID NO:213) | c | SMRYT (SEQ ID NO:225) | QQRYSADRT (SEQ ID NO:249) |
| 884_01_B11 | 2534 | 12 | GYTFTSYY (SEQ ID NO:208) | INPSGGSTNYN (SEQ ID NO:213) | c | SSRYT (SEQ ID NO:220) | QQRYSFNRT (SEQ ID NO:250) |
| 884_01_B12 | 3481 | 14 | GYTFTSYY (SEQ ID NO:208) | INPSGGSTNYN (SEQ ID NO:213) | c | SARYT (SEQ ID NO:221) | QQRYSLKRT (SEQ ID NO:234) |
| 884_01_C01 | 3002 | 12 | GYTFTSYY (SEQ ID NO:208) | INPSGGSTNYN (SEQ ID NO:213) | c | SSRYT (SEQ ID NO:220) | QQRYSYDRT (SEQ ID NO:251) |
| 884_01_C02 | 2645 | 10 | GYTFTSYY (SEQ ID NO:208) | INPSGGSTNYN (SEQ ID NO:213) | c | SDRYT (SEQ ID NO:223) | QQRYSSQRT (SEQ ID NO:252) |
| 884_01_C03 | 3011 | 12 | GYTFTSYY (SEQ ID NO:208) | INPSGGSTNYN (SEQ ID NO:213) | c | SSRYT (SEQ ID NO:220) | QQRYSYVRT (SEQ ID NO:253) |
| 884_01_C04 | 343 | 12 | GYTFTSYD (SEQ ID NO:210) | ISPFGGRTNYN (SEQ ID NO:215) | b | SDRYT (SEQ ID NO:223) | QQRYSLYRT (SEQ ID NO:254) |
| 884_01_C05 | 4155 | 10 | GYTFTSYY (SEQ ID NO:208) | INPSGGSTNYN (SEQ ID NO:213) | c | SMRYT (SEQ ID NO:225) | QQRYSADRT (SEQ ID NO:255) |
| 884_01_C06 | 1293 | 10 | GYTFTSYY (SEQ ID NO:208) | INPSGGSTNYN (SEQ ID NO:213) | c | SVRYT (SEQ ID NO:226) | QQRYSSMRT (SEQ ID NO:256) |
| 884_01_C07 | 4638 | 12 | GYTFTSYY (SEQ ID NO:208) | INPSGGSTNYN (SEQ ID NO:213) | c | SMRYT (SEQ ID NO:225) | QQRYSYYRT (SEQ ID NO:257) |
| 884_01_C08 | 5271 | 10 | GYTFTSYY (SEQ ID NO:208) | INPSGGSTNYN (SEQ ID NO:213) | c | SLRYT (SEQ ID NO:217) | QQRYSLIRT (SEQ ID NO:258) |
| 884_01_C09 | 3735 | 12 | GYTFTSYY (SEQ ID NO:208) | INPSGGSTNYN (SEQ ID NO:213) | c | SPRYT (SEQ ID NO:222) | QQRYSERRT (SEQ ID NO:259) |
| 884_01_C10 | 1413 | 10 | GYTFTSYY (SEQ ID NO:208) | INPSGGSTNYN (SEQ ID NO:213) | c | STRYT (SEQ ID NO:224) | QQRYS (SEQ ID NO:260) |
| 884_01_C11 | 4435 | 10 | GYTFTSYY (SEQ ID NO:208) | INPSGGSTNYN (SEQ ID NO:213) | c | SLRYT (SEQ ID NO:217) | QQRYSQMRT (SEQ ID NO:261) |
| 884_01_C12 | 2317 | 12 | GYTFTSYY (SEQ ID NO:208) | INPSGGSTNYN (SEQ ID NO:213) | c | nd | nd |
| 884_01_D01 | 2396 | 10 | GYTFTSYY (SEQ ID NO:208) | INPSGGSTNYN (SEQ ID NO:213) | c | SSRYT (SEQ ID NO:220) | QQRYSVNRT (SEQ ID NO:262) |
| 884_01_D02 | 928 | 12 | GYTFTSYY (SEQ ID NO:208) | INPSGGSTNYN (SEQ ID NO:213) | c | STRYT (SEQ ID NO:224) | QQRYSFFRT (SEQ ID NO:263) |
| 884_01_D03 | 2707 | 12 | GYTFTSYY (SEQ ID NO:208) | INPSGGSTNYN (SEQ ID NO:213) | c | SQRYT (SEQ ID NO:219) | QQRYSNVRT (SEQ ID NO:264) |
| 884_01_D04 | 4086 | 10 | GYTFTSYY (SEQ ID NO:208) | INPSGGSTNYN (SEQ ID NO:213) | c | SMRYT (SEQ ID NO:225) | QQRYSFART (SEQ ID NO:243) |
| 884_01_D05 | 2361 | 12 | GYTFTSYY (SEQ ID NO:208) | INPSGGSTNYN (SEQ ID NO:213) | c | SARYT (SEQ ID NO:221) | QQRYSAVRT (SEQ ID NO:265) |
| 884_01_D06 | 2560 | 10 | GYTFTSYY (SEQ ID NO:208) | INPSGGSTNYN (SEQ ID NO:213) | c | SLRYT (SEQ ID NO:217) | QQRYSDPRT (SEQ ID NO:266) |
| 884_01_D07 | 1152 | 0 | nd | nd | nd | SARYT (SEQ ID NO:221) | QQRYSMTRT (SEQ ID NO:267) |
| 884_01_D08 | 1226 | 10 | GYTFTSYY (SEQ ID NO:208) | INPSGGSTNYN (SEQ ID NO:213) | c | STRYT (SEQ ID NO:224) | QQRYSISRT (SEQ ID NO:268) |
| 884_01_D09 | 291 | 12 | GYTFTSYD (SEQ ID NO:210) | ISPFGGRTNYN (SEQ ID NO:215) | b | SDRYT (SEQ ID NO:223) | QQRYSLYRT (SEQ ID NO:269) |
| 884_01_D10 | 2331 | 10 | GYTFTSYY (SEQ ID NO:208) | INPSGGSTNYN (SEQ ID NO:213) | c | SDRYT (SEQ ID NO:223) | QQRYSNMRT (SEQ ID NO:270) |
| 884_01_D11 | 2363 | 10 | GYTFTSYY (SEQ ID NO:208) | INPSGGSTNYN (SEQ ID NO:213) | c | SDRYT (SEQ ID NO:223) | QQRYSQMRT (SEQ ID NO:271) |
| 884_01_D12 | 3715 | 10 | GYTFTSYY (SEQ ID NO:208) | INPSGGSTNYN (SEQ ID NO:213) | c | SMRYT (SEQ ID NO:225) | QQRYSADRT (SEQ ID NO:272) |
| 884_01_E01 | 796 | 10 | GYTFTSYY (SEQ ID NO:208) | INPSGGSTNYN (SEQ ID NO:213) | c | STRYT (SEQ ID NO:224) | QQRYSTIRT (SEQ ID NO:273) |
| 884_01_E02 | 2790 | 12 | GYTFTSYY (SEQ ID NO:208) | INPSGGSTNYN (SEQ ID NO:213) | c | SDRYT (SEQ ID NO:223) | QQRYSCART (SEQ ID NO:274) |
| 884_01_E03 | 111 | 22 | GYTFTSYA (SEQ ID NO:211) | ISPFGGRTNYN (SEQ ID NO:215) | a | SERYT (SEQ ID NO:218) | QQRYSNHRT (SEQ ID NO:275) |
| 884_01_E04 | 2565 | 10 | GYTFTSYY (SEQ ID NO:208) | INPSGGSTNYN (SEQ ID NO:213) | c | STRYT (SEQ ID NO:224) | QQRYSAKRT (SEQ ID NO:276) |
| 884_01_E05 | 1149 | 10 | GYTFTSYY (SEQ ID NO:208) | INPSGGSTNYN (SEQ ID NO:213) | c | SVRYT (SEQ ID NO:226) | QQRYSHRRT (SEQ ID NO:277) |

Figure 17 (continued)

| | | | | | | | |
|---|---|---|---|---|---|---|---|
| 884_01_E06 | 1382 | 12 | GYTFTSYY (SEQ ID NO: 208) | INPSGGSTNYN (SEQ ID NO: 213) | c | SVRYT (SEQ ID NO: 226) | QQRYSCTRT (SEQ ID NO: 278) |
| 884_01_E07 | 105 | 12 | nd | nd | nd | nd | nd |
| 884_01_E08 | 2009 | 12 | GYTFTSYY (SEQ ID NO: 208) | INPSGGSTNYN (SEQ ID NO: 213) | c | SNRYT (SEQ ID NO: 227) | QQRYSYMRT (SEQ ID NO: 279) |
| 884_01_E09 | 1012 | 10 | GYTFTSYY (SEQ ID NO: 208) | INPSGGSTNYN (SEQ ID NO: 213) | c | SVRYT (SEQ ID NO: 226) | QQRYSHFRT (SEQ ID NO: 280) |
| 884_01_E10 | 2897 | 10 | GYTFTSYY (SEQ ID NO: 208) | INPSGGSTNYN (SEQ ID NO: 213) | c | SERYT (SEQ ID NO: 218) | QQRYSSART (SEQ ID NO: 281) |
| 884_01_E11 | 2294 | 12 | GYTFTSYY (SEQ ID NO: 208) | INPSGGSTNYN (SEQ ID NO: 213) | c | nd | nd |
| 884_01_E12 | 4168 | **24** | GYTFTSYY (SEQ ID NO: 208) | INPSGGSTNYN (SEQ ID NO: 213) | c | SMRYT (SEQ ID NO: 225) | QQRYSNRRT (SEQ ID NO: 282) |
| 884_01_F01 | 162 | **26** | GYTFTSYY (SEQ ID NO: 208) | INPSGGSTNYN (SEQ ID NO: 213) | c | SYLES (SEQ ID NO: 228) | QHSRDLPLT (SEQ ID NO: 283) |
| 884_01_F02 | 4741 | **22** | GYTFTSYY (SEQ ID NO: 208) | INPSGGSTNYN (SEQ ID NO: 213) | c | SYRYT (SEQ ID NO: 229) | QQRYSTGRT (SEQ ID NO: 284) |
| 884_01_F03 | 2655 | 10 | GYTFTSYY (SEQ ID NO: 208) | INPSGGSTNYN (SEQ ID NO: 213) | c | SARYT (SEQ ID NO: 221) | QQRYSDTRT (SEQ ID NO: 285) |
| 884_01_F04 | 3780 | 12 | GYTFTSYY (SEQ ID NO: 208) | INPSGGSTNYN (SEQ ID NO: 213) | c | SLRYT (SEQ ID NO: 217) | QQRYSETRT (SEQ ID NO: 286) |
| 884_01_F05 | 494 | 12 | GYTFTSYA (SEQ ID NO: 211) | INPSGGSTNYN (SEQ ID NO: 213) | d | SYRYT (SEQ ID NO: 229) | QQRYSNSRT (SEQ ID NO: 287) |
| 884_01_F06 | 1241 | 8 | GYTFTSYY (SEQ ID NO: 208) | INPSGGSTNYN (SEQ ID NO: 213) | c | SNRYT (SEQ ID NO: 227) | QQRYSPPRT (SEQ ID NO: 288) |
| 884_01_F07 | 4532 | 12 | GYTFTSYY (SEQ ID NO: 208) | INPSGGSTNYN (SEQ ID NO: 213) | c | SLRYT (SEQ ID NO: 217) | QQRYSSART (SEQ ID NO: 289) |
| 884_01_F08 | 3007 | 8 | GYTFTSYY (SEQ ID NO: 208) | INPSGGSTNYN (SEQ ID NO: 213) | c | SERYT (SEQ ID NO: 218) | QQRYSLERT (SEQ ID NO: 290) |
| 884_01_F09 | 1203 | 10 | GYTFTSYY (SEQ ID NO: 208) | INPSGGSTNYN (SEQ ID NO: 213) | c | STRYT (SEQ ID NO: 224) | QQRYSHSRT (SEQ ID NO: 291) |
| 884_01_F10 | 1339 | 10 | GYTFTSYY (SEQ ID NO: 208) | INPSGGSTNYN (SEQ ID NO: 213) | c | SVRYT (SEQ ID NO: 226) | QQRYSVART (SEQ ID NO: 292) |
| 884_01_F11 | 160 | 10 | GYTFTSYD (SEQ ID NO: 210) | INPSGGSTNYN (SEQ ID NO: 213) | e | STRYT (SEQ ID NO: 224) | QQRYSLTRT (SEQ ID NO: 293) |
| 884_01_F12 | 4294 | 10 | GYTFTSYY (SEQ ID NO: 208) | INPSGGSTNYN (SEQ ID NO: 213) | c | SLRYT (SEQ ID NO: 217) | QQRYSHPRT (SEQ ID NO: 294) |
| 884_01_G01 | 5237 | 12 | GYTFTSYY (SEQ ID NO: 208) | INPSGGSTNYN (SEQ ID NO: 213) | c | SHRYT (SEQ ID NO: 230) | QQRYSDTRT (SEQ ID NO: 295) |
| 884_01_G02 | 2727 | 10 | GYTFTSYY (SEQ ID NO: 208) | INPSGGSTNYN (SEQ ID NO: 213) | c | SQRYT (SEQ ID NO: 219) | QQRYSNMRT (SEQ ID NO: 296) |
| 884_01_G03 | 2719 | 10 | GYTFTSYY (SEQ ID NO: 208) | INPSGGSTNYN (SEQ ID NO: 213) | c | SERYT (SEQ ID NO: 218) | QQRYSSKRT (SEQ ID NO: 297) |
| 884_01_G04 | 1228 | 12 | GYTFTSYY (SEQ ID NO: 208) | INPSGGSTNYN (SEQ ID NO: 213) | c | SVRYT (SEQ ID NO: 226) | QQRYSHFRT (SEQ ID NO: 298) |
| 884_01_G05 | 1477 | 10 | GYTFTSYY (SEQ ID NO: 208) | INPSGGSTNYN (SEQ ID NO: 213) | c | SERYT (SEQ ID NO: 218) | QQRYSPPRT (SEQ ID NO: 299) |
| 884_01_G06 | 3557 | 12 | GYTFTSYY (SEQ ID NO: 208) | INPSGGSTNYN (SEQ ID NO: 213) | c | SSRYT (SEQ ID NO: 220) | QQRYSESRT (SEQ ID NO: 300) |
| 884_01_G07 | 939 | 10 | GYTFTSYY (SEQ ID NO: 208) | INPSGGSTNYN (SEQ ID NO: 213) | c | SVRYT (SEQ ID NO: 226) | QQRYSVYRT (SEQ ID NO: 301) |
| 884_01_G08 | 233 | 0 | GYTFTSYA (SEQ ID NO: 211) | INPSGGSTNYN (SEQ ID NO: 213) | d | SMRYT (SEQ ID NO: 225) | QQRYSCIRT (SEQ ID NO: 302) |
| 884_01_G09 | 4788 | 12 | GYTFTSYY (SEQ ID NO: 208) | INPSGGSTNYN (SEQ ID NO: 213) | c | SLRYT (SEQ ID NO: 217) | QQRYSATRT (SEQ ID NO: 303) |
| 884_01_G10 | 4511 | 10 | GYTFTSYY (SEQ ID NO: 208) | INPSGGSTNYN (SEQ ID NO: 213) | c | SLRYT (SEQ ID NO: 217) | QQRYSATRT (SEQ ID NO: 304) |
| 884_01_G11 | 892 | 10 | GYTFTSYY (SEQ ID NO: 208) | INPSGGSTNYN (SEQ ID NO: 213) | c | SVRYT (SEQ ID NO: 226) | QQRYSDCRT (SEQ ID NO: 305) |
| 884_01_G12 | 2133 | 12 | GYTFTSYY (SEQ ID NO: 208) | INPSGGSTNYN (SEQ ID NO: 213) | c | SVRYT (SEQ ID NO: 226) | QQRYSMART (SEQ ID NO: 306) |
| 884_01_H01 | 3075 | 10 | GYTFTSYY (SEQ ID NO: 208) | INPSGGSTNYN (SEQ ID NO: 213) | c | SARYT (SEQ ID NO: 221) | QQRYSGERT (SEQ ID NO: 307) |
| 884_01_H02 | 2688 | 10 | GYTFTSYY (SEQ ID NO: 208) | INPSGGSTNYN (SEQ ID NO: 213) | c | SERYT (SEQ ID NO: 218) | QQRYSIRRT (SEQ ID NO: 308) |
| 884_01_H03 | 5182 | 12 | GYTFTSYY (SEQ ID NO: 208) | INPSGGSTNYN (SEQ ID NO: 213) | c | SLRYT (SEQ ID NO: 217) | QQRYSIMRT (SEQ ID NO: 309) |
| 884_01_H04 | 4873 | 12 | GYTFTSYY (SEQ ID NO: 208) | INPSGGSTNYN (SEQ ID NO: 213) | c | SLRYT (SEQ ID NO: 217) | QQRYSIDRT (SEQ ID NO: 310) |
| 884_01_H05 | 1997 | 12 | GYTFTSYY (SEQ ID NO: 208) | INPSGGSTNYN (SEQ ID NO: 213) | c | SARYT (SEQ ID NO: 221) | QQRYSYVRT (SEQ ID NO: 311) |
| 884_01_H06 | 4607 | 10 | GYTFTSYY (SEQ ID NO: 208) | INPSGGSTNYN (SEQ ID NO: 213) | c | SLRYT (SEQ ID NO: 217) | QQRYSSART (SEQ ID NO: 312) |
| 884_01_H07 | 3066 | 10 | GYTFTSYY (SEQ ID NO: 208) | INPSGGSTNYN (SEQ ID NO: 213) | c | SPRYT (SEQ ID NO: 222) | QQRYSINRT (SEQ ID NO: 313) |
| Bococizumab | 4604 | **26** | GYTFTSYY (SEQ ID NO: 208) | ISPFGGRTNYN (SEQ ID NO: 215) | f | SYRYT (SEQ ID NO: 229) | QQRYSLWRT (SEQ ID NO: 314) |
| 5A10i | 4748 | 10 | GYTFTSYW (SEQ ID NO: 212) | INPSNGRTNYN (SEQ ID NO: 216) | | SYRYT (SEQ ID NO: 229) | QQRYSTPRT (SEQ ID NO: 315) |
| Untransfected | 200 | 0 | -- | -- | -- | -- | -- |
| Untransfected | 141 | 0 | -- | -- | -- | -- | -- |
| Untransfected | nd | 0 | -- | -- | -- | -- | -- |

Figure 23

```
                                  >splice junction
          >HindIII                      |
                 |                      |      stop
     K    S>  L    S    L    S    P      G  K    *
J9   AAG TCC CTA AGC TTG TCT CC GG/GTAAA TGA GT GCC ACG GCC GGC AAG CCC CCG CTC
J10  AAG TCC CTA AGC TTG TCT CC AG/GTAAA TGA GT GCC ACG GCC GGC AAG CCC CCG CTC
J29  AAG TCC CTA AGC TTG TCT CC GG/GTAAG TGA GT GCC ACG GCC GGC AAG CCC CCG CTC
J30  AAG TCC CTA AGC TTG TCT CC AG/GTAAG TGA GT GCC ACG GCC GGC AAG CCC CCG CTC
```

(SEQ ID NO: 316)

Figure 24A

```
>Sequence: pInt17-J30 Range: 4801 to 8500

     >XhoI
      |
      |   4810         4820         4830         4840         4850         4860
  AGT CTC GAG TGC CTC CAC CAA GGG CCC TAG CGT CTT TCC TCT GGC CCC TTC CTC CAA GTC
  S>
  ___a_>
      S   S   A   S   T   K   G   P   S   V   F   P   L   A   P   S   S   K   S>
    __b___b___b___b___b___b___b____IGG1 CH1-3_b___b___b___b___b___b___b___b___>

          4870         4880         4890         4900         4910         4920
  TAC CTC TGG CGG CAC CGC TGC TCT GGG CTG CCT GGT GAA GGA CTA CTT CCC TGA GCC TGT
   T   S   G   G   T   A   A   L   G   C   L   V   K   D   Y   F   P   E   P   V>
  ___b___b___b___b___b___b___b___b__IGG1 CH1-3___b___b___b___b___b___b___b___b___>

          4930         4940         4950         4960         4970         4980
  GAC CGT GTC CTG GAA CTC TGG CGC CCT GAC CTC CGG CGT GCA TAC CTT CCC TGC CGT CCT
   T   V   S   W   N   S   G   A   L   T   S   G   V   H   T   F   P   A   V   L>
  ___b___b___b___b___b___b___b___b__IGG1 CH1-3___b___b___b___b___b___b___b___b___>

          4990         5000         5010         5020         5030         5040
  CCA GTC CTC CGG CCT GTA CTC CCT GTC CTC CGT GGT GAC CGT GCC TTC CTC CTC TCT GGG
   Q   S   S   G   L   Y   S   L   S   S   V   V   T   V   P   S   S   S   L   G>
  ___b___b___b___b___b___b___b___b__IGG1 CH1-3___b___b___b___b___b___b___b___b___>

          5050         5060         5070         5080         5090         5100
  CAC CCA GAC CTA CAT CTG CAA CGT GAA CCA CAA GCC TTC CAA CAC CAA GGT GGA CAA GAA
   T   Q   T   Y   I   C   N   V   N   H   K   P   S   N   T   K   V   D   K   K>
  ___b___b___b___b___b___b___b___b__IGG1 CH1-3___b___b___b___b___b___b___b___b___>

          5110         5120         5130         5140         5150         5160
  GGT GGA GCC TAA GTC CTG CGA CAA GAC CCA CAC CTG CCC TCC ATG TCC TGC CCC TGA GCT
   V   E   P   K   S   C   D   K   T   H   T   C   P   P   C   P   A   P   E   L>
  ___b___b___b___b___b___b___b___b__IGG1 CH1-3___b___b___b___b___b___b___b___b___>

          5170         5180         5190         5200         5210         5220
  GCT GGG CGG ACC CTC CGT GTT CCT GTT CCC TCC TAA GCC TAA GGA CAC CCT GAT GAT CTC
   L   G   G   P   S   V   F   L   F   P   P   K   P   K   D   T   L   M   I   S>
  ___b___b___b___b___b___b___b___b__IGG1 CH1-3___b___b___b___b___b___b___b___b___>

          5230         5240         5250         5260         5270         5280
  CCG GAC CCC TGA AGT GAC CTG CGT GGT GGT GGA CGT GTC CCA CGA AGA TCC TGA AGT GAA
```

Figure 24B

```
 R   T   P   E   V   T   C   V   V   V   D   V   S   H   E   D   P   E   V   K>
___b___b___b___b___b___b___b___b__IGG1 CH1-3___b___b___b___b___b___b___b___b___>

          5290          5300          5310          5320          5330          5340
GTT CAA TTG GTA CGT GGA CGG CGT GGA GGT GCA CAA CGC CAA GAC CAA GCC TCG GGA GGA
 F   N   W   Y   V   D   G   V   E   V   H   N   A   K   T   K   P   R   E   E>
___b___b___b___b___b___b___b___b__IGG1 CH1-3___b___b___b___b___b___b___b___b___>

          5350          5360          5370          5380          5390          5400
ACA GTA CAA CTC CAC CTA CCG GGT GGT GTC TGT GCT GAC CGT GCT GCA CCA GGA CTG GCT
 Q   Y   N   S   T   Y   R   V   V   S   V   L   T   V   L   H   Q   D   W   L>
___b___b___b___b___b___b___b___b__IGG1 CH1-3___b___b___b___b___b___b___b___b___>

          5410          5420          5430          5440          5450          5460
GAA CGG CAA AGA ATA CAA GTG CAA GGT GTC CAA CAA GGC CCT GCC TGC CCC TAT CGA AAA
 N   G   K   E   Y   K   C   K   V   S   N   K   A   L   P   A   P   I   E   K>
___b___b___b___b___b___b___b___b__IGG1 CH1-3___b___b___b___b___b___b___b___b___>

          5470          5480          5490          5500          5510          5520
GAC CAT CTC CAA GGC TAA GGG CCA GCC ACG GGA ACC TCA GGT CTA CAC ACT GCC TCC TAG
 T   I   S   K   A   K   G   Q   P   R   E   P   Q   V   Y   T   L   P   P   S>
___b___b___b___b___b___b___b___b__IGG1 CH1-3___b___b___b___b___b___b___b___b___>

          5530          5540          5550          5560          5570          5580
CCG GGA CGA GCT GAC CAA GAA CCA GGT GTC CCT GAC CTG TCT GGT GAA GGG CTT CTA CCC
 R   D   E   L   T   K   N   Q   V   S   L   T   C   L   V   K   G   F   Y   P>
___b___b___b___b___b___b___b___b__IGG1 CH1-3___b___b___b___b___b___b___b___b___>

          5590          5600          5610          5620          5630          5640
TTC CGA TAT CGC CGT GGA GTG GGA GTC TAA CGG CCA GCC TGA GAA CAA CTA CAA GAC CAC
 S   D   I   A   V   E   W   E   S   N   G   Q   P   E   N   N   Y   K   T   T>
___b___b___b___b___b___b___b___b__IGG1 CH1-3___b___b___b___b___b___b___b___b___>

          5650          5660          5670          5680          5690          5700
CCC TCC TGT GCT GGA CTC CGA CGG CTC CTT CTT CCT GTA CTC CAA GCT GAC CGT GGA CAA
 P   P   V   L   D   S   D   G   S   F   F   L   Y   S   K   L   T   V   D   K>
___b___b___b___b___b___b___b___b__IGG1 CH1-3___b___b___b___b___b___b___b___b___>

          5710          5720          5730          5740          5750          5760
GTC CCG GTG GCA GCA GGG CAA CGT GTT CTC CTG CTC CGT GAT GCA CGA GGC CCT GCA CAA
 S   R   W   Q   Q   G   N   V   F   S   C   S   V   M   H   E   A   L   H   N>
___b___b___b___b___b___b___b___b__IGG1 CH1-3___b___b___b___b___b___b___b___b___>

                                                 >splice donor
                                                >G>A    >A>G
                                                  |       |
          5770          5780          5790          5800  |   5810          5820
CCA CTA CAC CCA GAA GTC CCT GTC CCT AAG CTT GTC TCC AGG TAA GTG AGT GCC ACG GCC
 H   Y   T   Q   K   S   L   S   L   S   L   S   P   G   K> (SEQ ID NO: 318)
___b___b___b___b___b___b__IGG1 CH1-3___b___b___b___b___b___b___>
                                                           _c___c___INTRON__c___c___>

          5830          5840          5850          5860          5870          5880
GGC AAG CCC CCG CTC CCC AGG CTC TCG GGG TCG CGC GAG GAT GCT TGG CAC GTA CCC CGT
___c___c___c___c___c___c___c___c____INTRON_c___c___c___c___c___c___c___c___c___>

          5890          5900          5910          5920          5930          5940
CTA CAT ACT TCC CGG GCA CCC AGC ATG GAA ATA AAG CAC CCA GCG CTG CCC TGG GCC CCT
___c___c___c___c___c___c___c___c____INTRON_c___c___c___c___c___c___c___c___c___>

          5950          5960          5970          5980          5990          6000
GCG AGA CTG TGA TGG TTC TTT CCG TGG GTC AGG CCG AGT CTG AGG CCT GAG TGG CAT GAG
___c___c___c___c___c___c___c___c____INTRON_c___c___c___c___c___c___c___c___c___>

          6010          6020          6030          6040          6050          6060
GGA GGC AGA GCG GGT TCC ACT GTC CCC ACA CTG GCC CAG GCT GTG CAG GTG TGC CTG GGC
___c___c___c___c___c___c___c___c____INTRON_c___c___c___c___c___c___c___c___c___>

          6070          6080          6090          6100          6110          6120
CGC CTA GGG TGG GGC TCA GCC AGG GGC TGC CCT CGG CAG GGT GGG GGA TTT GCC AGC GTG
```

Figure 24C

```
____c___c___c___c___c___c___c___c____INTRON_c___c___c___c___c___c___c___c___c___>

         6130      6140      6150      6160      6170      6180
GCC CTC CCT CCA GCA GCA GCT GCC CTG GGC TGG GCC ACG GGA AGC CCT AGG AGC CCC TGG
____c___c___c___c___c___c___c___c____INTRON_c___c___c___c___c___c___c___c___c___>

         6190      6200      6210      6220      6230      6240
GGA CAG ACA CAC AGC CCC TGC CTC TGT AGG AGA CTG TCC TGT CCT GTG AGC GCC CTG TCC
____c___c___c___c___c___c___c___c____INTRON_c___c___c___c___c___c___c___c___c___>

         6250      6260      6270      6280      6290      6300
TCC GAC CTC CAT GCC CAC TCG GGG GCA TGC CTA GTC CAT GTG CGT AGG GAC AGG CCC TCC
____c___c___c___c___c___c___c___c____INTRON_c___c___c___c___c___c___c___c___c___>

         6310      6320      6330      6340      6350      6360
CTC ACC CAT CTA CCC CCA CGG CAC TAA CCC CTG GCT GCC CTG CCC AGC CTC GCA CCC GCA
____c___c___c___c___c___c___c___c____INTRON_c___c___c___c___c___c___c___c___c___>

         6370      6380      6390      6400      6410      6420
TGG GGA CAC AAC CGA CTC CGG GGA CAT GCA CTC TCG GGC CCT GTG GAG GGA CTG GTC CAG
____c___c___c___c___c___c___c___c____INTRON_c___c___c___c___c___c___c___c___c___>

         6430      6440      6450      6460      6470      6480
ATG CCC ACA CAC ACA CTC AGC CCA GAC CCG TTC AAC AAA CCC CGC GCT GAG GTT GGC CGG
____c___c___c___c___c___c___c___c____INTRON_c___c___c___c___c___c___c___c___c___>

         6490      6500      6510      6520      6530      6540
CCA CAC GGC CAC CAC ACA CAC ACG TGC ACG CCT CAC ACA CGG AGC CTC ACC CGG GCG AAC
____c___c___c___c___c___c___c___c____INTRON_c___c___c___c___c___c___c___c___c___>

         6550      6560      6570      6580      6590      6600
CGC ACA GCA CCC AGA CCA GAG CAA GGT CCT CGC ACA CGT GAA CAC TCC TCA GAC ACA GGC
____c___c___c___c___c___c___c___c____INTRON_c___c___c___c___c___c___c___c___c___>

         6610      6620      6630      6640      6650      6660
CCC CAC GAG CCC CAC GCG GCA CCT CAA GGC CCA CGA GCC GCT CGG CAG CTT CTC CAC ATG
____c___c___c___c___c___c___c___c____INTRON_c___c___c___c___c___c___c___c___c___>

         6670      6680      6690      6700      6710      6720
CTG ACC TGC TCA GAC AAA CCC AGC CCT CCT CTC ACA AGG TGC CCC TGC AGC CGC CAC ACA
____c___c___c___c___c___c___c___c____INTRON_c___c___c___c___c___c___c___c___c___>

         6730      6740      6750      6760      6770      6780
CAC ACA GGC CCC CAC ACA CAG GGG AAC ACA CGC CAC GTC GCG TCC CTG GCA CTG GCC CAC
____c___c___c___c___c___c___c___c____INTRON_c___c___c___c___c___c___c___c___c___>

         6790      6800      6810      6820      6830      6840
TTC CCA ATG CCG CCC TTC CCT GCA GCT GAG GTC ACA TGA GGT GTG GGC TTC ACC ATC CTC
____c___c___c___c___c___c___c___c____INTRON_c___c___c___c___c___c___c___c___c___>

         6850      6860      6870      6880      6890      6900
CTG CCC TCT GGG CCT CAG GGA GGG ACA CAG GAG ATG GGG AGC GGG TCC TGC TGA GGG CCA
____c___c___c___c___c___c___c___c____INTRON_c___c___c___c___c___c___c___c___c___>

         6910      6920      6930      6940      6950      6960
GGT CGC TAT CTA GGG CTG GGT GTC TGG CTG AGT CCC GGG GCC AAA GCT GGT GCC CAG GGC
____c___c___c___c___c___c___c___c____INTRON_c___c___c___c___c___c___c___c___c___>

         6970      6980      6990      7000      7010      7020
AGG CAG CTG TGG GGA GCT GAC CTC AGG ACA CTG CTG GCC CAT CCC GGC CGG GCC CTA CAT
____c___c___c___c___c___c___c___c____INTRON_c___c___c___c___c___c___c___c___c___>

         7030      7040      7050      7060      7070      7080
CCT GGG TCC TGC CAC AGA GGG AAT CAC CCC CAG AGG CCC GAG CCC AGC AGG ACA CAG TAT
____c___c___c___c___c___c___c___c____INTRON_c___c___c___c___c___c___c___c___c___>

         7090      7100      7110      7120      7130      7140
TGA CCA CCC ACT TCC TGT CCA GAG CTG CAA CTG GAG GAG AGC TGT GCG GAG GCG CAG GAC
                                 L   Q   L   E   E   S   C   A   E   A   Q   D>
____c___c_____INTRON_c____c____c_____    ____d___d___d___d___M1 EXON_d___d___d___d___d___>
```

Figure 24D

```
        7150        7160        7170         7180        7190        7200
GGG GAG CTG GAC GGG CTG TGG ACC ACC ATC ACC ATC TTC ATC ACA CTC TTC CTG CTA AGC
 G   E   L   D   G   L   W   T   T   I   T   I   F   I   T   L   F   L   L   S>
___d___d___d___d___d___d___d___d___M1 EXON_d___d___d___d___d___d___d___d___d___>

        7210        7220        7230         7240        7250        7260
GTG TGC TAC AGT GCC ACC ATC ACC TTC TTC AAG GTT AAA TAA TAA TAG CTT ACG ACG TGA
 V   C   Y   S   A   T   I   T   F   F   K   V   K> (SEQ ID NO: 319)
___d___d___d___d___d_M1 EXON___d___d___d___d___d___>


>BGH_pA
    |
    |   7270        7280        7290         7300        7310        7320
TCA GCC TCG ACT GTG CCT TCT AGT TGC CAG CCA TCT GTT GTT TGC CCC TCC CCC GTG CCT
TCC TTG ACC CTG GAA GGT GCC ACT CCC ACT GTC CTT TCC TAA TAA AAT GAG GAA ATT GCA
TCG CAT TGT CTG AGT AGG TGT CAT TCT ATT CTG GGG GGT GGG GTG GGG CAG GAC AGC AAG
GGG GAG GAT TGG GAA GAC AAT AGC AGG CAT GCT GGG GAA TTC TGG CCC GGG CAT GAT AAC
                                            >AscI     >AAVS1_right_homology_arm
                                            |         |
        7510        7520        7530        |7540     |    7550        7560
TTC GTA TAA TGT ATG CTA TAC GAA GTT ATG TAT ACG GCG CGC CCA CTA GGG ACA GGA TTG
GTG ACA GAA AAG CCC CAT CCT TAG GCC TCC TCC TTC CTA GTC TCC TGA TAT TGG GTC TAA
CCC CCA CCT CCT GTT AGG CAG ATT CCT TAT CTG GTG ACA CAC CCC CAT TTC CTG GAG CCA
TCT CTC TCC TTG CCA GAA CCT CTA AGG TTT GCT TAC GAT GGA GCC AGA GAG GAT CCT GGG
AGG GAG AGC TTG GCA GGG GGT GGG AGG GAA GGG GGG GAT GCG TGA CCT GCC CGG TTC TCA
GTG GCC ACC CTG CGC TAC CCT CTC CCA GAA CCT GAG CTG CTC TGA CGC GGC TGT CTG GTG
CGT TTC ACT GAT CCT GGT GCT GCA GCT TCC TTA CAC TTC CCA AGA GGA GAA GCA GTT TGG
AAA AAC AAA ATC AGA ATA AGT TGG TCC TGA GTT CTA ACT TTG GCT CTT CAC CTT TCT AGT
CCC CAA TTT ATA TTG TTC CTC CGT GCG TCA GTT TTA CCT GTG AGA TAA GGC CAG TAG CCA
GCC CCG TCC TGG CAG GGC TGT GGT GAG GAG GGG GGT GTC CGT GTG GAA AAC TCC CTT TGT
GAG AAT GGT GCG TCC TAG GTG TTC ACC AGG TCG TGG CCG CCT CTA CTC CCT TTC TCT TTC
TCC ATC CTT CTT TCC TTA AAG AGT CCC CAG TGC TAT CTG GGA CAT ATT CCT CCG CCC AGA
GCA GGG TCC CGC TTC CCT AAG GCC CTG CTC TGG GCT TCT GGG TTT GAG TCC TTG GCA AGC
CCA GGA GAG GCG CTC AGG CTT CCC TGT CCC CCT TCC TCG TCC ACC ATC TCA TGC CCC TGG

                                                              >SbfI
                                                              |
        8350        8360        8370         8380        8390        8400
CTC TCC TGC CCC TTC CCT ACA GGG GTT CCT GGC TCT GCT CTC CTG CAG GCG ATC TCT CGA

            >3'_beta_globin_insulator
                                |
        8410        8420|       8430         8440        8450        8460
TCT CTC GAT TTC GAT CAA GAC ATT CCT TTA ATG GTC TTT TCT GGA CAC CAC TAG GGG TCA
GAA GTA GTT CAT CAA ACT TTC TTC CCT CCC TAA TCT CAT T (SEQ ID NO: 317)
```

Figure 28.

```
Sequence: pINT 18-Tet1 Range: 1 to 7680

>AsiSI    >AAVS1_left_homology_arm
 |         |
 |         |10         20         30         40         50         60
GCG ATC GCT GCT TTC TCT GAC CTG CAT TCT CTC CCC TGG GCC TGT GCC GCT TTC TGT CTG
CAG CTT GTG GCC TGG GTC ACC TCT ACG GCT GGC CCA GAT CCT TCC CTG CCG CCT CCT TCA
GGT TCC GTC TTC CTC CAC TCC CTC TTC CCC TTG CTC TCT GCT GTG TTG CTG CCC AAG GAT
GCT CTT TCC GGA GCA CTT CCT TCT CGG CGC TGC ACC ACG TGA TGT CCT CTG AGC GGA TCC
TCC CCG TGT CTG GGT CCT CTC CGG GCA TCT CTC CTC CCT CAC CCA ACC CCA TGC CGT CTT
CAC TCG CTG GGT TCC CTT TTC CTT CTC CTT CTG GGG CCT GTG CCA TCT CTC GTT TCT TAG
GAT GGC CTT CTC CGA CGG ATG TCT CCC TTG CGT CCC GCC TCC CCT TCT TGT AGG CCT GCA
TCA TCA CCG TTT TTC TGG ACA ACC CCA AAG TAC CCC GTC TCC CTG GCT TTA GCC ACC TCT
CCA TCC TCT TGC TTT CTT TGC CTG GAC ACC CCG TTC TCC TGT GGA TTC GGG TCA CCT CTC
ACT CCT TTC ATT TGG GCA GCT CCC CTA CCC CCC TTA CCT CTC TAG TCT GTG CAA GCT CTT
CCA GCC CCC TGT CAT GGC ATC TTC CAG GGG TCC GAG AGC TCA GCT AGT CTT CTT CCT CCA
ACC CGG GCC CCT ATG TCC ACT TCA GGA CAG CAT GTT TGC TGC CTC CAG GGA TCC TGT GTC
CCC GAG CTG GGA CCA CCT TAT ATT CCC AGG GCC GGT TAA TGT GGC TCT GGT TCT GGG TAC

          790        800        810        820        830        840
TTT TAT CTG TCC CCT CCA CCC CAC AGT GGG GCA AGA TGC ATC TTC TGA CCT CTT CTC TTC
                                          _a___a___a___SYN INTRON__a___a___a___>

>Splice_acceptor
          |
          | 850        860        870        880        890        900
CTC CCA CAG GGC ATG GCA AAA CCT CTG AGC CAG GAA GAA AGC ACA CTG ATT GAA AGA GCA
                 M   A   K   P   L   S   Q   E   E   S   T   L   I   E   R   A>
                ____b___b___b___b___b___b_BLASTICIDIN___b___b___b___b___b___b___>
____a___a___a___>

          910        920        930        940        950        960
ACC GCT ACT ATC AAC AGC ATC CCC ATC TCC GAA GAC TAT TCT GTG GCT AGT GCC GCT CTG
 T   A   T   I   N   S   I   P   I   S   E   D   Y   S   V   A   S   A   A   L>
____b___b___b___b___b___b___b___b_BLASTICIDIN___b___b___b___b___b___b___b___b___>

          970        980        990       1000       1010       1020
TCC AGC GAC GGG AGA ATC TTC ACC GGT GTG AAC GTC TAC CAC TTT ACA GGC GGA CCA TGC
 S   S   D   G   R   I   F   T   G   V   N   V   Y   H   F   T   G   G   P   C>
____b___b___b___b___b___b___b___b_BLASTICIDIN___b___b___b___b___b___b___b___b___>

         1030       1040       1050       1060       1070       1080
GCA GAG CTG GTG GTC CTG GGG ACT GCA GCC GCT GCA GCC GCT GGT AAT CTG ACC TGT ATC
 A   E   L   V   V   L   G   T   A   A   A   A   A   A   G   N   L   T   C   I>
____b___b___b___b___b___b___b___b_BLASTICIDIN___b___b___b___b___b___b___b___b___>

|        1090       1100       1110       1120       1130       1140
GTG GCC ATT GGC AAC GAA AAT AGG GGC ATC CTG TCC CCA TGC GGC AGG TGT CGG CAG GTG
 V   A   I   G   N   E   N   R   G   I   L   S   P   C   G   R   C   R   Q   V>
____b___b___b___b___b___b___b___b_BLASTICIDIN___b___b___b___b___b___b___b___b___>

         1150       1160       1170       1180       1190       1200
CTG CTG GAT CTG CAT CCT GGC ATC AAG GCA ATT GTC AAA GAC TCT GAT GGA CAG CCT ACC
 L   L   D   L   H   P   G   I   K   A   I   V   K   D   S   D   G   Q   P   T>
____b___b___b___b___b___b___b___b_BLASTICIDIN___b___b___b___b___b___b___b___b___>

         1210       1220       1230       1240       1250       1260
GCC GTC GGT ATC CGT GAA CTG CTG CCT AGC GGC TAT GTC TGG GAG GGA TAA TGA GCT TGG
 A   V   G   I   R   E   L   L   P   S   G   Y   V   W   E   G   *   *> (SEQ ID NO: 321)
____b___b___b___b___b___b___b_BLASTICIDIN___b___b___b___b___b___b___b___>

                                                          >BGH_pA
                                                            |
         1270       1280       1290       1300          |1310       1320
CTT CGA AAC ACA CAG ATC TAC ACG GTA CCA GCT TAC GAC GTG ATC AGC CTC GAC TGT GCC
TTC TAG TTG CCA GCC ATC TGT TGT TTG CCC CTC CCC CGT GCC TTC CTT GAC CCT GGA AGG
TGC CAC TCC CAC TGT CCT TTC CTA ATA AAA TGA GGA AAT TGC ATC GCA TTG TCT GAG TAG
```

Figure 28 (continued)

```
GTG TCA TTC TAT TCT GGG GGG TGG GGT GGG GCA GGA CAG CAA GGG GGA GGA TTG GGA AGA


                                                   >CMV_promoter
                                                   |
        1510      1520      1530      1540      1550      1560
CAA TAG CAG GCA TGC TGG GGA CGA TCG TCA GCT GGA TCT AGT AAT CAA TTA CGG GGT CAT
TAG TTC ATA GCC CAT ATA TGG AGT TCC GCG TTA CAT AAC TTA CGG TAA ATG GCC CGC CTG
GCT GAC CGC CCA ACG ACC CCC GCC CAT TGA CGT CAA TAA TGA CGT ATG TTC CCA TAG TAA
CGC CAA TAG GGA CTT TCC ATT GAC GTC AAT GGG TGG AGT ATT TAC GGT AAA CTG CCC ACT
TGG CAG TAC ATC AAG TGT ATC ATA TGC CAA GTA CGC CCC CTA TTG ACG TCA ATG ACG GTA
AAT GGC CCG CCT GGC ATT ATG CCC AGT ACA TGA CCT TAT GGG ACT TTC CTA CTT GGC AGT
ACA TCT ACG TAT TAG TCA TCG CTA TTA CCA TGC TGA TGC GGT TTT GGC AGT ACA TCA ATG
GGC GTG GAT AGC GGT TTG ACT CAC GGG GAT TTC CAA GTC TCC ACC CCA TTG ACG TCA ATG
GGA GTT TGT TTT GGC ACC AAA ATC AAC GGG ACT TTC CAA AAT GTC GTA ACA ACT CCG CCC

                                                  >TATA_box
                                                   |
        2050      2060      2070      2080 |    2090      2100
CAT TGA CGC AAA TGG GCG GTA GGC GTG TAC GGT GGG AGG TCT ATA TAA GCA GAG CTG GTT

                                             >Nuclear_localisation_signal
                                                       |
        2110      2120      2130      2140 |    2150      2160
TAG TGA ACC GTC AGA TCA GAT CCA TCG ATC TAG GAA TTC ACC ATG CCA AAG AGA CCC AGA
                                                         M   P   K   R   P   R

        2170      2180      2190      2200      2210      2220
CCC TCT AGA TTA GAT AAA AGT AAA GTG ATT AAC AGC GCA TTA GAG CTG CTT AAT GAG GTC
 P   S   R   L   D   K   S   K   V   I   N   S   A   L   E   L   L   N   E   V>
____c___c___c___c___c___c___c___c___c___rTA___c___c___c___c___c___c___c___c___>

        2230      2240      2250      2260      2270      2280
GGA ATC GAA GGT TTA ACA ACC CGT AAA CTC GCC CAG AAG CTG GGT GTA GAG CAG CCT ACA
 G   I   E   G   L   T   T   R   K   L   A   Q   K   L   G   V   E   Q   P   T>
____c___c___c___c___c___c___c___c___c_rTA__c___c___c___c___c___c___c___c___c___>

        2290      2300      2310      2320      2330      2340
CTG TAT TGG CAT GTA AAA AAT AAG CGG GCT TTG CTC GAC GCC TTA GCC ATT GAG ATG TTA
 L   Y   W   H   V   K   N   K   R   A   L   L   D   A   L   A   I   E   M   L>
____c___c___c___c___c___c___c___c___c_rTA__c___c___c___c___c___c___c___c___c___>

        2350      2360      2370      2380      2390      2400
GAT AGG CAC CAT ACT CAC TTT TGC CCT TTA AAA GGG GAA AGC TGG CAA GAT TTT TTA CGC
 D   R   H   H   T   H   F   C   P   L   K   G   E   S   W   Q   D   F   L   R>
____c___c___c___c___c___c___c___c___c_rTA__c___c___c___c___c___c___c___c___c___>

        2410      2420      2430      2440      2450      2460
AAT AAC GCT AAA AGT TTT AGA TGT GCT TTA CTA AGT CAT CGC AAT GGA GCA AAA GTA CAT
 N   N   A   K   S   F   R   C   A   L   L   S   H   R   N   G   A   K   V   H>
____c___c___c___c___c___c___c___c___c_rTA__c___c___c___c___c___c___c___c___c___>

        2470      2480      2490      2500      2510      2520
TCA GAT ACA CGG CCT ACA GAA AAA CAG TAT GAA ACT CTC GAA AAT CAA TTA GCC TTT TTA
 S   D   T   R   P   T   E   K   Q   Y   E   T   L   E   N   Q   L   A   F   L>
____c___c___c___c___c___c___c___c___c_rTA__c___c___c___c___c___c___c___c___c___>

        2530      2540      2550      2560      2570      2580
TGC CAA CAA GGT TTT TCA CTA GAG AAC GCG TTA TAT GCA CTC AGC GCT GTG GGG CAT TTT
 C   Q   Q   G   F   S   L   E   N   A   L   Y   A   L   S   A   V   G   H   F>
____c___c___c___c___c___c___c___c___c_rTA__c___c___c___c___c___c___c___c___c___>
```

Figure 28 (continued)

```
          2590          2600          2610          2620          2630          2640
ACT TTA GGT TGC GTA TTG GAA GAT CAA GAG CAT CAA GTC GCT AAA GAA GAA AGG GAA ACA
 T   L   G   C   V   L   E   D   Q   E   H   Q   V   A   K   E   E   R   E   T>
____c___c___c___c___c___c___c___c___c_rTA__c___c___c___c___c___c___c___c___c___>

          2650          2660          2670          2680          2690          2700
CCT ACT ACT GAT AGT ATG CCG CCA TTA TTA CGA CAA GCT ATC GAA TTA TTT GAT CAC CAA
 P   T   T   D   S   M   P   P   L   L   R   Q   A   I   E   L   F   D   H   Q>
____c___c___c___c___c___c___c___c___c_rTA__c___c___c___c___c___c___c___c___c___>

          2710          2720          2730          2740          2750          2760
GGT GCA GAG CCA GCC TTC TTA TTC GGC CTT GAA TTG ATC ATA TGC GGA TTA GAA AAA CAA
 G   A   E   P   A   F   L   F   G   L   E   L   I   I   C   G   L   E   K   Q>
____c___c___c___c___c___c___c___c___c_RTTA__c___c___c___c___c___c___c___c___c___>

          2770          2780          2790          2800          2810          2820
CTT AAA TGT GAA AGT GGG TCC GCG TAC AGC CGC GCG CGT ACG AAA AAC AAT TAC GGG TCT
 L   K   C   E   S   G   S   A   Y   S   R   A   R   T   K   N   N   Y   G   S>
____c___c___c___c___c___c___c___c___c_rTA__c___c___c___c___c___c___c___c___c___>

          2830          2840          2850          2860          2870          2880
ACC ATC GAG GGC CTG CTC GAT CTC CCG GAC GAC GAC GCC CCC GAA GAG GCG GGG CTG GCG
 T   I   E   G   L   L   D   L   P   D   D   D   A   P   E   E   A   G   L   A>
____c___c___c___c___c___c___c___c___c_rTA__c___c___c___c___c___c___c___c___c___>

          2890          2900          2910          2920          2930          2940
GCT CCG CGC CTG TCC TTT CTC CCC GCG GGA CAC ACG CGC AGA CTG TCG ACG GCC CCC CCG
 A   P   R   L   S   F   L   P   A   G   H   T   R   R   L   S   T   A   P   P>
____c___c___c___c___c___c___c___c___c_rTA__c___c___c___c___c___c___c___c___c___>

          2950          2960          2970          2980          2990          3000
ACC GAT GTC AGC CTG GGG GAC GAG CTC CAC TTA GAC GGC GAG GAC GTG GCG ATG GCG CAT
 T   D   V   S   L   G   D   E   L   H   L   D   G   E   D   V   A   M   A   H>
____c___c___c___c___c___c___c___c___c_rTA__c___c___c___c___c___c___c___c___c___>

          3010          3020          3030          3040          3050          3060
GCC GAC GCG CTA GAC GAT TTC GAT CTG GAC ATG TTG GGG GAC GGG GAT TCC CCG GGT CCG
 A   D   A   L   D   D   F   D   L   D   M   L   G   D   G   D   S   P   G   P>
____c___c___c___c___c___c___c___c___c_rTA__c___c___c___c___c___c___c___c___c___>

          3070          3080          3090          3100          3110          3120
GGA TTT ACC CCC CAC GAC TCC GCC CCC TAC GGC GCT CTG GAT ATG GCC GAC TTC GAG TTT
 G   F   T   P   H   D   S   A   P   Y   G   A   L   D   M   A   D   F   E   F>
____c___c___c___c___c___c___c___c___c_rTA__c___c___c___c___c___c___c___c___c___>

                         <2827                                          >SV40pA
                           |                                               |
          3130          3140|         3150          3160          3170          3180
GAG CAG ATG TTT ACC GAT GCC CTT GGA ATT GAC GAG TAC GGT GGG TAG GGG GCG CGA GGA
 E   Q   M   F   T   D   A   L   G   I   D   E   Y   G   G   *> (SEQ ID NO: 322)
____c___c___c___c___c___c___c_RTTA__c___c___c___c___c___c___c___>

          3190          3200          3210          3220          3230          3240
TCC AGA CAT GAT AAG ATA CAT TGA TGA GTT TGG ACA AAC CAC AAC TAG AAT GCA GTG AAA
AAA ATG CTT TAT TTG TGA AAT TTG TGA TGC TAT TGC TTT ATT TGT AAC CAT TAT AAG CTG
CAA TAA ACA AGT TAA CAA CAA CAA TTG CAT TCA TTT TAT GTT TCA GGT TCA GGG GGA GGT
GTG GGA GGT TTT TTA AAG CAA GTA AAA CCT CTA CAA ATG TGG TAT GGC TGA TTA TGA TCC
TGC AAG CCT CGT CGT CCT GGC CGG ACC ACG CTA TCT GTG CAA GGT CCC CGG CCC CGG ACG
CGC GCT CCA TGA GCA GAG CGC CCG CCG CCG AGG CGA AGA CTC GGG CGG CGC CCT GCC CGT
CCC ACC AGG TCA ACA GGC GGT AAC CGG CCT CTT CAT CGG GAA TGC GCG CGA CCT TCA GCA
TCG CCG GCA TGT CCC CCT GGC GGA CGG GAA GTA TCC AGC TCG ACC ATG CTT GGC GAG ATT

                        >tetO_heptamer
                         |
          3670          3680          3690          3700          3710          3720
TTC AGG AGC TAA GGT AGC TTC GTC TTC ACA CGA GTT TAC TCC CTA TCA GTG ATA GAG AAC
GTA TGT CGA GTT TAC TCC CTA TCA GTG ATA GAG AAC GAT GTC GAG TTT ACT CCC TAT CAG
```

Figure 28 (continued)

```
TGA TAG AGA ACG TAT GTC GAG TTT ACT CCC TAT CAG TGA TAG AGA ACG TAT GTC GAG TTT
ACT CCC TAT CAG TGA TAG AGA ACG TAT GTC GAG TTT ATC CCT ATC AGT GAT AGA GAA CGT
ATG TCG AGT TTA CTC CCT ATC AGT GAT AGA GAA CGT ATG TCG AGG TAG GCG TGT ACG GTG


        3970        3980        3990        4000        4010        4020
GGA GGC CTA TAT AAG CAG AGC TCG TTT AGT GAA CCG TCA GAT CGC CTG GAT TCG AAT GAG
                                                                          M  R>
                                                                         __d___>

        4030        4040        4050        4060        4070        4080
GGC CTG GAT CTT CTT TCT CCT TTG CCT GGC CGG GAG GGC TCT GGC AGC TAG CGA GAT TGT
  A   W   I   F   F   L   L   C   L   A   G   R   A   L   A> (SEQ ID NO: 323)
___d___d___d___d___d____BM40 LEADER____d___d___d___d___d___d_>
                                                            L   A   R   L>
                                                          _e_MK3475-VL_e___>

        4090        4100        4110        4120        4130        4140
CCT GAC CCA GAG CCC CGC AAC ACT GTC CCT GTC CCC CGG AGA AAG AGC AAC CCT GTC CTG
S   *   P   R   A   P   Q   H   C   P   C   P   P   E   K   E   Q   P   C   P>
___e___e___e___e___e___e___e___e__MK3475-VL____e___e___e___e___e___e___e___e___>

        4150        4160        4170        4180        4190        4200
TAG AGC ATC AAA AGG TGT GTC TAC CAG TGG GTA CAG CTA TCT GCA CTG GTA CCA GCA GAA
V   E   H   Q   K   V   C   L   P   V   G   T   A   I   C   T   G   T   S   R>
___e___e___e___e___e___e___e___e__MK3475-VL____e___e___e___e___e___e___e___e___>

        4210        4220        4230        4240        4250        4260
GCC CGG ACA GGC CCC TAG GCT GCT GAT CTA CCT GGC TTC TTA TCT GGA GAG TGG AGT GCC
S   P   D   R   P   L   G   C   *   S   T   W   L   L   I   W   R   V   E   C>
___e___e___e___e___e___e___e___e__MK3475-VL____e___e___e___e___e___e___e___e___>

        4270        4280        4290        4300        4310        4320
AGC ACG GTT CTC AGG TTC CGG CAG CGG AAC AGA CTT TAC CCT GAC AAT TTC CAG CCT GGA
Q   H   G   S   Q   V   P   A   A   E   Q   T   L   P   *   Q   F   P   A   W>
___e___e___e___e___e___e___e___e__MK3475-VL____e___e___e___e___e___e___e___e___>

        4330        4340        4350        4360        4370        4380
GCC AGA AGA CTT CGC CGT GTA CTA TTG CCA GCA TTC CAG AGA TCT GCC CCT GAC TTT TGG
S   Q   K   T   S   P   C   T   I   A   S   I   P   E   I   C   P   *   L   L>
___e___e___e___e___e___e___e___e__MK3475-VL____e___e___e___e___e___e___e___e___>

        4390        4400        4410        4420        4430        4440
CGG AGG GAC CAA GGT CGA AAT CAA AAG GAC TGC GGC CGC AAC CGT GGC TGC CCC TTC CGT
A   E   G   P   R   S   K   S   K   G   L> (SEQ ID NO: 324)
___e___e___e____MK3475-VL__e___e___e___e___>
                                                    T   V   A   A   P   S   V>
                                                  __f___f_CL-KAPPA__f___f___>

        4450       |4460        4470        4480        4490        4500
GTT CAT CTT CCC TCC CTC CGA CGA GCA GCT GAA GTC CGG CAC CGC CTC TGT GGT GTG CCT
  F   I   F   P   P   S   D   E   Q   L   K   S   G   T   A   S   V   V   C   L>
___f___f___f___f___f___f___f___f___CL-KAPPA____f___f___f___f___f___f___f___f___>

        4510        4520        4530        4540        4550        4560
GCT GAA CAA CTT CTA CCC TCG GGA GGC CAA GGT GCA GTG GAA GGT GGA CAA CGC CCT GCA
  L   N   N   F   Y   P   R   E   A   K   V   Q   W   K   V   D   N   A   L   Q>
___f___f___f___f___f___f___f___f___CL-KAPPA____f___f___f___f___f___f___f___f___>

        4570        4580        4590        4600        4610        4620
GTC CGG CAA CTC CCA GGA ATC CGT CAC CGA GCA GGA CTC CAA GGA CTC TAC CTA CTC CCT
  S   G   N   S   Q   E   S   V   T   E   Q   D   S   K   D   S   T   Y   S   L>
___f___f___f___f___f___f___f___f___CL-KAPPA____f___f___f___f___f___f___f___f___>
```

Figure 28 (continued)

```
           4630         4640         4650          4660         4670         4680
GTC CTC CAC CCT GAC CCT GTC CAA GGC CGA CTA CGA GAA GCA CAA GCT GTA CGC CTG CGA
  S   S   T   L   T   L   S   K   A   D   Y   E   K   H   K   L   Y   A   C   E>
____f___f___f___f___f___f___f___f___CL-KAPPA_____f___f___f___f___f___f___f___f___>

           4690         4700         4710          4720         4730         4740
AGT GAC CCA CCA GGG CCT GTC CTC TCC CGT GAC CAA GTC CTT CAA CCG GGG CGA GTG CTC
  V   T   H   Q   G   L   S   S   P   V   T   K   S   F   N   R   G   E   C> (SEQ ID NO: 325)
___f___f___f___f___f___f___f___f__CL-KAPPA_f___f___f___f___f___f___f___f___f_>
>Furin_cleavage
        |
        |  4750         4760         4770          4780         4790         4800
TAG ACG AGC AAA GAG AGG CAG CGG CGC GAC CAA CTT TAG CCT GCT GAA ACA GGC GGG CGA
                        G   S   G   A   T   N   F   S   L   L   K   Q   A   G   D>
                      __g___g___g___g___g____P2A PEPTIDE____g___g___g___g___g___>

           4810         4820    |    4830          4840         4850         4860
TGT GGA AGA AAA CCC AGG ACC CGA GCT CAT GAG TTG GAG CTG TAT CAT CCT CTT CTT GGT
  V   E   E   N   P> (SEQ ID NO: 326)
____P2A PEPTIDE_____g_>
                                            M   S   W   S   C   I   I   L   F   L   V>
                                          __h___h___h___h__LEADER1__h___h___h___h___>

               >intron
                   |
           4870    |    4880         4890          4900         4910         4920
AGC AAC AGC TAC AGG TAA GGG GTT AAC AGT AGC AGG CTT GAG GTC TGG ACA TAT ATA TGG
  A   T   A   T> (SEQ ID NO: 327)
____LEADER1_____h_>

           4930         4940         4950          4960|        4970         4980
GTG ACA ATG ACA TCC ACT TTG CCT TTC TCT CCA CAG GCG CCA TGG CCC AGG TGC AGC TGG
                                                G> A
                                              _i___i_>
                                                        M   A   Q   V   Q   L>
                                                      _j___j_MK3475 VH_j___j___>

           4990         5000         5010          5020         5030         5040
TGC AGA GCG GCG TGG AAG TGA AAA AGC CTG GGG CAT CCG TGA AGG TCT CCT GTA AAG CAA
V   Q   S   G   V   E   V   K   K   P   G   A   S   V   K   V   S   C   K   A>
___j___j___j___j___j___j___j___j__MK3475 VH____j___j___j___j___j___j___j___j___>

           5050         5060         5070          5080         5090         5100
GCG GGT ACA CAT TCA CCA ACT ACT ATA TGT ACT GGG TGA GAC AGG CAC CAG GAC AGG GAC
S   G   Y   T   F   T   N   Y   Y   M   Y   W   V   R   Q   A   P   G   Q   G>
____j___j___j___j___j___j___j___j__MK3475 VH____j___j___j___j___j___j___j___j___>

           5110         5120         5130          5140         5150         5160
TGG AGT GGA TGG GCG GAA TCA ACC CTT CTA ATG GGG GTA CAA ACT TCA ACG AAA AGT TTA
L   E   W   M   G   G   I   N   P   S   N   G   G   T   N   F   N   E   K   F>
____j___j___j___j___j___j___j___j__MK3475 VH____j___j___j___j___j___j___j___j___>

           5170         5180         5190          5200         5210         5220
AAA ACA GGG TCA CTC TGA CCA CAG ATT CCA GCA CTA CCA CAG CCT ATA TGG AGC TGA AGT
K   N   R   V   T   L   T   T   D   S   S   T   T   T   A   Y   M   E   L   K>
____j___j___j___j___j___j___j___j__MK3475 VH____j___j___j___j___j___j___j___j___>

           5230         5240         5250          5260         5270         5280
CCC TCC AGT TCG ACG ATA CCG CCG TGT ACT ATT GCG CTA GGC GGG ACT ACA GGT TCG ATA
S   L   Q   F   D   D   T   A   V   Y   Y   C   A   R   R   D   Y   R   F   D>
____j___j___j___j___j___j___j___j__MK3475 VH____j___j___j___j___j___j___j___j___>
```

Figure 28 (continued)

```
         5290          5300          5310           5320          5330          5340
TGG GCT TTG ACT ATT GGG GGC AGG GAA CTA CCG TCA CAG TCT CGA GTG CCT CCA CCA AGG
M   G   F   D   Y   W   G   Q   G   T   T   V   T   V> (SEQ ID NO: 328)
___j___j___j___j___j__MK3475 VH_____j___j___j___j___j__>
                                                                S   S   A   S   T   K>
                                                              _k___k_IGG1 CH1-3____k___>

         5350          5360          5370           5380          5390          5400
GCC CTA GCG TCT TTC CTC TGG CCC CTT CCT CCA AGT CTA CCT CTG GCG GCA CCG CTG CTC
G   P   S   V   F   P   L   A   P   S   S   K   S   T   S   G   G   T   A   A>
___k___k___k___k___k___k___k___k__IGG1 CH1-3___k___k___k___k___k___k___k___k___>

         5410          5420          5430           5440          5450          5460
TGG GCT GCC TGG TGA AGG ACT ACT TCC CTG AGC CTG TGA CCG TGT CCT GGA ACT CTG GCG
L   G   C   L   V   K   D   Y   F   P   E   P   V   T   V   S   W   N   S   G>
___k___k___k___k___k___k___k___k__IGG1 CH1-3___k___k___k___k___k___k___k___k___>

         5470          5480          5490           5500          5510          5520
CCC TGA CCT CCG GCG TGC ATA CCT TCC CTG CCG TCC TCC AGT CCT CCG GCC TGT ACT CCC
A   L   T   S   G   V   H   T   F   P   A   V   L   Q   S   S   G   L   Y   S>
___k___k___k___k___k___k___k___k__IGG1 CH1-3___k___k___k___k___k___k___k___k___>

         5530          5540          5550           5560          5570          5580
TGT CCT CCG TGG TGA CCG TGC CTT CCT CCT CTC TGG GCA CCC AGA CCT ACA TCT GCA ACG
L   S   S   V   V   T   V   P   S   S   S   L   G   T   Q   T   Y   I   C   N>
___k___k___k___k___k___k___k___k__IGG1 CH1-3___k___k___k___k___k___k___k___k___>

         5590          5600          5610           5620          5630          5640
TGA ACC ACA AGC CTT CCA ACA CCA AGG TGG ACA AGA AGG TGG AGC CTA AGT CCT GCG ACA
V   N   H   K   P   S   N   T   K   V   D   K   K   V   E   P   K   S   C   D>
___k___k___k___k___k___k___k___k__IGG1 CH1-3___k___k___k___k___k___k___k___k___>
                                                                E   P   K   S   C   D>
                                                              _l___l___HINGE___l___l___>

         5650          5660          5670           5680          5690          5700
AGA CCC ACA CCT GCC CTC CAT GTC CTG CCC CTG AGC TGC TGG GCG GAC CCT CCG TGT TCC
K   T   H   T   C   P   P   C   P   A   P   E   L   L   G   G   P   S   V   F>
___k___k___k___k___k___k___k___k__IGG1 CH1-3___k___k___k___k___k___k___k___k___>
K   T   H   T   C   P   P   C   P   A   P   E   L   L   G   G   P> (SEQ ID NO: 330)
___l___l___l___l___l___l___l__HINGE_____l___l___l___l___l___l___l__>

         5710          5720          5730           5740          5750          5760
TGT TCC CTC CTA AGC CTA AGG ACA CCC TGA TGA TCT CCC GGA CCC CTG AAG TGA CCT GCG
L   F   P   P   K   P   K   D   T   L   M   I   S   R   T   P   E   V   T   C>
___k___k___k___k___k___k___k___k__IGG1 CH1-3___k___k___k___k___k___k___k___k___>

         5770          5780          5790           5800          5810          5820
TGG TGG TGG ACG TGT CCC ACG AAG ATC CTG AAG TGA AGT TCA ATT GGT ACG TGG ACG GCG
V   V   V   D   V   S   H   E   D   P   E   V   K   F   N   W   Y   V   D   G>
___k___k___k___k___k___k___k___k__IGG1 CH1-3___k___k___k___k___k___k___k___k___>

         5830          5840          5850           5860          5870          5880
TGG AGG TGC ACA ACG CCA AGA CCA AGC CTC GGG AGG AAC AGT ACA ACT CCA CCT ACC GGG
V   E   V   H   N   A   K   T   K   P   R   E   E   Q   Y   N   S   T   Y   R>
___k___k___k___k___k___k___k___k__IGG1 CH1-3___k___k___k___k___k___k___k___k___>

         5890          5900          5910           5920          5930          5940
TGG TGT CTG TGC TGA CCG TGC TGC ACC AGG ACT GGC TGA ACG GCA AAG AAT ACA AGT GCA
V   V   S   V   L   T   V   L   H   Q   D   W   L   N   G   K   E   Y   K   C>
___k___k___k___k___k___k___k___k__IGG1 CH1-3___k___k___k___k___k___k___k___k___>

         5950          5960          5970           5980          5990          6000
AGG TGT CCA ACA AGG CCC TGC CTG CCC CTA TCG AAA AGA CCA TCT CCA AGG CTA AGG GCC
K   V   S   N   K   A   L   P   A   P   I   E   K   T   I   S   K   A   K   G>
___k___k___k___k___k___k___k___k__IGG1 CH1-3___k___k___k___k___k___k___k___k___>
```

Figure 28 (continued)

```
          6010          6020          6030           6040          6050          6060
AGC CAC GGG AAC CTC AGG TCT ACA CAC TGC CTC CTA GCC GGG ACG AGC TGA CCA AGA ACC
Q   P   R   E   P   Q   V   Y   T   L   P   P   S   R   D   E   L   T   K   N>
____k____k____k____k____k____k____k____k__IGG1 CH1-3____k____k____k____k____k____k____k____k___>

          6070          6080          6090           6100          6110          6120
AGG TGT CCC TGA CCT GTC TGG TGA AGG GCT TCT ACC CTT CCG ATA TCG CCG TGG AGT GGG
Q   V   S   L   T   C   L   V   K   G   F   Y   P   S   D   I   A   V   E   W>
____k____k____k____k____k____k____k____k__IGG1 CH1-3____k____k____k____k____k____k____k____k___>

          6130          6140          6150           6160          6170          6180
AGT CTA ACG GCC AGC CTG AGA ACA ACT ACA AGA CCA CCC CTC CTG TGC TGG ACT CCG ACG
E   S   N   G   Q   P   E   N   N   Y   K   T   T   P   P   V   L   D   S   D>
____k____k____k____k____k____k____k____k__IGG1 CH1-3____k____k____k____k____k____k____k____k___>

          6190          6200          6210           6220          6230          6240
GCT CCT TCT TCC TGT ACT CCA AGC TGA CCG TGG ACA AGT CCC GGT GGC AGC AGG GCA ACG
G   S   F   F   L   Y   S   K   L   T   V   D   K   S   R   W   Q   Q   G   N>
____k____k____k____k____k____k____k____k__IGG1 CH1-3____k____k____k____k____k____k____k____k___>

          6250          6260          6270           6280          6290          6300
TGT TCT CCT GCT CCG TGA TGC ACG AGG CCC TGC ACA ACC ACT ACA CCC AGA AGT CCC TGT
V   F   S   C   S   V   M   H   E   A   L   H   N   H   Y   T   Q   K   S   L>
____k____k____k____k____k____k____k____k__IGG1 CH1-3____k____k____k____k____k____k____k____k___>

          6310          6320          6330           6340          6350          6360
CCC TGT CTC CTG GCA AGG AAC AAA AAC TCA TCT CAG AAG AGG ATC TGA ATG CTG TGG GCC
S   L   S   P   G   K> (SEQ ID NO: 329)
____k_IGG1 CH1-3_____k__>
                        E   Q   K   L   I   S   E   E   D   L> (SEQ ID NO: 331)
                      _m____m____m_____MYC-EPITOPE_____m____m____m__>
                                                                N   A   V   G>
                                                              _n___PDGFR TM_n____>

          6370          6380          6390           6400          6410          6420
AGG ACA CGC AGG AGG TCA TCG TGG TGC CAC ACT CCT TGC CCT TTA AGG TGG TGG TGA TCT
Q   D   T   Q   E   V   I   V   V   P   H   S   L   P   F   K   V   V   V   I>
____n____n____n____n____n____n____n____n____PDGFR TM_____n____n____n____n____n____n____n____n___>

          6430          6440          6450           6460          6470          6480
CAG CCA TCC TGG CCC TGG TGG TGC TCA CCA TCA TCT CCC TTA TCA TCC TCA TCA TGC TTT
S   A   I   L   A   L   V   V   L   T   I   I   S   L   I   I   L   I   M   L>
____n____n____n____n____n____n____n____n____PDGFR TM_____n____n____n____n____n____n____n____n___>

          6490          6500      | | 6510           6520      |6530          6540
GGC AGA AGA AGC CAC GTT AGT AAA AGC TTG TCA CTT GGA AAG TAA TAG TTT TTC CTG CAC
W   Q   K   K   P   R   *   *> (SEQ ID NO: 332)
____n____n__PDGFR TM_n____n____n__>

               >BGH_pA
                  |
          6550    |     6560          6570           6580          6590          6600
GGG TAG TAA TCA GCC TCG ACT GTG CCT TCT AGT TGC CAG CCA TCT GTT GTT TGC CCC TCC
CCC GTG CCT TCC TTG ACC CTG GAA GGT GCC ACT CCC ACT GTC CTT TCC TAA TAA AAT GAG
GAA ATT GCA TCG CAT TGT CTG AGT AGG TGT CAT TCT ATT CTG GGG GGT GGG GTG GGG CAG
GAC AGC AAG GGG GAG GAT TGG GAA GAC AAT AGC AGG CAT GCT GGG GAT GGC CCG GGC ATG

                                                               >AAVS-R
                                                                  |
                                                                  |
          6790          6800          6810           6820|         6830          6840
ATA ACT TCG TAT AAT GTA TGC TAT ACG AAG TTA TGT ATA CGG CGC GCC CAC TAG GGA CAG
GAT TGG TGA CAG AAA AGC CCC ATC CTT AGG CCT CCT CCT TCC TAG TCT CCT GAT ATT GGG
TCT AAC CCC CAC CTC CTG TTA GGC AGA TTC CTT ATC TGG TGA CAC ACC CCC ATT TCC TGG
```

Figure 28 (continued)

```
AGC CAT CTC TCT CCT TGC CAG AAC CTC TAA GGT TTG CTT ACG ATG GAG CCA GAG AGG ATC
CTG GGA GGG AGA GCT TGG CAG GGG GTG GGA GGG AAG GGG GGG ATG CGT GAC CTG CCC GGT
TCT CAG TGG CCA CCC TGC GCT ACC CTC TCC CAG AAC CTG AGC TGC TCT GAC GCG GCT GTC
TGG TGC GTT TCA CTG ATC CTG GTG CTG CAG CTT CCT TAC ACT TCC CAA GAG GAG AAG CAG
TTT GGA AAA ACA AAA TCA GAA TAA GTT GGT CCT GAG TTC TAA CTT TGG CTC TTC ACC TTT
CTA GTC CCC AAT TTA TAT TGT TCC TCC GTG CGT CAG TTT TAC CTG TGA GAT AAG GCC AGT
AGC CAG CCC CGT CCT GGC AGG GCT GTG GTG AGG AGG GGG GTG TCC GTG TGG AAA ACT CCC
TTT GTG AGA ATG GTG CGT CCT AGG TGT TCA CCA GGT CGT GGC CGC CTC TAC TCC CTT TCT
CTT TCT CCA TCC TTC TTT CCT TAA AGA GTC CCC AGT GCT ATC TGG GAC ATA TTC CTC CGC
CCA GAG CAG GGT CCC GCT TCC CTA AGG CCC TGC TCT GGG CTT CTG GGT TTG AGT CCT TGG
CAA GCC CAG GAG AGG CGC TCA GGC TTC CCT GTC CCC CTT CCT CGT CCA CCA TCT CAT GCC

                                                                      >Sbf1
                                                                        |
          7630         7640         7650          7660         7670     |    7680
CCT GGC TCT CCT GCC CCT TCC CTA CAG GGG TTC CTG GCT CTG CTC TCC TGC AGG CGA TCT
```

(SEQ ID NO: 320)

Sequence: PINT17-Tet Range: 1516 to 7793

```
   BglII
     |     10          20          30          40          50          60
GGA GAT CTT CCC CAG CAT GCC TGC TAT TGT CTT CCC AAT CCT CCC CCT TGC TGT CCT GCC
CCA CCC CAC CCC CCA GAA TAG AAT GAC ACC TAC TCA GAC AAT GCG ATG CAA TTT CCT CAT
TTT ATT AGG AAA GGA CAG TGG GAG TGG CAC CTT CCA GGG TCA AGG AAG GCA CGG GGG AGG

                                                <BGH_polyA
                                                     |
           190         200         210         220   |     230         240
GGC AAA CAA CAG ATG GCT GGC AAC TAG AAG GCA CAG TCG AGG CTC TAG ATT ATT AGC ACT
                                                                         <C  E
                                                                        <__a___

           250         260         270         280         290         300
CGC CCC GGT TGA AGG ACT TGG TCA CGG GAG AGG ACA GGC CCT GGT GGG TCA CTT CGC AGG
 <G   R   N   F   S   K   T   V   P   S   S   L   G   Q   H   T   V   E   C   A
<___a___a___a___a___a___a___a___a___C_KAPPA_a___a___a___a___a___a___a___a___a___

           310         320         330         340         350         360
CGT ACA GCT TGT GCT TCT CGT AGT CGG CCT TGG ACA GGG TCA GGG TGG AGG ACA GGG AGT
 <Y   L   K   H   K   E   Y   D   A   K   S   L   T   L   T   S   S   L   S   Y
<___a___a___a___a___a___a___a___a___C_KAPPA_a___a___a___a___a___a___a___a___a___

           370         380         390         400         410         420
AGG TAG AGT CCT TGG AGT CCT GCT CGG TGA CGG ATT CCT GGG AGT TGC CGG ACT GCA GGG
 <T   S   D   K   S   D   Q   E   T   V   S   E   Q   S   N   G   S   Q   L   A
<___a___a___a___a___a___a___a___a___C_KAPPA_a___a___a___a___a___a___a___a___a___

           430         440         450         460         470         480
CGT TGT CCA CCT TCC ACT GCA CCT TGG CCT CCC GAG GGT AGA AGT TGT TCA GCA GGC ACA
 <N   D   V   K   W   Q   V   K   A   E   R   P   Y   F   N   N   L   L   C   V
<___a___a___a___a___a___a___a___a___C_KAPPA_a___a___a___a___a___a___a___a___a___

           490         500         510         520         530         540
CCA CAG AGG CGG TGC CGG ACT TCA GCT GCT CGT CGG AGG GAG GGA AGA TGA ACA CGG AAG
 <V   S   A   T   G   S   K   L   Q   E   D   S   P   P   F   I   F   V   S   P (SEQ ID NO: 334)
<___a___a___a___a___a___a___a___a___C_KAPPA_a___a___a___a___a___a___a___a___a___
       NotI
         | 550         560         570         580         590         600
GGG CGG CCG CGG TAC GTT TGA TTT CCA CCT TGG TCC CTT GGC CGA ACG TCC TTG GGG TGC
 <A   A   A  <T   R   K   I   E   V   K   T   G   Q   G   F   T   R   P   T   S
<___a_        <__b___b___b___b___b___b___b__D1.3 VL_b___b___b___b___b___b___b___

           610         620         630         640         650         660
TCC AGA AGT GCT GGC AGT AGT AGG TGG CGA TGT CCT CTG GCT GGA GGC TGC TGA TGG TGA
 <W   F   H   Q   C   Y   Y   T   A   I   D   E   P   Q   L   S   S   I   T   F
<___b___b___b___b___b___b___b___b___D1.3 VL_b___b___b___b___b___b___b___b___b___

           670         680         690         700         710         720
AGG TGT AGT CGG TAC CGC TAC CGC TAC CGC TGA ATC TGC TTG GCA CAC CGT CAG CCA GGG
 <T   Y   D   T   G   S   G   S   G   S   F   R   S   P   V   G   D   A   L   T
<___b___b___b___b___b___b___b___b___D1.3 VL_b___b___b___b___b___b___b___b___b___

           730         740         750         760         770         780
TGG TGG TGT AGT AGA TCA GCA GCT TTG GAG CCT TAC CTG GCT TCT GCT GGT ACC AAG CCA
 <T   T   Y   Y   I   L   L   K   P   A   K   G   P   K   Q   Q   Y   W   A   L
<___b___b___b___b___b___b___b___b___D1.3 VL_b___b___b___b___b___b___b___b___b___

           790         800         810         820         830         840
GGT AGT TGT GGA TGT TAC CGC TGG CTC TAC AGG TGA TGG TCA CTC TGT CAC CCA CGC TGG
 <Y   N   H   I   N   G   S   A   R   C   T   I   T   V   R   D   G   V   S   A
<___b___b___b___b___b___b___b___b___D1.3 VL_b___b___b___b___b___b___b___b___b___
```

Figure 37

```
                                                                  <splice_acceptor
                                                              NheI        |
          850         860         870          880      |     890|        900
CGC TCA GGC TGC TTG GGC TCT GGG TCA TCT GGA TGT CTC CTC TGC TAG CTG AAA ATA TAC
 <S   L   S   S   P   S   Q   T   M   Q   I   D   G   R   S   A
<___b___b___b___b____D1.3 VL____b___b___b___b___b_<__c__LEAD_c___c_ <d_INTRON_d
             (SEQ ID NO: 335)                         (SEQ ID NO: 336)
          910         920         930          940         950         960
AGC AAA CAT CAG TAC AAC ATA AAT ATC TGT GTA TGA AAA TCA CCT TTA ATC TTG CTA GAC
<___d___d___d___d___d___d___d____LEADER INTRON__d___d___d___d___d___d___d___d___

          970         980         990         1000        1010        1020
ATG AAG AAA GAA TAT GCA ATA CAT TTT TAA AAT TAG GAT TTT AAA ATC AAG CCA AAA ATC
<___d___d___d___d___d___d___d____LEADER INTRON__d___d___d___d___d___d___d___d___

         1030        1040        1050         1060        1070        1080
ACC TAT TGC AGA GTC CCC AAT GAA AGA AAT TAC AGA TTG AAA GAA TAT CTC CGC CTA GGT
<___d___d___d___d___d___d___d____LEADER INTRON__d___d___d___d___d___d___d___d___

         1090        1100        1110         1120        1130        1140
TTG TGG AAA TAT TCT CAC CTG GAA CCC AGA GCA GCA GAA ACC CAA TGA GTT GTG ATG GCA
<____LEADER INTRON__d_    <P   V   W   L   L   L   F   G   I   L   Q   S   P   L
                          <__e___e___e___e___e___LEADER I_____e___e___e___e___e___

                           >TRE3G_BI_promoter
                                      |
         1150        1160        1170         1180        1190        1200
ACA TGG TGG CCA CTC CGG ATC TGA TCT GCG ATC TGA CGG TTC ACT AAA CGA GCT CTG CTT
 <M (SEQ ID NO: 337)
<___e_
                                                     >tet_operator
                                                            |
         1210        1220        1230         1240        1250        1260
ATA TAG GCC TCC CAC CGT ACA CGC CAC CTC GAC ATA CTC GTG TTT ACT CCC TAT CAG TGA

                        >tet_operator                            >tet_operator
                                  |                                          |
         1270        1280   |    1290         1300        1310        1320
TAG AGA ACG TAT GAA GAG TTT ACT CCC TAT CAG TGA TAG AGA ACG TAT GCA GAC TTT ACT

                                      >tet_operator
                                              |
         1330        1340        1350      |  1360        1370        1380
CCC TAT CAG TGA TAG AGA ACG TAT AAG GAG TTT ACT CCC TAT CAG TGA TAG AGA ACG TAT

     >tet_operator                                    >tet_operator
            |                                                |
         1390 |      1400        1410         1420        1430        1440
GAC CAG TTT ACT CCC TAT CAG TGA TAG AGA ACG TAT CTA CAG TTT ACT CCC TAT CAG TGA

                        >tet_operator
                                  |
         1450        1460   |    1470         1480        1490        1500
TAG AGA ACG TAT ATC CAG TTT ACT CCC TAT CAG TGA TAG AGA ACG TAT TAG CTT TAG GCG
TGT ACG GTG GGC GCC TAT AAA AGC AGA GCT CGT TTA GTG AAC CGT CAG ATC GCC TGG AGC
AAT TCC ACA ACA CTT TTG TCT TAT ACC AAC TTT CCG TAC CAC TTC CTA CCC TCG TAA AAG

         1630        1640        1650         1660        1670        1680
ATC AGA TCC ATC GAT TGG CCA CCA TGA GTT GGA GCT GTA TCA TCC TCT TCT TGG TAG CAA
                                 M   S   W   S   C   I   I   L   F   L   V   A>
                                _f___f___f___f___f___LEADER__f___f___f___f___f___>

         1690        1700        1710         1720        1730        1740
CAG CTA CAG GTA AGG GGT TAA CAG TAG CAG GCT TGA GGT CTG GAC ATA TAT ATG GGT GAC
T   A   T> (SEQ ID NO: 338)
____f___f__> ___g___g___g___g___g___g___g__INTRON____g___g___g___g___g___g___g___>
```

Figure 37 (continued)

```
                                                    >NcoI
                                                      |
            1750        1760        1770          |  1780        1790        1800
AAT GAC ATC CAC TTT GCC TTT CTC TCC ACA GGC GCC ATG GCC CAG GTC CAA CTG CAG GAG
                                         G   A   M   A > Q   V   Q   L   Q   E>
___g___g___g___g_INTRON____g___g___g___g_><___LEADER_h__><__i__D1.3VH__i___i___>
                                        (SEQ ID NO: 339)

            1810        1820        1830        1840        1850        1860
AGC GGT CCA GGT CTT GTG AGA CCT AGC CAG ACC CTG AGC CTG ACC TGC ACC GTG TCT GGC
 S   G   P   G   L   V   R   P   S   Q   T   L   S   L   T   C   T   V   S   G>
____i___i___i___i___i___i___i___i___D1.3 VH_i___i___i___i___i___i___i___i___i___>

            1870        1880        1890        1900        1910        1920
AGC ACC TTC AGC GGC TAT GGT GTA AAC TGG GTG AGA CAG CCA CCT GGA CGA GGT CTT GAG
 S   T   F   S   G   Y   G   V   N   W   V   R   Q   P   P   G   R   G   L   E>
____i___i___i___i___i___i___i___i___D1.3 VH_i___i___i___i___i___i___i___i___i___>

            1930        1940        1950        1960        1970        1980
TGG ATT GGA ATG ATT TGG GGT GAT GGA AAC ACA GAC TAT AAT TCA GCT CTC AAA TCC AGA
 W   I   G   M   I   W   G   D   G   N   T   D   Y   N   S   A   L   K   S   R>
____i___i___i___i___i___i___i___i___D1.3 VH_i___i___i___i___i___i___i___i___i___>

            1990        2000        2010        2020        2030        2040
GTG ACA ATG CTG GTA GAC ACC AGC AAG AAC CAG TTC AGC CTG AGA CTC AGC AGC GTG ACA
 V   T   M   L   V   D   T   S   K   N   Q   F   S   L   R   L   S   S   V   T>
____i___i___i___i___i___i___i___i___D1.3 VH_i___i___i___i___i___i___i___i___i___>

            2050        2060        2070        2080        2090        2100
GCC GCC GAC ACC GCG GTC TAT TAT TGT GCA AGA GAG AGA GAT TAT AGG CTT GAC TAC TGG
 A   A   D   T   A   V   Y   Y   C   A   R   E   R   D   Y   R   L   D   Y   W>
____i___i___i___i___i___i___i___i___D1.3 VH_i___i___i___i___i___i___i___i___i___>

            2110        2120        2130        2140        2150        2160
GGT CAA GGC AGC CTC GTC ACA GTC TCG AGT GCC TCC ACC AAG GGC CCT AGC GTC TTT CCT
 G   Q   G   S   L   V   T   V   S   S   A   S   T   K   G   P   S   V   F   P>
____i___i___i_D1.3 VH___i___i___i_><_j___j___j___j__IGG1 CH1-3___j___j___j___j___>
          (SEQ ID NO: 340)
            2170        2180        2190        2200        2210        2220
CTG GCC CCT TCC TCC AAG TCT ACC TCT GGC GGC ACC GCT GCT CTG GGC TGC CTG GTG AAG
 L   A   P   S   S   K   S   T   S   G   G   T   A   A   L   G   C   L   V   K>
____j___j___j___j___j___j___j___j__IGG1 CH1-3___j___j___j___j___j___j___j___j___>

            2230        2240        2250        2260        2270        2280
GAC TAC TTC CCT GAG CCT GTG ACC GTG TCC TGG AAC TCT GGC GCC CTG ACC TCC GGC GTG
 D   Y   F   P   E   P   V   T   V   S   W   N   S   G   A   L   T   S   G   V>
____j___j___j___j___j___j___j___j__IGG1 CH1-3___j___j___j___j___j___j___j___j___>

            2290        2300        2310        2320        2330        2340
CAT ACC TTC CCT GCC GTC CTC CAG TCC TCC GGC CTG TAC TCC CTG TCC TCC GTG GTG ACC
 H   T   F   P   A   V   L   Q   S   S   G   L   Y   S   L   S   S   V   V   T>
____j___j___j___j___j___j___j___j__IGG1 CH1-3___j___j___j___j___j___j___j___j___>

            2350        2360        2370        2380        2390        2400
GTG CCT TCC TCC TCT CTG GGC ACC CAG ACC TAC ATC TGC AAC GTG AAC CAC AAG CCT TCC
 V   P   S   S   S   L   G   T   Q   T   Y   I   C   N   V   N   H   K   P   S>
____j___j___j___j___j___j___j___j__IGG1 CH1-3___j___j___j___j___j___j___j___j___>

            2410        2420        2430        2440        2450        2460
AAC ACC AAG GTG GAC AAG AAG GTG GAG CCT AAG TCC TGC GAC AAG ACC CAC ACC TGC CCT
 N   T   K   V   D   K   K   V   E   P   K   S   C   D   K   T   H   T   C   P>
____j___j___j___j___j___j___j___j__IGG1 CH1-3___j___j___j___j___j___j___j___j___>
                                 E   P   K   S   C   D   K   T   H   T   C   P>
                                ____k___k___k___k____HINGE__k___k___k___k___k___>
```

Figure 37 (continued)

```
         2470        2480        2490         2500         2510        2520
CCA TGT CCT GCC CCT GAG CTG CTG GGC GGA CCC TCC GTG TTC CTG TTC CCT CCT AAG CCT
 P   C   P   A   P   E   L   L   G   G   P   S   V   F   L   F   P   P   K   P>
____j___j___j___j___j___j___j___j__IGG1 CH1-3___j___j___j___j___j___j___j___j___>
 P   C   P   A   P   E   L   L   G   G   P> (SEQ ID NO: 342)
____k___k___k___k__HINGE_____k___k___k___k____>

         2530        2540        2550         2560         2570        2580
AAG GAC ACC CTG ATG ATC TCC CGG ACC CCT GAA GTG ACC TGC GTG GTG GTG GAC GTG TCC
 K   D   T   L   M   I   S   R   T   P   E   V   T   C   V   V   V   D   V   S>
____j___j___j___j___j___j___j___j__IGG1 CH1-3___j___j___j___j___j___j___j___j___>

         2590        2600        2610         2620         2630        2640
CAC GAA GAT CCT GAA GTG AAG TTC AAT TGG TAC GTG GAC GGC GTG GAG GTG CAC AAC GCC
 H   E   D   P   E   V   K   F   N   W   Y   V   D   G   V   E   V   H   N   A>
____j___j___j___j___j___j___j___j__IGG1 CH1-3___j___j___j___j___j___j___j___j___>

         2650        2660        2670         2680         2690        2700
AAG ACC AAG CCT CGG GAG GAA CAG TAC AAC TCC ACC TAC CGG GTG GTG TCT GTG CTG ACC
 K   T   K   P   R   E   E   Q   Y   N   S   T   Y   R   V   V   S   V   L   T>
____j___j___j___j___j___j___j___j__IGG1 CH1-3___j___j___j___j___j___j___j___j___>

         2710        2720        2730         2740         2750        2760
GTG CTG CAC CAG GAC TGG CTG AAC GGC AAA GAA TAC AAG TGC AAG GTG TCC AAC AAG GCC
 V   L   H   Q   D   W   L   N   G   K   E   Y   K   C   K   V   S   N   K   A>
____j___j___j___j___j___j___j___j__IGG1 CH1-3___j___j___j___j___j___j___j___j___>

         2770        2780        2790         2800         2810        2820
CTG CCT GCC CCT ATC GAA AAG ACC ATC TCC AAG GCT AAG GGC CAG CCA CGG GAA CCT CAG
 L   P   A   P   I   E   K   T   I   S   K   A   K   G   Q   P   R   E   P   Q>
____j___j___j___j___j___j___j___j__IGG1 CH1-3___j___j___j___j___j___j___j___j___>

         2830        2840        2850         2860         2870        2880
GTC TAC ACA CTG CCT CCT AGC CGG GAC GAG CTG ACC AAG AAC CAG GTG TCC CTG ACC TGT
 V   Y   T   L   P   P   S   R   D   E   L   T   K   N   Q   V   S   L   T   C>
____j___j___j___j___j___j___j___j__IGG1 CH1-3___j___j___j___j___j___j___j___j___>

         2890        2900        2910         2920         2930        2940
CTG GTG AAG GGC TTC TAC CCT TCC GAT ATC GCC GTG GAG TGG GAG TCT AAC GGC CAG CCT
 L   V   K   G   F   Y   P   S   D   I   A   V   E   W   E   S   N   G   Q   P>
____j___j___j___j___j___j___j___j__IGG1 CH1-3___j___j___j___j___j___j___j___j___>

         2950        2960        2970         2980         2990        3000
GAG AAC AAC TAC AAG ACC ACC CCT CCT GTG CTG GAC TCC GAC GGC TCC TTC TTC CTG TAC
 E   N   N   Y   K   T   T   P   P   V   L   D   S   D   G   S   F   F   L   Y>
____j___j___j___j___j___j___j___j__IGG1 CH1-3___j___j___j___j___j___j___j___j___>

         3010        3020        3030         3040         3050        3060
TCC AAG CTG ACC GTG GAC AAG TCC CGG TGG CAG CAG GGC AAC GTG TTC TCC TGC TCC GTG
 S   K   L   T   V   D   K   S   R   W   Q   Q   G   N   V   F   S   C   S   V>
____j___j___j___j___j___j___j___j__IGG1 CH1-3___j___j___j___j___j___j___j___j___>

         3070        3080        3090         3100         3110        3120
ATG CAC GAG GCC CTG CAC AAC CAC TAC ACC CAG AAG TCC CTG TCC CTG TCT CCT GGC AAG
 M   H   E   A   L   H   N   H   Y   T   Q   K   S   L   S   L   S   P   G   K> (SEQ ID NO: 341)
____j___j___j___j___j___j___j___j__IGG1 CH1-3___j___j___j___j___j___j___j___j___>

         3130        3140        3150         3160         3170        3180
GAA CAA AAA CTC ATC TCA GAA GAG GAT CTG AAT GCT GTG GGC CAG GAC ACG CAG GAG GTC
 E   Q   K   L   I   S   E   E   D   L> <N   A   V   G   Q   D   T   Q   E   V>
____l___l___l MYC-EPITOPE___l___l___l____><____m___m___m____PDGFR TM_____m___m___m____>
      (SEQ ID NO: 343)
         3190        3200        3210         3220         3230        3240
ATC GTG GTG CCA CAC TCC TTG CCC TTT AAG GTG GTG GTG ATC TCA GCC ATC CTG GCC CTG
 I   V   V   P   H   S   L   P   F   K   V   V   V   I   S   A   I   L   A   L>
____m___m___m___m___m___m___m___m____PDGFR TM_____m___m___m___m___m___m___m___m___>
```

Figure 37 (continued)

```
          3250           3260           3270           3280           3290           3300
GTG GTG CTC ACC ATC ATC TCC CTT ATC ATC CTC ATC ATG CTT TGG CAG AAG AAG CCA CGT
 V   V   L   T   I   I   S   L   I   I   L   I   M   L   W   Q   K   K   P   R> (SEQ ID NO: 344)
___m___m___m___m___m___m___m___m___PDGFR TM___m___m___m___m___m___m___m___m___>

                                         >pre_polyA
                                              |
          3310           3320           3330  |        3340           3350           3360
TAG TAA AAG CTT GTC ACT TGG AAA GTA ATA GTT TTT CCT GCA CGG GTA GTA ATC AGC CTC
 *   *>
___m___>

          3370           3380           3390           3400           3410           3420
GAC TGT GCC TTC TAG TTG CCA GCC ATC TGT TGT TTG CCC CTC CCC CGT GCC TTC CTT GAC
CCT GGA AGG TGC CAC TCC CAC TGT CCT TTC CTA ATA AAA TGA GGA AAT TGC ATC GCA TTG
TCT GAG TAG GTG TCA TTC TAT TCT GGG GGG TGG GGT GGG GCA GGA CAG CAA GGG GGA GGA

                                     <BGH_polyA
                                           |
          3550           3560           3570           3580           3590           3600
TTG GGA AGA CAA TAG CAG GCA TGC TGG GGA TGG CCC GGG CAT GAT AAC TTC GTA TAA TGT

                    >Human\EF1a\Promoter
                               |
          3610           3620|          3630           3640           3650           3660
ATG CTA TAC GAA GTT ATG TAG AGT AAT TCA TAC AAA AGG ACT CGC CCC TGC CTT GGG GAA
TCC CAG GGA CCG TCG TTA AAC TCC CAC TAA CGT AGA ACC CAG AGA TCG CTG CGT TCC CGC
CCC CTC ACC CGC CCG CTC TCG TCA TCA CTG AGG TGG AGA AGA GCA TGC GTG AGG CTC CGG
TGC CCG TCA GTG GGC AGA GCG CAC ATC GCC CAC AGT CCC CGA GAA GTT GGG GGG AGG GGT
CGG CAA TTG AAC CGG TGC CTA GAG AAG GTG GCG CGG GGT AAA CTG GGA AAG TGA TGT CGT
GTA CTG GCT CCG CCT TTT TCC CGA GGG TGG GGG AGA ACC GTA TAT AAG TGC AGT AGT CGC
CGT GAA CGT TCT TTT TCG CAA CGG GTT TGC CGC CAG AAC ACA GGT AAG TGC CGT GTG TGG
TTC CCG CGG GCC TGG CCT CTT TAC GGG TTA TGG CCC TTG CGT GCC TTG AAT TAC TTC CAC
GCC CCT GGC TGC AGT ACG TGA TTC TTG ATC CCG AGC TTC GGG TTG GAA GTG GGT GGG AGA
GTT CGA GGC CTT GCG CTT AAG GAG CCC CTT CGC CTC GTG CTT GAG TTG AGG CCT GGC TTG
GGC GCT GGG GCC GCC GCG TGC GAA TCT GGT GGC ACC TTC GCG CCT GTC TCG CTG CTT TCG
ATA AGT CTC TAG CCA TTT AAA ATT TTT GAT GAC CTG CTG CGA CGC TTT TTT TCT GGC AAG
ATA GTC TTG TAA ATG CGG GCC ATG ATC TGC ACA CTG GTA TTT CGG TTT TTG GGG CCG CGG
GCG GCG ACG GGG CCC GTG CGT CCC AGC GCA CAT GTT CGG CGA GGC GGG GCC TGC GAG CGC
GGC CAC CGA GAA TCG GAC GGG GGT AGT CTC AAG CTG GCC GGC CTG CTC TGG TGC CTG GCC
TCG CGC CGC CGT GTA TCG CCC CGC CCT GGG CGG CAA GGC TGG CCC GGT CGG CAC CAG TTG
CGT GAG CGG AAA GAT GGC CGC TTC CCG GCC CTG CTG CAG GGA GCT CAA AAT GGA GGA CGC
GGC GCT CGG GAG AGC GGG CGG GTG AGT CAC CCA CAC AAA GGA AAA GGG CCT TTC CGT CCT
CAG CCG TCG CTT CAT GTG ACT CCA CGG AGT ACC GGG CGC CGT CCA GGC ACC TCG ATT AGT
TCA CGA GCT TTT GGA GTA CGT CGT CTT TAG GTT GGG GGG AGG GGT TTT ATG CGA TGG AGT
TTC CCC ACA CTG AGT GGG TGG AGA CTG AAG TTA GGC CAG CTT GGC ACT TGA TGT AAT TCT
CCT TGG AAT TTG CCC TTT TTG AGT TTG GAT CTT GGT TCA TTC TCA AGC CTC AGA CAG TGG
TTC AAA GTT TTT TTC TTC CAT TTC AGG TGT CGT GAG AGC TCG TTT AGT GAA CCG TCA GAT
CGC CTG GAG ACG CCA TCC ACG CTG TTT TGA CCT CCA TAG AAG ACA CCG GGA CCG ATC CAG

          5050           5060           5070           5080           5090           5100
CCT CCG CGG CCC CGA ATT CAC CAT GTC TAG ACT GGA CAA GAG CAA AGT CAT AAA CTC TGC
                             M   S   R   L   D   K   S   K   V   I   N   S   A>
                            ___n___n___n___n___n_TET-ON\3G_n___n___n___n___n___>

          5110           5120           5130           5140           5150           5160
TCT GGA ATT ACT CAA TGG AGT CGG TAT CGA AGG CCT GAC GAC AAG GAA ACT CGC TCA AAA
  L   E   L   L   N   G   V   G   I   E   G   L   T   T   R   K   L   A   Q   K>
___n___n___n___n___n___n___n___n__TET-ON\3G___n___n___n___n___n___n___n___n___>

          5170           5180           5190           5200           5210           5220
GCT GGG AGT TGA GCA GCC TAC CCT GTA CTG GCA CGT GAA GAA CAA GCG GGC CCT GCT CGA
  L   G   V   E   Q   P   T   L   Y   W   H   V   K   N   K   R   A   L   L   D>
___n___n___n___n___n___n___n___n__TET-ON\3G___n___n___n___n___n___n___n___n___>
```

Figure 37 (continued)

```
         5230        5240        5250        5260        5270        5280
TGC CCT GCC AAT CGA GAT GCT GGA CAG GCA TCA TAC CCA CTC CTG CCC CCT GGA AGG CGA
  A   L   P   I   E   M   L   D   R   H   H   T   H   S   C   P   L   E   G   E>
___n___n___n___n___n___n___n___n___TET-ON\3G___n___n___n___n___n___n___n___n___>

         5290        5300        5310        5320        5330        5340
GTC ATG GCA AGA CTT TCT GCG GAA CAA CGC CAA GTC ATA CCG CTG TGC TCT CCT CTC ACA
  S   W   Q   D   F   L   R   N   N   A   K   S   Y   R   C   A   L   L   S   H>
___n___n___n___n___n___n___n___n___TET-ON\3G___n___n___n___n___n___n___n___n___>

         5350        5360        5370        5380        5390        5400
TCG CGA CGG GGC TAA AGT GCA TCT CGG CAC CCG CCC AAC AGA GAA ACA GTA CGA AAC CCT
  R   D   G   A   K   V   H   L   G   T   R   P   T   E   K   Q   Y   E   T   L>
___n___n___n___n___n___n___n___n___TET-ON\3G___n___n___n___n___n___n___n___n___>

         5410        5420        5430        5440        5450        5460
GGA AAA TCA GCT CGC GTT CCT GTG TCA GCA AGG CTT CTC CCT GGA GAA CGC ACT GTA CGC
  E   N   Q   L   A   F   L   C   Q   Q   G   F   S   L   E   N   A   L   Y   A>
___n___n___n___n___n___n___n___n___TET-ON\3G___n___n___n___n___n___n___n___n___>

         5470        5480        5490        5500        5510        5520
TCT GTC CGC CGT GGG CCA CTT TAC ACT GGG CTG CGT ATT GGA GGA ACA GGA GCA TCA AGT
  L   S   A   V   G   H   F   T   L   G   C   V   L   E   E   Q   E   H   Q   V>
___n___n___n___n___n___n___n___n___TET-ON\3G___n___n___n___n___n___n___n___n___>

         5530        5540        5550        5560        5570        5580
AGC AAA AGA GGA AAG AGA GAC ACC TAC CAC CGA TTC TAT GCC CCC ACT TCT GAA ACA AGC
  A   K   E   E   R   E   T   P   T   T   D   S   M   P   P   L   L   K   Q   A>
___n___n___n___n___n___n___n___n___TET-ON\3G___n___n___n___n___n___n___n___n___>

         5590        5600        5610        5620        5630        5640
AAT TGA GCT GTT CGA CCG GCA GGG AGC CGA ACC TGC CTT CCT TTT CGG CCT GGA ACT AAT
  I   E   L   F   D   R   Q   G   A   E   P   A   F   L   F   G   L   E   L   I>
___n___n___n___n___n___n___n___n___TET-ON\3G___n___n___n___n___n___n___n___n___>

         5650        5660        5670        5680        5690        5700
CAT ATG TGG CCT GGA GAA ACA GCT AAA GTG CGA AAG CGG CGG GCC GAC CGA CGC CCT TGA
  I   C   G   L   E   K   Q   L   K   C   E   S   G   G   P   T   D   A   L   D>
___n___n___n___n___n___n___n___n___TET-ON\3G___n___n___n___n___n___n___n___n___>

         5710        5720        5730        5740        5750        5760
CGA TTT TGA CTT AGA CAT GCT CCC AGC CGA TGC CCT TGA CGA CTT TGA CCT TGA TAT GCT
  D   F   D   L   D   M   L   P   A   D   A   L   D   D   F   D   L   D   M   L>
___n___n___n___n___n___n___n___n___TET-ON\3G___n___n___n___n___n___n___n___n___>

         5770        5780        5790        5800        5810        5820
GCC TGC TGA CGC TCT TGA CGA TTT TGA CCT TGA CAT GCT CCC CGG GTA ACT AAG TAA GGA
  P   A   D   A   L   D   D   F   D   L   D   M   L   P   G   *> (SEQ ID NO: 345)
___n___n___n___n___n___n___TET-ON\3G___n___n___n___n___n___n___n_>

     >SV40\polyA\signal
              |
         5830 |      5840        5850        5860        5870        5880
TCC AGA CAT GAT AAG ATA CAT TGA TGA GTT TGG ACA AAC CAC AAC TAG AAT GCA GTG AAA
AAA ATG CTT TAT TTG TGA AAT TTG TGA TGC TAT TGC TTT ATT TGT AAC CAT TAT AAG CTG
CAA TAA ACA AGT TAA CAA CAA CAA TTG CAT TCA TTT TAT GTT TCA GGT TCA GGG GGA GGT
GTG GGA GGT TTT TTA AAG CAA GTA AAA CCT CTA CAA ATG TGG TAT GGC TGA TTA TGA TCC
TGC AAG CCT CGT CGT CCT GGC CGG ACC ACG CTA TCT GTG CAA GGT CCC CGG CCC CGG ACG
CGC GCT CCA TGA GCA GAG CGC CCG CCG CCG AGG CGA AGA CTC GGG CGG CGC CCT GCC CGT
CCC ACC AGG TCA ACA GGC GGT AAC CGG CCT CTT CAT CGG GAA TGC GCG CGA CCT TCA GCA

                                          BstZ17I
         6250        6260        6270      |6280
TCG CCG GCA TGT CCC CCT GGC GGA CGG GAA GTA TGT ATA C (SEQ ID NO: 333)
```

Figure 37 (continued)

```
                                                              CRISPR2
                                                           ____________
                1410        1420        1430        1440        1450
Human   CAGGGCCGGT  TAATGTGGCT  CTGGTTCTGG  GTACTTTTAT  CTGTCCCCTC   (SEQ ID NO: 346)
CHO     CGGGATC--C  TTCTG-----  --GATTCGGG  ATGCTTTTAT  CT--CCCCGT   (SEQ ID NO: 347)
        * **  *     *  **          * *** **  * *******  **   ****
                                                                 __

                  CRISPR1
         _____________________
        CRISPR2
        __________
               1460        1470        1480        1490        1500
Human   CACCCCACAG  -TGGGGCCAC  TAGGGACAGG  ATTGGTGAC  AGAAAAGCCCC   (SEQ ID NO: 346)
CHO     CATCCAAAAG  CTGGCATTGT  CAGGGACAAG  ATTAGTCAC  AGCAGAGCCCC   (SEQ ID NO: 347)
        ** ** * **   ***          ******* *  *** ** **  ** * ******
        ________________
            CRISPR3
```

Figure 46

```
Sequence: pINT17-BSD-CHO-D1.3 Range: 1 to 960 and 6321 to 7360

>CHO-AAVS-left_arm
         |
     >3199    >Ex-DraIII
         |         |
        10        20        30        40        50        60        70        80
GCGATCGCGA TGGCTTACAT CCCGTGCCTT TCCAGGCTGG TGGCTGCCCT GGCTGTGCCG CAGGCTTCCA GGGCCCAGCT

                                >3197     >Ex-NheI    <3200
                                    |         |         |
        90       100       110      |  120    |  130    | 140       150       160
CTGACTTGAC GCCCCCCCCC CAATCCCCCA CTCCCTCCTC TGAGTCTAGC CAGGCCCAGG CCCTTCAGTG TCACTTCTTT
TGGGGGGTCC ACCTTGTTCC CTACCCCACT TCCTGTGACC CGTGCTGTCC GCTGTGGCCT CAGGAGGGTC CTTTGCCCCT
CCAAGGCAGT GTACCCCTTT GTTCCCCTGG AGAAGAGGCG CTCCACCGTC TGTTGGGCCC CATCCCATAA CCTTCCTCCC
CTCCCCATGT CCTATTAATT CAATTCTCGG CTCATCCCCT TTTGGTGATC TTGCCACCCA CCCCCACCCC CCATAGGTTT
CTCCTCAACT CTCTCTCTCT CTCTCTCTCT CTCTCTCTCT CTCTCTCTCT CTCTCTCTCT CTGTCTCTCT CTCTCTGTGT
CCACATTGAT TTGCCTTTCT GGAAACTTCT AAGCATTCGG TCTTCCAAGC CCTATTTCTC TCTCCTCTGG TTTTGTTTTT
GTTGTTGTTT TTTGTTTTTT CCCCTGTGTA GCCCAGGCCA ACCTCAAATA CAGGTCCTGT GTCTCTGACC CCCTCATTTG

                >3195        >Ex-NcoI       <3198
                    |            |              |
       650       660 |      670   |  680       690       700       710       720
TGGGATTACA GGCATGCCCA CTCCACCTAC CACCTCATGG ACTATATTTG GGCAGCATCC TGCTTTAAAA ACTATGCCCT
GTCTCTTAGA TTTCCACCCT GTCACCTTCT AGAACCTACC CCACCAGGAC CCTGGGCGAC TCAGACACTG TGATTATCTT

                                                                        >AAVS-TALE-left
                                                                                 |
       810       820       830       840       850       860       870       880
TTTCCAGTGA TCTGTGCCCC GAGAGTGAGG ACCATCTTGT ATTGCCGGGA TCCTTCTGGA TTCGGGATGC TTTTATCTCC

                <3196
                    |
         >AAVS-Left_end    >branch_site           >Splice_acceptor
                  | |            |                      |
       890       900 |      910   |   920       930      | 940       950       960
CCGTCATCCA AAAGCTGGCA TAAGATGCAT CTTCTGACCT CTTCTCTTCC TCCCACAGGG CATGGCAAAA CCTCTGAGCC (SEQ ID NO: 348)
                                                                    M  A  K   P  L  S>  (SEQ ID NO: 349)
                                                                  ____BLASTICIDIN_____>
                                 _b_________SYN INTRON__b__________>


                                                           >3201
                                                               |
                                                               |
   >loxP                                            >CHO-AAVS-right_arm
      |                                                        |
      6330      6340      6350      6360      6370      |6380      6390      6400
GGGCATGATA ACTTCGTATA ATGTATGCTA TACGAAGTTA TGTATACGGC GCGCCTGTCA GGGACAAGAT TAGTCACAGC
AGAGCCCCCA TCCCCGTTCT TCTTCCTCCT GGCCACAGTG TTGGTTCACT TTCAGTCTTT CATGGCAACT TCCATCTCCT
GGGTTGTCGT CCTCTTGCTA GGATGCTCGT GGAGGTGGGG AATAAAGGTT CAGTGTTTCA CTCATCCAGG CAGAGGAAAA
ACAGAATCCG TCTGTCCTGG GCTGGGCTGT CTTTTAGACA GAGTGCTTGC CTAGAGTGCA GGAAGCCTCA GGTTCCAACC
CCAATACCAC AGAAATCAGG TGCTTGGAAA GTAGAGGCAG GAGGGTTGGA ATTCAGTGTC ACCTTCATCT ACACAGTGAC
TTTGAGGCCA TCTTGATAGC CCACATGAGA CCCAGTTGCA AAATCTTGAC CAAACAAAAA AAGTCCGTGC TGACTTTTTG
TGTCAGTCTG CTTCTTGTGT CTTGTATCTT GAGTGTCTTT TCTCGGTGCG CCTTAGTTTT TTTACCTGTA GAATGGGACC
AGTGGTCACC CCTGTCCCCA GAGGGACTCT ATGGTGAGAG GCGTCCTGTG GAAAACTTCC TTTATGGGGC CGGCGTGAGC
TGTGTGGGAC ATCGTCCTCT ATATATAGCA GGGTCCTGTT TTCCCGAGGC CACACTCAGG GTGTCAGCGT CTTTGACCAG

              >3203     >Ex-BclI       <3202
                  |         |              |
      7050      7060      7070      7080   |  7090      7100      7110      7120
TCCAGGAGAT CAGCTCAGGC TGCTCACATT ATCACCAAAG TCCCTGGCCC TCCCAAGAGT TCCCTCCCAA CTGCATCCCC
TTCCTCTGCA TCTGCTGGAG GTCCCTAGAG CATCCTCTCT GACAGGAACC TGTGACCTCA GGCCTGACGT GTCAGCCTTC

                                                                          >Sbf1
                                                                              |
      7210      7220      7230      7240      7250      7260      7270    |   7280
CAGGTGGGAC TCTCCTCCCG CCATGCAGAC ACCTTGGTGA CCTGACTCTT CAGGCCTTTG CAGGAGCCTG CAGGCGATCT

            >3'_beta_globin_insulator
                        |
      7290      7300      |7310      7320      7330      7340      7350      7360
CTCGATCTCT CGATTTCGAT CAAGACATTC CTTTAATGGT CTTTTCTGGA CACCACTAGG GGTCAGAAGT AGTTCATCAA (SEQ ID NO: 350)
```

Figure 47 i

```
                                 E   V   Q   L   V   Q   S   G   A   E   V
GCCTTTCTCTCCACA GGCGCCATGGCC GAA GTG CAG CTG GTG CAG TCT GGA GCT GAG GTG
                   NcoI
                                                                 CDR1
K   R   P   G   A   S   V   T   V   S   C   K   A   S   G   Y   T   F   T   N
AAG AGG CCT GGG GCC TCA GTG ACA GTT TCC TGC AAG GCT TCC GGT TAC ACC TTT ACC AAC

H   G   I   S   W   V   R   Q   A   P   G   Q   G   L   E   W   M   G   W   N
CAC GGT ATC AGC TGG GTG CGA CAG GCC CCT GGA CAA GGC CTT GAG TGG ATG GGA TGG AAC

      CDR2
S   P   Y   N   G   N   T   N   Y   A   Q   R   F   Q   G   R   V   T   M   T
AGC CCT TAC AAT GGA AAC ACA AAC TAT GCA CAG AGG TTC CAG GGC AGA GTC ACC ATG ACC

T   D   T   S   T   N   T   A   Y   M   E   L   R   T   L   T   S   D   D   T
ACA GAC ACA TCC ACG AAC ACA GCC TAC ATG GAG CTG AGG ACC CTG ACA TCT GAC GAC ACG

                                          CDR3
A   M   Y   Y   C   A   R   D   R   D   Y   Y   D   A   G   S   Y   W   G   Q
GCC ATG TAT TAC TGT GCC AGA GAT AGG GAT TAC TAT GAT GCG GGG AGC TAC TGG GGC CAG

G   T   L   V   T   V   S   S   a   s   t   k   g   p   s   v     (SEQ ID NO: 352)
GGA ACC CTG GTC ACC GTC TCG AGT GCC AGC ACC AAG GGC CCC AGC GTG   (SEQ ID NO: 351)
                          XhoI        ----------CH1---------->
```

ii

```
     A   S   S   Y   E   L   T   Q   P   P   S   V   S   V   S   P   G   Q
     GCT AGC TCC TAT GAG CTG ACT CAG CCA CCC TCG GTG TCA GTA TCC CCA GGA CAG
       NheI
                                              CDR1
T   A   R   I   T   C   S   G   D   S   L   P   K   Q   Y   A   Y   W   Y   Q
ACG GCC AGG ATC ACC TGC TCT GGA GAT TCA TTG CCA AAG CAA TAT GCT TAT TGG TAC CAG

                                                          CDR2
Q   K   P   G   Q   A   P   V   L   V   I   Y   K   D   S   E   R   P   S   G
CAA AAG CCA GGC CAG GCC CCT GTA TTA GTG ATA TAT AAA GAC AGC GAG AGG CCC TCA GGG

I   P   E   R   F   S   G   S   G   S   G   T   T   V   T   L   T   I   S   G
ATC CCT GAG CGA TTC TCT GGC TCC GGC TCA GGG ACA ACA GTC ACA TTG ACC ATC AGT GGA

                                                          CDR3
V   Q   A   E   D   E   A   D   Y   Y   C   Q   S   A   D   S   D   N   A   F
GTC CAG GCA GAA GAC GAG GCT GAC TAT TAT TGT CAA TCA GCA GAC AGT GAT AAT GCT TTT

V   F   G   R   G   T   K   L   T   V   L   G   Q   P   A   A   A
GTC TTT GGA AGA GGG ACC AAG CTG ACC GTC CTA GGT CAG CCC GCG GCC GCT   (SEQ ID NO: 353)
```

Figure 50a

Sequence: pINT17-Bi-CMV-Emicizumab: 1514 to 8904

```
BglII   >BGH_polyA
   |       |  10          20          30          40          50          60
 GAG ATC TTC CCC AGC ATG CCT GCT ATT GTC TTC CCA ATC CTC CCC CTT GCT GTC CTG CCC
 CAC CCC ACC CCC CAG AAT AGA ATG ACA CCT ACT CAG ACA ATG CGA TGC AAT TTC CTC ATT
 TTA TTA GGA AAG GAC AGT GGG AGT GGC ACC TTC CAG GGT CAA GGA AGG CAC GGG GGA GGG

                                                 <BGH_polyA
                                                      |
         190         200         210         220 |        230         240
 GCA AAC AAC AGA TGG CTG GCA ACT AGA AGG CAC AGT CGA GGC TCT AGA TTA TTA ACA TTC
                                                                 <*   C   E
                                                                <___b___b___

         250         260         270         280         290         300
 GCC CCG GTT GAA GCT CTT GGT CAC AGG GCT AGA AAG GCC CTG GTG GGT CAC TTC GCA GGC
 <G   R   N   F   S   K   T   V   P   S   S   L   G   Q   H   T   V   E   C   A
<___b___b___b___b___b___b___b___b___b__CL___b___b___b___b___b___b___b___b___b___

         310         320         330         340         350         360
 GTA CAC TTT GTG CTT CTC GTA GTC GGC CTT GCT CAG GGT CAG TGT GCT GCT CAG GCT GTA
 <Y   V   K   H   K   E   Y   D   A   K   S   L   T   L   T   S   S   L   S   Y
<___b___b___b___b___b___b___b___b___b__CL___b___b___b___b___b___b___b___b___b___

         370         380         390         400         410         420
 GGT AGA GTC CTT GCT GTC CTG CTC GGT CAC GCT CTC TTG GCT ATT GCC GCT CTG GAG GGC
 <T   S   D   K   S   D   Q   E   T   V   S   E   Q   S   N   G   S   Q   L   A
<___b___b___b___b___b___b___b___b___b__CL___b___b___b___b___b___b___b___b___b___

         430         440         450         460         470         480
 GTT GTC CAC CTT CCA CTG CAC CTT GGC TTC TCT GGG GTA GAA GTT GTT CAG CAG GCA CAC
 <N   D   V   K   W   Q   V   K   A   E   R   P   Y   F   N   N   L   L   C   V
<___b___b___b___b___b___b___b___b___b__CL___b___b___b___b___b___b___b___b___b___

         490         500         510         520         530         540
 GAC AGA GGC TGT GCC AGA CTT CAG CTG CTC GTC GCT AGG TGG AAA GAT GAA CAC GCT AGG
 <V   S   A   T   G   S   K   L   Q   E   D   S   P   P   F   I   F   V   S   P (SEQ ID NO: 355)
<___b___b___b___b___b___b___b___b___b__CL___b___b___b___b___b___b___b___b___b___

         550         560         570         580         590         600
 GGC GGC CGC TGT CCG CTT GAT TTC CAC CTT GGT GCC TCC GCC AAA TGT CAG TGG AGG GTC
 <A   A   A   T   R   K   I   E   V   K   T   G   G   G   F   T   L   P   P   D
<___b___<___c___c___c___c___c___c___c___c__VL___c___c___c___c___c___c___c___c___

         610         620         630         640         650         660
 GCT GTA CTG CTG GCA GTA GTA GGT GGC GAT ATC CTC AGG CTG GAG GCT GGA TAT TGT CAG
 <S   Y   Q   Q   C   Y   Y   T   A   I   D   E   P   Q   L   S   S   I   T   L
<___c___c___c___c___c___c___c___c___c__VL___c___c___c___c___c___c___c___c___c___

         670         680         690         700         710         720
 GGT GAA GTC GGT GCC GTA TCT GCT GCC GCT GAA TCT ATC GGG CAC GCC GCT TTC TTT TCT
 <T   F   D   T   G   Y   R   S   G   S   F   R   D   P   V   G   S   E   K   R
<___c___c___c___c___c___c___c___c___c__VL___c___c___c___c___c___c___c___c___c___

         730         740         750         760         770         780
 GCT GGC CTG ATA GAT CAG CAG CTC AGG AGC CTG TCC AGG CTT CTG CTG ATA CCA GGC CAG
 <S   A   Q   Y   I   L   L   E   P   A   Q   G   P   K   Q   Q   Y   W   A   L
<___c___c___c___c___c___c___c___c___c__VL___c___c___c___c___c___c___c___c___c___

         790         800         810         820         830         840
 CTG TCT CTC GAT GTT CCG GCT GGC CTT GCA TGT GAT GGT CAC TCT GTC TCC CAC GCT GGC
 <Q   R   E   I   N   R   S   A   K   C   T   I   T   V   R   D   G   V   S   A
<___c___c___c___c___c___c___c___c___c__VL___c___c___c___c___c___c___c___c___c___
```

Figure 51

```
                                                     >RG         <splice_acceptor
                                                     |                   |
          850         860         870         | 880         890         900
AGA CAG GCT GCT AGG GCT CTG TGT CAT CTG GAT GTC TCC TCT GCT AGC TGA AAA TAT ACA
<S   L   S   S   P   S   Q   T   M   Q   I   D   G   R  (SEQ ID NO: 356)
<___c___c___c___c___c__VL___c___c___c___c___c___

          910         920         930         940         950         960
GCA AAC ATC AGT ACA ACA TAA ATA TCT GTG TAT GAA AAT CAC CTT TAA TCT TGC TAG ACA
TGA AGA AAG AAT ATG CAA TAC ATT TTT AAA ATT AGG ATT TTA AAA TCA AGC CAA AAA TCA
CCT ATT GCA GAG TCC CCA ATG AAA GAA ATT ACA GAT TGA AAG AAT ATC TCC GCC TAG GTT


                <intron
         1090       | 1100        1110        1120        1130        1140
TGT GGA AAT ATT CTC ACC TGG AAC CCA GAG CAG CAG AAA CCC AAT GAG TTG TGA TGG CAA
                        <P   V   W   L   L   L   F   G   I   L   Q   S   P   L
                        <____g____g____g____g____g____LEADER I_____g____g____g____g____g____

                                                                    <TATA_box
                                                                         |
         1150        1160|        1170        1180        1190        |1200
CAT GGT GGC CAC TCC GGA TCT GAT CTG ACG GTT CAC TAA ACC AGC TCT GCT TAT ATA GAC
<M  (SEQ ID NO: 357)

      <minimal_CMV_promoter_from_M60321      >CMV_promoter
                                        |      |
         1210        1220        1230        |1240        1250        1260
CTC CCA CCG TAC ACG CCT ACC GCC CAT TTG GGA TCT AGT AAT CAA TTA CGG GGT CAT TAG
TTC ATA GCC CAT ATA TGG AGT TCC GCG TTA CAT AAC TTA CGG TAA ATG GCC CGC CTG GCT
GAC CGC CCA ACG ACC CCC GCC CAT TGA CGT CAA TAA TGA CGT ATG TTC CCA TAG TAA CGC
CAA TAG GGA CTT TCC ATT GAC GTC AAT GGG TGG AGT ATT TAC GGT AAA CTG CCC ACT TGG
CAG TAC ATC AAG TGT ATC ATA TGC CAA GTA CGC CCC CTA TTG ACG TCA ATG ACG GTA AAT
GGC CCG CCT GGC ATT ATG CCC AGT ACA TGA CCT TAT GGG ACT TTC CTA CTT GGC AGT ACA
TCT ACG TAT TAG TCA TCG CTA TTA CCA TGC TGA TGC GGT TTT GGC AGT ACA TCA ATG GGC
GTG GAT AGC GGT TTG ACT CAC GGG GAT TTC CAA GTC TCC ACC CCA TTG ACG TCA ATG GGA
GTT TGT TTT GGC ACC AAA ATC AAC GGG ACT TTC CAA AAT GTC GTA ACA ACT CCG CCC CAT

                                                  >TATA_box
                                                      |
         1750        1760        1770        1780        1790        1800
TGA CGC AAA TGG GCG GTA GGC GTG TAC GGT GGG AGG TCT ATA TAA GCA GAG CTG GTT TAG

                          >Cla1
                            |
         1810        1820|        1830        1840        1850        1860
TGA ACC GTC AGA TCA GAT CCA TCG ATT GGC CAC CAT GAG TTG GAG CTG TAT CAT CCT CTT
                                                M   S   W   S   C   I   I   L   F>
                                              __h___h___h__LEADER___h___h___h___>

                           >intron
         1870        1880   |     1890        1900        1910        1920
CTT GGT AGC AAC AGC TAC AGG TAA GGG GTT AAC AGT AGC AGG CTT GAG GTC TGG ACA TAT
 L   V   A   T   A   T> (SEQ ID NO: 358)
___h___h_LEADER_____h___h_>


                                                             >Nco1
                                                               |
         1930        1940        1950        1960        | 1970        1980
ATA TGG GTG ACA ATG ACA TCC ACT TTG CCT TTC TCT CCA CAG GCG CCA TGG CCC AGG TGC
                                                                        Q   V>
                                                                      _i___i___>
```

Figure 51 (continued)

```
          1990          2000          2010          2020          2030          2040
AGC TGG TTG AAT CTG GCG GAG GAC TGG TTC AGC CTG GCG GAT CTC TGA GAC TGT CTT GTG
Q   L   V   E   S   G   G   G   L   V   Q   P   G   G   S   L   R   L   S   C>
____i____i____i____i____i____i____i_____VH1-ANTI-FIXA__i____i____i____i____i____i____i____i____>

          2050          2060          2070          2080          2090          2100
CCG CCA GCG GCT TCA CCT TCA GCT ACT ACG ATA TCC AGT GGG TCC GAC AGG CCC CTG GCA
A   A   S   G   F   T   F   S   Y   Y   D   I   Q   W   V   R   Q   A   P   G>
____i____i____i____i____i____i____i_____VH1-ANTI-FIXA__i____i____i____i____i____i____i____i____>

          2110          2120          2130          2140          2150          2160
AAG GAC TTG AAT GGG TGT CCA GCA TCA GCC CCT CTG GCC AGT CCA CCT ACT ACC GGC GAG
K   G   L   E   W   V   S   S   I   S   P   S   G   Q   S   T   Y   Y   R   R>
____i____i____i____i____i____i____i_____VH1-ANTI-FIXA__i____i____i____i____i____i____i____i____>

          2170          2180          2190          2200          2210        | 2220
AAG TGA AGG GCA GAT TCA CCA TCA GCC GGG ACA ACA GCA AGA ACA CCC TGT ACC TGC AGA
E   V   K   G   R   F   T   I   S   R   D   N   S   K   N   T   L   Y   L   Q>
____i____i____i____i____i____i____i_____VH1-ANTI-FIXA__i____i____i____i____i____i____i____i____>

          2230          2240          2250          2260          2270          2280
TGA ACA GCC TGA GAG CCG AGG ACA CCG CCG TGT ACT ACT GCG CCA GAA GAA CCG GCA GAG
M   N   S   L   R   A   E   D   T   A   V   Y   Y   C   A   R   R   T   G   R>
____i____i____i____i____i____i____i_____VH1-ANTI-FIXA__i____i____i____i____i____i____i____i____>

          2290          2300          2310          2320          2330          2340
AGT ACG GCG GAG GCT GGT ACT TTG ATT ACT GGG GCC AGG GCA CCC TGG TCA CAG TCT CGA
E   Y   G   G   G   W   Y   F   D   Y   W   G   Q   G   T   L   V   T   V   S> (SEQ ID NO: 359)
____i____i____i____i____i____i____i_____VH1-ANTI-FIXA__i____i____i____i____i____i____i____i__>
                                                                                         _>

          2350          2360          2370          2380          2390          2400
GCG CCT CTA CAA AGG GCC CCA GCG TTT TCC CAC TGG CTC CCT GTA GCA GAA GCA CCA GCG
S   A   S   T   K   G   P   S   V   F   P   L   A   P   C   S   R   S   T   S>
_____j_____j_____j_____j_____j_____j_____CH1-3_HEAVY1-IGG2-KNOBS_j_____j_____j_____j_____j_____j_____j_____>

          2410          2420          2430          2440          2450          2460
AAT CTA CAG CCG CTC TGG GCT GCC TGG TCA AGG ACT ACT TTC CTG AGC CTG TGA CCG TGT
E   S   T   A   A   L   G   C   L   V   K   D   Y   F   P   E   P   V   T   V>
_____j_____j_____j_____j_____j_____j_____CH1-3_HEAVY1-IGG2-KNOBS_j_____j_____j_____j_____j_____j_____j_____>

          2470          2480          2490          2500          2510          2520
CCT GGA ACT CTG GCG CTC TGA CAT CTG GCG TGC ACA CCT TTC CAG CCG TGC TGC AAA GCA
S   W   N   S   G   A   L   T   S   G   V   H   T   F   P   A   V   L   Q   S>
_____j_____j_____j_____j_____j_____j_____CH1-3_HEAVY1-IGG2-KNOBS_j_____j_____j_____j_____j_____j_____j_____>

          2530          2540          2550          2560          2570          2580
GCG GCC TGT ACA GTC TGA GCA GCG TCG TGA CAG TGC CTA GCA GCT CTC TGG GCA CCC AGA
S   G   L   Y   S   L   S   S   V   V   T   V   P   S   S   S   L   G   T   Q>
_____j_____j_____j_____j_____j_____j_____CH1-3_HEAVY1-IGG2-KNOBS_j_____j_____j_____j_____j_____j_____j_____>

          2590          2600          2610          2620          2630          2640
CCT ACA CCT GTA ATG TGG ACC ACA AGC CTA GCA ACA CCA AGG TGG ACA AGC GCG TGG AAT
T   Y   T   C   N   V   D   H   K   P   S   N   T   K   V   D   K   R   V   E>
_____j_____j_____j_____j_____j_____j_____CH1-3_HEAVY1-IGG2-KNOBS_j_____j_____j_____j_____j_____j_____j_____>

          2650          2660          2670          2680          2690          2700
CTA AGT ACG GCC CTC CTT GTC CTC CAT GTC CTG CAC CTG AGT TTC TCG GCG GAC CCT CCG
S   K   Y   G   P   P   C   P   P   C   P   A   P   E   F   L   G   G   P   S>
_____j_____j_____j_____j_____j_____j_____CH1-3_HEAVY1-IGG2-KNOBS_j_____j_____j_____j_____j_____j_____j_____>

          2710          2720          2730          2740          2750          2760
TGT TCC TGT TTC CTC CAA AGC CTA AGG ACA CCC TGA TGA TCT CCA GAA CAC CCG AAG TGA
V   F   L   F   P   P   K   P   K   D   T   L   M   I   S   R   T   P   E   V>
_____j_____j_____j_____j_____j_____j_____CH1-3_HEAVY1-IGG2-KNOBS_j_____j_____j_____j_____j_____j_____j_____>
```

Figure 51 (continued)

```
        2770        2780        2790        2800        2810        2820
CCT GCG TGG TGG TGG ACG TTT CAC AAG AGG ACC CCG AGG TGC AGT TTA ATT GGT ACG TGG
T   C   V   V   V   D   V   S   Q   E   D   P   E   V   Q   F   N   W   Y   V>
____j____j____j____j____j____j____CH1-3_HEAVY1-IGG2-KNOBS_j____j____j____j____j____j____j____>

        2830        2840        2850        2860        2870        2880
ACG GCG TGG AAG TGC ACA ACG CCA AGA CCA AGC CTA GAG AGG AAC AGT ACA ACA GCA CCT
D   G   V   E   V   H   N   A   K   T   K   P   R   E   E   Q   Y   N   S   T>
____j____j____j____j____j____j____CH1-3_HEAVY1-IGG2-KNOBS_j____j____j____j____j____j____j____>

        2890        2900        2910        2920        2930        2940
ACA GAG TGG TGT CCG TGC TGA CAG TGC TGC ACC AGG ATT GGC TGA ACG GCA AAG AGT ACA
Y   R   V   V   S   V   L   T   V   L   H   Q   D   W   L   N   G   K   E   Y>
____j____j____j____j____j____j____CH1-3_HEAVY1-IGG2-KNOBS_j____j____j____j____j____j____j____>

        2950        2960        2970        2980        2990        3000
AGT GCA AGG TGT CCA ACA AGG GCC TGC CAA GCA GCA TCG AGA AAA CCA TCA GCA AGG CCA
K   C   K   V   S   N   K   G   L   P   S   S   I   E   K   T   I   S   K   A>
____j____j____j____j____j____j____CH1-3_HEAVY1-IGG2-KNOBS_j____j____j____j____j____j____j____>

        3010        3020        3030        3040        3050        3060
AGG GCC AGC CTA GGG AAC CCC AGG TTT ACA CAC TGC CTC CAA GCC AGA AAG AGA TGA CCA
K   G   Q   P   R   E   P   Q   V   Y   T   L   P   P   S   Q   K   E   M   T>
____j____j____j____j____j____j____CH1-3_HEAVY1-IGG2-KNOBS_j____j____j____j____j____j____j____>

        3070        3080        3090        3100        3110        3120
AGA ACC AGG TGT CCC TGA CCT GCC TCG TGA AGG GCT TCT ACC CTT CCG ATA TCG CCG TGG
K   N   Q   V   S   L   T   C   L   V   K   G   F   Y   P   S   D   I   A   V>
____j____j____j____j____j____j____CH1-3_HEAVY1-IGG2-KNOBS_j____j____j____j____j____j____j____>

        3130        3140        3150        3160        3170        3180
AAT GGG AGA GCA ATG GCC AGC CAG AGA ACA ACT ACA AGA CCA CAC CTC CTG TGC TGG ACA
E   W   E   S   N   G   Q   P   E   N   N   Y   K   T   T   P   P   V   L   D>
____j____j____j____j____j____j____CH1-3_HEAVY1-IGG2-KNOBS_j____j____j____j____j____j____j____>

        3190        3200        3210        3220        3230        3240
GCG ACG GCT CAT TCT TCC TGT ACA GCA AGC TGA CCG TGG ACA AGA GCA GAT GGC AAG AGG
S   D   G   S   F   F   L   Y   S   K   L   T   V   D   K   S   R   W   Q   E>
____j____j____j____j____j____j____CH1-3_HEAVY1-IGG2-KNOBS_j____j____j____j____j____j____j____>

        3250        3260        3270        3280        3290        3300
GCA ACG TGT TCA GCT GCA GCG TGA TGC ACG AGG CCC TGC ACA ACA GAT ACA CCC AGA AGT
G   N   V   F   S   C   S   V   M   H   E   A   L   H   N   R   Y   T   Q   K>
____j____j____j____j____j____j____CH1-3_HEAVY1-IGG2-KNOBS_j____j____j____j____j____j____j____>

                >Myc-epitope                           >PDGFR_TM
                    |                                      |
        3310        3320        3330        3340        3350        3360
CCC TGT CTC TGA GCC CCG AAC AAA AAC TCA TCT CAG AAG AGG ATC TGA ATG CTG TGG GCC
S   L   S   L   S   P> (SEQ ID NO: 360)
____CH1-3_HEAVY1-IG_j___>

    3370        3380        3390        3400        3410        3420
AGG ACA CGC AGG AGG TCA TCG TGG TGC CAC ACT CCT TGC CCT TTA AGG TGG TGG TGA TCT

    3430        3440        3450        3460        3470        3480
CAG CCA TCC TGG CCC TGG TGG TGC TCA CCA TCA TCT CCC TTA TCA TCC TCA TCA TGC TTT

                                                         >pre_polyA
                                                           |
        3490        3500        3510        3520        3530        3540
GGC AGA AGA AGC CAC GTT AGT AAA AGC TTG TCA CTT GGA AAG TAA TAG TTT TTC CTG CAC
GGG TAG TAA TCA GCC TCG ACT GTG CCT TCT AGT TGC CAG CCA TCT GTT GTT TGC CCC TCC
```

Figure 51 (continued)

```
CCC GTG CCT TCC TTG ACC CTG GAA GGT GCC ACT CCC ACT GTC CTT TCC TAA TAA AAT GAG
GAA ATT GCA TCG CAT TGT CTG AGT AGG TGT CAT TCT ATT CTG GGG GGT GGG GTG GGG CAG
                                                      <BGH_polyA
                                                           |
         3730          3740          3750           3760          |3770          3780
GAC AGC AAG GGG GAG GAT TGG GAA GAC AAT AGC AGG CAT GCT GGG GAT GCC CCG GGC ATG


                                          >Human\EF1a\Promoter
                                                       |
         3790          3800          3810           3820          3830          3840
ATA ACT TCG TAT AAT GTA TGC TAT ACG AAG TTA TGT AGA GTA ATT CAT ACA AAA GGA CTC
GCC CCT GCC TTG GGG AAT CCC AGG GAC CGT CGT TAA ACT CCC ACT AAC GTA GAA CCC AGA
GAT CGC TGC GTT CCC GCC CCC TCA CCC GCC CGC TCT CGT CAT CAC TGA GGT GGA GAA GAG
CAT GCG TGA GGC TCC GGT GCC CGT CAG TGG GCA GAG CGC ACA TCG CCC ACA GTC CCC GAG
AAG TTG GGG GGA GGG GTC GGC AAT TGA ACC GGT GCC TAG AGA AGG TGG CGC GGG GTA AAC
TGG GAA AGT GAT GTC GTG TAC TGG CTC CGC CTT TTT CCC GAG GGT GGG GGA GAA CCG TAT
ATA AGT GCA GTA GTC GCC GTG AAC GTT CTT TTT CGC AAC GGG TTT GCC GCC AGA ACA CAG
GTA AGT GCC GTG TGT GGT TCC CGC GGG CCT GGC CTC TTT ACG GGT TAT GGC CCT TGC GTG
CCT TGA ATT ACT TCC ACG CCC CTG GCT GCA GTA CGT GAT TCT TGA TCC CGA GCT TCG GGT
TGG AAG TGG GTG GGA GAG TTC GAG GCC TTG CGC TTA AGG AGC CCC TTC GCC TCG TGC TTG
AGT TGA GGC CTG GCT TGG GCG CTG GGG CCG CCG CGT GCG AAT CTG GTG GCA CCT TCG CGC
CTG TCT CGC TGC TTT CGA TAA GTC TCT AGC CAT TTA AAA TTT TTG ATG ACC TGC TGC GAC
GCT TTT TTT CTG GCA AGA TAG TCT TGT AAA TGC GGG CCA TGA TCT GCA CAC TGG TAT TTC
GGT TTT TGG GGC CGC GGG CGG CGA CGG GGC CCG TGC GTC CCA GCG CAC ATG TTC GGC GAG
GCG GGG CCT GCG AGC GCG GCC ACC GAG AAT CGG ACG GGG GTA GTC TCA AGC TGG CCG GCC
TGC TCT GGT GCC TGG CCT CGC GCC GCC GTG TAT CGC CCC GCC CTG GGC GGC AAG GCT GGC
CCG GTC GGC ACC AGT TGC GTG AGC GGA AAG ATG GCC GCT TCC CGG CCC TGC TGC AGG GAG
CTC AAA ATG GAG GAC GCG GCG CTC GGG AGA GCG GGC GGG TGA GTC ACC CAC ACA AAG GAA
AAG GGC CTT TCC GTC CTC AGC CGT CGC TTC ATG TGA CTC CAC GGA GTA CCG GGC GCC GTC
CAG GCA CCT CGA TTA GTT CAC GAG CTT TTG GAG TAC GTC GTC TTT AGG TTG GGG GGA GGG
GTT TTA TGC GAT GGA GTT TCC CCA CAC TGA GTG GGT GGA GAC TGA AGT TAG GCC AGC TTG
GCA CTT GAT GTA ATT CTC CTT GGA ATT TGC CCT TTT TGA GTT TGG ATC TTG GTT CAT TCT
CAA GCC TCA GAC AGT GGT TCA AAG TTT TTT TCT TCC ATT TCA GGT GTC GTG AGA GCT CGT
TTA GTG AAC CGT CAG ATC GCC TGG AGA CGC CAT CCA CGC TGT TTT GAC CTC CAT AGA AGA
CAC CGG GAC CGA TCC AGC CTC CGC GGC CCC GAA TTC AAC ATG GAC TGG ACC TGG AGG GTC
                                                 M   D   W   T   W   R   V>
                                                ____l___SIGPP-PART1_l____l___>
                         >Splice_donor
                                |
                                |          >intron
         5290          5300    |     5310 |          5320          5330          5340
TTC TGC TTG CTG GCT GTA GCT CCA GGT AAA GGG CCA ACT GGT TCC AGG GCT GAG GAA GGG
 F   C   L   L   A   V   A   P   G> (SEQ ID NO: 361)
____l___l___SIGPP-PART1_l____l____l___>


         5350          5360          5370           5380          5390          5400
ATT TTT TCC AGT TTA GAG GAC TGT CAT TCT CTA CTG TGT CCT CTC CGC AGG TGC TCA CTC

         5410          5420          5430           5440          5450          5460
CCA GGT TCA GCT GGT GCA GTC TGG CAG CGA GCT GAA AAA ACC TGG CGC CTC CGT GAA GGT
 Q   V   Q   L   V   Q   S   G   S   E   L   K   K   P   G   A   S   V   K   V>
___n____n____n____n____n____n____n___VH2-ANTI-FX-ACE910____n____n____n____n____n____n____n___>


         5470          5480          5490           5500          5510          5520
GTC CTG CAA GGC TTC TGG CTA CAC CTT TAC CGA CAA CAA CAT GGA CTG GGT CCG ACA GGC
 S   C   K   A   S   G   Y   T   F   T   D   N   N   M   D   W   V   R   Q   A>
____n____n____n____n____n____n____n___VH2-ANTI-FX-ACE910____n____n____n____n____n____n____n___>

         5530          5540          5550           5560          5570          5580
CCC TGG ACA AGG ACT TGA GTG GAT GGG CGA CAT CAA CAC CAG AAG CGG CGG CAG CAT CTA
 P   G   Q   G   L   E   W   M   G   D   I   N   T   R   S   G   G   S   I   Y>
____n____n____n____n____n____n____n___VH2-ANTI-FX-ACE910____n____n____n____n____n____n____n___>
```

Figure 51 (continued)

```
       5590        5600        5610        5620        5630        5640
CAA CGA AGA GTT CCA GGA CAG AGT CAT CAT GAC CGT GGA CAA GAG CAC CGA CAC CGC CTA
 N   E   E   F   Q   D   R   V   I   M   T   V   D   K   S   T   D   T   A   Y>
____n____n____n____n____n____n____n__VH2-ANTI-FX-ACE910___n____n____n____n____n____n____n___>

       5650        5660        5670        5680        5690        5700
CAT GGA ACT GAG CAG CCT GAG AAG CGA GGA CAC CGC CAC CTA TCA CTG CGC CAG AAG AAA
 M   E   L   S   S   L   R   S   E   D   T   A   T   Y   H   C   A   R   R   K>
____n____n____n____n____n____n____n__VH2-ANTI-FX-ACE910___n____n____n____n____n____n____n___>

       5710        5720        5730        5740        5750        5760
GAG CTA CGG CTA CTA CCT GGA CGA GTG GGG CGA GGG AAC ACT GGT CAC AGT GTC TAG CGC
 S   Y   G   Y   Y   L   D   E   W   G   E   G   T   L   V   T   V   S   S>  A (SEQ ID NO: 362)
____n____n____n____n____n____n____n__VH2-ANTI-FX-ACE910___n____n____n____n____n____n____n_>

       5770        5780        5790        5800        5810        5820
CAG CAC AAA GGG CCC TAG CGT TTT CCC ACT GGC TCC CTG TAG CAG AAG CAC CAG CGA ATC
 S   T   K   G   P   S   V   F   P   L   A   P   C   S   R   S   T   S   E   S>
____o____o____o____o____o____o____o__CH1-3 IGG4 - HOLES___o____o____o____o____o____o____o___>

       5830        5840        5850        5860        5870        5880
TAC AGC CGC TCT GGG CTG CCT CGT GAA GGA CTA CTT TCC TGA GCC TGT GAC CGT TAG CTG
 T   A   A   L   G   C   L   V   K   D   Y   F   P   E   P   V   T   V   S   W>
____o____o____o____o____o____o____o__CH1-3 IGG4 - HOLES___o____o____o____o____o____o____o___>

       5890        5900        5910        5920        5930        5940
GAA CAG CGG AGC ACT GAC AAG CGG CGT GCA CAC ATT TCC AGC CGT GCT GCA AAG CAG CGG
 N   S   G   A   L   T   S   G   V   H   T   F   P   A   V   L   Q   S   S   G>
____o____o____o____o____o____o____o__CH1-3 IGG4 - HOLES___o____o____o____o____o____o____o___>

       5950        5960        5970        5980        5990        6000
CCT GTA CTC TCT GAG CAG CGT CGT GAC AGT GCC TAG CAG CTC TCT GGG CAC CCA GAC CTA
 L   Y   S   L   S   S   V   V   T   V   P   S   S   S   L   G   T   Q   T   Y>
____o____o____o____o____o____o____o__CH1-3 IGG4 - HOLES___o____o____o____o____o____o____o___>

       6010        6020        6030        6040        6050        6060
CAC CTG TAA TGT GGA CCA CAA GCC TAG CAA CAC CAA GGT GGA CAA GCG CGT GGA ATC TAA
 T   C   N   V   D   H   K   P   S   N   T   K   V   D   K   R   V   E   S   K>
____o____o____o____o____o____o____o__CH1-3 IGG4 - HOLES___o____o____o____o____o____o____o___>

       6070        6080        6090        6100        6110        6120
GTA CGG CCC TCC TTG TCC TCC ATG TCC TGC TCC AGA GTT TCT CGG CGG ACC CTC CGT GTT
 Y   G   P   P   C   P   P   C   P   A   P   E   F   L   G   G   P   S   V   F>
____o____o____o____o____o____o____o__CH1-3 IGG4 - HOLES___o____o____o____o____o____o____o___>

       6130        6140        6150        6160        6170        6180
CCT GTT TCC TCC AAA GCC TAA GGA CAC CCT GAT GAT CTC CAG AAC ACC CGA AGT GAC CTG
 L   F   P   P   K   P   K   D   T   L   M   I   S   R   T   P   E   V   T   C>
____o____o____o____o____o____o____o__CH1-3 IGG4 - HOLES___o____o____o____o____o____o____o___>

       6190        6200        6210        6220        6230        6240
CGT GGT GGT GGA CGT TTC ACA AGA GGA CCC CGA GGT GCA GTT CAA TTG GTA CGT GGA CGG
 V   V   V   D   V   S   Q   E   D   P   E   V   Q   F   N   W   Y   V   D   G>
____o____o____o____o____o____o____o__CH1-3 IGG4 - HOLES___o____o____o____o____o____o____o___>

       6250        6260        6270        6280        6290        6300
CGT GGA AGT GCA CAA CGC CAA GAC CAA GCC TAG AGA GGA ACA GTA CAA CAG CAC CTA CAG
 V   E   V   H   N   A   K   T   K   P   R   E   E   Q   Y   N   S   T   Y   R>
____o____o____o____o____o____o____o__CH1-3 IGG4 - HOLES___o____o____o____o____o____o____o___>

       6310        6320        6330        6340        6350        6360
AGT GGT GTC CGT GCT GAC AGT GCT GCA CCA GGA TTG GCT GAA CGG CAA AGA GTA CAA GTG
 V   V   S   V   L   T   V   L   H   Q   D   W   L   N   G   K   E   Y   K   C>
____o____o____o____o____o____o____o__CH1-3 IGG4 - HOLES___o____o____o____o____o____o____o___>
```

Figure 51 (continued)

```
        6370        6380        6390        6400        6410        6420
CAA GGT GTC CAA CAA GGG CCT GCC AAG CAG CAT CGA GAA AAC CAT CAG CAA GGC CAA GGG
 K   V   S   N   K   G   L   P   S   S   I   E   K   T   I   S   K   A   K   G>
___o___o___o___o___o___o___o__CH1-3 IGG4 - HOLES___o___o___o___o___o___o___o___>

        6430        6440        6450        6460        6470        6480
CCA GCC TAG GGA ACC CCA GGT TTA CAC ACT GCC TCC AAG CCA AGA GGA AAT GAC CAA GAA
 Q   P   R   E   P   Q   V   Y   T   L   P   P   S   Q   E   E   M   T   K   N>
___o___o___o___o___o___o___o__CH1-3 IGG4 - HOLES___o___o___o___o___o___o___o___>

        6490        6500        6510        6520        6530        6540
CCA GGT GTC CCT GAC CTG CCT GGT CAA GGG CTT CTA CCC TTC CGA TAT CGC CGT GGA ATG
 Q   V   S   L   T   C   L   V   K   G   F   Y   P   S   D   I   A   V   E   W>
___o___o___o___o___o___o___o__CH1-3 IGG4 - HOLES___o___o___o___o___o___o___o___>

        6550        6560        6570        6580        6590        6600
GGA GAG CAA TGG CCA GCC AGA GAA CAA CTA CAA GAC CAC ACC TCC TGT GCT GGA CAG CGA
 E   S   N   G   Q   P   E   N   N   Y   K   T   T   P   P   V   L   D   S   D>
___o___o___o___o___o___o___o__CH1-3 IGG4 - HOLES___o___o___o___o___o___o___o___>

        6610        6620        6630        6640        6650        6660
CGG CTC ATT CTT CCT GTA CAG CAA GCT GAC TGT GGA TAA GAG CCG GTG GCA AGA GGG CAA
 G   S   F   F   L   Y   S   K   L   T   V   D   K   S   R   W   Q   E   G   N>
___o___o___o___o___o___o___o__CH1-3 IGG4 - HOLES___o___o___o___o___o___o___o___>

        6670        6680        6690        6700        6710        6720
CGT GTT CAG CTG TAG CGT GAT GCA CGA GGC CCT GCA CAA CCA CTA CAC CCA AGA GAG CCT
 V   F   S   C   S   V   M   H   E   A   L   H   N   H   Y   T   Q   E   S   L>
___o___o___o___o___o___o___o__CH1-3 IGG4 - HOLES___o___o___o___o___o___o___o___>

           >Myc-epitope                        >PDGFR_TM
                |                                   |
        6730    |   6740        6750        6760    |   6770        6780
GTC TCT GAG CCC TGA ACA AAA ACT CAT CTC AGA AGA GGA TCT GAA TGC TGT GGG CCA GGA
 S   L   S   P> (SEQ ID NO: 363)
___CH1-3 IGG4__o_>

        6790        6800        6810        6820        6830        6840
CAC GCA GGA GGT CAT CGT GGT GCC ACA CTC CTT GCC CTT TAA GGT GGT GGT GAT CTC AGC

        6850        6860        6870        6880        6890        6900
CAT CCT GGC CCT GGT GGT GCT CAC CAT CAT CTC CCT TAT CAT CCT CAT CAT GCT TTG GCA

                                                 >SV40\polyA\signal
                                                   |
        6910        6920        6930        6940   |    6950        6960
GAA GAA GCC ACG TTA GTA ACT AAG TCG ACA TCC AGA CAT GAT AAG ATA CAT TGA TGA GTT
TGG ACA AAC CAC AAC TAG AAT GCA GTG AAA AAA ATG CTT TAT TTG TGA AAT TTG TGA TGC
TAT TGC TTT ATT TGT AAC CAT TAT AAG CTG CAA TAA ACA AGT TAA CAA CAA CAA TTG CAT
TCA TTT TAT GTT TCA GGT TCA GGG GGA GGT GTG GGA GGT TTT TTA AAG CAA GTA AAA CCT
CTA CAA ATG TGG TAT GGC TGA TTA TGA TCC TGC AAG CCT CGT CGT CCT GGC CGG ACC ACG
CTA TCT GTG CAA GGT CCC CGG CCC CGG ACG CGC GCT CCA TGA GCA GAG CGC CCG CCG CCG
AGG CGA AGA CTC GGG CGG CGC CCT GCC CGT CCC ACC AGG TCA ACA GGC GGT AAC CGG CCT
CTT CAT CGG GAA TGC GCG CGA CCT TCA GCA TCG CCG GCA TGT CCC CCT GGC GGA CGG GAA

     BstZ191
        |
GTA TGT ATA C    (SEQ ID NO: 354)
```

Figure 51 (continued)

```
                                                  ____CDR1____                    __CDR2__
                               10         20         30         40         50         60
Emicizumab            DIQMTQSPSS LSASVGDRVT ITCKASRNIE RQLAWYQQKP GQAPELLIYQ ASRKESGVPD (SEQ ID NO: 364)
E30Y                  .......... .......... .........Y .......... .......... .......... (SEQ ID NO: 365)
E30Y_E55Y             .......... .......... .........Y .......... .......... ....Y..... (SEQ ID NO: 366)
E30Y_E55Y_D93S        .......... .......... .........Y .......... .......... ....Y..... (SEQ ID NO: 367)
E30Y_K54R_E55Y_D93S   .......... .......... .........Y .......... .......... ...RY..... (SEQ ID NO: 368)
```

```
                                                     ____CDR3____
                               70         80         90        100        110
Emicizumab            RFSGSRYGTD FTLTISSLQP EDIATYYCQQ YSDPPLTFGG GTKVEIKRTA (SEQ ID NO: 364)
E30Y                  .......... .......... .......... .......... .......... (SEQ ID NO: 365)
E30Y_E55Y             .......... .......... .......... .......... .......... (SEQ ID NO: 366)
E30Y_E55Y_D93S        .......... .......... .......... ..S....... .......... (SEQ ID NO: 367)
E30Y_K54R_E55Y_D93S   .......... .......... .......... ..S....... .......... (SEQ ID NO: 368)
```

Figure 53 a
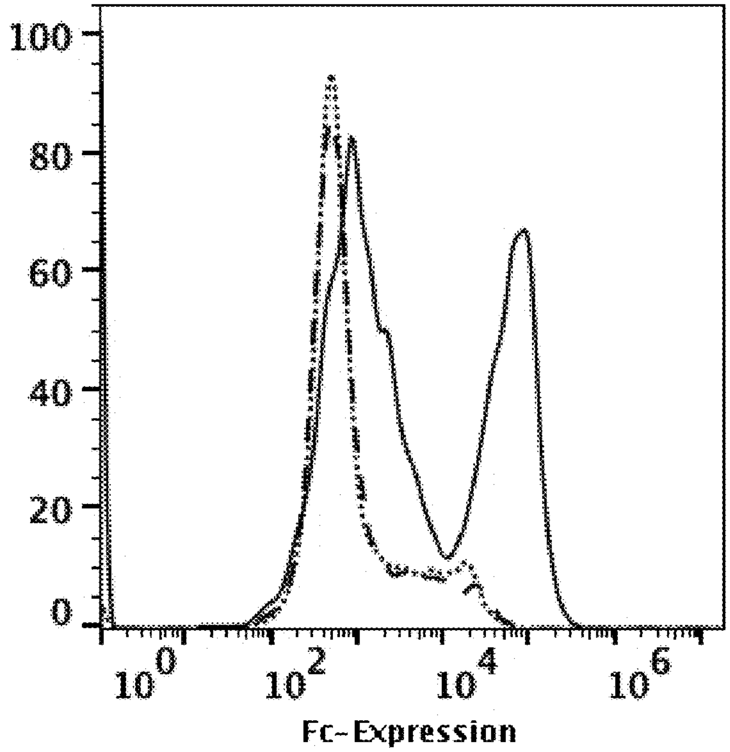
b
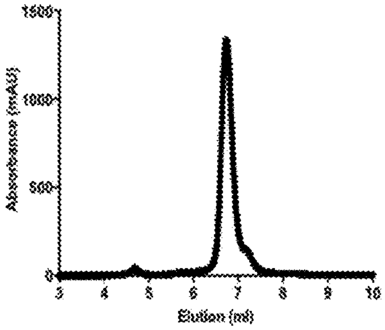
c
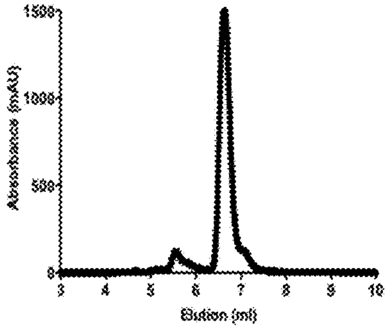
d
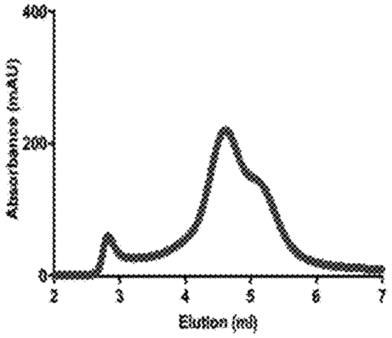
Figure 54

SELECTING FOR DEVELOPABILITY OF POLYPEPTIDE DRUGS IN EUKARYOTIC CELL DISPLAY SYSTEMS

CROSS-REFERENCE TO RELATED APPLICATION(S)

This patent application is the U.S. National Stage of International Application No. PCT/EP2018/083698, filed Dec. 5, 2018, which claims the benefit of priority of Great Britain Application Number 1720351.4, filed Dec. 6, 2017, which application is herein incorporated by reference.

SEQUENCE LISTING

The instant application contains a Sequence Listing which has been submitted electronically in ASCII format and is hereby incorporated by reference in its entirety. Said ASCII copy, created on Jan. 27, 2021, is named 51528-003002_Sequence_Listing_1.27.21_ST25 and is 234,767 bytes in size.

FIELD OF THE INVENTION

The present invention relates to identification of candidate polypeptide drugs having desirable developability characteristics such as solubility, capability to be formulated at high concentrations, low propensity for non-specific binding, and optimal half-life. The invention further relates to screening of binders in drug discovery, including antibody discovery.

BACKGROUND

Antibodies have proven to be a very successful class of drug with over 70 therapeutic antibodies approved to date and many more in the development pipeline. However, the production and formulation of polypeptide drugs such as antibodies is in many respects a more complex endeavour than for small molecule pharmaceuticals. A number of factors affect the practicality of developing polypeptide drugs such as antibodies, influencing whether a lead candidate antibody will be successfully developed into a drug that is not only efficacious but also manufacturable, stable and safe. Such factors include chemical stability (resistance to e.g., fragmentation, deamidation, oxidation and isomerisation), physical stability (e.g., conformational stability, propensity of the protein to unfold, aggregate and/or precipitate, colloidal stability), and solution properties (e.g., solubility, tendency to reversibly self-associate in solution, and viscosity at high concentrations). The ability of a polypeptide to be expressed at high yield in cell culture is also a relevant consideration, as the amount of polypeptide secreted from the host cells determines the yield of product that is recoverable from the culture medium. The immunogenicity of an antibody or polypeptide drug is also a consideration. All these factors can collectively be referred to as "developability" characteristics of the product. These are important considerations as they impact the product's cost and practicality of manufacture, safety profile, dosing schedule and mode of administration. Where developability problems are encountered, they can affect the utility or commercial success of antibodies, and may cause a lead molecule to fail during the development process. Aspects of antibody drug developability and methods to measure them have been reviewed[1-3].

Production of stable, soluble protein at high concentration is desired for administration to patients. For example antibody concentrations of 50 mg/ml and greater are sought for subcutaneous administration where a relatively large dose has to be administered in a low volume. An ideal polypeptide for therapeutic use is highly soluble in aqueous buffered solution and thus able to be concentrated to high levels. Success in producing soluble protein at high concentration depends at least in part on the polypeptides' resistance to self-association which can otherwise lead to increased viscosity and/or precipitation. When the solubility limit of a molecule is reached, further increase in dissolved concentration is not possible and undesirable effects occur such as precipitation of the molecule out of solution. As the solubility limit is approached, a solution may become viscous and/or the dissolved polypeptide may self-associate in solution (reversibly or otherwise)—such effects complicate handling and formulation of the solution. Even worse, the formation of aggregates by poorly soluble and/or unstable polypeptides can present a heightened risk of immunogenicity when the product is administered to patients[4,5]. An anti-drug immune response (e.g., anti-drug antibodies) may neutralise the therapeutic effect, and hypersensitivity can result in morbidity or mortality.

The ability of a polypeptide to be expressed at high levels can affect the economics of production. During the early steps of antibody discovery, yields achieved from optimised transient expression in mammalian cell culture can reach 50 μg/ml or greater. Transient expression is a temporary expression system in which a plasmid encoding the product of interest is transfected into a cell and is expressed for a period of time, usually declining after 2-7 days as the plasmid is lost from the cell. To achieve stably expressing recombinant cells for drug manufacture, the encoding DNA must be stably integrated into the cell genome. Following creation of stable manufacturing cell lines, cells may be cultured for one or two weeks to obtain higher yields, which may be around 1 mg/ml or better.

Low yields from transient expression may indicate potential developability problems with a candidate drug. For example an anti-angiopoietin antibody ("Ang2") that was prone to aggregation was reported to give yields of only 10 μg/ml, whereas an optimised variant of the antibody yielded 260 μg/ml[6]. However, even when good yields are obtained from transient expression (e.g., >50 μg/ml) and/or from stable cell lines (e.g., >1 mg/ml), biophysical problems may emerge when a polypeptide is concentrated above 1 mg/ml. Dobson et al (2016[7]) found that the anti-NGF antibody MEDI1912 had significant biophysical problems when compared with its parental antibody MEDI576 but this was not reflected in the levels of expression reported from transient culture which was around 200 μg/ml. Yields from expression in cell culture are thus only one aspect of developability and may not be predictive of other important aspects.

Over the last few decades, display technologies have permitted the creation of large diverse populations of antibodies and other proteins and peptides from which individual variants with desired target binding properties can be isolated. Desired binding properties include binding to an appropriate epitope on the target (e.g., to inhibit a receptor-ligand interaction) with an appropriate specificity (e.g., towards orthologues and paralogues) and with appropriate affinity. Display technologies can help find binders with desired properties by allowing some such aspects to be enriched during selection. For example, higher affinity antibodies can be selected by using limiting amounts of antigen to drive selection. Deselecting against binding to unwanted paralogues has also been described. In vitro binder display platforms, and their use in selecting for desired characteristics including some aspects of developability, have been reviewed[8]. Also known are in vivo methods of generating antibodies, including immunisation of laboratory animals such as mice. Many approved antibody drug molecules have been discovered by using an animal's immune system to create a panel of antibodies that is then screened in multi-well plates or by flow sorting for desirable properties (e.g., binding tumour associated antigen; cytokine neutralisation).

There is no guarantee that antibody genes isolated from "natural" sources, whether obtained directly from animals or built into combinatorial display systems such as yeast display or phage display, will encode antibodies that exhibit good developability characteristics. This applies to antibody genes obtained from naïve sources as well as to those generated in vivo following immunisation, there being no a prior reason to assume that such antibodies will have good developability properties. The immune system is directed toward creating high affinity antibodies rather than creating antibodies that lend themselves to industrial manufacture or formulation as pharmaceutical products. Antibodies generated either in vivo or in vitro will not necessarily have the capacity to be concentrated to levels that are suitable for pharmaceutical formulations. The average total concentration of IgG in human serum is 12 mg/ml, with any individual antibody being represented at a significantly lower concentration. There is also great variation in the proportions of individual antibodies, with differences in expression of 1000 fold being observed between individual B cells during an immune response[6]. Thus, irrespective of an antibody's origin (e.g., immunised animals/human donors, synthetic or semi-synthetic sources), its solubility at high concentration cannot be assumed.

Traditionally, the early phase of drug discovery focuses on identifying molecules having a desired mode of therapeutic action such as target binding properties, while assessment for developability is deferred to a later stage, often after a lead molecule or limited panel of molecules have been selected for pre-clinical development. An unfortunate consequence of this is that developability problems may only come to light at a relatively late stage in drug development, when significant time and money have already been expended. Such failures are expensive. While the biopharmaceutical industry recognises that failure of candidate drugs is a ubiquitous feature of drug discovery—a majority of potential drugs never reach the clinic—there is a desire for drugs to "fail early" to reduce wastage and enable resources to be diverted towards the rarer successes.

It has been shown that engineering antibodies with a focus on improving affinity can generate affinity enhanced variants with mutations that adversely affect biophysical properties such as the propensity for self-association. The anti-NGF antibody MEDI1912 is an example of this. MEDI1912 was reported to have a pM affinity for NGF[7], having been affinity matured from a parental antibody MEDI578. However, compared with MEDI578 the affinity matured MEDI1912 antibody exhibited poor solubility, colloidal instability, aggregation at low concentrations and short half-life.

Efforts have been made to integrate selection or screening for some aspects of developability into in vitro selection platforms such as phage display. For single domain antibodies or dAbs, which possess only a VH or VL domain, thermal challenge can reduce the proportion of antibodies with lower melting temperature (Tm), prior to selection against antigen. Increase in Tm has been linked with an overall improvement of biophysical characteristics such as reversible unfolding, resistance to aggregation, solubility, expression and purification yields in bacteria. However, molecules with similar Tm can exhibit differences in biophysical properties—see Dobson et al 2016[7] and Example 3. ScFv molecules have also been engineered to have improved stability for inclusion in bispecific platforms[9-11]. Further, phage display libraries have been built (e.g. Tiller et al (2013)[12] which seek to introduce diversity into the library while avoiding inclusion of any potential post-translational modification sites (e.g. deamidation sites, isomerization sites, protease cleavage sites, and oxidation sites).

A number of algorithms have been created for in silico prediction of molecular behaviour, such algorithms facilitating comparison of developability characteristics of relatively large numbers of potential candidate drug molecules. Algorithms of this type can assist in pinpointing possible reasons underlying developability problems by identifying features of the amino acid sequence that may be responsible. It is recognised for example that hydrophobic patches in a sequence can cause molecular "stickiness", exhibiting as non-specific binding and/or self-aggregation, which is more likely to occur at high concentrations since polypeptides are in close association. Protein unfolding may expose hydrophobic residues that are buried within the molecule in its native conformation.

Where developability problems arise, whether predicted or simply encountered during the process of development, attempts can be made to address the difficulties using protein engineering. Dudgeon et al.[13] identified specific positions in antibody VH and VL domains at which the introduction of aspartate or glutamate residues improved biophysical properties. The resulting antibodies were said to be non-aggregating, well-expressed and heat-refoldable. The identified mutations were reported to enhance aggregation resistance by altering the local charge distribution at specific positions, independent of the rest of the antibody sequence, and so were presented as a general template for engineering human antibody variable domains with superior biophysical properties. In other cases, particular antibody sequences have been examined for individual features that may constrain developability. For instance, the anti-angiopoietin antibody "Ang2", which was identified from a B cell hybridoma campaign, was found to have low level expression in transient culture and to be prone to aggregation[6]. Analysis of its sequence identified an unpaired cysteine at position 49 in the light chain variable domain framework. 20 individual variants were made, assessed for aggregation and a version with improved solubility was identified where cysteine 49 was changed to threonine (C49T). In this case the baseline expression of the parental clone was very low and an improvement in yield was also observed in the C49T variant without compromising binding.

Another example is the "repair" of the affinity-improved MEDI912 antibody mentioned above, which stalled in development[7]. Through a combination of hydrogen:deuterium exchange and structural modelling, 3 non-paratopic hydrophobic residues in the VH domain were identified and these were reverted to residues found in the parental antibody. Tryptophan at position 30, phenylalanine at position 31 and leucine at position 56 were converted to serine, threonine and threonine respectively (represented as W30S, F31T and L56T where number indicates amino acid position within the antibody chain, first letter represents the original amino acid and last letter represents the replacement amino acid). The developability-improved version, referred to as MEDI1912-STT, showed reduced aggregation and was improved in a number of other aspects including reduced non-specific binding and increased half-life.

Bethea et al (2012)[14] described an anti-IL-13 antibody with poor biophysical properties including self-aggregation leading to precipitation at 13 mg/ml. An aromatic triad in the CDR3 of the heavy chain consisting of phenylalanine, histidine and tryptophan was identified as a potential problem. The authors described introduction of several mutations, including a single amino acid change (substitution of alanine for a tryptophan residue at position 100a) which improved solubility and reduced non-specific interactions. In this case the change also reduced target binding.

The examples of MEDI912-STT and the anti-IL-13 antibody, in which sequence optimisation was able to simultaneously reduce both non-specific binding and other undesirable behaviours such as self-aggregation, indicates that multiple developability parameters may be interconnected and may have common underlying causes. However, other cases have been reported where there is little evidence of self-interaction although non-specific interactions are seen[2, 15].

Non-specific interactions are a significant consideration in drug development since they can adversely affect the performance, specificity, in vivo distribution or half-life of drug molecules. It has been shown that the in vivo half-life of antibodies can vary significantly[16] between antibodies having the same Fc region, indicating an influence of the antibody variable domains on half-life. This in many cases has been attributed to non-specific interactions. If an administered drug is drawn into a "sink" of non-specific binding interactions with non-target components, it will be less available for binding to its target molecule and may have a reduced ability to reach or penetrate a target tissue or site of pathology. Even low affinity non-specific interactions can be significant, particularly if the target is highly abundant. For example, antibodies in circulation are exposed to a vast area of endothelial glycocalyx (estimated area of 350 $m^2$) reported to reach depths of 0.5 mm or greater. The negatively charged glycocalyx is composed of various glycosaminoglycans such as hyaluronic acid and proteoglycans such as heparin sulphate which together constitute a major component. It also presents absorbed plasma proteins[17,18]. Low affinity association with this matrix and other surfaces presented to antibodies in circulation may have a significant effect on pharmacokinetics.

Methods exist for screening for non-specific interaction and these are usually carried out on a clone by clone basis after individual binders of interest have been identified. Hotzel et al (2012) described a strategy to help identify antibodies which exhibit non-specific interactions by screening for binding to baculoviral particles in ELISA[16]. Also, Xu et al described a polyspecificity reagent binding assay (PSR MFI) using labelled protein mixtures with a yeast display platform to identify antibodies exhibiting low specificity[19]. A number of chromatographic methods have also been developed to help identify antibodies that are prone to non-specific interactions. These typically involve immobilising an interaction partner, compound or surface of interest on a matrix such as sepharose and then passing the test antibody molecule over the matrix and comparing the degrees of retention of test and control antibodies through fixed or changing wash conditions. Methods such as cross-interaction chromatography (CIC)[15], hydrophobicity chromatography, and heparin have been used.

A further consideration for developability is the half-life of a therapeutic protein in vivo. To achieve optimal efficacy of many systemically administered drugs it is necessary to maintain their serum concentration at a particular level (or within a target range) for some duration of time. Polypeptide half-life and/or effective concentration in vivo can be influenced to an extent by non-specific binding interactions discussed above. Further, for antibodies and other molecules containing Fc regions, half-life can be strongly influenced by binding of the Fc region to FcRn, a receptor expressed in endothelial cells. Human IgGs have relatively long half-life compared with other circulating molecules and this has been attributed to their pH-dependent interactions with FcRn. Following pinocytosis and endosomal trafficking, a relatively high affinity interaction occurs between the antibody Fc and FcRn receptors which protect the antibodies from lysosomal degradation. At neutral pH the affinity between Fc and FcRn is low and upon recycling to the cell surface neutral pHs are encountered. Under these conditions the antibody is released back into circulation. Thus pH-dependent binding to FcRn receptors is an important property of IgG molecules. A crystal structure of FcRn in complex with rat IgG2a Fc[20] indicates FcRn binding to the $C_H2$ and $C_H3$ domains (at $C_H2$ residues 252-254 and 309-311, and $C_H3$ residues 434-436) and helps explain the important pH dependent binding. Fc variants with improved half-lives have been generated through Fc engineering.

Suzuki et al (2010) have shown a positive correlation between low affinity at neutral pH and long in vivo half-life[21] although it is clear that other factors can contribute. The anti-IL-12 antibodies briakinumab and ustekinumab have half-lives of 8 days and 22 days respectively despite having similar Fc domains. Using these antibodies and a series of cross-over variants Schoch et al (2015)[22] showed a good correlation between retained binding at neutral pH and in vivo half-life. They pointed to a large positively charged patch on the VL of briakinumab as causing increased electrostatic interactions with FcRn, thereby limiting FcRn-IgG dissociation at extracellular pH. Similar pH-dependent interactions are described in Kelly et al (2016) although they argue non-specific interactions with other proteins may also contribute to short half-life[23].

Usually the primary aim in drug discovery using display libraries is to enrich the libraries for clones expressing binders that have a high affinity for binding to a target molecule of interest. Phage display libraries can be used to enrich binders from non-binders and to enrich higher affinity clones relative to lower affinity clones. The relative enrichment on the basis of affinity has allowed phage display to be used for affinity maturation of antibodies. Typically biotinylated antigen is used to permit recovery of antibody: antigen complexes together with the associated display package (e.g., using streptavidin coated magnetic beads). At lower concentrations of antigen, higher affinity antibodies within a population are more likely to form complexes than lower affinity antibodies resulting in a relative enrichment of these.

However, for display of binders on eukaryotic cells, the approach of using limiting antigen coupled with solid phase recovery on beads may be less effective than phage display at enriching for high affinity binders. Unlike monovalent phage display, the eukaryotic cell is a multivalent display package with many copies of the same binder on its surface. The concentration of binders presented within a cell population during selection is potentially relatively high compared with the antigen concentration and/or the affinities which one seeks to resolve. This may mask affinity effects and make it difficult to resolve differences in affinity of binders displayed on different clones in a mixed population, consequently reducing the enrichment factor achieved compared with approaches such as phage display.

Boder & Wittrup[24] described a method that claimed to increase stringency and permit selection for affinity in a eukaryotic cell display library, using limiting concentrations of fluorescently labelled monovalent antigen in conjunction with flow cytometry to select for affinity, measuring the amount of antibody bound per cell to control for differences in expression. In this system, stringency of binding was reportedly increased by reducing the concentration of target relative to the binders, whereby higher affinity binders were said to be detected based on the level of signal detected from the target since more molecules of the target bound to higher affinity binders than to lower affinity binders.

A number of publications have described selections where target binding and antibody expression were examined simultaneously. In this way the extent of antigen binding can be normalised based on the level of display achieved. U.S. Pat. No. 8,771,960 (DKFZ) described selection for higher affinity monoclonal antibodies using a fluorescence activated cell sorter (FACS) method in which an antibody library or a group of different antigen-specific hybridoma cells was stained with PE-labelled antigen and counterstained with FITC-labelled protein G. Cells with the greatest quotient PE staining:FITC staining were selected in the FACS, followed by expanding individual cells each producing an antibody having comparatively high affinity for the target antigen used for selection. The ratio of antibody-bound antigens to antibody non-bound-antigens was thus used as a direct measure of the antibody affinity for its antigen.

Chao et al (2006)[25] described genes encoding a repertoire of scFvs genetically fused with the yeast agglutinin Aga2p subunit. In the Aga2p yeast display system, the binder of interest (here, scFv) is fused to an Aga2p subunit which attaches to the Aga1p subunit present in the yeast cell wall via disulphide bonds. Yeast cells expressing a target-specific binding molecule can be identified by flow cytometry using directly or indirectly labelled target molecule. For example biotinylated target can be added to cells and binding to the scFv presented within the cell wall can be detected with streptavidin-phycoerythrin. Limiting concentrations of the target molecule made it possible to enrich clones expressing higher affinity binders since those clones captured more target molecules and so exhibited brighter fluorescence. To control for variation in scFv expression in different cells Chao et al (2006)[25] used a fluorescently labelled anti-tag antibody to measure antibody expression level on the surface of each cell allowing normalisation for variation in expression level. This approach therefore allowed yeast cells displaying high affinity binding molecules to be differentiated from those cells expressing high levels of a lower affinity antibody. The purpose of measuring antibody display in this case was therefore to normalise for expression differences and thereby facilitate affinity selections.

Methods have also been described wherein display level was used as an indicator of potential expression yield of the same protein in a secreted form. In seeking to identify highly expressing cellular clones during the creation of stable cell lines for antibody production WO2015128509 (Glenmark Pharmaceuticals) described an approach wherein an antibody is expressed in a secreted form but a proportion is "sampled" for presentation on the cell surface. This sampling arises as a result of a splicing event which bypasses a first stop codon and in a fraction of the antibody mRNA splices the antibody gene onto an exon encoding a transmembrane domain. In this system the display level of the antibody was reported to correlate directly to the amount of soluble antibody expressed.

A number of studies with yeast have reported links between the level of surface presentation of binders on yeast cells, thermal stability of binders, and/or yield of binders from cell culture. Shusta et al.[26] fused soluble single chain T cell receptor (scTCR) variants to Aga2p and reported that thermal stability of the various mutants were strongly correlated with their soluble secretion levels and with the quantity of scTCR displayed as a fusion to Aga2p on the yeast cell wall. They proposed that intracellular proteolysis of thermodynamically unstable mutants by the quality control apparatus of the endoplasmic reticulum (ER) dictated the efficiency of protein expression. Kowalski et al.[27,28] examined soluble expression of variants of the soluble polypeptide fibronectin type III (FnIII) domain in yeast and also reported a correlation between the polypeptides' thermodynamic stability and their efficiency of secretion (and hence yield). Using a yeast display system, Hackel et al.[29] further investigated the effect of thermodynamic stability of FnIII domains. Hackel et al. cultured yeast expressing a range of Aga2p-fused FnIII variants mutated to reduce their thermal stability, and found a positive correlation between thermal stability and surface copy number. Thus, the more thermally unstable mutants exhibited reduced surface display levels.

WO2012/158739 described a two stage process for selecting polypeptides from libraries based on the FnIII domain, involving antigen-based selection from an in vitro ribosome display library followed by conversion of selected binders to a yeast display library for further antigen-based selection. The in vitro ribosome display system generated polypeptides which were largely aggregated whereas inclusion of the yeast display selection reduced the number of highly aggregated polypeptides in the selected population, although the fraction of clones producing monomers remained low. The modest improvement in expression behaviour of emerging clones was attributed to the yeast system being less permissive for expression of misfolded (e.g., thermally unstable) proteins, so that such proteins were less available for selection from the yeast library. Again this work involved an Aga1p:Aga2p-FnIII display system.

On the other hand, Julian et al[30] found that co-selecting for antigen binding and surface display of VH domains on yeast yielded antibodies with higher affinity but lower stability. The highest affinity VH domains were highly unstable. This study found only modest changes (1.6 fold) in display levels on yeast across a range of thermostabilities, and the authors reported that display level was unable to guide the selection of sets of mutations that improved both affinity and stability together.

A recent review of the relationship between antibody affinity, specificity, stability and solubility described how improvements in one property (e.g., affinity) can lead to deficits in other properties (e.g., stability) and how these trade-offs can be balanced to co-optimise multiple properties of antibodies[31].

Extensive work on multiple fronts has thus sought to identify and understand potential links between different characteristics of polypeptides that influence developability. Nevertheless there remains a lack of polypeptide drug discovery methods that conveniently integrate developability screening into the early stages of selection of candidate drugs, especially for aspects such as drug solubility and avoidance of non-specific binding.

SUMMARY OF THE INVENTION

The present invention provides methods and products facilitating the detection of developability issues in polypeptides during the phase of discovery from display libraries, enabling avoidance of molecules with developability liabilities and the enrichment of pools of candidate drug molecules for those with better developability characteristics.

The present inventors have surprisingly discovered that the level at which a polypeptide is presented on the surface of a eukaryotic host cell is associated with particular developability characteristics of the polypeptide, including its properties in solution such as its solubility and its resistance to self-association in solution. A host cell that expresses a polypeptide from a recombinant gene and displays the polypeptide on its surface may be used to assess or screen for such developability characteristics of the polypeptide by determining its level of presentation on the cell surface. This lends itself to high throughput screening of multiple host cell clones in parallel, allowing comparison of relative surface presentation and selection of clones displaying polypeptides having better developability characteristics. The surface presentation level of polypeptides thus represents a predictive indicator of developability in methods of screening polypeptide binders, such as in antibody discovery. Furthermore this association between level of surface presentation and biophysical properties such as self-association allows binders with such optimal biophysical properties to be selected from libraries of binders, or enriched within such libraries. Conversely, binders with poorer biophysical properties (e.g., lower solubility) can be selected against or excluded from libraries of binders.

The inventors have also devised methods of screening polypeptides expressed in higher eukaryotic cells in vitro for aspects of developability relating to in vivo properties of polypeptide drugs, such as non-specific binding, half-life and effective concentration in serum or in target organs and tissues.

Methods and uses according to the present invention have particular advantages during early stage screening, including screening of large and diverse libraries of binders such as antibodies. By integrating developability screening of candidate polypeptide drugs at the earliest stages of drug discovery, the invention reduces the risk of costly late-stage failures. Developability screening according to the present invention may also be used to select among a later-stage pool of candidate polypeptide drugs, optionally a "family" of antibodies sharing a common lineage, to enrich the pool for polypeptides having better developability and/or to inform decisions on lead molecule selection for drug development. Additionally, the techniques of the present invention may be used to identify improved variants of existing candidate polypeptide drugs, such as candidate drugs that have failed to meet one or more developability criteria or in which the improvement of one or more developability characteristics is desired. Thus, described herein are methods for the generation and rapid screening of derivative sequences that exhibit improved developability characteristics.

The polypeptide expression pathway in a mammalian cell begins with the translation machinery (ribosome, etc) on the endoplasmic reticulum, following which nascent polypeptides travel through the Golgi complex and are transported to the plasma membrane where they may be either secreted from the cell or retained at the cell surface (e.g., as membrane proteins). When a recombinantly-produced polypeptide is secreted it is immediately diluted into a large volume of culture medium and after several days/weeks of accumulation will be present at concentration of typically between 1-100 μg/ml. This is low compared with the desired concentration of a polypeptide drug in a medicament formulated for administration to a patient. In contrast with a secreted polypeptide, an expressed polypeptide that is retained at the cell surface can form high local concentrations on the cell surface. Retention of the expressed polypeptide on the cell surface massively reduces the volume available to the polypeptide and therefore provides an opportunity for high concentrations to be achieved. Concentrations may be especially high when the displayed polypeptide is expressed from a strong promoter such as the cytomegalovirus (CMV) promoter. Thus, the retention of polypeptide binders on the surface of mammalian and other eukaryotic cells in recombinant cell libraries results in binders being concentrated at locally high densities at the plasma membrane surface, especially when using host cells that strongly express recombinant genes where the encoded polypeptide represents a significant fraction of the total polypeptide synthesis. Applied across a panel of clones expressing a repertoire of polypeptides, inter-clonal variation in surface presentation levels of different polypeptides may reflect characteristics of the polypeptides such as their resistance to self-association. Polypeptides with a lower tendency to self-associate can concentrate to higher levels on the cell surface, assisted by their ability to resist aggregation when brought into close proximity. A eukaryotic cell display library in culture may thus function as an in vitro selection environment for binders exhibiting good developability characteristics. This is borne out by the evidence in the Examples presented herein.

In accordance with a first aspect of the present invention, the surface presentation level of polypeptide binders (e.g., antibodies) on the surface of cultured eukaryotic cell clones is used as a predictive indicator of developability characteristics of the binders, such as their solubility, resistance to self-associate in solution and/or capability to be concentrated in solution. Without wishing to be bound by theory, one element relating to solubility of a binder may be its hydrophilicity, with greater hydrophilicity (lower hydrophobicity) being associated with higher solubility, greater resistance to self-association in aqueous solution, and an ability to reach higher concentration in solution. Methods of the invention may thus be used to distinguish more hydrophilic binders (candidate polypeptide drugs) from less hydrophilic binders, based on their degree of surface presentation in eukaryotic cell display systems as described herein.

The invention provides a method comprising providing a library of higher eukaryotic (e.g., mammalian) cell clones each containing DNA encoding a binder, culturing the clones in vitro under conditions for expression of the binders, wherein the binders are presented on the cell surface, determining surface presentation levels of the binders on the plurality of clones, selecting one or more clones that exhibit higher surface presentation of binders compared with other clones, and identifying binders encoded by the one or more selected clones as having good developability characteristics.

The invention may be used to distinguish or rank binders according to their developability characteristics and/or to select one or more binders having good developability characteristics. Developability characteristics assessed in such a method may be solution properties of the binders, such as solubility, resistance to self-association, and/or capability to be concentrated in aqueous solution, as discussed in detail elsewhere herein.

Selection of clones exhibiting higher surface presentation provides a selected population of cells enriched for clones exhibiting higher surface presentation of binders, which may optionally then be used in one or more further methods such as additional rounds of screening.

Methods of determining surface presentation levels are described in detail elsewhere herein and optionally comprise labelling the binders with an agent incorporating a detectable (e.g., fluorescent) label. With antibodies and other binders that comprise an Fc region, it is convenient to label with an agent that binds the Fc region, e.g. the detection agent may be a labelled anti-IgG antibody. Methods may comprise determining surface presentation levels and observing a range of binder presentation levels in cells of the library. Examples of copy number range are found elsewhere herein.

A further aspect of the invention relates to assessment of non-specific binding during binder discovery in display libraries. It is advantageous to identify interactions with non-target molecules during initial binder discovery. Methods of the invention may be employed in screening populations of binders (e.g., antibodies) displayed on higher eukaryotic cells for optimal biophysical properties and low propensity for non-specific interaction with non-target molecules in vivo. Whereas it is routine to select candidate polypeptide drugs for desirable binding to a target molecule (e.g., the molecular target of the polypeptide drug, to which it binds in vivo and exerts a biological effect), problems with developability may be reduced if attention is also given to negatively selecting against candidate polypeptide drugs that exhibit undesirable binding to a non-target molecule (e.g., a component or class of molecules to which the binder shows non-specific binding, such as binding to negatively charged polymers like nucleic acids). The non-target molecule may be substituted for a target molecule in methods of selecting binders, except that binders that recognise the non-target molecule are then discarded rather than retained, thereby enriching for binders that do not recognise the non-target molecule.

The invention provides methods of selecting binders that exhibit lower tendency for non-specific binding, to enrich a pool of candidate drugs for those that exhibit less non-specific binding, and for comparing the predicted pharmacokinetic performance of different candidate drug products. Such methods may be used during drug discovery, optionally at early stages of screening, or to inform decisions on lead molecule selection for drug development.

The invention provides an in vitro screening method comprising;

(i) providing a library of eukaryotic cell clones each containing DNA encoding a binder, (ii) culturing the clones in vitro under conditions for expression of the binders, wherein the binders are presented on the cell surface, (iii) exposing the binders to a matrix of non-target molecules, allowing binding, (iv) discarding cells that exhibit a greater level of binding to the matrix, (v) selecting cells that exhibit a lower level of binding to the matrix, to provide a selected population of cells enriched for clones expressing binders having a low propensity to bind the non-target molecules. Binders, and thereby the cells that display them, are thus separated according to their relative binding to the matrix. Cells that bind to the matrix are discarded while non-binding cells are collected.

The high valency of antibodies displayed on a cell surface will facilitate the detection of low affinity cross-reactivities. When a population of cells displaying binders is passed over a matrix, binding to the matrix may be manifested by delayed passage. Cells displaying binders with low interaction potential progress through the matrix more readily and can be collected, in contrast to clones displaying binders exhibiting non-specific interactions which emerge later. Passing the library of clones over the matrix thus achieves separation of clones over time as those displaying binders exhibiting a greater propensity to bind one or more components of the matrix will take longer to pass over the matrix or may not even emerge from the matrix at all. The method may comprise collecting cells that pass more quickly over the matrix and discarding cells that pass more slowly and/or remain bound to the matrix. The matrix will generally comprise a solid or semi-solid substrate on which the one or more non-target components are immobilised (e.g., beads, optionally packed within a column). A number of non-target molecules may be tested, such as heparin sulphate proteoglycans and other abundant components encountered in the bloodstream. The matrix may comprise one or more components of the glycocalyx, e.g., hyaluronic acid, heparin sulphate. Alternatively flow sorting or sorting on magnetic beads may be used, with non-target molecules with collection parameters based on the extent of binding to an interaction partner, compound or surface of interest. The method may thus be used to enrich for cells expressing binders that exhibit a low propensity to bind in vivo with non-target molecules in a mammalian subject to whom the binder is administered.

Binders may be screened for binding to one or more non-target molecules in a method comprising (i) providing a library of eukaryotic cell clones each containing DNA encoding a binder, (ii) culturing the clones in vitro under conditions for expression of the binders, wherein the binders are presented on the cell surface, (iii) exposing the binders to one or more non-target molecules, allowing binding, (iv) discarding cells that exhibit a greater level of binding to one or more non-target molecules, and (v) selecting cells that exhibit a lower level of binding, to provide a selected population of cells enriched for clones expressing binders having a low propensity to bind the non-target molecules.

Such methods may be applied to cells (or a sample of cells) of a library of higher eukaryotic cells displaying binders, to enrich for cells expressing binders that exhibit a low propensity to bind the one or more non-target molecules.

To facilitate identification and/or separation of cells expressing binders that recognise the non-target molecule, the non-target molecule may be detectably labelled, e.g., with a fluorescent label. Use of fluorescence allows separation of the cells by flow sorting in a FACS, where non-stained (unlabelled) cells are distinguishable from stained (fluorescently labelled) cells and can be directed into a collected or discarded fraction accordingly. Conveniently, this may be combined with labelling to detect FcRn binding and/or to detect the presence and level of surface display of binders (e.g., using an anti-Fc antibody to bind binders that contain an Fc region) and/or to detect of target binding (e.g., using labelled antigen). Simultaneous labelling and sorting for combined properties is possible with the use of multiple distinct labels, e.g., fluorophores of different wavelength.

Further aspects of the invention relate to screening polypeptides for pH dependent interactions with the FcRn receptor. An antibody (or other Fc-containing drug) may have interactions with FcRn that either increase or shorten its half-life. As already noted, binders comprising Fc domains may interact with FcRn receptors on endothelial cells and be saved from degradation. Operation of the FcRn recycling pathway is pH dependent, requiring stronger binding within the low pH of the endosomal compartment to keep the polypeptide safely docked on the receptor, and lower affinity binding in the higher pH extracellular environment for release of the polypeptide back to the bloodstream. In some cases, it be desirable to increase binding to FcRn for reasons beyond controlling half-life. For example using "sweeping antibody" approaches[32] it is desirable for the administered antibody to engage well with FcRn at neutral pH to ensure there is preferential interaction compared with other natural antibodies in serum. The antibody in turn can deliver bound target molecules to the endosomal compartment where the bound target is released by the reduced pH and is subsequently degraded, e.g. within lysosomes.

One may wish to combine selection for multiple aspects of developability (e.g., according to any such aspect of the invention described herein) or with selection for binding to a target. To this end a selection may be performed by exposing the binders to the target, allowing recognition of the target by cognate binders, whereby clones displaying cognate binders become bound to the target. One or more clones displaying cognate binders is then selected. The target may carry a detectable (e.g., fluorescent) label to facilitate selection of clones displaying cognate binders. Conveniently, the method may comprise simultaneously determining surface presentation levels of the binders and levels of target binding by the binders, and co-selecting clones displaying cognate binders exhibiting higher surface presentation. The use of a fluorescence activated cell sorter (FACS) allows cells to be sorted according to their emitted fluorescence, and a parallel selection for surface presentation and target binding may be conducted by using different fluorescent labels to detect surface presentation vs bound target. Clones that exhibit surface presentation above a chosen threshold, and which also exhibit target binding, may thus be selected.

A further aspect of the invention relates to improvements in selection of binders having high affinity for binding to a target of interest. The inventors noted that while high level presentation of binders on the cell surface can have advantages in a display library, it may undesirably limit the sensitivity or stringency of affinity-based selection for target binding. The inventors realised that limiting the presentation level of binders in a display library could facilitate selection for higher affinity binders.

In accordance with this aspect, the invention provides a method comprising (a) providing an in vitro library of higher eukaryotic (e.g., mammalian) cell clones each containing DNA encoding a binder, wherein the encoded binder is expressed from a weakly active promoter and/or expressed on the cell surface at a copy number in the range of 100-60,000 per cell, (b) exposing the library to a target and allowing recognition of the target by cognate binders, whereby cells displaying cognate binders become bound to the target, and (c) isolating cells bound to the target to provide a selected population of cells displaying cognate binders.

Thus a pool of clones is obtained that is enriched for clones encoding binders with higher affinity for the target. The method may further comprise (d) exposing the selected population of cells to one or more further rounds of selection on the target, optionally wherein the concentration of target is progressively reduced to increase stringency of selection, and/or (e) selecting one or more clones displaying a cognate binder having the desired level of binding to the target.

The concentration of target used may be pre-determined or may be judged empirically based on using a range of target concentrations and choosing an antigen concentration where the extent of cell binding is higher than found on control cells (e.g., cells which do not express binders, or which express a binder that does not recognise the target).

Flow sorting may be used to identify the population of clones within a library with a desired level of binding under different conditions of target concentration and/or level of binder display. Selected clones may be identified based on the extent of fluorescence bound to the cell. As the number of bound target molecules reduces (through lower target concentration and/or reduced levels of binder display) the ability to distinguish labelled cells from non-labelled cells diminishes particularly if non-labelled cells exhibit a significant baseline of autofluorescence. In that case the use of recoverable target molecules (e.g., biotinylated target) and magnetic beads (e.g., streptavidin coated beads) for separation of labelled cells may allow separation of cells with a significantly reduced extent of labelling from non-labelled cells, thereby allowing increased stringency to be used in selection.

The method may be used to identify a binder that recognises a target molecule with desired affinity, to select binders according to affinity and/or to enrich a pool of clones for those expressing higher affinity binders for the target. The target may be any molecule of interest, such as a human receptor, ligand, enzyme or other polypeptide.

The invention provides libraries as defined under (a) above, and their use for selection of binders having a desired affinity for a target. Such libraries and methods of generating them are further described herein.

As outlined above, cell libraries may be used to distinguish binders based on different characteristics (developability and affinity) depending on the level at which the binders are expressed on the cell surface. During drug discovery one may naturally wish to select for both good affinity and good developability, in which case multiple aspects of the invention may be combined. For example, one may select binders to a target of interest using cells displaying binders at a relatively low level and thereby obtain a population of cells enriched for clones displaying high affinity binders. Their encoding DNA may then be provided in clones expressing the binders at a higher level, to select binders for desired developability traits. These selections may be performed in either order (selection for affinity followed by selection for developability or the other way around) and multiple rounds of selection may be included (e.g., initial affinity selection, then developability selection, then further rounds of affinity selection).

Dual-purpose display libraries can be constructed that are adaptable for use in selecting for both affinity and developability, by placing surface expression of binders under an externally controlled switch or modulatable element. For instance, DNA encoding binders may be operably linked to a promoter whose expression can be modulated by addition of an inducer or suppressor to the cell culture medium. Expression is then controlled from outside the cell, enabling the operator of the method to upregulate or downregulate the level of expression at will. Thus, in the case of an inducible promoter, addition of an inducer by an external operator causes the promoter to be activated so it may be regarded as externally inducible, albeit the induction is ultimately exerted within the cell. A number of inducible promoter systems have been described, a classic example being tetracycline-inducible promoters[33]. Dual-purpose libraries in which expression of binder DNA is under external control (e.g. under control of an inducible promoter) have the advantage that changing the level of binder gene expression is rapid and straightforward, without a need to reclone the encoding DNA into a new population of cells.

Methods of binder display involving such libraries form part of the present invention. A method of identifying a binder that recognises a target may comprise:

(i) providing a library of eukaryotic (e.g., mammalian) cell clones each containing DNA encoding a binder, wherein expression of the binder at the cell surface is externally modulatable (e.g., wherein surface expression of the binder is under control of an externally modulatable promoter), and wherein binders are presented on the cell surface, (ii) culturing cells of the library under conditions for low presentation on the cell surface (e.g., where the promoter is weakly active), (iii) exposing the library to the target, allowing recognition of the target by cognate binders, whereby cells displaying cognate binders become bound to the target, (iv) selecting cells displaying cognate binders, thereby providing a selected population of cells, (v) culturing the selected population of cells under conditions for increased presentation on the cell surface (e.g., where the promoter is more strongly active, optionally maximally active), (vi) determining surface presentation levels of the binders on the plurality of clones, optionally by labelling the binders with an agent incorporating a detectable (e.g., fluorescent) label, and (vii) selecting one or more clones that exhibit higher surface presentation of binders compared with other clones.

Binders having good developability characteristics (and the clones expressing them) are thus identified, selected and/or enriched for by selecting/enriching for binders (and hence clones) exhibiting higher surface presentation. The method can thus provide a pool of clones enriched for clones expressing binders that have good developability characteristics.

Such a method effectively combines multiple aspects of the invention that are described in detail elsewhere herein, namely the selection of binders to a target and the selection of cells based on surface presentation of binders. Features of these aspects as described elsewhere herein may be employed in the combined method, including e.g., the choice of target concentration for stringent selection, levels of surface presentation of binders, and methods of selecting cells.

The modulatable promoter may be an inducible promoter. Depending on the type of inducible promoter system used, low level or basal expression may be obtained in the absence of inducer (e.g., a tetracycline such as tetracycline or doxycycline) in the culture medium. Alternatively, a low concentration of inducer may be added. Expression from the promoter may be titred by addition of inducer or by increasing the concentration of inducer in the culture medium, preferably to obtain maximal promoter activity. An alternative to an inducible promoter is a repressible promoter, where the default state of the promoter is active, its activity being dampened or blocked by addition of a suppressor to the culture medium.

It will often be convenient to begin with the library in its basal expression state, and to conduct initial round(s) of selection on the target before upregulating activity of the promoter to increase cell surface presentation of binders and select for developability. However, in some cases it may be desirable to select for developability first, with the promoter activated, and then to suppress activity of the promoter or to allow its activity to decline (e.g., by removing the inducer from the culture medium), before conducting selection for affinity. This may be more convenient if using a repressible promoter. Thus, with reference to the numbered method steps set out above, one may conduct steps (ii)-(iv) followed by steps (v)-(vii), or one may conduct steps (v)-(vii) followed by steps (ii)-(iv).

The invention further provides libraries for use in the above method, an example of which is an in vitro display library of eukaryotic (e.g., mammalian) cell clones containing DNA encoding a repertoire of binders, wherein expression of the binder (and hence its presentation on the cell surface) is under control of a tetracycline-inducible promoter. Preferably the encoding DNA is integrated at a fixed locus in the cellular DNA. Such a library may be produced by a method comprising:

providing donor DNA molecules encoding the binders, and eukaryotic (e.g., mammalian) cells, introducing the donor DNA into the cells, thereby creating recombinant cells containing donor DNA integrated in the cellular DNA, wherein expression of the donor DNA is placed under control of a tetracycline-inducible promoter for presentation on the cell surface, and culturing the recombinant cells to produce clones, thereby providing a library of cell clones containing donor DNA encoding the repertoire of binders.

Optionally, integration of donor DNA is achieved by providing a site-specific nuclease within the cells, wherein the nuclease cleaves a recognition sequence in cellular DNA to create an integration site at which the donor DNA becomes integrated into the cellular DNA, integration occurring through DNA repair mechanisms endogenous to the cells.

Preferably the tetracycline-inducible promoter is on the donor DNA molecule encoding the binder, although it may be separately integrated if desired. Generally, the donor DNA and/or the cellular DNA of recombinant cells will contain DNA encoding the binder downstream of the promoter for expression. Following library construction, expression of donor DNA can be induced from the promoter and cells can be cultured under conditions for presentation of the binders on the cell surface.

Cells in which expression of binder DNA is placed under control of an inducible promoter also provide an opportunity to assess the rate at which cell surface presentation of binders on expressing clones reaches a certain level, and to compare rate across a plurality of clones by comparing presentation level after a short period of induction. This may be predetermined (e.g., 4 hours or 8 hours or 12 hours) or may be empirically derived by observing the appearance of binder presentation following induction. Cell surface presentation can be plotted over time, starting from the time point at which expression from the inducible promoter is initiated, to observe the rate of increase in expression and surface presentation. Polypeptide expression will typically increase over time until it reaches a stable or equilibrium level on the cell surface. By determining and comparing cell surface presentation between clones at an early stage, before the final expression level has been reached, initial indications of aspects of developability may already be seen. These developability aspects may include the capability of the polypeptide to be concentrated in solution, its solubility, resistance to self-association in solution, and/or other developability characteristics discussed herein, in addition to the yield recoverable from expression.

The rate of turnover, degradation or internalisation of binders displayed on higher eukaryotic cells can also be used as an indicator of such developability characteristics. This may optionally be assessed under conditions where the displayed binder is not being continuously replenished with newly expressed binder (so manifesting as depletion of binder from the cell surface, i.e., reduced level of surface presentation). One may label the binders, wash away unbound label and observe the rate at which labelled binder is depleted from the cell surface over time due to degradation and/or internalisation. Higher levels of depletion of binder may be observed on some clones relative to others. Selecting clones with the higher levels of surface presentation will select those clones with the better developability characteristics (e.g., higher solubility, better resistance to self-association in solution, lower non-specific binding).

Within a library of cells it may be observed that some clones exhibit a greater rate of increase in surface presentation than others. This may be used as an early indication of the developability potential of a polypeptide allowing selection of clones with optimal properties from the library.

In accordance with methods of the invention generally, once one has selected clones or selected a population of cells enriched in clones having desired characteristics, the selected clones or population may then be used in one or more further screening methods, examples of which are provided herein. Selected clones may be cultured, either together or individually. Methods may be combined so that clones are screened for multiple characteristics, including target binding and various developability characteristics described herein.

Methods of the invention may be used to assess the behaviour of antibodies at high concentrations in the earliest stages of antibody discovery. In preferred embodiments, the propensity for self-interaction of antibodies or other polypeptide binders at high concentrations is detected by screening libraries of clones using library selection techniques such as flow sorting, bead-based selection or chromatography.

Following selection of one or more clones containing DNA encoding a desired binder in any aspect of the present invention, nucleic acid encoding the binder may be recovered and/or the sequence of the nucleic acid encoding the binder may be determined. Nucleic acid (e.g., DNA) encoding the binder may be provided in isolated form, e.g., in a recombinant vector.

DNA encoding a binder of interest may be expressed in a host cell in vitro, optionally under conditions for expression of the binder in soluble form. Thus, the host cell may secrete the binder, facilitating its recovery from cell culture medium. The yield of binder (e.g., from a stably transfected host cell) may be at least 0.5 mg/ml, at least 1 mg/ml, at least 2 mg/ml or at least 5 mg/ml for example. The binder may be purified and/or concentrated to provide an aqueous solution of the binder. Advantageously, a binder may be provided in solution at a concentration of at least 1 mg/ml, optionally at least 10 mg/ml, at least 50 mg/ml or at least 100 mg/ml. In some embodiments, the binder is provided in solution at a concentration of between 50 mg/ml and 200 mg/ml, e.g., between 50 mg/ml and 100 mg/ml.

Binders that are identified or selected using methods according to the invention are themselves also provided as aspects of the invention herein, including those described in the Examples (including, without limitation, binders comprising the disclosed sequences such as the antibody VH and/or VL domain sequences set out herein) as well as further binders that are obtained as a result of conducting the methods of the invention. A binder of interest may be formulated into a composition comprising a pharmaceutically acceptable excipient. The invention extends to such compositions and to their clinical use, including binders for use in methods of treatment of the human or animal body by therapy. The method may comprise administration of a composition containing the binder by subcutaneous administration. A composition comprising the binder in solution may be provided in a pre-filled syringe for injection, optionally within a kit comprising one or more additional components such as a needle and/or product information leaflet comprising directions for administration of the composition by injection, e.g., subcutaneous injection.

Eukaryotic cells in the context of the present invention are preferably higher eukaryotic cells, such as mammalian cells. Mammalian cells are commonly used for large-scale expression of polypeptide drug products (e.g., antibodies) intended for clinical use. Consequently there are advantages to using mammalian cells when assessing characteristics of candidate polypeptides in drug discovery. A polypeptide binder may be expressed in its final intended molecular format during the early stages of discovery in mammalian cells. For example, where the desired clinical product is a full-length antibody (e.g., IgG), mammalian cells expressing full-length antibodies (e.g., IgG) may be used in methods of the invention.

The present invention may be used to best advantage in cell populations where there is a constant number (preferably one) of integrated binder genes per genome to avoid copy number effects or heterogeneity arising from differences in the number or identity of binder genes being expressed in different clones in a population. Additionally, the binder-encoding DNA is preferably integrated at the same locus in the cellular DNA of all clones, to avoid the complication of extrinsic effects on expression from variation in the position of integration of the encoding DNA, which may otherwise arise from genomic regions differing in their transcriptional activity. This has the benefit of transcriptional normalisation of binder expression. Thus, preferably the invention employs a plurality (e.g., a large library) of mammalian cell clones each containing DNA encoding a different binder sequence, wherein the encoding DNA is at a fixed locus in the cellular DNA and wherein the encoded binder is presented on the cell surface. Nevertheless, benefits of the invention may still be obtained using clones in which the encoding DNA is randomly integrated in the cellular DNA or provided on a plasmid for transient expression (e.g. Example 11). Integration of binder-encoding DNA at a single or limited number of loci will also enable better control of expression if required e.g., using inducible promoters, and preferably the binder-encoding DNA is present once per cell or once per chromosomal copy in a diploid genome. Thus, clones of a library each preferably express only one or two members of a repertoire of binders.

Various features of the invention are further described below. Headings used throughout this specification are to assist navigation only and should not be interpreted as definitive. Embodiments described in different sections may be combined as appropriate.

DETAILED DESCRIPTION OF THE INVENTION

Headings and sub-headings within this document are included purely to assist navigation and should not be construed as limiting. Multiple aspects and embodiments of the invention may be combined, and methods of selecting polypeptide drugs based for developability will desirably encompass sequential and/or parallel combinations of individual features and steps described herein.

Developability

It is desirable to integrate screening for multiple developability characteristics into the process of drug discovery to provide insight into developability at an early stage and to allow developability risks to be reduced. Binders (and their encoding cell clones) may be identified and selected for one or more desired developability characteristics as detailed here. It will be understood that screening or selection for developability in the present invention generally refers to predicted developability, where what is being assessed is a surrogate marker indicative of developability traits, enabling high throughput selection and integration of developability selection in early-stage discovery. The invention allows developability risks to be identified and reduced through enrichment for binders having more favourable developability traits. Developability characteristic(s) of individual polypeptides may then be directly confirmed by methods such as those described below. Identifying a binder as having a certain characteristic may thus comprise concluding that the binder is predicted to have that characteristic, based on data obtained from a method of the invention.

Identifying a binder as a candidate binder for development, or identifying a binder as having good developability characteristics, may comprise generating a report identifying the binder as having good developability characteristics. Identifying a pool of binders as being enriched for binders having good developability characteristics may comprise generating a report identifying the pool as being enriched for binders having good developability characteristics. Similarly, identifying selected cells as expressing binders (or as being enriched for clones expressing binders) that have good developability characteristics may comprise generating a report identifying the cells (e.g., selected cell population) as expressing binders (or being enriched for expression of binders) that have good developability characteristics. A report may be a written report, which may be provided in electronic form and/or in print. The report may provide quantitative and/or qualitative information on developability including, for example, data from one or more methods described herein.

Solubility, Concentration and Self-Association in Solution

A recombinantly expressed polypeptide will usually need to be purified from the cell culture and formulated at a higher concentration, e.g., for use as a medicament. For example the protein may be expressed in transient cell culture at 100 μg/ml or in stable cell culture at 1 mg/ml, with a requirement to provide the protein to patients at a higher concentration e.g., at 50 mg/ml or greater for subcutaneous administration.

A number of straightforward techniques for expression, purification and quantitation of soluble binders such as antibodies will be known to those skilled in the art e.g., Walker et al (2008)[34], Janson et al (2012)[35]. The concentration of a purified polypeptide binder in solution can be determined in a number of ways. For example the solution's absorbance of light at a wavelength of 280 nm can be measured and the value used to determine the concentration based on the extinction coefficient of the polypeptide. Alternatively the test sample may be compared to a standard protein of known concentration, for which various colorimetric and fluorescent assays are known to those skilled in the art.

A desired developability characteristic is high solubility in aqueous solution. A polypeptide may desirably be soluble at 10 mg/ml, 20 mg/ml, 50 mg/ml, 75 mg/ml, 100 mg/ml, 150 mg/ml, 200 mg/ml or greater. The solution may be an aqueous buffered solution such as PBS. The solubility limit of the polypeptide may be greater than 10 mg/ml, >20 mg/ml, >50 mg/ml, >75 mg/ml, >100 mg/ml, >150 mg/ml or >200 mg/ml. It is advantageous to provide the polypeptide in solution at a concentration substantially below its solubility limit, to minimise self-interaction of the molecule and other undesirable effects that may occur as the solubility limit is approached more closely. Self-association of the polypeptide can lead to undesirable outcomes in terms of product quality and stability, including increased viscosity or phase separation. When the solubility limit of a molecule is reached, further increase in dissolved concentration is not possible and undesirable effects such as precipitation of the molecule will occur. In some embodiments, solubility limit of a selected polypeptide binder (e.g., an improved variant) is between 10 mg/ml and 200 mg/ml, e.g., between 50 mg/ml and 100 mg/ml.

It may be possible to drive a polypeptide solution to the point of precipitation and then, following filtration or centrifugation determine the concentration of the remaining soluble material, to determine its solubility limit. This can also be referred to as the maximal solubility of the protein. There are however more sensitive ways to measure the onset of self-association, which may occur at a concentration lower than that required for precipitation. For example at a critical concentration monomeric molecules will begin to form dimers and higher order soluble aggregates. Such aggregates can be detected in various ways. The "critical concentration" is defined as the concentration at which self-interaction is evident using one or more of these methods. A desired developability characteristic of a binder is that its critical concentration is high, so that medicinal formulations of the binder in solution are comfortably below the critical concentration. The critical concentration is preferably greater than 10 mg/ml, >20 mg/ml, >50 mg/ml, >75 mg/ml, >100 mg/ml, >150 mg/ml or >200 mg/ml. In some embodiments, critical concentration of a selected polypeptide binder (e.g., an improved variant) is between 10 mg/ml and 200 mg/ml, e.g., between 50 mg/ml and 100 mg/ml.

Some of the consequences of self-interaction, such as precipitation, may occur over an extended time and this is relevant to the shelf life of the product. The buffer composition, pH and temperature may also be influential. Parameters such as concentration may thus be determined under a set of reference conditions, e.g., at 4° C. with a standard buffer such as PBS at pH 7.4. Resistance of a polypeptide to self-interaction may be confirmed after an extended duration of time, e.g., by testing after (and optionally at additional points during) a 4 week period of storage under these conditions. The polypeptide may optionally resist self-interaction under such conditions for at least six months, confirming that the solution is below its critical concentration.

A polypeptide with poor developability characteristics in this respect would be one where signs of self-aggregation are apparent even at lower concentrations in solution, such as 1 mg/ml or less in standard buffer such as PBS, e.g., at 4° C. An ideal polypeptide will have a critical concentration of 100 mg/ml or greater, i.e., it will resist such self-interaction allowing it to be concentrated to 100 mg/ml. Between these extremes there may be cases where an improved polypeptide selected using the methods outlined herein exhibits a critical concentration which is improved by 1.5 fold or more over a starting polypeptide. Thus "improvement" can be defined in relation to a starting polypeptide, such as in methods described elsewhere herein where variants are being compared with a parent binder. Differences can also be compared between binders from different clones more generally, such as between different derivatives or variants of a parent binder, or across a population of clones in a library, whether a naïve library or an enriched population derived from another method (optionally a population of clones derived from the output of phage display selection or an antibody population derived from immunisation). Clones encoding binders which present at higher levels on the cell surface using the present invention may be compared to clones encoding polypeptides with lower levels of surface presentation within the same population which have been deselected. The biophysical behaviour of a polypeptide from a selected clone can be compared to the polypeptide derived from a deselected clone exhibiting lower levels of surface presentation from the same population. An antibody or other binder benefitting from discovery using the present invention will be one where it can be shown by any method that higher concentration levels can be achieved before the onset of self-interaction or where the degree of self-interaction is reduced within a given assay compared to a comparator polypeptide. For example a starting polypeptide with evidence of self-aggregation at 10 mg/ml could be improved to 15 mg/ml or greater. Alternatively an optimal polypeptide selected from a library may resist self-aggregation at 10 mg/ml while other polypeptides derived from rejected clones in the same population may exhibit self-interaction at 10 mg/ml or less. In each case we refer to parental polypeptide or the polypeptide derived from rejected clones as the "comparator polypeptide".

As a control for self-association and other biophysical properties selected for in the present invention, an antibody with known desirable properties could be used and the relative performance of the parental antibody and its improved derivative (or a selected library member versus a deselected member) compared to this. The National Institute of Standards and Technology have used an antibody NIST RM 8671 as a "gold standard" reference antibody which has been extensively characterised by over 100 collaborators with the comparison published as part of a three part volume published by the American Chemical Society[36]. The NIST RM 8671 antibody was shown to have minimal self-interaction (Saro D et al, Developability Assessment of a proposed NIST monoclonal antibody[37]). Alternatively the antibody adalimumab has been shown to exhibit minimal self and cross-interaction and has been used as a control in some studies e.g., by Jain et al (2017)[2] and Sun et al (2013)[38]. The critical concentration or solubility of a binder, especially an antibody, as described herein may be compared with one or more such reference antibodies for benchmarking purposes.

Self-interaction can be determined in a number of ways allowing a direct and quantifiable comparison between an antibody selected for a high level of surface presentation compared to an antibody deselected based on a lower display level. Size exclusion chromatography (SEC), e.g., high pressure liquid chromatography (HPLC), allows the separation of monomer and multimeric forms (including dimer and higher order forms) of the polypeptide. The proportion of material in the dimer and/or multimer form can be quantitated and the extent of multimer formation can be compared between binders (e.g., between a parent binder and an improved variant) may be detected as an increased retention time and/or a broader elution peak following passage over the column. The HPLC-SEC profile may be determined at a single concentration and the proportion of multimer and/or retention time compared. Any detectable, reproducible reduction in retention time or peak width will be deemed an improvement. A reduction of the multimer peaks to 60% of their value in the parental clone will be deemed an improvement. Alternatively the critical concentration where a threshold of multimerisation occurs can be determined for each clone by testing a range of concentrations and determining a concentration where this threshold of multimerisation (e.g., 5%) occurs. Alternatively the increase in multimerisation can be plotted over time and the rate of multimer accumulation compared[2]. In each case an increase in the critical concentration represents an improvement. The magnitude of improvement in the critical concentration may be e.g., at least 1.5 fold or at least 2 fold.

Improvement in solubility limit, or improvement in critical concentration, is optionally between 1.5 fold and 50 fold, e.g., between 1.5 fold and 15 fold, between 1.5 fold and 10 fold, or between 2 fold and 10 fold.

Methods of determining self-association of a polypeptide include self-interaction chromatography (SIC). In this technique, a binder such as an antibody is immobilised on a matrix and a solution of the same binder is passed over the matrix. An extended retention time compared to control antibodies indicates self-interaction[38] (or interaction with the matrix). Alternatively a high throughput approach can be used in which different binders are immobilised on a biolayer interferometry chip (BLI) and tested for self-interaction by immersing a solution of its soluble form yielding a signal related to the amount of soluble binder that binds. This "Antibody Clone Self-Interaction using Biolayer Interferometry" (CSI-BLI) approach was shown to have good correlation with more laborious approaches such as SIC and required less material. In each case the retention time of the test binder (in the case of SIC) and the signal achieved in the case of (CSI-BLI) can be compared with the parental binder and a control binder known to resist self-aggregation (such as a benchmark antibody mentioned above).

In affinity capture self-interaction nanoparticle spectroscopy (AC-SINS), test antibodies are presented on a cell surface and their potential for avid self-interactions with antibodies presented on other beads is assessed[39-41] The reduction in inter-particle distance ensuing from interaction can be detected as an increase in plasmon wavelength of gold colloidal solutions. AC-SINS is a preferred technique for determining critical concentration, as it is a sensitive and straightforward assay. In preferred embodiments, improvements in developability of binders are detectable as an increase in critical concentration of the polypeptide in solution, where critical concentration is measurable by determining change in plasmon wavelength in an AC-SINS assay.

Self-association can also be measured by static and dynamic light scattering (DLS)[42,43], in which the hydrodynamic radius and percent polydispersity of molecules in a sample can be calculated providing information on the size and shape of molecules in solution. With DLS mutual diffusion coefficient is evaluated in relation to antibody concentration as a measure of self-association. Other methods for measuring self-interaction such as analytical ultracentrifugation[44] membrane osmometry[45] and neutron scattering[46] can be used.

Methods of the invention may comprise selecting one or more clones that exhibit higher surface presentation of binders compared with other clones, and identifying binders encoded by the one or more selected clones as having good solubility and/or resistance to self-association in solution, wherein the binder or binders have a critical concentration that is increased by at least 10%, at least 25%, or at least 50% as compared with binders encoded by one or more other clones in the population or as compared with a parent binder of which the selected binder is a variant, and/or wherein the binder or binders have a critical concentration that is increased by at least 1.5×, at least 2×, at least 3×, at least 5×, at least 10×, at least 20× or at least 100× as compared with binders encoded by one or more other clones in the population or as compared with a parent binder of which the selected binder is a variant.

As discussed, methods herein can be used to exclude (or diminish frequency or prevalence of) binders with poor developability characteristics, and favour the selection of (by increasing frequency or prevalence of, enriching) those with better developability characteristics. Such methods are not limited to merely identifying and avoiding "problem" binders. The sensitivity of the techniques described herein allows their use in distinguishing the best (e.g., most soluble) candidates among multiple binders that exhibit good solubility. The invention can also be used to apply selective pressure in favour of maintained or enhanced developability during affinity-based selection.

A comparator polypeptide may be any binder from a non-selected population of clones (or clones exhibiting binder presentation level at less than the determined threshold level). A comparator polypeptide may have a solubility limit of at least 5 mg/ml, at least 10 mg/ml, at least 20 mg/ml, at least 30 mg/ml, at least 40 mg/ml or at least 50 mg/ml, e.g. as determined by any method described herein. A comparator polypeptide may optionally have a critical concentration of at least 5 mg/ml, at least 10 mg/ml, at least 20 mg/ml, at least 30 mg/ml, at least 40 mg/ml or at least 50 mg/ml, e.g. as determined by any method described herein. A binder from a selected clone may exhibit at least 10%, at least 20%, at least 30%, at least 40%, at least 50%, at least 60%, at least 70%, at least 80%, at least 90% or at least 100% improvement in a developability characteristic, e.g., solubility limit or critical concentration, compared with a comparator polypeptide (e.g., a clone from the non-selected population, or parent binder). The binder from a selected clone may exhibit at least 1.5 fold improvement in a developability characteristic compared with a comparator polypeptide, e.g., increased solubility limit or increased critical concentration. Comparator polypeptides may optionally have a critical concentration of at least 10 mg/ml, at least 20 mg/ml, at least 30 mg/ml, at least 40 mg/ml or at least 50 mg/ml. It will be understood when comparing properties of a polypeptide against a comparator polypeptide, the comparison is made under identical conditions as is standard with the use of controls in the art.

The method may comprise confirming the improvement in critical concentration, e.g., by experimentally measuring the critical concentration by determining change in plasmon wavelength in an AC-SINS assay. Standard buffer conditions for determining parameters such as solubility limit and critical concentration include PBS pH 7.4 at 4° C. Parameters may be measured immediately after freshly synthesised polypeptide is formulated into said aqueous buffered solution. Alternatively parameters may be measured after a period of storage, e.g., a storage time of 1 hour, 1 week, 2 weeks, 28 days or 6 months under the standard buffer conditions.

One may wish to determine parameters after exposure to higher temperature, in which case the temperature may be increased, e.g., to 25° C., 37° C. or 50° C., for the duration of storage before returning the solution to 4° C. for measurement.

Non-Specific Binding

Non-specific binding, "polyreactivity", "polyspecificity" or "low specificity" may refer to interaction of a binder with a plurality of non-target molecules in addition to its cognate target, e.g., the polypeptide may bind non-specifically to hydrophobic, negatively charged or positively charged surfaces. A polyreactive polypeptide may be described as showing "stickiness", reflecting its binding to non-target molecules though interactions of this type, in addition to the specific recognition between the binder polypeptide and its target. In many cases, non-specific binding manifests as a low affinity interaction, but it may nevertheless be problematic where the non-target molecule is abundant. Polyreactivity may be attributable to clustered hydrophobic or charged amino acid residues on the surface of the binder polypeptide—in the case of antibodies this may be on the heavy and/or light variable domain—leading to a class of non-specific interactions with other (non-target) molecules. For example, a polypeptide may exhibit binding to hydrophobic surfaces, which may occur if the polypeptide displays one or more hydrophobic patches on its surface or if hydrophobic patches are exposed through unfolding of the polypeptide in solution. Alternatively, a polypeptide may exhibit binding to negatively charged surfaces or molecules carrying a net negative charge (at neutral pH), such as the negatively charged backbone of DNA, or other negatively charged polymers such as heparin or heparan sulphate. Regardless of the underlying molecular motifs responsible for these non-specific interactions, polyreactivity is generally an undesirable feature for a candidate polypeptide drug. Polyreactivity of polypeptide drugs is linked with poor pharmacokinetics such as short half-life in vivo and/or poor tissue uptake of the drug from circulation.

In aspects of the present invention, cells expressing binders (e.g. a library, or a sample of cells from a library) are exposed to one or more non-target molecules or "polyreactivity probes". This can be used to distinguish cellular clones within a population presenting a binder which interacts with said polyreactivity probe from those cellular clones with absent or lower binding to such probes. A polyreactivity probe may comprise any one or more of nucleic acid (e.g., DNA), streptavidin, heparin, heparan sulphate, chondroitin sulphate, carboxyl dextran, other sulphated proteoglycans, insulin, lipopolysaccharide, baculovirus, KLH, FcRn, laminin, collagen, trigger factor, Hsp70, Hsp90 or other heat shock protein or chaperone protein, hyaluronic acid or other glycocalyx component. The non-target molecule may be presented in isolated form or as a mixed preparation, e.g., membrane preparations from mammalian cells (e.g., CHO cells) can be used to test for polyreactivity. The non-target molecule may be one which is found in vivo, e.g., in mammals, e.g., in human. It may be found in the extracellular matrix or bloodstream, and/or on cell surfaces. Synthetic surrogates for the non-target molecules may also be prepared and used as polyreactivity probes.

The polyreactivity probe will be selected to screen for a particular mode of non-specific binding, e.g., to detect non-specific binding to negatively charged surfaces, one may select a polyreactivity probe carrying a net negative charge at neutral pH, such as heparin sulphate, DNA or streptavidin, and/or a molecule bearing an extended negatively charged surface region such as. FcRn. Suitable polyreactivity probes may be identified based on their calculated isoelectric point (pI). The pI is a measurement of protein charge and is defined as the pH at which the protein carries no net electrical charge. A polyreactivity probe with a pI of less than 6 may be chosen for detecting binders showing non-specific binding to negatively charged surfaces. Examples are known to the skilled person and include streptavidin, nucleic acid and sulphated proteoglycans such as heparin sulphate or carboxyl dextran. Conversely, to detect non-specific binding to positively charged surfaces one may select a polyreactivity probe having a positively charged surface region and/or a basic pI (e.g., pI greater than 8). Such a probe may also be used to detect binders having negatively charged surface patches which could result in undesirable electrostatic repulsion from negatively charged cell surfaces in vivo. To probe for polyreactivity through hydrophobic attraction one may select a polyreactivity probe having one or more hydrophobic regions on its surface, e.g., Hsp70 or Hsp90.

A number of methods are available to screen individual clones for low specificity. Cross-interaction chromatography (CIC)[47] is a method wherein a target molecule or mixture, often a polyclonal antibody preparation, is immobilised on a chromatographic matrix and the retention time of various antibodies measured. Delayed retention either through interaction with the immobilised molecule or the resin itself is an indication of low specificity. This approach has been used in a number of studies to characterise recombinant antibodies e.g.[2,15,38]. Size exclusion chromatography, as described above, may also be used to determine interaction of a binder with a matrix. In the present context it will be understood that the non-target molecule(s) of interest occupy the place of the "target" in these methods, being the molecular component against which interaction of the binder is being tested.

Interaction with alternative matrices or target molecules has also been used in characterisation of antibodies and other polypeptides. For example cells may be screened for their binding to abundant molecules present in the glycocalyx e.g. heparan sulphate proteoglycans (HSPGs) which are composed of a core protein with heparan sulphate (HS) glycosaminoglycan (GAG) chains attached. Given the large surface area and quantity of such molecules in the glycocalyx, this is a particularly appropriate class of molecules to test. Heparin affinity chromatography involves passing a sample over a matrix containing immobillised heparin[48]. Pre-prepared resins are available from a number of sources (Heparin Sepharose (Pharmacia), Bio-Gel Heparin (Bio-Rad, Vienna, Austria) Eupergit Heparin (Riihm Pharma, Weiterstadt, Germany) and Toyopearl Heparin 650 M (Toso-Haas, Stuttgart, Germany). Binding substances will be retained or delayed in their passage. Non-binding substances will pass through or be removed upon washing. Bound material is removed using altered buffer conditions, e.g., increasing salt concentrations. This method can be used for screening soluble antibodies and determining the extent to which they interact with heparin. Hydrophobic interaction chromatography could also be used to characterise antibodies by their tendency to interact with hydrophobic matrices[49,50].

Where the one or more non-target molecules are presented on a matrix, binding of binders to the matrix may be manifested as increased binding of cells to the matrix, e.g., retardation of cells passing over the matrix, or binding to beads (e.g., magnetic beads) coated with the non-target molecule(s). Binders that show greater binding to the one or more non-target molecules may thus be separated by removing (discarding, or not selecting) a fraction of cells showing greater binding, whereas those cells showing less binding may be recovered and optionally selected for use in further steps. As discussed above comparator polypeptides and control polypeptides can be used to confirm improvement arising from the present invention. Improvement may be determined by identifying a concentration at which non-specific interactions are apparent, the concentration optionally being defined under standard conditions. Alternatively the extent of non-specific interaction may be determined at a fixed concentration. Methods of assaying non-specific binding may generate a "stickiness measure" for the binder, providing a quantitative measure of non-specific binding that may be compared against other binders. Thus the "stickiness measure" for any given assay will be the difference between the value for the test polypeptide compared to a control polypeptide known to have very low non-specific interactions. For example the approved antibody adalimumab[2,38] or the antibody NIST RM 8671 have minimal self-interactions or association with other polyclonal IgG molecules as estimated by self-interaction chromatography (SIC) and cross-interaction chromatography (CIC) methods. (Saro D et al, Developability Assessment of a proposed NIST monoclonal antibody[37]). An approved polypeptide according to the present invention is one where an improvement in "stickiness measure" is observed compared to a comparator clone. A comparator clone may be the starting clone which is being improved or may be a clone which is deselected by the use of the invention.

A number of methods including these chromatographic methods are typically used to characterise individual antibodies and generate a "stickiness measure". Chromatography matrices can be used to separate cells on the basis of their interaction with immobilised molecules. For example lectins immobilised onto cyanogen bromide activated sepharose has been used to separate T cell populations[51]. Such a system could be modified to separate antibody-expressing cells based on their interaction with immobilised target such as polyclonal antibodies, heparin sulphate or other test molecules. Where there is interaction with the immobilised target or support matrix, cells bearing such antibodies would be retained or delayed relative to non-interacting cells. Loading or washing buffers could be modified to achieve the desired stringency when used for separating cells displaying antibodies with differing binding tendencies.

It is also possible to use non-chromatographic methods to identify and quantitate low specificity within individual antibodies. For example Hotzel et al (2012) use binding of antibodies to baculoviral particles in ELISA to identify antibodies which exhibit non-specific interactions[16]. In a similar way other test molecules (eg heparin sulphate) could be immobilised or presented on beads to test for interactions with individual antibodies. Non-chromatographic methods such as these could be adapted to identify clones which exhibit low specificity from libraries displayed on higher eukaryotes.

Mixtures of detergent solubilised membrane proteins have been prepared, biotinylated and used to identify clones within yeast libraries displaying antibodies with low specificity[19]. The presences of detergent may be tolerated using yeast libraries but are unlikely to be suitable for display systems based on higher eukaryotes such as mammalian cells. Test molecules or mixtures used to identify low specificity interactions could be labelled with fluorophores or molecules such as biotin which facilitate labelling or recovery of the molecule and its complexes on streptavidin coated surfaces. For example molecules such as fluorophore labelled chondroitin sulphate or heparin sulphate (eg from AMS Cat No. AMS.CSR.FACS-A1, C1 or D1 or E1 or AMS.CSR.FAHS-P1) could be used to separate clones in flow sorting according to the extent of interaction with the labelled test molecules. High avidity expression of polypeptides on the cell surface add to the sensitivity of the approach, particularly if a multivalent target molecule is used. Clones within a library could be separated by flow cytometry based on the binding of fluorescent molecules. These test molecules could be used in conjunction with other labelled molecules to select in advance, simultaneously or subsequently for other desirable properties such as binding to target, or other binding/avoidance of other molecules of interest such as Fc receptors. Other methods include AC-SINS as mentioned above. In this technique, test binders are presented on a cell surface and their potential for interactions with one or more non-target components presented on other cells or on beads is assessed[39]. The reduction in inter-particle distance ensuing from interaction can be detected as an increase in plasmon wavelength of gold colloidal solutions.

Cells expressing binders may be exposed to the one or more non-target molecules wherein a mixture of clones (e.g., a library, or sample therefrom) are together in one vessel—this is convenient with methods such as FACS for example, or with chromatographic techniques. In other cases the cells expressing binders may be exposed to the one or more non-target molecules in separate vessels, e.g., one clone per vessel, and the resulting interactions or binding levels can then be individually measured and compared—this may be more convenient with methods that measure interparticle distance, such as AC-SINS, or when relatively small numbers of binder-expressing clones are being compared.

Thus a fluorescently labelled polyreactivity probe can be mixed with a population of cells and detection or separation methods used to distinguish cellular clones which express polyreactive binders (as identified by binding to the polyreactivity probe), from binder-expressing clones which do not. Cellular clones which fail to bind the labelled probe can be separated by flow sorting, magnetic bead separation and other separation methods to achieve enrichment over clones expressing polyreactive antibodies. Example 6 demonstrates that it is not only possible to achieve sufficient discrimination between polyreactive clones and non-polyreactive clones within a population, but that this can be performed using straightforward practical steps that allow their separation.

Identifying Developable Variants of Candidate Drugs

While the invention may be used at all stages of drug discovery, including early stage selection of binders (e.g., from naive libraries or selected populations derived from immunisation or other display approaches), and later on for comparing qualities of a short-listed panel of candidate molecules, it also finds use in situations where a binder of interest has already been identified but is then discovered to require improvement in one or more developability characteristics. Binders identified from any source may be found to exhibit less than ideal developability characteristics, and in such cases it may be preferable to refine the sequence of the existing molecule rather than to begin again from scratch with a new drug discovery program to find an alternative molecule.

Methods of the invention may be used to identify variants of a binder, wherein the binder has been identified as requiring improvement in one or more developability characteristics (e.g., self-association, solubility, non-specific binding, and/or others as discussed), and wherein invention is used to predict whether or not one or more variants will exhibit improved developability. The selection methods of the invention may thus be performed on populations of cells that display variants of a "parent" binder. While these may be referred to as a library, and will in some cases display a large and diverse population of variant binders, the number of clones for comparison in some cases may be relatively small, e.g., up to 10. Methods of the invention may thus comprise providing a library or plurality of clones wherein binders are presented on the cell surface, wherein the clones are produced by generated variant sequences of a parent binder sequence and introducing DNA encoding the variants into cells so that the DNA is integrated into the cellular DNA. Suitable methods and techniques are detailed in other sections of this document.

The "parent" binder, from which the variants are generated, may be one that has been identified as requiring improvement due to poor performance in on or more developability assays. Alternatively it may simply be desired to investigate whether its developability is improvable through sequence variation. Various aspects of developability are discussed herein and a parent molecule may be identified as requiring improvement in any of these. The parent molecule may be found to have a solubility limit (maximum solubility) of less than 50 mg/ml, less than 20 mg/ml, less than 10 mg/ml, less than 5 mg/ml or less than 1 mg/ml for example. The parent molecule may be found to have a critical concentration of less than 50 mg/ml, less than 20 mg/ml, less than 10 mg/ml, less than 5 mg/ml or less than 1 mg/ml for example. The parent may exhibit undesirable aggregation in solution and/or may be unable to be concentrated above 1 mg/ml in solution without aggregating and/or precipitating. The parent may show non-specific binding to one or more non-target molecules. The parent may be identified as requiring improvement in binding to and/or dissociating from FcRn.

Optionally, bioinformatics assessment of the parent polypeptide sequence is performed to identify potential features of the sequence where mutation is predicted to reduce the identified developability issues and thus improve performance. Thus, one or more amino acid positions may be identified that are predicted to be associated with developability (e.g., solubility, self-association, non-specific binding).

Such bioinformatics assessment can be used to inform the mutation strategy. Thus, variants of the parent polypeptide sequence can be generated, optionally including mutation of the one or more amino acid positions identified in the bioinformatics assessment. Mutation may thus be performed at one or more amino acid residues of the polypeptide sequence of the parent binder that are predicted to promote self-association, aggregation and/or non-specific binding, and/or to reduce solubility. Mutation generates DNA encoding one or more variants of the parent sequence, which may be introduced into higher eukaryotic cells to generate a population of cells encoding the variant binders (methods for which are described herein). Cells may be cultured under conditions for expression of the binders, wherein the binders are presented on the cell surface. A plurality of cells expressing the binders may be used as a library as described herein and selections may be performed to identify clones having higher surface presentation of binders, as an indicator of improved developability characteristics.

In various examples as described herein, sequence analysis is used to identify potential problematic residues. Alternatively, random sequence variation can be used. Methods of generating variants and derivative libraries are described elsewhere herein. Individual variants can be are produced and assessed for improved biophysical characteristics. The ability to create large libraries of many such variants and select directly for improved characteristics such as resistance to self-aggregation would greatly facilitate the discovery of antibodies and other binders with optimal solubility properties. Since changes that benefit solubility can simultaneously diminish target binding, particularly if paratopic residues are involved[14], methods of the invention may combine selection for developability with selection for retained target binding. Such selections are optionally performed simultaneously, and methods for simultaneously or sequentially screening for affinity and solubility are described.

Methods of the invention comprising selection based on the level of surface presentation of binders may be used to identify variants having improved solution properties, as discussed. For example, a method of improving the developability characteristics of a "parent" binder (e.g., antibody) may comprise introducing mutations in the amino acid sequence of the binder to generate variants, introducing DNA encoding the variants into eukaryotic (e.g., mammalian) cells to provide a plurality of cell clones each containing DNA encoding a derivative antibody, introducing DNA encoding the parent binder into eukaryotic (e.g., mammalian) cells to provide a cell clone containing DNA encoding the parent, culturing the clones in vitro under conditions for presentation of the binders on the cell surface, determining surface presentation levels of the binders on the plurality of clones, selecting one or more clones that exhibit higher surface presentation of a derivative antibody compared with the clone expressing the parent, and identifying one or more variant binders encoded by the one or more selected clones as having improved developability characteristics compared with the parent antibody.

There is a relationship between propensity for self-interaction and propensity for non-target interaction. It has been found that a small number of amino acid changes (1-3) can have a beneficial effect on both aspects[6,7,14]. In other cases there may be limited self-interaction with evidence of low specificity. In either case, methods of the invention comprising selection for binders that exhibit lower non-specific binding may also be used. Thus, as discussed elsewhere herein, the system may be used to identify undesired non-specific interactions with other molecules, also referred to as "low specificity" and "polyspecificity". The present invention has the benefit of conducting such screening in the context of expression on higher eukaryotic cells, such as mammalian cells, with modifications such as glycosylation that more closely reflects that found in production cell lines typically used for production of the product used in the clinic. High presentation levels[23] of the polypeptide on the cell will increase the avidity of any interaction thereby serving to increase the sensitivity of the system in detecting low affinity undesired interactions. Furthermore, the surface of the higher eukaryote itself (or the environment of the endoplasmic reticulum and Golgi apparatus) can act as a matrix where the binder may be exposed, at relatively high concentrations, to a diversity of polypeptides allowing a binder with low specificity to interact with non-target molecules on the same or neighbouring cells. This in turn will lead to lower presentation levels. This may also lead to aggregation of the presenting cell with other cells in the population. The resulting cellular aggregates can be removed (e.g. by filtration or sedimentation) leading to depletion of such clones from the population. Removal of aggregated cells could also be used to reduce the representation of self-interacting clones.

In a further application, a host cell expressing unwanted targets from endogenous or exogenous genes could be used to deplete cross-reactive clones. For example endothelial cells expressing components of the glycocalyx or mammalian cells transfected with a gene of interest. Clones which bind to the target may be depleted based on low surface expression or cellular aggregation.

The value of the biophysical measurement at a single concentration of polypeptide may be compared between the starting clone and an improved clone generated using the invention. Alternatively the concentration at which a unwanted biophysical parameter is measured may be compared. Methods may comprise selecting variants exhibiting improvement in one or more desired developability characteristics, e.g., greater solubility, lower propensity for self-association in solution, lower non-specific binding to non-target molecules, higher critical concentration, etc. A fold difference or % difference may be measurable and example values are provided elsewhere herein. Comparison will usually be made to the parent binder. However, comparison between a variant polypeptide from a clone selected by the present invention and a comparator polypeptide deselected by the present invention could also be used to confirm and quantitate improvement when the present invention is used to select for other biophysical properties described herein.

Methods of Generating Variants and Derivative Libraries

Following any selection method described herein, DNA encoding displayed binders can be recovered from one or more selected cells, optionally mutated to generate variants, and/or sub-cloned e.g., to allow additional rounds of selection within a second display system. This could be another eukaryotic display system that results in a different level of surface presentation or could be an entirely different display system such as phage display. The second system may use secreted expression and/or may allow direct functional selection as previously described—see refs[52-54] and WO2015/166272. Alternatively the input DNA encoding binders could be a population of binders from an unselected library or a population derived from immunisation or another display technology such as yeast or phage display.

Accordingly, following production of a library by the method of the invention, one or more library clones may be selected and used to produce a further, second generation library. When a library has been generated by introducing DNA into eukaryotic cells as described herein, the library may be cultured to express the binders, and one or more clones expressing binders of interest may be recovered, for example by selecting binders against a target as described elsewhere herein. These clones may subsequently be used to generate a derivative library containing DNA encoding a second repertoire of binders.

In other instances it is desirable to generate variants of a parent binder, in order to provide a plurality of variants from which to select variants exhibiting improved developability characteristics.

To generate the derivative library, donor DNA of the one or more recovered clones is mutated to provide the second repertoire of binders. Similarly, to generate variants, DNA encoding the parent binder is mutated. Mutations may be addition, substitution or deletion of one or more nucleotides. Mutation will change the sequence of the encoded binder by addition, substitution or deletion of one or more amino acids. Mutation may be focused on one or more regions, such as one or more CDRs of an antibody molecule, providing a repertoire of binders of a common structural class which differ in one or more regions of diversity, as described elsewhere herein.

In general, manipulation and/or modification of nucleic acid sequences may be undertaken at the DNA or RNA level. Reference to DNA herein may thus be generalised to include equivalent other nucleic acid (e.g., RNA), unless the context requires otherwise. Provision, isolation or mutation of binder-encoding RNA is thus an alternative to the provision, isolation or mutation of binder encoding DNA. RNA is optionally used to generate cDNA.

Generating a derivative library may comprise isolating nucleic acid encoding the binder (e.g., isolating donor DNA, or its encoded RNA) from the one or more recovered clones, introducing mutation into the nucleic acid (e.g., DNA) to provide a derivative population of donor DNA molecules encoding a second repertoire of binders, and introducing the derivative population of donor DNA molecules into cells to create a derivative library of cells containing DNA encoding the second repertoire of binders.

Isolation of the binder-encoding nucleic acid (e.g., the donor DNA) may involve obtaining and/or identifying the DNA or RNA from the clone. Such methods may encompass amplifying the DNA encoding a binder from a recovered clone, e.g., by PCR and introducing mutations. DNA may be sequenced and mutated DNA synthesised.

Mutation may alternatively be introduced into the donor DNA in the one or more recovered clones by inducing mutation of the DNA within the clones. The derivative library may thus be created from one or more clones without requiring isolation of the DNA, e.g., through endogenous mutation in avian DT40 cells. Alternatively the gene encoding the binder may be present within the genome and mutagenesis carried out by introduction of oligonucleotides with short homology arms. It has been shown that transfection efficiencies of up to 45% have been achieved using single stranded oligonucleotides of 80 bp to repair a defective GFP gene (Igoucheva, O., Alexeev, V., Yoon, K., 2001. Targeted gene correction by small single-stranded oligonucleotides in mammalian cells. Gene Ther. 8 (5), 391-399[55], Liang, et al (2017). Enhanced CRISPR/Cas9-mediated precise genome editing by improved design and delivery of gRNA, Cas9 nuclease, and donor DNA. *J. Biotechnology,* 241, 136-146[56]).

Antibody display lends itself especially well to the creation of derivative libraries. Once antibody genes are isolated, it is possible to use a variety of mutagenesis approaches (e.g., error prone PCR, oligonucleotide-directed mutagenesis, chain shuffling) to create display libraries of related clones from which improved variants can be selected. For example, with chain-shuffling the DNA encoding the population of selected VH clone, oligoclonal mix or population can be sub-cloned into a vector encoding a suitable antibody format and encoding a suitably formatted repertoire of VL chains[57]. Alternatively and again using the example of VHs, the VH clone, oligomix or population could be introduced into a population of eukaryotic cells which encode and express a population of appropriately formatted light chain partners (e.g., a VL-CL chain for association with an IgG or Fab formatted heavy chain). The VH population could arise from any of the sources discussed above including B cells of immunised animals or scFv genes from selected phage populations. In the latter example cloning of selected VHs into a repertoire of light chains could combine chain shuffling and re-formatting (e.g., into IgG format) in one step.

Cell Surface Presentation of Binders

Retention of binders at the cell surface is a feature of display libraries as it provides a physical association between the binder and the encoding DNA, facilitating retrieval of the DNA following physical isolation of cells expressing binders with desired properties. Surface presentation (or simply "presentation") of binders may also be referred to as display or surface expression of binders. The level of surface presentation of a binder reflects its expression level and its retained presentation level following extended exposure to high concentrations on the surface of the cell. In methods described herein, the relative level of surface presentation of binders is compared across clones expressing different binders and is used to identify binders that have a lower propensity for self-association, greater solubility and that can be formulated into aqueous buffered solutions at concentrations suitable for pharmaceutical use. Thus presentation level can be used to select clones with desired properties. Surface presentation of binders on display libraries thus represents an in-built feature that can be used for selection of developability characteristics.

Various means of immobilisation at the cell surface can be employed. Binders may comprise or be linked to a membrane anchor, such as a transmembrane domain, for extracellular display of the binder. This may involve direct fusion of the binder to a membrane localisation signal such as a GPI recognition sequence or to a transmembrane domain such as the transmembrane domain of the PDGF receptor.[58]

Other methods of achieving retention of binder on the cell surface include indirect association of a binder with another cell surface retained molecule expressed within the same cell. This associated molecule could itself be part of a heterodimeric binder, such as tethered antibody heavy chain in association with a light chain partner that is not directly tethered. WO2015/166272 (incorporated herein by reference) describes a variety of techniques for retaining expressed binders on their host cells, including methods that allow a combination of secreted expression and membrane display. Thus, a proportion of the expressed binder may be retained at the cell surface while other copies of the same binder are secreted in soluble form from the same cell. Cells may retain a majority of binder (e.g., 80% or more, or 90% or more) presented on the cell surface, with the minority being secreted into the culture medium. Optionally, the binder is only retained at the cell surface and is not secreted in soluble form.

As illustrated in Example 1, the heavy chain of an antibody may be fused to the PDGFRTM domain and expressed together with its cognate light chain for surface presentation of full length immunoglobulins, e.g., IgG. The gene encoding the binder or polypeptide subunit thereof (e.g., antibody heavy chain) within the cell may comprise DNA encoding a leader sequence for secretion, via the endoplasmic reticulum (ER), to the cell surface. The binder-encoding gene may comprise DNA encoding a membrane anchor such as a transmembrane domain, e.g., a TM domain of a mammalian (e.g., human) protein. Alternatively, it may comprise DNA encoding an attachment signal for a post-translational membrane anchor such as a glycosylphosphatidylinositol (GPI) anchor. The C-terminal region of polypeptide binders is usually chosen for membrane anchor attachment or fusion of TM domains.

Methods of influencing the level of cell surface expression include controlling the level at which the binder is expressed from its encoding DNA, e.g., using promoters, and methods for this are described elsewhere herein. Surface expression level can alternatively be controlled by influencing the extent to which DNA encoding an expressed binder is spliced to an exon encoding a transmembrane domain, for instance as described in WO2015128509 (Glenmark Pharmaceuticals). This approach is also exemplified herein—see Example 8a and Example 8b, which describe expression systems that may be usefully employed in methods of the invention where varying levels of surface presentation of binders is desired.

In embodiments of the invention, binders are expressed in the cell and transported to the plasma membrane where they are retained at the cell surface as membrane proteins, e.g., a binder may comprise one or more polypeptides having at least one transmembrane domain or membrane anchor. For example, where the polypeptide binder comprises an antibody heavy chain (or part thereof) and an antibody light chain (or part thereof), and comprises a transmembrane domain or membrane anchor linked to the heavy and/or light chain, the binder is synthesised within the ER and budded off into the Golgi apparatus, from where it is transported to the cell surface in an intracellular vesicle which fuses with the plasma membrane, whereupon the binder is retained by virtue of its transmembrane domain or membrane anchor and is presented extracellularly. Integration of the binder into the membrane thus occurs within the cell, prior to transportation to the cell surface. Where applicable, assembly of multi-subunit binders (e.g., antibodies comprising separate heavy and light chains, or parts thereof) would also typically occur within the cell.

The level of cell surface presentation may be measured in terms of copy number (number of displayed binders per cell). A number of methods are available, including comparison to calibration beads and Scatchard plots of ligand concentration and receptor occupancy[59-61]. With the knowledge of the cell radius and certain assumptions about the available volume or surface area this can be used to estimate concentration or density respectively (Example 3). At the level of generality with which the present invention is concerned, copy number is related to the concentration achieved with higher concentrations found as the presentation level increases. The relationship between copy number and concentration on the cell surface is also affected by cell size. Presentation of the same number of binders on a small cell and a large cell will give rise to different concentrations since the antibodies will occupy a greater volume on the bigger cell (see example 3 comparing cell size and concentration achieved).

A great number of recombinant expression systems are available and the absolute number of displayed binders on the cell surface will vary between different systems. The skilled person will be able to calibrate methods of the invention as appropriate for the range of presentation levels observed when using different cells (e.g., of different sizes), different promoters, different induction mechanisms, different splicing mechanisms, transport efficiencies, etc. The following guidance is however provided by way of example.

With a weakly active promoter, binders may be presented on the cell surface at a copy number in the range of 100-100,000 per cell. The number of binders per cell may be at least 100, at least 1,000 or at least 10,000. The number of binders per cell may be up to 1,000, up to 10,000 or up to 100,000. In preferred embodiments, copy number is about 80,000 or less, about 60,000 per cell or less, about 50,000 per cell or less, or about 40,000 per cell or less. To facilitate detection, copy number may be at least 100, at least 1,000, or at least 10,000 per cell. Copy number may thus for example be in the range of 1,000-60,000 per cell. It may be about 10,000, about 50,000 or about 60,000.

With a strongly active promoter, binders may be presented on the cell surface at a copy number in the range of 100,000-10,000,000 per cell. The number of binders per cell may be at least 100,000 or at least 1,000,000. The number of binders per cell may be up to 1,000,000 or up to 10,000,000. It may be about 1,000,000.

Of course, there will be variation in the exact number of binders on different cells even for a single clone, although such variation in copy number between cells of a clone is minor compared with the inter-clonal copy number variation which is exploited by the selection and enrichment methods described herein. The example numbers and ranges represent approximate averages (means). The copy number may be the average (mean) copy number for cells in a population. Lower copy numbers are preferred when selecting for affinity, in order to increase the stringency of binding and enrich for high affinity clones, whereas higher copy numbers are preferred when selecting for developability, e.g., solution properties of the binders.

Copy number within a library of binder-expressing cells may range from relatively low (e.g., 10,000, 50,000, 100,000 or 250,000 copies per cell) to relatively high (e.g., 1,000,000 copies per cell). Copy numbers cited herein are a guide only, and are based on copy numbers observed in libraries of HEK cells in suspension culture, which have a radius in the order of 10 μm[95]. A polypeptide presented at a given density on the surface of a large cell will be at higher copy number than when presented at the same density on a small cell, so the absolute copy number observed in libraries generated from larger or smaller cells may vary accordingly. See Example 3b.

When conducting the methods of the invention, one will usually be interested in relative presentation levels as compared between clones, in which case it is not the absolute number of binders (absolute copy number per cell) that matters but rather the ability to rank or distinguish clones according to the different levels at which binders are displayed at the cell surface.

Surface presentation levels can be determined for a representative sample of clones from a library, and used to estimate the average (mode, mean or median) and spread (range) of surface presentation level present in clones of the library.

Any suitable method can be used to determine the level at which polypeptides are present on the cell surface, in order to compare their relative quantities. A preferred way to measure relative differences in binder presentation between cells is to expose the cells to an agent carrying a detectable (e.g., fluorescent) label, allow binding of the agent to the binders, and detect the relative quantities of label on cells, wherein a stronger signal from the detectable label (e.g., more fluorescence units) indicates a higher presentation level of binder on the cell. When the detectable label is fluorescent, sorting may be performed using a fluorescence activated cell sorter (FACS). Alternatively, or additionally with FACS, selection with magnetic beads can be used.

One will generally select an agent that binds to a constant region of the binders so that all binders can be equally labelled independent of their sequence. With antibodies and other binders that comprise an Fc region, it is convenient to label with an agent that binds the Fc region. For example, where the binders are IgG antibodies, cells may be contacted with a detectable agent that binds to the IgG Fc region, e.g., a labelled anti-IgG antibody. Adaptations of the method can be made where appropriate, e.g., where a library comprises binders that vary in the sequence of their Fc regions, an agent that binds a non-diverse part of the Fc or other region of the binder molecule can be employed. Peptide expression tags (e.g., hemagglutinin (HA), c-Myc) may be incorporated into a binder polypeptide (e.g., incorporated into an antibody scaffold), making it possible to detect displayed binders by detecting an agent bound to the tag. This has been described previously in the context of selecting correctly assembled antibodies in order to normalise the antigen-binding signal based on the antibody expression level[24,62]. Agents for detection of surface presentation level of binders may be used alone, i.e., without co-detection of or co-selection for other features such as antigen-binding or target specificity. Thus, in some embodiments, the step of detecting binder presentation level using an agent that binds a constant region of the binders does not include detecting binders using labelled target. In other embodiments, multiparametric selections may be performed. A wide range of surface presentation levels may be exhibited by binder-expressing clones of a library, reflecting a high level of inter-clonal variation. Surface presentation level can be plotted against the frequency with which that presentation level was observed, for a representative sample of cells from the library, e.g., following detection by FACS. Some embodiments of this are described in Example 10 with reference to and illustrated in FIG. 31. The median surface presentation level or the modal surface presentation level detected for the sample, and the spread of presentation levels and their deviation from the median or mode can be observed and/or calculated. Modal surface presentation can conveniently be visualised as the highest peak in a plot of surface presentation level against cell count.

The spread of surface presentation levels observed in a population of clones may be represented by the degree of variance from the modal value (mode). A population of clones may show wide variation in the level of surface presentation between clones, especially where the binders exhibit a large degree of variation in structure (e.g., different primary sequences), so that some clones display binders at much higher density than others. In some populations of clones the inter-clonal variation in the level of surface presentation may be lower, but nevertheless the present methods may be used to set a threshold presentation level and to distinguish higher presenting clones from lower presenting clones. One statistical measure of spread is the interquartile range, which is the difference between the upper quartile ($75^{th}$ percentile) and lower quartile (25th percentile). The copy number at the $75^{th}$ percentile (represented as the lower boundary of the upper quartile) may differ from that at the $25^{th}$ percentile (represented by the upper boundary of the lower quartile) by at least 1.5-fold, at least 2-fold, at least 2.5-fold, at least 3-fold, at least 3.5-fold, at least 4-fold, at least 4.5-fold or at least 5 fold.

In some embodiments, the range of surface presentation levels, and the fold-difference in surface presentation between the reference points mentioned above, may be observed to decrease with each round of selection for surface presentation level, as the population of cells is progressively enriched for clones with high surface presentation of binders. In some embodiments, the mode may be observed to progressively increase with each enrichment for higher surface presentation. Following selection, methods of determining or observing increase in surface presentation level in a population of binders may comprise determining or observing an increase in the average (e.g., median or modal) copy number as measured e.g., by FACS or similar method described herein. A selected population (or a clone thereof) may be observed to have an average surface presentation level that is higher than that of the unselected population or of a clone expressing a comparator polypeptide, e.g., than that of a clone expressing the parental binder from which the population was derived. For example the modal or median copy number for the selected clone or selected population may be at least 5%, at least 10%, at least 20% or at least 25% higher than that of the comparator or parent—and that clone may be selected on the basis of that improvement in surface presentation level.

To select clones expressing higher surface presentation of binders, or to select a population of clones enriched for clones encoding binders exhibiting higher surface presentation, cells can be sorted into a collected fraction and a discarded fraction according to the level of surface presentation of binders on the cells. Cells having surface presentation above a pre-determined threshold are sorted into the collected fraction and cells having surface presentation below the pre-determined threshold are sorted into the discarded fraction. Surface presentation is optionally the sole basis on which the selection/enrichment is performed during this step. This can be facilitated by using a detectable agent that labels all binders, optionally in the absence of detecting target recognition by the binders.

By discarding a fraction of cells exhibiting the lower surface presentation of binders, clones expressing binders having poor developability characteristics are depleted from the population. Selection of all or a fraction of the remaining cells provides a selected population of cells enriched for clones expressing binders having higher surface presentation of binders compared with other clones. The selected cells, clones or population can thus be identified as having better developability characteristics compared with the starting population or library and compared with the non-selected cells, clones or population.

As noted above, the absolute number of binders on a cell surface will vary, and the skilled person will determine the threshold suitable for the system in use. For example, the threshold may be pre-determined to select a particular percentage of clones within the population expressing the highest surface presentation of binders, e.g., based on an initial test sample of the library. The threshold may be set to select e.g., the top 50% of cells, the top 30%, top 25%, top 20%, top 15%, top 10% or top 5%.

Having determined surface presentation levels for a representative sample of cells from a library, and having observed or calculated the mode, median, spread and/or interquartile range of copy number for the sample, an appropriate threshold copy number can be set. For use of FACS, this will correspond to threshold fluorescence intensity per cell, e.g., if the FACS threshold for collection of cells is set to collect cells of the library having a median fluorescence intensity corresponding to the mode of the sample, then cells having that level of fluorescence or above will be collected. For even greater enrichment of surface presentation levels, the FACS threshold for collection of cells may be set to collect cells of the library having a fluorescence intensity corresponding to that of the $75^{th}$ percentile of cells in the sample.

The threshold may represent a number of binders presented per cell of at least about 100,000, at least about 500,000 or at least about 1,000,000.

Selection and Enrichment

Selecting clones, selecting cells or selecting a population may comprise physically separating the clones, cells or population from other clones or cells or from a wider population or library. The selected clones, cells or population may be provided in isolated form.

Where selection comprises physical separation of multiple cells or clones, this will typically comprise generating a collected fraction and a discarded fraction. The collected fraction will be enriched for clones displaying binders with characteristics that have been selected for in the method. Enrichment means that the relative abundance of these clones in the population is increased. Enrichment is relative to the pool of cells or clones before the selection step, e.g., the library or starting population. By discarding a fraction of cells during selection (e.g., cells exhibiting lower surface presentation of binders, cells with lower affinity, etc.) clones expressing binders having less desirable characteristics (e.g., poor developability characteristics) are excluded. Thus, the relative abundance of cells/binders with less desirable characteristics is reduced in the population as a result of the selection step. All or a fraction of the selected cells (collected fraction) may be taken forward into further selection methods if desired, and optionally one or more clones are selected for individual culture in isolation. Optionally one or more selected cells or binders or a selected population may be used for creation of a derivative library as described elsewhere herein.

In selecting a collected fraction of clones, the operator of the method may take a set percentage or fraction of the "top" or "best" clones. Embodiments of this principle have been discussed in detail with reference to selection for high surface presentation. It is to be understood that the same principles apply when selecting for other characteristics, such as binding to a target or non-target molecule. Thus, when selecting for clones expressing binders that recognise a target (e.g., affinity selections), the operator may select a set percentage or fraction of clones exhibiting the highest binding to target (e.g., as measured by quantity of detectable label bound to the clones in a method using labelled target). When selecting for clones expressing binders that show reduced (or absent) non-specific binding to a non-target molecule, the operator may select a set percentage or fraction of clones exhibiting the lowest binding to the non-target molecule (e.g., as measured by quantity of detectable label bound to the clones in a method using labelled non-target molecule, such as any of the various polyreactivity probes mentioned herein). In general, when selecting positively for "good" characteristics (e.g., surface presentation level, affinity for target), one will be selecting for clones exhibiting higher levels of that characteristic relative to other clones, whereas when selecting against "bad" characteristics (e.g., non-specific binding), one will be selecting clones exhibiting lower levels of that characteristic relative to other clones.

As discussed elsewhere herein, selection thresholds may be determined by the operator according to the situation in hand and may be guided by an initial assessment of a sample of the population (e.g., representative sample of clones from a library). The threshold may be set to enrich for clones with the highest level of signal, e.g., the top 50% of cells, the top 30%, top 25%, top 20%, top 15%, top 10% or top 5% in the case of a desired characteristic (e.g., based on quantity of detectable label bound, representing level of surface presentation or level of target binding, or based on inter-particle distance as determined by AC-SINS, or based on monomeric proportion in solution). The selected top % of clones become the collected fraction while others are discarded. In selections against undesirable characteristics, e.g., based on quantity of detectable label bound to a polyreactivity probe, or extent of retardation on a matrix to detect non-specific binding, the threshold may be set to enrich for clones with the lowest level of signal, e.g., to select a percentage of clones (e.g., 50%, 30%, 25%, 20%, 15%, 10% or 5%) exhibiting the lowest quantity of detectable label bound, or the lowest degree of retardation on a matrix. The example % for collection are of course guidelines only, and numerical exactness is unimportant provided that the operator adheres to the principles of the method.

Quantifying and Measuring Differences

Various methods of the invention involve comparing properties of binders and/or their encoding clones, e.g., for properties such as presentation level, binding, concentration (e.g., critical concentration), solubility limit, and so on. Methods may comprise identifying binders that are better as compared with other binders in a population (e.g., as compared with one or more others or as compared with the population average (mean)), and/or that are improved in one or more characteristics relative to a parent molecule from which they are derived. Comparison may also be made to a benchmark binder—in the example of antibodies this may be the NIST RM 8671 antibody (Saro D et al, Developability Assessment of a proposed NIST monoclonal antibody[37]). Desirable properties for selection and improvement are discussed elsewhere herein and include greater solubility, greater critical concentration, lower non-specific binding, and/or higher affinity for target. Relative terms such as "greater" or "lesser", "higher level" or "lower level", "better" or "poorer", "more" or "less" generally refer to differences observed in the relevant experimental context that allow binders or clones to be distinguished based on their properties. Differences may be statistically significant. Differences may optionally be quantified in % terms, e.g., a difference of at least 10%, at least 25%, or at least 50%. Alternatively fold-difference can be considered, e.g., at least 1.5×, at least 2×, at least 3×, at least 5×, at least 10×, at least 20× or at least 100×.

Target Binding

Binders may be selected for binding to a target molecule of interest, which may optionally be another polypeptide such as a receptor, enzyme and/or a disease-associated polypeptide such as a tumour-associated antigen. Other target molecule classes include nucleic acids, carbohydrates, lipids and small molecules. Exemplary binders and targets are detailed elsewhere herein. A classic example is a library of antibody molecules, which may be screened for binding to a target antigen of interest. Other examples include screening a library of TCRs against a target MHC:peptide complex or screening a library of MHC:peptide complexes against a target TCR.

Selecting for clones that encode binders that recognise a target (cognate binders) may comprise contacting a display library as described herein with the target, thereby exposing binders to the target, allowing recognition of the target by cognate binders (if present), and detecting whether the target is recognised by a cognate binder. One or more clones displaying cognate binders may then be selected.

The target may be provided in soluble form. The target may be labelled to facilitate detection, e.g., it may carry a fluorescent label or it may be biotinylated. Cells expressing a target-specific binder may be identified using a directly or indirectly labelled target molecule, where the binder captures the labelled molecule. For example, cells that are bound, via the binder:target interaction, to a fluorescently labelled target can be detected and sorted by flow cytometry to isolate the desired cells. Selections involving cytometry require target molecules which are directly fluorescently labelled or are labelled with molecules which can be detected with secondary reagents, e.g., biotinylated target can be added to cells and binding to the cell surface can be detected with fluorescently labelled streptavidin such as streptavidin-phycoerythrin. A further possibility is to immobilise the target molecule or secondary reagents which bind to the target on a solid surface, such as magnetic beads or agarose beads, to allow enrichment of cells which bind the target. For example cells that bind, via the binder: target interaction, to a biotinylated target can be isolated on a substrate coated with streptavidin, e.g., streptavidin-coated beads. Magnetic beads are convenient for capture of cells which have bound to biotinylated antigen, by magnetic recovery of the beads. The optimal target concentration may be pre-determined or may be determined empirically by using a range of concentrations and comparing to background controls.

Methods of selecting for binding to a target may comprise sorting cells into a collected fraction and a discarded fraction according to the level of bound target on the cells, whereby cells having bound target above a pre-determined threshold are sorted into the collected fraction and cells having bound target below the pre-determined threshold are sorted into the discarded fraction. The threshold may be set relative to negative control cells that do not display cognate binders. In FACS a negative control peak will typically be observed when sorting cells displaying cognate and non-cognate binders. The threshold may be set so that all cells displaying fluorescence at a level that is statistically significantly higher than the negative control are sorted into the collected fraction, or a higher threshold may be chosen to achieve greater confidence in selection of cognate binders and greater enrichment for clones displaying cognate binders. As already discussed with reference to determination of cell surface presentation of binders, calibration may be performed using a sample of cells to determine suitable threshold values. Enrichment of binders from non-binders can be achieved. Methods of enriching for higher affinity binders are further described elsewhere herein.

Selection against a target may be incorporated as an additional step before or following, or included within, other methods of the invention. Construction of a library of variants by mutagenesis of a starting domain to improve aspects of developability such as solubility or low specificity or optimal FcRn binding, may in some library members compromise binding to target (e.g. if mutagenesis of contact CDRs is carried out). For example, clones selected for binder presentation level may subsequently be selected against a target. Simultaneous determination of surface presentation level and target binding is also possible, using co-selection of clones displaying cognate binders at high surface presentation levels. Such methods may comprise the use of an agent incorporating a detectable label for determining binder presentation level as described elsewhere herein, and may further comprise exposing the binders to the target wherein the target is labelled with a second agent incorporating a second detectable label to enable detection of target binding. Where fluorescent labels are used, FACS may be used to sort the cells simultaneously for both binder presentation and target recognition. Labels may be chosen that fluoresce at different wavelengths to enable their different signals to be distinguished.

Thus, methods of the present invention may comprise co-detection of binder presentation level and target binding level, using different detectable labels for each. In other embodiments, target binding is detected in the absence of determining binder presentation levels on the cells, e.g., the step of detecting binders using labelled target does not include detecting binder presentation level using an agent that binds a constant region of the binders.

Following detection of target recognition by a cognate binder, cells of a selected clone containing DNA encoding the cognate binder may be recovered. DNA encoding the binder may then be identified, amplified and/or provided in isolated form, thereby obtaining DNA encoding a binder that recognises the target.

Multiple Selections

The idea of performing multiple selections in parallel can be extended to co-sorting of cells based on any two or more characteristics described herein. In the discussion above, simultaneous co-selection of cells is performed by simultaneously determining surface presentation levels of the binders and levels of target binding by the binders, and co-selecting clones displaying cognate binders exhibiting higher surface presentation. Other methods of the invention can also be employed in parallel. Methods may comprise simultaneously determining any two or more of:

(i) surface presentation levels
(ii) levels of non-specific binding to non-target molecules
(iii) levels of target binding,
(iv) level of FcRn binding, and co-selecting clones accordingly. FACS enables parallel selection to be performed using multiple labels emitting fluorescence at different wavelengths.

Advantages and synergies may be obtained by performing multiple types of selections in series or in parallel, e.g., combining selection for solubility with selection against non-specific binding. Each selection that is applied to the population of clones in the library generates an evolutionary pressure in favour of variants that meet that selection criterion (e.g., high surface presentation level). Repeated selection for a single parameter may drive evolution towards this characteristic (e.g., high solubility) at the expense of other qualities (e.g., affinity for target binding) which are at risk of being depleted or lost[31]. This can occur for example when mutations that increase solubility also reduce affinity. Judicious combination of selection methods may steer the evolution of the population towards clones that express polypeptides with multiple desired characteristics, allowing the identification of polypeptides that perform optimally (or at least acceptably) across the full range of requirements demanded of the polypeptide drug.

Selection against non-specific binding may be performed before or after selection for increased surface presentation level. For example, one may perform a method of distinguishing or ranking binders according to their solubility and/or resistance to self-association in solution, and/or enriching for binders exhibiting greater solubility and/or greater resistance to self-association in solution, resulting in a selected a population of clones, and then screen the selected population for clones expressing binders that exhibit a low propensity to bind one or more non-target molecules, thereby identifying one or more clones that express binders which also have low non-specific binding.

In some embodiments, screening for non-specific binding can be integrated simultaneously with screening for surface presentation level. For example, dual exposure of cells to (i) an agent for binding all presented binders, carrying a detectable label (e.g., fluorescently labelled anti-Fc) and (ii) one or more non-target molecules (e.g., heparin or other molecule to which non-specific binding is to be avoided) carrying a different detectable label (e.g., of different fluorescent wavelength) can be performed. Dual staining of the clones allows clones to be distinguished on the basis of both surface presentation level and non-specific or off-target binding. Sorting thresholds may be set to collect cells exhibiting greater surface presentation levels and lower binding to the non-target molecule. This will eliminate, or at least reduce the prevalence of, antibodies with poor developability in selected clones.

Similarly, selection against binding to non-target molecules (e.g., heparin or other molecule to which non-specific binding is to be avoided) can be combined with selection for FcRn binding in methods described herein.

In some situations, selecting for one characteristic (e.g., selecting for high level of surface presentation) will enrich for binders that have multiple beneficial qualities, as a result of the inter-linking of certain aspects of developability. For instance, some clones may express polyreactive binders that interact with non-target molecules (e.g., proteoglycans) on the cell surface—e.g., they may bind non-specifically to heparin. In a higher eukaryotic cell display system, the binder-expressing cell clones themselves may express the same or similar non-target molecules (e.g., proteoglycans endogenous to the cell), a resulting effect being that a surface-displayed binder interacts non-specifically with one or more molecules on the cell on which it is displayed. This may lead to the binder being internalised within the cell, thus exhibiting a lower level of surface presentation, resulting in de-selection of its expressing clone. In such a case, selecting clones that display higher levels of surface presentation of binders will enrich or select in parallel for clones expressing binders that have better developability qualities on multiple fronts, e.g., being both more soluble and less prone to non-specific binding.

A different example of this is that by enriching for binders that have a lower propensity for self-aggregation, methods may promote selection of binders that will show a lower degree of immunogenicity in vivo, by excluding from selection those binders that would tend to form immunogenic aggregates if used in pharmaceutical formulations.

On top of this, as noted, further dimensions of parallel selection can be incorporated by including further labelled detection agents, e.g., labelled FcRn, labelled target, other labelled polyreactivity probe. The ready availability of a range of different labels (e.g., fluorophores of different wavelengths), and the ability of FACS machines to conduct multiplex detection and sorting, can assist the design of such parallel selections.

Affinity Selection

In selecting binders to a target it is often useful to be able to select binders based on affinity, allowing enrichment for clones expressing binders having a high affinity for target binding.

Affinity is commonly expressed as $K_D$, the equilibrium dissociation constant. $K_D$ is the ratio of k(off)/k(on) for the interaction between a binder and its target (e.g., between the antibody and its antigen). The $K_D$ value relates to the concentration of binder and so the lower the $K_D$ value (lower concentration) the higher the affinity of the binder. A binder that specifically recognises its target, in the manner of an antibody recognising its antigen, may be referred to as a cognate binder. Recognition of a target by a cognate binder is desirably a high affinity interaction. $K_D$ of binder:target interaction may be less than 1 μM, preferably less than 10 nM.

Methods of the invention may comprise enriching populations of cells for those encoding (and presenting) higher affinity binders to a target. Stringency of selection can be enhanced by using eukaryotic cells on which binders are presented at relatively low copy number, to drive selection for affinity. Methods of selecting binders that bind to a target of interest may employ libraries of higher eukaryotic cell clones each containing DNA encoding a binder, wherein the binder is presented on the cell surface, wherein the encoded binder is expressed from a weakly active promoter and/or expressed on the cell surface at a relatively low copy number. This may be from expression driven from a weakly active promoter or as a result of transcript instability or non-optimal splicing, translation, transport to the surface, or retention on the cell surface.

The presentation of a dense suspension of higher eukaryotic cells (e.g. $10^7$/ml with a high level of surface presentation (e.g. $6\times10^5$ binding sites/cell presents a relatively high concentration of antibody (10 nM in this example). In that situation, even when a low concentration of antigen is used in an attempt to drive the stringency of a selection e.g. 0.1 nM, the high concentration of antibody will drive association limiting the relative enrichment between high and low affinity clones (see Example 8a and Example 8b). An input concentration of binder of 1 nM or less would be preferred. Even if cell density was lower, there is a potential problem of target rebinding in the presence of a high density of immobilised binder. This problem is particularly well recognised and documented in surface based affinity measurement such as surface plasmon resonance (BIAcore manual) and would have the effect of reducing differential binding between a high and a low affinity clone. Thus copy number may for example be in the range of 100-100,000 per cell. In preferred embodiments, copy number is about 60,000 per cell or less, optionally about 50,000 per cell or less, or about 40,000 per cell or less. To facilitate detection, copy number may be at least 100, at least 1,000, or at least 10,000 per cell. Copy number may thus for example be in the range of 1,000-60,000 per cell. Copy number and methods of determining copy number in the context of surface presentation of binders are discussed elsewhere herein.

The library is exposed to the target (e.g., by adding the target to a suspension of cells expressing binders of the library), contacting the binders with the target and thus allowing recognition of the target by cognate binders, if present. Cells displaying cognate binders become bound to the target. By using a limited concentration of target, higher affinity binders are preferentially bound by the target. Cells displaying binders that do not recognise the target or which recognise the target with lower affinity will not bind the target or will display fewer molecules of target per cell, compared with cells displaying higher affinity binders. Cells bound to the target can then be isolated, thereby selecting a population of cells that is enriched for cells displaying cognate binders.

The selection procedure can optionally be repeated using decreasing concentrations of target, to progressively increase stringency of selection and increase the degree of enrichment for higher affinity clones. Mutation may be introduced in binders of a selected population to generate variants, prior to further enrichment for high affinity binders. Generation of derivative libraries is described elsewhere herein.

The concentration of target used may be below the $K_D$ of interaction of the binders that are sought to be isolated by the method.

One or more clones having a desired affinity for the target can then be selected, and optionally the encoding DNA can then be recovered and the binder expressed from individually cultured recombinant cells, as described elsewhere herein.

To achieve the low level of surface presentation on cells, binder genes may be expressed at low level, for example operably linked to a weakly active promoter or as a result of transcript instability or non-optimal splicing, translation, transport to the surface, or retention on the cell surface. Inducible promoters and other controllable expression systems are described in detail elsewhere herein. See for instance Example 8a or Example 8b.

Libraries

A collection of cell clones, each containing recombinant DNA encoding a binder, together form a library. Diversity of the library is a function of the number of different binders encoded by the clones. In drug discovery it is advantageous to provide large, diverse libraries to maximise the potential for identifying a binder that meets all desired criteria. Each clone of a library may be generated by integrating DNA encoding a binder into cellular DNA to form a recombinant cell, as described elsewhere herein. DNA may be introduced into many cells in parallel to generate a population of recombinant cells, each encoding at least one binder from a diverse repertoire. Following integration of donor DNA into the cellular DNA, the resulting recombinant cells are cultured to allow their replication, generating a clone of cells from each initially-produced recombinant cell. Each clone is thus derived from one original cell into which donor DNA was integrated (e.g., at an integration site created by a site-specific nuclease or by other methods as described herein). A library according to the present invention may contain at least 100, $10^3$, $10^4$, $10^5$, $10^6$, $10^7$, $10^8$, $10^9$ or $10^{10}$ clones.

A library in accordance with the present invention may have any one or more of the following features:

Diversity. A library may encode and/or express at least 100, $10^3$, $10^4$, $10^5$ $10^6$, $10^7$, $10^8$ or $10^9$ different binders. Binders of varying sequence make up the repertoire.

Uniform integration. A library may consist of clones containing donor DNA integrated at a fixed locus, or at a limited number of fixed loci in the cellular DNA. Each clone in the library therefore preferably contains donor DNA at the fixed locus or at least one of the fixed loci. Preferably clones contain donor DNA integrated at one or two fixed loci in the cellular DNA. As explained elsewhere herein, the integration site can be at a recognition sequence for a site-specific nuclease. Integration of donor DNA to produce recombinant DNA is described in detail elsewhere herein and can generate different results depending on the number of integration sites. Where there is a single potential integration site in cells used to generate the library, the library will be a library of clones containing donor DNA integrated at the single fixed locus. All clones of the library therefore contain the binder genes at the same position in the cellular DNA. Alternatively where there are multiple potential integration sites, the library may be a library of clones containing donor DNA integrated at multiple and/or different fixed loci. Preferably, each clone of a library contains donor DNA integrated at a first and/or a second fixed locus. For example a library may comprise clones in which donor DNA is integrated at a first fixed locus, clones in which donor DNA is integrated at a second fixed locus, and clones in which donor DNA is integrated at both the first and second fixed loci. In preferred embodiments there are only one or two fixed loci in the clones in a library, although it is possible to integrate donor DNA at multiple loci if desired for particular applications. Therefore in some libraries each clone may contain donor DNA integrated at any one or more of several fixed loci, e.g., three, four, five or six fixed loci.

For libraries containing binder subunits integrated at separate sites, clones of the library may contain DNA encoding a first binder subunit integrated at a first fixed locus and DNA encoding a second binder subunit integrated at a second fixed locus, wherein the clones express multimeric binders comprising the first and second subunits.

Uniform transcription. Relative levels of transcription of the binders between different clones of the library is kept within controlled limits due to donor DNA being integrated at a controlled number of loci, and at the same locus in the different clones (fixed locus). Relatively uniform transcription of binder genes leads to comparable levels of expression of binders on or from clones in a library. Binders displayed on the surface of cells of the library may be identical to (having the same amino acid sequence as) other binders displayed on the same cell. The library may consist of clones of cells which each display a single member of the repertoire of binders, or of clones displaying a plurality of members of the repertoire of binders per cell. Alternatively a library may comprise some clones that display a single member of the repertoire of binders, and some clones that display a plurality of members (e.g., two) of the repertoire of binders. Preferably clones of a library express one or two members of the repertoire of binders.

For example, a library of eukaryotic cell clones according to the present invention may express a repertoire of at least $10^3$, $10^4$, $10^5$ $10^6$, $10^7$, $10^8$ or $10^9$ different binders, e.g., IgG, Fab, scFv or scFv-Fc antibody fragments, each cell containing donor DNA integrated in the cellular DNA. The donor DNA encodes the binder and may further comprise a genetic element for selection of cells into which the donor DNA is integrated. Cells of the library may contain DNA encoding an exogenous site-specific nuclease.

Binders displayed on the surface of cells of the library may be identical to (having the same amino acid sequence as) other binders displayed on the same cell. The library may consist of clones of cells which each display a single member of the repertoire of binders, or of clones displaying a plurality of members of the repertoire of binders per cell. Alternatively a library may comprise some clones that display a single member of the repertoire of binders, and some clones that display a plurality of members (e.g., two) of the repertoire of binders. Accordingly, a library according to the present invention may comprise clones encoding more than one member of the repertoire of binders, wherein the donor DNA is integrated at duplicate fixed loci or multiple independent fixed loci.

It is easiest to identify the corresponding encoding DNA for a binder if the corresponding clone expresses only one binder. Typically, a molecule of donor DNA will encode a single binder. The binder may be multimeric so that a molecule of donor DNA includes multiple genes or open reading frames corresponding to the various subunits of the multimeric binder.

As noted, a library according to the present invention may encode at least 100, $10^3$, $10^4$, $10^5$ or $10^6$, $10^7$, $10^8$, $10^9$ or $10^{10}$ different binders. Where the binders are multimeric, diversity may be provided by one or more subunits of the binder. Multimeric binders may combine one or more variable subunits with one or more constant subunits, where the constant subunits are the same (or of more limited diversity) across all clones of the library. In generating libraries of multimeric binders, combinatorial diversity is possible where a first repertoire of binder subunits may pair with any of a second repertoire of binder subunits.

These and other features of libraries according to the present invention are further described elsewhere herein, and examples of suitable libraries and methods for their construction and use are also set out in WO2015/166272 (Iontas Limited), the content of which is incorporated herein by reference. Suitable loci may be identified for targeted integration of encoding DNA into cell chromosomes, and several examples are known in the art. The AAVS locus may be used as exemplified herein. Other suitable integration sites include the ROSA26, HPRT and FUT8 loci (e.g., within CHO cells). Although targeted integration can have advantages, random integration is a suitable alternative and may be used in many situations. Apart from nuclease-mediated targeted integration, methods of generating libraries of surface-expressed polypeptides include transfecting eukaryotic cells with vectors encoding the polypeptides, e.g., using lentivirus, adenovirus, adeno associated virus, or transposons, or using genomically embedded recombinase sites such as Flp, Bxb2 recombinase, or endogenous cryptic recombinase sites such as phi recombinase sites. Libraries created by these or any other technique may be employed in the methods described herein. The present invention extends to the library either in pure form, as a population of library clones in the absence of other eukaryotic cells, or mixed with other eukaryotic cells. Other cells may be eukaryotic cells of the same type (e.g., the same cell line) or different cells. Further advantages may be obtained by combining two or more libraries according to the present invention, or combining a library according to the invention with a second library or second population of cells, either to facilitate or broaden screening or for other uses as are described herein or which will be apparent to the skilled person.

A library according to the invention, one or more clones obtained from the library, or host cells into which DNA encoding a binder from the library has been introduced, may be provided in a cell culture medium. The cells may be cultured and then concentrated to form a cell pellet for convenient transport or storage.

Libraries will usually be provided in vitro. The library may be in a container such as a cell culture flask containing cells of the library suspended in a culture medium, or a container comprising a pellet or concentrated suspension of eukaryotic cells comprising the library. The library may constitute at least 75%, 80%, 85% or 90% of the eukaryotic cells in the container. Selection steps may be performed on libraries in mixed culture, thus facilitating a high throughput.

As an alternative to co-culturing a mixture of clones of a library, it may sometimes be convenient to individually culture clones, each in their own separate flask or other vessel. Individual cultures may be used where a relatively small number of clones is being compared, such as where a parent binder has been mutated to generate one or more variants (e.g., up to 10 variants) and the invention is being used to compare the qualities of the variants relative to the parent and/or each other.

The selection methods described herein may be applied to naïve libraries, i.e., libraries that have not undergone affinity-based selection. Methods may thus be used to enrich a library for clones that have higher solubility and/or lower non-specific binding (conversely depleting the library in clones that exhibit low solubility and/or higher non-specific binding), prior to performing any affinity-based selection. Such a library, which has been "pre-selected" for more developable clones, is then highly suitable for performing affinity-based selection using a target of interest. Clones obtained in the affinity-selection step are more likely to exhibit good solubility, high critical concentration, low non-specific binding and/or other developable qualities, compared with clones selected from a library which had not been pre-screened for developability.

Eukaryotic Cells

Eukaryotic cells according to the present invention are preferably higher eukaryotic cells, defined here as cells with a genome greater than that of *Saccharomyces cerevisiae* which has a genome size of $12\times10^6$ base pairs (bp). The higher eukaryotic cells may for example have a genome size of greater than $2\times10^7$ base pairs. This includes, for example, mammalian, avian, insect or plant cells. Eukaryotic cells of the present invention preferably lack a cell wall. Preferably they are not yeast cells or other fungal cells. Preferably the cells are mammalian cells, e.g., mouse or human. The cells may be primary cells or may be cell lines. Chinese hamster ovary (CHO) cells are commonly used for antibody and protein expression but any alternative stable cell line may be used in the invention. HEK293 cells are used in several Examples herein.

The display of binders using higher eukaryotes, such as mammalian cells, has advantages since the manufacture of antibodies for research, diagnostic and therapeutic application is typically carried out in these cells. Conducting drug discovery on mammalian cells exhibiting the same expression environment and the same post-translation modifications will give a better indication of potential issues or benefits for downstream manufacturing allowing early identification of clones with optimal expression properties. Bacterial and yeast cells in contrast do not fully recapitulate the glycosylation, expression and secretion machinery of higher eukaryotes. Thus display on mammalian cells could help identify clones with better presentation levels or stability properties with implications for future research use or downstream manufacturing. The ability to display large libraries of antibodies on the surface of mammalian cells will allow the screening of millions of clones directly for binding and presentation properties with the potential to use manufacturing cell lines during the discovery phase of antibody development.

The CHO cell line was originally isolated in 1957[63] and derivatives of this cell line have become the production cell line for the majority of therapeutic antibodies[64]. For example, Herceptin (the anti-HER-2 antibody approved for treating breast cancer) is produced at more than one metric ton per year by expression in CHO cells. Compared with human cells, CHO cells have an advantage for producing products for administration to humans because they do not propagate most human pathogenic viruses. In addition, they allow integration of foreign DNA into their genomes and grow quickly and robustly. The properties of antibodies and other polypeptide binders, including biophysical properties, stability pharmacokinetics and immunogenicity, can be affected by their post-translational modifications such as glycosylation[65], which are acquired within the secretory pathway of cells such as the endoplasmic reticulum (ER) and Golgi apparatus. Here monosaccharide units such as mannose (Man), galactose (Gal), fucose (Fuc), N-acetylglucosamine (GlcNAc), N-acetylgalactosamine (GalNAc) and sialic acids are covalently attached to specific amino acids. "O-linked" or "N-linked" glycosylation refers to either glycans attached to the oxygen atom of serine or threonine residues or glycans attached to the amide nitrogen atom of asparagine residues. Complexity in the glycosylation can be introduced by the glycosylation being either linear or branched and the atomic positions and conformation of the glycosidic linkage (e.g. $\alpha$ or $\beta$) at various position within the monosaccharide unit. The precise nature of antibody glycosylation profiles can be affected by the host cell line used for expression[65]. It is therefore an advantage during antibody and therapeutic protein screening to produce the recombinant protein in a host cell line which is as close as possible to the final production cell line. This ensures that the post-translational modifications of the polypeptides to be screened, and therefore their properties, are identical, or as similar as possible, to those that will be acquired during their large-scale manufacture. Since the majority of human therapeutic antibodies are produced in CHO cells it therefore an advantage to perform higher eukaryotic display in a CHO host cell line. Example 12 demonstrates developability-based selection of candidate polypeptide drugs in a CHO cell library.

In methods and uses of the present invention generally, the plurality of cell clones may be a library of at least 1000 clones, optionally cultured together in the same culture medium within a single vessel. It may be a naive library, i.e., one that encodes a repertoire of binders that has not previously undergone selection for binding to a target. This will often be the case in early stage discovery, although it may be desirable to use a library encoding a repertoire of binders that are the result of one or more previous rounds of selection for binding to a target. For example, the selection output of a phage display library may be introduced into the eukaryotic cell library.

The invention is described in the present specification with particular reference to mammalian cells, and mammalian cells were used to illustrate the invention in the Examples. However, unless the context requires otherwise, it should be understood that other higher eukaryotic cells may be used instead. For example, insect or chicken cells may be used.

Binders

A "binder" in accordance with the present invention is a binding molecule, representing a specific binding partner for another molecule. Typical examples of specific binding partners are antibody-antigen and receptor-ligand. Many principles of the invention extend to polypeptides that may not classically be regarded as "binders", such as enzymes, co-factors, clotting factors and their inhibitors, complement factors and their inhibitors and so forth. In many cases such polypeptides represent candidate clinical drugs which it is desirable to produce at large scale and/or to provide at high concentrations. Their developability qualities are therefore a significant consideration. For example, factor VIII is used in haemophilia but has considerable developability issues. Aspects of the invention relating to developability can be applied to all such polypeptides. Thus, unless the context requires otherwise, the invention should not be interpreted as being limited to classical specific binding molecules like antibodies, and should be understood as extending generally to polypeptides that are designed to interact with one or more other molecules.

The present invention is concerned with binders that are polypeptides, i.e., polymers of amino acids, expressed from encoding DNA in a cell and optionally subject to post-translational modifications such as cleavage, glycosylation and so on. Binders may comprise short peptides of around e.g., 10 to 30 amino acids. Binders may also be longer polypeptides and may optionally comprise multiple subunits.

Binders preferably comprise polypeptides of mammalian, e.g., human, origin. The binders may comprise human antibodies (optionally chimeric antigen receptors (CARs) comprising human antibodies), human TCRs or other receptors, or other human polypeptides. Binders may be soluble peptides or polypeptides (e.g., cytokines, chemokines, complement proteins or complement regulators, enzymes (including enzymes for industrial use), blood clotting factors e.g., factor VIII). Binders may be mammalian (e.g., human) membrane proteins, or may be soluble mammalian (e.g., human) proteins/peptides that have been engineered to comprise one or more TM domains or other membrane anchors. Binders may be native, naturally occurring polypeptides, or (frequently) will be synthetic variants. For example, a library of human factor VIII polypeptides may comprise binders having at least 70% amino acid sequence identity with human factor VIII (e.g., at least 80%, or at least 90%).

The repertoire of binders encoded by a library will usually share a common structure and have one or more regions of diversity. The library therefore enables selection of a member of a desired structural class of molecules, such as a peptide or a scFv antibody molecule. In a library or population of binders according to the present invention, the binder polypeptides may thus share a common structure (e.g., a related secondary and/or tertiary structure, optionally including a region of highly similar or identical amino acid sequence—a "constant region") and may have one or more regions of amino acid sequence diversity—a "variable region".

This can be illustrated by considering a repertoire of antibodies. These may be antibodies of a common structural class, e.g., IgG, Fab, scFv-Fc or scFv, differing in one or more regions of their sequence. Antibodies typically have sequence variability in their complementarity determining regions (CDRs), which are the regions primarily involved in antigen recognition. A repertoire of binders in the present invention may be a repertoire of antibody molecules which differ in one or more CDRs, for example there may be sequence diversity in all six CDRs, or in one or more particular CDRs such as the heavy chain CDR3 and/or light chain CDR3.

Antibodies and other binders are described in more detail elsewhere herein. The potential of the present invention however extends beyond antibody display to include display of libraries of peptides or engineered proteins, including receptors, ligands, individual protein domains and alternative protein scaffolds[66-68]. Examples are polypeptides that have monomeric binding domains such as DARPins and lipocalins, affibodies and adhirons. The invention can also be used with complex multimeric binders. For example T cell receptors (TCRs) are expressed on T cells and have evolved to recognise peptide presented in complex with MHC molecules on antigen presenting cells. Libraries encoding and expressing a repertoire of TCRs may be generated, and may be screened to identify binding to MHC peptide complexes.

For multimeric binders, donor DNA encoding the binder may be provided as one or more DNA molecules. For example, where individual antibody VH and VL domains are to be separately expressed, these may be encoded on separate molecules of donor DNA. The donor DNA integrates into the cellular DNA at multiple integration sites, e.g., the binder gene for the VH at one locus and the binder gene for the VL at a second locus. Methods of introducing donor DNA encoding separate binder subunits are described in more detail elsewhere herein and in WO2015/166272 (Iontas Limited), incorporated herein by reference. Alternatively, both subunits or parts of a multimeric binder may be encoded on the same molecule of donor DNA which integrates at a fixed locus.

A binder may be an antibody or a non-antibody protein that comprises an antigen-binding site. An antigen binding site may be provided by means of arrangement of peptide loops on non-antibody protein scaffolds such as fibronectin or cytochrome B etc., or by randomising or mutating amino acid residues of a loop within a protein scaffold to confer binding to a desired target. (Haan & Maggos (2004) BioCentury, 12(5): A1-A6[69,70], Protein scaffolds for antibody mimics are disclosed in WO/0034784 in which the inventors describe proteins (antibody mimics) that include a fibronectin type III domain having at least one randomised loop. A suitable scaffold into which to graft one or more peptide loops, e.g., a set of antibody VH CDR loops, may be provided by any domain member of the immunoglobulin gene superfamily. The scaffold may be a human or non-human protein.

Use of antigen binding sites in non-antibody protein scaffolds has been reviewed previously (Wess, L. In: BioCentury, The Bernstein Report on BioBusiness, 12(42), A1-A7, 2004). Typical are proteins having a stable backbone and one or more variable loops, in which the amino acid sequence of the loop or loops is specifically or randomly mutated to create an antigen-binding site having for binding the target antigen. Such proteins include the IgG-binding domains of protein A from *S. aureus*, transferrin, tetranectin, fibronectin (e.g. 10th fibronectin type III domain) and lipocalins. Other approaches include small constrained peptide e.g., based on"knottin" and cyclotides scaffolds[71]. Given their small size and complexity particularly in relation to correct formation of disulphide bond, there may be advantages to the use of eukaryotic cells for the selection of novel binders based on these scaffolds. Given the common functions of these peptides in nature, libraries of binders based on these scaffolds may be advantageous in generating small high affinity binders with particular application in blocking ion channels and proteases. WO2017/118761 (Iontas Limited) described libraries of binding members that each comprise a fusion protein which contains a donor diversity scaffold domain, such as a cysteine rich protein, inserted within a recipient diversity scaffold domain such as an antibody constant or variable domain. Such binders and libraries as described in WO2017/118761 may be used in the present invention and the document is incorporated by reference herein. Thus, in some embodiments, binders according to the present invention are "knotbodies" comprising a cysteine rich protein inserted within an antibody variable domain. See Example 15 herein.

In addition to antibody sequences and/or an antigen-binding site, a binder may comprise other amino acids, e.g., forming a peptide or polypeptide, such as a folded domain, or to impart to the molecule another functional characteristic in addition to ability to bind antigen. A binder may carry a detectable label, or may be conjugated to a toxin or a targeting moiety or enzyme (e.g., via a peptidyl bond or linker). For example, a binder may comprise a catalytic site (e.g., in an enzyme domain) as well as an antigen binding site, wherein the antigen binding site binds to the antigen and thus targets the catalytic site to the antigen. The catalytic site may inhibit biological function of the antigen, e.g., by cleavage.

Optionally, the binders of the library are a population of polypeptides for which the thermal stability (e.g., as determined by the melting temperature) is not predictive of the binders' solubility or resistance to self-association in solution. This non-correlation between thermal stability and solubility/resistance to self-association in solution may apply when considering all binders in the library that have a solubility or critical concentration of at least 10 mg/ml (methods for determining which are described elsewhere herein). It may apply when considering all binders having a surface presentation of at least $10^3$, at least $10^4$ per cell, at least $10^5$ per cell or at least $10^6$ per cell (methods for determining which are described elsewhere herein, e.g., FACS gating). Optionally, it may apply when considering the total population of surface-expressed binders in the library.

Antibodies

Antibodies are preferred binders. They may be whole antibodies or immunoglobulins (Ig), which have four polypeptide chains—two identical heavy chains and two identical light chains. The heavy and light chains form pairs, each having a VH-VL domain pair that contains an antigen binding site. The heavy and light chains also comprise constant regions: light chain CL, and heavy chain CH1, CH2, CH3 and sometimes CH4. The two heavy chains are joined by disulphide bridges at a flexible hinge region. An antibody molecule may comprise a VH and/or a VL domain.

The most common native format of an antibody molecule is an IgG which is a heterotetramer consisting of two identical heavy chains and two identical light chains. The heavy and light chains are made up of modular domains with a conserved secondary structure consisting of a four-stranded antiparallel beta-sheet and a three-stranded antiparallel beta-sheet, stabilised by a single disulphide bond. Antibody heavy chains each have an N terminal variable domain (VH) and 3 relatively conserved "constant" immunoglobulin domains (CH1, CH2, CH3) while the light chains have one N terminal variable domain (VL) and one constant domains (CL). Disulphide bonds stabilise individual domains and form covalent linkages to join the four chains in a stable complex. The VL and CL of the light chain associates with VH and CH1 of the heavy chain and these elements can be expressed alone to form a Fab fragment. The CH2 and CH3 domains (also called the "Fc domain") associate with another CH2:CH3 pair to give a tetrameric Y shaped molecule with the variable domains from the heavy and light chains at the tips of the "Y". The CH2 and CH3 domains are responsible for the interactions with effector cells and complement components within the immune system. Recombinant antibodies have previously been expressed in IgG format or as Fabs (consisting of a dimer of VH:CH1 and a light chain). In addition the artificial construct called a single chain Fv (scFv) could be used consisting of DNA encoding VH and VL fragments fused genetically with DNA encoding a flexible linker.

IgG is one of the preferred classes of antibody for therapeutic use. An advantage of using higher eukaryotic, especially mammalian, cells is that one can work with antibodies in IgG format. This enables drug discovery and screening to be performed directly in the production cell type used for IgG manufacture.

Binders may be human antibody molecules. Thus, where constant domains are present these are preferably human constant domains.

Binders may be antibody fragments or smaller antibody molecule formats, such as single chain antibody molecules. For example, the antibody molecules may be scFv molecules, consisting of a VH domain and a VL domain joined by a linker peptide. In the scFv molecule, the VH and VL domains form a VH-VL pair in which the complementarity determining regions of the VH and VL come together to form an antigen binding site.

Other antibody fragments that comprise an antibody antigen-binding site include, but are not limited to, (i) the Fab fragment consisting of VL, VH, CL and CH1 domains; (ii) the Fd fragment consisting of the VH and CH1 domains; (iii)

the Fv fragment consisting of the VL and VH domains of a single antibody; (iv) the dAb fragment[72-74], which consists of a VH or a VL domain; (v) isolated CDR regions; (vi) F(ab')2 fragments, a bivalent fragment comprising two linked Fab fragments (vii) scFv, wherein a VH domain and a VL domain are linked by a peptide linker which allows the two domains to associate to form an antigen binding site[75,76] (viii) bispecific single chain Fv dimers (PCT/US92/09965) and (ix) "diabodies", multivalent or multispecific fragments constructed by gene fusion (WO94/13804,[77]). Fv, scFv or diabody molecules may be stabilised by the incorporation of disulphide bridges linking the VH and VL domains[78].

Various other antibody molecules including one or more antibody antigen-binding sites have been engineered, including for example $Fab_2$, $Fab_3$, diabodies, triabodies, tetrabodies and minibodies (small immune proteins). Antibody molecules and methods for their construction and use have been described[79].

Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

A dAb (domain antibody) is a small monomeric antigen-binding fragment of an antibody, namely the variable region of an antibody heavy or light chain. VH dAbs occur naturally in camelids (e.g., camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™".

Synthetic antibody molecules may be created by expression from genes generated by means of oligonucleotides synthesized and assembled within suitable expression vectors, for example as described by Knappik et al. or Krebs et al[80,81].

Bispecific or bifunctional antibodies form a second generation of monoclonal antibodies in which two different variable regions are combined in the same molecules[63]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways, e.g., prepared chemically or from hybrid hybridomas, or may be any of the bispecific antibody fragments mentioned above[82]. These antibodies can be obtained by chemical methods[83,84] or somatic methods[85,86]) but likewise and preferentially by genetic engineering techniques which allow the heterodimerisation to be forced and thus facilitate the process of purification of the antibody sought[87]. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

In some embodiments of the present invention, binders are bispecific antibodies and their encoding clones comprise two different antibody heavy chains and optionally either two different antibody light chains or preferably a common light chain. Successful heterodimer pairing between the heavy chains leads to cell surface presentation of bispecific antibody, each antibody comprising the heterodimeric pair of heavy chains, and optionally each heavy chain being paired with a light chain, optionally a common light chain (i.e., the light chains paired with each heavy chain have the same amino acid sequence). Where an Fc region is included, the invention may be used to assess Fc sequence variants that may improve heterodimerisation. In previous studies where the Fc region has been engineered to improve heterodimerisation, the developability profile has been compromised by the changes[67]. The present invention provides an opportunity to screen such variants for developability (eg solubility and polyspecificity) alongside their heterodimerisation potential.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful. Diabodies (and many other polypeptides, such as antibody fragments) of appropriate binding specificities can be readily selected. If one arm of the diabody is to be kept constant, for instance, with a specificity directed against an antigen of interest, then a library can be made where the other arm is varied and an antibody of appropriate specificity selected. Bispecific whole antibodies may be made by alternative engineering methods as described in Ridgeway et al. (*Protein Eng.,* 9, 616-621, (1996)).

Alternative formats of bispecific antibodies include $mAb^2$ ("mAb squared") molecules comprising immunoglobulins which loop regions of the CH3 have been engineered to provide an antigen binding site (see, e.g., WO2006072620, WO2008003103, WO2008003116). The modified CH3 region is termed an Fcab. One binding specificity is provided by the antibody antigen-binding site of the Fv regions, and a different binding specificity (or further valency) is provided by the binding site in the Fcab.

A library according to the invention may be used to select an antibody that binds one or more antigens of interest. Selection from libraries is described in detail elsewhere herein. Following selection, the antibody may be engineered into a different format and/or to contain additional features. For example, the selected antibody may be converted to a different format, such as one of the antibody formats described above. The selected antibodies, and antibodies comprising the VH and/or VL CDRs of the selected antibody molecules, are an aspect of the present invention. Antibodies and their encoding nucleic acid may be provided in isolated form.

Antibody fragments can be obtained starting from an antibody molecule by methods such as digestion by enzymes e.g. pepsin or papain and/or by cleavage of the disulphide bridges by chemical reduction. In another manner, the antibody fragments can be obtained by techniques of genetic recombination well known to the person skilled in the art or else by peptide synthesis by means of, for example, automatic peptide synthesisers, or by nucleic acid synthesis and expression.

It is possible to take monoclonal and other antibodies and use techniques of recombinant DNA technology to produce other antibodies or chimaeric molecules that bind the target antigen. Such techniques may involve introducing nucleic acid (e.g., DNA) encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature.

Antibody molecules may be selected from a library and then modified, for example the in vivo half-life of an antibody molecule can be increased by chemical modification, for example PEGylation, or by incorporation in a liposome.

Binders may comprise antibody variable domains that exhibit sequence diversity, optionally in one or more complementarity determining regions. Binders may also, or alternatively, comprise antibody constant regions or Fc regions, which optionally exhibit sequence diversity. Features of Fc regions are discussed further below.

Fc Regions

A binder may be a polypeptide comprising an Fc region. The binders may be antibodies, knotbodies or other polypeptides, optionally fusion proteins, comprising an Fc region. The Fc region may be or may comprise the constant region of the binders, i.e., having a highly similar or identical amino acid sequence as compared between binders of a library. In some cases constant domains of the antibody (e.g. the Fc region, or CL or CH1 domains) may be or may comprise variable amino acid sequences, thus exhibiting sequence diversity across the repertoire of binders in a library. Sequence diversity may optionally be in CH3 domains of the Fc. For example, binders may comprise Fcabs or $mAb^2$ in which the binding loops of the Fcabs are diverse within the library. $mAb^2$ may comprise diverse Fcab regions and either non-variant or diverse antigen binding sites of the Fv regions. Amino acid sequence diversity of binders may be restricted to the Fc region, optionally restricted to the CH3 domain.

Using the display libraries of the present invention, libraries of Fc domains may be screened for altered function and for developability criteria, optionally simultaneously.

Various engineering approaches have been taken to engineer the interaction of Fc domains with its interaction partners. For example the "knobs into holes" approach modifies two paired Fc sequences such that their co-expression from a cell (or their expression in co-cultured cells) leads to mainly heterodimer formation between the two variant Fcs domains, which is advantageous in the generation of bispecific antibodies. Unfortunately such mutations can have an effect on developability[88]. The present invention may be used to assess Fc variants, including Fc domains containing candidate "knobs into holes" mutations, for developability potential.

Fc engineering has also been used to alter affinity or specificity with Fc gamma receptors e.g., to create "null variants" with reduced Fc gamma receptor interaction. Mutation of antibody constant domain and selection of variants with desired binding qualities can degrade stability and manufacturability. Again, the present invention may be used to assess libraries of variant Fc domains to enrich for those with improved properties.

Modifications have also been made to increase or decrease the interaction of Fc with FcRn for the purpose of positively or negatively modifying half-life[89]. For example a triplet of mutations of M252Y/S254T/T256E (so-called "YTE mutation") have increased IgG half-life prolonging half-life and reducing dosing frequency and cost.

It is recognised that introduction of mutations in the Fc domain can also have a detrimental effect on biophysical properties of the variant leading to aggregation and poor developability. For example Borrok et al (2017)[90] review mutations which affect interaction with FcRn and mutations affecting interaction with other Fc receptors. They describe an antibody which combines mutations which increase half-life (M252Y, S254T, T256E, the so called the "YTE mutation") and others diminish interaction of CH2 domain with Fc gamma receptors (L234F, L235E, P331S, the so-called TM mutant)[90]. Compared with wild type this TM-YTE mutant had lowered thermostability, greater conformational flexibility, increased self-association, poorer solubility and poorer aggregation profiles. By selecting candidate mutations they were able to create a new FQQ-YTE variant (L234F/L235Q/K322Q/M252Y/S254T/T256E) which had significantly improved conformational and colloidal stability, while retaining extended half-life and lack of antibody-dependent cell-mediated cytotoxicity and complement-dependent cytotoxicity activity.

The present invention offers an opportunity to screen large numbers of variants simultaneously for altered binding properties of Fc domains alongside developability criteria such as self-aggregation or low specificity. Thus, in various embodiments of the invention the binders may comprise Fc regions exhibiting sequence diversity, e.g., in one or more amino acid residues of the CH3 domain. Binders that exhibit sequence diversity in one or more variable regions (e.g., antibody heavy chain variable and/or light chain variable domain) outside the Fc domain, and which optionally have a constant Fc domain of invariant sequence, may also be screened to identify effects of the variable region sequence on the FcRn interaction (see Example 9). Such effects may be indirect e.g., affecting conformation of the molecule or otherwise influencing binding more remotely, in the absence of direct binding of the variable region to the receptor.

Screening for FcRn binding characteristics of polypeptides may be integrated into drug discovery. Methods may comprise selecting for optimal pH dependent FcRn interactions within libraries of sequence variants. Described herein are methods of identifying or selecting for binders having an extended or reduced in vivo half-life resulting from the nature of their interaction with FcRn.

A method according to the present invention may comprise:

providing a plurality of eukaryotic (e.g., mammalian) cell clones each containing DNA encoding a binder comprising an Fc domain, culturing the clones in vitro under conditions for presentation of the binders on the cell surface, exposing the clones to FcRn receptor at low pH (e.g. about pH 6.0) or neutral pH (e.g. about pH7.4) allowing recognition of FcRn by the Fc domains, eluting at higher pH (e.g., about pH 7.4) and selecting one or more clones expressing binders that exhibit higher affinity binding at about pH 6.0 compared with binding at higher pH (e.g. about pH 7.4).

The selected clones can be obtained from the eluted fraction. Binders from the eluted clones may be identified as having an extended half-life in vivo.

Alternatively binders which are retained following a switch to a higher pH may be collected if retained binding at higher pH is desired, for example for reduced half-life or for use with "sweeping antibody" approaches[32]. In such cases the method may comprise:

providing a plurality of eukaryotic (e.g., mammalian) cell clones each containing DNA encoding a binder comprising an Fc domain, culturing the clones in vitro under conditions for presentation of the binders on the cell surface, exposing the clones to FcRn receptor at low pH (e.g. about pH 6.0) allowing recognition of FcRn by the Fc domains, washing at higher pH (e.g., about pH 7.4) and selecting one or more clones expressing binders that exhibit lower or similar affinity binding at about pH 6.0 compared with binding at higher pH (e.g. about pH 7.4).

The selected clones can be obtained from the retained fraction that is not eluted at the higher pH wash. Such clones can be eluted at more extreme pH, above pH 7.4 or below pH 6. Higher affinity binding at the lower pH (e.g., about pH 6.0) can be selected for by reducing the concentration of FcRn used at that pH during selection thereby increasing the stringency of the selection.

Binders exhibiting a greater difference in affinity between the two pHs may be preferentially selected, as these may show the greatest half-life extension. Conversely if shorter half-life is sought, one would select clones expressing binders where there is a smaller differential in affinity for FcRn between the two pHs (or no significant difference). The method may thus be adapted to select either for shorter or longer half-life. Populations of clones are thus enriched for clones expressing binders with the desired half-life.

Binding to biotinylated FcRn may be carried out at pH 6.0 to ensure binding is occurring, then eluted samples collected following washing with buffers of increasing pH. Alternatively selection for retention or loss of fluorescent label could be carried out using flow sorting. FcRn-based affinity chromatography methods in conjunction with pH gradient elution have been described[91] for characterising antibodies. Such methods could be used with libraries of antibody variants displayed on cells where clones with desired pH dependent binding properties could be collected and the antibody genes recovered.

Some embodiments of the invention use anti-Fc detection agents to determine the level of surface presentation of the binders. Such agents may still be used in connection with binders having Fc sequence diversity provided that the diversity does not affect binding of the detectable agent, for example if it can be ensured that the detection agent binds a region of the Fc where the binders share a common sequence. In alternative embodiments, the binders comprise Fc regions that do not exhibit sequence diversity.

Cell Culture and Binder Expression

To provide a repertoire of binders for screening against a target of interest and/or for developability characteristics, a library may be cultured to express the binders from the encoding DNA. As discussed, binders may contain a transmembrane domain, membrane anchor or may associate with a membrane-bound partner molecule, for extracellular display. Culturing cells for expression of binders will generally involve incubating the cells in a suitable culture medium, optionally in suspension culture, and at a temperature conducive to growth of the cells (e.g., 37 degrees C. for mammalian cells). Expression of the polypeptide binder from the encoding DNA is initiated under control of the promoter (and optionally other elements such as enhancers) and surface presentation of the binder will begin to be observed after a duration, and should be detectable within e.g., 12 hours although a longer duration (e.g., 24 h or 48 h) may be required for binder presentation to reach a final or equilibrium concentration on the cell surface.

Promoters

In cells according to the present invention, DNA encoding a binder is operably linked to a promoter for expression. A heterologous promoter may be used, meaning that it is not the promoter associated with the encoding DNA in nature, e.g., DNA encoding an antibody may be operably linked to a promoter other than the promoter from the immunoglobulin locus. It will generally be convenient to integrate the promoter into the cellular DNA, optionally in cis (on the same donor DNA as the sequence encoding the binder) although an alternative is to express the integrated binder DNA from a promoter endogenous to the host cell.

Where expression of the DNA encoding the binders is under control of a strong promoter, e.g., a constitutive promoter or an inducible promoter from which expression has been maximally induced, high levels of binder presentation may be achieved. Conversely, where expression of DNA encoding the binders is under control of a weakly active promoter, e.g., a weak promoter or an inducible promoter from which expression has been minimally induced or which exhibits only a basal level of activity, low levels of binder presentation may be achieved. Strength of a promoter can be quantified using a reporter gene and determining the level of expression of the reporter, e.g., expression of GFP can be detected as fluorescence, which may be quantified. A weakly active or weak promoter may for example show about 1-10% of the activity of a fully active or constitutive promoter, e.g., as compared with the CMV promoter.

A convenient method to control cell surface presentation of binders is to provide an inducible promoter operably linked to the binder-encoding DNA in the cells. Tetracycline-inducible promoters are suitable, and a variety of these are available. Gossen et al. described a first generation rtTA protein (EP0804565 and Gossen et al., 1995[92]). The VP16 activation domain was fused with a mutant Tet repressor from *Escherichia coli* to generate the transcriptional transactivator "rtTA", which requires certain tetracycline (Tc) derivatives for specific DNA binding. Doxycycline is an inducer in this system, and its addition to cultured cells in which gene expression is under control of the rtTA can undergo a 1000× increase in expression from the inducible promoter. A second generation "TetO/CMV" promoter named pTight or Ptet-14 was designed with optimised 7 TetO spacing and a truncated minimal CMV promoter, which exhibits reduced basal expression levels (Clontech: pTRE-Tight Vectors. Clontechniques 2003, 18(3):13-14). The promoter sequence is:

```
                                        (SEQ ID NO: 1)
TTCGTCTTCACACGAGTTTACTCCCTATCAGTGATAGAGAACGTATGTCG
AGTTTACTCCCTATCAGTGATAGAGAACGATGTCGAGTTTACTCCCTATC
AGTGATAGAGAACGTATGTCGAGTTTACTCCCTATCAGTGATAGAGAACG
TATGTCGAGTTTACTCCCTATCAGTGATAGAGAACGTATGTCGAGTTTAT
CCCTATCAGTGATAGAGAACGTATGTCGAGTTTACTCCCTATCAGTGATA
GAGAACGTATGTCGAGGTAGGCGTGTACGGTGGGAGGCCTATATAAGCAG
AGCTCGTTTAGTGAACCGTCAGATCGCC.
```

This inducible promoter, or a variety of other modulatable promoters, may be used to control binder presentation levels in the present invention. Any inducible system could be employed where a DNA binding domain is fused to a protein domain capable of binding an inducer molecule which results in a protein conformational change or a change in affinity for a DNA recognition sequence. This will result in either derepression or activation of transcription leading to protein expression. For example, in the case of the T-Rex or cumate switch systems, the binding of inducer to a repressor protein results in loss of DNA binding and derepression of transcription. Alternatively binding of an inducer to a DNA binding domain fused to a transcription activation domain fusion protein would result in DNA binding and the recruitment of transcription factors as is the case for the Tet-on[92, 114] or the GAL4 GeneSwitch systems[121].

The tetracycline-inducible promoter systems mentioned above may be convertable to a more tuneable homogeneous and titratable induction by reduction in the number of TetO repeat sequences to between one and six[118] or by modification of the rTA protein. Example 8b describes a third generation inducible tet promoter system, which achieved an improved range of expression. Details are illustrated in FIG. 37. Alternative inducible expression systems could also be employed including the cumate switch[119], T-Rex[120] or GAL4 systems[121].

Recovery of Binders and Encoding Nucleic Acid

Following selection of a binder or clone of interest from the library, a common next step will be to isolate, identify and/or amplify the nucleic acid (e.g., DNA or RNA) encoding the binder. Optionally, it may be desired to modify the nucleic acid encoding the binder, for example to restructure the binder and/or to insert the encoding sequence into a different vector. Nucleic acid (DNA or RNA) encoding a displayed binder can be recovered from the selected cell, cloned into an expression vector and the encoded polypeptide expressed either in a secreted form or for display. This can be done on individual clones.

When the population of donor DNA molecules that is used to create the library contains multiple copies of the same sequence, two or more clones may be obtained that contain DNA encoding the same binder. It can also be the case that a clone may contain donor DNA encoding more than one different binder, for example if there is more than one recognition sequence for the site-specific nuclease, as detailed elsewhere herein. Thus, the diversity of the library, in terms of the number of different binders encoded or expressed, may be different from the number of clones obtained.

Clones in the library preferably contain donor DNA encoding one or two members of the repertoire of binders and/or preferably express only one or two members of the repertoire of binders. A limited number of different binders per cell is an advantage when it comes to identifying the clone and/or DNA encoding a particular binder identified when screening the library against a given target. This is simplest when clones encode a single member of the repertoire of binders. However it is also straightforward to identify the relevant encoding DNA for a desired binder if a clone selected from a library encodes a small number of different binders, for example a clone may encode two members of the repertoire of binders. As discussed elsewhere herein, clones encoding one or two binders are particularly convenient to generate by selecting a recognition sequence for the site-specific nuclease that occurs once per chromosomal copy in a diploid genome, as diploid cells contain duplicate fixed loci, one on each chromosomal copy, and the donor DNA may integrate at one or both fixed loci. Thus, clones of the library may each express only one or two members of the repertoire of binders.

Where the binder is an antibody molecule, a method may comprise isolating DNA encoding the antibody molecule from cells of a clone, amplifying DNA encoding at least one antibody variable region, preferably both the VH and VL domain, and inserting DNA into a vector to provide a vector encoding the antibody molecule. A multimeric antibody molecule bearing a constant domain may be converted to a single chain antibody molecule for expression in a soluble secreted form. Antibodies may be presented in different formats but whatever format an antibody is selected in, once the antibody gene is isolated it is possible to reconfigure it in a number of different formats. Once VH or VL domains are isolated, they can be re-cloned into expression vectors encompassing the required partner domains DNA encoding a selected binder may be integrated into a host cell chromosome for expression. Expression of recombinant protein typically involves introducing into a cell the gene encoding the desired protein under the control of a promoter which is expressed in that cell. For example the gene may be under the control of a cytomegalovirus enhancer/promoter and may be introduced into a mammalian cell such as the commonly used human embryonic kidney 293 (HEK293) cell or the Chinese Hamster Ovary (CHO) cell. Standard methods for introducing expression constructs into host cells are well known. For production of secreted, soluble protein the encoded gene is preceded by a leader sequence which directs the encoded protein to the endoplasmic reticulum. In the absence of a transmembrane domain the encoded gene is secreted into the culture medium from which it may be purified and concentrated.

Following any method of the invention, a desired binder may be provided in isolated form in solution, e.g., after secretion from a host cell stably transfected for expression of the binder. Properties of the soluble binder may then be tested to confirm its performance, e.g., to assess developability traits such as solubility, self-association, non-specific binding, FcRn interaction, and others, or to assess affinity. Suitable assays for determining each of these features are provided in the relevant sections of this document, and may be performed to confirm that a binder exhibits the desired property and/or shows an improvement in the relevant characteristic, e.g., that it is improved compared with a parent molecule.

Pharmaceutical Formulation of Binders

Binders obtained using methods of the invention may be provided in purified and/or isolated form, and may be formulated into compositions comprising one or more additional components. Compositions may contain suitable carriers, excipients, and other agents that are incorporated into formulations to provide improved transfer, delivery, tolerance, etc. Example formulations are described in Remington's Pharmaceutical Sciences. Binders intended for in vivo use may be formulated for the desired route of administration to a patient, e.g., in a liquid (optionally aqueous solution) for injection. Various delivery systems are known and can be used to administer a pharmaceutical composition comprising the binder. Methods of administration include intradermal, intramuscular, intraperitoneal, intravenous, subcutaneous, intranasal, epidural, and oral routes. The composition may be administered by any convenient route, by infusion or bolus injection, by absorption through epithelial or mucocutaneous linings (e.g., oral mucosa, rectal and intestinal mucosa, etc.) and may be administered together with other biologically active agents. Administration can be systemic or local.

The binder, or composition comprising it, may be contained in a medical container such as a phial, syringe, IV container or an injection device. In an example, a kit is provided comprising the binder, packaging and instructions for use in a therapeutic method. The method may comprise subcutaneous administration to a patient.

The binder may be formulated into a composition, optionally an aqueous buffered solution, comprising the binder at a concentration of at least (or above): 50 mg/ml, 60 mg/ml, 70 mg/ml, 80 mg/ml, 90 mg/ml or 100 mg/ml. The binder may be at a concentration of between 50-200 mg/ml, e.g., between 50-150 mg/ml, e.g., between 50 and 100 mg/ml.

A number of methods for concentrating expressed recombinant protein are known to those skilled in the art but may include column chromatography (e.g., affinity chromatography, ion exchange chromatography) and ultrafiltration[27].

Clauses

The following numbered clauses represent statements of invention and are part of the description.

1. Use of the surface presentation level of binders on cultured higher eukaryotic cells in vitro as a predictive indicator of the solubility of the binders and/or their resistance to self-association in solution.

2. Use according to clause 1, wherein the cultured cells are clones of a display library expressing a diverse repertoire of binders.

3. Use of a cultured library of higher eukaryotic cells for in vitro selection of binders for higher solubility and/or a lower propensity for self-association in solution, wherein the library is a library of higher eukaryotic cell clones each containing DNA encoding a binder, wherein the encoded binder is presented on the cell surface.

4. A binder discovery method in which the surface presentation level of binders on the surface of cultured higher eukaryotic cell clones of a display library is used as a predictive indicator of the solubility of the binders and/or their resistance to self-association in solution.

5. A method of distinguishing or ranking binders according to their solubility and/or resistance to self-association in solution, and/or enriching for binders exhibiting greater solubility and/or greater resistance to self-association in solution, comprising (i) providing a library of higher eukaryotic cell clones each containing DNA encoding a binder, (ii) culturing the clones in vitro under conditions for expression of the binders, wherein the binders are presented on the cell surface, (iii) determining surface presentation levels of the binders on the clones, optionally by labelling the binders with an agent incorporating a detectable (e.g., fluorescent) label, (iv) selecting one or more clones that exhibit higher surface presentation of binders compared with other clones, and (v) identifying binders encoded by the one or more selected clones as having good solubility and/or resistance to self-association in solution, and optionally providing the selected clones for use in one or more further screening steps.

6. Use according to any of clauses 1 to 3 or a method according to clause 4 or clause 5, wherein the binders are transmembrane domain-containing polypeptides.

7. A method according to clause 4 or clause 5, comprising determining surface presentation levels of the binders on the clones by labelling the binders with an agent incorporating a detectable (e.g., fluorescent) label, wherein the agent binds to a constant region of the binders, optionally wherein the binders comprise an Fc region and the agent binds to the Fc region.

8. A method according to any of clauses 4 to 7, comprising sorting cells into a collected fraction and a discarded fraction according to the level of surface presentation of binders on the cells, whereby cells displaying surface presentation above a pre-determined threshold are sorted into the collected fraction and cells displaying surface presentation below the pre-determined threshold are sorted into the discarded fraction.

9. A method according to clause 8, wherein discarded fraction comprises cells expressing comparator polypeptides that have a critical concentration of at least 10 mg/ml and wherein the collected fraction comprises cells expressing binders that have a critical concentration at least 1.5-fold higher than the comparator polypeptides in the discarded fraction.

10. A method according to clause 8 or clause 9, wherein sorting is performed by a fluorescence activated cell sorter (FACS).

11. A method according to any of clauses 4 to 10, wherein step (ii) comprises culturing the clones of the library as a mixture in one vessel.

12. A method according to any of clauses 4 to 10, wherein step (ii) comprises culturing each clone of the library in a separate vessel.

13. A method according to any of clauses 4 to 12, wherein the binders are sequence variants of a parent binder.

14. A method according to clause 13, wherein the parent binder has been identified as requiring improvement in solubility or resistance to self-association in solution.

15. A method according to clause 13 or clause 14, wherein the method comprises generating sequence variants of the parent binder and integrating DNA encoding the sequence variants into cellular DNA of higher eukaryotic cells to provide the library of cell clones containing DNA encoding the binders, optionally wherein the method comprises analysing the polypeptide sequence of the parent, identifying one or more amino acid residues that are predicted to promote self-association and/or reduce solubility, and generating mutation at the one or more amino acid residues.

16. A method according to any of clauses 13 to 15, wherein the parent binder has a critical concentration of less than 50 mg/ml in phosphate buffered saline solution (PBS) and/or has a solubility limit of less than 50 mg/ml in phosphate buffered saline solution (PBS), and/or wherein the method comprises identifying binders encoded by the one or more selected clones as having a critical concentration and/or a solubility limit at least 1.5 fold higher than that of the parent binder.

17. A method according to any of clauses 4 to 16, comprising predicting hydrophilicity of binders based on their surface presentation level on the cell clones and/or identifying binders of one or more selected clones as being more hydrophilic.

18. An in vitro method of screening a library of higher eukaryotic cells displaying binders, to enrich the library for cells expressing binders that exhibit a low propensity to bind one or more non-target molecules in a mammal in vivo, the method comprising (i) providing a library of higher eukaryotic cell clones each containing DNA encoding a binder, (ii) culturing the clones in vitro under conditions for expression of the binders, wherein the binders are presented on the cell surface, (iii) exposing the binders to the one or more non-target molecules, allowing binding between the binders to the one or more non-target molecules, (iv) discarding cells that exhibit greater binding to the one or more non-target molecules, (v) selecting cells that exhibit lower binding to the one or more non-target molecules, to provide a selected population of cells enriched for clones expressing binders having a low propensity to bind to the non-target molecules, and optionally providing the selected population for use in one or more further screening steps 19. A method according to clause 18, comprising (iii) exposing the binders to a matrix comprising the one or more non-target molecules, allowing binding to the matrix, (iv) discarding cells that exhibit greater binding to the matrix, (v) selecting cells that exhibit lower binding to the matrix, to provide a selected population of cells enriched for clones expressing binders having a low propensity to bind to the non-target molecules, and optionally providing the selected population for use in one or more further screening steps.

20. A method according to clause 18 or clause 19, wherein the non-target molecules comprise DNA, heparin, heparan sulphate, chondroitin sulphate, a chaperone protein, hyaluronic acid or one or more components of the glycocalyx.

21. A method according to any of clauses 18 to 20, wherein the binding to non-target molecules is low affinity non-specific binding.

22. A method according to any of clauses 18 to 21, comprising culturing the clones of the library as a mixture in one vessel and exposing the mixture to the matrix.

23. A method according to any of clauses 18 to 21, comprising culturing each clone of the library in a separate vessel.

24. A method according to any of clauses 18 to 23, wherein the binders are sequence variants of a parent binder.

25. A method according to clause 24, wherein the parent binder has been identified as requiring reduction in binding to one or more non-target molecules.

26. A method according to clause 24 or clause 25, wherein the method comprises generating sequence variants of the parent binder and integrating DNA encoding the sequence variants into cellular DNA of higher eukaryotic cells to provide the library of cell clones containing DNA encoding the binders, optionally wherein the method comprises analysing the polypeptide sequence of the parent, identifying one or more amino acid residues that are predicted to promote non-specific binding, and generating mutation at the one or more amino acid residues.

27. A method according to any of clauses 24 to 26, wherein the parent binder exhibits significant binding to one or more non-target molecules.

28. A method according to any of clauses 18 to 27, comprising (iii) exposing the binders to cells or beads presenting the one or more non-target molecules.

29. A method according to clause 28, comprising detecting interaction of binder-expressing cells with the cells or beads presenting the one or more non-target molecules.

30. A method according to clause 29, comprising detecting interparticle distance using AC-SINS, and selecting binders presented by cells that exhibit higher interparticle distance.

31. A method according to clause 18, wherein the one or more non-target molecules are detectably labelled.

32. A method according to clause 31, wherein the one or more non-target molecules are fluorescently labelled.

33. A method according to clause 32, comprising flow sorting cells by FACS into a collected fraction and a discarded fraction according to the level of binding to the one or more non-target molecules, whereby cells displaying fluorescence from the labelled non-target molecule above a pre-determined threshold are sorted into the collected fraction and cells displaying fluorescence from the labelled non-target molecule below the pre-determined threshold are sorted into the discarded fraction.

34. A method according to any of clauses 4 to 33, wherein expression of the DNA encoding the binders is under control of a strong promoter.

35. A method according to clause 34, wherein the promoter is a constitutive promoter.

36. A method according to clause 35, wherein the promoter is the CMV promoter.

37. A method according to clause 34, wherein the promoter is an inducible promoter from which expression has been maximally induced.

38. A method according to any of clauses 18 to 37, further comprising subsequently performing a method according to any of clauses 5 to 17.

39. A method according to any of clauses 18 to 37, further comprising initially performing a method according to any of clauses 5 to 17.

40. A method of selecting one or more binders for a target, comprising performing a method as defined in any of clauses 5 to 39, further comprising exposing the binders to the target, allowing recognition of the target by cognate binders, whereby cells displaying cognate binders become bound to the target, and selecting one or more clones displaying cognate binders.

41. A method according to any preceding clause, comprising (i) simultaneously determining surface presentation levels of the binders and levels of target binding by the binders, and co-selecting clones displaying cognate binders exhibiting higher surface presentation compared with other clones; or (ii) simultaneously determining surface presentation levels of the binders and levels of non-specific binding to non-target molecules, and co-selecting clones displaying binders exhibiting higher surface presentation and lower non-specific binding compared with other clones; or (iii) simultaneously determining levels of target binding and levels of non-specific binding to non-target molecules by the binders, and co-selecting clones displaying cognate binders exhibiting lower non-specific binding compared with other clones.

42. A method of identifying a binder that recognises a target with a desired affinity, the method comprising (a) providing an in vitro library of higher eukaryotic cell clones each containing DNA encoding a binder, wherein the binder is presented on the cell surface, and wherein the encoded binder is expressed from a weakly active promoter and/or expressed on the cell surface at a copy number in the range of 100-60,000 per cell, (b) exposing the library to the target and allowing recognition of the target by cognate binders, whereby cells displaying cognate binders become bound to the target, (c) isolating cells bound to the target to provide a selected population of cells that is enriched for cells displaying cognate binders, and optionally (d) exposing the selected population of cells to one or more further rounds of selection on the target, optionally wherein the concentration of target is progressively reduced to increase stringency of selection, and optionally (e) selecting one or more clones displaying a cognate binder having the desired affinity for the target.

43. A method according to clause 42, comprising providing the selected population of cells enriched for cells displaying cognate binders, and subsequently:

providing binder-encoding DNA from the selected population of cells under control of a strongly active promoter within an in vitro library of higher eukaryotic cell clones, and performing a method according to any of clauses 5 to 17.

44. A method according to clause 42, comprising performing the method defined in any of clauses 5 to 17 to provide selected clones displaying higher surface presentation of binders, and subsequently:

expressing the binders from a weakly active promoter in an in vitro library of higher eukaryotic cell clones each containing DNA encoding a binder, and subsequently performing the method of clause 42.

45. A method of identifying a binder that recognises a target, comprising:

(i) providing a library of higher eukaryotic cell clones each containing DNA encoding a binder, wherein expression of the binder is under control of an inducible promoter for presentation on the cell surface, (ii) culturing cells of the library under conditions where the inducible promoter is weakly active, (iii) exposing the library to the target, allowing recognition of the target by cognate binders, whereby cells displaying cognate binders become bound to the target, (iv) selecting cells displaying cognate binders, thereby providing a selected population of cells, (v) culturing the selected population of cells under conditions for increased expression of binders from the inducible promoter, (vi) determining surface presentation levels of the binders on the plurality of clones, optionally by labelling the binders with an agent incorporating a detectable (e.g., fluorescent) label, (vii) selecting one or more clones that exhibit higher surface presentation of binders compared with other clones.

46. A method of identifying a binder that recognises a target, comprising:

(i) providing a library of higher eukaryotic cell clones each containing DNA encoding a binder, wherein expression of the binder is under control of an inducible promoter for presentation on the cell surface, (ii) culturing the library under conditions for strong expression of binders from the inducible promoter, (iii) determining surface presentation levels of the binders on the plurality of clones, optionally by labelling the binders with an agent incorporating a detectable (e.g., fluorescent) label, (iv) selecting a population of clones that exhibit higher surface presentation of binders compared with other clones, (v) culturing the selected population under conditions for weak expression of binders from the inducible promoter, (vii) exposing the library to the target, allowing recognition of the target by cognate binders, whereby cells displaying cognate binders become bound to the target, (iv) selecting one or more clones displaying cognate binders.

47. A method according to any of clauses 42 to 46, wherein the promoter is a tetracycline-inducible promoter.

48. A method according to any of clauses 42 to 47, wherein the target is labelled with a detectable agent such as a fluorescent label.

49. A method according to clause 48, wherein the method comprises sorting cells into a collected fraction and a discarded fraction according to the level of bound target on the cells, whereby cells displaying bound target above a pre-determined threshold are sorted into the collected fraction and cells displaying bound target below the pre-determined threshold are sorted into the discarded fraction.

50. A method according to clause 49, wherein sorting is performed by a fluorescence activated cell sorter (FACS).

51. A method according to any of clauses 5 to 50, comprising determining the sequence of the DNA encoding the binder from the one or more selected clones, and providing isolated nucleic acid encoding the binder.

52. A method according to any of clauses 5 to 51, further comprising determining the sequence of the DNA encoding the binder from the one or more selected clones, and expressing DNA encoding the binder in a host cell in vitro under conditions for secretion of the binder in soluble form.

53. A method according to clause 52, wherein the secreted binder is obtained at a yield of at least 1 mg/ml.

54. A method according to clause 52 or clause 53, further comprising purifying and/or concentrating the binder to obtain an aqueous solution of the binder at a concentration of at least 10 mg/ml.

55. A method according to clause 54, wherein the concentration is at least 50 mg/ml.

56. A method according to clause 55, wherein the concentration is at least 100 mg/ml.

57. A method according to any of clauses 52 to 56, comprising formulating the binder into a composition comprising a pharmaceutically acceptable excipient.

58. A method according to clause 57, comprising providing the composition in a pre-filled syringe for injection, optionally within a kit comprising one or more additional components such as a needle and/or product information leaflet comprising directions for administration of the composition by injection.

59. A method of identifying a binder that interacts with FcRn, the method comprising providing a plurality of higher eukaryotic cell clones each containing DNA encoding a different binder having an Fc domain, culturing the clones in vitro under conditions for presentation of the binders on the cell surface, exposing the clones to FcRn receptor at about pH 6.0 and about pH 7.4, allowing recognition of FcRn by the Fc domains, selecting one or more clones expressing binders that exhibit higher affinity binding at about pH 6.0 compared with at about pH 7.4, that exhibit lower affinity binding at about pH 6.0 compared with at about pH 7.4, or that exhibit about the same affinity binding at about pH 6.0 compared with at about pH 7.4, and optionally providing the selected clones for use in one or more further screening steps.

60. A method according to clause 59, comprising selecting one or more clones expressing binders that exhibit higher affinity binding at about pH 6.0 compared with at about pH 7.4, and identifying the binders encoded by the one or more selected clones as having the extended half-life in vivo.

61. A method according to clause 59 or clause 60, wherein the binders comprise variable domains exhibiting sequence diversity, optionally in one or more complementarity determining regions.

62. A method according to any of clauses 59 to 61, wherein the binders comprise Fc regions exhibiting sequence diversity, optionally in their CH3 domains.

63. A method according to any of clauses 59 to 61, wherein the Fc regions of the binders do not exhibit sequence diversity.

64. A clone, a binder expressed by a clone, or nucleic acid encoding the binder, substantially as described herein and/or that is identified or selected by a method according to any preceding clause.

65. An in vitro library of higher eukaryotic cell clones each containing DNA encoding a binder, wherein the encoding DNA is optionally at a fixed locus in the cellular DNA, and wherein the encoded binder is expressed on the cell surface at a copy number in the range of 100-1000 per cell.

66. Use of a library as defined in clause 65 for affinity-based selection of binders to a target.

67. An in vitro display library of higher eukaryotic cell clones containing DNA encoding a repertoire of binders, wherein expression of binders is under control of a tetracycline-inducible promoter for presentation on the cell surface.

68. A method of producing a library of higher eukaryotic cell clones containing DNA encoding a repertoire of binders, comprising providing donor DNA molecules encoding the binders, and higher eukaryotic cells, introducing the donor DNA into the cells, thereby creating recombinant cells containing donor DNA integrated in the cellular DNA, wherein expression of the binders is under control of a tetracycline-inducible promoter for presentation on the cell surface, and culturing the recombinant cells to produce clones, thereby providing a library of higher eukaryotic cell clones containing donor DNA encoding the repertoire of binders.

69. A method according to clause 68, wherein the recombinant cells are created by introducing the donor DNA into the cells and by providing a site-specific nuclease within the cells, wherein the nuclease cleaves a recognition sequence in cellular DNA to create an integration site at which the donor DNA becomes integrated into the cellular DNA, integration occurring through DNA repair mechanisms endogenous to the cells.

70. A method according to clause 68 or clause 69, further comprising inducing expression of donor DNA from the tetracycline-inducible promoter and culturing the cells under conditions for expression of the binders, obtaining presentation of binders on the cell surface.

71. A method according to clause 69 or clause 70, further comprising using the library in the method or use as defined in any preceding clause.

72. A use, method or library according to any preceding clause, wherein the higher eukaryotic cells are mammalian cells.

73. A use, method or library according to any preceding clause, wherein the mammalian cells are a human cell line or a CHO cell line.

74. A use, method or library according to any preceding clause, wherein the higher eukaryotic cells are in suspension culture.

75. A use, method or library according to any preceding clause, wherein DNA encoding the binders is integrated at a fixed locus in the cellular DNA.

76. A use, method or library according to any preceding clause, wherein the binders are antibodies.

77. A use, method or library according to clause 76, wherein the antibodies are full length immunoglobulins.

78. A use, method or library according to clause 77, wherein the antibodies are IgG.

79. A use, method or library according to any of clauses 76 to 78, wherein the antibodies comprise a heavy chain fused to a transmembrane domain, and a light chain.

80. A use, method or library according to any of clauses 1 to 79, wherein the binders are fusion proteins comprising a donor diversity scaffold domain inserted within a recipient diversity scaffold domain, optionally comprising a partner domain associated with the fusion protein, wherein the donor diversity scaffold domain comprises a donor scaffold and a donor interaction sequence and the recipient diversity scaffold domain comprises a recipient scaffold and a recipient interaction sequence.

81. A use, method or library according to clause 80, wherein the fusion protein is a knotbody comprising a cysteine rich peptide inserted within an antibody variable domain.

82. A use, method or library according to clause 81, wherein the knotbody comprises an antibody heavy chain fused to a transmembrane domain, and an antibody light chain.

83. A use, method or library according to any preceding clause, wherein the binders comprise antibody variable domains exhibiting sequence diversity, optionally in one or more complementarity determining regions.

84. A use, method or library according to any preceding clause, wherein the binders comprise Fc regions exhibiting sequence diversity, optionally in their CH3 domains.

85. A use, method or library according to any preceding clause, wherein the binders are multispecific, comprising a first binding site for a first target and a second binding site for a second target.

86. A use, method or library according to any preceding clause, wherein the library comprises at least $10^3$ clones.

87. A use, method or library according to any preceding clause, wherein the library is a naive library.

88. A use, method or library according to any of clauses 1 to 86, wherein the clones of the library have been pre-selected for binding to a chosen target.

89. A use, method or library according to clause 88, wherein the target is a human polypeptide.

90. A use, method or library according to clause 88 or clause 89, wherein the clones of the library have been pre-selected for bispecific binding to two different targets.

Those skilled in the art will recognise, or be able to ascertain using no more than routine experimentation, many equivalents to the specific embodiments of the invention described herein. Such equivalents are intended to be encompassed by the appended claims.

Other aspects and embodiments of the invention provide the aspects and embodiments described above with the term "comprising" replaced by the term "consisting of" and the aspects and embodiments described above with the term "comprising" replaced by the term "consisting essentially of".

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Unless defined otherwise, all technical and scientific terms used herein have the same meaning as commonly understood by one of ordinary skill in the art to which this invention belongs. Although any compositions and methods similar or equivalent to those described herein can be used in the practice or testing of the methods of the disclosure, exemplary compositions and methods are described herein. Any of the aspects and embodiments of the disclosure described herein may also be combined. For example, the subject matter of any dependent or independent claim disclosed herein may be multiply combined (e.g., one or more recitations from each dependent claim may be combined into a single claim based on the independent claim on which they depend).

As used herein and in the claims, the singular forms "a," "and," and "the" include plural reference unless the context clearly dictates otherwise. Thus, for example, reference to "a peptide chain" is a reference to one or more peptide chains and includes equivalents thereof known to those skilled in the art.

All documents and sequence database entries mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

BRIEF DESCRIPTION OF THE DRAWINGS

Embodiments of the invention will now be described in more detail, with reference to the drawings, which are as follows.

pINT17-BSD-D1.3, a dual promoter antibody expression cassette for surface expression of the anti-lysozyme antibody D1.3. The full annotated nucleic acid sequence is shown.

Features:

AAVS left homology arm 9-812
Blasticidin resistance gene 853-1254
pEF promoter 1522-2705
BM40 leader 2745-2799
Humanised D1.3 VL 2799-3130
Human C kappa 3138-3443
BGH poly A 3468-3682
CMV promoter 3701-4273
Mouse VH leader with intron 4299-4426
Humanised D1.3 VH 4432-4779
Optimised human IgG1 CH1-CH3 4780-5775
Myc tag 5776-5805
PDGFR anchor 5806-5961
BGH polyA 6011-6225
AAVS right homology arm 6288-7124
f1 replication origin 7282-7695
pUC replication origin 7916-8590
Kanamycin resistance gene 9310-10104

Figure 2:
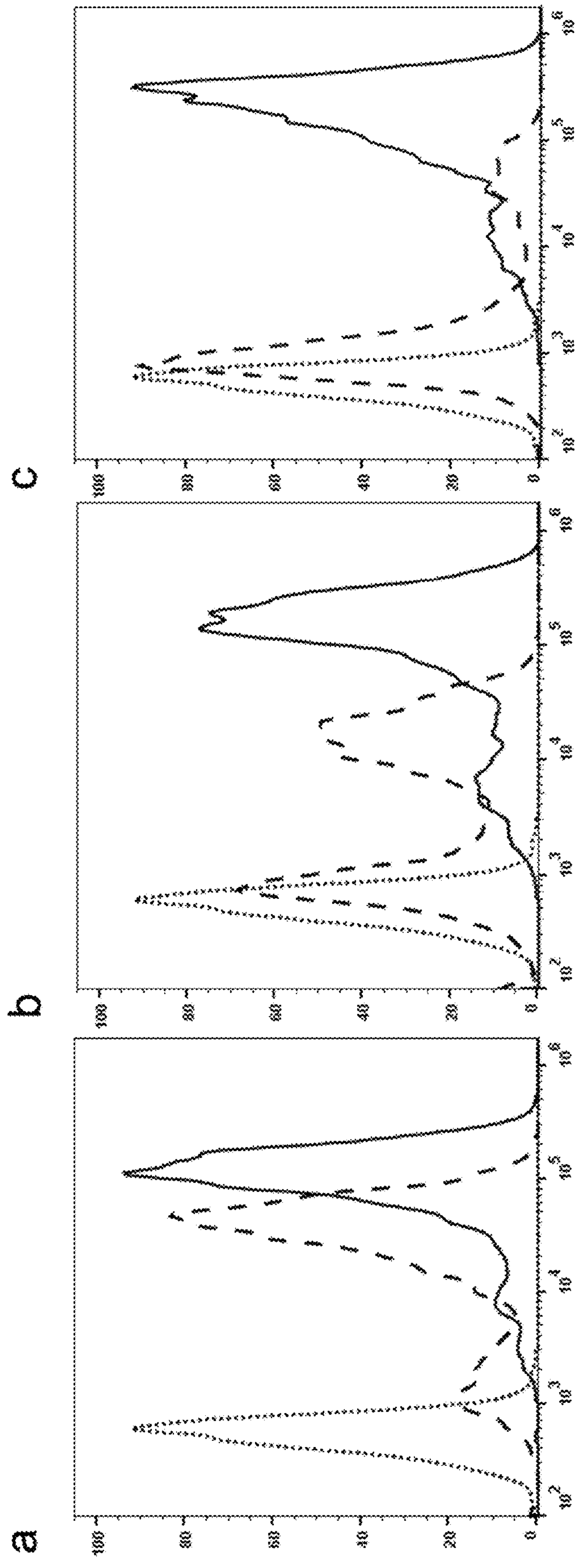

FIG. 2. Expression of IgG on cell surface.

Analysis was focused on viable cells using forward scatter and staining in the FL3 channel. Cells positive for staining in the FL3 channel (representing non-viable cells which took up 7-AAD) were excluded. HEK293 cells were transfected with pINT17-antibodies in presence of the AAVS TALENs. Stable populations were selected with Blasticidin. 14 days post-transfection, cells were stained with anti-Fc PE (FL2). Panels depicting fluorescence intensity (anti-Fc-PE, x-axis) plot against cell count (y-axis) and include the CNTO607 (a), MEDI1912 (b) and Ang2mAb (c) pairs. For all panels the plots include stained HEK293 cells (dotted line), parental antibody (dashed line), improved mutant (solid black line).

Figure 3:
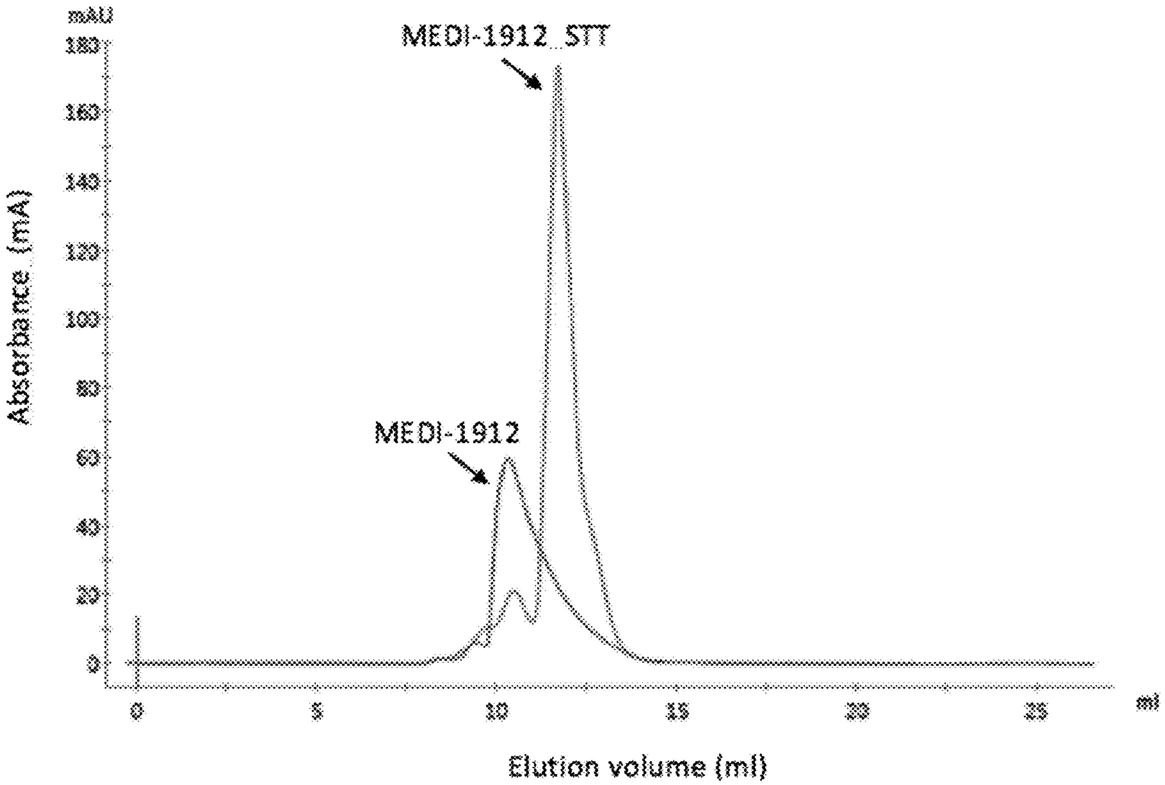

FIG. 3. Preparative size exclusion chromatography of MEDI-1912 and MEDI-1912-STT. Antibodies were expressed by transient transfection of Expi293 cells followed by protein A affinity purification and dialysis. Purified MEDI-1912 (0.5 ml, 1.1 mg/ml) or MEDI-1912-STT (0.5 ml, 1.7 mg/ml) were loaded onto a Superdex 200 10/300 column connected to an AKTA Pure system using a PBS (pH 7.4) running buffer. The elution volume (ml) us plotted on the x axis against the absorbance at 280 nm (mAU) on the y-axis. The elution volume (Ve) for MEDI-1912 and MEDI-1912-STT was 10.3 ml and 11.7 ml respectively. MEDI-1912 shows an earlier elution volume indicating self-interaction.

FIG. 4. DNA and protein sequence of MED-1912 variable heavy (VH) chain. Primers employed for library creation are labelled above the nucleic acid sequence.

FIG. 5. FACS separation of mixed cell displayed antibody populations based on antibody expression.

An equal mix of MEDI-1912 and MEDI-1912_STT IgG genes were targeted via nuclease-directed integration into the AAVS locus of HEK293 cells. This mixed cell population, 15 days post-transfection, was separated on the basis of antibody expression by FACS using a BD Influx sorter. Cells were stained with anti-Fc labelled with phycoerythrin (PE) and NGF-biotin/streptavidin labelled with allophycocyanin (APC). Analysis was focused on viable cells using forward scatter and staining. Cells positive for staining in the λem=450/40, λexc=355 channel (representing non-viable cells which took up 7-AAD) were excluded.

a. Histogram plot of fluorescence intensity for anti-Fc-PE against cell counts for the mixed input population (dashed line), and monoclonal HEK293 cell lines displaying MEDI-1912 (grey line) and MEDI-1912_STT (black line).

b. The dot-plot shows fluorescence intensity for anti-Fc-PE (x-axis), representing antibody expression level, plotted against fluorescence intensity for antigen binding (NGF-biotin/NGF-biotin/streptavidin-APC) on the y-axis. The gates chosen to separate the high and low antibody expression populations are labelled P5 and P6 and are shown as black boxes on the dot-plot. The total event count was $3.9\times10^6$ cells and the number of cells sorted in the P5 and P6 gates was $2.5\times10^5$ and $2.8\times10^5$ cell respectively.

Figure 6:
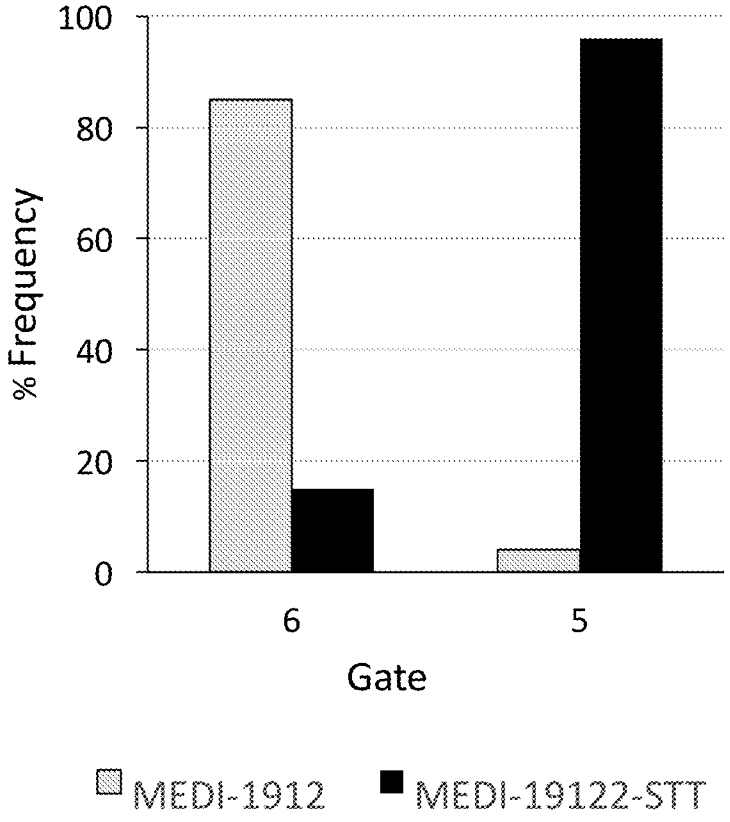

FIG. 6. Enrichment of antibodies selected by mammalian cell display level. Cells sorted in gates 5 and 6 (FIG. 5) were expanded, genomic DNA prepared and antibody VH genes isolated by PCR. The two antibody populations were analysed by Nextgen sequencing to determine the proportion of MEDI-1912 and MEDI-1912_STT in the two gated populations. The histogram shows the percentage frequency of MEDI-1912 (hatched bars) and MEDI-1912_STT (solid black bars) in the low antibody expression population (Gate 6) and the high antibody expression population (Gate 5).

Figure 7:
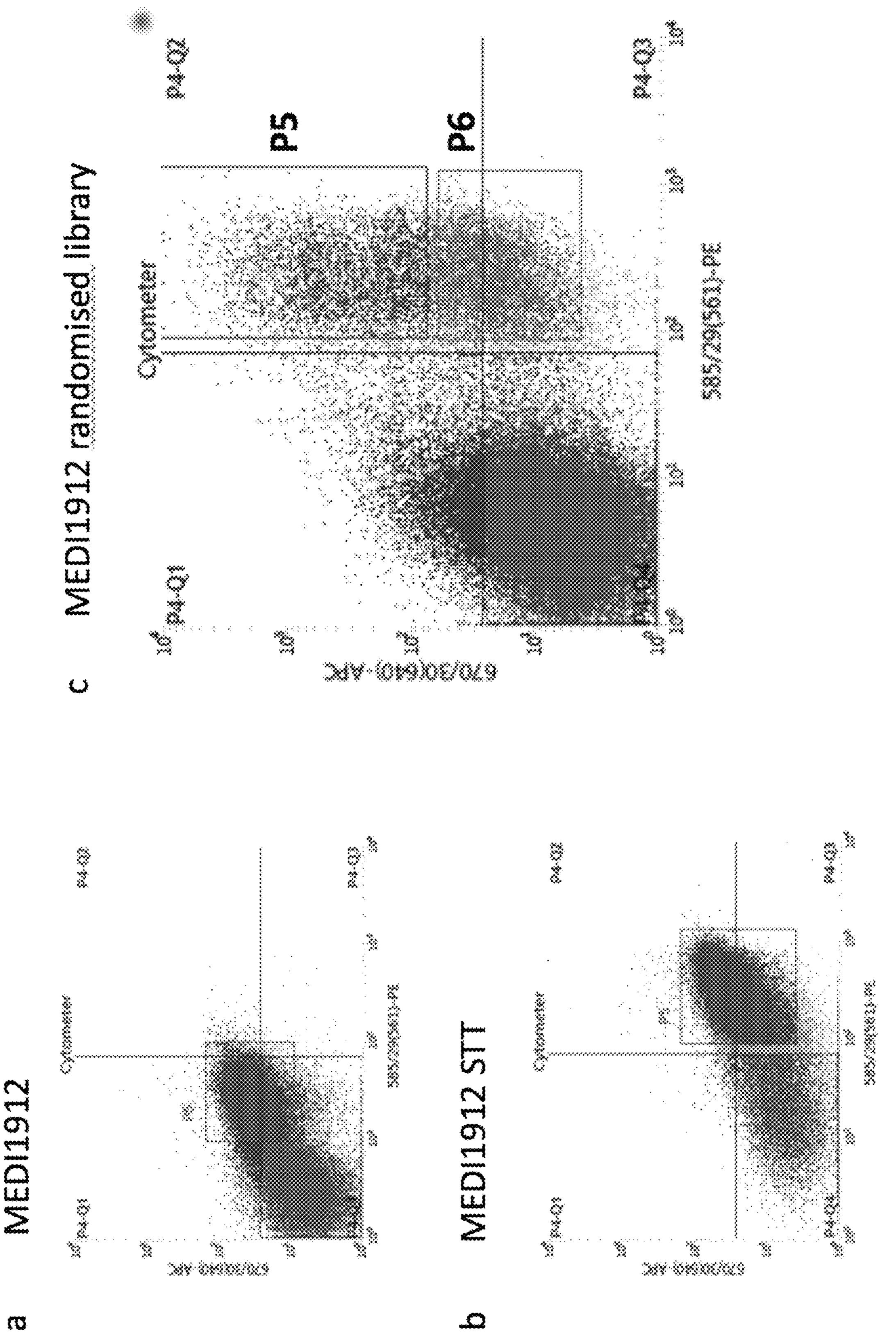

FIG. 7. FACS separation of the MEDI-1912 library antibody populations based on antibody expression.

A library of MEDI-1912 IgG genes, where NNS oligonucleotide-directed mutagenesis was used to randomly mutate the codon encoding W30, F31 and L56, were targeted via nuclease-directed integration into the AAVS locus of HEK293 cells. This mixed cell population, 15 days post-transfection, was separated on the basis of antibody expression and antigen binding by FACS using a BD Influx sorter. Cells were stained with anti-Fc labelled with phycoerythrin (PE) and NGF-biotin/streptavidin labelled with allophycocyanin (APC). Analysis was focused on viable cells using forward scatter and staining. Cells positive for staining in the λem=450/40, λexc=355 channel (representing non-viable cells which took up 7-AAD) were excluded. The dot-plot shows fluorescence intensity for anti-Fc-PE (x-axis), representing antibody expression level, plotted against fluorescence intensity for antigen binding (NGF-biotin/NGF-biotin/streptavidin-APC) on the y-axis for the parental MEDI-1912 displaying monoclonal cell line (a), the MEDI-1912_STT displaying monoclonal cell line (b) and the MEDI-1912 amino-acid position 30, 31 and 56 random library (c). The gates chosen for analysis are labelled P5 and P6 and are shown as boxes on the dot-plot.

Figure 8:
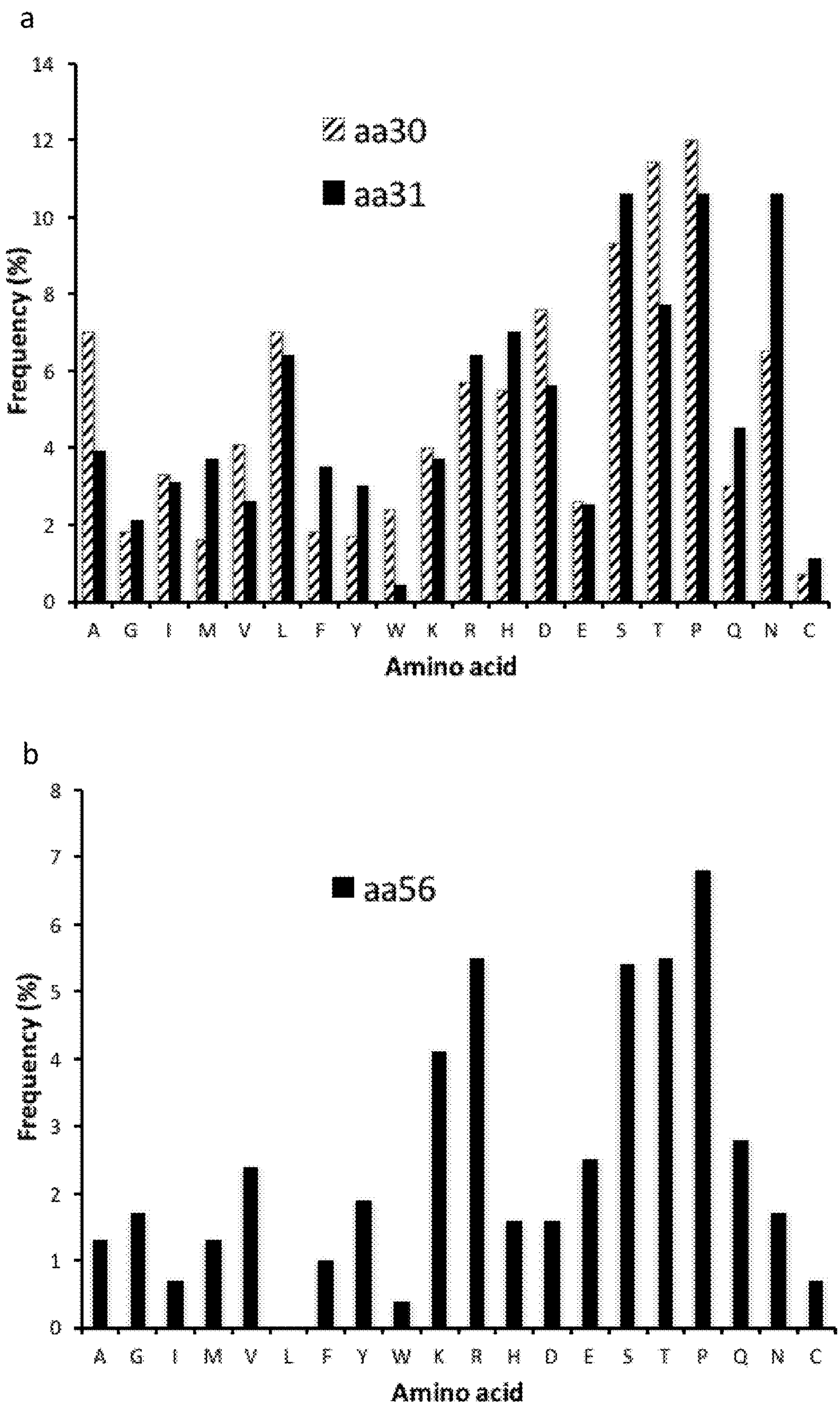

FIG. 8. Sequence distribution of selected MEDI-1912 variants.

Histogram plots of amino acid identity frequency at MEDI-1912 VH positions 30, 31 and 56 for the MEDI-1912 VH library after mammalian display and FACS gated on Fc expression and NGF binding (P5 gate, FIG. 7). Amino acid (single letter code) is plotted on the x-axis against frequency (percentage occurrence) on the y-axis for the adjacent amino acids 30, hatched bars and 31, black bars (a) and amino acid 56 (b). Leucine in position 56 was excluded from the analysis.

FIG. 9. Alignment of Bococizumab mouse parental antibody 5A10 VH (A) and VL (B) with the humanized intermediate antibody 5A10-i and Bococizumab.

CDRs are indicated by bars above the sequence and residues to be mutated are highlighted in bold and underlined. Paratopic residues (amino acids that contribute to direct binding to PCSK9) are highlighted in italic and underlined. Dots indicate identity with the parental mouse mAb 5A10.

Figure 10:
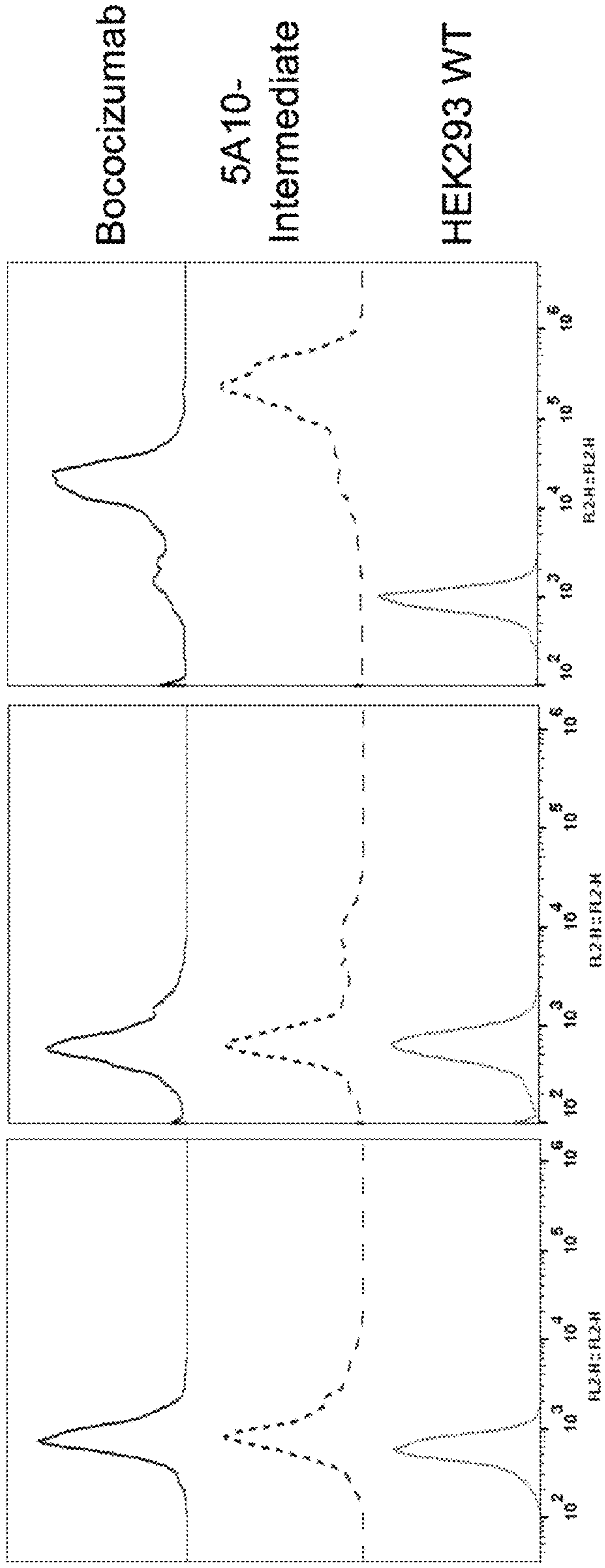

FIG. 10. Antibody mammalian display expression of Bococizumab and the parental humanized intermediate antibody 5A10-i Targeting vector pINT17 encoding Bococizumab or 5A10-i) IgG were integrated into the AAVS locus of Hek293 cells via TALE nuclease. Cell ($10^6$) were stained with anti-Fc-PE at 1, 8 or 21 days post transfection (dpt) and 106 cells analysed by flow cytometry with an iQue Intellicyte flow cytometer. Dead cells were excluded from the analysis. Histogram plots show fluorescence intensity (anti-Fc-PE) against cell count for the Bococizumab and 5A10-i cell display populations at 1, 8 and 21 days post transfection (dpt) with a staining of wild-type HEK293 cells included as a negative control.

FIG. 11. Alignment of Bococizumab VH with human germ-line sequences (IMGT). Bococizumab VH (Query_1) was subject to an Ig Basic Local Alignment Search (Ig-BLAST) against the human VDJ database. The results are presented as an alignment to the query sequence encompassing framework region 1 (FR1), complementarity determining region 1 (CDR1), FR2, CDR2 and FR3 in order of percentage identity (second column). The human germ-line is shown in column 1. Residue identity to the Bococizumab VH sequence (.) and differences (single amino acid code) is shown in the multiple alignment.

FIG. 12. DNA sequences encoding the Bococizumab VH variants and VL plus stop codon template. Variations compared with the original "wild-type" Bococizumab (row f) are highlighted in bold and underlined. The flanking 5' and 3' VH restriction sites (NcoI and XhoI) or VL restriction sites (NheI and NotI) are underlined. The VL stop codon are highlighted in bold and underlined.

Figure 13:
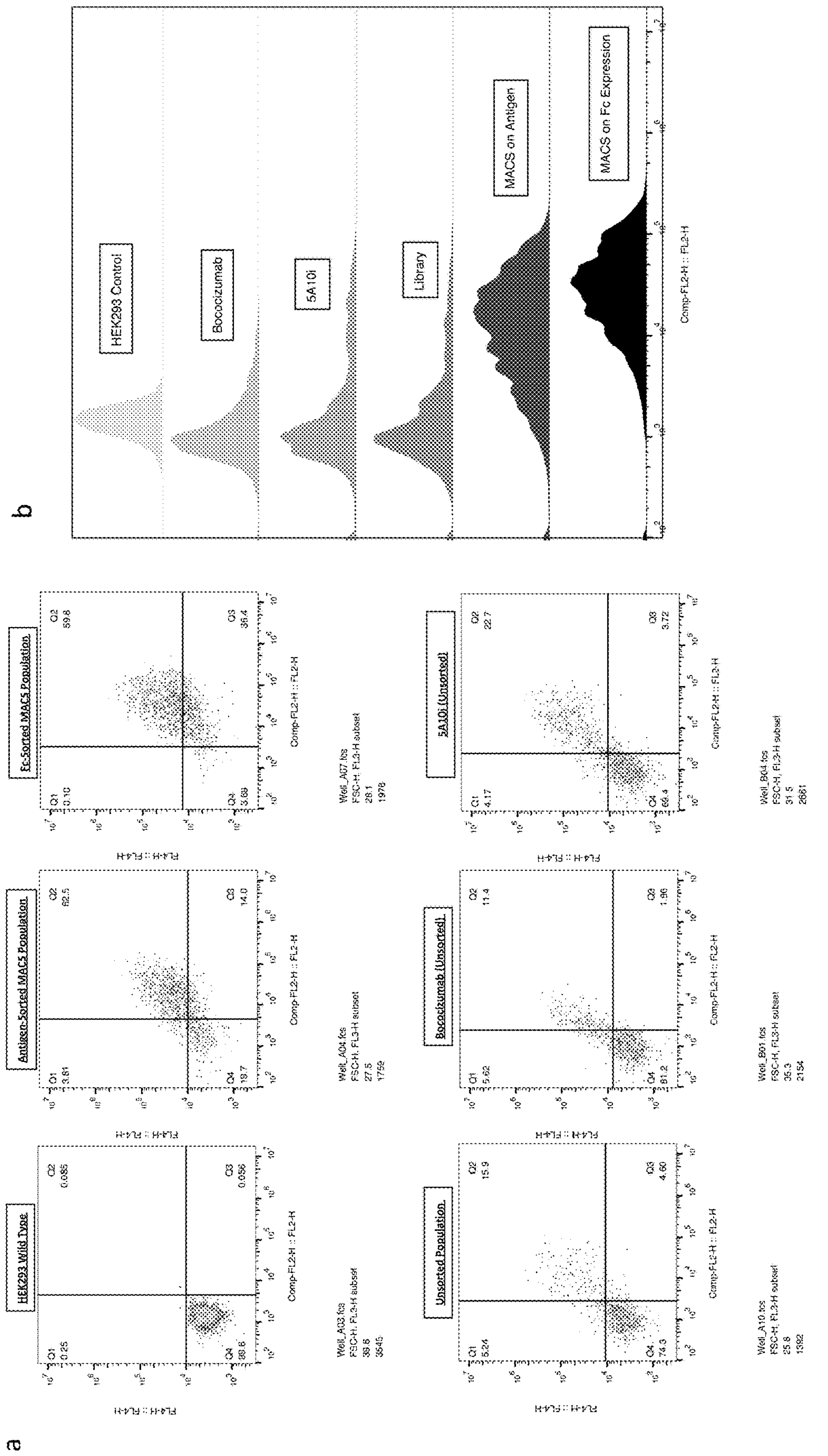

FIG. 13. Analytical flow cytometry analysis post-MACS purification of the Bococizumab libraries Hek293 cells transfected with the Bococizumab library were MACS purified 7 dpt with either anti-Fc or PCSK9i. (a) Flow cytometry dot plots are shown of anti-Fc expression (FL2, x-axis) plotted against PCSK9 binding (FL4, y-axis) for the post-MACS purified libraries, HEK293 cells and the unsorted library, Bococizumab and 5A10i transfectants, 9dpt. (b) Histogram of fluorescence intensity (anti-Fc, FL2, x-axis) plotted against cell count. Plots are (from top to bottom) the HEK293 control, Bococizumab, 5A10i, Bococizumab Library, anti-PCSK9 MACS purified Bococizumab Library, and anti-Fc MACS purified Bococizumab Library.

FIG. 14. BD Influx sorter dot plots of Bococizumab libraries previously MACS purified based on antigen binding or anti-Fc.

A library of Bococizumab IgG genes were targeted via nuclease-directed integration into the AAVS locus of HEK293 cells. This mixed cell population was first MACS purified based on PCSK9 binding (a) or anti-Fc (b). 16 days post-transfection the MACS enriched libraries were separated on the basis of antibody expression and antigen binding by FACS using a BD Influx sorter. Cells were stained with anti-Fc labelled with phycoerythrin (PE) and PCSK9-biotin/streptavidin labelled with allophycocyanin (APC). Analysis was focused on viable cells using forward scatter and staining. Cells positive for staining in the λem=450/40, λexc=355 channel (representing non-viable cells which took up 7-AAD) were excluded. The dot-plot shows fluorescence intensity for anti-Fc-PE (x-axis), representing antibody expression level, plotted against fluorescence intensity for antigen binding (PCSK9-biotin/streptavidin-APC) on the y-axis. The gate chosen for analysis are labelled P5 and P6 are shown as boxes on the dot-plot.

Figure 15:
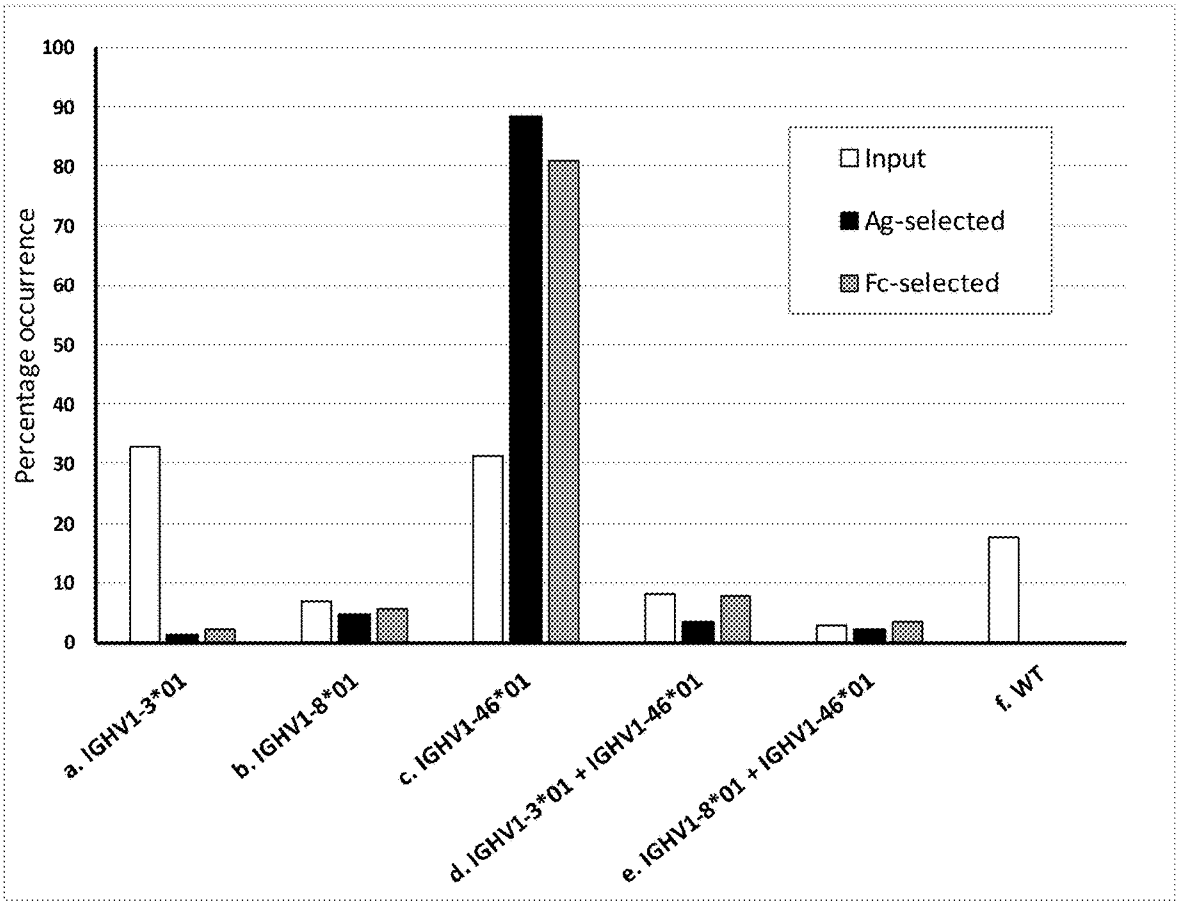

FIG. 15. Bococizumab VH distribution after mammalian display selection. Random unselected input clones (84), antigen sorted (75) and Fc selected (85) were sequenced and the VH identity determined. A histogram plot shows the VH germ-line identity on the x-axis plotted against the percentage occurrence for the input (white filled bars), antigen MACS followed by antigen and anti-Fc FACS selected (black filled bars) and anti-Fc MACS followed by antigen and anti-Fc FACS selected (grey filled bars) mammalian cell display selected populations.

Figure 16:
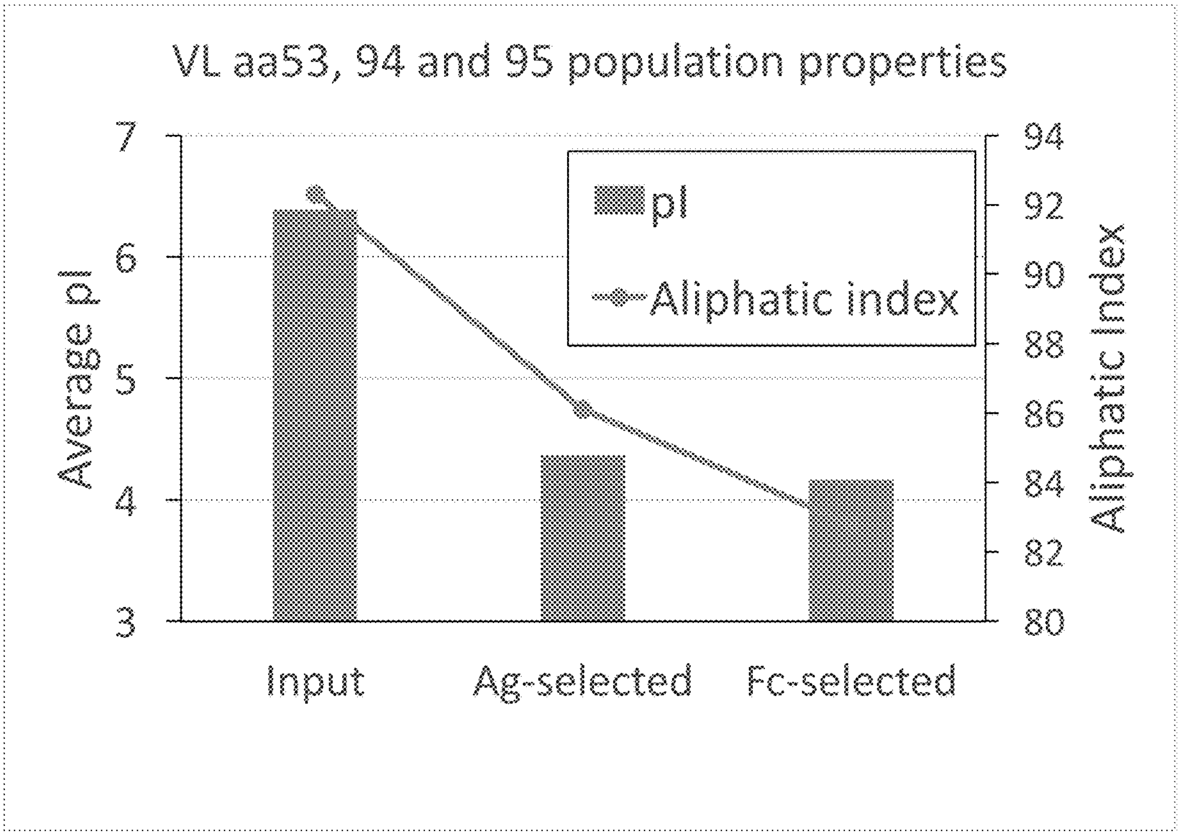

FIG. 16. Bococizumab VL sequence analysis after mammalian display selection. Random un-selected input clones (84), antigen sorted (75) and Fc selected (85) were sequenced and the VL sequence determined. The average pI and aliphatic index was calculated for the 3 mutated codons. This showed a reduction in both pI and aliphatic index for the mammalian display selected antibodies.

FIG. 17. Table listing the mammalian display Bococizumab clones, enriched for antigen binding by MACS followed by FACS enrichment for both antibody display level (anti-Fc) and antigen binding.

Clones were sequenced and the VH CDR1 and CDR2 and VL CDR2 and CDR3 single letter amino acid sequences are shown with variations from the original Bococizumab sequence highlighted in bold and red. Targeted amino acids which retained the Bococizumab sequence are underlined. Binding of antibodies, including the original parental antibodies Bococizumab and 5A10-i, to antigen in a capture ELISA was performed and the binding signal in fluorescence units is shown in column 2. The AC-SINS assay was performed as described previously by Liu et al, 2014[30] and column 3 shows the maximal absorbance wavelength shift compared to a no antibody PBS control (nm). The selected human VH germ-line is also indicated in column 6 by letter as detailed in Example 5:

a: VH Y33A-IGHV1-3*01 b: VH Y33D-IGHV1-8*01 c: VH S52N, F54S, R57S-IGHV1-46*01 d: VH Y33A, S52N, F54S, R57S (a. and c. mutants combined)

e: VH Y33D, S52N, F54S, R57S (b. and c. mutants combined)

f: Bococizumab "wild-type" sequence

Figure 18:
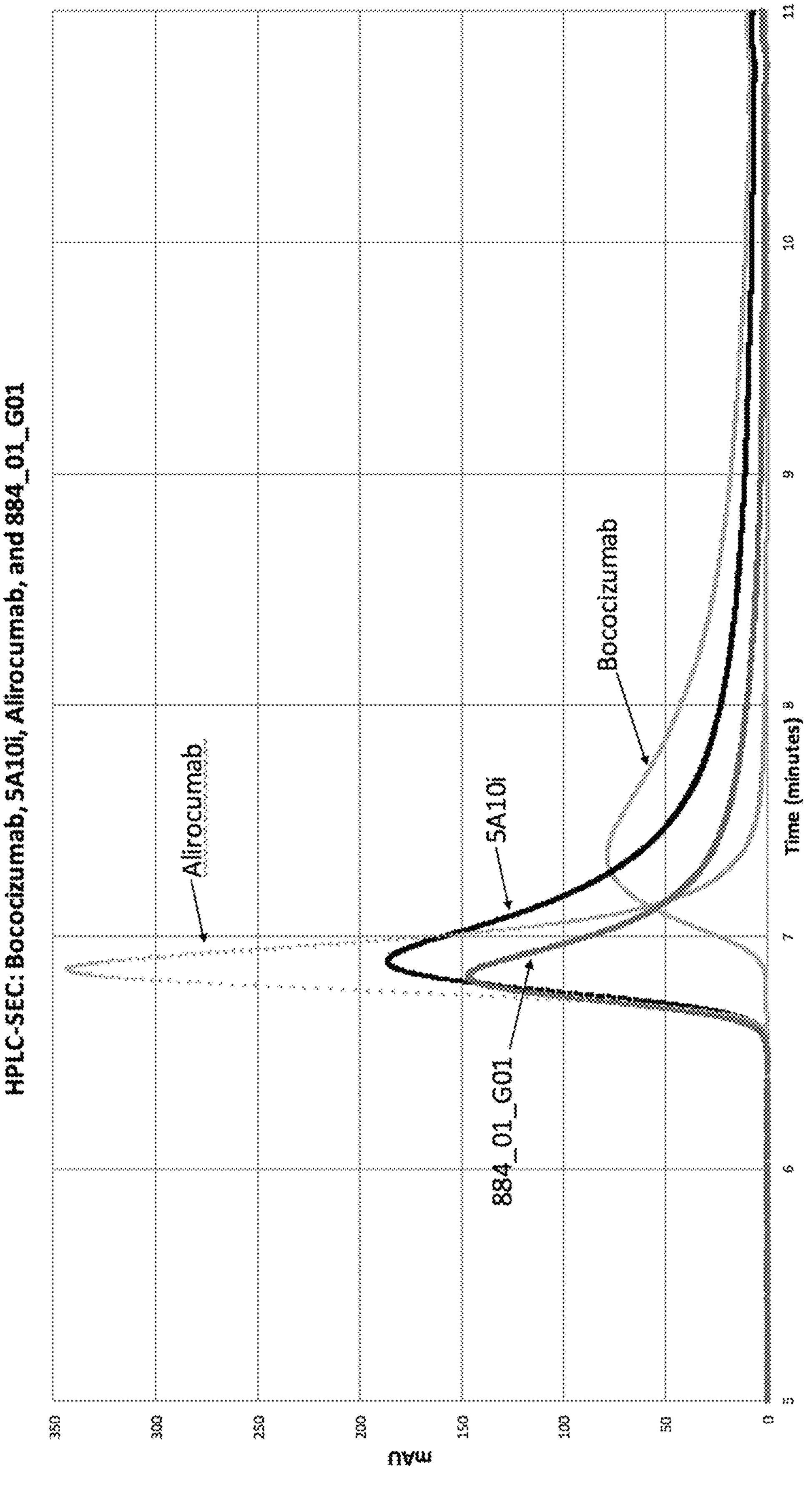

FIG. 18. HPLC-SEC of anti-PCSK9 IgG1 antibodies.

Antibodies were expressed by transient transfection of Expi-293 cells, affinity purified by protein A chromatography and dialysed. Samples (2 μl at 1 mg/ml) were loaded onto an Agilent AdvancedBio SEC 300A, 2.7 um, 4.6×300 mm column (Agilent Technologies, Cat. No. PL1580-5301) at a flow rate of 0.35 ml/min using an Agilent 1100 HPLC instrument. A plot of retention time against absorbance is shown for selected antibodies. From black to progressively lighter shades of grey are: 5A10-i, 884_01_G01 (identified by mammalian cell display), Bococizumab and Alirocumab.

Figure 19:
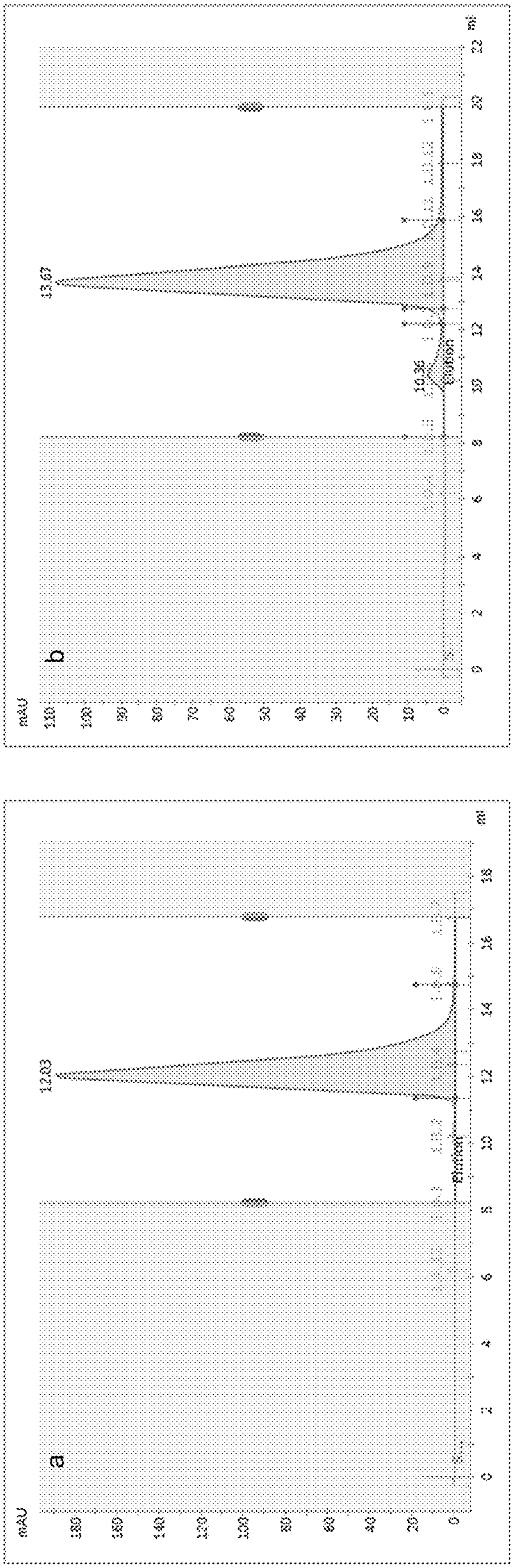

FIG. 19. Gel filtration analysis Nivolumab (a) and Vesencumab (b).

Antibodies were expressed by transient transfection of Expi293 cells followed by protein A affinity purification and dialysis. Purified Nivolumab (0.5 ml, 1.3 mg/ml) or Vesencumab (0.5 ml, 1.2 mg/ml) were loaded onto a Superdex 200 10/300 column connected to an AKTA Pure system using a PBS (pH 7.4) running buffer. The elution volume (ml) us plotted on the x axis against the absorbance at 280 nm (mAU) on the y-axis. The elution volume (Ve) for Nivolumab and Vesencumab was 12.0 ml and 13.7 ml respectively.

Figure 20:
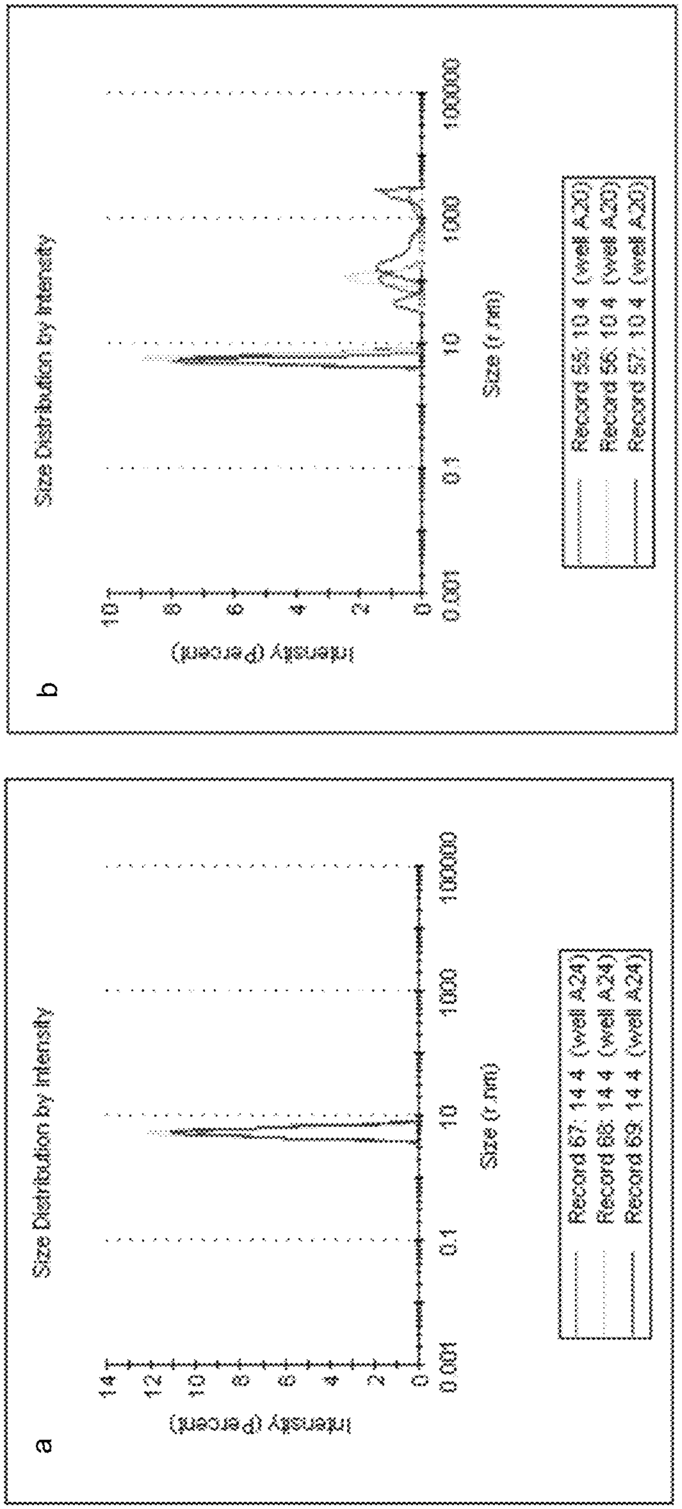

FIG. 20. Stability determination of Nivolumab (a) and Vesencumab (b) after storage at 4° C., 2 weeks.

Vesencumab and Nivolumab were purified by size exclusion chromatography (see FIG. 19) and their concentrations adjusted to 0.5 mg/ml in PBS (pH7.4). The antibodies were then stored at 4° C. for 2 weeks. Dynamic light scattering measurements were performed at 20° C. using a Zetasizer APS (Malvern Instruments, Malvern, UK) according to the manufacturer instructions. The hydrodynamic radius was evaluated with the Einstein-Stokes equation and plotted against scatter intensity. A single mono-disperse peak was observed for Nivolumab (a) in comparison to multiple aggregate peaks for Vesencumab (b).

Figure 21:
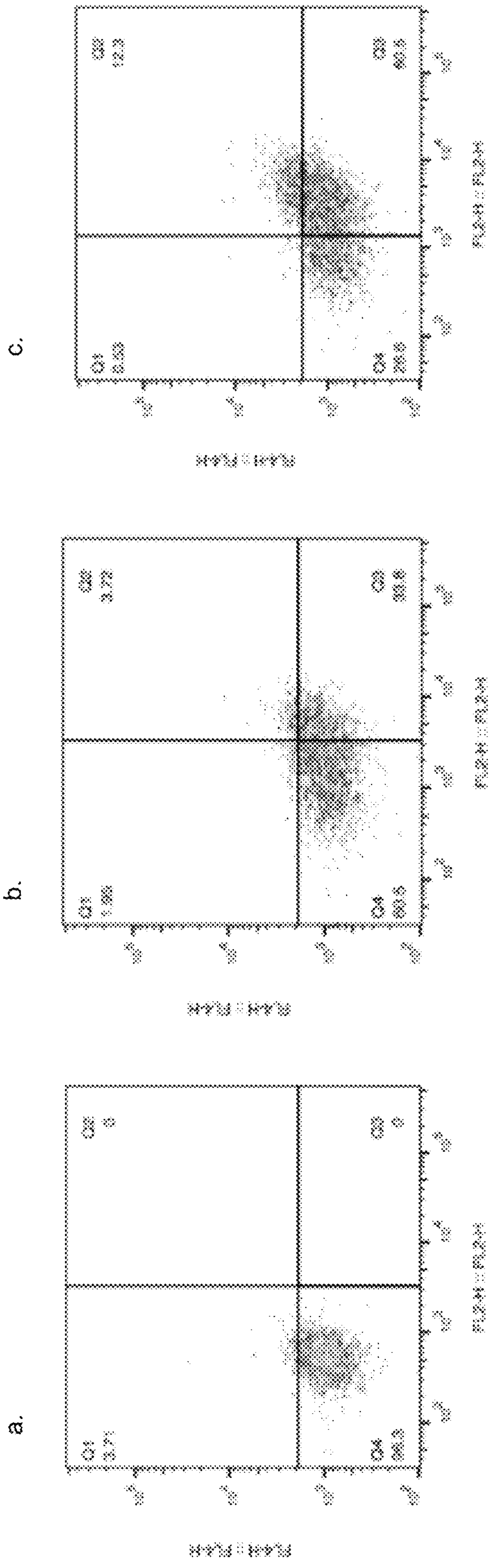

FIG. 21. Human serum binding to IgG on cell surface.

Analysis was focused on viable cells using forward scatter and staining in the FL3 channel. Cells positive for staining in the FL3 channel (representing non-viable cells which took up 7-AAD) were excluded. Cells were transfected with pINT17-Nivolumab or pINT17-Vesencumab in presence of the AAVS TALENs. Stable populations were selected with Blasticidin. 20 days post-transfection, cells were stained with anti-Fc PE (FL2) and human serum (H4522, Sigma) labelled with Dylight 633 (325-0000, Innova). Panels are untransfected HEK293 cells (a), pINT17-Nivolumab (b) or pINT17-Vesencumab (c) transfected HEK293 cells.

FIG. 22. Relationship between affinity, concentration of antigen and concentration of antibody a Concentration of complex using 0.1 nM antigen with differing concentrations of antibody of either $K_D$ 10 nM (dashed line) or 0.1 nM (solid line).

bi Relative selectivity of binding to 0.1 nM antigen for higher affinity antibody ($K_D$ 0.1 nM) versus lower affinity ($K_D$ 10 nM) at different antibody concentrations Even with low ("stringent") antigen concentrations, there is relatively little selectivity at high antibody concentrations but this increases as the antigen concentration drops.

FIG. 23. Splice acceptor/donor variants to control antibody display level.

The nucleic acid sequence from the HindIII site to the 5' intron, including the splice donor region is shown for the pINT17-J9, J10, J29 and J30 variants. The original human "wild-type" sequence is J9 and the nucleotides varying from J9, at the splice junction, for J10, J29 and J30 are underlined.

FIGS. 24A-24D. pINT17-J30, a dual promoter antibody IgG expression cassette for reduced display surface expression. The annotated nucleic acid sequence is shown between the XhoI (4804) and SbfI (8387) restriction sites. Features:

IgG1 CH1-3 4805-5808
Splice junction 5801-5802
Intron 5802-7104
M1 exon 7105-7239
BGH pA 7264-7478
AAVS right homology arm 7544-8381
3'β-globin insulator 8421-8492

Figure 25:
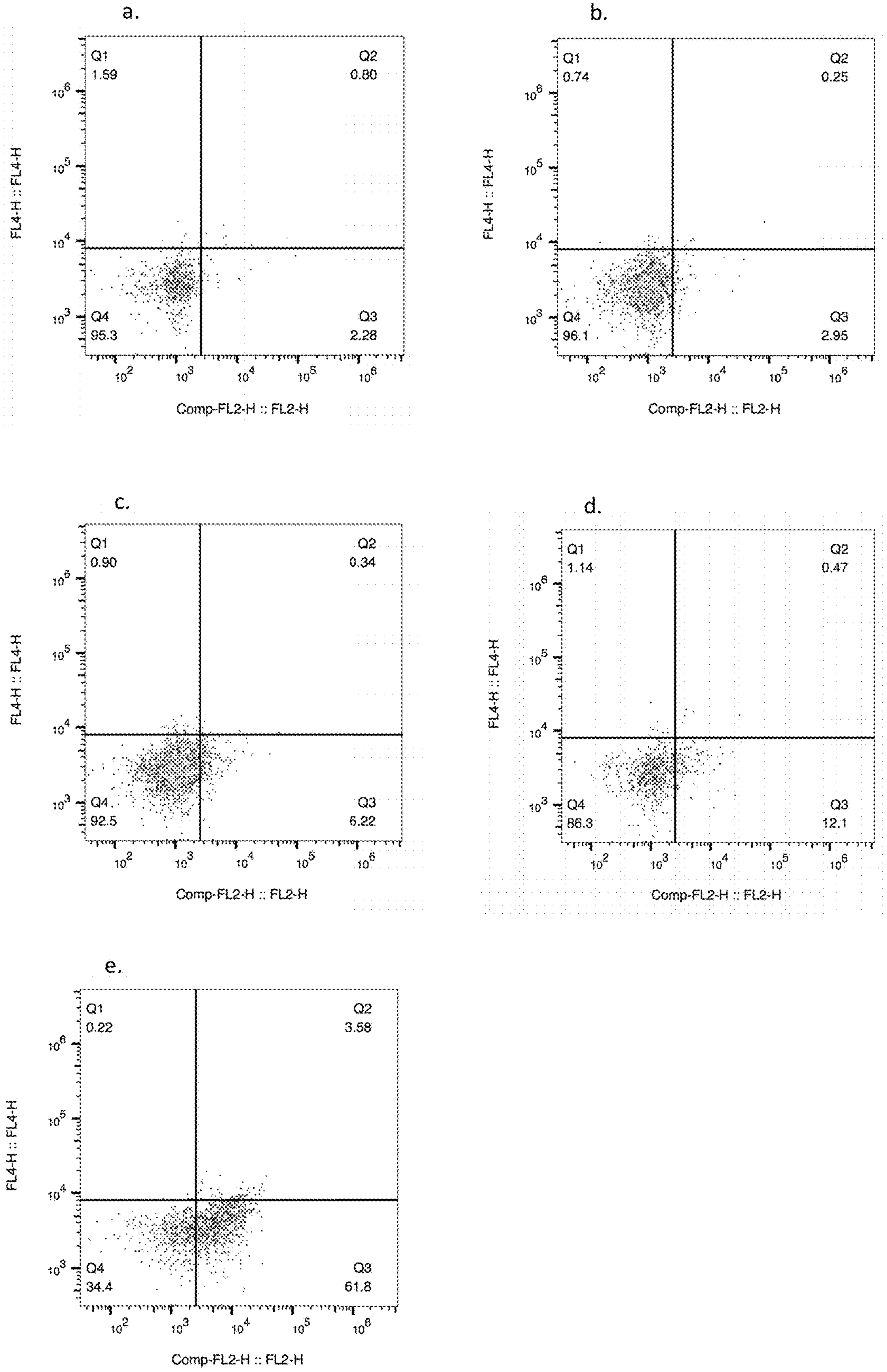

FIG. 25. Reduced surface expression of IgG on the cell surface using alternative transmembrane domain and splice variants.

Analysis was focused on viable cells using forward scatter and staining in the FL3 channel. Cells positive for staining in the FL3 channel (representing non-viable cells which took up 7-AAD) were excluded. Cells were transfected with pINT17 targeting vectors in presence of the AAVS TALENs. Stable populations were selected with Blasticidin. 27 days post-transfection, cells were stained with anti-Fc PE (FL2). Flow cytometry dot-plot panels include pINT17-J9-Nivolumab (a), pINT17-J10-Nivolumab (b), pINT17-J29-Nivolumab (c), pINT17-J30-Nivolumab (d) and pINT17-BSD-Nivolumab (e).

Figure 26:
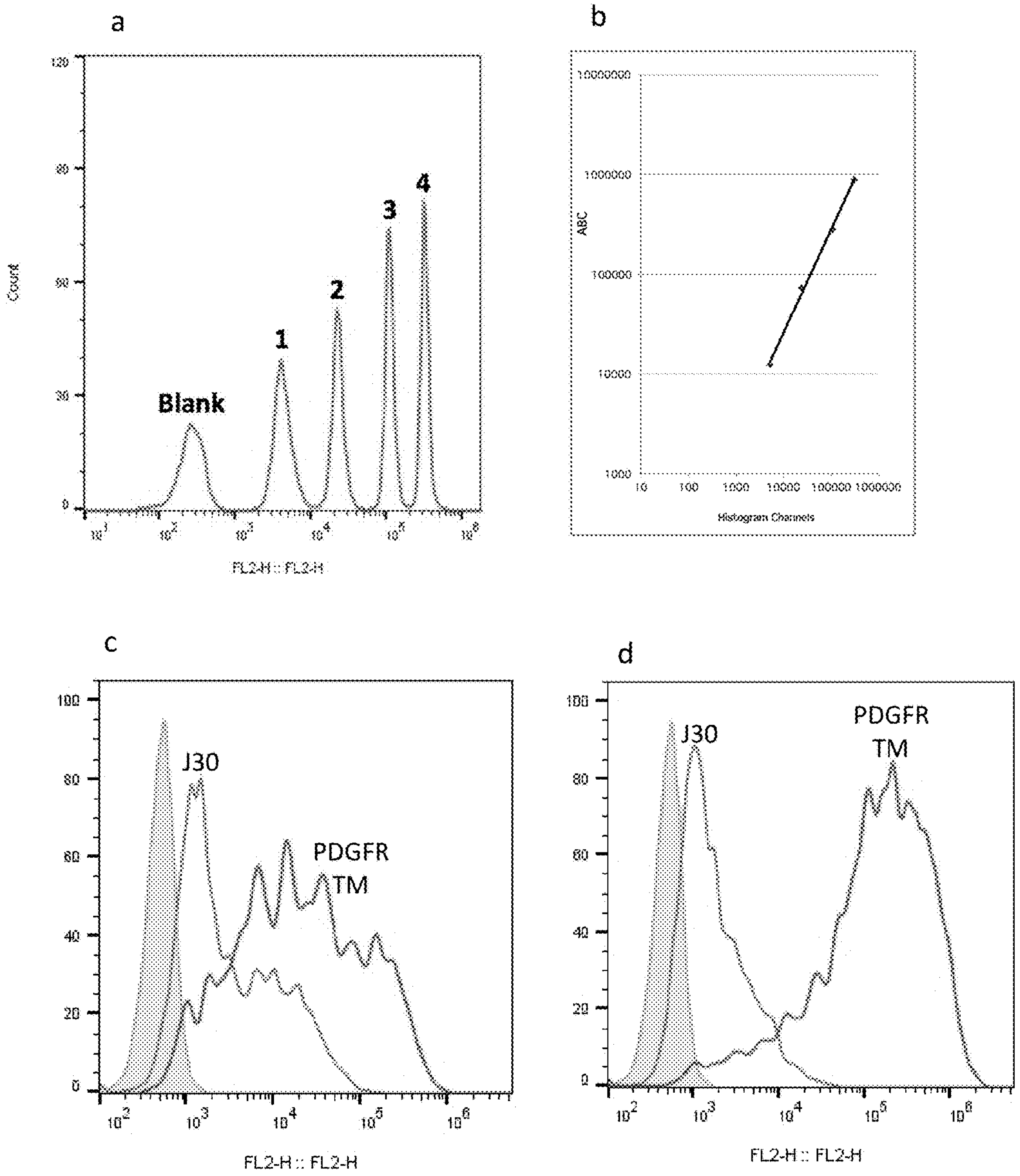

FIG. 26. Quantitation of IgG display level on the cell surface for antibodies expressed from the pINT17-BSD or pINT17-J30 targeting vectors Calibration beads FL2 staining was performed as described in the manufacturer instructions for the Quantum Simply Cellular anti-mouse IgG beads (catalogue number 815, Bangs Laboratories Inc) stained with mouse IgG-PE label. (a) Labelled histogram plot shows staining of the calibration bead set with peaks labelled 1, 2, 3 and 4 representing bead copy numbers of 12257, 72745, 283360, 886417 respectively. The blank peak represents bead with no capture antibody. (b) Calibration graph showing median fluorescence intensity (x-axis) plotted against copy number (y-axis). Cells-lines displaying 337_1_C08 (c) and Nivolumab (d) from either the pINT17-BSD or pINT17-J30 expression cassette were stained with anti-Fc-PE (5 μl, 0.1 mg/ml; $10^5$ cells). Analysis was focused on viable cells using forward scatter and staining in the FL3 channel. Cells positive for staining in the FL3 channel (representing non-viable cells which took up 7-AAD) were excluded. Histogram plots show fluorescence intensity against cell count for the pINT17-BSD with PDGFR TM (labelled and solid black line), pINT17-J30 (labelled and dotted line) and wild-type HEK293 cell lines (grey solid line) for cells displaying 337_1_C08 (c) and Nivolumab (d) respectively.

FIG. 27. Separation of antibodies with different affinities for their target by mammalian display is enabled by a reduction in cell display copy number.

Hek293 cells displaying Nivolumab and 337_1_C08 antibodies were labelled with 50 nM cell tracker green and 50 nM cell tracker red respectively. (a) demonstrates the display using the J30 splice variant and (b) demonstrates the display using PDGFR transmembrane domain encoded by the pINT17-BSD vector. Labelled cells were mixed equally and MACS sorted based on antigen binding. Sorted cells were analysed using the intellicyt flow cytometer. Dot plots represents Nivolumab on x-axis (FL1) and 337_1_C08 on y-axis (FL4). Panel i, ii, iii and iv represents 10 nM, 1 nM, 0.1 nM and no antigen respectively employed for MACS purification.

FIG. 28. pINT18-Tet1, an inducible promoter antibody IgG expression vector for reduced display surface expression. The annotated nucleic acid sequence is shown between the AsiS1 (5) and SbfI (7672) restriction sites. The vector backbone exterior to the AsiSI and SbfI sites (7673-10922 and 1-4) encompassing the origins of replication and kanamycin resistance gene is identical to pINT17-BSD (FIG. 1).

Key Features:
AAVS left homology arm 9-812
Blasticidin resistance gene 853-1254
CMV promoter 1540-2112
Reverse Tet activator (tTA) CDS 2164-3168
SV40 pA 3178-3395
tetO heptamer 3679-3932
Minimal CMV promoter (PminCMV) 3946-4005
BM40 leader 4016-4066
Anti-PD1 MK3475 VL 4068-4413
Human C kappa 4421-4738
Furin cleavage site 4745-4756
P2A peptide 4757-4816
Mouse VH leader with intron 4829-4960
Anti-PD1 MK3475 VH 4962-5321
Optimised human IgG1 CH1-CH3 5322-6317
Myc tag 6318-6347
PDGFR anchor 6348-6503
BGH polyA 6553-6767
AAVS right homology arm 6829-7666
3' β-globin insulator 7706-7777
f1 replication origin 7824-8237
pUC replication origin 8458-9132
Kanamycin resistance gene 9852-10646

Figure 29:
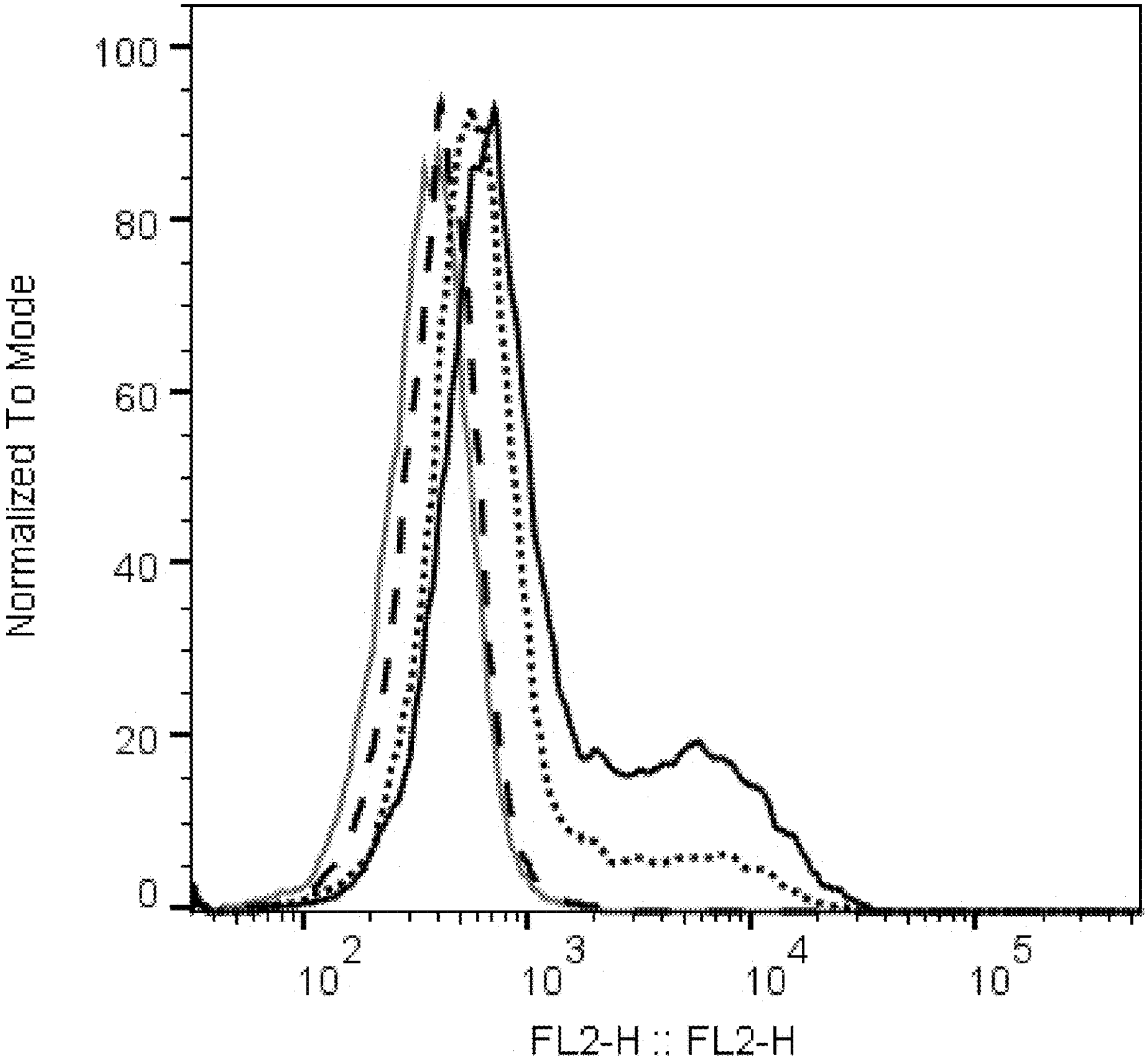

FIG. 29. Inducible mammalian display expression
Histogram representing staining results from a HEK293 cell line co-transfected with pINT18-Tet1-377_1_C08 and TALE nucleases and a stable cell population selected for 20 days in the presence of blasticidin. The sample was split into $5\times10^5$ cells/ml in 20 mls and induced with either 20 ng/ml, 2 ng/ml and 0 ng/ml Doxycycline. 24 hours post induction, a flow staining was carried out using $1\times10^6$ cells from each doxycycline induced sample. Cells were stained using anti-Fc-PE and TOPRO-3 viability stain. The histogram shows the fluorescence intensity on the FL2 channel (anti-Fc-PE) plotted against cell count. HEK293 WT control (grey solid line), HEK293-pINT18-Tet1-377_1_C08 stable cell line induced with 0 ng/ml doxycycline (black dashed line), 2 ng/ml doxycycline (black dotted line) and 20 ng/ml doxycycline (black solid line).

Figure 30:
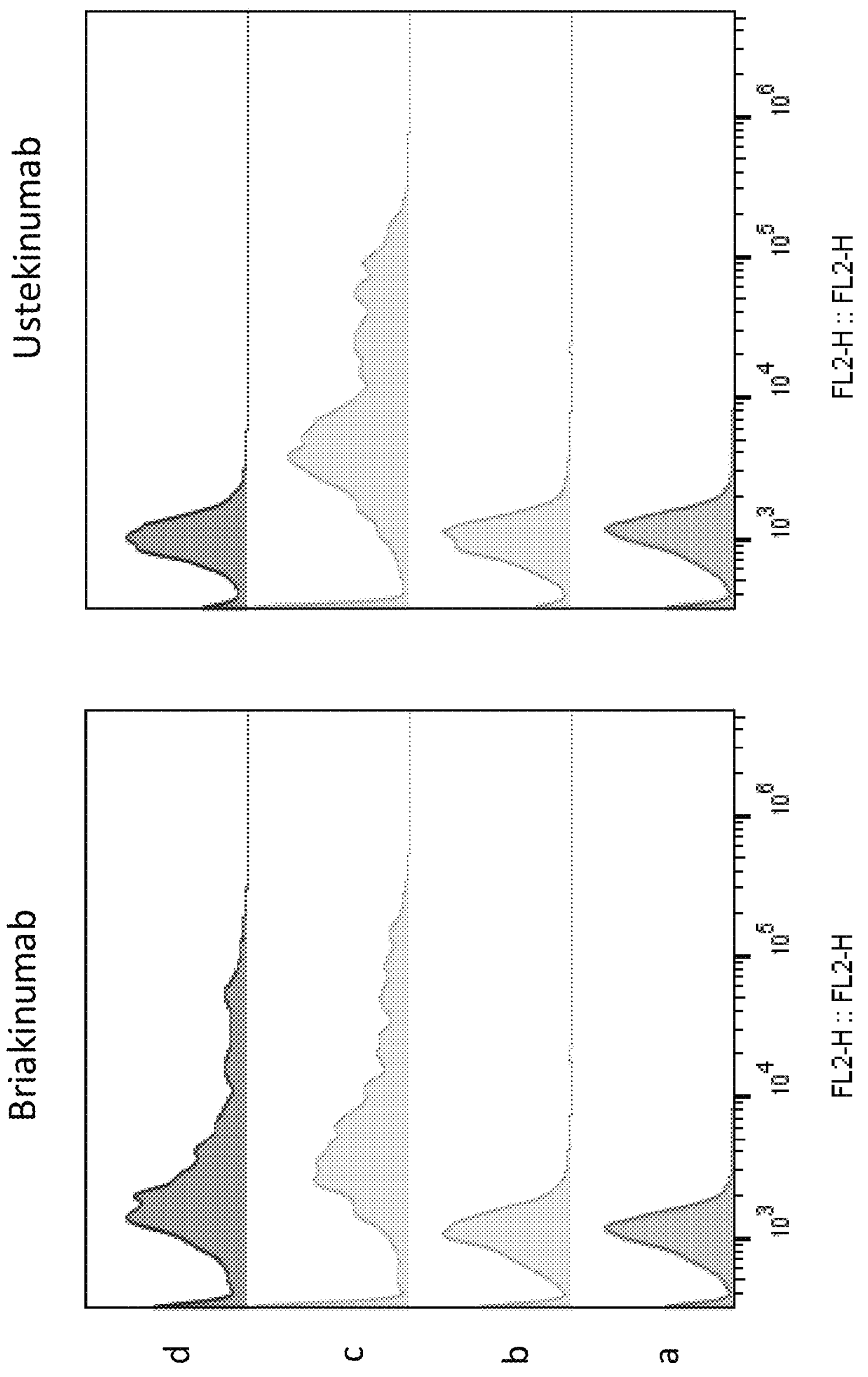

FIG. 30. Binding of cell displayed antibodies to FcRn. HEK293 cells expressing Briakinumab and Ustenkinumab were stained with biotinylated FcRn (50 nM) preconjugated with streptavidin PE (11 nM) using different buffers:
a. Hek293 WT
b. Streptavidin PE-control
c. Cells stained with buffer pH6.0
d. Cells stained with buffer pH7.4

Figure 31:
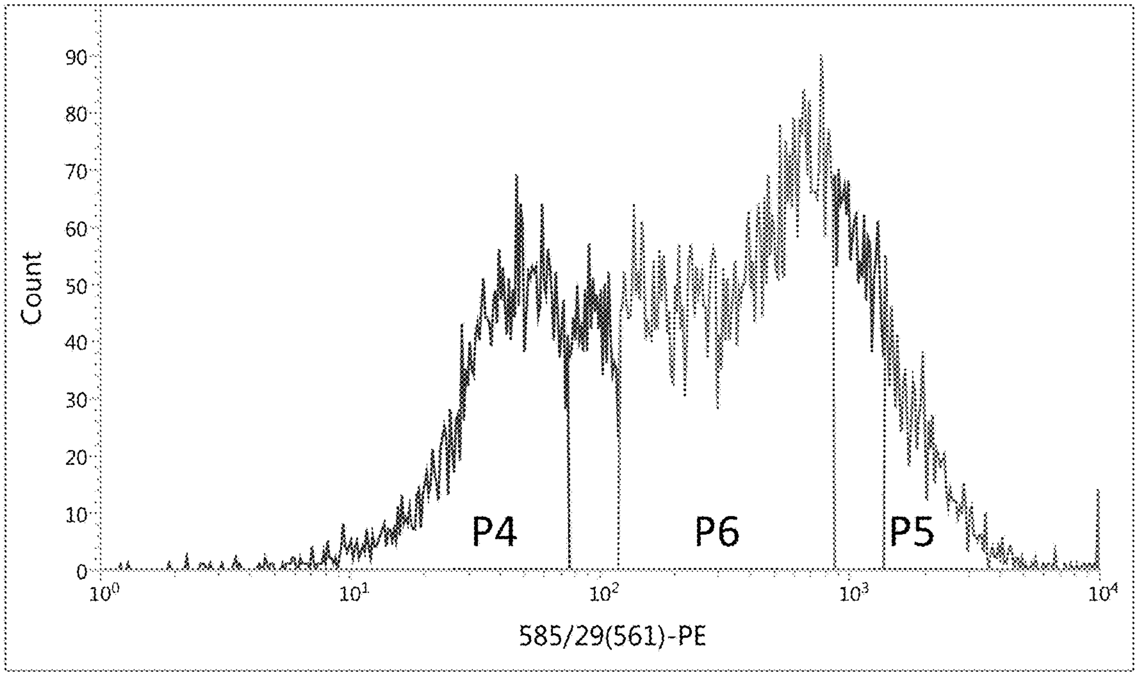

FIG. 31. FACS separation of HEK293 cell displayed anti-Mesothelin IgG by display level.
A population of anti-Mesothelin antibody genes were integrated into the human AAVS locus of HEK293 cells by nuclease mediated gene transfer. The polyclonal population of HEK293 cell displayed antibodies were separated by FACS according to antibody display level by staining with anti-human Fc-PE. 16 days post-transfection the MACS enriched libraries were separated on the basis of antibody expression by FACS using a BD Influx sorter. Cells were stained with anti-Fc labelled with phycoerythrin (PE). Analysis was focused on viable cells using forward scatter and staining. Cells positive for staining in the λem=450/40, λexc=355 channel (representing non-viable cells which took up DAPI) were excluded. The histogram shows fluorescence intensity for anti-Fc-PE (x-axis), representing antibody expression level, plotted against cell count on the y-axis. The gate chosen for analysis are labelled P4, P6 and P5 representing the low, medium and high display level populations respectively.

Figure 32:
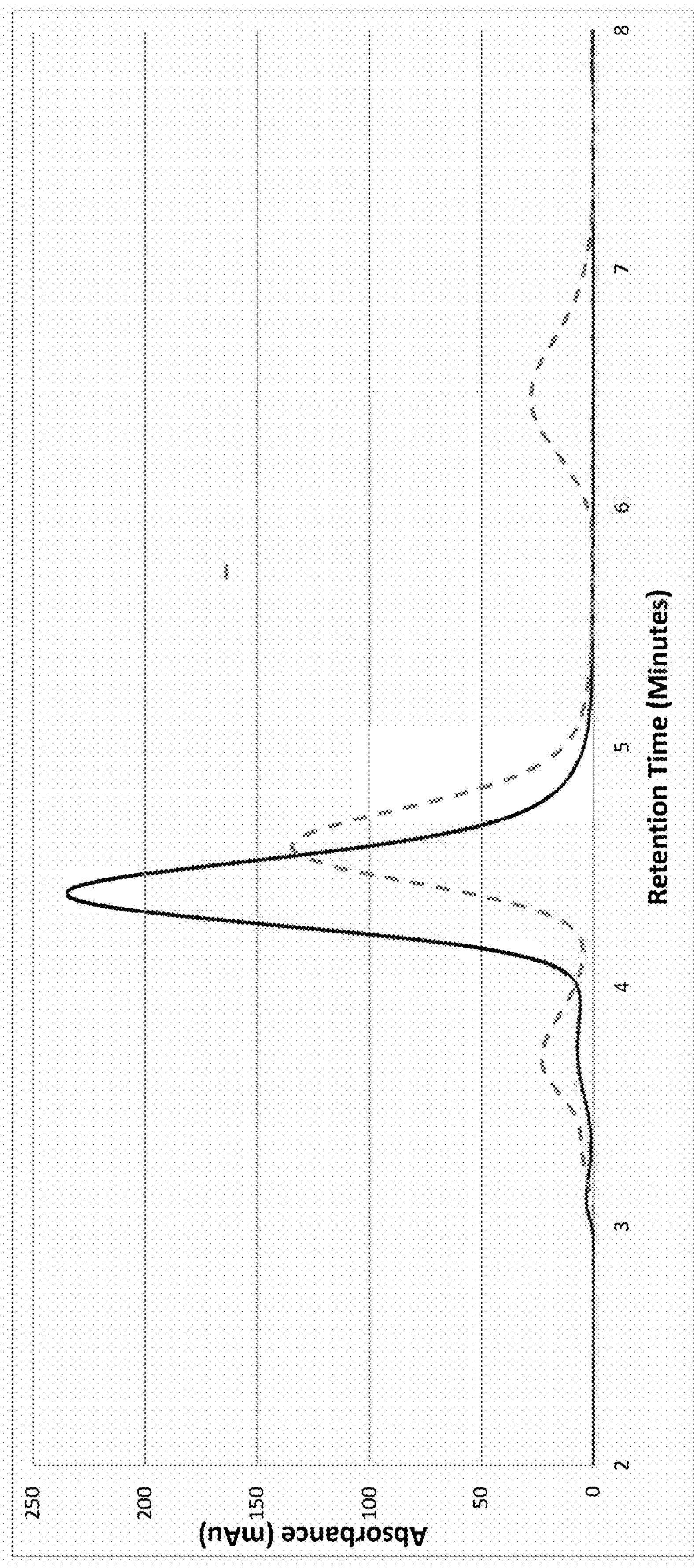

FIG. 32. HPLC-SEC of two anti-mesothelin IgG1 antibody clones originating from the high display level group (solid line) and low display level group (dotted line) respectively.

Figure 33:
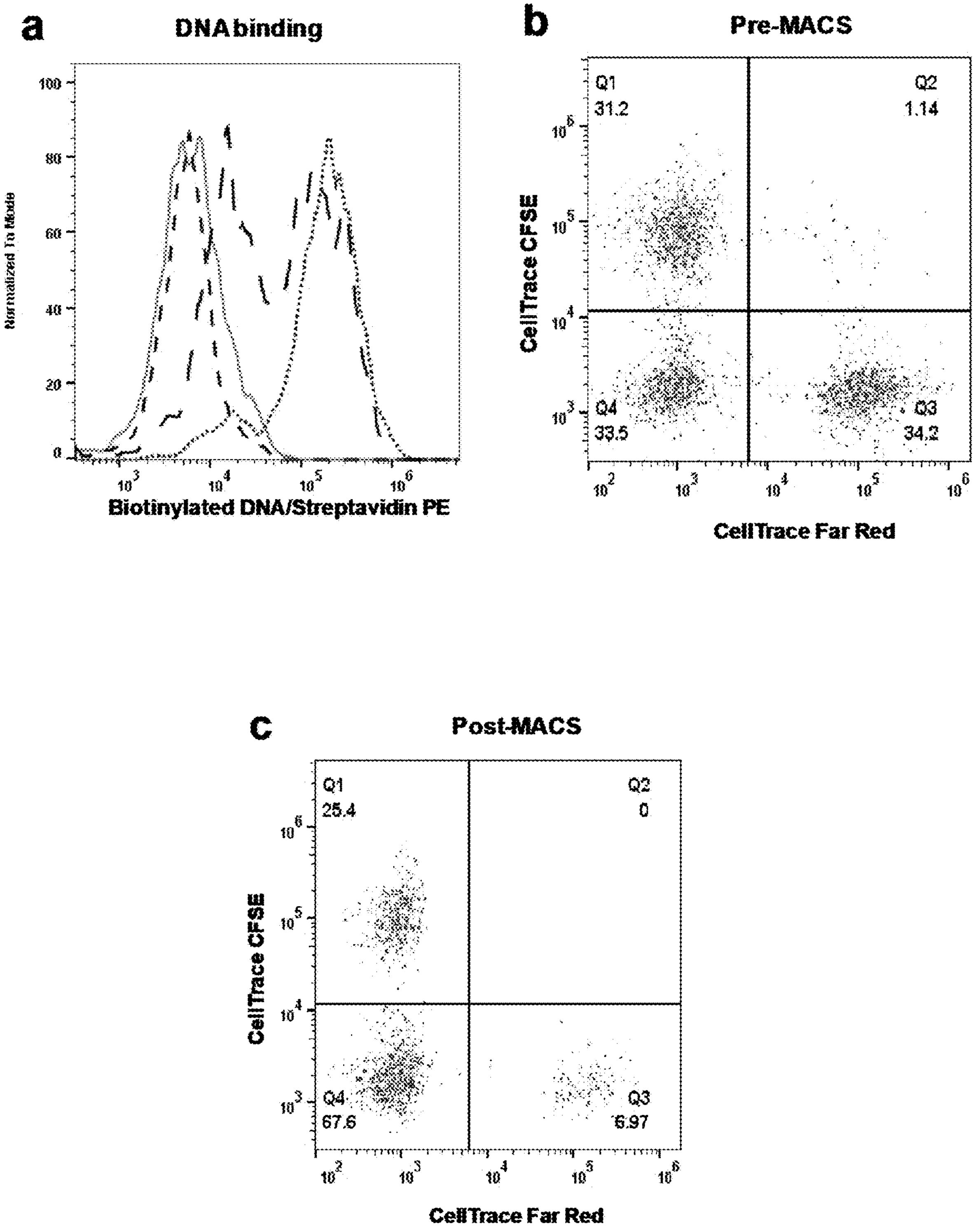

FIG. 33. DNA binding and depletion of DNA binders using MACS. (A) Overlay of HEK293 cells (solid grey), or HEK293 cells displaying ustekinumab (dashed), briakinumab (long dashed) and amatuximab (dotted) stained with biotinylated DNA detected with streptavidin PE; (B) Dot plot representing the mixture of three antibody cell populations displaying ustekinumab (unlabelled, Q4), amatuximab (labelled with CellTace Far red, X-axis) and briakinumab (labelled with CellTrace CFSE, Y-axis) stained with DNA before MACS sorting; (C) Dot plot of flow-through showing the depletion of DNA binders.

Figure 34:
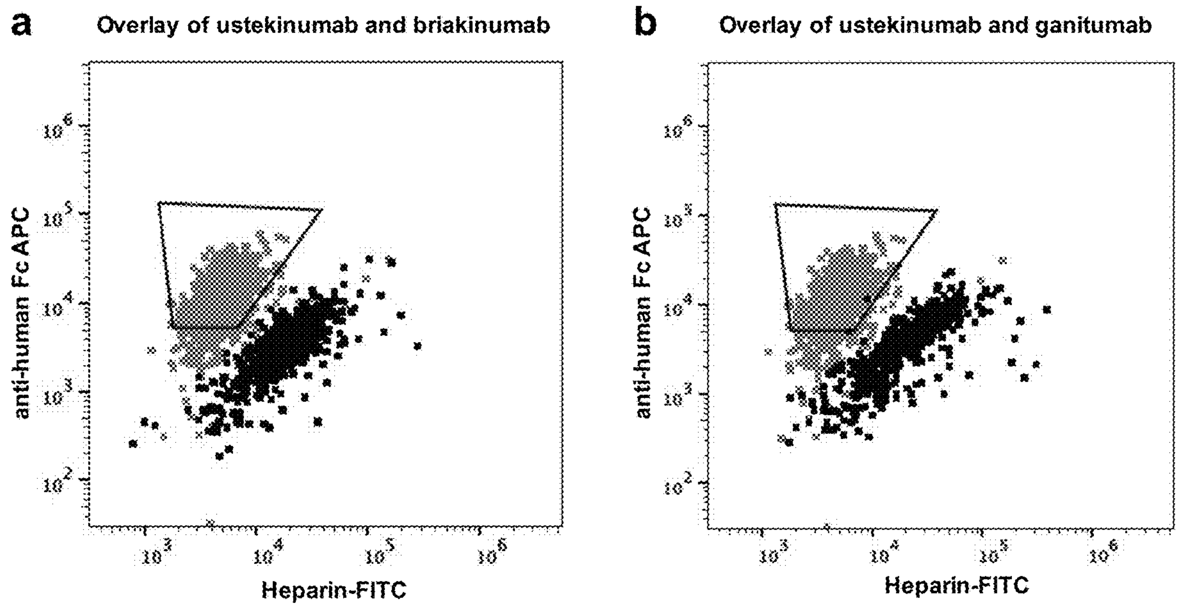

FIG. 34. Dual staining with Heparin-FITC (x-axis) and anti-human Fc APC (y-axis). (a) Dot plot showing overlay of ustekinumab (grey) and briakinumab (black). (b) Dot plot showing overlay of ustekinumab (grey) and ganitumab (black). Gate within the overlay plots indicates the cells to be high expressers and non-binders to heparin.

Figure 35:
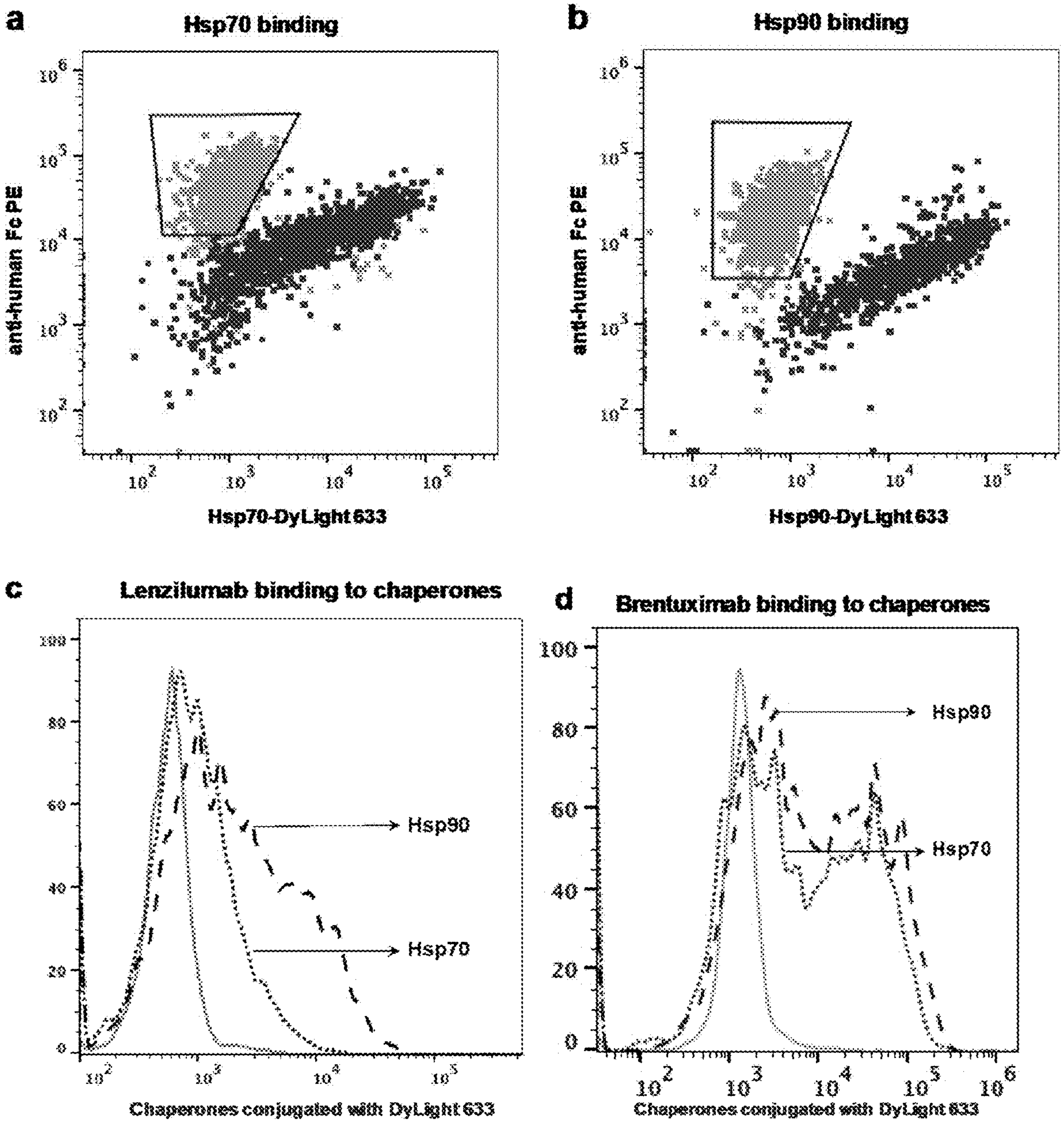
Figure 36A:
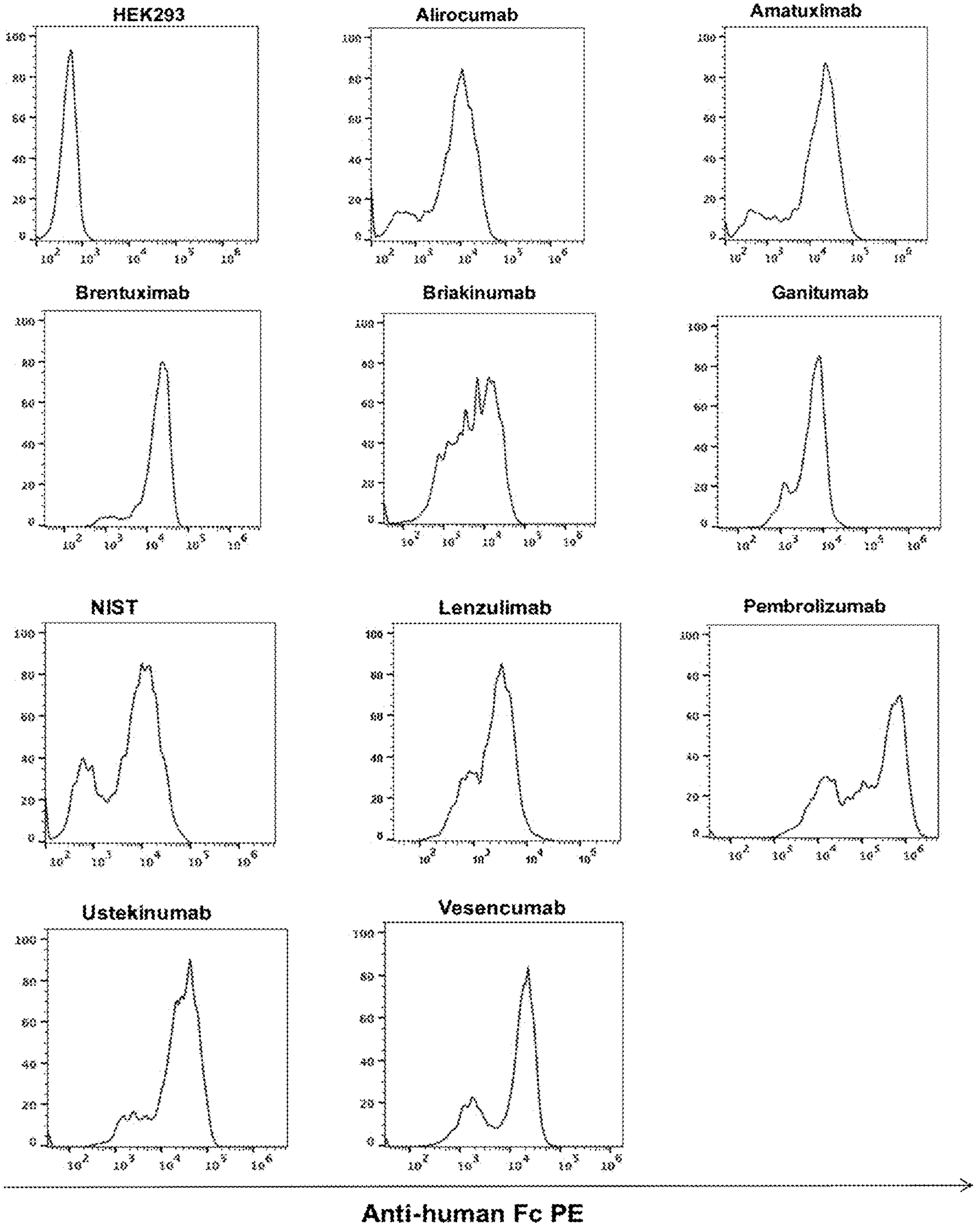
Figure 36B:
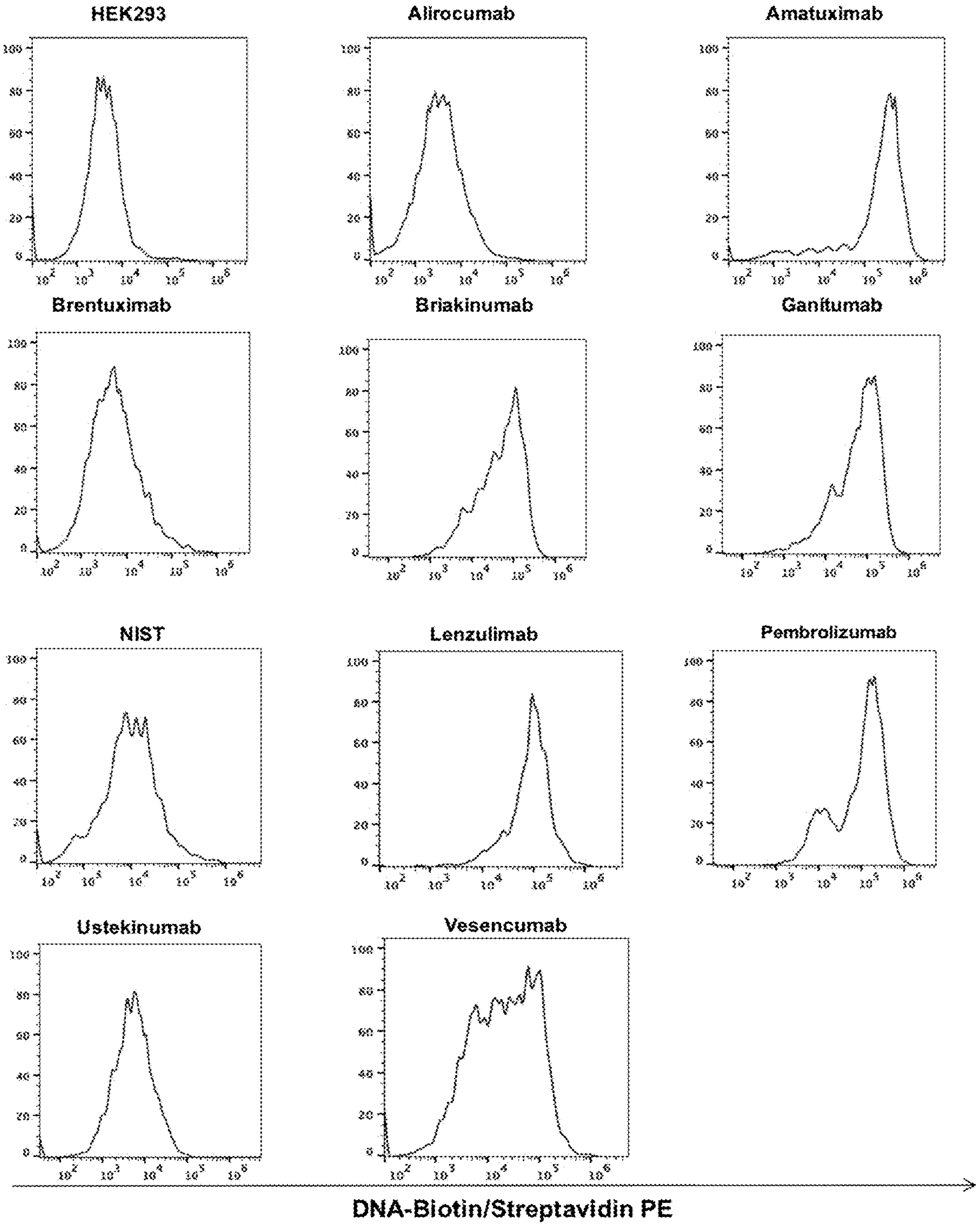
Figure 36C:
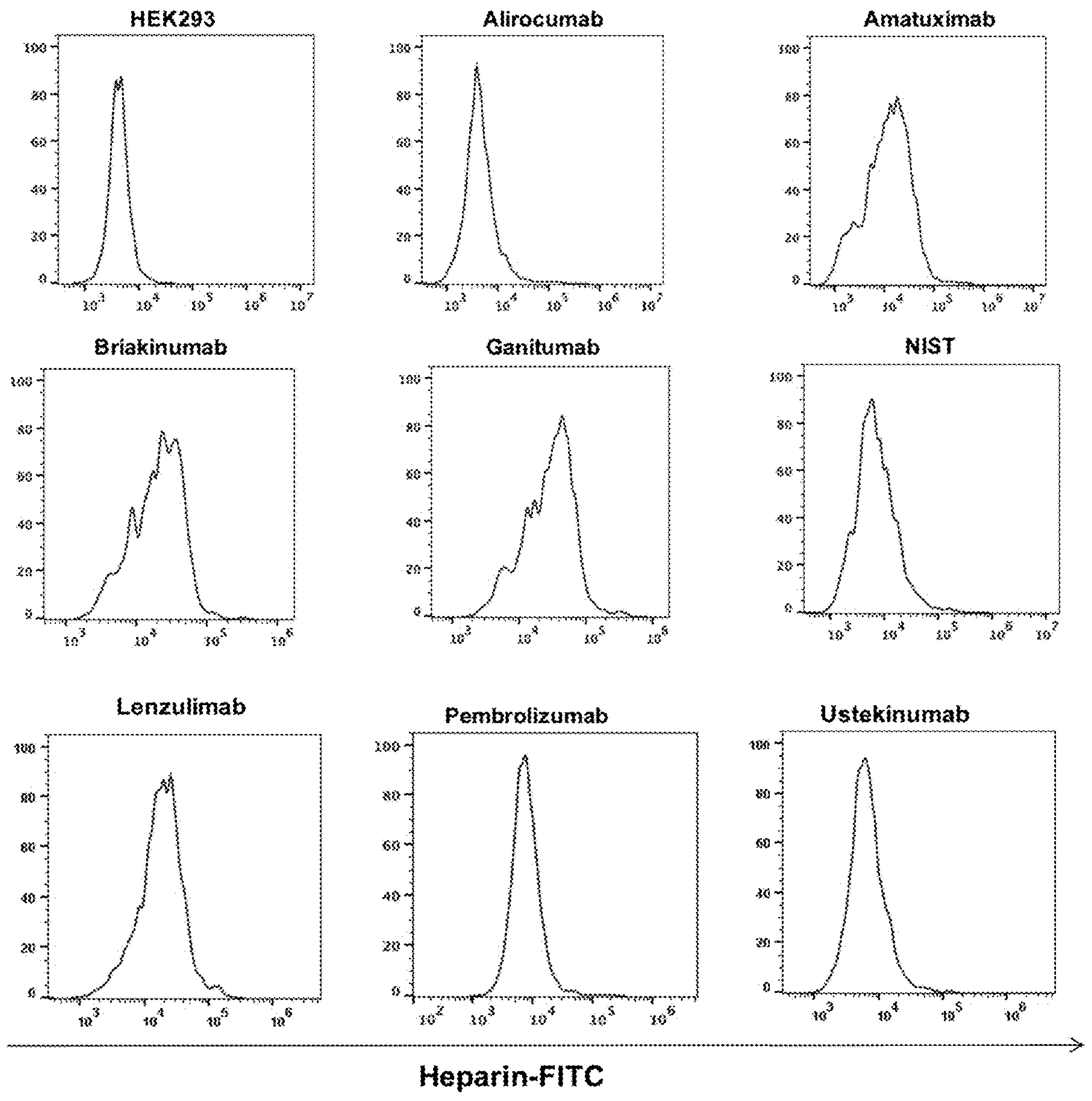
Figure 36D:
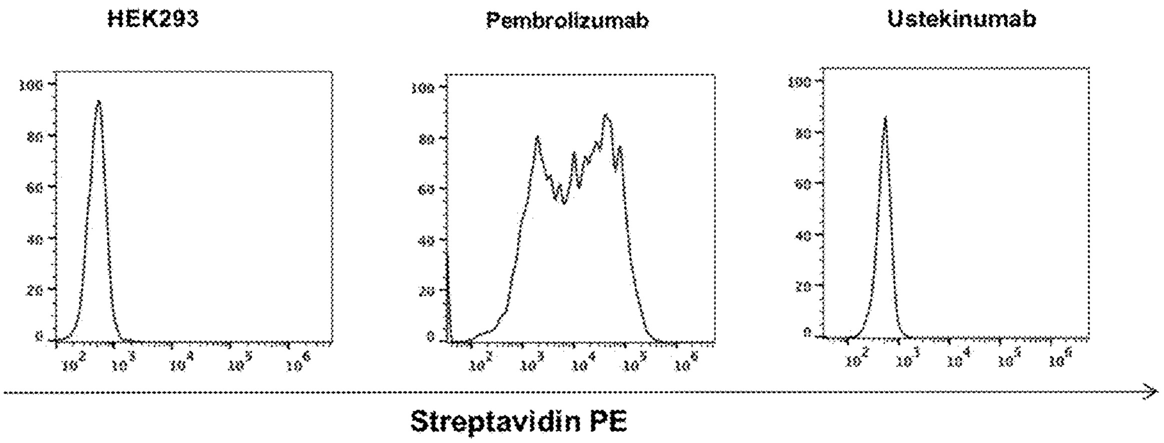
Figure 36E:
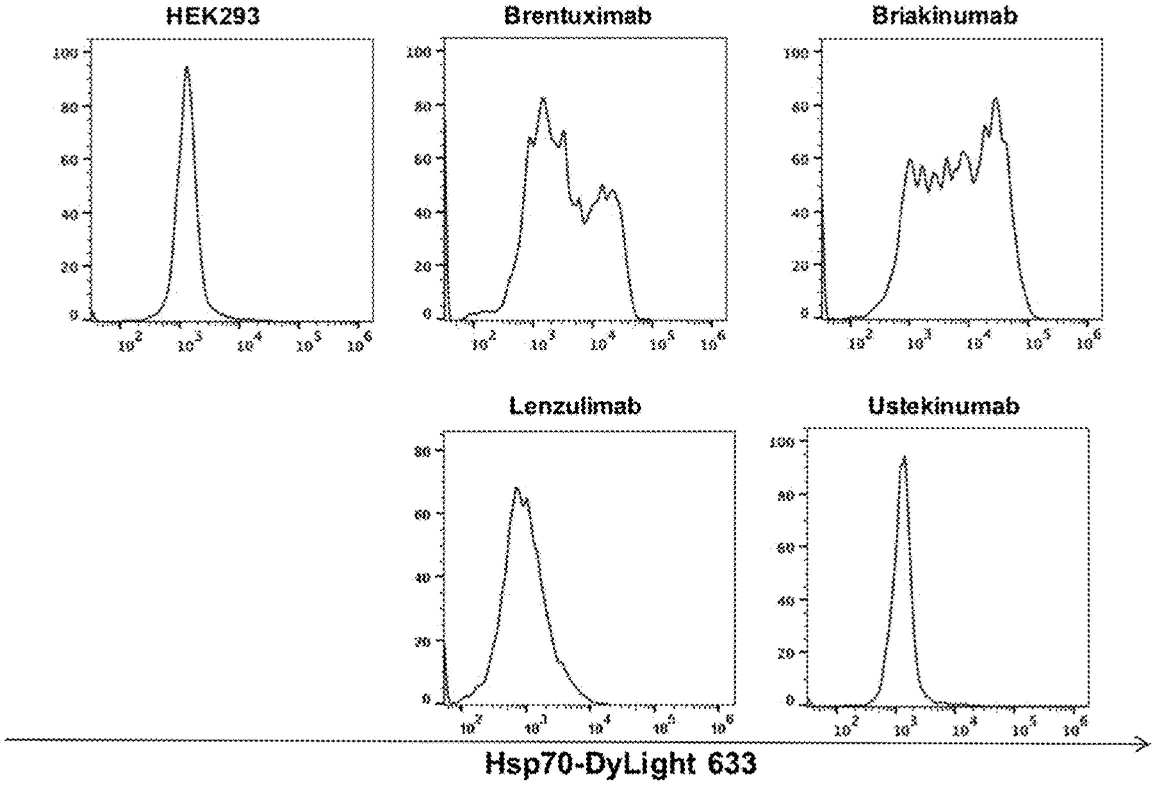
Figure 36F:
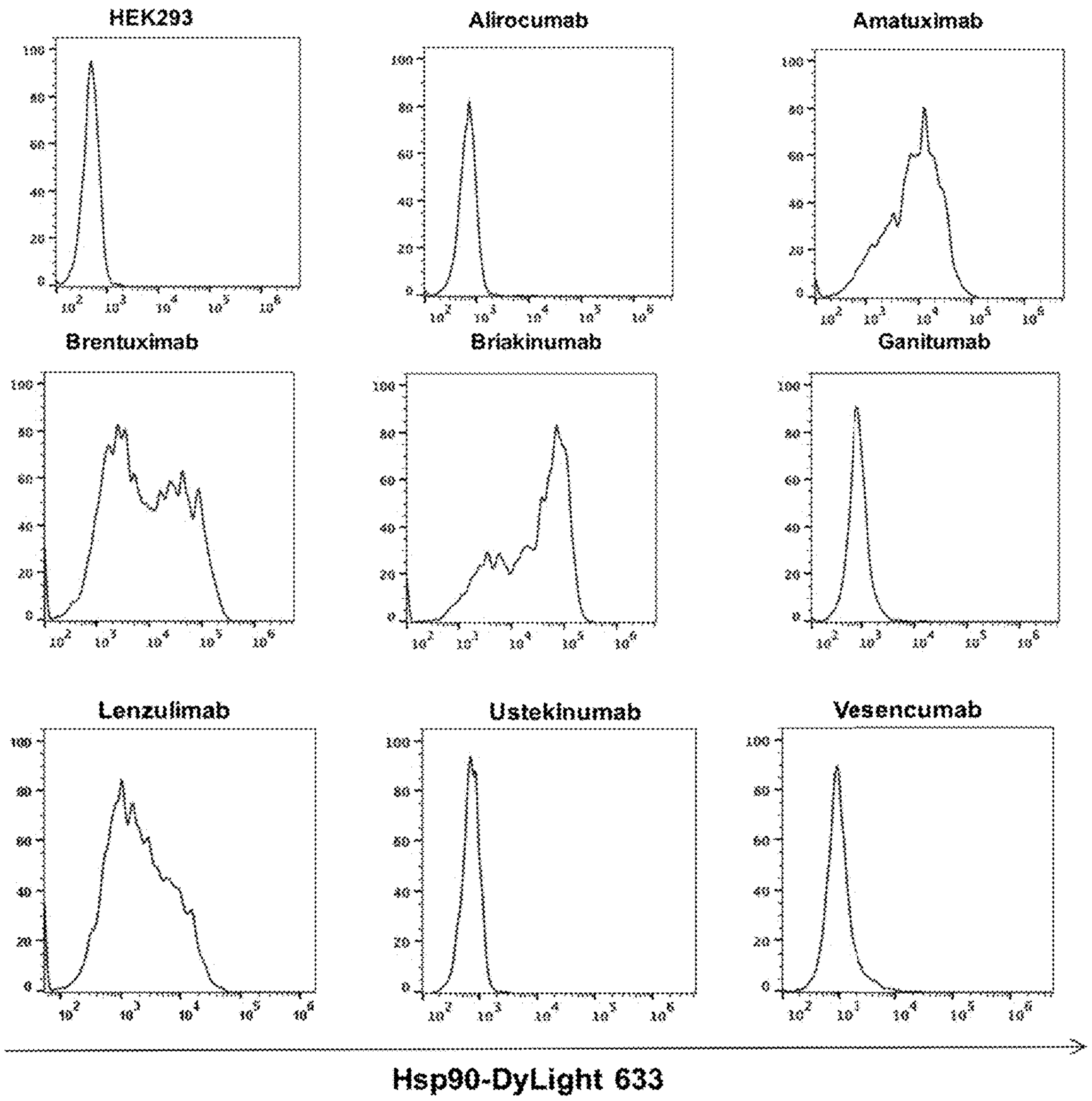
Figure 36G:
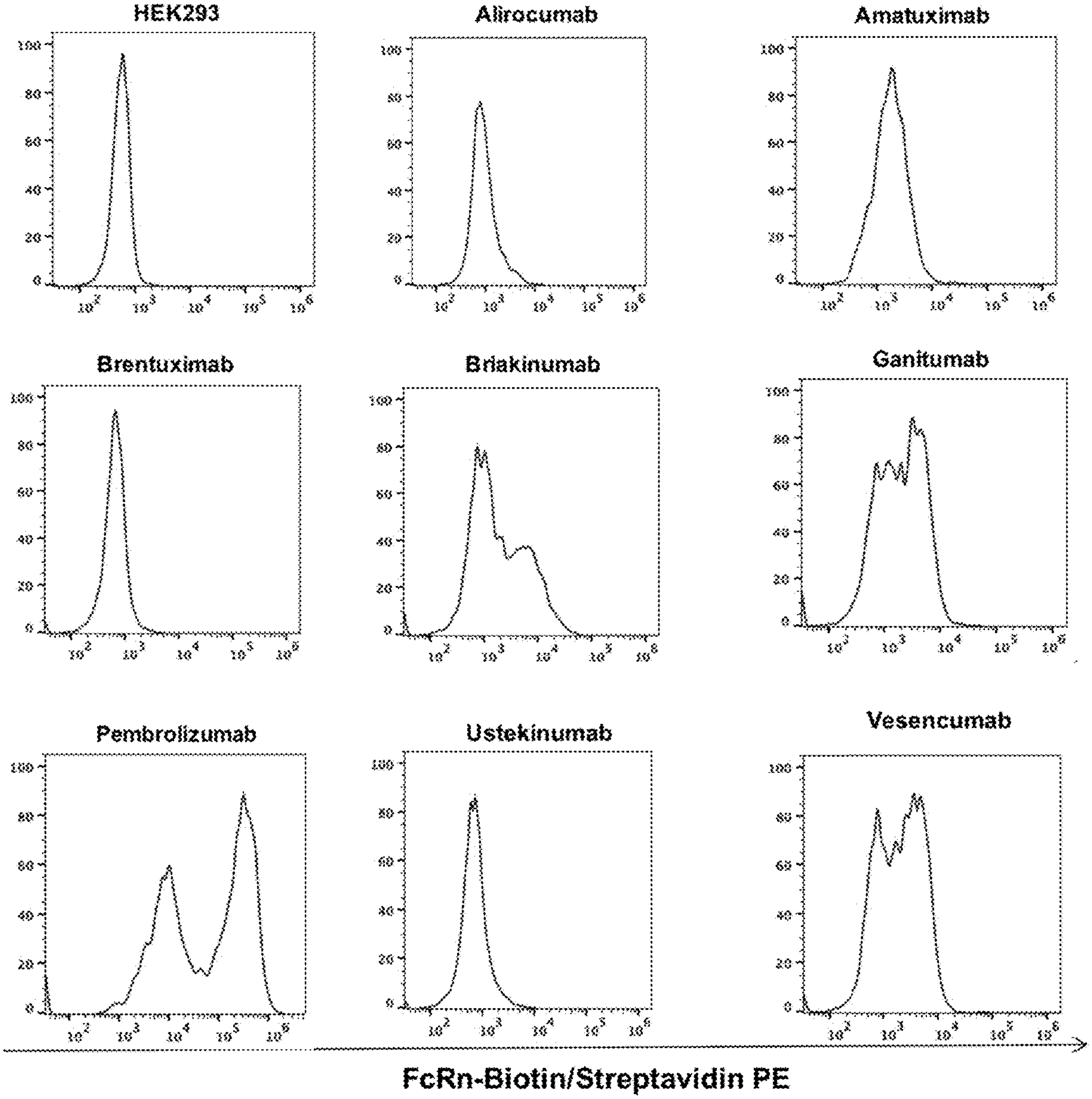

FIG. 35. Dual staining with chaperones conjugated with DyLight 633 (x-axis) and anti-human Fc PE (y-axis). (a) Dot plot showing overlay of ustekinumab (grey) and briakinumab (black) double-stained with Hsp70-DyLight 633 and anti-human Fc PE. (b) Dot plot showing overlay of ustekinumab (grey) and briakinumab (black) double-stained with Hsp90-DyLight 633 and anti-human Fc PE. Gate within the overlay plots indicates the cells to be high expressers and non-binders to chaperones (Hsp70 and Hsp90). (c and d) Overlay histogram plot shows lenzilumab and brentuximab binding Hsp70 and Hsp90 respectively.

FIG. 36. Histogram plots for antibodies stained with anti-human Fc PE and various polyreactivity probes. Stable monoclonal HEK293 cell lines, displaying a selection of antibodies, were created by nuclease mediated gene integration. Histograms plots of cell count (y-axis) against fluorescence intensity (x-axis) are shown for different antibodies displayed on the surface of HEK293 cells with the following probes: (a) anti-human Fc-PE, (b) biotinylated DNA detected using streptavidin PE, (c) Heparin-FITC, (d) Streptavidin PE, (e) Hsp70-DyLight 633, (f) Hsp90-DyLight 633 and (g) FcRn pre-conjugated with streptavidin PE.

FIG. 37. pINT17-Tet-D1.3, an inducible antibody IgG mammalian display expression vector. The full annotated nucleic acid sequence is shown between the AAVS homology arms and promoter-less blasticidin gene from the BglII to BstZ171 restriction sites. Numbering is from the BglII restriction site. Key features are listed below.
BGH poly A 223-9 (reverse strand)
Human C kappa 544-236 (reverse strand)
D1.3 VL 877-549 (reverse strand)
Human VL leader with intron 1168-883 (reverse strand)
TRE3G promoter 1230-1618
CMV promoter 1237-1809
VH leader with intron 1644-1782
D1.3 VH 1783-2127
IgG1 CH1-3 2125-3120
Myc tag 3121-3150
PDGFR anchor 3151-3306
BGH poly A 3356-3570 pEF promoter 3621-4955
rtTA-3G 5063-5809
SV40 poly A 5832-6274

Figure 38:
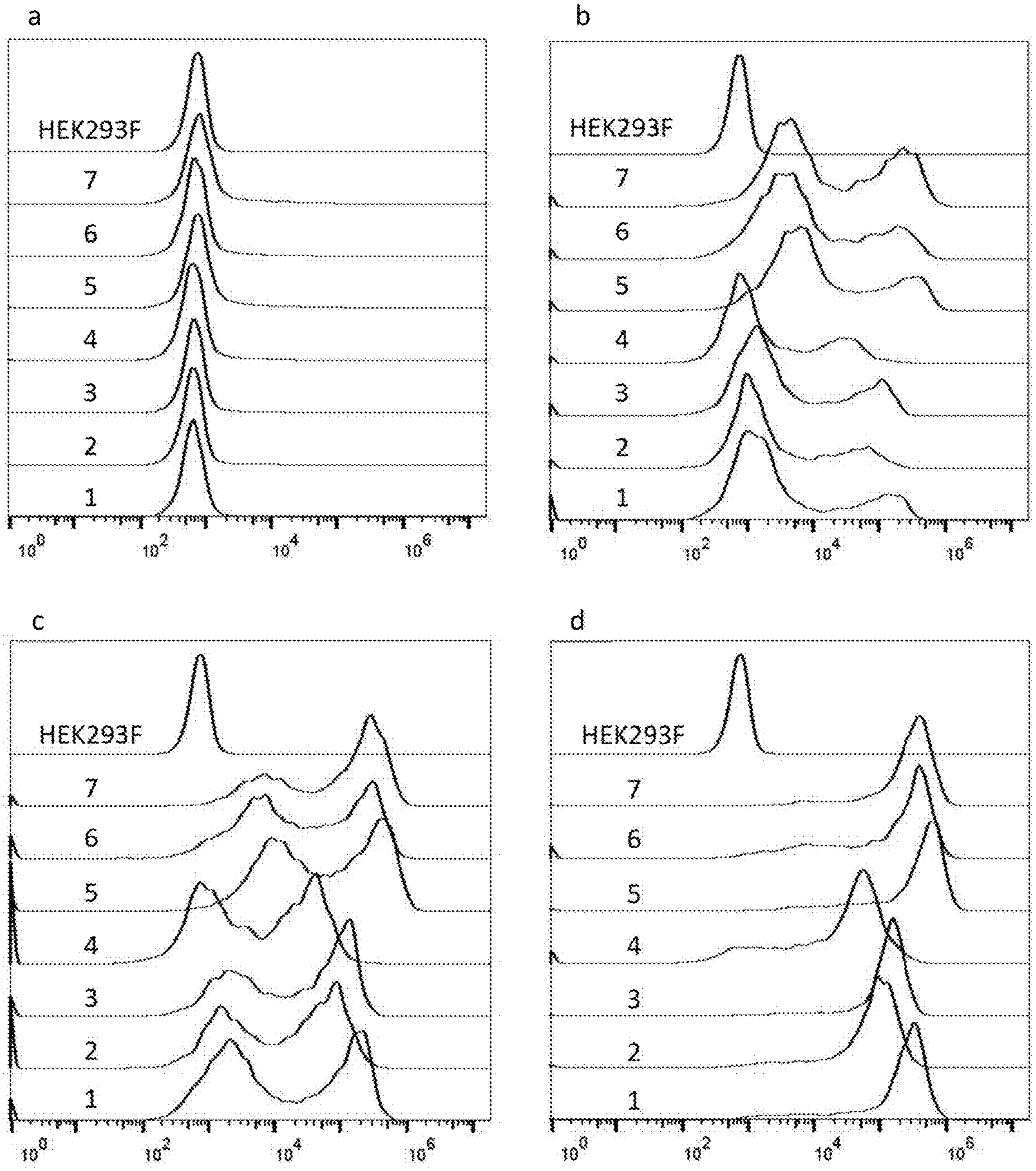

FIG. 38. Inducible IgG mammalian display cell lines. 1549_02_D06 (1), 1535_01_E03 (2), and 337_1_C08 (3), bococizumab (4), 884_01_G01 (5), 5A10i (6) and alirocumab (7). 27 dpt the cell lines were induced by the addition of 0 (a), 2 (b), 4 (c) or 100 (d) ng/ml doxycycline. 24 hours post induction the cells were stained with anti-Fc-PE. Histograms of fluorescence intensity (anti-Fc, FL2, x-axis) plotted against cell count.

Figure 39:
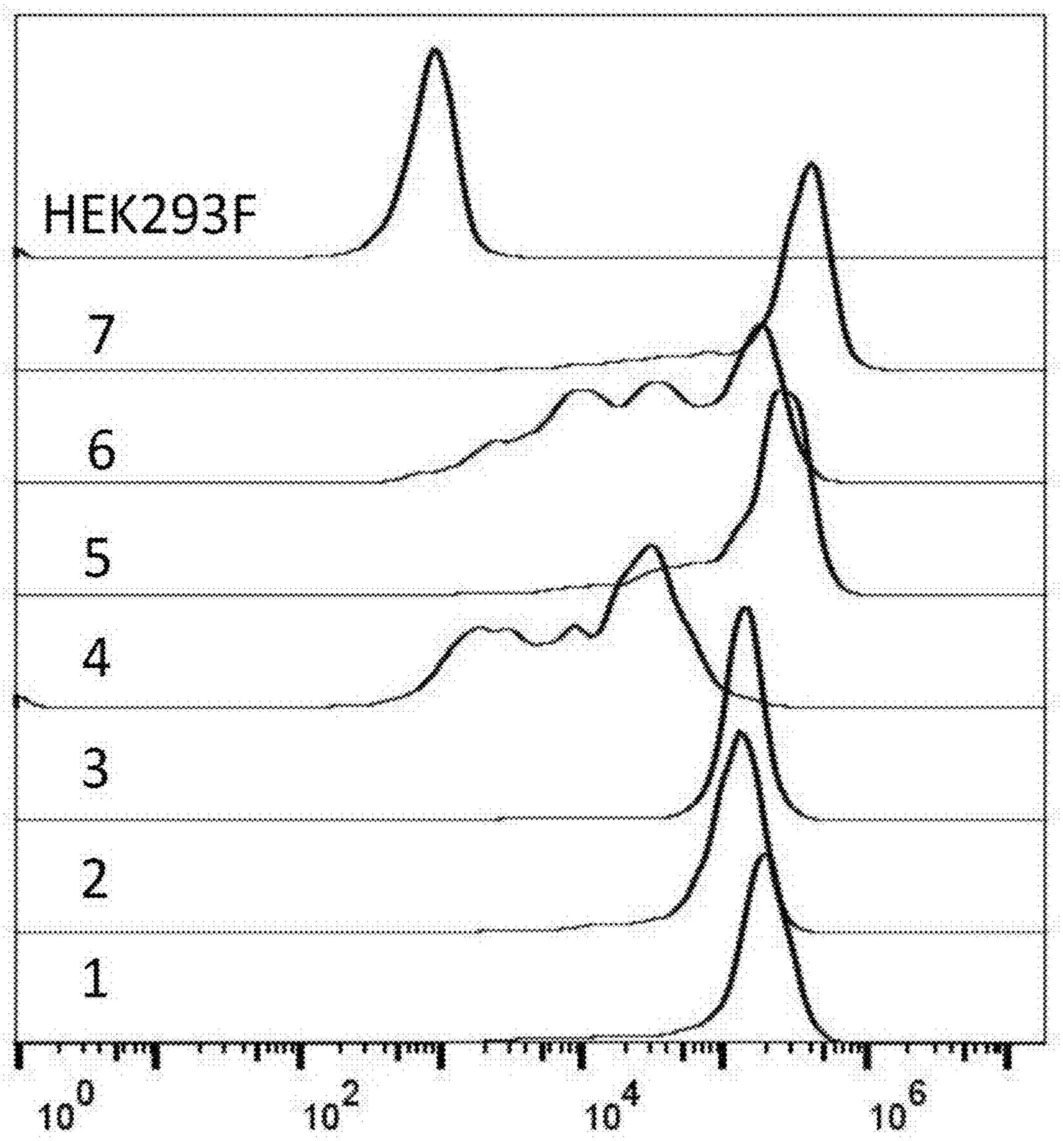

FIG. 39. Inducible IgG mammalian display cell lines: cell surface IgG turn-over pINT17-Tet harbouring the VH and VL of anti-PD1 antibodies: 1549_02_D06 (1), 1535_01_E03 (2), and 337_1_C08 (3) and the anti-PCSK9 antibodies bococizumab (4), 884_01_G01 (5), 5A10i (6) and alirocumab (7) was used to create stable HEK293 cell lines by AAVS TALE nuclease mediated gene integration and blasticidin selection. 27 dpt the cell lines were induced by the addition of 100 ng/ml doxycycline. 48 hours post induction the cells were stained with anti-Fc-PE. Histograms of fluorescence intensity (anti-Fc, FL2, x-axis) are shown plotted against cell count.

FIG. 40. Cell lines displaying the anti-PD1 antibodies 1549_02_D06 ($K_D$=2.9 nM for PD-1) and 337_1_C08 ($K_D$=74 nM for PD-1) were induced with (a) 0, (b) 2, (c) 4 and (d) 100 ng/ml doxycycline respectively. Dot plots of fluorescence in the FL1 channel (y-axis) against forward side-scatter (FSC, x-axis) are shown. Labelled cells displaying 1549_02_D06 are shown in the upper quadrant in each dot plot and unlabelled cells displaying 337_1_C08 are shown in the lower quadrant. Panels i, ii, iii and iv represent 0.1, 1, 10 nM concentration of PD-1-biotin respectively employed for MACS purification. Panel iv represents the input pre-MACS population. The percentage of each cell population is shown within each quadrant.

Figure 41:
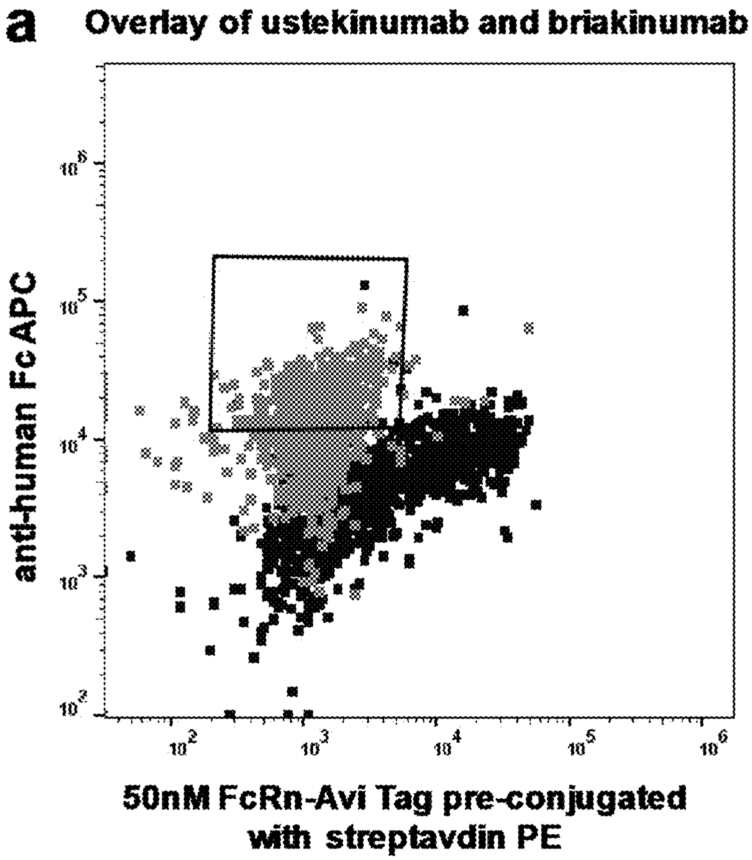

FIG. 41. Overlay dot plot of double-stained population of ustekinumab (grey) and briakinumab (black). Dual staining with 50 nM FcRn-Avi tag pre-conjugated with streptavidin PE (x-axis) and anti-human Fc APC (y-axis). The gate within the plot represents ustekinumab as the FcRn non-binder which can be FACS sorted from the FcRn binder.

Figure 42:
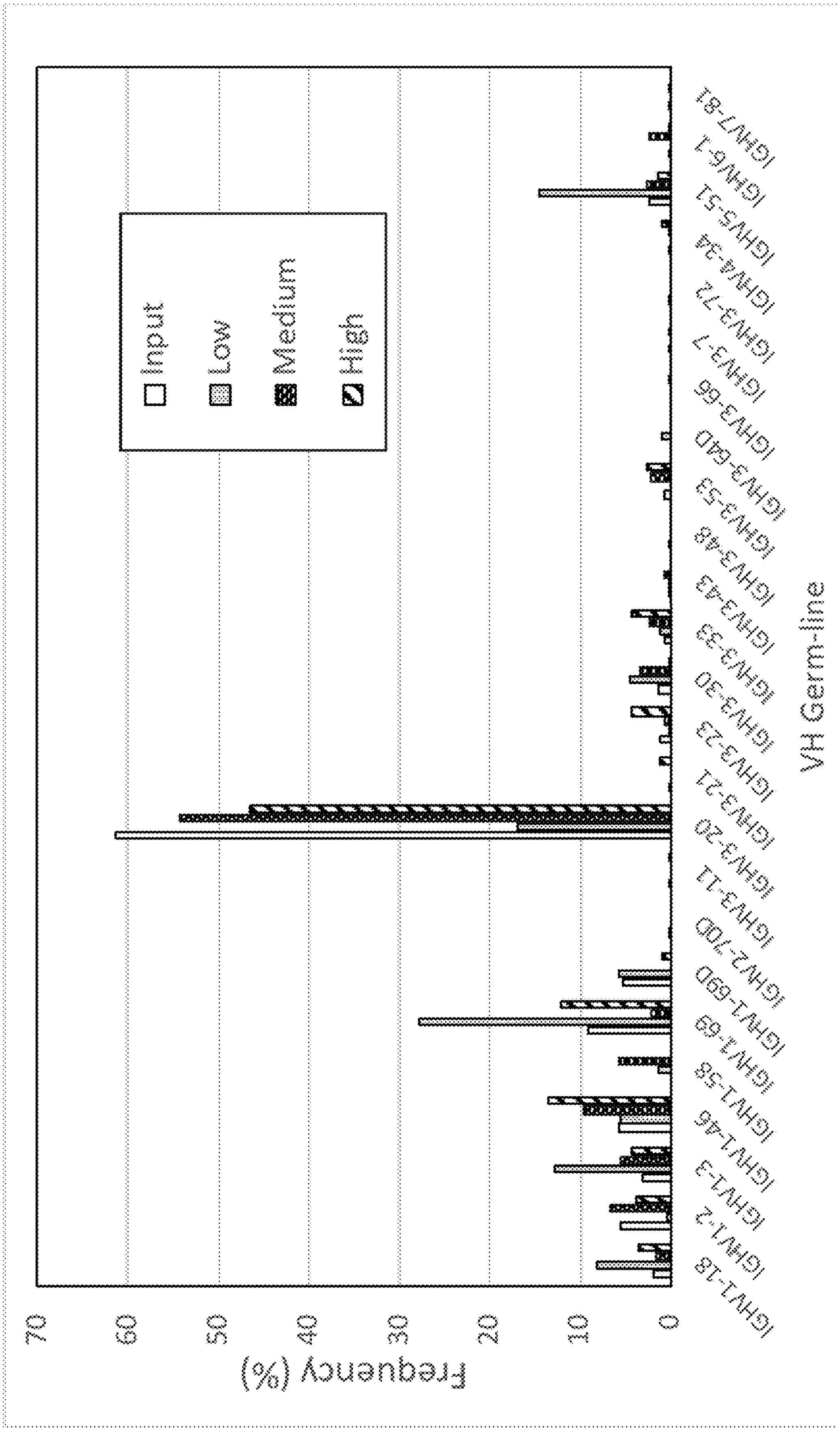

FIG. 42. Germ-line analysis of the anti-mesothelin variable heavy (VH) domain antibody populations. The chart plots frequency of occurrence in the input and low, medium and high mammalian display gated populations for each VH germ-line.

Figure 43:
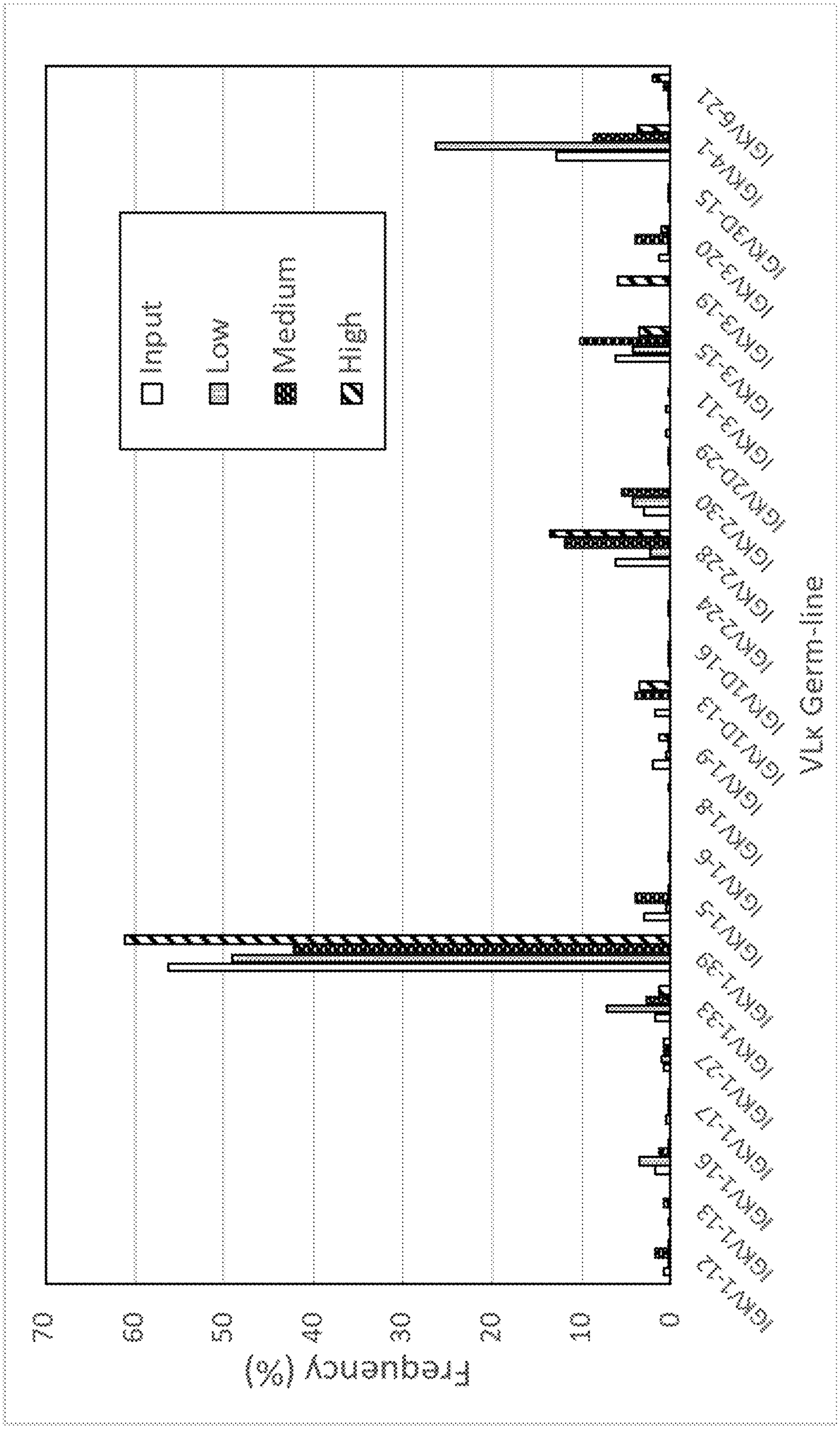

FIG. 43. Germ-line analysis of the anti-mesothelin variable light kappa (VLκ) domain antibody populations. The chart plots frequency of occurrence in the input and low, medium and high mammalian display gated populations for each VLκ germ-line.

Figure 44:
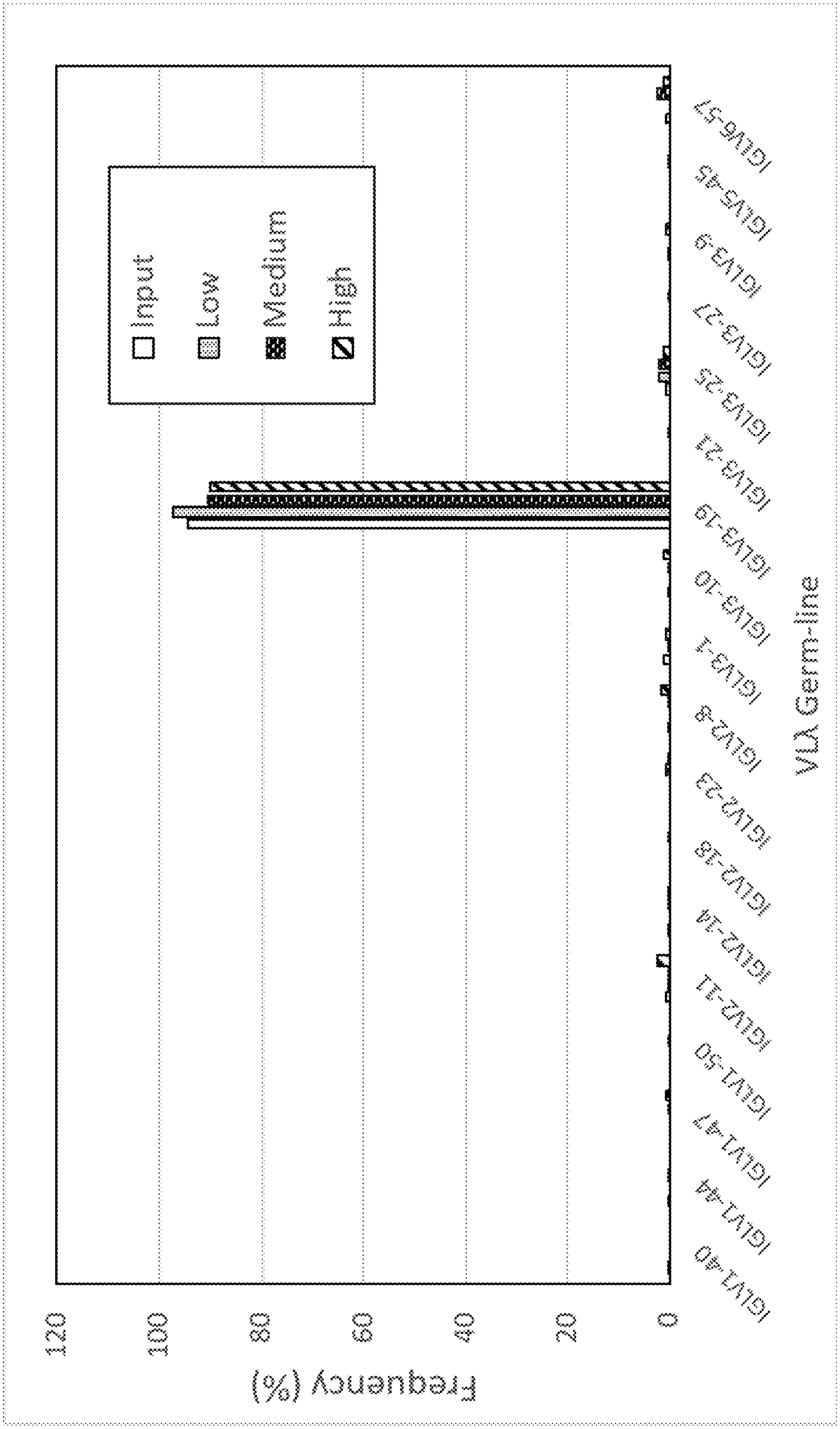

FIG. 44. Germ-line analysis of the anti-mesothelin variable light lambda (VLλ) domain antibody populations. The chart plots frequency of occurrence in the input and low, medium and high mammalian display gated populations for each VLλ germ-line.

Figure 45:
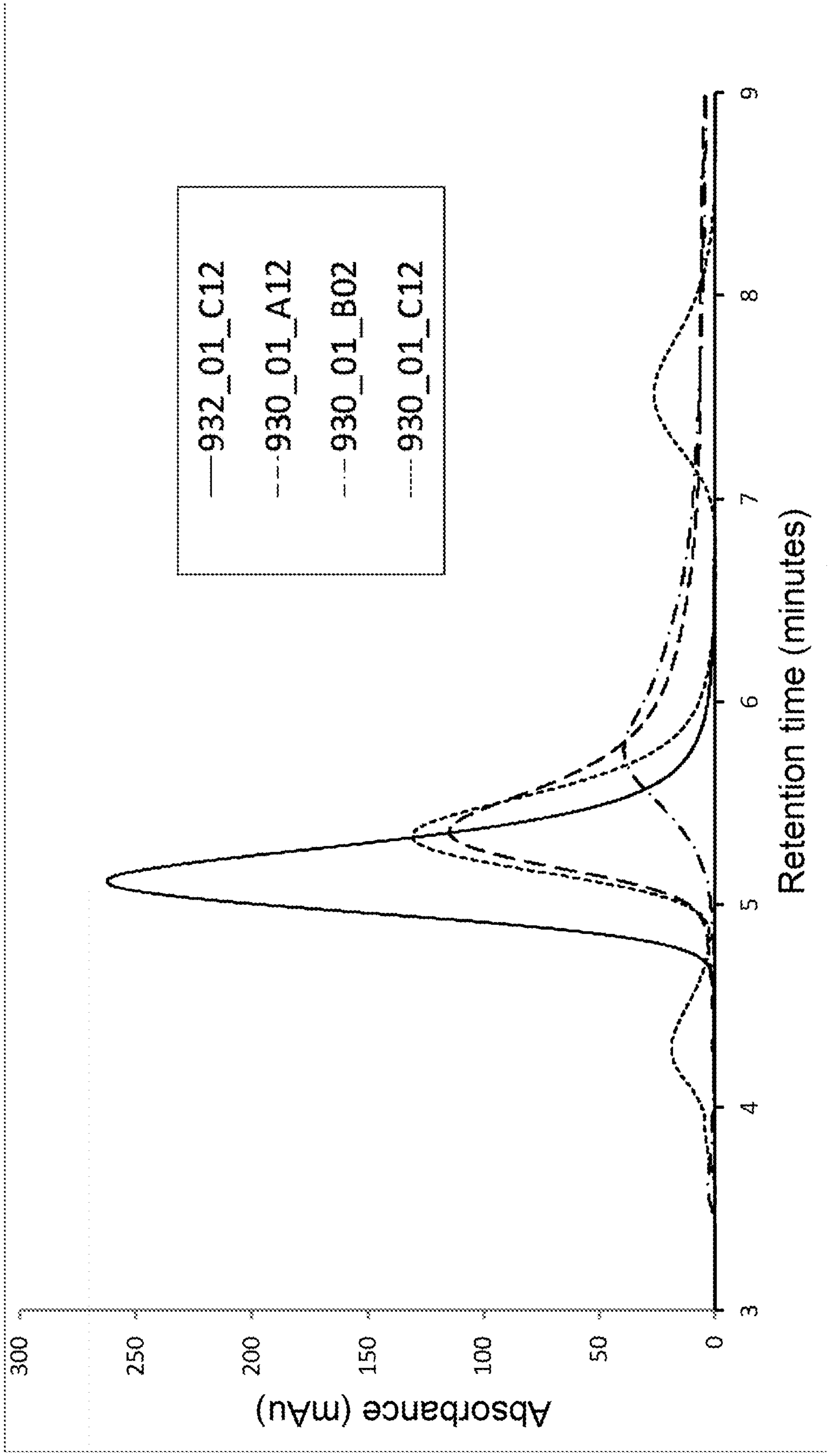

FIG. 45. HPLC-SEC of anti-mesothelin IgG1 antibodies. Antibodies were expressed by transient transfection of Expi-293 cells, affinity purified by protein A chromatography and dialysed. Samples (2 μl at 1 mg/ml) were loaded onto an Agilent AdvancedBio SEC 300A, 2.7 um, 4.6×300 mm column (Agilent Technologies, Cat. No. PL1580-5301) at a flow rate of 0.35 ml/min using an Agilent 1100 HPLC instrument. A plot of absorbance at 215 nm against retention time is shown for selected anti-Mesothelin antibodies: 932_01_A03 (black line), originating from the high display level group and 930_01_A12 (alternating dot and dash) 930_01_1B02 (long dash), 930_01_C12 (short dash line) originating from the low display level group.

FIG. 46. Alignment of the human and CHO AAVS intron 1 TALE-nuclease (TALEN) target binding sites. The CHO AAVS intron 1 DNA sequence was obtained from the ENSEMBL annotated CHO-K1 glutamine synthetase (GS) knockout cell line, accession: CHOK1GS_HDv1:scaffold_52:2374828:2406177:1. Numbering is referenced to human PPP1R12C intron 1 start. Bold indicates the left and right arms of the human TALEN target sites. Asterisks indicate homology between the human and CHO sequence and dash (-) indicates a deletion. Underline and italic indicate the ends of the AAVS left and right homology arms within the pINT17 targeting vector. This alignment was used to design CHO AAVS homology arms within the pINT17-CHO targeting vector and, for comparison, CRISPR/Cas9 guide RNAs. Sense or anti-sense CRISPR guide RNA recognition sites numbered 1 to 3 are shown above or below the sequence respectively.

FIG. 47. CHO AAVS homology arms within the vector pINT17-BSD-CHO, a dual promoter antibody IgG expression cassette for surface expression on CHO cells. An annotated DNA sequence is shown for the left and right CHO AAVS homology arms within the vector. All remaining features, including those not shown in this figure, encompassing the dual promoter antibody expression cassette, are as described for the vector pINT17-BSD (FIG. 1) and are listed below Features:
CHO AAVS left homology arm 9-899
Blasticidin resistance gene 942-1343
pEF promoter 1611-2794
BM40 leader 2834-2885
Humanised D1.3 VL 2888-3219
Human C kappa 3227-3532
BGH poly A 3468-3682
CMV promoter 3790-4362
Mouse VH leader with intron 4388-4515
Humanised D1.3 VH 4521-4868
Optimised human IgG1 CH1-CH3 4869-5864
Myc tag 5865-5894
PDGFR anchor 5895-6050
BGH polyA 6100-6314
CHO AAVS left homology arm 6376-7266
f1 replication origin 7424-7837
pUC replication origin 8058-8732
Kanamycin resistance gene 9452-10246

Figure 48:
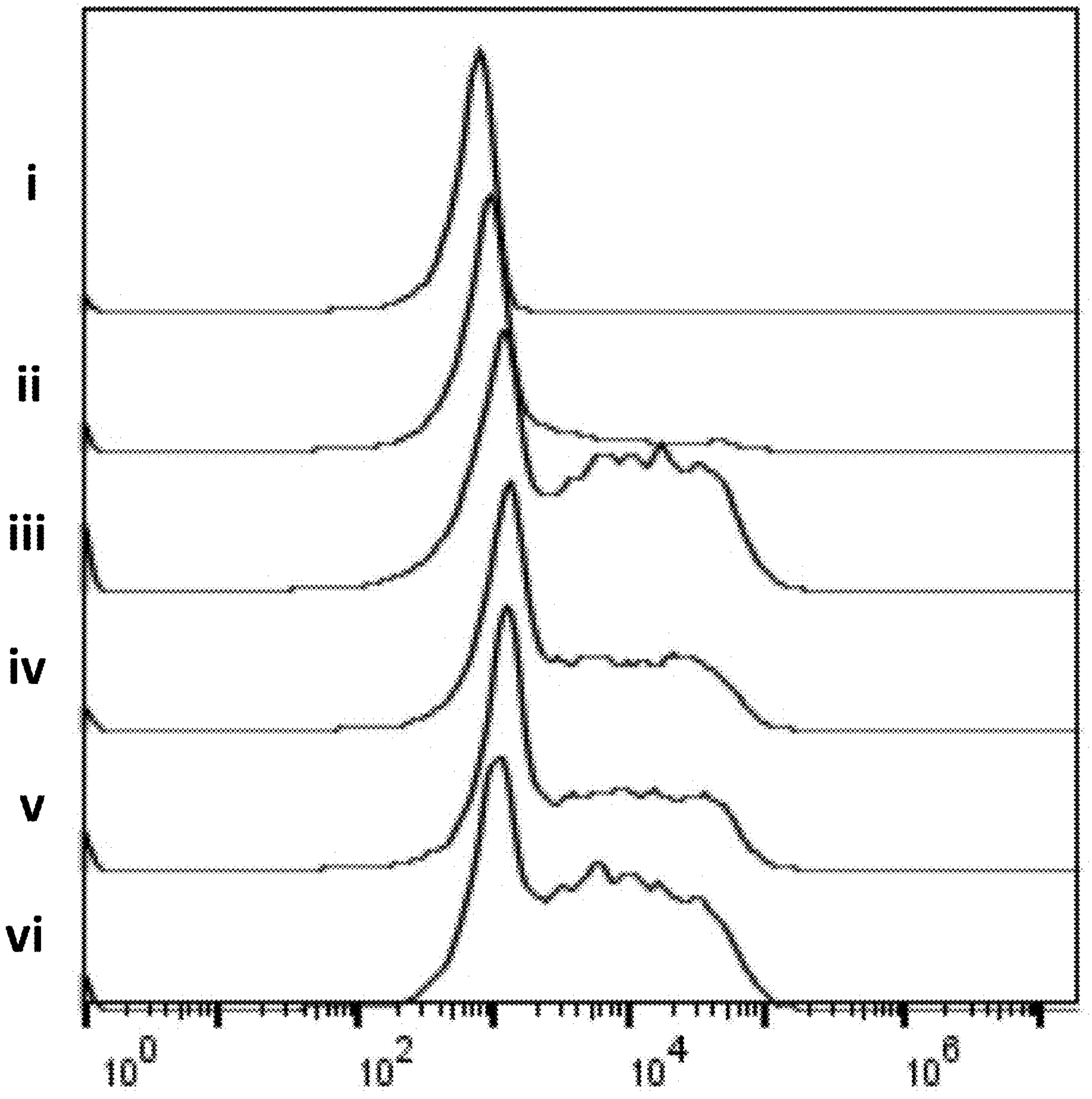

FIG. 48. Display of antibodies on the surface of CHO cells by TALEN or CRISPR/Cas9 nuclease mediated gene integration. Histograms of fluorescence intensity (anti-Fc, FL2, x-axis) plotted against cell count. Plots are (from top to bottom) the CHO control, pINT17-BSD-CHO V2-Nivolumab minus nuclease, pINT17-BSD-CHO V1-Nivolumab minus nuclease, pINT17-BSD-CHO V1-Nivolumab plus CHO TALENs, pINT17-BSD-CHO V1-Nivolumab plus CRISPR3, pINT17-BSD-CHO V1-Nivolumab plus CRISPR2, pINT17-BSD-CHO V1-Nivolumab plus CRISPR1.

Figure 49:
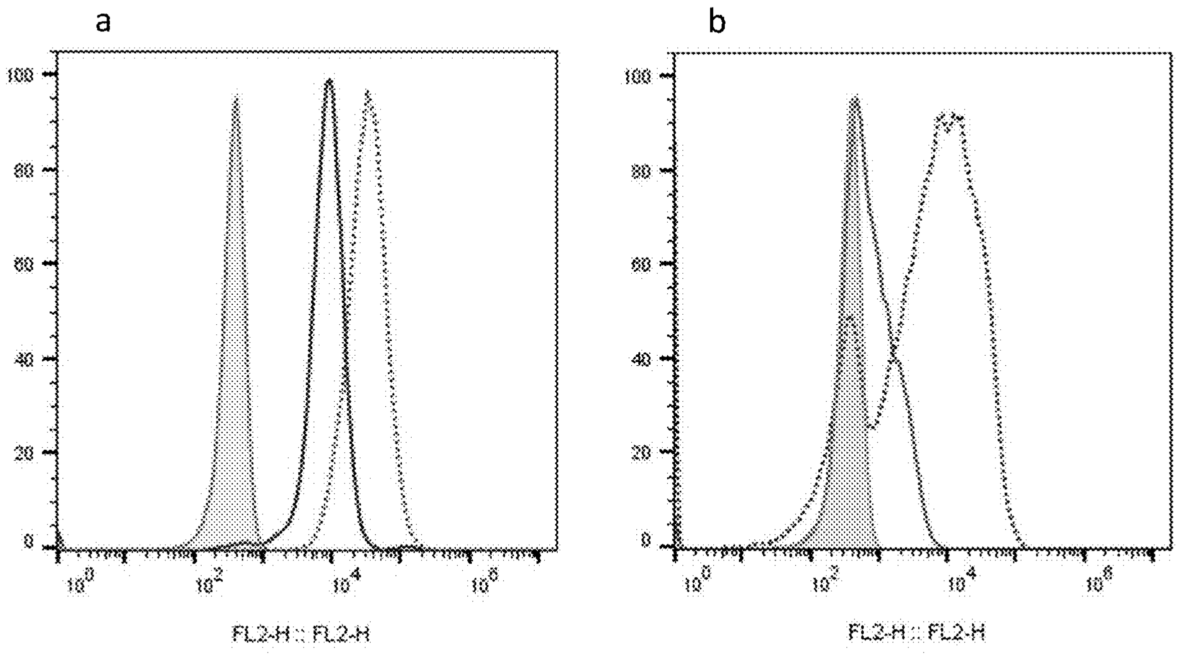

FIG. 49. Display levels of antibodies on the surface of CHO. Histograms of fluorescence intensity (anti-Fc, FL2, x-axis) plotted against cell count for CHO cells (filled plot) (a) Bococizumab (solid line) and 884_01_G01 (dashed line). (b) MEDI-1912 (solid line) and MEDI-1912-STT (dashed line).

FIG. 50. Creation of a "developability enhanced" population using mammalian display for subsequent binding selection a. Sequences of anti-PD1 337_1_C08 VH (i) and VL (ii) chains. Nucleotide sequences are shown with translation single letter amino acid code above the codons. CDRs are annotated (under-lined) and CDR3 amino-acids subject to site-directed mutagenesis highlighted in bold.

b. The anti-PD1 antibody VH and VL CDR3 mammalian display library was separated by FACS on the basis of high, medium and low antibody cell display levels and the analysed by analytical flow cytometry by staining with anti-Fc-PE. Histogram plots of cell count (y-axis) against Fc expression (x-axis) are shown (from top to bottom) the high (i), medium (ii) and low (iii) anti-PD1 populations. For reference, the starting anti-Fc MACS population (iv), the "wild-type" 337_1_C08 parental clone (v) and HEK293 cells with no displayed antibody (vi) are shown.

FIG. 51. pINT17-Bi-CMV-Emicizumab, a bi-directional CMV and elongation factor (pEF) promoter containing plasmid for cell surface expression of the bi-specific "knobs-into-holes", common light chain IgG Emicizumab. This is a tri-cistronic targeting vector with three promoters driving the expression of three genes: the anti-FIXa heavy chain, the anti-FX heavy chain and common light chain. The full annotated nucleic acid sequence is shown between the AAVS homology arms from the BgIII to BstZ171 restriction sites. Numbering is from the BgIII restriction site. Key features are listed below.

BGH poly A 222-8 (reverse strand)
Human C kappa 546-232 (reverse strand)
Emicizumab VL 876-547 (reverse strand)
Human VL leader with intron 1143-884 (reverse strand)
Minimal CMV promoter 1230-1167 (reverse strand)
CMV promoter 1237-1809
Mouse VH leader with intron 1835-1973
Emicizumab anti-FIXa VH 1974-2339
Emicizumab anti-FIXa CH1-3 2340-3317
Myc tag 3318-3347
PDGFR anchor 3348-3503
BGH poly A 3553-3767
pEF promoter 3818-5152
Human VH leader with intron 5260-5401
Emicizumab anti-FX VH 5402-5758
Emicizumab anti-FX CH1-3 5759-6733
Myc tag 6734-6763
PDGFR anchor 6764-6916
SV40 poly A 6942-7384

Figure 52:
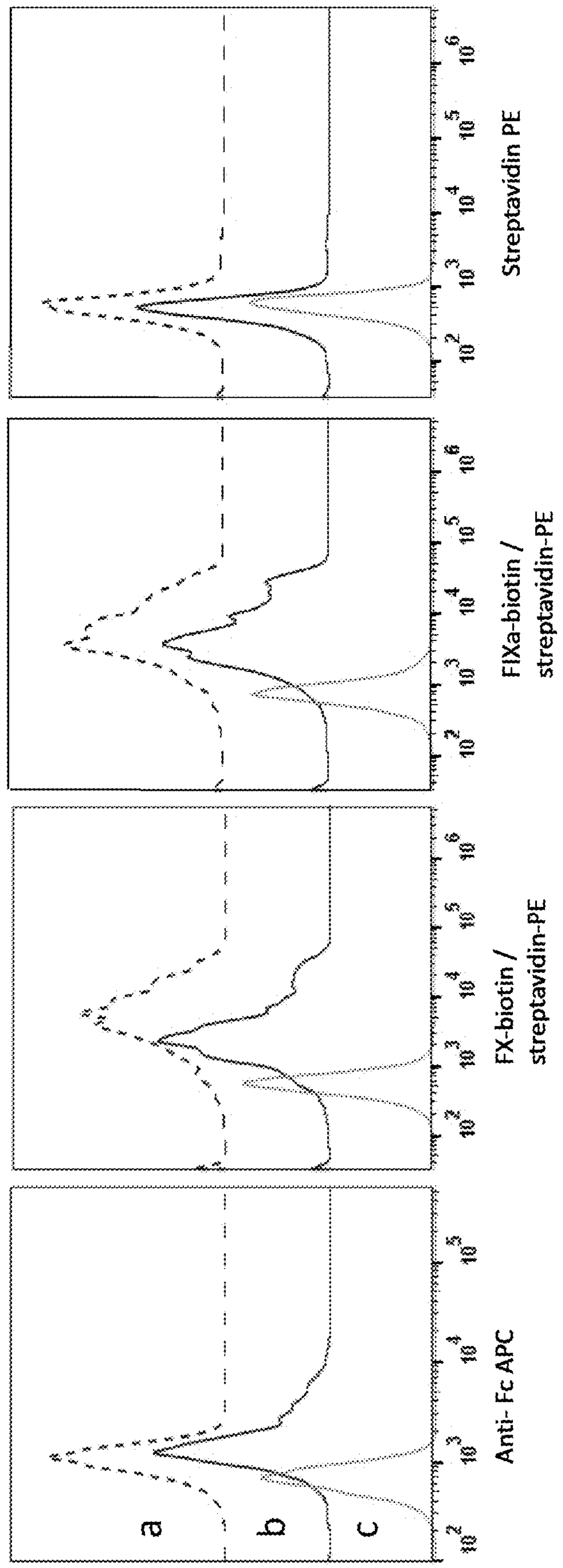

FIG. 52. Binding of FIXa and FX to the bi-specific antibody Emicizumab displayed on the surface of HEK293 cells pINT17-Bi-CMV-Emicizumab or pINT17-BSD-anti-FIXa was used to transfect HEK293 cells in the presence of plasmids encoding the AAVS TALENs. 24 hours post transfection the cells were analysed antibody display and the ability to bind the antigens FIXa or FX. The histogram plots depict cell count against fluorescence intensity when stained with, from left to right: anti-Fc-APC, FX-biotin or FIXa-biotin, pre-conjugated with streptavidin-PE or streptavidin-PE alone for HEK293 cells displaying (a) Bi-specific Emicizumab (black dash line), (b) anti-FIXa IgG (solid blck line), (c) HEK293 cells.

FIG. 53. Alignment of Emicizumab VL with parental Emicizumab VLs. CDRs are indicated by bars above the sequence. Dots indicate identity with the final Emicizumab VL. Residues contributing to the positive charge patch are highlighted in bold.

FIG. 54. Relationship between display of knotbodies on the surface of HEK293 cells and their biophysical properties (a) HEK293 cells were transfected with pINT17-knotbodies in presence of the AAVS TALENs. Stable populations were selected with Blasticidin. 7 days post-transfection, cells were stained with anti-Fc PE (FL2) and analysed by flow cytometry. The histogram depicts cell count (y-axis) plot against fluorescence intensity (anti-Fc-PE, x-axis) and include the KB_A12 EETI-II (black solid line), KB_A12 Hstx1 (dotted line) and KB_A12 ProTxIII (dashed line). The traces of KB_A12 Hstx1 (dotted line) and KB_A12 ProTxIII (dashed line) over-lap and appear merged.

Knotbodies were expressed by transient transfection of Expi293 cells and purified by Protein A affinity chromatography. The knotbodies were analysed by HPLC-SEC as described above and plots of absorbance against elution volume are shown for (b) KB_A12 EETI-II, (c) Trastuzumab and (d) KB_A12 ProTx-III.

Figure 55:
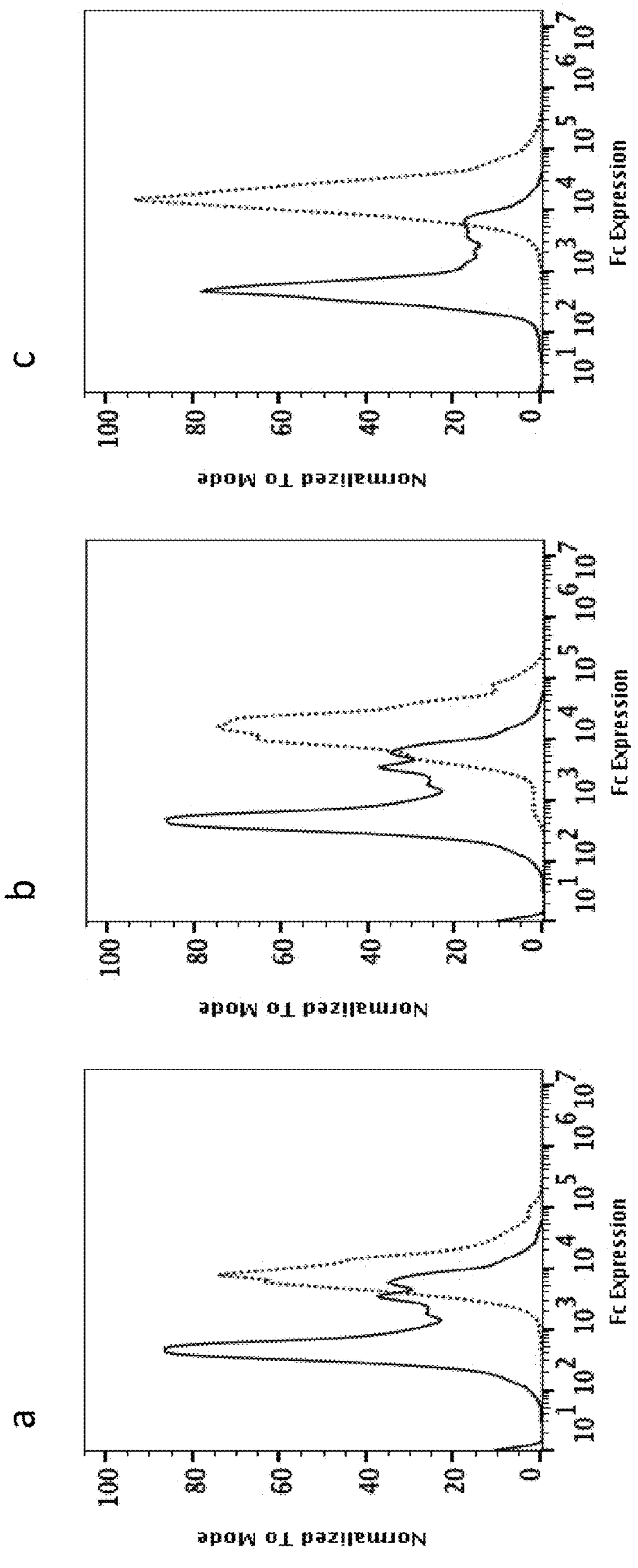

FIG. 55. Mutant libraries of knotbodies contain clones with improved display levels compared with the parental knotbodies. HEK293 cells displaying knotbodies were stained with anti-Fc-PE and analysed by flow cytometry. Histogram plots of cell count against fluorescence intensity are shown for the three libraries (after anti-Fc MACS purification) compared to their relevant parental knobody control displaying cell line. (From Left to Right): (a) KB_A12 ProTxIII Library Set A (dotted line) with KB_A12 ProTxIII Control (filled line), (b) KB_A12 ProTxIII Library Set B (dotted line) with KB_A12 ProTxIII Control (filled line), (c) KB_A12 HsTx1 library (dotted line) with KB_A12 HsTx1 Control (filled line).

EXAMPLES

Example 1. Construction of Targeting Vectors for Soluble Expression and Cell Surface Displayed IgG Formatted Antibodies To enable the display of binder molecules, including antibodies, on the surface of higher eukaryotic cells and their subsequent genetic selection, vectors may be used to target the binder gene to a particular location in the host genome. The vector may encode a selectable marker, to enable selection of stable cell lines and this selectable marker may encode genes conferring resistance to blasticidin, G418/Geneticin, hygromycin, puromycin or zeocin. The targeting vector may contain an exogenous promoter to drive expression of the gene encoding the selectable marker. Alternatively, the transgene may be integrated into the cellular DNA at a location downstream of an endogenous promoter to enable the preferential selection of the correctly integrated transgenes. The targeting vector will also encode homology arms to allow homologous recombination to the relevant chromosomal locus and promoters to drive expression of the binder molecule and polyadenylation (pA) sites. The binder molecule gene will be fused to DNA encoding a leader sequence to allow secretion, via the endoplasmic reticulum (ER), to the cell surface and a membrane anchor such as a transmembrane domain or glycosylphosphatidylinositol (GPI) anchor.

Figure 1A:
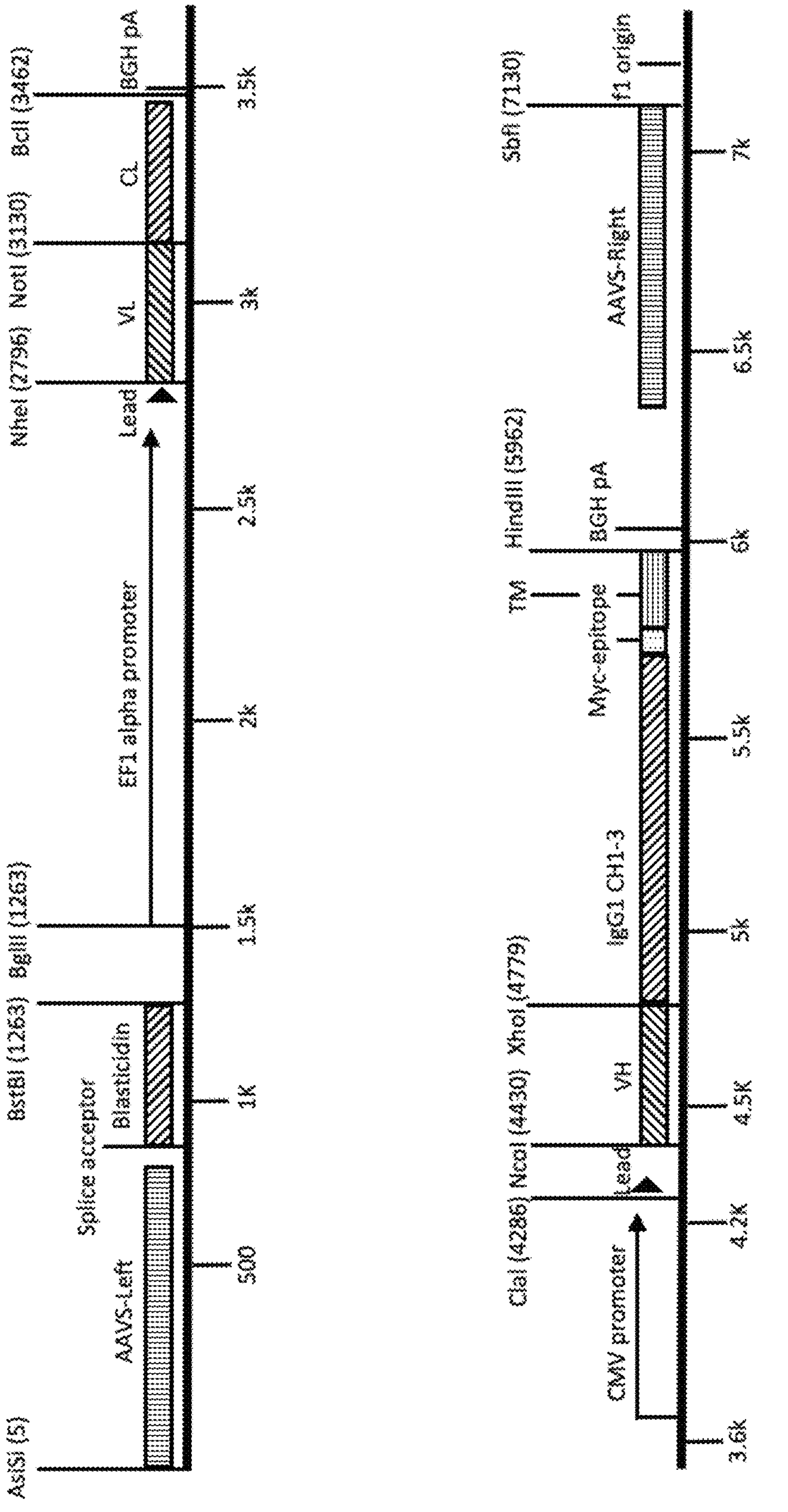
FIG. 1. pINT17-BSD, a dual promoter antibody IgG expression cassette for surface expression pINT17-BSD, a schematic map is shown depicting the key features (1-7500 bp)

A schematic map of the targeting vector used here is shown in FIG. 1*a* and the full annotated DNA sequence is shown in FIG. 1*b*. The plasmid includes the AAVS homology arms, flanking the expression cassette, to allow homologous recombination of the transgene into the human AAVS site. The AAVS locus was originally identified as a common integration site of the adeno-associated virus and is a "safe harbour" locus for insertion and expression of heterologous genes in human cells[93]. After nuclease mediated cleavage within the AAVS site, the AAVS homology arms in the targeting vector promote the integration of the expression cassette by homologous recombination. The blasticidin gene lacks a promoter within the vector, but is preceded by a splice acceptor that creates an in-frame fusion with the upstream exon from the AAVS locus. The details of the antibody heavy and light chain expression cassette are described below and in FIG. 1.

The targeting vector pINT17-BSD (FIGS. 1*a* and 1*b*) was constructed by polymerase chain reaction (PCR) amplification of selected fragments from vectors previously described (WO2015166272A2) with the addition of restriction sites to enable their subsequent assembly. The origins of the various elements of pINT17-BSD are now described. DNA encoding the AAVS-left homology arm, splice acceptor, blasticidin resistance gene, poly-adenylation site and the elongation factor 1 alpha promoter (pEF1α) originated from the pD2 plasmid (WO2015166272A2) by PCR amplification (1511 bp) with the addition of the 5' AsiSI and 3' BglII restriction enzymes. DNA encoding the Myc-tag and PDGFR transmembrane domain was PCR amplified from the pD2 plasmid with the addition of a 5' IgG1 CH3 homology sequence and 3'-HindIII site. DNA encoding the light chain BM40 leader, variable light chain (VL) of the anti-lysozyme antibody D1.3[94], the human constant light (CL), bovine growth hormone (BGH) pA, the immediate early cytomegalovirus promoter (CMV promoter), a mouse heavy chain leader split by an intron, variable heavy chain (VH) of the anti-lysozyme antibody D1.3 and the IgG1 antibody constant heavy domain 1 to 3 (IgG1 CH1-3) was PCR amplified from the previously described pINT3 plasmid (WO2015166272A2) with a 5' BglII site and 3' addition of DNA encoding the Myc-tag. The two fragments encoding the 4446 bp region of pINT17-BSD from BglII to HindIII were combined by PCR assembly to add the PDGR transmembrane domain directly to the CH3 terminus. The region from HindIII to SbfI, encoding the AAVS right homology arm was PCR amplified (1168 bp) from the pD2 plasmid (WO2015166272A2) with the addition of the HindIII and SbfI restriction sites. The vector backbone encompassing the f1 and pUC origin of replications and Kanamycin resistance gene from the SbfI to AsiSI sites originated from pSF-EF1 alpha (Oxford Genetics OG43). The example shown in FIG. 1*b* encodes the VL and VH of a human anti-lysozyme antibody but this can be conveniently substituted for other specificities using standard molecular biology techniques (for example using the flanking restriction enzymes to replace the VL and VH genes).

Example 2. Comparison of Surface Presentation Level of Parental and Developability Enhanced Clones for 3 Pairs of Antibodies We examined three antibody pairs where the original parental antibody possesses a poor developability profile and their re-engineered daughter molecules, which were altered to improve their self-interaction and cross-interaction properties. The panel included CNTO607, a monoclonal antibody against interleukin IL-13, and its modified counterpart CNTO607 W100A[14]. CNTO607 is poorly soluble at neutral pH, precipitates in PBS buffer at high concentrations and displays self-interaction as measured in an affinity-capture self-interaction nanoparticle spectroscopy (AC-SINS) assay[39]. Structure determination of CNTO697 revealed a hydrophobic patch in the heavy chain CDR3. The VH CDR3 mutation W100A improved both its antibody solubility and cross-interaction chromatography (CIC) profile[47]. CIC measures binding to human serum polyclonal antibodies immobilized on a column matrix. A second example is a monoclonal antibody, named Ang2mAb, which targets Angiopoietin 2, a soluble ligand for the Tie2 receptor and regulator of pathological angiogenesis. However, Ang2mAb was reported to exhibit both poor expression and aggregation. A combination of structural modelling and experimental screening of 19 variants led to the engineering of the better expressing Ang2mAb C49T[6], which mutated an unpaired cysteine residue. Finally, we included MEDI-1912, an anti-nerve growth factor (NGF) antibody that inhibits signaling via the TrkA and p75 receptors[7]. MEDI-1912 could potentially be used in the treatment of chronic pain, but shows precipitation and aggregation in solution and a poor pharmacokinetic profile. MEDI-1912 binds to NGF with pico-molar affinity and was affinity matured from a "grand-parental" antibody named MEDI-578 which was well-behaved in terms of self-aggregation. By hydrogen/deuterium exchange—mass spectrometry (HDX-MS) and molecular modelling, a hydrophobic patch was identified on the VH domain caused by residues within VH CDR1 and CDR2. This allowed the prediction of the amino acids responsible for self-association and consequent aggregation. This in turn enabled the design of a triple mutant (MEDI-1912_STT) with mutations W30S, F31T and L56T that interrupted the self-interaction interface whilst retaining potency and affinity for NGF[7].

Synthetic DNA encoding the CNTO607, CNTO607-W100A, Ang2mAb, Ang2mAb-C49T, MEDI-1912 and MEDI-1912_STT heavy and light variable domains (see Table 1) for sequences) were cloned into the mammalian display vector pINT17-BSD (see Example 1 for vector maps and sequences), DNA sequence confirmed and transfection quality plasmid DNA prepared. Suspension adapted HEK293 cells were seeded at $5\times10^5$ cells per ml in HEK FreeStyle 293 expression media one day before transfection. PEI-transfection was performed when the cells reached a density of $1\times10^6$ cells/ml in 10 ml. pINT17-harboring antibody genes (1 ug), left and right TALEN plasmids (5 ug each) were mixed and diluted in unsupplemented HEK FreeStyle 293 expression media (1 ml). Polyethylenimine (PEI), linear, 25000 Da MW (10 ul, 1 mg/ml, Polysciences) was added, incubated for 10 minutes at room-temperature. The plasmid DNA/PEI mix was then added to HEK293 suspension cells ($1\times10^6$ cells/ml in 10 ml HEK FreeStyle 293 expression media). Blasticidin selection was started 48 hours after transfection at a concentration of 7 μg/ml. The population was kept under selection for the duration of the experiment. After 15 days post-transfection (dpt) cells were stained with anti-human Fc PE (Biolegend). The monoclonal cell lines displaying antibodies were then stained by the following protocol. HEK293 cell lines displaying antibodies or wild-type HEK293 cells (one million cells) were pelleted (200 g, 3 minutes in an Eppendorf tube (1.5 ml). The pellet was resuspended in PBS (1 ml) and centrifuged (600 g, 2.5 min). The pellet was resuspended in 1% BSA, PBS (100 μl) containing anti-Fc PE (5 μl, Biolegend). The mix was incubated, shielded from light, at 4° C. for 30 min. 0.1% BSA, PBS (900 μl) was added and cells pelleted (600 g, 2.5 min). The cells were resuspended in 0.1% BSA, PBS (1 ml) and this wash step was repeated once. The cells were resuspended in 0.1% BSA, PBS (200 µl) with 7-AAD (5 µl per million cells). Labelled cells (50 µl) were analysed using the Intellicyte iQue screener. Flow cytometry analysis (FIG. 2) showed increased antibody display levels for the improved display levels for the improved daughter molecules for all three antibody pairs compared with the original problematic parental molecules.

TABLE 1

Protein sequence of VH and VL genes of test antibodies. Amino acid sequences in single letter code are shown of the variable antibody heavy and light chains. The variable domains are underlined. Variant residues between antibody pairs are highlighted in bold.

| Chain | Protein Sequence |
|---|---|
| Ang2 VH | QVQLVESGGGVVQPGRSLRLSCAASGFTFTNYG MHWGRQAPGKGLEWVAVISHDGNNKYYVDSVKG RFTISRDNSKNTLYLQMNSLRAEDTAVYYCARE GIDFWSGLNWFDPWGQGTLVTVSS (SEQ ID NO: 2) |
| Ang2 VL | EIVLTQSPGTLSLSPGERATLSCRASQSITGSY LAWYQQKPGQAPRLLICGASSWATGIPDRFSGS GSGTDFTLTISRLEPEDFAVYYCQQYSSSPITF GQGTRLEIK (SEQ ID NO: 3) |
| Ang2 VL C49T | EIVLTQSPGTLSLSPGERATLSCRASQSITGSY LAWYQQKPGQAPRLLI**T**GASSWATGIPDRFSGS GSGTDFTLTISRLEPEDFAVYYCQQYSSSPITF GQGTRLEIK (SEQ ID NO: 4) |
| CNT607 VH | QVQLVESGGGLVQPGGSLRLSCAASGFTFNSYW INWVRQAPGKGLEWVSGIAYDSSNTLYADSVKG RFTISRDNSKNTLYLQMNSLRAEDTAVYYCARG LGAFHWDMQPDYWGQGTLVTVSSAS (SEQ ID NO: 5) |
| CNT607 VH W100A | QVQLVESGGGLVQPGGSLRLSCAASGFTFNSYW INWVRQAPGKGLEWVSGIAYDSSNTLYADSVKG RFTISRDNSKNTLYLQMNSLRAEDTAVYYCARG LGAFH**A**DMQPDYWGQGTLVTVSS (SEQ ID NO: 6) |
| CNT607 VL | SYELTQPPSVSVAPGQTARISCSGDNIGGTFVS WYQQKPGQAPVLVIYDDNDRPSGIPERFSGSNS GNTATLTISGTQAEDEADYYCGTWDMVTNNVFG GGTKLTVL (SEQ ID NO: 7) |
| MEDI-1912 VH | QVQLVQSGAEVKKPGSSVKVSCKASGGTFWFGA FTWVRQAPGQGLEWMGGIIPIFGLTNLAQNFQG RVTITADESTSTVYMELSSLRSEDTAVYYCARS SRIYDLNPSLTAYYDMDVWGQGTMVTVSS (SEQ ID NO: 8) |
| MEDI1912 VH STT | QVQLVQSGAEVKKPGSSVKVSCKASGGTF**ST**GA FTWVRQAPGQGLEWMGGIIPIFG**T**TNLAQNFQG RVTITADESTSTVYMELSSLRSEDTAVYYCARS SRIYDLNPSLTAYYDMDVWGQGTMVTVSS (SEQ ID NO: 9) |
| MEDI-1912 VL | QSVLTQPPSVSAAPGQKVTISCSGSSSDIGNNY VSWYQQLPGTAPKLLIYDNNKRPSGIPDRFSGS KSGTSATLGITGLQTGDEADYYCGTWDSSLSAW VFGGGTKLTVL (SEQ ID NO: 10) |
| Vesencumab VH | EVQLVESGGGLVQPGGSLRLSCAASGFTFSSYA MSWVRQAPGKGLEWVSQISPAGGYTNYADSVKG RFTISADTSKNTAYLQMNSLRAEDTAVYYCARG ELPYYRMSKVMDVWGQGTLVTVSS (SEQ ID NO: 11) |

TABLE 1-continued

Protein sequence of VH and VL genes of test antibodies. Amino acid sequences in single letter code are shown of the variable antibody heavy and light chains. The variable domains are underlined. Variant residues between antibody pairs are highlighted in bold.

| Chain | Protein Sequence |
|---|---|
| Vesencumab VL | DIQMTQSPSSLSASVGDRVTITCRASQYFSSYL AWYQQKPGKAPKLLIYGASSRASGVPSRFSGSG SGTDFTLTISSLQPEDFATYYCQQYL GSPPTFGQGTKVEIK (SEQ ID NO: 12) |

Example 3a. The Relationship Between Cell Surface Presentation Level and Self-Interaction at High Concentrations To examine the properties of the antibodies described in Example 2, antibody expression and purification was performed. Synthetic DNA encoding CNTO607, CNTO607-W100A, Ang2mAb, Ang2mAb-C49T, MEDI-1912 and MEDI-1912_STT heavy and light variable domains (see Table 1 for sequences) were cloned into a dual promoter IgG soluble expression vector based on pINT3 (WO2015166272A2) and correct cloning confirmed by DNA sequencing.

Plasmid DNA was prepared and this was used to transfect Expi293 cells (30 ml final culture volume scale) using the transfection reagent ExpiFectamine according to the manufacturer instructions (A14525, ThermoFisher Scientific). Cells were seeded at a density of 2×106 cells/ml in 25.5 ml of Expi293 Expression Medium 24 hours prior to transfection. Plasmid DNA (30 µg) was diluted in Opti-MEM Medium (1.5 ml) and ExpiFectamine 293 Reagent (80 µl) was diluted in Opti-MEM Medium (1.5 ml) and incubated for 5 minutes at room temperature. The diluted plasmid DNA (30 µg in 1.5 ml Opti-MEM Medium) was then added to the diluted ExpiFectamine 293 Reagent (80 µl ExpiFectamine in 1.5 ml Opti-MEM Medium) and incubated for 20 minutes at room temperature. The cells were incubated at 37° C., 5% CO2, 5% humidity and agitated at 130 rpm (25 mm orbital throw, ISF1-X, Climo-Shaker, Kuhner). Following 5 days of expression, culture supernatant was harvested by centrifugation (2000 g, 20 min).

The culture supernatants in 50 ml centrifuge tubes were pH adjusted by the addition of 1/10 volume of PBS (pH7.4) and Protein A sepharose FF resin (300 µl, Generon, PC-A100) added and incubated by agitation for 1 hour at room-temperature. The 50 ml tubes were centrifuged at 2000 g for 5 mins to collect the beads and supernatant discarded leaving approximately 1 ml behind of bead slurry. This slurry was resuspended loaded onto a column with a frit (*Proteus* "1 step batch" midi spin column. Generon, GEN-1SB08), centrifuged (50 g, 1 min at 4° C.) and flow through discarded The column was washed with 2×PBS (2×10 ml) followed by centrifugation (50 g, 1 min at 4° C.) after each wash step. Antibody was eluted using elution buffer (900 ul, 0.2 M Glycine pH 2.6) which was added to the column matrix and the eluate immediately neutralized using neutralisation buffer (300 ul, 1 M Tris-HCl, pH 8). Antibodies were then eluted from the Protein A sepharose column by centrifugation (50 g, 1 min at 4° C.) directly into the neutralisation buffer. The antibodies were buffer exchanged by transfer to a GeBAflex maxi tube (8 kDa molecular weight cut-off, Generon, D045) and dialysed in 4 litres of PBS and incubation for at least 3-18 hours at 4° C. This dialysis step was repeated with a second 4 L PBS dialysis step. The antibody yield and concentration was determined by measurement of the absorbance at 280 nm and calculating using the Beer-Lambert Law using an estimated extinction coefficient of 1.4 to approximate the concentration.

The yield of polypeptide generated by transient expression may be considered as an indicator of developability potential. Although comparison of the expression yields in transient transfection between the 3 pairs of antibodies from example 2 showed lower expression of the parental antibody, the significant difference in developability potential was not apparent simply by comparing yield in transient transfection (Table 2). For example, the expression yield of the parental CNTO607 antibody was 34 mg/L whereas the solubility improved CNTO607-W100A antibody expression yield was 55 mg/L. Similarly, the expression yields of parental antibodies MEDI-1912 was 33 compared with 53 mg/l for the improved version. The yield of Ang2mAb was 13 mg/L compared with 34 mg/L for the engineered off-spring Ang C49T.

The melting temperature of a polypeptide is sometimes taken as a surrogate to predict "developability" and in some instances antibodies have been selected for improved melting temperature in the expectation of generating more developable antibodies[9-11]. The melting temperature (Tm) and temperature of the onset of aggregation (Tagg) were determined using Prometheus NT.4B (Nanotemper) according to the manufacturer instructions. Small capillaries were used to take up approximately 8-10 μl of antibody solution at 0.5 mg/ml. The capillaries were then clipped in place for fluorescent scanning by the Prometheus instrument for thermal melt analysis. The Prometheus fitting software was used to determine the temperature for the onset of melting and the temperature for the onset of scattering. The melting temperature (Tm) and the aggregation temperature (Tagg) of the antibodies were similar (see Table 2), both between the antibody pair sets and compared to the clinically approved positive control anti-PD1 antibody, Nivolumab. This data indicates that the melting and aggregation temperatures of this antibody set are not predictive of their biophysical profiles of self-interaction and non-specific cross-interaction.

During preparative size exclusion chromatography MEDI-1912 displayed an earlier elution profile compared with MEDI-1912_STT (FIG. 3), indicating that it exists as a higher molecular weight species and is prone to self-interaction. The remaining antibodies eluted with a similar profile to Nivolumab. To enable measurement of antibody self-interaction by dynamic light scattering (DLS), the size purified antibodies were concentrated by ultra-filtration. The antibody concentration achieved for each antibody pair is shown in Table 2. This revealed that it was not possible to concentrate the parental antibodies MEDI-1912 and CNTO607 beyond 1.4 mg/ml and 1.8 mg/ml respectively before antibody precipitation occurred which blocked the ultra-filtration membrane. In contrast, it was possible to concentrate the solubility enhanced daughter molecules MEDI-1912_STT and CNTO607_W100A to 29 and 30 mg/ml respectively with no evidence of precipitation. No precipitation was observed for the concentrated Ang2mAb pair. Dynamic light scattering (DLS) detected higher order aggregated species for the parental antibodies MEDI-1912 and CNTO607 (Table 2), but not for the daughter molecules MEDI-1912_STT and CNTO607_W100A, as judged from the calculated polydispersity index (PDI) and the cumulant (or z-average) size. For example, PDI for the parental CNTO607 and MEDI-1912 were 0.22 and 0.15 respectively, whereas the PDI for the daughter molecules was 0.1 and 0.12 respectively indicating a more homogenous, mono-disperse state (Table 2). Similarly, the average particle size of the parental MEDI-1912 was 22 nm respectively, whereas the average particle size for the daughter molecule MEDI-1912-STT was 13 nm indicating a lower order aggregation state (Table 2). Thus significant self-interaction is occurring resulting in detectable self-interaction at lower concentrations and precipitation at higher concentrations.

This example demonstrates a very clear relationship between the mammalian cell display level of an antibody and its biophysical properties for three different antibody

TABLE 2

IgG biophysical properties.

| Clone ID | Antibody | $T_m$ (° C.) | $T_{agg}$ (° C.) | Expression Yield (mg/L) | C-Max (mg/ml) | Zav (nm) | PDI |
|---|---|---|---|---|---|---|---|
| 1 | CNTO607 - parental | 62.6 | 75.6 | 33.6 | 1.8 | 16.2 | 0.22 |
| 2 | CNTO607 (W100A) | 61.4 | 75.4 | 55.2 | >30 | 14.8 | 0.1 |
| 3 | MEDI-1912-parental | 71.5 | 73.2 | 33.2 | 1.4 | 21.5 | 0.15 |
| 4 | MEDI-1912 (STT) | 70.8 | 74.8 | 52.8 | >29 | 12.5 | 0.05 |
| 5 | Ang2mAb-parental | 63.8 | 65.0 | 13.4 | >21 | 13.1 | 0.12 |
| 6 | Ang2mAb C49T | 66.5 | 65.2 | 34.4 | >18 | 12.7 | 0.09 |
| 14 | Nivolumab | 67.6 | 67.3 | 102.8 | >50 | nd | nd |

The melting temperature ($T_m$) and temperature of the onset of aggregation ($T_{agg}$) were determined using Prometheus NT.4B (Nanotemper) according to the manufacturer instructions. The expression yield in terms of amount of antibody expressed (mg) per liter of culture volume was determined by transient transfection of Expi293 cells at 30 ml scale (ThermoFisher) followed by affinity purification (Protein A) and the yield of purified antibody determined from the absorbance at 280 nm and estimated antibody extinction coefficient of 1.4. Antibodies were further purification by size-exclusion chromatography on a Superdex 200 10/300 using the AKTA Pure system with PBS (pH 7.4) running buffer. Dynamic light scattering measurement were performed with a Nano S DLS (Malvern Instruments, Malvern, UK) on samples and polydispersity index (PDI) and the cumulant (or z-average) size (Zav) calculated using the zetasizer software (Malvern Instruments, Malvern, UK).

pairs. Parental antibodies specific to IL-13 (CNTO607), Angiopoietin2 (Ang2mAb) and Nerve growth factor (MEDI-1912), with documented problems regarding self-interaction, cross-interaction and poor pharmaco-kinetics (MEDI-1912) all resulted in lower cell display levels compared with their solubility enhanced daughter molecules (FIG. 2).

Example 3b. Supporting Theory on Antibody Concentration at the Cell Surface

This Example presents underlying reasoning that may assist in understanding the inventors' proposal that strong polypeptide expression in a eukaryotic cell can potentially achieve high local concentrations when the polypeptide is retained on the cell surface.

In the work described here, suspension adapted HEK293 cells are used for antibody display. The HEK293 cell line is of mammalian (human) origin. The cells are approximately spherical with a radius of 10 microns[95]. If we treat the suspension HEK293 cell as a sphere we can calculate the volume occupied by an antibody on its surface. (We assume for the sake of this example that all areas of the cell surface are equally accessible for antibody display. Higher local concentrations of antibody would be achieved if this were not the case.) The radius (r) of a sphere can be calculated from the formula $4/3\pi r^3=4.18\ r^3$. Taking an antibody to be of height 150 angstroms (Å) (=15 nm), it will be present in a larger sphere of volume $4.18(r+150\ Å)^3$. Thus the antibody volume is the difference between this and the volume of the cell.

The volume of a cell of 10 micron radius is:

$4.18\times10^{-15}\ m^3(4180\times10^{-15}$ litre).

The volume of the larger sphere including the antibody is:

$4.198\times10^{-15}\ m^3(4198\times10^{-15}$ litre).

Thus the displayed antibody occupies a volume of $0.018\times10^{-15}\ m^3(18\times10^{-15}$ litre).

In a similar way we can calculate the difference in volume for different sized cells.

Knowing the number of antibodies/cell, the molecular weight and the volume occupied we can then calculate the concentration achieved at the cell surface. Using Avogadro's constant we know that $6\times10^{23}$ antibody molecules/l will have a concentration of 150,000 mg/ml. Thus $6\times10^{18}$ antibody molecules/ml will have a concentration of 1.5 mg/ml (10 μM). By this approach the concentrations shown in Table 3 are calculated.

TABLE 3

| Cell radius | 5 micron | 10 micron | 15 micron | 20 micron |
|---|---|---|---|---|
| Cell volume ($\times10^{-15}$ litres) | 522.5 | 4180 | 14107.5 | 33440 |
| volume occupied by cell plus antibody ($\times10^{-15}$ litres) | 527.2 | 4198 | 14150 | 33515 |
| volume occupied by antibody ($\times10^{-15}$ litres) | 4.7 | 18 .8 | 42.3 | 75 |
| No. Abs/litre ($\times10^{18}$) if $10^6$ displayed/cell | 212 | 53.2 | 23.64 | 13.3 |
| Concentration (mg/ml) assuming $10^6$ displayed antibodies | 53 | 13.2 | 5.9 | 3.3 |

TABLE 3-continued

| Cell radius | 5 micron | 10 micron | 15 micron | 20 micron |
|---|---|---|---|---|
| Concentration (microM) assuming $10^6$ displayed antibodies | 354 | 88 | 39 | 22 |
| Copy number providing 1 mg/ml | 19,000 | 75,000 | 170,000 | 300,000 |

In these calculations the number of antibodies on the cell surface is taken to be $10^6$ copies/cell. Methods of experimentally determining copy number are detailed elsewhere herein and illustrated in Example 7.

We see from Table 3 that display of $10^6$ antibodies/cell on a cell of 10 micron radius (such as a HEK293 cell in suspension culture) is estimated to give a concentration in excess of 10 mg/ml. At such concentrations, problems of protein self-interaction can potentially occur. Antibodies with a tendency to aggregate may thus have a reduced representation on the cell surface due to reduced passage through the endoplasmic reticulum[96] and increased degradation. As a result, a lower level of display would be observed for an antibody prone to self-aggregation compared with a non self-interacting antibody.

Example 4. Enriching "Developability Enhanced" Anti-NGF Antibodies on the Basis of Surface Presentation Level In Example 3 the relationship between the biophysical properties of an antibody, particularly self-aggregation and their mammalian cell display levels was described. This was illustrated by taking three antibody pairs where the original parental antibody had poor biophysical properties in terms of self and cross-interaction and these properties were improved by changing selected amino acids to create daughter molecules with improved biophysical properties. In all three cases the daughter molecules with improved biophysical properties display on the surface of HEK293 cells at increased levels compared with the problematic parental antibodies. In this example we demonstrate that it is possible to enrich for antibodies with superior biophysical properties from a mixed population of clones by mammalian display. The parental anti-NGF MEDI-1912, which has self-interaction properties and poor pharmaco-kinetics in a mouse model[7], and the improved daughter MEDI-1912_STT were chosen for this study. A model experiment was carried out where we created a mixed population of HEK293 cells displaying MEDI-1912 or MEDI-1912_STT by transfecting HEK293 cells with equal quantities of mammalian display plasmid (example 1) encoding the parental and modified antibodies along with plasmids encoding the TALE nuclease pair which directed the donor plasmid to the AAVS locus, as previously described (WO2015166272A2) Following drug selection fluorescence activated cell sorting (FACS) was carried out and cell were selected based on high antibody presentation level, isolation of the selected antibody genes and sequence analysis we demonstrate the selected enrichment of antibodies with improved biophysical properties from a mixed population.

pINT17-MEDI-1912 and pINT17-MEDI-1912_STT (see Example 2 for description) were mixed at a 1:1 ratio and this mix was integrated into the genome of HEK293 cells using nuclease-mediated gene targeting into HEK293 cells. Mid-log-phase HEK293 suspension cells (grown to a cell density of $1\times10^6$ cells/ml) were harvested by centrifugation at 200 g for 10 min and resuspended in MaxCyte electroporation buffer at a density of $1\times10^8$ cells/ml. Plasmid DNA mix consisting of pINT17-MEDI-1912 (1 μg), pINT17-MEDI-1912_STT (1 μg), AAVS directed TALEN vector pair (10 μg each) was added to HEK293 cells (100 μl, $1\times10^7$ cells total in MaxCyte electroporation buffer) and transferred into a OC100 electroporation cuvette and electroporated using a MaxCyte STX electroporation system. Following electroporation, cells were recovered at 37° C. for 20 min, diluted in HEK FreeStyle 293 expression media and maintained at 120 rpm, 37° C. under 5% CO2. Blasticidin selection was started 48 hours after transfection at a concentration of 7 μg/ml. The population was kept under selection for the duration of the experiment. 15 days post-transfection cells were stained as described in Example 2 except that DAPI stain replaced the 7-AAD stain, NGF-biotin/Streptavidin-APC stain was employed to detect antigen binding and the quantities scaled up to stain 10 million cells. The MEDI-1912/MEDI-1912_STT mixed HEK293 mammalian display population was analysed for antibody presentation level by flow-cytometry (FIG. 5*a*) and this revealed two main cell populations displaying different antibody levels. The two populations correlated with the monoclonal MEDI-1912 and MEDI-1912_STT antibody display levels as shown in the overlay plot (FIG. 5*a*). The mixed population was sorted by FACS into two populations: antibody presentation level low and high presentation level groups (Gates 5 and 6 respectively, FIG. 5*b*).

Genomic DNA was prepared from the FACS sorted cell populations (Gates 5 and 6, FIG. 5*b*). DNA encoding the IgG insert was amplified by nested PCR using KOD Hot Start DNA polymerase (Merck Millipore). Outer PCR was performed with the following genome-specific primers: Forw: CCGGAACTCTGCCCTCTAAC (SEQ ID NO: 13) and Rev: TCCTGGGATACCCCGAAGAG (SEQ ID NO: 14). PCR product from the outer PCR was used as a template to amplify the integrated IgG insert with following primers; Forw: GAGGGCCTGGATCTTCTTTCTC (SEQ ID NO: 15) and Rev: GAAGTAGTCCTTGACCAGGCAG (SEQ ID NO: 16) using KOD polymerase (71086, Merck) according to manufacturer conditions. PCR products were barcoded by following the manufacturer instructions (20015964, Illumina) and sequenced with the Illumina MiSeq sequencing platform. Approximately one million reads were analysed and this revealed that population sorted for high antibody presentation level (Gate 5, FIG. 5*b*) was enriched for the MEDI-1922_STT antibody (96%, FIG. 6). The population sorted for low antibody presentation was enriched for the parental MEDI-1912 antibody (85%, FIG. 6). This example demonstrates the selected enrichment of antibodies with improved biophysical properties by mammalian display, from a mixed population, by selecting clones on the basis of antibody cell surface display levels. This was exemplified by the enrichment of MEDI-1912_STT, with superior biophysical properties compared to its parental antibody MEDI-1912 from a mixed population of stable cell-lines.

We demonstrate that it is possible to enrich for an antibody with superior biophysical properties in a mixed population and we show that it is possible to identify improved antibodies from a large library of variants based only on presentation levels by mammalian display. As discussed residues W30, F31 and L56 on the VH MEDI1912 have potential to form a hydrophobic patch on the surface of this antibody[7]. These residues were chosen for randomization and a VH library was constructed by PCR assembly mutagenesis from a synthetic DNA template (see FIG. 4 for amino acid and nucleic acid sequences and position of primers). Three PCR products were amplified from the VH template using KOD polymerase (71086-3, Merck) according the manufacturer instructions):

```
a. VH1 (95 bp) amplified with primers
MEDI-1912-F3
                                        (SEQ ID NO: 17)
(CCATGGCCCAGGTTCAGCTG)
and

MEDI1912_W30NNS_F31NNS
                                        (SEQ ID NO: 18)
(CTGTCGGACCCATGTAAAGGCGCCSNNSNNAAAGGTGCCGCCGCTTGC

TTTGCA).

b. VH2 (102 bp) amplified with primers
MEDI-1912-F
                                        (SEQ ID NO: 19)
(GGCGCCTTTACATGGGTCCGACAG)
and

MEDI-1912_L56NNS
                                        (SEQ ID NO: 20)
(CTGGAAGTTCTGGGCCAGATTGGTSNNGCCGAAGATAGGGATGATGCC

GCC).

c. VH3 (213 bp) amplified with primers
MEDI-1912-F2
                                        (SEQ ID NO: 21)
(ACCAATCTGGCCCAGAACTTCCAG)
and

MEDI-1912-R
                                        (SEQ ID NO: 22)
(ACTCGAGACGGTGACCATTGTG)
```

The three PCR products (VH1, VH2 and VH3) listed above were combined (10 ng each) and assembled in a PCR reaction with outer primers MEDI-1912-F3 and MEDI-1912-R using KOD polymerase (71086-3, Merck) according the manufacturer instructions). The PCR product was digested with NcoI and XhoI and ligated with Nco1/Not 1 digested pINT17-MEDI-1912 (the pINT17 mammalian display vector (FIG. 1) encoding the VL of MEDI1912), (100 ng). This ligation mix was then was purified using the mini-Elute PCR purification kit (Qiagen) and purified ligation mix was transformed into 50 μl E. cloni 10G elite electrocompetent cells (60061-1, Lucigen). Cells were pulsed using a 0.1 cm cuvette, recovered with 2 ml recovery medium and grown for 1 h at 37° C., 250 rpm. In order to calculate the library size, cells were diluted 1 in 1000 and plated 10 μl and 100 μl in a 10 cm diameter 2TY-Kanamycin plates. The remaining cells were spun down and plated in 2×10 cm diameter 2TY-Kanamycin plates and incubated at 37° C. overnight. Colonies were counted from the 10 ul plate and a library size of $1.1\times10^6$ was calculated. Since a library constructed by randomizing three residues using NNS codons encodes 32,768 variants, the experimental library size exceeded the theoretical library size by 34-fold. The transformant plates were scraped, the cell density measured by reading the absorbance at 600 nm (OD600), the equivalent of 2 OD units of culture (2×OD600) used to inoculate 50 ml Circlegrow culture, culture grown 3 to 4 hours at 37° C. in a 250 ml baffled flask, approximately 400×OD600 units harvested and midiprep plasmid DNA prepared (pINT17-MEDI-1912-library).

The pINT17-MEDI-1912-library was used for nuclease mediated gene targeting into HEK293 cells. Mid-log-phase HEK293 suspension cells (grown to a cell density of $1\times10^6$ cells/ml) were harvested by centrifugation at 200 g for 10 min and resuspended in MaxCyte electroporation buffer at a density of 1×10[8] cells/ml. Plasmid DNA mix consisting of pINT17-MEDI-1912-library (8 μg), AAVS directed TALEN vector pair (40 μg each) was added to HEK293 cells (400 μl, 4×10[8] cells total in MaxCyte electroporation buffer) and transferred into a OC400 electroporation cuvette and electroporated using a MaxCyte STX electroporation system. Following electroporation, cells were recovered at 37° C. for 20 min, diluted in HEK FreeStyle 293 expression media and maintained at 120 rpm, 37° C. under 5% CO2. Blasticidin selection was started 48 hours after transfection at a concentration of 7 μg/ml. The population was kept under selection for the duration of the experiment. 15 days post-transfection cells were analysed were stained as described in Example 3. Flow cytometry analysis of the HEK293 displayed MEDI-1912-library (FIG. 7*c*) indicated that the library possessed cells within the mixed population that displayed equivalent antibody display levels as the MEDI-1912_STT monoclonal cell line (FIG. 7*b*) and higher display levels than the parental MEDI-1912 monoclonal cell line (FIG. 7*a*). This suggested that clones were present in the MEDI-1912 population that were equivalent to MEDI-1912_STT in terms of display level.

The library population was sorted by FACS according to antibody presentation level (FIG. 7*c*), antibody genes were recovered from the P5 and P6 gated populations and the VH gene sequenced by "next generation sequencing". (NextGen) as described above. FIG. 8 shows amino acid identity histogram plots for residues 30, 31 and 56 for the mammalian display selected population. This showed an enrichment of amino acids S, T, P at position 31, enrichment of amino acids S, P, N at position 32 and an enrichment of amino acids R, S, T and P at position 56.

To enable a biophysical characterization of the mammalian display selected antibodies, VH genes were PCR amplified from the genomic DNA of the selected population (Gates P5 and P6 FIG. 7), as described in Example 3. VH inserts were cloned into pINT17-MEDI-1912, NcoI and XhoI cut vector harbouring the MEDI-1912 VL, as described above and the ligation mix used to transform *E. coli* DH10B cells. 188 transformants were picked, plasmid DNA prepared and these were DNA sequenced to identify the identity of the codons at positions 30, 31 and 56. Selected clones, based on the frequency of occurrence by NextGen sequencing (FIG. 8), were then picked for expression by transient transfection and affinity purification as described in Example 2. Antibodies were concentrated prior to analysis by dynamic light scattering (DLS) by ultra-filtration. All the antibodies were able to be concentrated to between 8-fold and 29-fold greater than the parental MEDI-1912 antibody (Table 4), with no evidence of precipitation at these concentrations, indicating that the selected antibodies had higher solubility than the parental antibody. DLS also showed that the selected antibodies had lower average particle size (Z-Ave) and less polydispersity (PDI) than the parental antibody MEDI-1912 (Table 4). Four selected clones (P5_C06, P5_F01, P6_C08 and P6_F02) showed superior or equivalent mono-dispersity compared to the previously reported improved clone MEDI-1912_STT. The improved variants, selected by random sub-library creation and mammalian display selection, on average changed the original hydrophobic residues to hydrophilic residues.

TABLE 4

Selected MEDI-1912 variant biophysical properties.

| ID | aa30 | aa31 | aa56 | C (mg/ml) | Z-Ave (d.nm) | PDI |
|---|---|---|---|---|---|---|
| P5_C06 | T | S | R | 52.1 | 13.81 | 0.06 |
| P5_C11 | P | P | N | 42.3 | 24.77 | 0.135 |
| P5_F01 | T | H | T | 48.4 | 13.48 | 0.037 |
| P5_F07 | N | T | L | 43.9 | 18.86 | 0.108 |
| P5_F12 | D | H | L | 38.3 | 15.5 | 0.113 |
| P5_G12 | H | S | L | 31.8 | 16.44 | 0.103 |
| P6_B08 | T | P | L | 40.8 | 15.05 | 0.075 |
| P6_C08 | S | T | A | 30.7 | 12.73 | 0.054 |
| P6_C11 | S | L | L | 15.2 | 31.97 | 0.207 |
| P6_E07 | R | P | L | 33.9 | 19.54 | 0.177 |
| P6_F02 | R | S | Y | 39.1 | 12.96 | 0.036 |
| MEDI-1912_STT | S | T | T | 53.1 | 14 | 0.048 |
| MEDI-1912 | W | F | L | 1.8 | 23.2 | 0.148 |

Antibodies were expressed by transient transfection of Expi293 cells at 30 ml scale (ThermoFisher) followed by affinity purification (Protein A). Antibodies were further purification by size-exclusion chromatography on a Superdex 200 10/300 using the AKTA Pure system with PBS (pH 7.4) running buffer. Antibodies were concentrated by centrifugal filtration and the concentration obtained are shown (C) in milligrams per ml (mg/ml). Dynamic light scattering measurement were performed with a Nano S DLS (Malvern Instruments, Malvern, UK) on samples and polydispersity index (PDI) and the cumulant (or z-average) size (Zav) calculated using the zetasizer software (Malvern Instruments, Malvern, UK). Amino acid identity is shown in single letter code for positions 30, 31 and 32.

This example demonstrates that it is possible transform an antibody with poor biophysical properties to one with improved properties in terms of solubility and low self-interaction by mammalian display selection. This was achieved by the random mutagenesis of selected residues and the creation of a large random antibody variant library displayed on the surface of HEK293 cells. Current state of the art techniques to assess an antibody developability profile (e.g. solubility) require large scale expression and purification at the multi-mg scale to enable complete biophysical and PK measurements. In this example using differences in polypeptide presentation level, as judged by differences in mean fluorescence intensity (MFI) we demonstrate that it is possible to create millions of variants and select for antibodies which are subsequently shown to have improved biophysical properties. This process could be applied where novel antibodies are being selected from a naïve library or a library pre-selected in another system such as phage display. Alternatively, the present invention could also be applied during the affinity maturation or humanization of an antibody where a library of variants is created and displayed on the surface of mammalian cells.

Example 5. Construction of Variant Library and Selection of Developability Enhanced Anti-PSK9 Clones Bococizumab is an anti-proprotein convertase substilisin/kexin type 9 (PCSK9) mAb that was in development by Pfizer to reduce low-density lipoprotein cholesterol (LDL-C) in serum. The mechanism of action of Bococizumab is to inhibit the PCSK9 mediated degradation of LDL receptor (LDLR) and thereby decrease serum LDL-cholesterol (LDL-C)[97]. This antibody was withdrawn from development in November 2016 with Pfizer announcing "it was not likely to provide value for patients, physicians or shareholders". It has been reported that the biophysical properties of bococizumab are not optimal[2] and this may be a reason for its clinical failure. For example, Bococizumab displayed both self-aggregation and cross-interaction in a variety of assays[2]. In contrast, the FDA approved anti-PCSK9 Alirocumab (Regeneron) antibody did not display the same levels of self-aggregation and cross-interaction in the same assays.

Bococizumab was originally discovered by immunization of PCSK9 knockout mice and screening monoclonal antibodies (mAbs) producing hybridoma clones for their ability to inhibit PCSK9 activity[98]. The mouse mAb 5A10 (U.S. Pat. No. 8,399,646 B2) was then humanized by cloning DNA encoding the complementarity determining regions (CDRs) from the variable heavy (VH) and variable light (VL) domains into a human framework[99] with an amino acid substitution in VH CDR1 and VH CDR2 to give the humanized mAb 5A10-i. This humanized antibody 5A10-i was further affinity matured, as described previously[100], to give Bococizimab. A sequence alignment for the VH and VL domains for the parental mouse mAb 5A10, the humanized intermediate antibody 5A10-i and Bococizumab is shown in FIG. 9. The affinities (equilibrium dissociation constants or $K_D$) of 5A10, 5A10-i and Bococizimab for PCSK9 are 1 nM, 1.5 nM and 7 pM respectively as determined by surface plasmon resonance (SPR) or KinExA (U.S. Pat. No. 8,399,646 B2). The crystal structure of Bococizimab Fab fragment complexed with PCSK9 has been determined[98] and this has shown the antibody binds to the catalytic domain of PSK9 through both light and heavy chains, with the main contribution through VH CDR3.

After nuclease-mediated antibody gene integration into HEK293 cells and display on the cell surface we have observed reduced cell surface presentation of Bococizumab, compared with the humanized intermediate version 5A10-i from which it was derived (FIG. 10). The aim of this example is to demonstrate that, from a library of variants, a variant of Bococizumab can be selected by mammalian display with good presentation level indicating improved biophysical properties of stability, reduced self-aggregation and reduced cross-interaction properties or "stickiness" with retained target antigen binding. It is important to first identify regions or "patches" of the antibody which may contribute to its poor biophysical properties. For example, it is known that contiguous hydrophobic amino-acid residues within a polypeptide sequence can give rise to poor expression levels of that protein[101]. Also hydrophobic patches on antibodies can give rise to poor biophysical properties.[6,7,14] Similarly, positive charge patches on the antibody surface from clustered lysine or arginine residues can also give rise to cross-interaction by non-specific binding to the neonatal Fc receptor (FcRn)[22] or cell expressed negatively charged molecules such as heparin sulphate[23].

The process of creating an improved binder using the present invention begins with the identification of residues within a sequence as candidates for changing within a library. These positions can act as sites for randomization using more than one alternative amino acid or could be sites for substitution with a single amino acid. Mutagenesis may be carried out using approaches known to those skilled in the art, such as oligonucleotide-directed mutagenesis ([102]Molecular Cloning: a Laboratory Manual: 3rd edition, Russell et al., 2001, Cold Spring Harbor Laboratory Press, and references therein). In this case of Bococizumab the three dimensional structure was available, this was analysed and candidate amino acid residues were identified for mutagenesis. Structural modelling may be used as an alternative to help identify target amino acids for mutagenesis.

The facility to create and screen millions of variants within the present invention means that a thorough search of sequence variants can be conducted even in the absence of any 3D structural information or model e.g. by looking at linear sequences. This could be done by analysing linear sequence for features such as hydrophobicity or charge clustering. As an alternative, mutational scans focused on individual amino acids can be carried out in order to guide larger scale, combinatorial mutagenic campaigns during affinity maturation campaigns[103]. By the same approach individual amino acids may be substituted with alternative sets of amino acids to identify individual residues with potential for improving biophysical properties. These may subsequently form the basis for combinatorial mutagenesis wherein multiple positions are changed simultaneously. In the case of antibody genes an alignment with germ-line sequences may help identify optimal amino acid changes for improving expression. This approach was taken for non-paratopic amino-acid residues on the VH. Residues that contributed to hydrophobic or charge patches were Y33 within VH CDR1, F54 and R57 within VH CDR2 (FIG. 9). A multiple alignment with human VH germ-line sequences is shown in FIG. 11. Based on this alignment the non-paratopic bococizumab VH amino acids contributing to hydrophobic or charge patches were reverted to germ-line sequences listed below:

a. VH Y33A (reversion to germline IGHV1-3*01)
b. VH Y33D (reversion to germline IGHV1-8*01)
c. VH S52N, F54S, R57S (triple mutant reversion to germline IGHV1-46*01)
d. VH Y33A, S52N, F54S, R57S (a. and c. mutants combined)
e. VH Y33D, S52N, F54S, R57S (b. and c. mutants combined)

For paratopic residues, random mutant libraries were created to enable selection for both presentation and retained antigen binding (FIG. 9). Candidate problematic residues within the VL were: Y53, L94 and W95. From the co-crystal structure of Bococizumab with PCSK9 these residues either directly interact with the target antigen or indirectly contribute to binding through allosteric interactions (for example VL CDR3 residue W95 appears to pack against VH CDR3 residues and may maintain the VH CDR3 conformation for optimal binding to PCSK9. By the construction of random libraries in these positions and selection it will be possible to explore whether there is an optimal amino acid combination for improved biophysical properties with retained antigen binding. An alternative library design could have involved the random mutagenesis of selected non-paratopic residues within the VH CDR1 and CDR2.

Synthetic VH geneblocks were designed and synthesised encoding the following constructs listed (a) to (e) above and the original wild-type Bococizumab (f). The DNA sequences encoding these synthetic genes are shown FIG. 12. These geneblocks were PCR amplified with primers 3054 and 3055 (Table 5) to yield a 375 bp product. This product was spin column purified, digested with NcoI/XhoI and spin column purified. The 6 digested VH inserts were then ligated with pINT17-blasticidin NcoI/XhoI cut vector, ligations used to transform *E. coli* DH5α, individual colonies picked, mini-prep plasmid DNA prepared and DNA sequence confirmed.

TABLE 5

| Primer sequences. | |
|---|---|
| 3052 TTTTTTGCCATGGCCCAAGTG (SEQ ID NO: 23) | 7A2-VH-F |
| 3053 AAAAAAACTCGAGACGGTGACC (SEQ ID NO: 24) | 7A2, 107_A07-VH-R |
| 3054 TTTTTTGCCATGGCCCAGG (SEQ ID NO: 25) | Bococizumab-VH-F |
| 3055 AAAAAAACTCGAGACTGTCACGG (SEQ ID NO: 26) | Bococizumab-VH, 7D4-intermediate-R |
| 3056 TTTTTTGCTAGCGACATCCAGATG (SEQ ID NO: 27) | Bococizumab, 7D4-intermediate-VL-F |
| 3057 TTTTTTGCCATGGCCCAGGTTC (SEQ ID NO: 28) | Bococizumab-VL-R |
| 3052 TTTTTTGCCATGGCCCAAGTG (SEQ ID NO: 29) | 7A2-VH-F |
| 3053 AAAAAAACTCGAGACGGTGACC (SEQ ID NO: 30) | 7A2, 107_A07-VH-R |
| 3069 CTGGGCACGCCGGTGTATCTSNNGCTGGCGCTGTAGATCAGCAG (SEQ ID NO: 31) | Bococizumab-VL-R-Y53-random |
| 3070 GTGCCCTGGCCAAATGTCCGSNNSNNAGAGTACCGCTGCTGGCAGTAG (SEQ ID NO: 32) | Bococizumab-VL-R-L94W95-random |
| 3071 TTTTTTGCTAGCGACATCCAGATG (SEQ ID NO: 33) | Bococizumab-VL-F1 |
| 3072 GCTGGCGCTGTAGATCAGCAG (SEQ ID NO: 34) | Bococizumab-VL-R1 |
| 3073 AGATACACCGGCGTGCCCAG (SEQ ID NO: 35) | Bococizumab-VL-F2 |
| 3074 AGAGTACCGCTGCTGGCAGTAG (SEQ ID NO: 36) | Bococizumab-VL-R2 |
| 3075 AAAAAAGCGGCCGCGGTACGCTTGATTTCCAGCTTGGTGCCCTGGCCAAATGTCCG (SEQ ID NO: 37) | Bococizumab-VL-R3-extension |
| 3076 TTTTTTGCCATGGCCCAGGTTCAG (SEQ ID NO: 38) | Bococizumab-VH-F1 |
| 3077 AAAAAAACTCGAGACTGTCACGGTGG (SEQ ID NO: 39) | Bococizumab-VH-R1 |

The VL Y53, L94, W95 codons was randomized by NNS PCR assembly mutagenesis using a VL gene template containing stop codons at the positions subject to mutagenesis (see FIG. 12 for VL gene template sequence). The following PCRs were performed:

a) The Bococizumab VL plus stops geneblock (see FIG. 12 for sequence) was PCR amplified with primers 3071/3047 (Table 5) to give a 353 bp product.
b) A PCR was performed with template (a) above with primers 3071/3069 (Table 5) to give 191 bp product.
c) A PCR was performed with template (a) above with primers 3073/3070 to give a 146 bp product.
d) A PCR assembly reaction was performed with the products of PCR reactions b and c above with outer primers 3071/3075 to give a 353 bp insert. The product was digested with NheI/NotI and purified by spin column.

The 6 VH variants a to f above (see FIG. 12) were PCR assembled with a "stuffer" fragment encoding the constant kappa light chain (CL-kappa), polyA, CMV promoter and signal sequence and the VL NNS library. The stuffer fragment was amplified from pINT3 plasmid (WO2015166272A2) using primers Kappa stuffer F4 (GTACCGCGGCCGCACCTTCCG (SEQ ID NO: 40)) and Lambda stuffer R3 (CAGCCATGGCGCCTGTG-GAGAGAAAGG (SEQ ID NO: 41)). The assembled inserts were digested with NheI and XhoI, spin column purified and ligated (50 ng insert per ligation reaction) with pINT17-BSD targeting vector (100 ng), pre-digested with NheI and XhoI. Ligation mixture (20 μl) was purified using the mini-Elute PCR purification kit (Qiagen) and purified ligation mix (4 μl) was transformed into E. cloni 10G elite electrocompetent cells (50 μl, 600512, Lucigen). Cells were pulsed using a 0.1 cm cuvette, recovered with 2 ml recovery medium and grown for 1 h at 37° C., 250 rpm. In order to calculate the library size, cells were diluted 1 in 1000 and plated (10 μl and 100 μl) in a 10 cm diameter 2TY-Kanamycin plates. The remaining cells were spun down and plated in 2×10 cm diameter 2TY-Kanamycin plates and incubated at 37° C. overnight. Colonies were counted from the 10 μl plate and library size was calculated to be $2\times10^6$ transformants. In order to represent every variant the required library size $1.2\times10^5$ clones. ($32^3=3.4\times10^4$ per library×6 VH mutants) so the library generated represented a 16-fold over-representation of the required library diversity. The transformant plates were scraped, OD600 measured, 2 OD600 used to inoculate 50 ml circlegrow culture, culture grown 3 to 4 hours at 37° C. in a 250 ml baffled flask, approximately 400 OD600 units harvested and 6 midiprep plasmid DNA prepared representing the 6 VH Bococizumab variants combined with the three NNS codon VL library (FIG. 12). The 6 midiprep plasmid DNAs were quantitated by reading the absorbance at 260 nm and mixed at an equimolar ratio to give the Bococizimab targeting vector library pINT17-BSD-Boco1-library.

Suspension adapted HEK293 cells were seeded at $2.5\times10^5$ cells per ml in HEK FreeStyle 293 expression media two days before transfection. On the day of transfection cells were centrifuged and re-suspended in a final volume of $10^8$ cells/ml in the manufacturer's electroporation buffer (1 ml, Maxcyte Electroporation buffer, Thermo Fisher Scientific Cat. No. NC0856428) containing pINT17-BSD-Bococizumab-library (20 μg) and plasmids encoding the AAVS left and right TALE nucleases (TALENs, 100 μg each). The HEK293/plasmid DNA mix (0.4 ml) was transferred to a single OC-400 Cuvette (MaxCyte, Cat. No. OC-400R10) and pulsed on the HEK293 setting with the MaxCyte STXG2. The controls (minus TALENs and pINT17-BSD-Bococizumab and pINT17-BSD-5A10-i) were transfected using OC-100 Cuvettes (MaxCyte, Cat. No. OC-100R10) on the same setting. After transferring the electroporated cells into an Erlenmeyer flask (250 ml) the cells were allowed to rest for 30 minutes before FreeStyle 293 Expression Media (40 ml, LifeTech. Cat. No. 12338018) was added. The cells were resuspended thoroughly and placed in a orbital shaking incubator set to 130 RPM, 37° C. and 5% $CO_2$.

After 24 hours, $1\times10^6$ cells were stained with Anti-Human Fc PE (Cambridge Bioscience, Cat. No. 409304) to confirm transient expression. Briefly, the cells were centrifuged at 600×g for 2.5 minutes. The supernatant was discarded and cells re-suspended in 0.1% BSA (Diluted from 7.5% solution: LifeTech, Cat. No. 15260037). These were centrifuged again and resuspended in 100 μl of 1% BSA, PBS with 1 μl of anti-human Fc PE added. These were incubated for 30 minutes in the dark at 4° C. The cells were washed twice with 1 ml of 0.1% BSA, PBS and resuspended in 0.5 ml of 0.1% BSA, PBS containing 5 μl of 7-AAD (eBioscience, Cat. No. 00-6993-50). 50 μl was removed and added to wells of a 96 well plate. The IntelliCyt flow cytometer was used to analyse the presentation levels and this showed transient cell surface antibody for the transfection. As transient expression was observed the cultures were taken forward for selection using the antibiotic Blasticidin S HCl (LifeTech, Cat. No. R21001) at a concentration of 7.5 μg/ml. Cells were seeded at $0.25\times10^6$ cells per ml in Erlenmeyer flasks. Cells were also plated into 10 cm dishes (Corning, Cat. No. 353003) in DMEM (LifeTech, Cat. No. 41965039) with 10% FBS (Sigma Aldrich, Cat. No. F9665-500ML) and 1% Penicillin Streptomycin (Sigma Aldrich, Cat. No. P0781-100ML) at either 10,000 cells, or 1000 cells in 10 ml. These were allowed to attach for 24 hours before Blasticidin S HCl (LifeTech, Cat. No. R21001) was added at 7.5 μg/ml. After 12 days of transfection the plates were stained with 2% methylene blue. The percentage transfection efficiency was calculated by counting the number of blasticidin colonies achieved for a given input of total cells. The integration efficiency was calculated to be 2% and the library size achieved for a 40 million cell transfection was 800,000, 7-fold greater than the required theoretical library size (120,000). Thus a mammalian display library was constructed encoding all possible combination of variants.

After 5 days of Blasticidin S HCl (LifeTech, Cat. No. R21001) selection the cells were enriched using MACS beads and columns (Miltenyi, Cat. No. 130-048-801 & Cat. No. 130-042-401). The library had been expanded to over 200 million cells. 100 million cells were centrifuged at 200×g and washed in 0.1% BSA-PBS. These were resuspended in 9.9 ml of 1% BSA-PBS and 100 μl of anti-human Fc PE antibody (Cambridge Bioscience, Cat. No. 409304) added. The remaining 100 million were also spun down, washed, and incubated with biotinylated PCSK9 antigen (10 nM, PC9-H82E7, AcroBiosystems, 10 ml, diluted in 1% BSA-PBS). Both were incubated in the dark at 4° C. for 30 minutes. From this point, autoMACS Rinsing Solution (Miltenyi, Cat. No. 130-091-221) was used. The cells were washed in autoMACS Rinsing Solution (10 ml, 1×PBS+2 mM EDTA+0.5% BSA), centrifuged at 200×g and resuspended in 800 μl of autoMACS Rinsing Solution. 200 μl of either anti-PE (Miltenyi, Cat. No. 130-048-801) microbeads or Streptavidin (Miltenyi, Cat. No. 130-048-101) microbeads were added. These were incubated for 10 minutes in the dark at 4° C. before washing in 10 ml of autoMACS Rinsing Solution and resuspended in 5 ml ready to be applied to the columns. The MACS LS Columns (Miltenyi, Cat. No. 130-042-401) were pre-washed with 3 ml of autoMACS Rinsing Solution before the cells were added. 4× columns were used for each set of cells. Once ¼ (roughly 1.25 ml) of cells were added to each column, the columns were washed 3× times with 3 ml of buffer. The LS columns were removed from the magnetic holder and 5 ml of buffer was added. This was pushed through the column using the plunger into a 15 ml Falcon tube to elute the bound cells. To further purify the population, this 5 ml was added to a fresh column (pre-washed as before) and processed as before. The cells were counted and were found to be roughly $1.5\times10^6$ cells/ml in 5 ml. These were spun down and resuspended in 30 ml of FreeStyle media FreeStyle 293 Expression Media (LifeTech. Cat. No. 12338018) with blasticidin at 7.5 μg/ml) and incubated at 37° C., 5% CO2 until ready to passage.

48 hours post-MACS the cells were stained for Fc presentation and antigen binding (FIG. 13). Thus 2 populations were created based on a first round selection on either antigen or Fc expression (selection numbers 884 and 885 respectively). These were subsequently selected on a combination of antigen and Fc expression by flow cytometry. The procedure was the same as for the 24-hour stain described previously, with the following adjustment: the cells were incubated with 10 nM Biotinylated Human PCSK9, Avi-Tag (Cat. No. PC9-H82E7-25 μg, ACRObiosystems) for 30 minutes at 4° C. before washing and incubation with a mix of Anti-Human Fc PE (1 μl per $1\times10^6$ cells) (Cambridge Bioscience, Cat. No. 409304) and Anti-strep APC (Invitrogen, Cat. No. SA1005) (0.5 μl per $1\times10^6$ cells). 7-AAD (eBioscience, Cat. No. 00-6993-50) was used to assess viability as before. The cells were washed and analyzed using the IntelliCyt instrument as described previously (FIG. 10). After 14 days of selection, FACS was carried out using the BD Influx. $20\times10^6$ cells of the MACS sorted populations sorted on Antigen binding or Fc Presentation were incubated (as previously) with the 10 nM Biotinylated Human PCSK9 (PC9-H82E7-25 μg, ACRObiosystems) before washing and incubation with a mix of anti-Human Fc PE (1 μl per $1\times10^6$ cells) (Cambridge Bioscience, Cat. No. 409304) and anti-strep APC (0.5 μl per $1\times10^6$, SA1005, Invitrogen). DAPI was added (1 μl/million cells) immediately before sorting. The cells were sorted into two further populations: a higher antigen binding population (gate P5) and a lower antigen binding population (gate P6) as shown in FIG. 14. These FACS purified populations were grown without blasticidin but with 1% penicillin streptomycin to avoid contamination from the cell sorting process. After 4 days in culture $1\times10^6$ cells for each population were taken for genomic DNA extraction.

DNA encoding the IgG was amplified by nested PCR using KOD Hot Start DNA polymerase (Merck Millipore) as described in Example 4. PCR products were gel purified and digested with NheI and XhoI, cloned into the pINT3 mammalian expression vector and used to transform *E. coli* DH10B cells.

Random un-selected input clones (84), antigen sorted (75) and Fc selected (85) were sequenced and the VH identity determined. From the set of sequenced clones derived from a cycle of mammalian display selection, none had the original Bococizumab VH gene and there was a strong bias towards the variant composed of the IGHV1-46*01 germline (see FIG. 15). The VL sequences were determined for the same clone sets. The average pI and aliphatic index was calculated for the 3 mutated codons. This showed a reduction in both pI and aliphatic index for the mammalian display selected antibodies (FIG. 16), indicating a switch away from the original hydrophobic amino acids in CDR2 and 3.

To show that the mammalian display selected Bococizumab variants had superior biophysical properties compared with the parental antibodies, selected antibodies were next expressed. Clones were picked into 96-well plates per selection (91 per population): MACS on PCSK9 (named selection 884) or MACS on anti-Fc (named selection 885). These colonies were used to prepare two plates of DNA for transfection using the Qiagen Plasmid Plus 96 Miniprep Kit (Qiagen, Cat. No. 16181) following the manufacturers instructions. This DNA was used to transfect two 96 well plates of Expi293 cells using the Expi293 transfection system (LifeTech, Cat. No. A14525) following the manufacturers instructions. After 5 days these were harvested and the supernatants kept at 4° C. To determine the propensity of the antibodies to aggregate a method called AC-SINS (Affinity-capture self interaction nanoparticle spectroscopy) was used. The method used was essentially as described by Liu et al., 2014[39] with the following modifications. Once the gold nanoparticles (AuNP, citrate-stabilized 20 nm gold nanoparticles, 15705, Ted Pella Inc.) were blocked with PEG Thiol, the AuNP were stored until needed (up to one week) at 4° C. Rather than using a syringe filter to concentrate to 10×, the AuNP were centrifuged at 15,000 RPM for 10 minutes at 4° C. with 95% of the supernatant removed and further centrifuged at the same conditions. The final AuNP were resuspended in ⅒th of the starting volume. 10 μl was added to each well of a polypropylene 96 well plate (containing 100 μl of test antibody, either in supernatant or purified in PBS. The plate was incubated for 2 hours at room temperature on a shaking platform set to 700 RPM. As stated in Liu et al. (2014)[39] the contents were carefully transferred to a polystyrene UV transparent plate. Absorbance data are collected from 450 to 650 nm at in increment of 2 nm using a BMG Pherastar instrument. The wavelength of maximum absorbance is identified and 10 points either side are averaged with the points directly before and after to reduce error from noise. The highest point from these averages is taken as the maximum absorbance. FIG. 17 lists the results of the AC-SINS assay together with the antibody CDR sequences. The majority (86/91) of selected variant clones displayed AC-SINS wavelength shifts of 12 nm or less, equivalent to the humanized intermediate clone 5A10-i. This wavelength indicates that self-association is not occurring to any great extent in these samples. In contrast Bococizumab gave a wavelength shift of 26 nm (FIG. 17) by AC-SINS and only 5 clones in the selected set resulted in a wavelength shift of greater than 20 nm. Therefore, Bococizumab variant clones have been selected by mammalian cell display with a lower propensity to self-aggregate than the original parental clone as judged by the AC-SINS assay.

The supernatants from the expressed plate were also used to compare ability of the antibodies to retain binding to PCSK9. This was performed in a capture ELISA assay with monomeric antigen, which has been shown to be an effective way to affinity rank antibodies for binding to their target. Briefly, 96-well Maxisorp plates (Nunc, Cat. No. 437111) were coated with anti-human Fc antibody (Jackson ImmunoResearch, Cat. No. 209-005-098) at 3 μg/ml in PBS overnight at 4° C. The following day the plates were washed 3 times with 1×PBS and subsequently blocked with 300 μl of 3% (w/v) dried milk (Marvel) in 1×PBS (M-PBS) for 1 hour at room temperature. These were washed 3 times with 1×PBS, and 30 μl of 6% (w/v) dried milk (Marvel) added to each well. 30 μl of each supernatant was added and incubated for 1 hour at room temperature. The plates were then washed 3 times with 1×PBS-Tween (0.1%) and then 3 times with 1×PBS. 60 μl/well of 0.1 nM Biotinylated Human PCSK9, Avi-Tag (ACRObiosystems, Cat. No. PC9-H82E7) was added to each well and the plates incubated for 1 hour at room temperature. The plates were washed as previously with 1×PBS-Tween followed by 1×PBS. 60 μl/well of Streptavidin-Europium (Perkin Elmer, Cat. No. 1244-360) in DELFIA assay buffer (Perkin Elmer, Cat. No. 1244-111) (1 in 500 dilution) was added and incubated for 1 hour at room temperature. The plates were washed a final time with 1×PBS-Tween and 1×PBS before addition of 50 μl/well of DELFIA enhancement solution (Perkin Elmer, Cat No. 4001-0010). The plates were placed on a plate shaker for 5 minutes at 300 RPM and read on a BMG Labtech PHERAStar Plate reader (Excitation 340 nm, Emission 615 nm). This showed that the majority of antibodies retained binding for PCSK9 with several displaying a capture ELISA signal equivalent to Bococizumab ($K_D$=7 pM) and the 5A10-i ($K_D$=1.5 nM) intermediate clone (FIG. 17). This shows that by library creation and mammalian display selection it is possible to target antibody paratope residues and simultaneously select for antibodies with improved biophysical properties and the retained ability to bind to target antigen.

Clones were then selected, based on the AC-SINS culture supernatant score of a low AC-SINS wavelength shift and retention of antigen binding (FIG. 17). These clones, together with Bococizumab, 5A10-i and Alirocumab (an approved anti-PCSK9 antibody) were then expressed by transient transfection of Expi-293 cells (50 ml scale) and purified by Protein A affinity chromatography, followed by dialysis, as described in Example 3. The antibodies were then analysed by HPLC-SEC and this showed that all the selected antibodies displayed equivalent HPLC retention times and peak widths at the control Alirocumab antibody and 5A10-i (FIG. 18). In contrast, Bococizumab was retarded on the column and displayed a longer retention time. Also Bococizumab showed a non-symmetrical peak also indicating that it possesses cross-interaction properties and was non-specifically binding to the column matrix. The purified antibodies were also analysed by AC-SINS and this showed wavelength shifts equivalent to Alirocumab and 5A10-i ($\Delta\lambda$=8 to 12 nm), whereas Bococizumab displayed a longer AC-SINS wavelength shift indicating that it possessed self-interaction properties ($\Delta\lambda$=39 nm). The expression yields, AC-SINS wavelength shifts, HPLC-SEC retention times and HPLC-SEC peak widths are summarised in Table 6.

This example has therefore exemplified that it is possible to use binder display on higher eukaryotic cells to select variants with an improved developability profile including reduced self-interaction and with reduced non-specific interactions while retaining binding to the target. In this example, this was achieved by first identifying hydrophobic and positive charge patches on the surface of an antibody, random or targeted mutagenesis to create a variant library and the use of nuclease mediated binder gene targeting to enable a single gene copy per cell. The cell display library was then sorted on the basis of cell display level and antigen binding to identify variants of the parental antibody with improved biophysical properties.

TABLE 6

Comparison of biophysical properties of Bococizumab and improved variants (including wavelength shift (nm) in an AC-SINS assay, HPLC-SEC retention time, peak width and expression yield).

| Test Clone or Control | AC-SINS Δλ (nM) | HPLC-SEC Retention Time (min) | Peak Width (min) | Expression in Expi293 (mg/L) |
|---|---|---|---|---|
| 884_01_G01 | 9 | 6.84 | 0.45 | 15 |
| 884_01_A01 | 10 | 6.87 | 0.42 | 14 |
| 884_01_A04 | 9 | 6.86 | 0.41 | 16 |
| 884_01_F02 | 12 | 6.91 | 0.42 | 16 |
| 884_01_E12 | 9 | 6.97 | 0.65 | 16 |
| Bococizumab | 39 | 7.35 | 1.14 | 11 |
| 5A10-i | 10 | 6.91 | 0.56 | 33 |
| Alirocumab | 8 | 6.87 | 0.26 | 14 |

Example 6a. Developability Enhancement by Selection for Non-Cross-Interacting Clones Antibodies which possess the property of non-specific binding to molecules other than their target tend have poor half-life in vivo, can give rise to “off-target” binding resulting in poor pharmaco-kinetics (PK) and pharmacodynamics (PD). In addition, the properties of cross-interaction or “stickiness” can give rise to problems during the manufacture of the antibodies leading, for example, to retardation to a column matrix during purification or formulation problems.

This example demonstrates that it is possible to use antibody mammalian display to differentiate between an antibody with known “stickiness” or cross-interaction problems from an antibody that is well-behaved and has been approved for clinical use. The anti-neuropilin-1 antibody Vesencumab (or MNRP1685A) was chosen as an example of a “sticky” antibody. This antibody is known to be retarded during size exclusion chromatography and non-specifically binds to the column matrix. This is thought to contribute to its poor half-life in animal models[104]. In addition, the clinical development of this antibody was halted after the observation of the side-effect of proteinuria[105]. The anti-PD1 antibody Nivolumab was chosen as an example of a well-behaved antibody that has been approved for clinical use[106]. Vesencumab also displayed some self-interaction in an affinity-capture self-interaction nanoparticle spectroscopy (AC-SINS) assay[39].

TABLE 7

Protein sequences of Vesencumab and Nivolumab heavy and light chains. The amino acid sequences in single letter code are shown of the complete antibody heavy and light chains. The variable domains are underlined.

| Chain | Protein Sequence |
|---|---|
| Vesencumab (heavy chain) | EVQLVESGGG LVQPGGSLRL SCAASGFTFS SYAMSWVRQA PGKGLEWVSQ ISPAGGYTNY ADSVKGRFTI SADTSKNTAY LQMNSLRAED TAVYYCARGE LPYYRMSKVM DVWGQGTLVT VSSASTKGPS VFPLAPSSKS TSGGTAALGC LVKDYFPEPV TVSWNSGALT SGVHTFPAVL QSSGLYSLSS VVTVPSSSLG TQTYICNVNH KPSNTKVDKK VEPKSCDKTH TCPPCPAPEL LGGPSVFLFP PKPKDTLMIS RTPEVTCVVV DVSHEDPEVK FNWYVDGVEV HNAKTKPREE QYNSTYRVVS VLTVLHQDWL NGKEYKCKVS NKALPAPIEK TISKAKGQPR EPQVYTLPPS REEMTKNQVS LTCLVKGFYP SDIAVEWESN GQPENNYKTT PPVLDSDGSF FLYSKLTVDK SRWQQGNVFS CSVMHEALHN HYTQKSLSLS PGK (SEQ ID NO: 42) |

TABLE 7-continued

Protein sequences of Vesencumab and Nivolumab heavy and light chains. The amino acid sequences in single letter code are shown of the complete antibody heavy and light chains. The variable domains are underlined.

| Chain | Protein Sequence |
|---|---|
| Vesencumab (light chain) | DIQMTQSPSS LSASVGDRVT ITCRASQYFS SYLAWYQQKP GKAPKLLIYG ASSRASGVPS RFSGSGSGTD FTLTISSLQP EDFATYYCQQ YLGSPPTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC (SEQ ID NO: 43) |
| Nivolumab (heavy chain) | QVQLVESGGG VVQPGRSLRL DCKASGITFS NSGMHWVRQA PGKGLEWVAV IWYDGSKRYY ADSVKGRFTI SRDNSKNTLF LQMNSLRAED TAVYYCATND DYWGQGTLVT VSSASTKGPS VFPLAPCSRS TSESTAALGC LVKDYFPEPV TVSWNSGALT SGVHTFPAVL QSSGLYSLSS VVTVPSSSLG TKTYTCNVDH KPSNTKVDKR VESKYGPPCP PCPAPEFLGG PSVFLFPPKP KDTLMISRTP EVTCVVVDVS QEDPEVQFNW YVDGVEVHNA KTKPREEQFN STYRVVSVLT VLHQDWLNGK EYKCKVSNKG LPSSIEKTISK AKGQPREPQV YTLPPSQEEM TKNQVSLTC LVKGFYPSDI AVEWESNGQP ENNYKTTPPV LDSDGSFFLY SRLTVDKSRW QEGNVFSCSV MHEALHNHYT QKSLSLSLGK (SEQ ID NO: 44) |
| Nivolumab (light chain) | EIVLTQSPAT LSLSPGERAT LSCRASQSVS SYLAWYQQKP GQAPRLLIYD ASNRATGIPA RFSGSGSGTD FTLTISSLEP EDFAVYYCQQ SSNWPRTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFNRGEC (SEQ ID NO: 45) |

Synthetic DNA encoding the Vesencumab and Nivolumab heavy and light variable domains (see Table 7 for sequences) were cloned into a dual promoter IgG soluble expression vector based on pINT3 (WO2015166272A2) and DNA sequence confirmed. To examine the properties of the soluble antibody, plasmid DNA was prepared of pINT3-Vesencumab and pINT3-Nivolumab and this was used to transfect Expi293 cells (30 ml final culture volume scale) using the transfection reagent ExpiFectamine according to the manufacturer instructions (A14525, ThermoFisher Scientific). Cells were seeded at a density of $2\times10^6$ cells/ml in 25.5 ml of Expi293 Expression Medium 24 hours prior to transfection. Plasmid DNA (30 μg) was diluted in Opti-MEM Medium (1.5 ml) and ExpiFectamine 293 Reagent (80 μl) was diluted in Opti-MEM Medium (1.5 ml) and incubated for 5 minutes at room temperature. The diluted plasmid DNA (30 μg in 1.5 ml Opti-MEM Medium) was then added to the diluted ExpiFectamine 293 Reagent (80 μl ExpiFectamine in 1.5 ml Opti-MEM Medium) and incubated for 20 minutes at room temperature. The cells were incubated at 37° C., 5% CO2, 5% humidity and agitated at 200 rpm (50 mm orbital throw, ISF1-X, Climo-Shaker, Kuhner). Following 5 days of expression, culture supernatant was harvested by centrifugation (2000 g, 20 min) and purified by Protein A affinity chromatography as described above (Example 3). The antibody yield and concentration was determined by measurement of the absorbance at 280 nm and calculating using the Beer-Lambert Law using an estimated extinction coefficient of 1.4 to approximate the concentration. The expression yields of Vesencumab and Nivolumab were similar (95 mg/L and 103 mg/L respectively). Again the expression yield achieved in transient transfection efficiency is no guide to impending problems when the concentration of antibodies are increased.

The biophysical properties of Nivolumab and Vesencumab were determined by several techniques. The melting temperature ($T_m$) and temperature of the onset of aggregation ($T_{agg}$) were determined using Prometheus NT.4B (Nanotemper) as described above (Example 3). The melting temperature ($T_m$) and the aggregation temperature ($T_{agg}$) of the two antibodies were similar (see Table 8a). This again demonstrates that melting temperature is not predictive of impending problems.

TABLE 8a

Vesencumab and Nivolumab IgG biophysical properties.

| Antibody | $T_m$ (° C.) | $T_{agg}$ (° C.) | Expression Yield (mg/L) | Ve (ml) | PDI | Zav (nm) | $MW_{est}$ (KDa) | Poly-dispersity (%) |
|---|---|---|---|---|---|---|---|---|
| Vesencumab | 69.9 | 70.4 | 94.8 | 13.7 | 0.163 | 7.7 | 401 | 66 |
| Nivolumab | 67.6 | 67.3 | 103 | 12.0 | 0.053 | 5.1 | 156 | 0 |

The melting temperature (Tm) and temperature of the onset of aggregation (Tagg) were determined using Prometheus NT.4B (Nanotemper) according to the manufacturer instructions. The expression yield in terms of amount of antibody expressed (mg) per liter of culture volume was determined by transient transfection of Expi293 cells at 30 ml scale (ThermoFisher) followed by affinity purification (Protein A) and the yield of purified antibody determined from the absorbance at 280 nm and estimated antibody extinction coefficient of 1.4. Antibodies were further purification by size-exclusion chromatography on a Superdex 200 10/300 using the AKTA Pure system with PBS (pH 7.4) running buffer. Dynamic light scattering measurement were performed with a Nano S DLS (Malvern Instruments, Malvern, UK) on samples and polydispersity index (PDI) and the cumulant (or z-average) size (Zav) calculated using the zetasizer software (Malvern Instruments, Malvern, UK).

However, during preparative size exclusion chromatography significant column matrix binding and retardation was observed (Table 8a and FIG. 19), as described previously. The elution volume (Ve) for Nivolumab and Vesencumab was 12.0 ml and 13.7 ml respectively, indicating retardation of Vesencumab and non-specific interaction with the column matrix. An additional elution peak at 10.4 ml indicated the presence of some higher molecular weight aggregated antibody, not observed for Nivolumab. To investigate the stability of the antibodies during storage, size purified antibodies were incubated at 4° C. for 2 weeks in PBS pH7.4. Dynamic light scattering (DLS) detected higher order aggregated species for Vesencumab, but not for Nivolumab (see FIG. 20 and Figure legend for methodology). Dynamic light scattering measurement were performed with a Zetasizer APS (Malvern Instruments, Malvern, UK) on samples that had been stored at 4° C. for 2 weeks. The DLS derived biophysical parameters of calculated percentage polydispersity, the polydispersity index (PDI), the cumulant (or z-average) size and average molecular weight are shown in Table 8 and show indicate significant aggregation of Vesencumab upon storage at 4° C. for 2 weeks compared with Nivolumab which is mono-disperse when stored under the same conditions.

Synthetic DNA encoding the Vesencumab and Nivolumab heavy and light variable domains were cloned into the mammalian display vector pINT17-BSD (see Example 1 for vector maps and sequences), DNA sequence confirmed and transfection quality plasmid DNA prepared. HEK293 cells were transfected with TALE nucleases and stable cell lines created as described above un Example 2. After 14 days post-transfection (dpt) cells were stained with anti-human Fc PE (409303, Biolegend) for 30 min at 4° C. to determine antibody display presentation level (see Example 2). The monoclonal cell lines displaying either Nivolumab or Vesencumab were then stained with labelled human serum by the following protocol.

Heat inactivated, human AB Serum (5 μl, 40 mg/ml H4522, Sigma) was diluted in PBS (195 μl) to give a final concentration of 1 mg/ml. This diluted human serum was then labelled with Dylight 633 using the Lightning-Link® Rapid Dylight® 633 kit (325-0000, Innova) according to the manufacturer instructions. HEK293 cell lines displaying Nivolumab or Vesencumab or wild-type HEK293 cells (one million cells) were pelleted (200 g, 3 minutes in am Eppendorf tube (1.5 ml). The pellet was resuspended in PBS (1 ml) and pelleted (600 g, 2.5 min). The pellet was resuspended in 1% BSA, PBS (100 μl) containing anti-Fc PE (0.5 μl, 409303, Biolegend) and either AB serum Dylight 633 labelled (5 μl, 0.5 mg/ml). The mix was incubated, shielded from light, at 4° C. for 30 min. 0.1% BSA, PBS (900 μl) was added and cells pelleted (600 g, 2.5 min). The cells were resuspended in 0.1% BSA, PBS (1 ml) and this wash step was repeated once. The cells were resuspended in 0.1% BSA, PBS (200 μl) with 7-AAD (5 μl per million cells). Labelled cells (50 μl) were analysed using the Intellicyte iQue screener. Flow cytometry analysis (FIG. 21) showed increased binding of labelled human serum to HEK293 cells displaying Vesencumab compared with Nivolumab (12.3% and 3.7% respectively) double positive for antibody and human serum binding respectively)

Vesencumab is an antibody that failed to be developed beyond Phase 1 clinical trials[105] and is an antibody with known self-aggregation and cross-interaction properties[39, 104]. We have also shown that this antibody displays non-specific interaction with a size exclusion column matrix (FIG. 19) and aggregates upon storage (FIG. 20 and Table 8) compared with the clinically approved anti-PD1 antibody Nivolumab which shows no cross-interaction during size exclusion chromatography and remains mono-disperse after storage. We here show that we can differentiate between Vesencumab and Nivolumab when they are displayed on the surface of HEK293 cells in a cross-interaction flow cytometry assay. It is likely that this assay can be optimized to allow even greater discrimination between "sticky" and well-behaved antibodies. For example, the human serum could be biotinylated and conjugated to fluorophore labelled streptavidin conjugated to increase avidity. Alternatively one could modify any number of cross-interaction assays[2] for flow cytometry as described previously and including, but not exclusively labelled baculovirus[16,19] or a labelled mix of proteins, DNA and heparin sulphate containing molecules[107].

Example 6b. Improvements in Polyreactivity Screening

Using known antibodies with known polyreactivity profiles, we further exemplify the possibility of discriminating polyreactive binders from non-polyreactive binders within a population of binder-displaying cell clones, based on differences in binding to a non-target molecule (a polyreactivity probe). We demonstrate enrichment of clones which fail to bind the polyreactivity probe.

Individual populations of HEK293 cells were prepared using nuclease-directed integration to express ustekinumab, briakinumab and amatuximab. The individual populations were stained with biotinylated DNA. Binding to DNA was detected on cells expressing briakinumab and amatuximab whereas cells expressing ustekinumab were not stained. DNA binding was normalised to mode. FIG. 33A. Staining with anti-Fc antibodies revealed that the briakinumab population was a mixture of IgG expressing and non-expressing cells accounting for an approximate 50:50 mix of DNA binding and DNA non-binding cells within the population. The different cell populations were labelled with cell-tracker dyes and mixed in equal proportion. Amatuximab cells were labelled with CellTrace Far Red (shown on x axis in Q3—FIGS. 33B and C), briakinumab with CellTrace CFSE (shown on y axis in Q1—FIGS. 33B and C) and ustekinumab remained unlabelled (double negative population in Q4—FIGS. 33B and C). The mixed population was stained with biotinylated DNA (20 μg DNA per 1 million cells in 200 μl 1% BSA) and labelled with anti-biotin microbeads. The population was sorted using MiniMACS beads in combination with the MS column. The flow through fraction from the MACS sort was analysed using the Intellicyt flow cytometer to count cells. 7-AAD was used as viability stain and dead cells were excluded from analysis. Ustekinumab, which did not bind DNA, was observed to enriched compared with briakinumab and amatuximab (FIG. 33B, FIG. 33C, Table 8b).

TABLE 8b

Relative cell counts (normalised to the number of ustekinumab cells and normalised to 10,000 counts) for each antibody before and after MACS.

| Sample | Briakinumab | Mix | Amatuximab | Ustekinumab |
|---|---|---|---|---|
| Pre-MACS | 3120 | 114 | 3420 | 3350 |
| Post-MACS | 2540 | 0 | 697 | 6790 |

The relative percentage of briakinumab-displaying cells was reduced to 37% and the amatuximab-displaying cells were reduced to 10% compared with the ustekinumab-displaying cells. It is likely that the enrichment factors can be even higher since the input population of briakinumab included a relatively high proportion of non-antibody expressing cells and these will be retained in the "unbound population" which is selected here. This background could be reduced further by pre-sorting, post-sorting or co-sorting the cells for IgG expression or antigen binding as described earlier.

Here we successfully used MACS, but the resolution and effective enrichment would be expected to be even greater with flow sorting by FACS.

Additional polyreactivity probes were also tested for their ability to discriminate between cellular clones expressing either polyreactive and non-polyreactive antibodies.

We found that cells expressing ustekinumab could be distinguished and separated from cells expressing briakinumab or ganitumab based on the extent of heparin sulphate binding. Briefly, 250,000 cells were stained with 9 μM Heparin-FITC (Creative PEGWorks) using the standard staining protocol as described previously in Example 5. Briakinumab and ganitumab showed heparin binding. Overlay plots are shown in FIG. 34. This non-specific binding possibly occurs through positively charged patches in the heavy chain CDRs of briakinumab and ganitumab.

Chaperone proteins represent further polyreactivity probes which may be used as non-target molecules for de-selecting polyspecific binders. Chaperones are functionally related and assist in protein folding. Heat shock proteins (Hsp) are overexpressed in stressful conditions such as high temperature. Most chaperones are also abundantly expressed in normal cells where they recognise and bind non-native proteins thus preventing aggregation.

A variety of therapeutic antibodies were displayed on HEK293 cells and tested for binding to Hsp70 and Hsp90.

Of the antibodies tested in our experiment, brentuximab and lenzilumab showed binding to Hsp70 and Hsp90. Brentuximab (Vedotin) is an anti-CD30 antibody-drug conjugate that failed in a clinical trial to treat Hodgkin's lymphoma. It was previously shown to exhibit self-interaction and cross-interaction[2]. Lenzilumab is an anti-GM-CSF (granulocyte-macrophage colony-stimulating factor) antibody that failed a phase II trial for severe asthma.

FIG. 35 shows an overlay of ustekinumab and briakinumab double stained with anti-human Fc PE and heat shock proteins (Hsp70 and 90) conjugated with DyLight 633. The gate within the overlay plots indicates cells that did not show detectable interaction with chaperones (Hsp70 and Hsp90) and which can be FACS sorted to provide a selected population of clones in which binders that recognise chaperones have been depleted (and preferably eliminated).

Pooled data from multiple experiments with a variety of different antibodies and different polyreactivity probes are depicted in FIG. 36. The individual ampules were tested in separate, independent experiments but the Intellicyt flow cytometer has a fixed voltage so the fluorescence intensity is expected to be consistent for all samples. Additionally, Hek293 was used an internal control for each experiment. Table 8c below summarises data from the panel of antibodies tested for binding to the polyreactivity probes.

TABLE 8c

Summary of antibody polyreactivity screening.

| Antibodies | DNA | Heparin | Chaperones | FcRn |
|---|---|---|---|---|
| Alirocumab | No | No | No | No |
| Amatuximab | Yes | Yes | Yes | Yes |
| Brentuximab | ND | ND | Yes | No |
| Briakinumab | Yes | Yes | Yes | Yes |
| Ganitumab | Yes | Yes | No | Yes |
| Lenzulimab | ND | Yes | Yes | No |
| Ustekinumab | No | No | No | No |
| Vesencumab | ND | ND | No | Yes |

Yes = antibody showed binding to polyreactivity probe.
No = antibody did not show binding to polyreactivity probe.
ND = binding to the polyreactivity probe was not determined.

Amatuximab, brentuximab, briakinumab and lenzilumab showed binding to chaperone proteins. The polyreactivity of these antibodies may arise due to hydrophobic clusters of amino acids within the antibody variable domains, giving rise to van der Waals interactions with proteins that also possess hydrophobic regions such as the chaperone proteins. Other reasons for polyreactivity can be the presence of positively charge patches of amino acids (e.g., consisting of arginine or lysine residues) which interact with molecules that have a net negative charge such as DNA or heparan sulphate or with proteins such as FcRn that have a positive charge patch on their surface[22]. Amatuximab, briakinumab, ganitumab and lenzulimab all bound DNA and heparin in our experiment. Antibodies that possess both hydrophobic and positively charged patches on their surface may have increased polyreactivity. Based on our data, examples of antibodies capable of both binding chaperone proteins via hydrophobic patches and binding DNA, heparain sulphate or FcRn at neutral pH include briakinumab, amatuximab and lenzulimab. These data are consistent with earlier reports of non-specific binding shown by briakinumab[2].

Example 7. Quantitation of Display Level for Parental and Improved Clones

In Example 2 we observed higher eukaryotic cell display-level differences for three pairs of antibodies, after nuclease mediated transgene integration into HEK293 cells and the selection of stable cell lines. The display level, judged by staining the cells with PE labelled anti-Fc and measuring the mean fluorescence intensity by flow cytometry, correlated by the antibody self-interaction and cross-interaction properties (Example 3). In this Example 7 we quantitate the antibody display copy number on the cell surface and show that the display copy number correlates with the antibody biophysical properties. Quantitative measurement was done using bead based calibration curve where beads have a precisely defined number of Fc-specific capture antibodies.

Quantum Simply Cellular (QSC) microspheres kit (815, Bangs laboratories, Inc.) has 5 bead populations—one blank and four bead populations with increasing amount of Fc-specific capture antibody (goat anti-mouse IgG). QSC beads are stained with the same flurochrome-conjugated antibody that is used to label cells and analysed on the flow cytometer according to manufacturers instructions. Briefly one drop of QSC microspheres was added to a microcentrifuge tube and 50 μL of staining buffer (1% BSA) was added and the tube was gently flicked. 5 ul of PE anti-human IgG Fc Antibody was added to the QSC microspheres, mixed gently and incubated in dark for 30 minutes. QSC microspheres was washed twice with 1 ml wash buffer (PBS containing 0.1% BSA) by centrifuging at 2500×G for 5 minutes. Bead pellet was resuspended in 150 ul wash buffer. Stained bead populations and blank population are combined (10 ul per population) in a single well and run in the Intellicyt. In parallel cell staining was performed for the HEK293 cells expressing different antibodies on the cell surface as described in the Example 2.

A calibration curve is generated by plotting the median fluorescent intensity (FIG. 26) of each bead population versus its assigned antibody binding capacity. Fluorescence intensity of the antibody expressing population is compared with the antibody binding capacity of the beads and linear regression is calculated using QuickCal (Bangs laboratories, Inc.) to enable the calculation of antibody display copy number (Table 9).

TABLE 9

Copy number of antibodies displayed on HEK293 cells calculated using Quantum Simply Cellular beads

| Antibody | Copy Number ($\times 10^3$) |
|---|---|
| CNTO607 | 113 |
| CNTO607-W100A | 313 |
| MEDI-1912 | 48 |
| MEDI1-912_STT | 433 |
| Ang2mAb | 125 |
| Angiopoietin2-C49T | 570 |
| Briakinumab | 273 |
| Ustenikumab | 706 |
| Pembrolizumab | 910 |

The clinically approved anti-PD1 antibody Pembrolizumab, known to have good biophysical characteristics in terms of low self-interaction properties[2] had the highest copy number of this test set. The most intense calibration bead had 886,000 copies/bead and this was in excess of that (approximately 910,000 copies/cell). Similarly, the anti-IL12 antibody Ustekinumab, approved for the clinical treatment of Crohns disease, displayed a higher copy number on cells (706,000) compared with the anti-IL-12 antibody Briakinumab (273,000 copies), which showed poor efficacy in a Phase III human clinical trial to treat psoriasis. Briakinumab is described as having increased self- and cross-interaction properties, as measured in a variety of assays, compared to Ustekinumab including the self-interaction assay AC-SINS and cross-interaction assays with a poly-specificity reagent and baculovirus particles[2,23].

For all three antibody pairs the copy number was lower than controls, the re-engineered daughter clones with improved biophysical properties had higher cell display copy numbers. For example, the improved daughter antibodies CNTO607-W100A, MED-1912_STT and Ang2mAb_C49 had display copy numbers of 313 thousand, 433 thousand and 570 thousand copies respectively representing a 2.8-fold, 9-fold and 4.6-fold increase in copy number compared to the original parental molecules with known problem of self and cross-interaction.

In this example we show a clear relationship between the antibody copy number displayed on the cell surface, after nuclease mediated transgene integration into the host genome and stable cell line selection, and the biophysical properties of the antibody displayed. Antibodies with the properties of self-interaction and cross-interaction displayed a lower copy number compared with antibodies that did not score highly in assays designed to measure self and cross-interaction. The better behaved antibodies with a good biophysical profile of low self-interaction and low cross-interaction properties displayed a high copy number on the surface of higher eukaryotic cells.

Example 8a. Combining High Level Expression for Developability and Low Level Expression for Affinity Stringency High level polypeptide expression, e.g. for antibodies where the antibody heavy and light chains genes are driven by strong constitutive promoters, has been demonstrated to be useful in the enrichment from populations of antibodies with superior biophysical properties, such as low self-interaction (as described above in Examples 3, 4 and 5). The presentation of high polypeptide concentrations on a cell can help detect self-interaction and increased avidity allows sensitive detection of undesired non-specific interactions with other molecules. One adverse consequence of this however is that there may be a reduction in the achieved rate of enrichment of high affinity over low affinity even when low concentrations of antigen are used to drive stringency. An additional consequence of this “low powered” enrichment is that there may in fact be a preferential selection for surface presentation even when the goal is to enrich higher affinity binders. The rate of enrichment could be enhanced however by using a lower density of binder presentation on the cell surface. In the discussion below we will use antibodies and their antigens as an example to represent in general interactions of binders of different affinities.

If we consider $10^6$ cells in a 100 microlitres volume displaying $6\times10^5$ monovalent binding sites/cell then we have $6\times10^{11}$ molecules/100 microlitre or $6\times10^{15}$ molecules/ l. This number of binding sites in this volume would be equivalent to a concentration of 10 nM. Using antigen concentrations below 10 nM in this situation means that the antibody will be in excess over antigen and the relatively high antibody concentration will help drive association even for lower affinity antibodies. For example if one is trying to separate rare cells expressing an antibody with $K_D$ 0.1 nM from an excess of cells expressing an antibody with a lower affinity of $K_D$ 10 nM, then under the conditions outlined above, (i.e., the equivalent of an antibody concentration of 10 nM) a significant proportion of the antigen will be in complex with the lower affinity antibody.

The law of mass action deals with two interacting molecules forming a complex. These formulae are intended to cover interactions in free solution and we are dealing with antibodies immobilised on suspension cells. The calculations of selectivity below consider the concentration of complex formed in each case for a single antibody in solution. Nonetheless we can use this knowledge of the behaviour of molecules in solution from the law of mass action to better understand the relationship between affinity, antibody concentration, antigen concentration and the formation of complex as it might affect surface presented antibodies.

If two interacting molecules e.g. monovalent antibody (A) and antigen (B) are mixed, they can form a complex (A:B) and eventually reach equilibrium. The position of the equilibrium is dependent on the concentration of antibody and antigen but can be described by the dissociation constant, $K_D$ as follows (where [A]. [B] and [AB] denote the concentration at equilibrium):

$$K_D = \frac{[A][B]}{[A{:}B]}$$

This equation can be re-arranged to calculate the concentration of complex (AB) formed under different conditions of $K_D$, concentration of A and concentration of B.

If you have a binding reaction that is in equilibrium:

$$A+B \leftrightarrow AB \quad (1)$$

then the dissociation constant ($K_D$) is defined as:

$$K_D = \frac{[A][B]}{[AB]} \quad (2)$$

where [A], [B], and [AB] are the concentrations of the reactants at equilibrium. The total concentrations of the reactants ($A_T$ and $B_T$, which are the concentrations you added to the "test tube") are as follows:

$$[A_T]=[A]+[AB] \text{ which can be rearranged as } [A]=[A_T]-[AB] \quad (3)$$

$$[B_T]=[B]+[AB] \text{ which can be rearranged as } [B]=[B_T]-[AB] \quad (4)$$

Substitute eq. 3 and eq. 4 into eq. 2:

$$K_D = \frac{([A_T]-[AB])([B_T]-[AB])}{[AB]} \quad (9)$$

Rearrange the Equation:

$$K_D[AB]=([A_T]-[AB])([B_T]-[AB]) \quad (10)$$

Multiply it out and rearrange (concentration brackets are removed for clarity):

$$AB^2-(A_T+B_T+K_D)(AB)+(A_TB_T)=0 \quad (11)$$

into the form $$ax^2+bx+c=0 \quad (12)$$

where, $$a=1 \quad (14)$$

$$b=-(A_T+B_T+K_D) \quad (15)$$

$$c=(A_TB_T) \quad (16)$$

which allows for solving via the quadratic equation:

$$x = \frac{-b \pm \sqrt{b^2-4ac}}{2a} \quad (16)$$

$$AB = \frac{(A_T+B_T+K_D) - \sqrt{(A_T+B_T+K_D)^2 - 4(A_TB_T)}}{2} \quad (17)$$

Figure 22A:
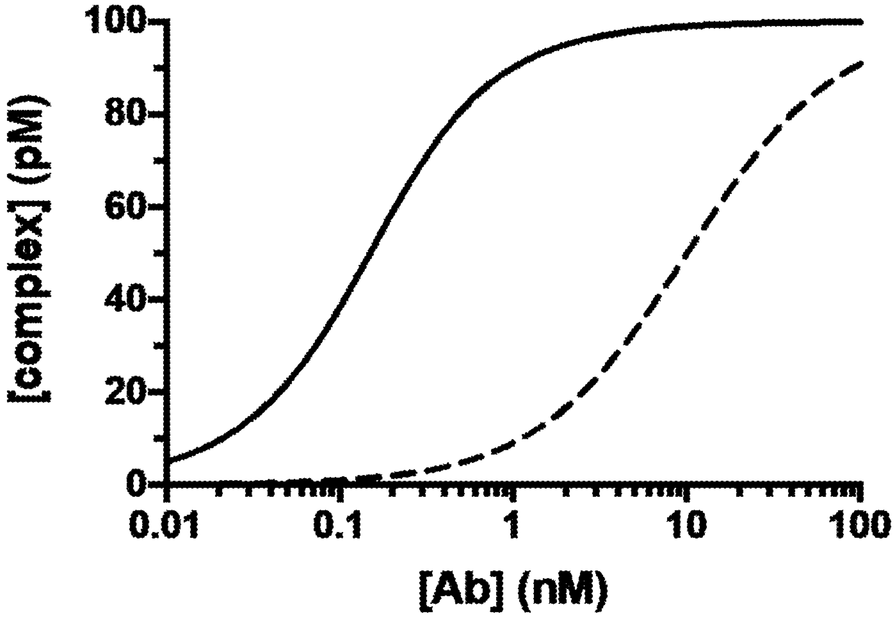
Figure 22B:
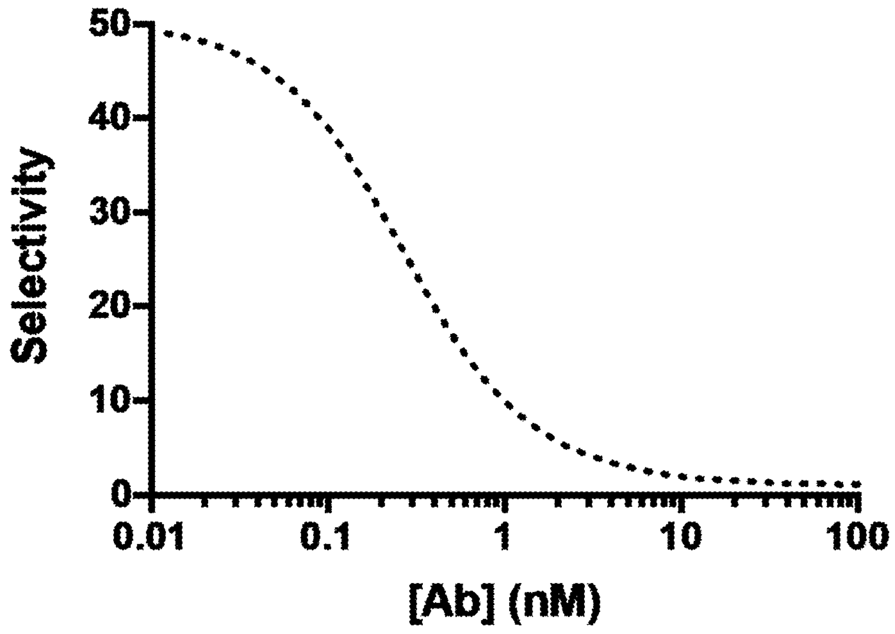

Assuming an antigen concentration of 0.1 nM is used, FIG. 22*a* shows the effect of varying concentration of antibody (A) for 2 antibodies of different affinities ($K_D$ equal to 10 nM for Ab1 or 0.1 nM for Ab2). FIG. 22*b* shows the relative "selectivity" between the 2 antibodies being the ratio of concentration of complex formed when the antibodies are individually incubated with 0.1 nM antigen and varying antibody concentrations.

This shows that despite using an antigen concentration well below the $K_D$ of the interaction, the concentration of complex is 50 pM representing 50% of the antigen in complex when Ab1 is present at a concentration of 10 nM. (10 nM is the concentration calculated in the example above for cell surface display at $6\times10^5$ copies/cell). Under the same conditions using the high affinity Ab2 antibody the concentration of complex will be 99 pM (representing 99% of the antigen) so there is only a 2 fold difference in selectivity (Table 10). If however the antibody concentration is reduced to 0.1 nM (equivalent to reducing the display level by 100 fold in this example) then the concentration of complex drops to 1 pM for Ab1 while a concentration of complex of 38.2 pM will be achieved with Ab2 (Table 10) representing a selectivity of 38-fold. Reduced density also has the advantage of reducing the potential for target rebinding. The problem of rebinding in the presence of a high density of immobilised binder is particularly well recognised and documented in surface based affinity measurement such as surface plasmon resonance (BIAcore manual).

With flow sorting one is measuring the relative concentration of complex by detecting the presence of fluorescently labelled antigen (either directly or indirectly labelled) on the surface of the cell. The fluorescent signal on the cell detected within the flow cytometer is therefore an indication of the concentration of complex formed on the cell under the conditions used. Thus under more limiting conditions of antibody presentation a greater separation will be achieved between clones presenting high and low affinity antibodies.

TABLE 10

Concentration of complex formed in solution using 0.1 nM antigen and different concentrations of a high affinity ($K_D$ 0.1 nM) and a low affinity ($K_D$ 10 nM) antibody

| [Ab in nM] | [complex in pM] for Ab1 ($K_D$ 10 nM) | [complex in pM] for Ab2 ($K_D$ 0.1 nM) | Selectivity |
|---|---|---|---|
| 10 | 49.9 | 99.0 | 2 |
| 1 | 9.0 | 90.1 | 10 |
| 0.1 | 1.0 | 38.2 | 39 |

During the process of selecting for the optimal antibody, during an antibody discovery campaign, it can be desirable to select for antibodies with higher affinity to their target. A method to increase stringency and enrich for clones with improved affinity for their target during antibody phage display selection is to reduce the concentration of the target antigen during selection[57] (Fellouse F A, Sidhu S S: Making antibodies in bacteria. In: *Making and Using Antibodies: A Practical Handbook*. Edited by Howard G C, Kaser M R: CRC Press; 2007: 157-180[108]). In mammalian display selections, the labelled antigen concentration can also be reduced during FACS or MACS to enable the selective enrichment of clones with improved affinity. However, the high display level achieved, where the antibody expression is driven by strong constitutive promoters can equate to a concentration of antibody above the desired target affinity. It therefore may be desirable to reduce the antibody cell display level on HEK293 cells e.g. to below 60,000 per cell giving a 10 fold selectivity between 10 nM and 0.1 nM in the example above. This will enable superior enrichment of antibodies with improved affinity over lower affinity clones.

Antibody display level could be reduced by several different methods at the transcriptional, post-transcriptional, translational or post-translational stages of antibody. For example, weak promoters could be employed to reduce the rate of production of primary mRNA transcript, non-optimal splice/acceptor sites could be incorporated to reduce the efficiency and rate of the production of mature mRNA and export from the nucleus to the cytoplasm. The stability of the mRNA could be reduced thus reducing the transcript half-life and effective concentration. Translational control of expression could be by altering the Kozak consensus sequence to affect ribosomal binding to the mRNA. An example of post-translational control could be by the use of non-optimal leader sequences to reduce the efficiency of transport to the endoplasmic reticulum.

In this example we show the use of splice/acceptor site engineering to reduce the antibody display level. This reduced display system was shown to enable the more efficient separation of HEK293 cell line mixtures displaying antibodies with different affinities for their target.

We have devised a way to combine surface display with antibody secretion that is based on the natural system used in B cells. During B cell maturation antibodies are expressed in a membrane bound form and this switches to a mainly secreted form as plasma cells mature. This matches the requirements for eukaryotic display where the ability to effect cell surface display relies on expression of the transmembrane form. Alternatively, the ability to express the antibody in a secreted form once a clone has been selected would allow immediate production of free, soluble antibody for further characterization.

The balance between surface display and secretion in B cells is driven largely by the balance between poly A addition (leading to secreted IgG) and splicing (leading to membrane tethering)[109,110]. A "proximal" polyadenylation site is found 100-200 bp after the end of the CH3 domain and this generates an mRNA which stops translation at the end of the CH3 domain resulting in a secreted product. Near the end of the CH3 domain there is also a potential splice donor site which can splice to a downstream exon (M1) to create an in-frame fusion with a "hinge" and transmembrane domain. (The M1 exon in turn splices to an M2 exon encoding an intracellular domain). The balance of secreted versus membrane bound IgG presentation depends on the balance between polyadenylation at the proximal poly A site and splicing to the M1 exon. This is distinct from more recently published methods where one of 2 alternative exons are used to switch between secreted and membrane bound[111].

Splicing normally occurs through U1 small nuclear RNA (snRNA) which is required to initiate spliceosome assembly leading to intron removal. The splice donor site at the end of CH3 is sub-optimal compared to consensus splice donor sites. The non-optimal splice donor is conserved throughout evolution and would be expected to give non-optimal base-pairing to U1 snRNA. In fact it has been shown that mutation of the non-optimal splice donor site to a consensus splice donor sequence changes the balance from processed RNA encoding a predominantly secreted form to a predominantly membrane bound as a result of increased splicing[86]. This represents an early example of modifying a splice donor to alter the balance between splicing versus polyadenylation to effect a significant change in the balance between secretion and polyadenylation. Based on the work of Peterson et al[109,110] it would be anticipated that the degree of optimization of the splice donor would affect the balance between splicing and polyadenylation therefore affecting the proportion of displayed antibody. In order to find the optimal balance between membrane and secreted forms a number of alternative splice donor sites were created at the end of the CH3 exon.

The sequence of U1 snRNA involved in splicing initiation is shown above the mRNA sequence generated from IgG2 CH3 domain. Positions of mismatch are underlined:

```
U1 snRNA                  uc/cauuca
IgG2 CH3 splice donor     gg/guaaau
```

Four variants were designed around the splice donor including wild type (J9—GG/GTAAT), partial optimisation (J10—AG/GTAAA), partial optimisation (J29—GG/GTAA G) and fully optimized (J30—AG/GTAAG) as shown in FIG. 23. From the hybridization with the U1snRNA, it would be expected that the J30 variant would allow the most efficient splicing, resulting in a greater proportion of membrane tethered antibody at the cell surface compared with the "wild-type" sequence J9 where less efficient splicing would result in a lower level of membrane tethered antibody and a greater proportion of secretion. The J10 and J29, partially optimized variants would expect to give rise to antibody display levels intermediate between J9 and J30.

Variants of the antibody display targeting vector pINT17-BSD were constructed where an embedded HindIII restriction site was added to the DNA encoding the C-terminus of the IgG1 CH3 domain and the human IgG intron and M1 exon, encoding a transmembrane domain replaced the PDGFR transmembrane domain encoded by pINT17-BSD (Example 1). The splice donor variants J9, 10, 29 and 30 were constructed by a combination of synthetic gene synthesis, PCR assembly and restriction enzyme cloning. The annotated DNA sequence of the pINT17-J30 vector is shown in FIGS. 24A-24D from the XhoI to SbfI restriction enzyme sites. The vector backbone, exterior to the XhoI—SbfI insert and not shown in FIGS. 24A-24D, is identical to pINT17-BSD (FIG. 1).

DNA encoding the VH and VL chains of the anti-PD1 antibody Nivolumab was cloned into the four splice donor variant targeting vectors pINT17-J9, pINT17-J10, pINT17-J29 and pINT17-J30 and used to create stable cell lines by nuclease mediated gene integration as described in Example 2. For comparison Nivolumab was also cloned into the standard pINT17_BSD vector shown in FIG. 1. This construct fuses the antibody CH3 domain directly to the PDGFr transmembrane domain without splicing and is referred to in this example as pINT17-PDGFR. After 27 days of blasticidin selection, the cells were stained with anti-Fc labelled with PE and analysed by flow cytometry as described above (FIG. 25). This showed that the antibody display level was greater for pINT17-PDGFR, the antibody expressed with a direct fusion between the IgG1 CH3 domain and a PDGFR transmembrane, (FIG. 25*e*) compared with the constructs with the native IgG transmembrane domain with an intron placed between CH3 and transmembrane domains (FIG. 25*a* to *d*). J30 is completely complementary to the U1 snRNA and so would be expected to result in more efficient splicing with the M1 exon, encoding the transmembrane domain than the J9, J10 or J29 variants. FIG. 25*d* show that this is indeed the case with the J30 variant showing the highest level. It also shows however that the level of expression is significantly lower even for J30 variant compared with that found on the pINT17-PDGFr construct (FIG. 25*d*) used throughout the earlier examples.

To demonstrate that a reduction in antibody display copy number can aid the differentiation and separation of antibodies with different affinities, a test pair of anti-PD1 antibodies was chosen with different affinities for their target. The antibodies chosen were Nivolumab and another PD1 antibody (337_1_C08) with equilibrium dissociation constant ($K_D$) affinities, determined by surface plasmon resonance (SPR), of 3 nM[112] and 74 nM respectively. DNA encoding the VH and VL chains of the anti-PD1 antibodies were cloned into the targeting vectors pINT17-J30 and pINT17-PDGFr (also referred to as pINT17-BSD) and used to create stable cell lines by nuclease mediated gene integration as described in Example 2. The quantitation of antibody display levels by quantitative flow cytometry analysis was performed as described previously[113] and in the manufacturer instructions (Quantum Simply Cellular anti-mouse IgG beads, catalogue number 815, Bangs Laboratories Inc), (FIG. 26) for cells 21 days post blasticidin selection. The copy number on cells, calculated from measurement of the median fluorescence intensity of cells stained with anti-Fc-PE compared with a reference bead set (catalogue number 815, Bangs Laboratories Inc) (FIG. 26). As shown in Table 11A, the cell display copy number was reduced for pINT17-J30 (plus intron) expression cassettes compared with the pINT17-BSD expression cassette, with no intron between the CH3 and transmembrane domains, for both antibodies.

TABLE 11A

Copy number calculation

| | Copy Number ($\times 10^3$) | |
|---|---|---|
| Antibody | pINT17-BSD | pINT17-J30 |
| Nivolumab | 61 | 18 |
| 337_1_C08 | 607 | 11 |

As the copy number of antibody and concentration of antigen diminishes, the intensity of signal observed by flow cytometry also diminishes (FIG. 25). It is possible to enrich labeled cells below the sensitivity limits of flow cytometry using magnetic bead sorting and this was employed here. To test if reduced copy number on the cell surface would aid the separation of antibodies with different affinities, the Nivolumab or 337_1_C08 expressing cell lines were each stained with different fluorophore dyes This will allow the relative enrichment of one cell over the other to be observed. The labelled cells were mixed, incubated with varying concentrations of biotinylated PD1 and separated by MACS. Flow cytometry analysis was then performed to determine if there was enrichment of cells expressing the antibody with a higher affinity for PD1. Four HEK293 cell lines were tested in this example, originally transfected with:

a. pINT17-BSD-Nivolumab
b. pINT17-J30-Nivolumab
c. pINT17-BSD-337_1_C08
d. pINT17-J30-337_1_C08

The pINT17-BSD expression cassette (with a direct fusion between the antibody CH3 and transmembrane domains) was shown above to express a higher antibody display level than from the pINT17-J30 expression cassette. The Nivolumab expressing cells ($5\times10^6$) were stained with Cell Tracker Green (50 nM, C7025, Thermo Fisher) and the 337_1_C08 expressing cells were stained with Cell Tracker Deep Red (50 nM, C34565, Thermo Fisher) according to the manufacturer instructions. Briefly cells were washed with PBS, incubated with PBS containing tracker dye (50 nM) and incubated at 37° C. for 10 minutes. Cells were then washed with PBS. The pre-stained cells expressing Nivolumab or 337_1_C08, derived from the pINT17-J30 expression cassette were mixed at a 1:1 ratio ($5\times10^6$ cells each in a volume of 10 ml). The mixed cells were pelleted (100 g, 3 minutes) and each cell pellet resuspended in PBS (1 ml) containing either 0, 0.1, 1, or 10 nM biotinylated PD1 (PD1-H82E4, AcroBiosystems) and this was incubated at 4° C. for 30 minutes. Cells were washed with 0.1% BSA, PBS and Streptavidin beads (10 µl) and 90 µls of 1% BSA was added to each sample and mixed. Samples were incubated in the fridge (4° C.) for 15 minutes. Cells were washed using 2 ml of 0.1% BSA and spun down at 200×G for 4 minutes. The pellet was re-suspended in 500 µls of Separation Buffer (MACS Rinsing Buffer consisting of 1×PBS+2 mM EDTA+0.5% BSA). LS columns were washed with 3 ml Separation Buffer. The cell suspension was added to columns, one sample per column. Uncaptured cells were collected by washing the columns with 3 ml separation buffer three times and the flow through was collected. The column was placed in a new collection tube and 5 ml separation buffer was added to each column and immediately flushed out using the supplied column plunger. Elution samples and flow through samples were counted using cell counter and trypan blue to determine cell recovery rate. $1\times10^6$ cells for each sample was diluted into 500 µl 0.1% BSA, PBS. 50 µl of diluted cells were analysed by flow cytometry.

Figure 27A:
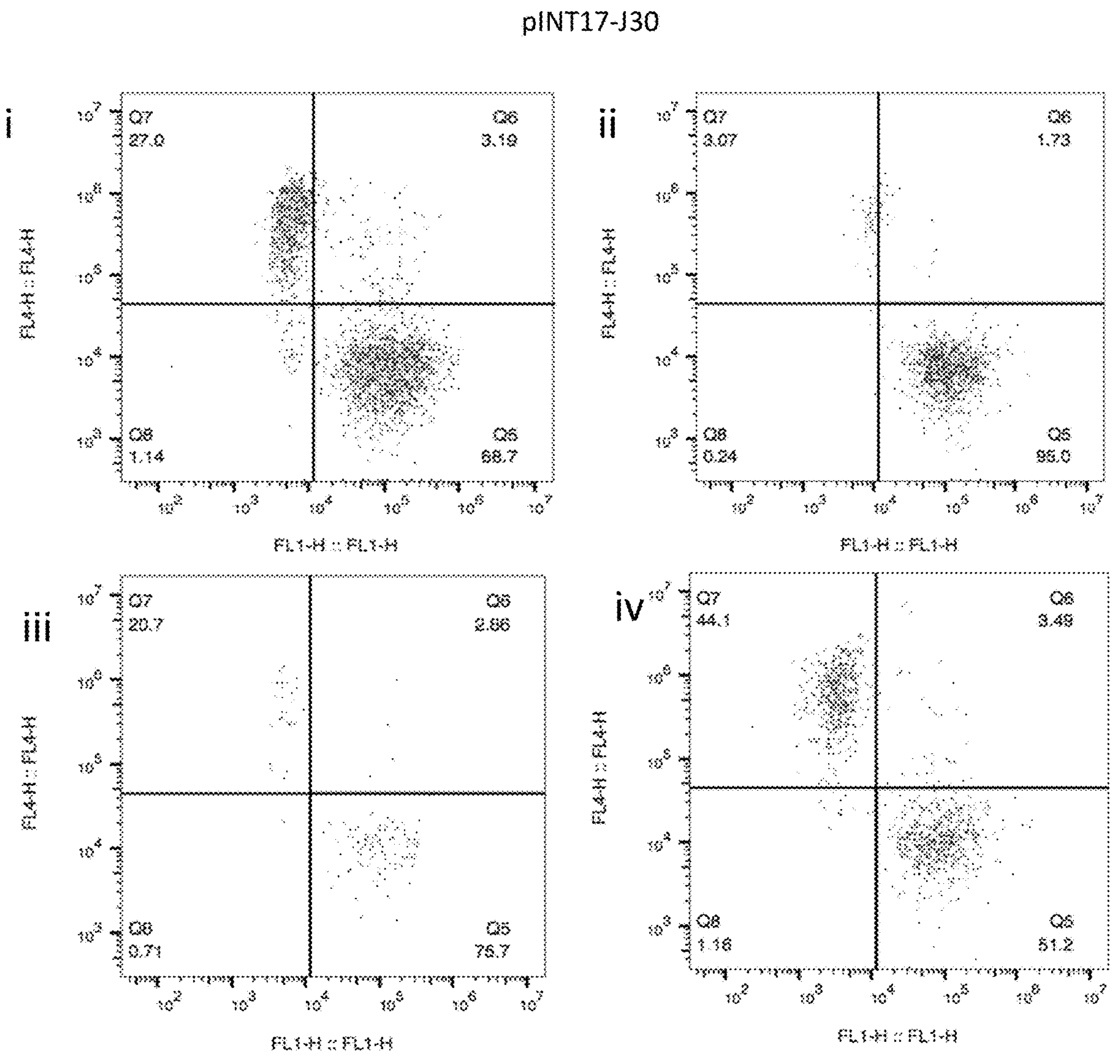
Figure 27B:
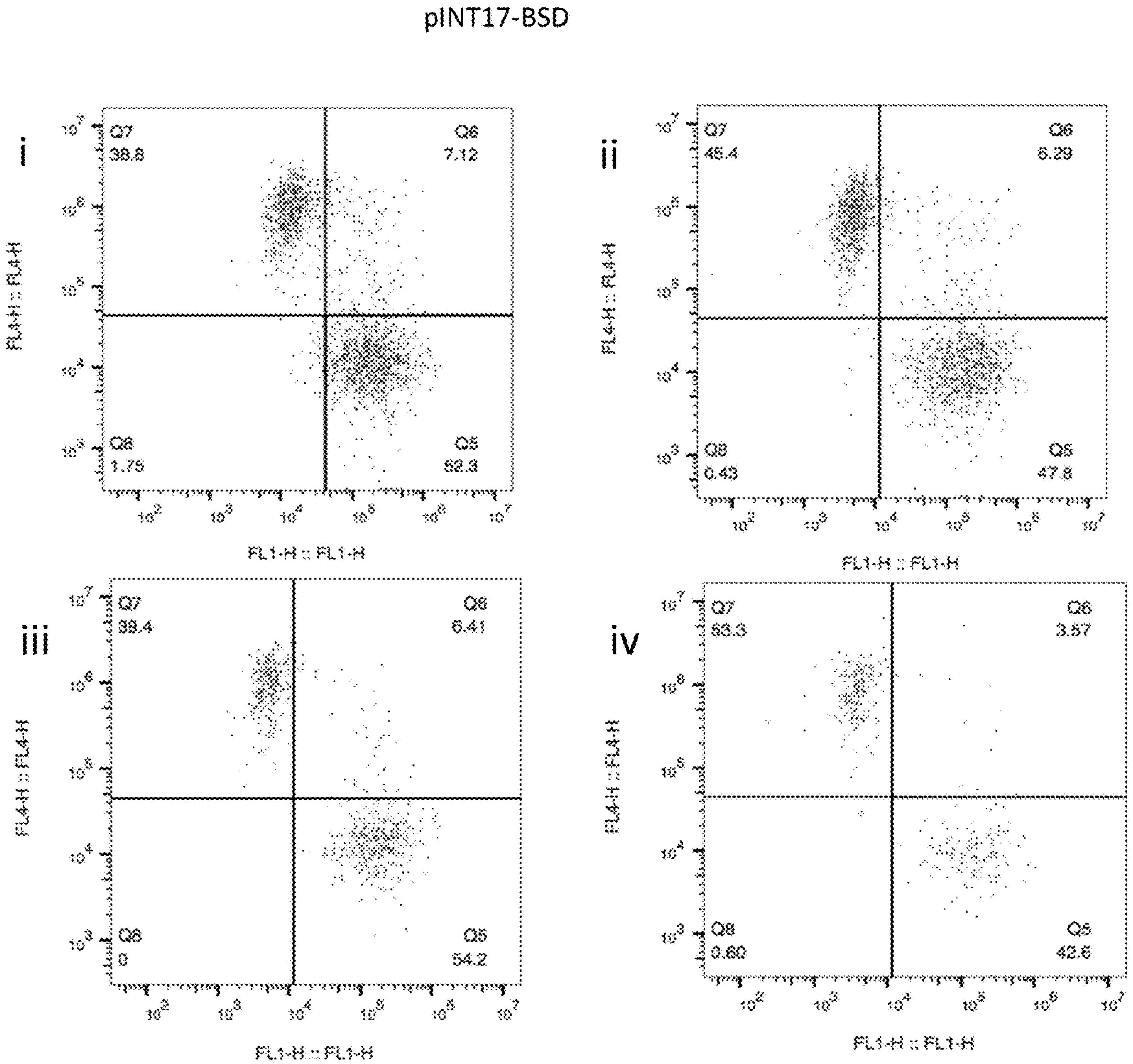

When the low density display vector pINT17-J30 was employed, it was possible to selectively separate the cell line displaying the low affinity anti-PD1 antibody 337_1_C08 from the higher affinity anti-PD1 antibody Nivolumab expressing cells. This is shown in FIG. 27*a* where dot-plot flow cytometry results are presented for either the MACS elution or flow through populations. Each panel shows a dot-plot where the green fluorescence intensity is plotted on the x-axis (FL1, Nivolumab expressing cells) and the red fluorescence intensity on the y-axis (FL4, 337_C08 expressing cells) for the elution and flow-through fractions pre-incubated with 0, 0.1, 1, or 10 nM biotinylated PD1. For example, upon incubation of the cell-line mix with 1 nM biotinylated PD1 followed by MACS separation, this resulted in 95% enrichment for the green dye stained high affinity anti-PD1 Nivolumab displaying cells compared with the red dye stained lower affinity anti-PD1 337_1_C08 antibody. In contrast, the unbound cells in the flow through contained predominantly the lower affinity red stained anti-PD1 337_1_C08 antibody displaying cells. Also, superior separation was observed with 1 nM PD1 compared with 10 nM PD1 incubations. However, when the same experiment was performed with the higher copy number cell lines, derived from the pINT17-BSD cassette, no preferential enrichment was observed between the Nivolumab and 337_1_C08 expressing cells (FIG. 27*b*).

This example has therefore illustrated that reducing the antibody display level on the cell surface can increase the enrichment of high affinity antibodies over lower affinities, particularly as high affinities are achieved within the population. Optimal cell display separation of a high affinity antibody from an antibody with lower affinity for its target was achieved by a combination of a reduction in antibody display level and a reduction in the concentration of labelled target antigen employed during selection. The ability to separate antibodies, during eukaryotic cell display selection, according to affinity is important during an antibody discovery campaign depending on the required target candidate profile of the desired antibody. It is also important to enrich for antibodies with improved affinity for their target during affinity maturation. This example has shown the importance of cell display copy number in helping to discriminate antibodies with high affinity for their target.

Example 8b. Improvements Using Inducible Tet Promoter

It is advantageous to create a vector that enables the inducible expression of mammalian cell displayed antibodies. This facilitates the combination of selection steps at different surface presentation levels, e.g., selection of low display levels required for stringent selection can be followed by the induction of high display levels required for the selection of antibodies with improved biophysical properties as exemplified in Examples 4 and 5.

An inducible antibody display targeting vector (pINT18-Tet1) was constructed by a combination of synthetic gene synthesis, PCR assembly and restriction enzyme mediated cloning (FIG. 28). pINT18-Tet1 contains the same vector back-bone, AAVS homology arms and promoter-less blasticidin resistance gene as pINT17-BSD. FIG. 28 shows and the annotated nucleic acid sequence of pINT18-Tet1 between the AAVS homology arms. The key features of this vector include a CMV promoter driving the expression of a reverse Tet activator (rtTA) protein[114], a Tet operator (TetO) tetrad followed by a minimal CMV promoter, BM40 leader fused to the light chain genes (VL and CL), a P2A peptide[115] to enable ribosome "skipping", followed by the antibody heavy chain coding sequence. The heavy and light variable genes (VH and VL) of Pembrolizumab, Nivolumab and 337_1_C03 were cloned into this inducible targeting vector and a stable HEK293 cell lines were created by nuclease mediated gene integration as described above. FIG. 29 shows low basal antibody display in the absence of doxycycline when cells are stained with anti-Fc-PE and analysed by flow cytometry. However, 24 hours after the addition of 20 ng/ml doxycycline antibody expression is observed on the cell surface. This display level can be controlled as shown by a reduction in Fc staining when the doxycycline concentration is titrated to 2 ng/ml. Thus, the exemplification of an inducible cell displayed binder is shown and the ability to control display levels by varying the concentration of inducer.

An improved ("third generation") inducible targeting vector was later constructed to enable an improved range of antibody display levels. pINT17-Tet was constructed by a combination of synthetic gene synthesis, PCR assembly and restriction enzyme mediated cloning. pINT17-Tet contains the same vector back-bone, AAVS homology arms and promoter-less blasticidin resistance gene as pINT17-BSD. FIG. 37 shows the annotated nucleic acid sequence of pINT17-Tet between the AAVS homology arms. This plasmid includes an elongation factor promoter driving the expression of the reverse Tet activator (rtTA-3G). rtTA-3G is a modified form of the original rtTA protein[114] which was evolved to display higher sensitivity to the inducer doxycycline[116]. pINT17-Tet also contains a b-directional inducible promoter (pTRE3G) to drive the expression of the antibody heavy and light chains. pTRE3G was optimised to widen the window between low basal expression and high maximal expression after induction[117]. It consists of 7 repeats of a 19 bp tet operator (TetO) sequence with two flanking minimal CMV promoters.

The VH and VL genes of the anti-PD-1 antibodies: 1549_02_D06, 1535_01_E03 and 337_1_C08 and the anti-PCSK9 antibodies bococizumab, 884_01_G01, 5A10i and alirocumab were cloned into pTet17-Tet. The anti-PD1 antibody 337_1_C08 was described in Example 8 with an affinity for PD1 of 74 nM. The antibodies 1549_02_D06 and 1535_01_E03 are affinity matured daughter clones of the parental antibody 337_1_C08 which have an affinity ($K_D$) for PD-1 of 2.9 nM and 17 nM respectively. The VH and VL genes of the anti-PCSK9 antibodies bococizumab, 884_01_G01, 5A10i. and alirocumab (all described previously in Example 5) were also cloned into pINT17-Tet.

The pINT17-Tet targeting vector harbouring the genes of the anti-PD1 and anti-PCSK9 antibodies were used to transfect HEK293 cells with plasmids encoding the AAVS TALE nucleases as described above. After 25 days of blasticidin drug selection, the stable cell lines were induced with 0, 2, 4 or 100 ng/ml doxycycline. 24 hours post induction the induced cell lines were stained with anti-Fc-PE and cells analysed by flow cytometry. Histogram plots of the cell-lines were generated by plotting cell number against fluorescence intensity.

The cell lines showed very low basal expression in the absence of doxycycline (FIG. 38*a*). Full induction was observed by the addition of doxycycline at a concentration of 100 ng/ml (FIG. 38*d*) 24 hours post induction. Intermediate induction was achieved by the addition of doxycycline concentrations of 2 and 4 ng/ml (FIGS. 38*b* and 38*c*). This resulted in a lower average display level compared with full induction, but did result in a spread of induction resembling the bi-modal gene expression observed previously with the seven TetO repeats[118].

The average displayed copy number of antibodies was quantitated by the method described in Example 7. Here the average mean fluorescence intensity (MFI) of the cell lines, induced with varying amounts of doxycycline, was determined and this used to convert to copy number using a calibration plot generated using the Quantum Simply Cellular anti-mouse IgG beads (catalogue number 815, Bangs Laboratories Inc) stained with mouse IgG-PE label. Tables 11c and 11d show the calculated display copy numbers 24 or 48 hours post induction (hpi). Very low basal expression was observed for the antibodies in the absence of doxycycline, which fell below the limits of detection when staining with anti-Fc-PE in some instances. There was detectable basal expression for all the antibodies for 48 hpi and this may be because the cells would have reached a stationary growth phase compared with 24 hpi. The average display level increased for all the antibodies as the concentration of doxycycline increased from 2 ng/ml to 4 ng/ml to 100 ng/ml doxycycline. Increasing the concentration of doxycycline above 100 ng/ml did not result in an increase in display level and so maximal induction was achieved at a concentration of 100 ng/ml doxycycline.

Display level differences were observed between the anti-PCSK9 IgG bococizumab, which is prone to self-interaction and polyreactivity 2, and the well behaved parental antibody 5A10i. The parental antibody 5A10i was displayed on the surface of HEK293 cells with a copy number of 235,000 whereas bococizumab displayed on the surface of HEK293 cells with a copy number of 36,000 when cells were induced with 100 ng/ml doxycycline and display levels determine 24 hours post induction (hpi). This represents a 6.5-fold reduction in display level of bococizumab compared to the parental antibody 5A10i. This observed reduction in cell displayed copy number for bococizumab compared with 5A10i was observed previously (Example 5, FIG. 10) when the antibody expression was driven by constitutive promoters. Therefore, this inducible system, at full induction, is able to differentiate between antibodies that have different developability profiles in terms of self-interaction and polyreactivity as we demonstrated previously with a constitutive promoter display system.

We also displayed a variant of bococizumab which was identified by mammalian display library screening named 884_01_G01 (Example 5). This antibody was shown to be well behaved biophysically in an AC-SINS assay and by HPLC-SEC (Table 6, Example 5 and FIG. 18, Example 5). This antibody displayed to high levels on the surface of HEK293 cells 24 hpi (100 ng/ml doxycycline) with a display copy number of 768,000 (Table 11B). The well-behaved antibody alirocumab[2] also displayed to high levels on the surface of HEK293 cells 24 hpi under full induction conditions (Table 11B).

Doxycycline is known to degrade in culture supernatant with a half-life of approximately one day, depending on culture conditions. Examining the display level of antibodies at different time points post induction with no replenishment of doxycycline provides some evidence regarding the dynamic turn-over of antibodies on the cell surface. Alternatively, induction could occur in the presence of doxycycline for a 24-hour period followed by a complete media change so the cells are no longer exposed to doxycycline. Here we simply re-examined the display levels 48 hours post induction (Table 11C). Several well-behaved antibodies such as alirocumab maintained or increased their cell surface display levels 48 hpi. Other antibodies such as bococizumab showed a greater than 2-fold reduction in cell surface display level at 48 hpi compared with 24 hpi (FIG. 39). The rate of turn-over, degradation or internalisation of an antibody displayed on a cell, where the displayed antibody is not being continuously replenished with newly expressed antibody, is an additional means to select antibodies based on their developability characteristics in terms of self-interaction and stability (see also Example 11).

TABLE 11B

Copy number of antibodies displayed on HEK293 cells calculated using Quantum Simply Cellular beads 24 hpi with 0, 2, 4 or 100 ng/ml Doxyclicycline (Dox) induction. nd, not detectable.

| | Copy Number ($\times 10^3$) | | | |
|---|---|---|---|---|
| | Dox (0 ng/ml) | Dox (2 ng/ml) | Dox (4 ng/ml) | Dox (100 ng/ml) |
| 1549_02_D06 | Nd | 4.5 | 21.9 | 356 |
| 1535_01_E03 | Nd | 3.3 | 16.5 | 137 |
| 337_1_C08 | Nd | 5.6 | 31.0 | 251 |
| Bococizumab | Nd | 2.4 | 5.1 | 36.1 |
| 884_01_G01 | Nd | 26.7 | 115 | 768 |
| 5A10i | 0.1 | 14.0 | 48 | 235 |
| Aliricocumab | 0.4 | 32.8 | 144 | 557 |

TABLE 11C

Copy number of antibodies displayed on HEK293 cells calculated using Quantum Simply Cellular beads 48 hpi with 0, 2, 4 or 100 ng/ml Doxyclicycline (Dox) induction.

| | Copy Number ($\times 10^3$) | | | |
|---|---|---|---|---|
| | Dox (0 ng/ml) | Dox (2 ng/ml) | Dox (4 ng/ml) | Dox (100 ng/ml) |
| 1549_02_D06 | 0.4 | 11.1 | 51.5 | 317 |
| 1535_01_E03 | 0.7 | 6.1 | 46.8 | 238 |
| 337_1_C08 | 0.4 | 20.4 | 108 | 294 |
| Bococizumab | 0.7 | 2.0 | 5 | 17.5 |
| 884_01_G01 | 0.6 | 26.4 | 112 | 417 |
| 5A10i | 5.2 | 20.7 | 40.2 | 73.5 |
| Aliricocumab | 1.7 | 101 | 339 | 668 |

pINT17-Tet therefore represents an example of an inducible mammalian display targeting vector that can be used to create monoclonal cell lines by nuclease mediated gene integration that can be switched to high expression, full induction mode to enable the developability screening described above for antibody self-interaction and polyreactivity screening. Cell lines created with pINT17-Tet can also be switch to low copy display mode by either basal display levels, in the absence of inducer, or adding limiting concentrations of doxycycline. This low copy number display mode will enable the more efficient separation of antibody clones with different affinities as described in Example 8a.

To demonstrate the utility of inducible mammalian display cell lines for the separation of antibodies displayed on the cell surface with different affinities for their target, HEK293 cells displaying the high affinity anti-PD1 antibody 1549_02_D06 ($K_D$=2.9 nM for PD-1) or the low affinity anti-PD-1 antibody 337_1_C08 ($K_D$=74 nM for PD-1) were created by nuclease mediated gene integration with the pINT17-Tet targeting vector. Hek293 cells displaying the 1549_02_D06 antibody were labelled with CellTrace CFSE Cell Proliferation Kit (Thermo cat #C34554—Excitation/emission wavelengths—492 nm/517 nm) and cells displaying the 337_1_C08 antibody were not labelled. Cells were induced with 0, 2, 4 or 100 ng/ml doxycycline. 48 hours post induction (hpi), the cells displaying 1549_02_D06 were stained with CellTrace CFSE Cell Proliferation Kit (C34554, ThermoFisher Scientific) and mixed with unlabelled cells displaying 337_1_C08. The labelled and unlabelled cells were mixed equally and MACS purification was then performed on the mixed IgG display cell populations with 0.1, 1 or 10 nM PD-1-biotin as described in detail in Example 8a. The cells were then analysed by flow cytometry (FIG. 40) to determine the relative enrichment of the high affinity anti-PD1 IgG compared to the low affinity anti-PD1 IgG.

Figure 40A:
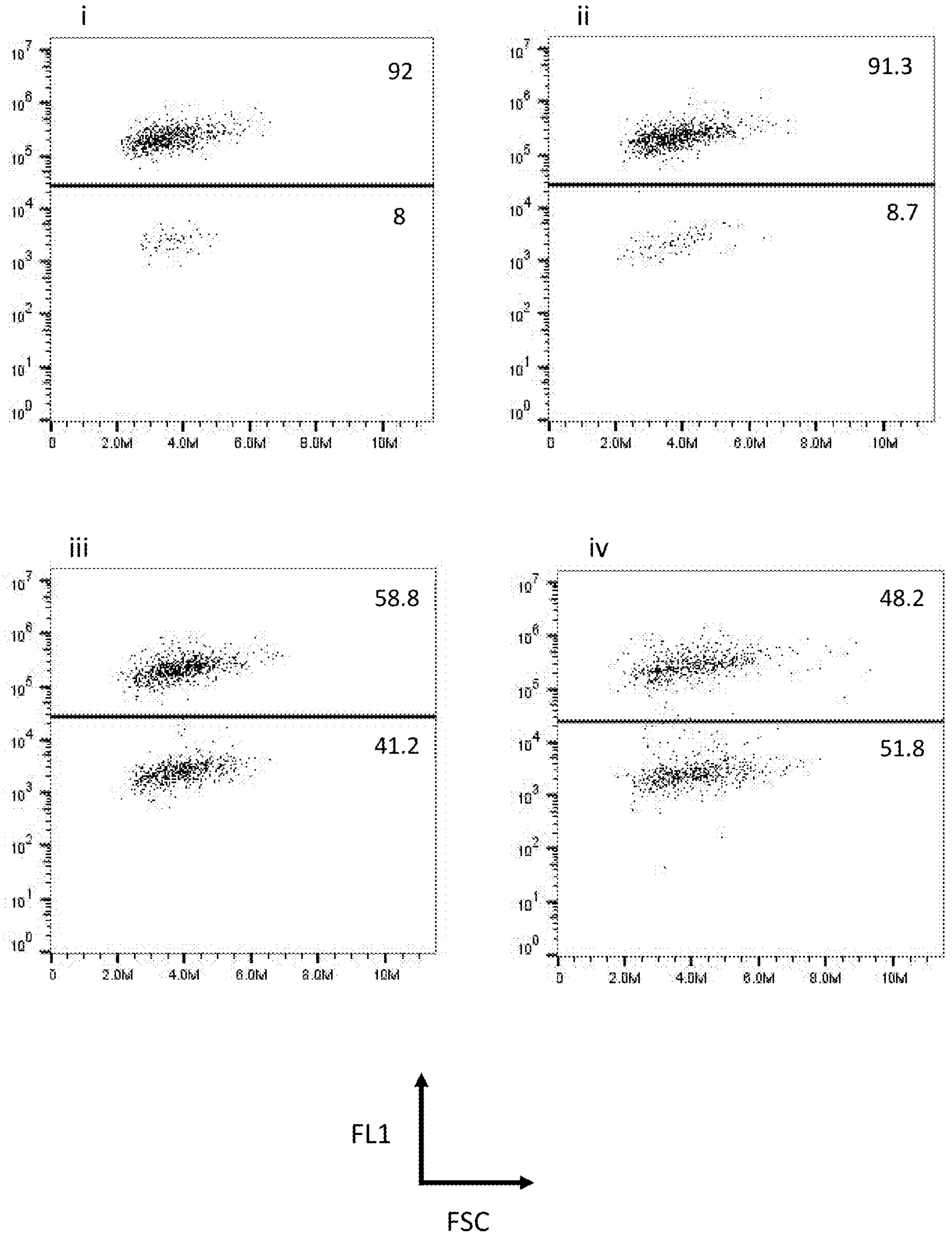
Figure 40B:
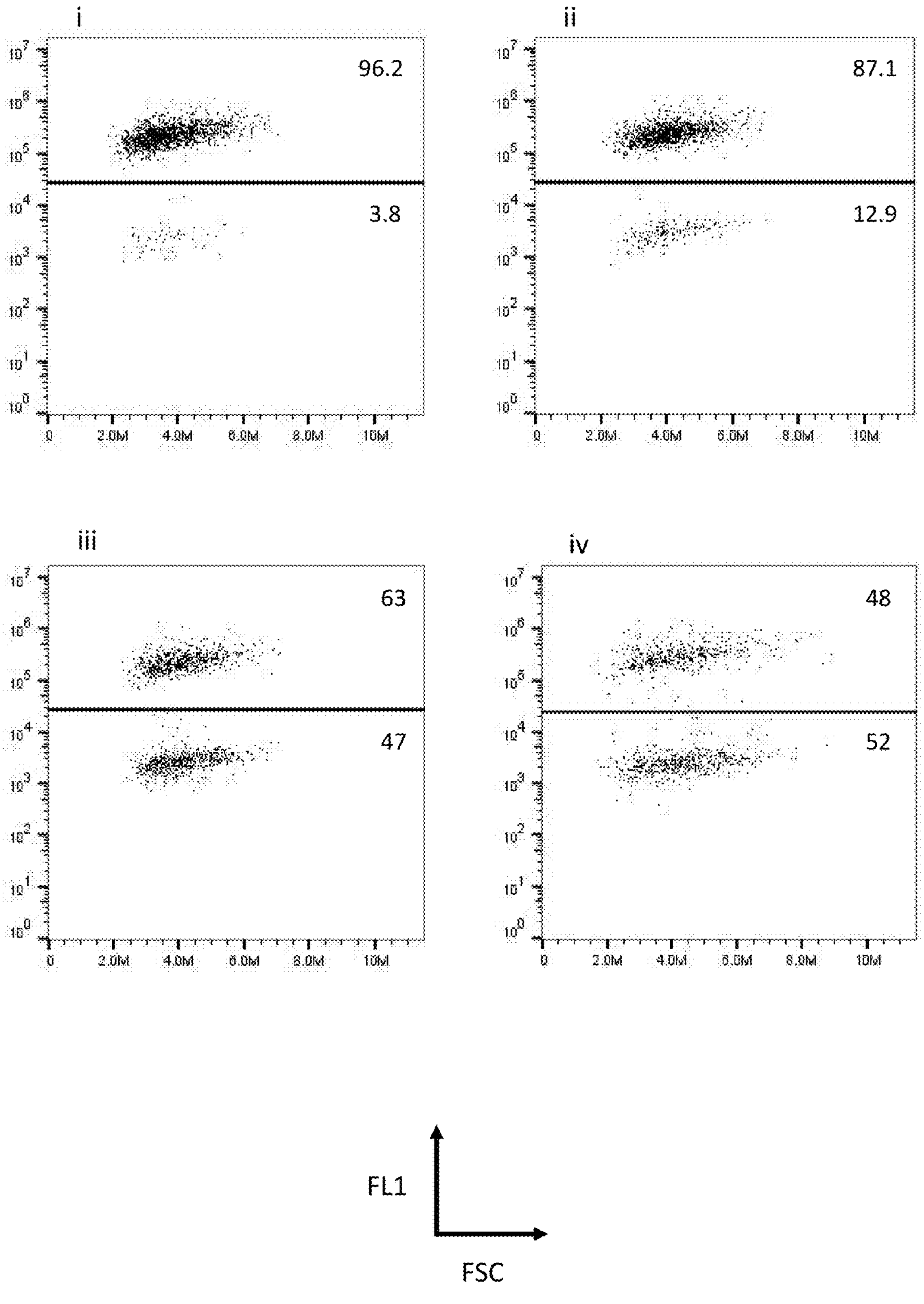
Figure 40C:
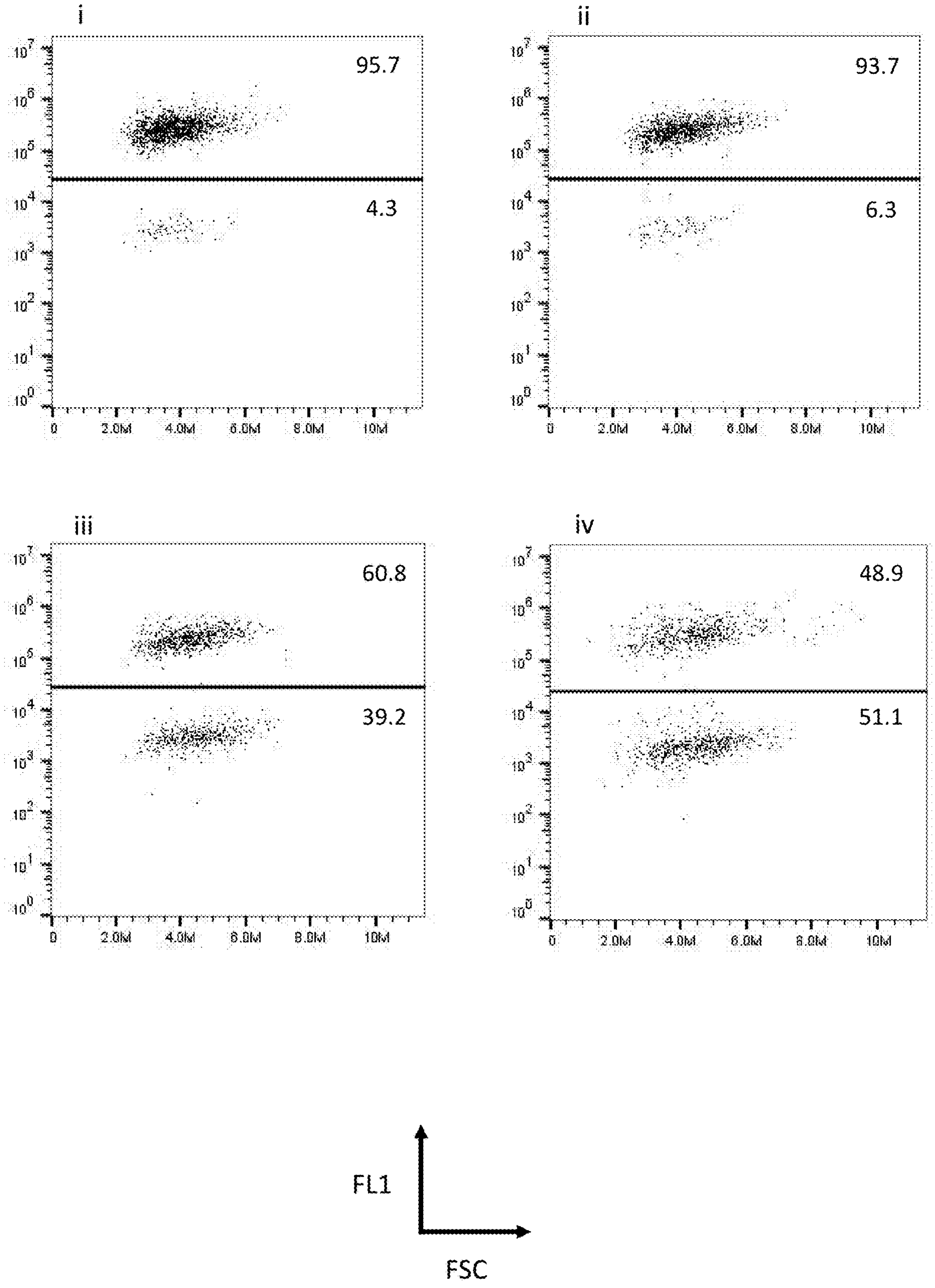
Figure 40D:
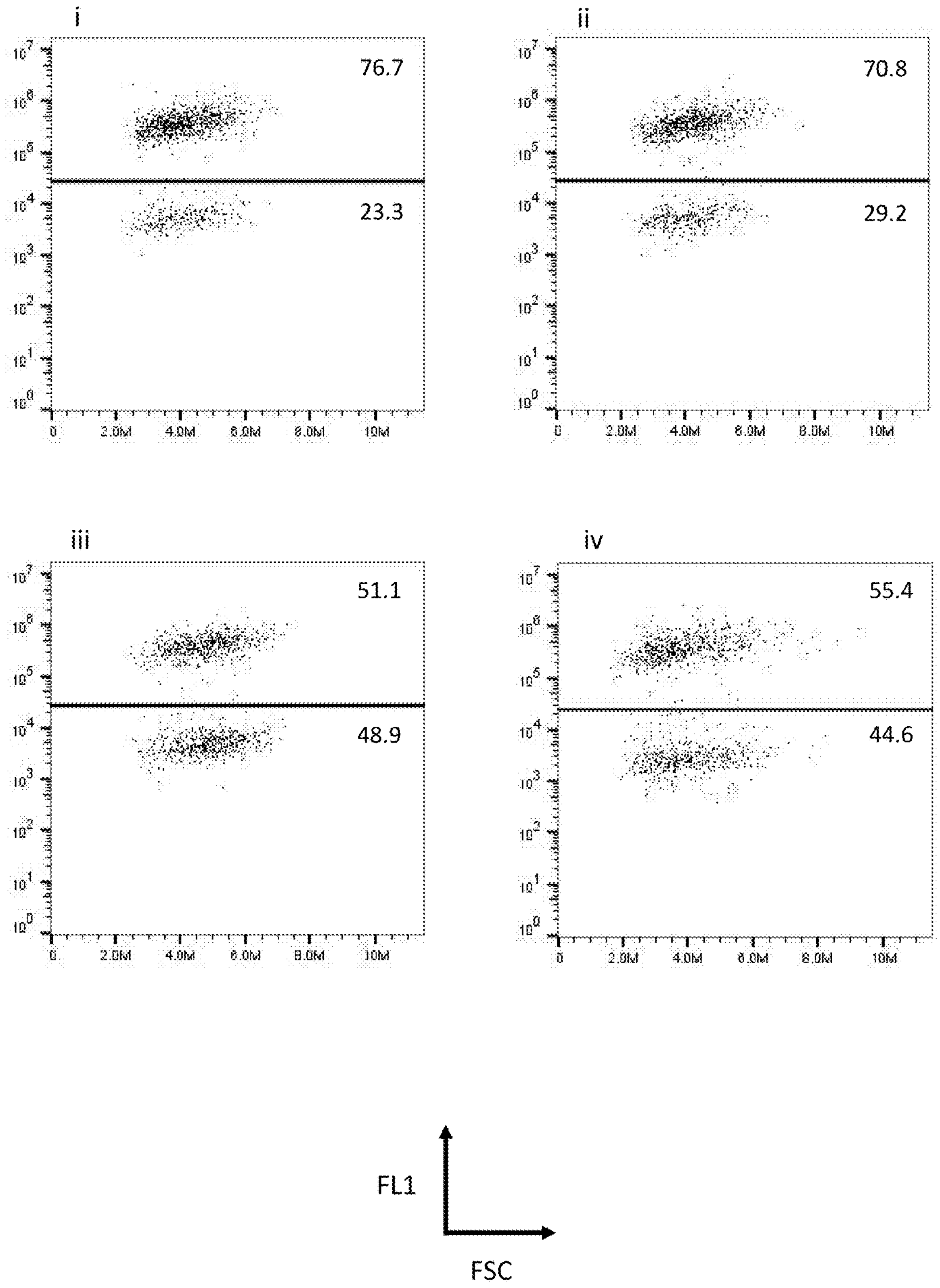

The most efficient separation of cells displaying the high and low affinity anti-PD-1 antibodies occurred when the cells were induced with a limiting doxycycline concentration of 2 ng/ml to reduce the displayed antibody level and 0.1 nM PD-1-biotin was employed in a MACS purification. Here an enrichment of the population was achieved for the high affinity clone to 96% of the population (FIG. 40*bi*). When the cells were induced with 2 ng/ml doxycycline, the cell copy number 48 hpi was 11,000 and 20,000 respectively for the high and low affinity anti-PD-1 clones. In contrast, when the cell-lines were fully induced, MACS with 0.1 nM PD-1 only achieved a 77% enrichment of the high affinity clone (FIG. 40*di*). When the cells were fully induced with 100 ng/ml doxycycline, the cell copy number 48 hpi was 317,000 and 294,000 respectively for the high and low affinity anti-PD-1 clones. This provides further evidence, in addition to the data in Example 8, that a reduction in cell surface antibody display level (copy number) will increase the efficiency of separation of displayed antibodies with different affinities for their target. As the concentration of PD-1 used for MACS was increased, this led to less efficient enrichment of the high affinity clone as expected from the theoretical analysis in Example 8 (FIGS. 40*bii* and 40*iii*).

In this Example, we have demonstrated the utility of an inducible promoter system for higher eukaryotic cell display, to enable both high copy display for self-interaction and aggregation propensity screening and low copy number display for the stringent selection of high affinity antibodies. Here we used limiting concentrations of inducer to give a low display level for the efficient separation of a clone with an affinity for its target of 2.9 nM from a second clone with an affinity of 74 nM for the same target. It is envisaged that by controlling the copy number of the displayed antibody on the cell surface and the concentration of the target antigen used for MACS separation, that it would increase the efficiency of the separate clones with an affinity ($K_D$) for its target of less than 1 nM from clones with single digit nM affinity.

Example 9. Developability Enhancement by Selection for Optimal Interaction with Fc Receptors Example 6 demonstrated that it is possible to differentiate between eukaryotic cell displayed antibodies that have different cross-interaction properties. This was achieved by incubating the cells with labelled human serum and detecting binding by flow cytometry. Vesencumab, an antibody with known cross-interaction properties[39], that did not proceed further than a Phase 1 clinical trial[82] resulted in greater binding to human serum compared with the clinically approved antibody Nivolumab which is considered to be a well-behaved antibody. Vesencumab has a short half-life in vivo[105]. "Stickiness" or cross-interaction properties of an antibody is generally correlated with poor pharmacokinetics and a short half-life in vivo is thought to be caused by systemic clearance by the non-specific binding to disseminated tissue[23,122,123].

Antibody half-life in vivo is also critically dependent of the interaction between the IgG, via its CH2 and CH3 domains, and the neonatal Fc receptor (FcRn)[124]. Long antibody half-life in circulation is achieved by the cellular internalization of IgG by unspecific pinocytosis or Fc receptor mediated uptake. Once internalized, IgG binds with high affinity to FcRn within the endosome at pH5-6, thereby protecting the IgGs from lysosomal degradation. Finally IgGs are transported to the cell surface and released back into circulation because the affinity between IgG and FcRn is very weak at physiological pH 7.4. The anti-IL12 Briakinumab[20] did not show efficacy in a Phase III clinical trial to treat psoriasis and is known to have a short half-life in vivo. Briakinumab has positive charge patches, consisting of arginine and lysine residues, within its variable domain that can bind to a negative charge patch on FcRn resulting in increased affinity for binding to FcRn at pH7.4. The binding of Briakinumab to FcRn at pH7.4 has been shown to correlate with poor half-life in vivo in mice. Also, the anti-IL12 antibody Ustekinumab, clinically approved to treat Crohn's disease, does not possess a positive charge patch within its variable domain, is known to bind weakly to FcRn at pH7.4 and has superior in vivo half-life compared with Briakinumab. In this example we show it is possible to differentiate between antibodies with known differing affinities for FcRn at pH7.4 by higher eukaryotic cell display and the detection of FcRn binding by flow cytometry.

Synthetic DNA encoding Briakinumab and Ustekinumab heavy and light variable domains (see Table 12 for sequences) were cloned into the pINT17-BSD targeting vector (see Example 1 for vector map and sequence) and DNA sequence confirmed.

TABLE 12

| Sequences of Briakinumab and Ustekinumab VH and VL chains | |
|---|---|
| Briakinumab VH | QVQLVESGGGVVQPGRSLRLSCAASGFTFSSYGMHW VRQAPGKGLEWVAFIRYDGSNKYYADSVKGRFTISR DNSKNTLYLQMNSLRAEDTAVYYCKTHGSHDNWGQG TMVTVS (SEQ ID NO: 46) |
| Briakinumab VL | QSVLTQPPSVSGAPGQRVTISCSGSRSNIGSNTVKW YQQLPGTAPKLLIYYNDRQPSGVPDRFSGSKSGTSA SLAITGLQAEDEADYYCQSYDRYTHPALLFGTGTKV TVLGQP (SEQ ID NO: 47) |
| Ustekinumab VH | EVLQVQSGAEVKKPGESLKISCKGSGYSFTTYWLGW VRQMPGKGLDWIDIMSPVDSDIRYSPSFQGQVTMSV DKSITTAYLQWNSLKASDTAMYYCARRRPGQGYFDF WGQGTLVTVS (SEQ ID NO: 48) |
| Ustekinumab VL | DIQMTQSPSSLSASVGDRVTITCRASQGISSWLAWY QQKPEKAPKSLIYAASSLQSGVPSRFSGSGSGTDFT LTISSLQPEDFATYYCQQYNIYPYTFGQGTKLEIKR TA (SEQ ID NO: 49) |

Suspension adapted HEK293 cells were seeded at $5\times10^5$ cells per ml in HEK FreeStyle 293 expression media one day before transfection. On day of transfection cells were centrifuged and re-suspended in a final volume of $10^8$ cells/ml in the manufacturer's electroporation buffer (Maxcyte Electroporation buffer, Thermo Fisher Scientific Cat. No. NC0856428). 100 µl was pulsed using an OC-100 cuvette (Maxcyte). Two days after transfection cells were seeded at $2.5\times10^5$ cells per ml and 7.5 µg/ml Blasticidin was added. 57 days after transfection cells were labeled with biotinylated FcRn (50 nM) preconjugated with streptavidin PE (11 nM). Preconjugation was done in either of the staining buffer at different pH (PBS containing 1% BSA, pH7.4 or 20 mM MES containing 140 mM NaCl and 1% BSA, pH6.0). Briefly $1\times10^6$ cells were spun down, washed once with either PBS at pH7.4 or 20 mM MES buffer at pH 6.0. Cell pellet was resuspended in 100 ul staining buffer and washed twice with 1.0 ml wash buffer (PBS containing 0.1% BSA, pH7.4 or 20 mM MES containing 140 mM NaCl and 0.1% BSA, pH6.0). Cell pellets were resuspended in 500 ul wash buffer containing viability dye 7AAD (5 ul per million cells). Cells were analysed using the Intellicyt flow cytometer. Dead cells were excluded during the analysis. Histogram plots were generated using FlowJo software (FIG. 30).

At pH6, both Briakinumab and Ustekinumab bound to FcRn when the antibodies were displayed on the surface of HEK293 cells (FIG. 30). At pH 7.4, only Briakinumab displayed significant binding to FcRn, unlike Ustekinumab where no binding of FcRn was observed. This example demonstrates that it is possible to differentiate between clones with different binding affinities to FcRn at pH7.4 by higher eukaryotic cell display and analysis of FcRn binding by flow cytometry. This will enable the prediction of an antibody pharmacokinetic (PK) profile. Also when selecting from a library of cell displayed binders, this technique could be employed to eliminate clones that bind to FcRn at pH7.4 and therefore select for clones expected to possess a favourable PK profile. For example, binding of cell displayed antibodies to MACS beads could be achieved at pH6. Washing the beads at pH7.4 should elute the clones with low affinity at pH7.4 and these clones would be expected to display a longer half-life in vivo compared to the binding clones which retain binding at pH7.4.

FcRn binding to IgG is known to be partially dependent on post-translational glycosylation of the IgG. Therefore, performing the selections described with higher eukaryotic cells has the advantage that authentic glycosylation will occur to enable FcRn binding, unlike display in unmodified lower eukaryotic cell display systems such as yeast.

We further demonstrated that it is possible to isolate antibody that shows reduced binding to FcRn from a mixed antibody population. Two populations of higher eukaryotic cell clones expressing different anti-IL-12 antibodies, briakinumab and ustekinumab, respectively, were co-cultured. Cells expressing briakinumab were shown to bind to FcRn at pH 7.4 (FIG. 30). The binding could be due to its positive charge patch within its variable domain binding to negatively charged side chains of FcRn (see Example 6, in which briakinumab was shown to bind negatively-charged polyreactivity probes). Ustekinumab did not show binding to FcRn at pH 7.4 (FIG. 30). The mixed antibody expressing population was dual stained and enriched by FACS for cells displaying ustekinumab. FIG. 41. We thus demonstrated that it is possible to enrich FcRn non-binders from a mixed population which also contains FcRn binders. The same technique may be applied for more diverse mixtures of clones, e.g., a library containing millions of different antibodies.

The antibody Fc region is known to elicit multiple effector functions including Fc receptor[139] and complement binding[140]. By the creation of libraries of Fc domains followed by selection with known effector molecules such as Fc gamma receptors, NK receptors, FcRn or members of the complement cascade it would be possible to use higher eukaryotic cell display to select for variants which either enhance or reduce binding to effector function molecules. This would select for Fc variants that may enhance, reduce or silence antibody-dependent cellular cytotoxicity (ADCC), complement-dependent cytotoxicity (CDC) or increase antibody half-life in vivo. Fc variants could also be selected which bind to Fc receptors to increase their agonism of target receptors and therefore their potency[141,142]. Fc variants can reduce the stability of antibodies and negatively affect their biophysical properties[134,143]. An advantage of selecting for Fc variants by higher eukaryotic cell display is that variants that display to a high level on the cell surface can be selected for and these variants would be expected to possess superior biophysical properties.

Example 10. Selection of Optimal Developability Clones within a Selected Population by Mammalian Display (Mesothelin Selections)

Here we demonstrate that it is possible to use higher eukaryotic (mammalian) cell display to select for antibodies with optimal developability potential from a highly diverse input panel of antibodies. A complex mixture of antibodies of different germline sequences was separated, allowing antibodies to be grouped and selected based upon their self-interaction properties.

We show this by first generating an enriched panel of anti-mesothelin antibodies by antibody phage display selection, then cloning the antibodies into a mammalian cell display library and comparing the characteristics of binders from cell clones exhibiting high, medium or low surface presentation respectively.

Mesothelin is an antigen over-expressed in several human tumours and is therefore of interest as a therapeutic antibody target to treat cancer. To generate an enriched population of anti-human mesothelin, two rounds of antibody phage display selection was performed where the antigen was directly immobilized on a polystyrene surface, as described previously[8]. A naïve human antibody library was employed (WO2015166272A2), described previously and constructed in a similar way to a previously described human naïve antibody library[8]. Selections were performed with VL lambda and VL kappa germ-lines separately and the round 1 output numbers were $2\times10^5$ (average). Conversion to IgG format and cloning into the pINT17-BSD targeting vector was performed "en masse", as described previously (WO2015166272A2). *E. coli* transformants for the lambda and kappa enriched populations were plated onto agar plates as described in Examples 4 and 5 to create a combined library size of $2.4\times10^6$ clones (a 12-fold excess of the input antibody population). Transfection quality plasmid DNA was prepared encoding the anti-Mesothelin antibodies in the pINT17-BSD vector. The library was transfected with AAVS TALE nucleases as described above (Examples 2, 4 and 5) using a single OC-400 Cuvette ($10^8$ cells total, MaxCyte, Cat. No. OC-400R10), on the HEK293 setting on the MaxCyte STXG2. The controls were transfected using OC-100 Cuvettes (MaxCyte, Cat. No. OC-100R10) on the same setting. After transferring the electroporated cells into an appropriate sized Erlenmeyer flask the cells were allowed to rest for 30 minutes before an appropriate amount of FreeStyle 293 Expression Media (LifeTech. Cat. No. 12338018) was added. The cells were resuspended and placed in an orbital shaking incubator set to 130 rpm, 37° C. and 5% $CO_2$. Stable transfection efficiency was calculated as described above (Examples 4 and 5) to be 4.2% to give a total library size of $4.2\times10^6$ stable antibody display HEK293 cell lines. After 19 days of blasticidin selection, FACS was carried out according as described above (Examples 4 and 5) using a BD Influx cell sorter. $100\times10^6$ cells were incubated with Anti-Human Fc PE (1 µl per 1×10⁶ cells) (Cambridge Bioscience, Cat. No. 409304) and DAPI was added (1 µl/million cells) immediately before sorting. Three gates were drawn allowing for a low display level population (P4), a medium display level population (P6), and a high display level population (P5). The Influx sorter can only sort two populations at a time, therefore 50×10⁶ cells were sorted for gate P4 and P5, and the other 50×10⁶ cells were sorted for P6 (FIG. 31). Genomic DNA was extracted from the three populations, as described above (Examples 4 and 5), antibody genes cloned into pINT3 vector (WO2015166272A2) and the VH and VL genes sequenced.

TABLE 13

Sequence analysis of the anti-Mesothelin mammalian display selected clone populations. The populations gated in FACS for low, medium and high display levels (FIG. 30) were DNA sequence analysed and compared with the input antibody generation used to produce the starting anti-Mesothelin display library. Germ-lines and VL CDR1, 2 and 3 and VH CDR1 and 2 followed IMGT nomenclature whereas VH CDR3 was defined by the Kabat numbering system.

|  | Input | Low Display | Medium Display | High Display |
| --- | --- | --- | --- | --- |
| Total sequenced | 79 | 89 | 92 | 85 |
| Unique VH CDR3 | 56 (71%) | 38 (49%) | 62 (67%) | 63 (74%) |
| Unique VL CDR3 | 49 (62%) | 32 (36%) | 57 (62%) | 48 (56%) |
| Unique VH + VL CDR3 | 69 (87%) | 43 (48%) | 79 (89%) | 71 (84%) |
| VH germ-lines | 14 | 10 | 10 | 12 |
| VL$_K$ germ-lines | 11 | 12 | 10 | 11 |
| VLλ germ-lines | 3 | 2 | 5 | 5 |

Sequence analysis revealed great diversity within all sub-populations (Table 13). In order to ensure that this was not due to a sampling issue, we focused the analysis on clones which appeared more than once to determine whether "binning" of different clone groups into the different display groups was occurring. Thus an overlap analysis was performed for antibodies where duplicate clones had been identified (based on the VH and VL CDR3 sequence) in the low, medium and high display level populations (Table 14). There were 13 such clones in the high display level population and 28 clones which appeared multiple times in the low display level population with no overlap between them. The group of clones identified as "medium expressors" had 11 sequences that appeared more than once and again these were not found in the other groups. There were 4 clones which appeared in the "medium" group which overlapped in 3 cases with the low group and in one case with the high group. This result is evidence that sorting based on display level in mammalian cells selects for specific sub-populations of sequence that are unique to that group.

TABLE 14

Antibody clone overlap analysis for the anti-Mesothelin antibodies pooled according to high, medium and low HEK293 cell display levels. Mammalian cell display selected anti-Mesothelin antibodies were pooled according to cell surface display level (FIG. 31). Clones from the high, medium and low display level populations were DNA sequenced and the unique clones (based on VH and VL CDR3 sequences) that appeared more than once were characterised according to the number of appearances in the high, medium or low display groups. The numbers in the Table indicate the number of appearances.

| Clone number | VH Germline | VL Germline | No of occurrences in the High display group | No. of occurrences in the Medium display group | No of occurrences in the Low display group |
| --- | --- | --- | --- | --- | --- |
| 1 | IGHV1-69 | IGKV2-28 | 3 | 0 | 0 |
| 2 | IGHV4-34 | IGLV2-8 | 2 | 0 | 0 |
| 3 | IGHV1-46 | IGKV1-5 | 2 | 0 | 0 |
| 4 | IGHV1-46 | IGKV6-21 | 2 | 0 | 0 |
| 5 | IGHV3-9 | IGLV3-19 | 2 | 0 | 0 |
| 6 | IGHV3-9 | IGLV3-19 | 2 | 0 | 0 |
| 7 | IGHV1-46 | IGKV3-15 | 3 | 0 | 0 |
| 8 | IGHV3-9 | IGLV3-19 | 1 | 1 | 0 |

TABLE 14-continued

Antibody clone overlap analysis for the anti-Mesothelin antibodies pooled according to high, medium and low HEK293 cell display levels. Mammalian cell display selected anti-Mesothelin antibodies were pooled according to cell surface display level (FIG. 31). Clones from the high, medium and low display level populations were DNA sequenced and the unique clones (based on VH and VL CDR3 sequences) that appeared more than once were characterised according to the number of appearances in the high, medium or low display groups. The numbers in the Table indicate the number of appearances.

| Clone number | VH Germline | VL Germline | No of occurrences in the High display group | No. of occurrences in the Medium display group | No of occurrences in the Low display group |
|---|---|---|---|---|---|
| 9 | IGHV3-9 | IGLV3-19 | 1 | 1 | 0 |
| 10 | IGHV3-9 | IGLV3-19 | 2 | 0 | 0 |
| 11 | IGHV1-2 | IGKV3-15 | 2 | 0 | 0 |
| 12 | IGHV3-9 | IGLV3-19 | 3 | 0 | 0 |
| 13 | IGHV3-9 | IGLV3-19 | 1 | 1 | 0 |
| 14 | IGHV3-9 | IGLV3-19 | 0 | 0 | 2 |
| 15 | IGHV5-51 | IGKV1-39 | 0 | 0 | 6 |
| 16 | IGHV1-3 | IGKV1-39 | 0 | 0 | 10 |
| 17 | IGHV1-2 | IGKV4-1 | 0 | 0 | 4 |
| 18 | IGHV1-18 | IGKV1-33 | 0 | 0 | 3 |
| 19 | IGHV1-46 | IGKV2-30 | 0 | 0 | 3 |
| 20 | IGHV1-69 | IGKV1-39 | 0 | 0 | 3 |
| 21 | IGHV1-69 | IGKV1-39 | 0 | 0 | 2 |
| 22 | IGHV1-69 | IGKV4-1 | 0 | 0 | 5 |
| 23 | IGHV3-30/33rn | IGKV4-1 | 0 | 0 | 4 |
| 24 | IGHV3-9 | IGLV3-19 | 0 | 0 | 3 |
| 25 | IGHV3-9 | IGLV3-19 | 0 | 0 | 2 |
| 26 | IGHV1-46 | IGKV1-39 | 0 | 0 | 2 |
| 27 | IGHV1-69 | IGKV1-39 | 0 | 1 | 3 |
| 28 | IGHV5-51 | IGKV4-1 | 0 | 0 | 2 |
| 29 | IGHV3-30/33rn | IGKV2-28 | 0 | 0 | 2 |
| 30 | IGHV1-69 | IGKV4-1 | 0 | 0 | 6 |
| 31 | IGHV3-9 | IGKV1-39 | 0 | 2 | 0 |
| 32 | IGHV3-9 | IGLV3-19 | 0 | 2 | 0 |
| 33 | IGHV3-9 | IGLV3-19 | 0 | 2 | 0 |
| 34 | IGHV1-69 | IGKV2-28 | 0 | 2 | 0 |
| 35 | IGHV3-9 | IGLV3-19 | 0 | 2 | 0 |
| 36 | IGHV3-9 | IGKV3-20 | 0 | 2 | 0 |
| 37 | IGHV3-9 | IGLV3-19 | 0 | 3 | 0 |
| 38 | IGHV3-9 | IGLV3-19 | 0 | 2 | 0 |
| 39 | IGHV3-9 | IGLV3-19 | 0 | 2 | 0 |
| 40 | IGHV3-9 | IGLV3-19 | 0 | 2 | 0 |
| 41 | IGHV3-9 | IGLV3-19 | 0 | 2 | 0 |

The distinctness of the cell populations selected on the basis of surface presentation was confirmed by an in-depth analysis of the antibody populations using next generation sequencing (NGS). In brief, paired variable domain genes of antibodies from the high, medium and low display level populations and from the input population were amplified, sequenced and demultiplexed using asymmetrical barcodes,[125,126] and the output BAM files were then converted to FASTQ file format to enable antibody sequence analysis with Geneious Biologics software.

A total of 19792 paired VL and VH gene reads resulted from this analysis. After de-multiplexing the populations, this resulted in 2998, 1516, 6180 and 9098 CCS reads for the input and high, medium and low display level populations respectively. Antibody sequences were annotated to map their framework and complementarity determining regions (CDRs) and heavy and light chain germ-lines were assigned according to the IMGT database[127]. A summary of the results of this analysis for the clones which had annotated VH and VL CDR3 sequences with no stop codons is in Table 15. The antibody input population, which was pre-selected by performing two rounds of antibody phage display selection against Mesothelin with a naïve antibody phage display library[8], was highly diverse with 51% of the clones being VH CDR3 sequence unique and 88% of the clones being VH and VL CDR3 sequence unique. This input population was also antibody germ-line diverse with 19, 18 and 10 VH, VLκ and VLλ germ-line identified respectively per 1000 clones sequenced. This diversity both in terms of CDR3 sequences and germ-lines was reduced when analysing the high, medium and low mammalian display gated populations. The diversity of the low display level population was markedly reduced with the number of VH CDR3 unique antibodies dropping to less than 4% and the number of VH, VLκ and VLλ germ-line per 1000 clones sequenced dropping to 4, 2 and 3 respectively. This reduction in antibody diversity compared with the input population indicates that certain clones are being enriched in the display level gated antibody populations, thus increasing the redundancy in the populations.

The ratio of the VLκ and VLλ germ-lines was also examined in the different populations. Although the starting input population had an almost 2-fold excess of VLλ compared with VLκ antibodies, this ratio was reversed for the low display level gated population which had an over four-fold excess of VLκ antibodies. These results indicate that the low display group is enriching for a particular sub-set of antibodies with particular light chain germ-line sequences.

TABLE 15

Sequence analysis of the anti- Mesothelin mammalian display selected clone populations generated by PacBio sequencing. The populations gated in FACS for low, medium and high display levels (FIG. 30) were DNA sequence analysed and compared with the input antibody generation used to produce the starting anti-Mesothelin display library. Germ-lines and VL CDR1, 2 and 3 and VH CDR1 and 2 followed IMGT nomenclature whereas VH CDR3 was defined by the Kabat numbering system.

| | Input | Low Display | Medium Display | High Display |
|---|---|---|---|---|
| Total sequenced and annotated | 1132 | 7378 | 3837 | 968 |
| Unique VH CDR3 | 575 (51%) | 284 (3.8%) | 547 (14%) | 236 (24%) |
| Unique VL CDR3 | 535 (47%) | 196 (2.7%) | 446 (11.6%) | 185 (19%) |
| Unique VH + VL CDR3 | 995 (88%) | 1170 (15.9%) | 2204 (57%) | 637 (66%) |
| Total VH germ-lines | 22 | 14 | 18 | 16 |
| Total $VL_K$ germ-lines | 20 | 19 | 19 | 17 |
| Total VLλ germ-lines | 11 | 4 | 17 | 9 |
| VH germ-lines per 1000 clones | 19.4 | 1.9 | 4.7 | 16.5 |
| $VL_K$ germ-lines per 1000 clones | 17.7 | 2.6 | 5.0 | 17.6 |
| VLλ germ-lines per 1000 clones | 9.7 | 0.5 | 4.4 | 9.3 |
| $VL_K$/VLλ ratio | 0.54 | 4.4 | 0.82 | 1.3 |

To enable a more detailed germ-line analysis of the input population and the clones that were selected using higher eukaryotic mammalian display on the basis of low, medium and high display levels, antibodies were assigned to their closest matching VH, VLκ and VLλ germ-lines and the frequency of occurrence of the germ-lines were calculated for each group. The results are shown in both tabular format (Tables 16, 17 and 18) and as histogram plots (FIGS. 42, 43 and 44). This indicated that in the populations sequenced, several germ-lines were either enriched or absent in the low or high display level groups, indicating that mammalian display selection on the basis of antibody display levels enables the selective enrichment of antibody germ-lines. For example, the IGHV3-23 and IGHV1-2 germ-lines were enriched by 105 and 9-fold respectively in the high display group compared with the low display group. The IGHV3-53, IGHV3-21 and IGHV4-34 germ-lines occurred at a frequency of 2.7%, 1.1% and 0.9% respectively in the high display group but were completely absent in the low display group. The IGHV3-23 germ-line is considered to be a well-behaved germ-line and is represented in several therapeutic antibodies that have been approved for clinical use including alirocumab, bevacizumab, certolizumab, daratumumab, denosumab, dupilumab, emicizumab, ocrelizumab, ranibizumab, and siltuximab. The IGHV3-21 and IGHV3-53 germ-lines are considered to be well-behaved have been included in human synthetic antibody library designs[12]. Five VH germ-lines were found to be enriched in the low display group: IGHV1-69D, IGH3-30, IGHV5-51, IGHV1-58 and IGH3-64D. Previously it has been observed that the IGH3-30 germ-line, when paired with certain light chains, is prone to self-interaction as determined by dynamic light scattering measurements[12].

Analysis of the frequency of occurrence of the antibody light chain germ-lines also showed enrichment of certain germ-lines in the high display group compared with the low display group. For example, IGKV1 D-13 and IGKV3-19 occurred at a frequency 3.5% and 6% respectively in the high display group but were completely absent in the low display group. The IGKV1-12, IGKV1-17, IGKV2-28, IGKV2D-29 and IGKV6-21 germ-lines were enriched by 11-, 22-, 6-, 11-, and 132-fold respectively in the high display group compared with the low display group. The IGKV2-28 and related germ-line IGKV2D-29 are considered to be well-behaved and is represented in several antibodies either approved for clinical use or under-going clinical evaluation including cantuzumab, dupilumab, lucatumumab, mogamulizumab, obinutuzumab, sevirumab, tenatumomab and zatuximab. Four VLκ germ-lines were found to be enriched in the low display group: IGKV1-16, IGKV1-33, IGKV2-30 and IGKV4-1. The VHλ germ-line analysis is less clear because of the domination of a single VHλ germ-line in the input population (IGLV3-19). Nevertheless the following VHλ germ-lines were enriched in the high display group: IGLV1-47, IGLV2-11, IGLV2-14, IGLV2-23, IGLV2-8, IGLV3-10 and IGLV6-57. The Vλ1-47 and Vλ2-14 light chains are known to be well behaved and have been included as the scaffold in synthetic library designs[12,128]. IGLV2-14 is the light chain present in the clinically approved anti-PCSK9 antibody Evolocumab which is a well behaved antibody[2]

This analysis enables the "binning" of human antibody germ-lines into either the mammalian display high or low display groups. It was previously shown that high level display correlates with well-behaved biophysical properties in terms of a low propensity for protein self-interaction (Example 3). Therefore, the observation of enrichment of certain germ-lines in the mammalian display high display level group is due to their inherent biophysical properties. Therefore, mammalian display enables the enrichment and identification of antibody germ-lines with well-behaved biophysical properties in terms of a low propensity for self-interaction.

TABLE 16

Variable heavy (VH) germ-line analysis of the anti- Mesothelin mammalian display selected clone populations. Antibodies were assigned to the closest matching human VH germ-line sequence and the frequency of occurrence in the input and low, medium and high mammalian display gated populations is shown. The last column shows a ratio of occurrence of the germ-lines for the high and low display level gated populations where germ-lines were found in both populations.

| | Frequency of occurrence (%) | | | | High/Low |
|---|---|---|---|---|---|
| VH | Input | Low | Medium | High | Ratio |
| IGHV1-18 | 1.9 | 8.1 | 1.8 | 3.5 | 0.43 |
| IGHV1-2 | 5.5 | 0.42 | 6.7 | 3.9 | 9.34 |
| IGHV1-3 | 3.0 | 13 | 5.6 | 4.3 | 0.34 |
| IGHV1-46 | 5.8 | 5.6 | 9.7 | 13 | 2.40 |
| IGHV1-58 | | 1.4 | 5.9 | 0 | 0.00 |
| IGHV1-69 | 9.3 | 28 | 2.1 | 12 | 0.44 |
| IGHV1-69D | 5.4 | 5.8 | 0 | 0.83 | 0.14 |
| IGHV2-70D | 0.18 | 0 | 0 | 0 | — |
| IGHV3-11 | 0.18 | 0 | 0 | 0.31 | — |
| IGHV3-20 | 61 | 17 | 54 | 47 | 2.75 |
| IGHV3-21 | 0.18 | 0 | 0 | 1.1 | — |
| IGHV3-23 | 1.1 | 0.04 | 0.57 | 4.2 | 104 |
| IGHV3-30 | 1.5 | 4.5 | 3.3 | 0.21 | 0.05 |
| IGHV3-33 | 0.71 | 1.1 | 2.4 | 4.2 | 3.9 |
| IGHV3-43 | 0.18 | 0.11 | 0.57 | 0 | — |
| IGHV3-48 | 0.09 | 0 | 0 | 0 | — |
| IGHV3-53 | 0.80 | 0 | 2.19 | 2.7 | — |
| IGHV3-64D | 0 | 0.84 | 0 | 0 | — |
| IGHV3-66 | 0 | 0 | 0.03 | 0 | — |
| IGHV3-7 | 0.09 | 0 | 0.03 | 0 | — |
| IGHV3-72 | 0.09 | 0 | 0 | 0 | — |
| IGHV4-34 | 0.09 | 0 | 0.16 | 0.93 | — |
| IGHV5-51 | 2.5 | 15 | 2.50 | 1.34 | — |
| IGHV6-1 | 0.18 | 0 | 2.32 | 0.21 | — |
| IGHV7-81 | 0.09 | 0 | 0.08 | 0 | 0.43 |

TABLE 17

Variable heavy ($VL_K$) germ-line analysis of the anti- Mesothelin mammalian display selected clone populations. Antibodies were assigned to the closest matching human $VL_K$ germ-line sequence and the frequency of occurrence in the input and low, medium and high mammalian display gated populations is shown. The last column shows a ratio of occurrence of the germ-lines for the high and low display level gated populations where germ-lines were found in both populations.

| | Frequency of occurrence (%) | | | | High/Low |
|---|---|---|---|---|---|
| $VL_K$ | Input | Low | Medium | High | Ratio |
| IGKV1-12 | 0.76 | 0.02 | 1.85 | 0.18 | 11 |
| IGKV1-13 | 0.25 | 0 | 0.75 | 0 | — |
| IGKV1-16 | 1.76 | 3.47 | 1.45 | 0.18 | 0.05 |
| IGKV1-17 | 0.50 | 0.02 | 0.41 | 0.36 | 22 |
| IGKV1-27 | 0.76 | 1.16 | 0.87 | 0.73 | 0.6 |
| IGKV1-33 | 1.76 | 7.14 | 2.72 | 1.28 | 0.18 |
| IGKV1-39 | 56.2 | 49.2 | 42.2 | 61.2 | 1.2 |
| IGKV1-5 | 3.02 | 0.70 | 4.05 | 0.18 | 0.26 |
| IGKV1-6 | 0 | 0.03 | 0 | 0 | — |
| IGKV1-8 | 0 | 0 | 0 | 0.18 | — |
| IGKV1-9 | 2.02 | 0.56 | 0.29 | 1.28 | 2.3 |
| IGKV1D-13 | 1.76 | 0 | 4.05 | 3.46 | — |
| IGKV1D-16 | 0.25 | 0.05 | 0.12 | 0 | — |
| IGKV2-24 | 0.25 | 0.07 | 0 | 0 | — |
| IGKV2-28 | 6.30 | 2.19 | 11.93 | 13.66 | 6.2 |
| IGKV2-30 | 3.02 | 4.19 | 5.50 | 0 | — |
| IGKV2D-29 | 0.25 | 0.05 | 0 | 0.55 | 11 |
| IGKV3-11 | 0.50 | 0 | 0.12 | 0 | — |

TABLE 17-continued

Variable heavy ($VL_K$) germ-line analysis of the anti- Mesothelin mammalian display selected clone populations. Antibodies were assigned to the closest matching human $VL_K$ germ-line sequence and the frequency of occurrence in the input and low, medium and high mammalian display gated populations is shown. The last column shows a ratio of occurrence of the germ-lines for the high and low display level gated populations where germ-lines were found in both populations.

| | Frequency of occurrence (%) | | | | High/Low |
|---|---|---|---|---|---|
| $VL_K$ | Input | Low | Medium | High | Ratio |
| IGKV3-15 | 6.30 | 4.39 | 10.19 | 3.64 | 0.83 |
| IGKV3-19 | 0 | 0 | 0 | 6.01 | — |
| IGKV3-20 | 1.26 | 0.40 | 4.00 | 1.09 | 2.7 |
| IGKV3D-15 | 0 | 0.02 | 0.06 | 0 | — |
| IGKV4-1 | 12.85 | 26.36 | 8.63 | 3.83 | 0.15 |
| IGKV6-21 | 0.25 | 0.02 | 0.87 | 2.19 | 131 |

TABLE 18

Variable heavy (VLλ) germ-line analysis of the anti- Mesothelin mammalian display selected clone populations. Antibodies were assigned to the closest matching human VLλ germ-line sequence and the frequency of occurrence in the input and low, medium and high mammalian display gated populations is shown. The last column shows a ratio of occurrence of the germ-lines for the high and low display level gated populations where germ-lines were found in both populations.

| | Frequency of occurrence (%) | | | | High/Low |
|---|---|---|---|---|---|
| VLλ | Input | Low | Medium | High | Ratio |
| IGLV1-40 | 0.14 | 0 | 0 | 0 | — |
| IGLV1-44 | 0.14 | 0 | 0.33 | 0 | — |
| IGLV1-47 | 0 | 0 | 0.28 | 0.72 | — |
| IGLV1-50 | 0 | 0 | 0.24 | 0 | — |
| IGLV2-11 | 1.09 | 0.07 | 0.24 | 2.63 | 36 |
| IGLV2-14 | 0.41 | 0 | 0.14 | 0.48 | — |
| IGLV2-18 | 0 | 0 | 0.09 | 0 | — |
| IGLV2-23 | 0 | 0 | 0.85 | 0.24 | — |
| IGLV2-8 | 0.14 | 0 | 0.19 | 1.67 | — |
| IGLV3-1 | 1.50 | 0.29 | 0.95 | 0 | — |
| IGLV3-10 | 0.14 | 0 | 0.47 | 1.43 | — |
| IGLV3-19 | 94.55 | 97.64 | 90.57 | 90.21 | 0.9 |
| IGLV3-21 | 0 | 0 | 0.09 | 0 | — |
| IGLV3-25 | 1.09 | 1.99 | 2.13 | 1.19 | 0.60 |
| IGLV3-27 | 0 | 0 | 0.24 | 0 | — |
| IGLV3-9 | 0.14 | 0 | 0.71 | 0 | — |
| IGLV5-45 | 0 | 0 | 0.05 | 0 | — |
| IGLV6-57 | 0.68 | 0 | 2.42 | 1.43 | — |

TABLE 19

Antibody clone cluster analysis for the anti-Mesothelin antibodies from the high, medium and low HEK293 cell display levels. Mammalian cell display selected anti-Mesothelin antibodies were pooled according to cell surface display level (Figure 31). The high (H), medium (M) and low (L)display level populations were DNA sequenced by PacBio NGS and the top 10 most abundant clones in each group were identified and are depicted in this table with the VH and VH CDR3 sequences shown in single letter amino acid code separated by a dash. Antibodies which were previously identified by Sanger sequencing of individual clones are assigned a clone name shown in the second column. The percentage abundance of each clone in the high, medium and low display groups is shown. The cells are shaded if an antibody is present in more than one display level group. Selected clones were expressed, purified and tested in an AC-SINS assay[40] and the wave-length shift (ΔAC-SINS) in nm is shown. HPLC-SEC retention volume is shown in the last column (nd, not done).

| Clone | Clone name | Display Group | VH-VL CDR3 | Heavy chain germline | Light chain germline | High Display (%) | Medium display (%) | Low Display (%) | Input (%) | ΔAC-SINS (nm) | HPLC-SEC Rentention Volume (ml) |
|---|---|---|---|---|---|---|---|---|---|---|---|
| 1 | 932_01_D10 | H | DSRPPYYGMDV (SEQ ID NO: 50)-MQALQTPPT (SEQ ID NO: 51) | IGHV1-69 | IGKV2-28 | **3.17** | **0.62** | 0.00 | 0.47 | 1 | nd |
| 2 | 932_01_C12 | H | DGRGGFDY (SEQ ID NO: 52)-QQFNSYHLLT (SEQ ID NO: 53) | IGHV3-43 | IGKV1-39 | 1.69 | 0.00 | 0.00 | 0.00 | 2.5 | 1.53 |
| 3 | 932_01_A03 | H | GRSSVIDYGMDV (SEQ ID NO: 54)-NSRDSSGNHVV (SEQ ID NO: 55) | IGHV3-20 | IGLV3-19 | **1.19** | **0.40** | 0.00 | 0.00 | 2 | 1.54 |
| 4 | N/A | H | DRVAATHYYYYGMDV (SEQ ID NO: 56)-QQSYGSPFT (SEQ ID NO: 57) | IGHV3-30 | IGKV1-39 | **1.09** | **0.20** | 0.00 | 0.00 | nd | nd |
| 5 | N/A | H | GLLEKGAFDI (SEQ ID NO: 58)-QQSYSTPQT (SEQ ID NO: 59) | IGHV1-46 | IGKV1-39 | 0.99 | 0.00 | 0.00 | 0.00 | nd | nd |
| 6 | N/A | H | DSRPPYYGMDV (SEQ ID NO: 60)-QQSYNSRPYT (SEQ ID NO: 61) | IGHV1-69 | IGKV2-28 | **0.79** | **0.07** | 0.00 | 0.00 | nd | nd |
| 7 | 932_01_A06 | H | TSPYSGSYNN (SEQ ID NO: 62)-SSYGGNYKYL (SEQ ID NO: 63) | IGHV4-34 | IGLV2-8 | 0.79 | 0.00 | 0.00 | 0.00 | 3 | 1.59 |
| 8 | 932_01_F02 | H | GLSSTWAGGAFDI (SEQ ID NO: 64)-NSRDSSGNHVV (SEQ ID NO: 65) | IGHV3-20 | IGLV3-19 | **0.69** | **1.52** | **0.02** | 1.41 | 2 | 1.54 |
| 9 | N/A | H | GAHSGYDSDFDY (SEQ ID NO: 66)-QQYNSYPLT (SEQ ID NO: 67) | IGHV1-18 | IGKV1-39 | **0.69** | 0.00 | **0.02** | 0.00 | nd | nd |
| 10 | 932_01_B01 | H | VSGSSNHAFDI (SEQ ID NO: 68)-HQSSSFPLT (SEQ ID NO: 69) | IGHV1-2 | IGKV1-2 | **0.69** | 0.00 | **0.02** | 0.00 | 1 | 1.55 |
| 11 | 931_01_F01 | M | DTSSRYAGGAFDI (SEQ ID NO: 70)-NSRDSSGNHVV (SEQ ID NO: 71) | IGHV1-69D | IGLV1-50 | **0.30** | **0.62** | 0.00 | 0.71 | 6 | 1.58 |
| 12 | 932_01_C04 | M | DTGSSARGGDFDY (SEQ ID NO: 72)-NSRDSSGNHVV (SEQ ID NO: 73) | IGHV3-20 | IGLV3-19 | **0.30** | **0.75** | **0.20** | 0.55 | 2 | 1.54 |

TABLE 19-continued

Antibody clone cluster analysis for the anti-Mesothelin antibodies from the high, medium and low HEK293 cell display levels. Mammalian cell display selected anti-Mesothelin antibodies were pooled according to cell surface display level (Figure 31). The high (H), medium (M) and low (L)display level populations were DNA sequenced by PacBio NGS and the top 10 most abundant clones in each group were identified and are depicted in this table with the VH and VH CDR3 sequences shown in single letter amino acid code separated by a dash. Antibodies which were previously identified by Sanger sequencing of individual clones are assigned a clone name shown in the second column. The percentage abundance of each clone in the high, medium and low display groups is shown. The cells are shaded if an antibody is present in more than one display level group. Selected clones were expressed, purified and tested in an AC-SINS assay[40] and the wave-length shift (ΔAC-SINS) in nm is shown. HPLC-SEC retention volume is shown in the last column (nd, not done).

| Clone | Clone name | Display Group | VH-VL CDR3 | Heavy chain germline | Light chain germline | High Display (%) | Medium display (%) | Low Display (%) | Input (%) | ΔAC-SINS (nm) | HPLC-SEC Rentention Volume (ml) |
|---|---|---|---|---|---|---|---|---|---|---|---|
| 13 | 931_01_B10 | M | DERYYGDMDV (SEQ ID NO: 74)-MQGLQTPRT (SEQ ID NO: 75) | IGHV1-69 | IGKV2-28 | **0.10** | **0.47** | 0.00 | 0.31 | nd | nd |
| 14 | 930_01_A01 | M | DYSSGWSGDAFDI (SEQ ID NO: 76)-NSRDSSGNHVV (SEQ ID NO: 77) | IGHV1-3 | IGKV1-39 | **0.10** | **0.40** | 0.39 | 0.08 | nd | nd |
| 15 | 931_01_B02 | M | RGTRGYYYYGMDV (SEQ ID NO: 78)-QQSYNSRPYT (SEQ ID NO: 79) | IGHV1-69D | IGKV1-39 | **0.10** | **0.65** | **3.63** | 2.36 | 23 | 1.61 |
| 16 | N/A | M | TNNGFIDY (SEQ ID NO: 80)-SQASHWPYT (SEQ ID NO: 81) | IGHV6-1 | IGKV2-30 | 0.00 | 1.12 | 0.00 | 0.08 | nd | nd |
| 17 | N/A | M | GRGRRYFDL (SEQ ID NO: 82)-QQSYSTPRT (SEQ ID NO: 83) | IGHV1-2 | IGKV1-39 | 0.00 | 0.55 | 0.00 | 0.00 | nd | nd |
| 18 | 931_01_E03 | M | DGDEGELGAFDI (SEQ ID NO: 84)-QQSYGSPFT (SEQ ID NO: 85) | IGHV1-46 | IGKV1-39 | 0.00 | 0.42 | 0.00 | 0.00 | nd | nd |
| 19 | 930_01_D09 | L | GDNNYYFDY (SEQ ID NO: 86)-QQYYSRPIT (SEQ ID NO: 87) | IGHV1-69 | IGKV4-1 | 0.00 | 0.00 | 1.88 | 0.00 | 5 | 1.55 |
| 20 | 930_01_A09 | L | ETGEGRWELLGY (SEQ ID NO: 88)-MQGTHWPRT (SEQ ID NO: 89) | IGHV1-46 | IGKV2-30 | 0.00 | 0.00 | 2.22 | 0.00 | 4 | nd |
| 21 | N/A | L | LSHTAPLVDY (SEQ ID NO: 90)-QQYSKWPLT (SEQ ID NO: 91) | IGHVS-51 | IGKV3-15 | 0.00 | **0.12** | **2.26** | 0.63 | nd | nd |
| 22 | 930_01_C02 | L | AIAPRRYYYGMDV (SEQ ID NO: 92)-QQSYSTPRT (SEQ ID NO: 93) | IGHV1-69 | IGKV1-39 | 0.00 | **0.22** | **2.65** | 1.18 | nd | nd |
| 23 | 930_01_A12 | L | AIAPRRYYYGMDV (SEQ ID NO: 94)-QQYNSYPLT (SEQ ID NO: 95) | IGHV1-69 | IGKV1-39 | 0.00 | 0.00 | 2.90 | 0.08 | 20 | 1.61 |
| 24 | 930_01_A08 | L | DGYNSDY (SEQ ID NO: 96)-QQYYSKPLT (SEQ ID NO: 97) | IGHV1-39 | IGKV1-33 | 0.00 | 0.00 | 3.70 | 0.00 | 1 | 1.55 |

TABLE 19-continued

Antibody clone cluster analysis for the anti-Mesothelin antibodies from the high, medium and low HEK293 cell display levels. Mammalian cell display selected anti-Mesothelin antibodies were pooled according to cell surface display level (Figure 31). The high (H), medium (M) and low (L)display level populations were DNA sequenced by PacBio NGS and the top 10 most abundant clones in each group were identified and are depicted in this table with the VH and VH CDR3 sequences shown in single letter amino acid code separated by a dash. Antibodies which were previously identified by Sanger sequencing of individual clones are assigned a clone name shown in the second column. The percentage abundance of each clone in the high, medium and low display groups is shown. The cells are shaded if an antibody is present in more than one display level group. Selected clones were expressed, purified and tested in an AC-SINS assay[40] and the wave-length shift (ΔAC-SINS) in nm is shown. HPLC-SEC retention volume is shown in the last column (nd, not done).

| Clone | Clone name | Display Group | VH-VL CDR3 | Heavy chain germline | Light chain germline | High Display (%) | Medium display (%) | Low Display (%) | Input (%) | ΔAC-SINS (nm) | HPLC-SEC Rentention Volume (ml) |
|---|---|---|---|---|---|---|---|---|---|---|---|
| 25 | 930_01_C07 | L | RRYNWDYDYVDV (SEQ ID NO: 98)-QQSYSTPRT (SEQ ID NO: 99) | IGHV5-51 | IGKV1-39 | 0.00 | 0.00 | 5.79 | 0.08 | 25 | 1.56 |
| 26 | 930_01_A05 | L | DKPVGSSGWYPFDY (SEQ ID NO: 100)-QQSYSTPYT (SEQ ID NO: 101) | IGHV1-3 | IGKV1-39 | 0.00 | 0.00 | 10.50 | 0.00 | nd | nd |
| 27 | 930_01_B02 | L | QINWGYYFDY (SEQ ID NO: 102)-MQALQTPPT (SEQ ID NO: 103) | IGHV1-69 | IGKV4-1 | 0.00 | 0.00 | 11.68 | 0.00 | 22 | 1.73 |

Cluster analysis was performed to generate a list of sequence unique VH and VL CDR3 clones with their frequency of occurrence for each of the four anti-Mesothelin antibody populations. The top 10 clones, by frequency of occurrence, are shown in Table 19 for the high, medium and low display level anti-Mesothelin antibodies FACS gated as depicted in FIG. 31. For comparison, the frequency of occurrence of the clones in the input and alternate populations is also shown. As was previously shown with a more limited clone set, there was no over-lap between the top 7 most abundant clones in the high display level group with the low display group. The 7 most abundant clones in the high display level group were completely absent in the low display level group. The 9 most abundant clones in the low display level group were completely absent in the high display level group. For the most abundant medium display level group there was some over-lap with the high and low display level groups: three clones were only present in the medium display level group, two clones were only present in the medium and high display level groups and three clones were present in all three display level groups. For clones originating from the high display level group where there was some over-lap with the low display level group (e.g. clones 8, 9 and 10) there was an enrichment of these clones in the high display level group by a factor of over 41-fold.

The binning of the antibodies into the high, medium and low display level groups according to their sequence indicates that separation based on eukaryotic cell antibody display level is due to the properties of that antibody as determined by their polypeptide sequences. The frequency of occurrence of antibodies as determined by PacBio NGS analysis agreed well with the results from sequencing a more limited set of clones by Sanger sequencing. By PacBio NGS 9, 8 and 6 of the top 10 most abundant clones in the low, medium and high display level groups had been previously identified by Sanger sequencing.

Selected antibodies from the high and low display level groups were then expressed and purified and their biophysical properties determined by AC-SINS[41] or HPLC-SEC. The AC-SINS results are shown in the penultimate column of Table 19. The average AC-SINS wavelength-shift of clones originating from the high or low display groups was 1.9 and 15.2 respectively. The significantly higher average AC-SINS wavelength shift observed from the clones originating from the low display level group compared with the high display level group indicates that the antibodies the low display level group are more prone to self-interaction and aggregation than the antibodies in the high display level group. Selected antibodies were also examined by HPLC-SEC. FIG. 45 shows an example of four clones: one from the high display group (932_01_A03) and three from the low display group (930_01_A12, 930_01_B02 and 930_01_C12) which were expressed and purified and analysed by HPLC-SEC. This shows that antibody 932_01_A03, isolated from the high display level group, is 96% monomeric. In contrast, the antibody 930_01_C12 is 82% monomeric with 18% dimer and also shows some retardation on the column with a later elution profile indicating some non-specific interaction with the column. This clone also included a small fragment (16 kDa molecular weight) indicating that it may have fragmented during expression or purification. Two additional clones from the low display group (930_01_A12, 930_01_B02) also displayed a delayed retention time on the column indicating that the antibodies were non-specifically absorbing to the column matrix. The HPLC-SEC retention volume (last column, Table 19) is a measure on non-specific antibody interacting with the column matrix. Here a larger retention volume can give rise to a broader HPLC-SEC peak and indicate non-specific interaction with the HPLC-SEC column matrix. The average HPLC-SEC retention volume in the high display group clones was 1.55 ml whereas the average HPLC-SEC retention volume in the low display group clones was 1.6 ml proving evidence that the clones in the low display group were more prone to non-specific HPLC-SEC column matrix interaction than the clones in the high display group. One clone in the low display level group (930_01_C07) precipitated after attempted concentration by ultra-filtration. A second clone in the low display level group failed expression and purification. None of the clones originating from the high display level group demonstrated any problems during their expression, purification and subsequent analysis. This included the ability to be concentrated by ultra-filtration to greater than 12 mg/ml in PBS (pH7.4).

Therefore, this example has exemplified that it is possible to use higher eukaryotic mammalian cell display to separate antibodies present within a complex mixture, including antibodies with different germ-line sequences, based upon their self-interaction and cross-interaction properties.

Example 11. Selecting Developable Clones on the Basis of Rapid Accumulation on Cell Surface In the examples above we have noted the relationship between constitutive antibody display level on the surface of a stable population of higher eukaryotic cells and the biophysical properties of that antibody. Here we also note display level differences are observed 24 hours after transfection. In Example 5, FIG. 10 we observed display level differences between Bococizumab and the parental antibody 5A10i at the 1-day post transfection (1 dpt) time point (FIG. 10, left panel). This initial rate of accumulation difference of displayed antibody correlates with the display levels differences in the stable cell lines (FIG. 10, right panel, 21 dpt) at equilibrium and the biophysical properties of the antibodies. It was shown in Example 5 that Bococizumab has high self-interaction and cross-interaction properties compared with the parental antibody 5A10-i as measured in the AC-SINS assay and HPLC-SEC. Bococizumab displayed at a lower level both at the 24-hour post transfection transient phase and the stable cell line phase, 21 days post-transfection (FIG. 10), compared with the parental antibody 5A10-i. Therefore, the initial transient antibody cell display level is predictive of the antibody cell display level in the stable cell line, created after several days of drug selection.

We have therefore shown a relationship between the rate of display of an antibody on the surface of a higher eukaryotic cell surface and the biophysical properties of the antibody. The demonstrated relationship between the initial transient display of antibodies and their biophysical properties will be useful for enriching antibodies with superior biophysical characteristics from a population or library of antibodies at an earlier stage compared with the generation of stable cell lines. It will also be useful for the screening of individual sets of antibodies by individual monoclonal transfection. Also differences in the initial rate of cell surface display of antibodies may be useful where antibody expression is regulated by an inducible promoter and selection of the population on the basis of cell surface display level is initiated post induction.

Example 12. Selection for Developability of IgG Based on Surface Presentation Level in CHO Cell Library IgG antibodies can be displayed on the surface of CHO cells, with the level of display correlating with the biophysical properties of the individual antibody including its propensity to self-interact and aggregate. In this Example we show antibody display on the surface of CHO cells after two alternative nuclease-mediated antibody gene integration methods, and we demonstrate that the level of display correlates with the biophysical properties of the displayed antibodies.

A gene targeting vector was designed and used for integration of an antibody gene expression cassette into intron 1 of the CHO AAVS gene, orthologous to the human AAVS genomic locus described in Example 1[93]. TALEN nucleases targeting intron 1 of the CHO AAVS gene locus created a double strand break at this location. For comparison, CRISPR/Cas9 nucleases were also tested in a parallel method.

Antibody display on CHO cells was successfully achieved using both the TALEN-directed and the CRISPR/Cas9-directed integration method. The best display levels were achieved using the TALEN nuclease pair or the CRISPR 1 design. The alternative CRISPR designs (CRISPR 2 and CRISPR 3) were also successful although slightly lower levels of antibody display were observed. FIG. 48.

We further demonstrated that the cell surface levels of antibodies displayed on CHO cells correlated with the biophysical characteristics of the displayed antibody, mirroring the results seen with HEK293 cells. Selected antibodies were cloned into the pINT17-BSD-CHO targeting vector: MEDI-1912, MEDI-1912-STT, bococizumab, 884_01_G01.

MEDI-1912 (anti-NGF) has poor biophysical properties in terms of its propensity to self aggregate[7]. Reduced cell surface display levels were observed on the CHO cells for MEDI-1912 compared with the solubility enhanced daughter clone MEDI1012-STT. 884_01_G01 is a derivative of bococizumab and was identified by mutagenesis and mammalian display selection on the basis of display level and retained binding to PCSK9 (Example 5). 884_01_G01 was previously shown to be "well behaved" in terms of giving a low AC-SINS score and a monomeric peak by HPLC-SEC. Reduced CHO cell surface display levels were also observed for bococizumab compared with the improved daughter clone 884_01_G01. FIG. 49.

The example therefore confirms the utility of CHO cells for the display of antibodies and the differentiation of antibodies with different biophysical properties based on their cell surface display levels. The antibodies with different biophysical properties are able to be well separated by flow cytometry, enabling the isolation of antibodies with better biophysical properties by CHO cell display within complex mixtures.

Materials & Methods

DNA encoding the CHO AAVS left and right homology arms was PCR amplified from suspension adapted CHO cell line genomic DNA, isolated from CHO cells with primer pairs 3165/3166 and 3169/3170 (Table 20) to generate PCR products of sizes 1.2 kb and 1.35 kb respectively. These PCR products were then used as templates to generate the left and right CHO AAVS homology arms while simultaneously knocking out various restriction site required for subsequent antibody gene cloning. The CHO left AAVS homology arm was created, with mutation of the existing NcoI, NheI, NsiI and DraIII sites by PCR amplification with the PCR primer pairs 3195/3196; 3197/3198; 3199/3200 using the CHO AAVS left arm template described above to create three PCR products with sizes of 241 bp, 576 bp and 142 bp respectively. The fragments were then assembled using primers 3199 and 3196 (Table 20) to generate a product of 893 bp in size. An additional assembly PCR reaction was performed except that primer 3123 was employed in place of 3196 to give a slightly shorter AAVS-left homology arm (880 bp). The reason for generating this slightly shorter left homology arm is to avoid the CRISPR 2 and 3 design recognition sites within the targeting vector (FIG. 46). The assembled AAVS left homology arms were digested with AsiSI and NsiI restriction enzymes and cloned into the pINT17-BSD vector pre-cut with AsiSI and NsiI. To PCR amplify the CHO AAVS homology arm and knock-out the BclI restriction two separate PCR reactions were performed with primer pairs 3201/3202 and 3203/3204 to create PCR products of sizes 707 bp and 208 bp respectively which were then PCR assembled with primers 3201 and 3204 to generate a PCR product of size 900 bp. The assembled AAVS right homology arms were digested with BstZ171 and SbfI restriction enzymes and cloned into the pINT17-BSD vector pre-cut with BstZ171 and SbfI and then cloned into BstZ171 and SbfI cut pINT17-BSD cut vector which already harboured the left CHO AAVS homology arm. This then created the CHO targeting vector pINT17-BSD-CHO, which is identical to pINT17-BSD (FIG. 1) except that the human AAVS homology arms have been replaced by CHO AAVS homology arms.

TABLE 20

Primer sequences to enable amplification of the CHO AAVS left and right homology arms and knock-out the restriction sites and CRISPR guide RNA primers. Restriction sites are underlined and mutations to knock out NheI, NcoI, BclI and DraIII restriction sites shown in bold.

| Name | Primer sequence | Description |
|---|---|---|
| 3165 | GGTGCTCGACTCCACCAA (SEQ ID NO: 104) | CHO-AAVS-Left-F |
| 3166 | GATGGAAGTTGCCATGAAAGA (SEQ ID NO: 105) | CHO-AAVS-Left-R |
| 3169 | TCTTGTATTGCCGGGATCCTTC (SEQ ID NO: 106) | CHO-AAVS-Right-F |
| 3170 | TAACTCCCAGCCCTACCTACTC (SEQ ID NO: 107) | CHO-AAVS-Right-R |
| 3195 | CTCCACCTACCACC**T**CATGGACTATATTTG (SEQ ID NO: 108) | CHO-AAVS-left-F1-exNcoI |
| 3196 | TTTTTTATGCATCTTATGCCAGCTTTTGGATGACGG (SEQ ID NO: 109) | CHO-AAVS-left-R1-exNsiI |
| 3197 | CTCCTCTGAG**T**CTAGCCAGGCC (SEQ ID NO: 110) | CHO-AAVS-left-F2-exNheI |
| 3198 | CAAATATAGTCCATG**A**GGTGGTAGGTGGAG (SEQ ID NO: 111) | CHO-AAVS-left-R2-exNcoI |
| 3199 | TTTTTTGCGATCGCGATGGCTTACA**T**CCCGTGCCTTTC (SEQ ID NO: 112) | CHO-AAVS-left-F3 + AsiS1-exDraIII |
| 3200 | GGCCTGGCTAG**A**CTCAGAGGAG (SEQ ID NO: 113) | CHO-AAVS-left-R3-exNheI |
| 3201 | TATATTGTATACGGCGCGCCTGTCAGGGACAAGATTAGTCACAG (SEQ ID NO: 114) | CHO-AAVS-right-F4-exBstZ171 + AscI |
| 3202 | GACTTTGGTGATAATGTGAGCAGC (SEQ ID NO: 115) | CHO-AAVS-right-R4-ex-BclI |
| 3203 | GCTGCTCACATTATCACCAAAGTC (SEQ ID NO: 116) | CHO-AAVS-right-F5-ex-BclI |
| 3204 | TATATTCCTGCAGGCTCCTGCAAAGGCCTGAAGAG (SEQ ID NO: 117) | CHO-AAVS-right-R5 + SbfI |
| 3213 | TTTTTTATGCATCTTGATGACGGGGAGATAAAAGCATC (SEQ ID NO: 118) | CHO-AAVS-left-R1 + NsiI-CRISPR2 + 3 |
| 3201 | TATATTGTATACGGCGCGCCTGTCAGGGACAAGATTAGTCACAG (SEQ ID NO: 119) | CHO-AAVS-right-F4 + BstZ171 + AscI |
| 3202 | GACTTTGGTGATAATGTGAGCAGC (SEQ ID NO: 120) | CHO-AAVS-right-R4-ex-BclI |
| 3203 | GCTGCTCACATTATCACCAAAGTC (SEQ ID NO: 121) | CHO-AAVS-right-F5-ex-BclI |
| 3204 | TATATTCCTGCAGGCTCCTGCAAAGGCCTGAAGAG (SEQ ID NO: 122) | CHO-AAVS-right-R5 + SbfI |

TABLE 20-continued

Primer sequences to enable amplification of the CHO AAVS left and right homology arms and knock-out the restriction sites and CRISPR guide RNA primers. Restriction sites are underlined and mutations to knock out NheI, NcoI, BclI and DraIII restriction sites shown in bold.

| Name | Primer sequence | Description |
|---|---|---|
| 3213 | TTTTTTATGCATCTTGATGACGGGGAGATAAAAGCATC (SEQ ID NO: 123) | CHO-AAVS-left-R1 + NsiI-CRISPR2 + 3 |
| 3220 | GGAATCATGGGAAATAGGCCCT (SEQ ID NO: 124) | CRISPR1-R-vector |
| 3221 | CGCTCACAATTCCACACAACAT (SEQ ID NO: 125) | CRISPR1-F-vector |
| 3222 | AGGGCCTATTTCCCATGATTCC (SEQ ID NO: 126) | CRISPR-seqR |
| 3223 | ATGTTGTGTGGAATTGTGAGCG (SEQ ID NO: 127) | CRISPR-seqR |

A TALEN pair was designed to recognise the CHO AAVS locus which recognised the TAL target sequences: TCCCCGTCATCCAAAAGC (SEQ ID NO: 128) and TCTGCTGTGACTAATCTT (SEQ ID NO: 129) as shown in FIG. 46. For comparison against site-specific DNA cleavage by TALEN, we also tested the performance of an alternative nuclease—the nucleic acid guided nuclease CRISPR/Cas9. Three CRISPR/Cas9 guide RNAs were designed to target the CHO AAVS locus, and the recognition sequences are shown in FIG. 46.

The nucleic acid sequence of the CHO AAVS homology arms cloned into the targeting vector is shown in FIG. 47. Synthetic geneblocks were designed encoding the U6 RNA polymerase promoter guide RNA and tracrRNA and PCR amplified with primers 3222 and 3223 (Table 21). The CRISPR/Cas9 vector (A21177, Geneart) was PCR amplified with primers 3220/3221 to generate a 9375 bp product. This was then assembled with the three CRISPR geneblocks (Table 20) using the NEB Builder (New England Biolabs), to generate the three CRISPR/Cas9 vectors encoding the three guide RNAs depicted in FIG. 46.

TABLE 21

Geneblock sequences encoding the CHO CRISPR sequences. The CHO CRISPR guide and tracrRNA sequences are shown in bold and italics respectively. The U6 RNA polymerase promoter is shown underlined.

| CHO CRISPR | Geneblock sequence |
|---|---|
| 1 | AGGGCCTATTTCCCATGATTCCTTCATATTTGCATATACGATACAAGGCTGTTAGAGAGATAATTAGAATTAATTTGACTGTAAACACAAAGATATTAGTACAAAATACGTGACGTAGAAAGTAATAATTTCTTGGGTAGTTTGCAGTTTTAAAATTATGTTTTAAAATGGACTATCATATGCTTACCGTAACTTGAAAGTATTTCGATTTCTTGGCTTTATATATCTTGTGGAAAGGACGAAACACCG**ATCCAAAAGCTGGCATTGTC**G*TTTTAGAGCTAGAAATAGCAAGTTAAAATAAGGCTAGTCCGTTATCAACTTGAAAAAGTGGCACCGAGTCGGTGCTTTT*TTCTAGTATACCGTCGACCTCTAGCTAGAGCTTGGCGTAATCATGGTCATAGCTGTTTCCTGTGTGAAATTGTTATCCGCTCACAATTCCACACAACAT (SEQ ID NO: 130) |
| 2 | AGGGCCTATTTCCCATGATTCCTTCATATTTGCATATACGATACAAGGCTGTTAGAGAGATAATTAGAATTAATTTGACTGTAAACACAAAGATATTAGTACAAAATACGTGACGTAGAAAGTAATAATTTCTTGGGTAGTTTGCAGTTTTAAAATTATGTTTTAAAATGGACTATCATATGCTTACCGTAACTTGAAAGTATTTCGATTTCTTGGCTTTATATATCTTGTGGAAAGGACGAAACACCG**TCTCCCCGTCATCCAAAAGC**G*TTTTAGAGCTAGAAATAGCAAGTTAAAATAAGGCTAGTCCGTTATCAACTTGAAAAAGTGGCACCGAGTCGGTGCTTTT*TTCTAGTATACCGTCGACCTCTAGCTAGAGCTTGGCGTAATCATGGTCATAGCTGTTTCCTGTGTGAAATTGTTATCCGCTCACAATTCCACACAACAT (SEQ ID NO: 131) |
| 3 | AGGGCCTATTTCCCATGATTCCTTCATATTTGCATATACGATACAAGGCTGTTAGAGAGATAATTAGAATTAATTTGACTGTAAACACAAAGATATTAGTACAAAATACGTGACGTAGAAAGTAATAATTTCTTGGGTAGTTTGCAGTTTTAAAATTATGTTTTAAAATGGACTATCATATGCTTACCGTAACTTGAAAGTATTTCGATTTCTTGGCTTTATATATCTTGTGGAAAGGACGAAACACCG**ATGCCAGCTTTTGGATGACG**G*TTTTAGAGCTAGAAATAGCAAGTTAAAATAAGGCTAGTCCGTTATCAACTTGAAAAAGTGGCACCGAGTCGGTGCTTTT*TTCTAGTATACCGTCGACCTCTAGCTAGAGCTTGGCGTAATCATGGTCATAGCTGTTTCCTGTGTGAAATTGTTATCCGCTCACAATTCCACACAACAT (SEQ ID NO: 132) |

The targeting vector pINT17-BSD-CHO with either the 893 bp or 880 bp AAVS left homology arms (named V1 or V2 respectively) harbouring the Nivolumab antibody heavy and light chain genes was used to transfect Freestyle CHO—S cells (Thermo Fisher Scientific) in the absence or presence of plasmids encoding either the CHO AAVS TAL-1F and CHO AAVS TAL-1R TALEN pair (M3770, Thermo Fisher Scientific) or the CRISPR/Cas9 with CHO AAVS specific guide RNAs and subject to blasticidin drug selection (7.5 μg/ml). The transfection method was as described in Example 2 for the TALEN transfection. For the CRISPR/Cas9 transfection a CRISPR/Cas9, pINT17-BSD-CHO plasmid DNA ratio of 10:1 was employed. Cells were stained with anti-Fc PE 14 days post transfection (dpt). Fluorescence intensity (anti-Fc) was plotted against cell count.

The heavy and light chain genes of two antibody pairs were cloned into the CHO targeting vector pINT17-BSD-CHO with the 893 bp AAVS left homology arms (FIG. 47): the anti-NGF antibodies MEDI-1912 or MED-1912-STT[7] or anti-PCSK9 Bococizumab or the Bococizumab derivative clone 884_01_G01 (see Example 5). The resultant targeting vectors were used to transfect Freestyle CHO-S cells (Thermo Fisher Scientific) in the presence of plasmids encoding the CHO AAVS TAL-1F and CHO AAVS TAL-1R TALEN pair (M3770, Thermo Fisher Scientific) and subject to blasticidin drug selection (7.5 μg/ml). 15 dpt cells were stained with anti-Fc-PE as described in Example 2. 15 dpt CHO cells displaying the antibodies were purified by anti-Fc-PE MACS and stained with anti-Fc PE. Fluorescence intensity (anti-Fc) was plotted against CHO cell count.

Example 13. Creation of a "Developability Enhanced" Population Using Mammalian Display for Subsequent Binding Selection Example 10 demonstrates that a population of clones pre-selected on antigen (in this example from phage display selection) can be further resolved based on different presentation levels which in turn correlate with biophysical properties. As described elsewhere binding to polyreactivity probes could also be used to identify and remove clones with polyreactivity properties. Thus, problematic clones that might otherwise be selected for further characterisation or development can be eliminated.

In example 10 the antibody population was initially selected based on binding properties (using phage display in this example) followed by subsequent selection based on biophysical properties. It is also possible to reverse the order of selection and generate a population of clones that have been selected for optimal biophysical properties based on presentation level in higher eukaryotes or binding to polyreactive probes. For example, a display library of binders could be made in mammalian cells or other higher eukaryotes and selected for presentation level using an agent that binds to a constant region of the binders so that all binders can be equally labelled independent of their sequence. For example, where the binders are IgG antibodies, cells may be contacted with a detectable agent that binds to the IgG Fc region, e.g., a labelled anti-IgG antibody. A fraction of the population showing presentation level higher than the mode or median can then be selected e.g. by flow cytometry. For example, the top 5%, 10% or 25% of clones based on presentation level can be selected in one or more rounds of sorting using methods described herein. This will create a "developability enhanced" population of binders which can be used for subsequent selection based on binding to different antigens.

Using the approach of example 10, a large phage display library of $4\times10^{10}$ clones was selected to generate a sub-population of binders which were then incorporated into a mammalian display library for selection based on presentation level. One potential disadvantage of reversing the order i.e. preselecting for biophysical properties in higher eukaryotes prior to selection of binders is that the creation of a large library in mammalian cells is more laborious and costly than creating a library for use with in vitro systems such as ribosome display or bacterial systems (e.g. phage display). Thus, if a starting mammalian display library of $10^7$ clones for example is used and the top 10% selected based on presentation level then the potential diversity of the library to be used for subsequent selection for antigen binding will be reduced e.g. to $10^6$ clones reducing the likelihood of selecting high affinity binders. An alternative strategy is to pre-select components of the library in mammalian display e.g. in the case of an antibody separately selected for optimal VH and optimal VL components and then and then recombining them to benefit from the combinatorial diversity.

Thus in one branch a mammalian display library may be created with antibodies in an IgG or scFv format containing a single or limited selection of VLs and a large diversity of VH chains to select optimal VH genes. The single or limited partner VL gene(s) may be randomly chosen or chosen based on poor biophysical properties with a view to selecting VH genes which rescue the poor biophysical properties of the partner chain. Alternatively, a VL gene with good biophysical properties may be chosen to identify and remove those VH genes which compromise presentation levels. Using the same numbers as the example above a library of $10^7$ clones with VH diversity may be created and the top 10% of VH genes selected based on presentation level potentially generating $10^6$ selected VH clones. In a parallel branch a single or limited number of VH genes may be combined with a diversity of VL genes to select optimal VL genes. The combinatorial diversity of bring the different selected VH and VL genes together will be significantly higher than the number of individual selected chains. Thus selecting the top $10^6$ VH and the top $10^6$ VL genes in each branch creates a potential combinatorial diversity of $10^{12}$ variants. The selected VH and VL domains may be presented within any display system allowing selection for target binding including phage display, ribosome display, yeast display and display on higher eukaryotes. In this way selection for optimal biophysical properties using the present invention may be used to generate a "developability enhanced" library within other display systems. For example a phage display library which is pre-disposed to yield clones with optimal biophysical properties.

In a further example of the above approach the selection for optimal biophysical properties may be directed to regions within an individual domain. For example, a VH domain includes 3 different complementary determining region (CDR1, CDR2 and CDR3) and biophysical liabilities may be caused by sequences within individual CDR or combination of CDRs. For example the CDR1 and 2 regions of VH genes a non-immunised antibody repertoire may be recovered combined with a single or limited number of VH CDR3 regions and VL partner chains and the resulting antibody population, with diversity focused within CDR1 and 2 selected for optimal biophysical property. The selected CDR1 and 2 regions can then be combined with a diversity of CDR3 segments and VL segments which may be unselected or may have been selected for optimal biophysical properties in a similar way. The potential combinatorial diversity increases by this "shuffling" approach. The example above describes selection for optimal biophysical properties on CDR 1 and CDR2 segments but it will be obvious how the same approach can be used with different CDR regions alone or in combination. In some case the input library to be selected for optimal biophysical properties may be a naïve library from a non-immunised source or from diversification of a starting scaffold. Alternatively, the input library may be diversified library based on an input starting clone or selection of clones with a view to improving biophysical properties potentially alongside affinity.

In each case the approaches described above will use standard molecular biology techniques known to those skilled in the art. In addition, methods for the construction and use of libraries, including chain shuffled libraries are also set out in WO2015/166272 (Iontas Limited), the content of which is incorporated herein by reference. Combining different regions within a VH or VL domain will benefit from the use of optimal PCR primers to amplify individual regions within VH and VL domains. Germline sequences of antibody VH and VL genes are readily available e.g. the IMGT database[132] allowing design of such primers. Furthermore examples in WO2017/118761 (Iontas Limited) describe methods for introducing diversity and combining different CDR regions to re-constitute an intact VH:VL combination.

The example below is used for illustration. Diversity was introduced into the VH CDR3 and VL CDR3 of an initial PD1 binding antibody clone and the resulting population selected for optimal presentation on mammalian cells. The same approach could be taken to introduce diversity into other starting frameworks and other CDRs including the CDR 1 and 2 of germline encoded genes. For example, Table 16 identifies germline genes that frequently appear in populations selected for high levels of presentation on mammalian cells e.g. IGHV1-2, IGHV3-23 and IGKV6-21 and these may be chosen as starting frameworks for further diversification and selection for developability. Similarly sub-regions for binding domains other than antibodies may be identified for separate selection for optimal biophysical properties.

By way of example an anti-PD1 antibody (337_1_C08) which blocked the interaction of PD-1 with PD-L1 was identified by phage display (FIG. 50*a*). The affinity ($K_D$) of 337_1_C08 for PD-1 is 74 nM. This was used to create a mutagenised library with diversification focused on VH CDR3 and VL CDR3. A variety of methods for diversification are known to those skilled in the art. Diversification for example may involve creation of a mutagenic library by saturation mutagenesis where randomizing codons such as NNS (encoding all 20 amino acids within 32 codons) are used. An alternative is to retain sequence information while exploring the surrounding sequence space. To achieve this oligonucleotides were designed to a continuous stretch of 8 amino acids in the CDR3 of VH and VLs such that every possible 2-mer and 1-mer variant, using all amino acids (with the exception of cysteine) were included (FIG. 50*a*).

Thus, the library was designed to retain at least 6 of the original 8 amino acids in each CDR3 region. It was possible to accomplish this by synthesis of 9216 oligonucleotides directed to each of VH CDR3 or VL CDR3. Geneblocks of the VH and VL where every 2-mer amino acid variation was encompassed within an 8-amino acid window (9216 variants) were synthesised by TWIST Biosciences. The presence of all 9216 oligonucleotides in each set was confirmed by high throughput sequencing (Twist Bioscience). The VH gene was amplified using the primer pairs primers Forward: 5'-CTTTCTCTCCACAGGCGCCCATGGCCGAAGTGCAGCC-3' (SEQ ID NO: 133) and Reverse: 5'-TTTTTTCTCGAGACGGTGACCAGGGTTC-3' (SEQ ID NO: 134). The VL gene was amplified using the primer pairs primers Forward: 5'-TTTTTTGCTAGCTCCTATGAGCTGACTC-3' (SEQ ID NO: 135) and Reverse: 5'-GTCACGCTTGGTGCGGCCGCGGGCTGACCTAG-3' (SEQ ID NO: 136). A "stuffer" fragment encoding the constant light (CL) and CMV promote was PCR amplified from the pINT17-BSD vector using the primer pair Forward: 5'-GGCCGCACCAAGCGTGAC-3' (SEQ ID NO: 137) and Reverse: 5'-GGCGCCTGTGGAGAGAAAG-3' (SEQ ID NO: 138). The three gene fragments were first assembled in a "mock" PCR with no amplification primers to ensure no bias introduced by partial assembly and subsequent amplification. The mock PCR was performed by mixing the three PCR products above at an equimolar ratio (90 nM each) and performing a PCR reaction with the KOD Hot Start Master Mix (Sigma, 71842) according to the manufacturer's instructions with an annealing temperature of 60° C. and elongation temperature of 68° C. (45 s). The assembled product was subsequently amplified using the primer pairs primers Forward: 5'-TTTTTTGCTAGCTCCTATGAGCTGACTC-3' (SEQ ID NO: 139) and Reverse: 5'-TTTTTTCTCGAGACGGTGACCAGGGTTC-3' (SEQ ID NO: 140). The assembled anti-PD-1 VH and VL CDR3 library was digested with NheI and XhoI restriction enzymes and cloned into the pINT17-BSD targeting vector and by electroporation of E. cloni 10G SUPREME Electrocompetent Cells (Lucigen cat #60081-1), a library size of $1.1\times10^8$ was created, as determined by counting individual kanamycin resistant colonies on agar plates plated with dilutions of the transformation mix. Transfection quality plasmid DNA was prepared and used to co-transfect HEK293 suspension cells ($1.35\times10^9$ cells) by Maxcyte electroporation with TALE AAVS left and right arm nucleases to enable single copy antibody gene integration. The efficiency of gene targeting was 0.8%, as determined by counting blasticidin resistant colony forming units (CFUs) in dilution plates post transfection, to yield a mammalian display library size of 10.8 million. The library was propagated for 7 days under blasticidin selection and then selected by anti-Fc MACS to remove clones which were not expressing IgG.

Figure 50B:
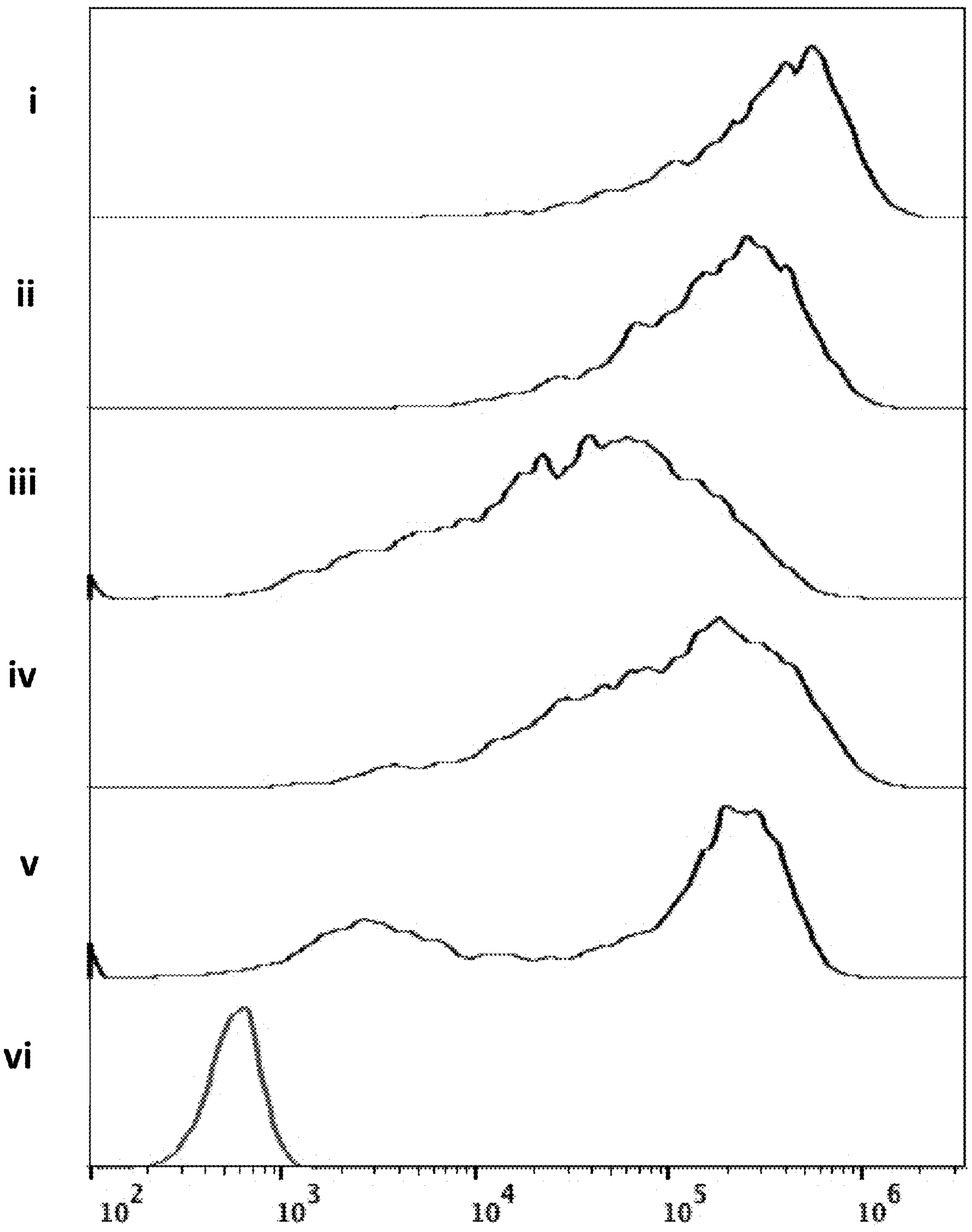

As described in example 10, the population of Fc positive cells were separated by flow cytometry on the basis of expression level using binding of a fluorescently labelled anti-Fc antibody (FIG. 50*b*). The separate populations were cultured for several days and re-analysed for Fc expression. FIG. 50*b* shows that distinct sub-populations with different modal values for expression have been generated. This including a population with inferior presentation levels as well as a population with presentation levels equivalent to the parental. As described in example 10, antibody genes can be recovered from these cells to generate a sub-population with optimal biophysical properties. In this example cells were sorted on the basis of biophysical properties only but it is also possible to conduct a selection based on antigen binding together or in sequence.

Example 14. Display of Bi-Specific Antibodies on the Surface of Mammalian Cells Bi-specific antibodies or alternative formats (reviewed by Spiess et al, 2015[129]) have enabled new therapeutic mechanisms of action (MOA), not previously possible with mono-specific antibodies or proteins. Examples of the use of bi-specific therapeutics include redirecting the cytotoxic activity of T-cells as cancer therapeutics, enabling the crossing of the blood-brain barrier, blocking two signalling pathways simultaneously and the tissue specific delivery or activity of antibodies[130]. Bi-specific formats can face the same developability hurdles as traditional mono-specific antibodies in terms of their propensity for self or cross-interaction properties. It is an advantage to screen the final format of a bi-specific moiety because each binding region can have different properties which may either compensate or compound its self-interaction or cross-interaction properties. These properties may not be apparent when screening the individual binding "arms" of a bi-specific because avidity can increase the affinity for off-target molecules such as heparin sulphate by several orders of magnitude. The property of self-interaction may also be different for a bi-specific molecule compared to its individual binding regions because the overall surface properties such as hydrophobicity may change. Bi-specific antibody (bsAb) formats can exist in many different forms[129], but can be broadly grouped into: IgG-like bsAbs such as κ/λ-bodies[131], common light chain, knobs-into-holes[132], charge pair and crossmab format[130]; fragment based bsAbs such as BiTE format, appended IgGs such as DVD-IgGs or antibodies engineered to possess additional binding regions in their constant domains such as Fcab or mAb2 format[133]. However, the alteration of the structural framework of the CH3 domain of Fcabs was found to reduce their thermal stability[134] and additional engineering of the Fcab molecule was required to increase their developability[134]. In this example, we demonstrate that higher eukaryotic mammalian display can be applied to the display of bi-specific antibodies by displaying the bi-specific antibody Emicizumab on the surface of HEK293 cells and showing that this can bind the antigens FIXa and FX.

Emicizumab is a bi-specific antibody generated using the heavy chain "knobs into holes" technology with a common light chain described previously[132] which was developed to treat haemophilia and acts as a Factor VIII mimetic[135]. One arm of Emicizumab is specific to Factor IXa (FIXa) and the second arm is specific to Factor X (FX). A tri-cistronic targeting vector was constructed by cloning the Emicizumab anti-FIXa heavy chain, anti-FX heavy chain and common light chain genes (Table 22) into the inducible targeting vector pINT17-Tet. The common light chain gene including the downstream poly-adenylation (pA) site was cloned into the BglII and NheI restriction sites of pINT17-Tet. The anti-FIXa heavy chain gene including the PDGFR transmembrane domain was cloned between the NcoI and HindIII restriction sites of pINT17-Tet. The anti-FX heavy chain gene including the signal peptide, PDGFR transmembrane domain and SV40 pA was cloned between the EcoRI and BstZ171 restriction sites of pINT17-Tet. The final vector (pINT17-Bi-CMV-Emicizumab) contained coding sequences between the AAVS homology arms. FIG. 51. The Emicizumab anti-FIXa and VL genes were also cloned into the pINT17-BSD targeting vector to enable display of a monospecific anti-FIXa IgG antibody.

To demonstrate HEK293 cell surface display of the bi-specific antibody Emicizumab pINT17-Bi-CMV-Emicizumab or pINT17-BSD-anti-FIXa was used to transfect HEK293 cells in the presence of plasmids encoding the AAVS TALENs as described above. 24 hours post transfection the cells were analysed for antibody display with anti-Fc-APC (FIG. 52). This showed that HEK293 cells transfected with the mono-specific anti-FIXa arm in IgG format or the bi-specific antibody Emicizumab had detectable antibody expression on the cell surface. However, the expression of the bi-specific Emicizumab with "knobs-in-holes" heavy chains was reduced compared to the standard mono-specific antibody format. It is envisaged that through the creation of a library of Fc variants followed by selection for high level expression by mammalian display that Fc variants could be selected to enable more efficient heterologous heavy chain pairing and increased cell display levels. In this way, new antibody CH2 or CH3 variants or a combination of CH2 and CH3 variants could be selected that are both more efficient in heterologous heavy chain pairing to create bi-specific antibodies but also would have superior developability properties including a low propensity to self-aggregate. The Fc variant libraries could also be screened for a low propensity to cross-interact with other molecules.

The ability of the displayed bi-specific Emicizumab to bind its target antigens was also demonstrated by flow cytometry. FIXa and FX (Complement Technology Inc) were chemically biotinylated (EZ-Link Sulfo-NHS-Biotin, ThermoFisher Scientific). Since the affinity of Emicizumab for FIXa and FX is relative low ($K_D$ in the micro-molar range[136]). The antigens were pre-conjugated with tetrameric streptavidin-PE, to increase the binding avidity, prior to cell staining at an antigen complex concentration of 100 nM. HEK293 cells displaying the bi-specific Emicizumab were shown to bind both FIXa and FX with no binding to unconjugated streptavidin-PE (FIG. 52*a*). This demonstrates functional display of a bi-specific antibody on the surface of HEK293 cells. Display of the mono-specific anti-FIXa arm in IgG format on the surface of HEK293 cells also bound to FIXa (FIG. 52*b*). The anti-FIXa antibody also showed some binding to FX, although to a lower level than Emicizumab and this may be due either to the common light chain or the anti-FIXa heavy chain cross-reacting with FX.

Example 6b described the differential binding of heparin sulphate to the anti-IL12 antibodies briakinumab and ustekinumab displayed on the surface of HEK293 cells. Briakinumab has a positive charge patch within its variable domain, which is likely to contribute to its binding a negative charge patch on FcRn[22]. The positive charge patch on briakinumab is also likely to be the cause of it its cross-interaction with negatively charge heparin sulphate. Binding of antibodies to heparin sulphate can lead to increased non-specific clearance in vivo resulting in a decreased half-life[137,138]. Therefore, the binding of antibodies or therapeutic proteins, including bi-specific molecules, to heparin is an undesired property. Example 6b demonstrated that it is possible to differentiate antibodies that bind heparin sulphate and so it will be possible to separate and eliminate heparin sulphate binding proteins by higher eukaryotic mammalian display selection. From the data presented in this example, it would be possible to envisage the demonstration of differentiation a series of anti-FIXa/anti-FX bi-specific antibodies on the basis of their ability to bind heparin sulphate.

During the course of development of Emicizumab, a precursor humanised antibody was discovered named hBS106[136]. This molecule was found to have poor pharmacokinetics in mice with rapid clearance and short in vivo half-life compared with human IgG4. This rapid clearance in vivo was attributable to a positive charge patch on the VH and VL anti-FIXa arm. The amino acids on the common light chain contributing to the positive charge patch included K24, R27 and R31 within VL CDR1 and R53 and R54 within VL CDR2 and R61 within FW3 (FIG. 53). VH amino acids contributing to the positive charge patch included R60 and R95. The lysine and arginine residues contributing to the positive charge patch were paratopic residues indispensable for FIXa binding. Therefore, negatively charged amino acid residues (glutamate or aspartate) were introduced to disrupt the positive charge patches and also lower the isoelectric point (pI) of the antibody. The introduction of negatively charged amino acid changes in the common light chain resulted in an 8-fold reduction in clearance rate in mice and an almost 6-fold increase in maximal in vivo plasma concentration (Cmax). FIG. 53 shows an alignment of the common VL chain of Emicizumab with a series of precursor VLs (US 2016/0222129) which have three to one less negative charge amino acids compared with the final Emicizumab VL. The naming of the Emicizumab parental antibodies are relative to Emicizumab. For example, the clone: E30Y_E55Y_D93S has tyrosine, tyrosine and serine residue at positions 30, 55 and 93 in place of glutamate, glutamate and aspartate respectively relative to Emicizumab.

Emicizumab pre-cursor VL anti-FIXa genes (Table 23) could be cloned into the pINT17-Bi-CMV-Emicizumab targeting vector nd this used to co-transfect HEK293 cells with the human AAVS TALEN pair as described above to enable nuclease mediated antibody gene integration. After 14 dpt, HEK293 cells could be stained with heparin sulphate (FITC labelled) and anti-Fc-PE as described in Example B. Flow cytometry analysis would show that the mammalian cell displayed anti-FIXa Emicizumab clones E30Y_K54R_E55Y_D93S and E30Y_E55Y_D93S would display enhanced binding to heparin sulphate compared with anti-FIXa Emicizumab and the E30Y VL clone. The E30Y_K54R_E55Y_D93S and E30Y_E55Y_D93S clones possess the most intact positive charge patch and these clones would result in detectable heparin sulphate binding to cells displaying these antibodies. This example has shown how it would be possible to use higher eukaryotic mammalian display to differentiate between clones with point mutation differences in their ability to bind to heparin sulphate. This will enable the elimination of bi-specific clones within a complex library that bind heparin sulphate and therefore remove clones that possess positive charge patches within their variable domains which may contribute to poor pharmacokinetics in vivo.

This example has illustrated the potential of bi-specific antibody or alternative bi-specific format screening by mammalian display. The number of variants required to be screened in a bispecific discovery campaign is multiplied by several orders of magnitude compared to a single target antibody discovery project. For example, to identify the lead starting molecule in the Emicizumab discovery campaign 200 anti-FIXa antibodies were crossed with 200 anti-FX antibodies to create 40,000 bi-specific molecules that were then screened by laborious plate based screening. The lead bi-specific molecule then had to proceed through several iterations including humanisation, affinity and specificity optimisation and developability enhancement regarding reducing cross-interaction with heparin sulphate by the disruption of variable domain positive charge patches[136]. The ability to perform multi-dimensional FACS on millions of bi-specific antibody clones by mammalian display including affinity for the target(s), specificity, display level (to screen for a low propensity to self-aggregate) and cross-interaction would enable a faster, more efficient bi-specific antibody screening process on a greater number of clones with a greater screening depth.

TABLE 22

Emicizumab heavy and light chain genes. Variable and PDGFR transmembrane domain encoding regions are highlighted in italic and bold respectively. Restriction sites are underlined.

| Gene | Gene sequence |
|---|---|
| Emicizumab VL-CL | TAATAAGCTAGCAGAGGA*GACATCCAGATGACACAGA*<br>*GCCCTAGCAGCCTGTCTGCCAGCGTGGGAGACAGAGT*<br>*GACCATCACATGCAAGGCCAGCCGGAACATCGAGAGA*<br>*CAGCTGGCCTGGTATCAGCAGAAGCCTGGACAGGCTC*<br>*CTGAGCTGCTGATCTATCAGGCCAGCAGAAAAGAAAG*<br>*CGGCGTGCCCGATAGATTCAGCGGCAGCAGATACGGC*<br>*ACCGACTTCACCCTGACAATATCCAGCCTCCAGCCTG*<br>*AGGATATCGCCACC*TACTACTGCCAGCAGTACAGCGA<br>CCCTCCACTGACATTTGGCGGAGGCACCAAGGTGGAA<br>ATCAAGCGGACAGCGGCCGCCCCTAGCGTGTTCATCT |

TABLE 22-continued

Emicizumab heavy and light chain genes. Variable and PDGFR transmembrane domain encoding regions are highlighted in italic and bold respectively. Restriction sites are underlined.

| Gene | Gene sequence |
|---|---|
| | TTCCACCTAGCGACGAGCAGCTGAAGTCTGGCACAGC<br>CTCTGTCGTGTGCCTGCTGAACAACTTCTACCCCAGA<br>GAAGCCAAGGTGCAGTGGAAGGTGGACAACGCCCTCC<br>AGAGCGGCAATAGCCAAGAGAGCGTGACCGAGCAGGA<br>CAGCAAGGACTCTACCTACAGCCTGAGCAGCACACTG<br>ACCCTGAGCAAGGCCGACTACGAGAAGCACAAAGTGT<br>ACGCCTGCGAAGTGACCCACCAGGGCCTTTCTAGCCC<br>TGTGACCAAGAGCTTCAACCGGGGCGAATGTTAATAA<br>TCTAGAGCCTCGACTGTGCCTTCTAGTTGCCAGCCAT<br>CTGTTGTTTGCCCCTCCCCCGTGCCTTCCTTGACCCT<br>GGAAGGTGCCACTCCCACTGTCCTTTCCTAATAAAAT<br>GAGGAAATTGCATCGCATTGTCTGAGTAGGTGTCATT<br>CTATTCTGGGGGGTGGGGTGGGGCAGGACAGCAAGGG<br>GGAGGATTGGGAAGACAATAGCAGGCATGCTGGGGAA<br>GATCTTAATAA<br>(SEQ ID NO: 141) |
| Emicizumab anti-FIXa VH-CH1-CH2-CH3 | TTATTAGCCATG*GCCCAGGTGCAGCTGGTTGAATCTG*<br>*GCGGAGGACTGGTTCAGCCTGGCGGATCTCTGAGACT*<br>*GTCTTGTGCCGCCAGCGGCTTCACCTTCAGCTACTAC*<br>*GATATCCAGTGGGTCCGACAGGCCCCTGGCAAAGGAC*<br>*TTGAATGGGTGTCCAGCATCAGCCCCTCTGGCCAGTC*<br>*CACCTACTACCGGCGAGAAGTGAAGGGCAGATTCACC*<br>*ATCAGCCGGGACAACAGCAAGAACACCCTGTACCTGC*<br>*AGATGAACAGCCTGAGAGCCGAGGACACCGCCGTGTA*<br>*CTACTGCGCCAGAAGAACCGGCAGAGAGTACGGCGGA*<br>*GGCTGGTACTTTGATTACTGGGGCCAGGGCACCCTGG*<br>*TCACAGT*CTCGAGCGCCTCTACAAAGGGCCCCAGCGT<br>TTTCCCACTGGCTCCCTGTAGCAGAAGCACCAGCGAA<br>TCTACAGCCGCTCTGGGCTGCCTGGTCAAGGACTACT<br>TTCCTGAGCCTGTGACCGTGTCCTGGAACTCTGGCGC<br>TCTGACATCTGGCGTGCACACCTTTCCAGCCGTGCTG<br>CAAAGCAGCGGCCTGTACAGTCTGAGCAGCGTCGTGA<br>CAGTGCCTAGCAGCTCTCTGGGCACCCAGACCTACAC<br>CTGTAATGTGGACCACAAGCCTAGCAACACCAAGGTG<br>GACAAGCGCGTGGAATCTAAGTACGGCCCTCCTTGTC<br>CTCCATGTCCTGCACCTGAGTTTCTCGGCGGACCCTC<br>CGTGTTCCTGTTTCCTCCAAAGCCTAAGGACACCCTG<br>ATGATCTCCAGAACACCCGAAGTGACCTGCGTGGTGG<br>TGGACGTTTCACAAGAGGACCCCGAGGTGCAGTTTAA<br>TTGGTACGTGGACGGCGTGGAAGTGCACAACGCCAAG<br>ACCAAGCCTAGAGAGGAACAGTACAACAGCACCTACA<br>GAGTGGTGTCCGTGCTGACAGTGCTGCACCAGGATTG<br>GCTGAACGGCAAAGAGTACAAGTGCAAGGTGTCCAAC<br>AAGGGCCTGCCAAGCAGCATCGAGAAAACCATCAGCA<br>AGGCCAAGGGCCAGCCTAGGGAACCCCAGGTTTACAC<br>ACTGCCTCCAAGCCAGAAAGAGATGACCAAGAACCAG<br>GTGTCCCTGACCTGCCTCGTGAAGGGCTTCTACCCTT<br>CCGATATCGCCGTGGAATGGGAGAGCAATGGCCAGCC<br>AGAGAACAACTACAAGACCACACCTCCTGTGCTGGAC<br>AGCGACGGCTCATTCTTCCTGTACAGCAAGCTGACCG<br>TGGACAAGAGCAGATGGCAAGAGGGCAACGTGTTCAG<br>CTGCAGCGTGATGCACGAGGCCCTGCACAACAGATAC<br>ACCCAGAAGTCCCTGTCTCTGAGCCCCGAACAAAAAC<br>TCATCTCAGAAGAGGATCTG**AATGCTGTGGGCCAGGA**<br>**CACGCAGGAGGTCATCGTGGTGCCACACTCCTTGCCC**<br>**TTTAAGGTGGTGGTGATCTCAGCCATCCTGGCCCTGG**<br>**TGGTGCTCACCATCATCTCCCTTATCATCCTCATCAT**<br>**GCTTTGGCAGAAGAAGCCACGTTAGTAA**AAGCTTTTA<br>TTA<br>(SEQ ID NO: 142) |
| Emicizumab anti-FX VH-CH1-CH2-CH3 | TTATTAGAATTCAACATGGACTGGACCTGGAGGGTCT<br>TCTGCTTGCTGGCTGTAGCTCCAGGTAAAGGGCCAAC<br>TGGTTCCAGGGCTGAGGAAGGGATTTTTTCCAGTTTA<br>GAGGACTGTCATTCTCTACTGTGTCCTCTCCGCAGGT<br>GCTCACTCC*CAGGTTCAGCTGGTGCAGTCTGGCAGCG*<br>*AGCTGAAAAAACCTGGCGCCTCCGTGAAGGTGTCCTG*<br>*CAAGGCTTCTGGCTACACCTTTACCGACAACAACATG*<br>*GACTGGGTCCGACAGGCCCCTGGACAAGGACTTGAGT*<br>*GGATGGGCGACATCAACACCAGAAGCGGCGGCAGCAT*<br>*CTACAACGAAGAGTTCCAGGACAGAGTCATCATGACC*<br>*GTGGACAAGAGCACCGACACCGCCTACATGGAACTGA* |

TABLE 22-continued

Emicizumab heavy and light chain genes. Variable and PDGFR transmembrane domain encoding regions are highlighted in italic and bold respectively. Restriction sites are underlined.

| Gene | Gene sequence |
|---|---|
| | *GCAGC*CTGAGAAGCGAGGACACCGCCACCTATCACTG<br>CGCCAGAAGAAAGAGCTACGGCTACTACCTGGACGAG<br>TGGGGCGAGGGAACACTGGTCACAGTGTCTAGCGCCA<br>GCACAAAGGGCCCTAGCGTTTTCCCACTGGCTCCCTG<br>TAGCAGAAGCACCAGCGAATCTACAGCCGCTCTGGGC<br>TGCCTCGTGAAGGACTACTTTCCTGAGCCTGTGACCG<br>TTAGCTGGAACAGCGGAGCACTGACAAGCGGCGTGCA<br>CACATTTCCAGCCGTGCTGCAAAGCAGCGGCCTGTAC<br>TCTCTGAGCAGCGTCGTGACAGTGCCTAGCAGCTCTC<br>TGGGCACCCAGACCTACACCTGTAATGTGGACCACAA<br>GCCTAGCAACACCAAGGTGGACAAGCGCGTGGAATCT<br>AAGTACGGCCCTCCTTGTCCTCCATGTCCTGCTCCAG<br>AGTTTCTCGGCGGACCCTCCGTGTTCCTGTTTCCTCC<br>AAAGCCTAAGGACACCCTGATGATCTCCAGAACACCC<br>GAAGTGACCTGCGTGGTGGTGGACGTTTCACAAGAGG<br>ACCCCGAGGTGCAGTTCAATTGGTACGTGGACGGCGT<br>GGAAGTGCACAACGCCAAGACCAAGCCTAGAGAGGAA<br>CAGTACAACAGCACCTACAGAGTGGTGTCCGTGCTGA<br>CAGTGCTGCACCAGGATTGGCTGAACGGCAAAGAGTA<br>CAAGTGCAAGGTGTCCAACAAGGGCCTGCCAAGCAGC<br>ATCGAGAAAACCATCAGCAAGGCCAAGGGCCAGCCTA<br>GGGAACCCCAGGTTTACACACTGCCTCCAAGCCAAGA<br>GGAAATGACCAAGAACCAGGTGTCCCTGACCTGCCTG<br>GTCAAGGGCTTCTACCCTTCCGATATCGCCGTGGAAT<br>GGGAGAGCAATGGCCAGCCAGAGAACAACTACAAGAC<br>CACACCTCCTGTGCTGGACAGCGACGGCTCATTCTTC<br>CTGTACAGCAAGCTGACTGTGGATAAGAGCCGGTGGC<br>AAGAGGGCAACGTGTTCAGCTGTAGCGTGATGCACGA<br>GGCCCTGCACAACCACTACACCCAAGAGAGCCTGTCT<br>CTGAGCCCTGAACAAAAACTCATCTCAGAAGAGGATC<br>TG**AATGCTGTGGGCCAGGACACGCAGGAGGTCATCGT**<br>**GGTGCCACACTCCTTGCCCTTTAAGGTGGTGGTGATC**<br>**TCAGCCATCCTGGCCCTGGTGGTGCTCACCATCATCT**<br>**CCCTTATCATCCTCATCATGCTTTGGCAGAAGAAGCC**<br>**ACGTTAGTAA**CTAAGTCGACATCCAGACATGATAAGA<br>TACATTGATGAGTTTGGACAAACCACAACTAGAATGC<br>AGTGAAAAAAATGCTTTATTTGTGAAATTTGTGATGC<br>TATTGCTTTATTTGTAACCATTATAAGCTGCAATAAA<br>CAAGTTAACAACAACAATTGCATTCATTTTATGTTTC<br>AGGTTCAGGGGGAGGTGTGGGAGGTTTTTTAAAGCAA<br>GTAAAACCTCTACAAATGTGGTATGGCTGATTATGAT<br>CCTGCAAGCCTCGTCGTCCTGGCCGGACCACGCTATC<br>TGTGCAAGGTCCCCGGCCCCGGACGCGCGCTCCATGA<br>GCAGAGCGCCCGCCGCCGAGGCGAAGACTCGGGCGGC<br>GCCCTGCCCGTCCCACCAGGTCAACAGGCGGTAACCG<br>GCCTCTTCATCGGGAATGCGCGCGACCTTCAGCATCG<br>CCGGCATGTCCCCCTGGCGGACGGGAAGTATGTATAC<br>TTATTA<br>(SEQ ID NO: 143) |

TABLE 23

VL and VH synthetic geneblock DNA sequences of the anti-FIXa Emicizumab and Emicizumab parental antibodies. Emicizumab parental antibodies are named by the single letter amino acid substitutions relative to Emicicuzumab. For example, parental antibody Emicizumab VL E30Y indicates that Emicizumab glutamate is replaced by tyrosine at position 30. Changes relative to the final Emicizumab VL are highlighted in bold. Flanking restriction sites are underlined.

| Gene | Gene sequence |
|---|---|
| Emicizumab anti-FIXa VH | TTATTAGCCATGGCCCAGGTGCAGCTGGTTGAATCT<br>GGCGGAGGACTGGTTCAGCCTGGCGGATCTCTGAGA<br>CTGTCTTGTGCCGCCAGCGGCTTCACCTTCAGCTAC<br>TACGATATCCAGTGGGTCCGACAGGCCCCTGGCAAA<br>GGACTTGAATGGGTGTCCAGCATCAGCCCCTCTGGC |

TABLE 23-continued

VL and VH synthetic geneblock DNA sequences of the anti-FIXa Emicizumab and Emicizumab parental antibodies. Emicizumab parental antibodies are named by the single letter amino acid substitutions relative to Emicicuzumab. For example, parental antibody Emicizumab VL E30Y indicates that Emicizumab glutamate is replaced by tyrosine at position 30. Changes relative to the final Emicizumab VL are highlighted in bold. Flanking restriction sites are underlined.

| Gene | Gene sequence |
|---|---|
| | CAGTCCACCTACTACCGGCGAGAAGTGAAGGGCAGA<br>TTCACCATCAGCCGGGACAACAGCAAGAACACCCTG<br>TACCTGCAGATGAACAGCCTGAGAGCCGAGGACACC<br>GCCGTGTACTACTGCGCCAGAAGAACCGGCAGAGAG<br>TACGGCGGAGGCTGGTACTTTGATTACTGGGGCCAG<br>GGCACCCTGGTCACAGTCTCGAGTTATTA<br>(SEQ ID NO: 144) |
| Emicizumab VL | TTATTAGCTAGCGACATCCAGATGACACAGAGCCCT<br>AGCAGCCTGTCTGCCAGCGTGGGAGACAGAGTGACC<br>ATCACATGCAAGGCCAGCCGGAACATCGAGAGACAG<br>CTGGCCTGGTATCAGCAGAAGCCTGGACAGGCTCCT<br>GAGCTGCTGATCTATCAGGCCAGCAGAAAAGAAAGC<br>GGCGTGCCCGATAGATTCAGCGGCAGCAGATACGGC<br>ACCGACTTCACCCTGACAATATCCAGCCTCCAGCCT<br>GAGGATATCGCCACCTACTACTGCCAGCAGTACAGC<br>GACCCTCCACTGACATTTGGCGGAGGCACCAAGGTG<br>GAAATCAAGCGGACAGCGGCCGCTTATTA<br>(SEQ ID NO: 145) |
| Emicizumab VL E30Y | TTATTAGCTAGCGACATCCAGATGACACAGAGCCCT<br>AGCAGCCTGTCTGCCAGCGTGGGAGACAGAGTGACC<br>ATCACATGCAAGGCCAGCCGGAACATC**TAT**AGACAG<br>CTGGCCTGGTATCAGCAGAAGCCTGGACAGGCTCCT<br>GAGCTGCTGATCTATCAGGCCAGCAGAAAA**TAT**AGC<br>GGCGTGCCCGATAGATTCAGCGGCAGCAGATACGGC<br>ACCGACTTCACCCTGACAATATCCAGCCTCCAGCCT<br>GAGGATATCGCCACCTACTACTGCCAGCAGTACAGC<br>GACCCTCCACTGACATTTGGCGGAGGCACCAAGGTG<br>GAAATCAAGCGGACAGCGGCCGCTTATTA<br>(SEQ ID NO: 146) |
| Emicizumab VL E30Y E55Y | TTATTAGCTAGCGACATCCAGATGACACAGAGCCCT<br>AGCAGCCTGTCTGCCAGCGTGGGAGACAGAGTGACC<br>ATCACATGCAAGGCCAGCCGGAACATC**TAT**AGACAG<br>CTGGCCTGGTATCAGCAGAAGCCTGGACAGGCTCCT<br>GAGCTGCTGATCTATCAGGCCAGCAGAAAAGAAAGC<br>GGCGTGCCCGATAGATTCAGCGGCAGCAGATACGGC<br>ACCGACTTCACCCTGACAATATCCAGCCTCCAGCCT<br>GAGGATATCGCCACCTACTACTGCCAGCAGTACAGC<br>GACCCTCCACTGACATTTGGCGGAGGCACCAAGGTG<br>GAAATCAAGCGGACAGCGGCCGCTTATTA<br>(SEQ ID NO: 147) |
| Emicizumab VL E30Y E55Y D935 | TTATTAGCTAGCGACATCCAGATGACACAGAGCCCT<br>AGCAGCCTGTCTGCCAGCGTGGGAGACAGAGTGACC<br>ATCACATGCAAGGCCAGCCGGAACATC**TAT**AGACAG<br>CTGGCCTGGTATCAGCAGAAGCCTGGACAGGCTCCT<br>GAGCTGCTGATCTATCAGGCCAGCAGAAAA**TAT**AGC<br>GGCGTGCCCGATAGATTCAGCGGCAGCAGATACGGC<br>ACCGACTTCACCCTGACAATATCCAGCCTCCAGCCT<br>GAGGATATCGCCACCTACTACTGCCAGCAGTACAGC<br>**AGC**CCTCCACTGACATTTGGCGGAGGCACCAAGGTG<br>GAAATCAAGCGGACAGCGGCCGCTTATTA<br>(SEQ ID NO: 148) |
| Emicizumab VL E30Y K54R E55Y D935 | TTATTAGCTAGCGACATCCAGATGACACAGAGCCCT<br>AGCAGCCTGTCTGCCAGCGTGGGAGACAGAGTGACC<br>ATCACATGCAAGGCCAGCCGGAACATC**TAT**AGACAG<br>CTGGCCTGGTATCAGCAGAAGCCTGGACAGGCTCCT<br>GAGCTGCTGATCTATCAGGCCAGCAGA**AGATAT**AGC<br>GGCGTGCCCGATAGATTCAGCGGCAGCAGATACGGC<br>ACCGACTTCACCCTGACAATATCCAGCCTCCAGCCT<br>GAGGATATCGCCACCTACTACTGCCAGCAGTACAGC |

TABLE 23-continued

VL and VH synthetic geneblock DNA sequences of the anti-FIXa Emicizumab and Emicizumab parental antibodies. Emicizumab parental antibodies are named by the single letter amino acid substitutions relative to Emicicuzumab. For example, parental antibody Emicizumab VL E30Y indicates that Emicizumab glutamate is replaced by tyrosine at position 30. Changes relative to the final Emicizumab VL are highlighted in bold. Flanking restriction sites are underlined.

| Gene | Gene sequence |
|---|---|
| | **AGC**CCTCCACTGACATTTGGCGGAGGCACCAAGGTG GAAATCAAGCGGACAGCGGCCGCTTATTA (SEQ ID NO: 149) |

Example 15. Selection for Developability of KnotBodies Based on Surface Presentation Level Example 14 demonstrated that it is possible to display the "knobs-in holes" bi-specific antibody Emicizumab on the surface of HEK293 cells. Bi-specific molecules can also be created by the fusion of polypeptides to antibody heavy or light chains or engineering of the heavy or light chains to confer novel binding specificities[133]. The ability to display bi-specific molecules on the surface of mammalian cells will enable screening for binding to both targets combined with selecting for bi-specific molecules with well-behaved biophysical properties as described above. A KnotBody is a novel antibody fusion format where a cysteine rich peptide (knottin) is incorporated into a peripheral CDR loop of an antibody domain (WO2017/118761) and the VH or VL domain is available to bind a second epitope on the same antigen or on a different antigen. The aim of this example was to demonstrate the ability of mammalian display technology to differentiate and separate KnotBodies that have different properties regarding their self-interaction and polyreactivity properties.

The KnotBody patent WO2017/118761, described the generation of two trypsin binding KnotBodies (KB_A07 and KB_A12) by inserting the trypsin binding knottin EETI-II into the VL CDR2 position of antibodies. The KnotBodies tested in this example were KB_A12 ProTx-III 2 M (hereafter referred as KB_A12 ProTx-III) and KB_A12 HsTx1. These KnotBodies were created by replacing the EETI-II knottin at the VL CDR2 position of KB_A12 KnotBody with ion channel blocking knottins or toxin peptides ProTx-III 2 M (PCT/EP2018/068855 filed 11 Jul. 2018) and HsTxI (PCT/EP2018/068856 filed 11 Jul. 2018). The VL sequences of KB_A12 EETI-II, KB_A12 ProTx-III and KB_A12 HsTx1 are shown in

TABLE 24

KnotBody VL sequences. The knottin with linker amino acids inserted in the CDR2 is highlighted in bold

| KnotBody | KnotBody VL sequence |
|---|---|
| KB_A12 EETI-II | QSVLTQPPSVSEAPRQRVTITCSGSSSNIGNNAVNWYQ QLPGKAPKLLIYAAGR**CPRILMRCKQDSDCLAGCVCGP NGFCG**ANSGVSDRFSAAKSGTSASLAINGLRSEDEADY YCAAWDDSLNGYVFGTGTKLTVLG (SEQ ID NO: 150) |
| KB_A12 ProTx-III | QSVLTQPPSVSEAPRQRVTITCSGSSSNIGNNAVNWYQ QLPGKAPKLLIYAAGR**GCLKFGWKCNPRNDKCCSGLKC** |

TABLE 24-continued

KnotBody VL sequences. The knottin with linker amino acids inserted in the CDR2 is highlighted in bold

| KnotBody | KnotBody VL sequence |
|---|---|
| | **GSNHNWCKWHI**GANSGVSDRFSAAKSGTSASLAINGLR SEDEADYYCAAWDDSLNGYVFGTGTKLTVLG (SEQ ID NO: 151) |
| KB_A12 HsTxI | QSVLTQPPSVSEAPRQRVTITCSGSSSNIGNNAVNWYQ QLPGKAPKLLIYAAGR**ASCRTPKDCADPCRKETGCPYG KCMNRKCKCNRC**ANSGVSDRFSAAKSGTSASLAINGLR SEDEADYYCAAWDDSLNGYVFGTGTKLTVLG (SEQ ID NO: 152) |

Genes encoding the knotBodies KB_A12 EETI-II, ProTx-III and HsTxI were cloned into the targeting vector pINT17-BSD and this was used to create stable cell lines by nuclease mediated gene integration into HEK293 cells as described above. FIG. 54*a* shows that the display level of KB_A12 EETI-II on the surface of HEK293 cells was higher than KB_A12 ProTx-III or KB_A12 HsTxI. KB_A12 ProTx-III or KB_A12 HsTxI displayed on the surface of HEK293 cells at a relatively low level and the flow cytometry histogram plots of cell count against Fc expression (FIG. 54*a*) are equivalent. The knotBodies were expressed by transient transfection of Expi293 cells, purified by Protein A affinity chromatography and analysed by HPLC-SEC. FIG. 54*b* shows that KB_A12 EETI-II displayed a monomeric peak with an equivalent retention time and volume as the well behaved anti-HER2 antibody Trastuzumab (FIG. 54*c*). In contrast, KB_A12 ProTx-III showed evidence of dimer and multimer formation as illustrated by an earlier retention time (FIG. 54*d*). The larger elution volume of KB_A12 ProTx-II compared with Trastuzumab and KB_A12 EETI-II is evidence of KB_A12 ProTx-III heterogeneous multimer and aggregate formation. KB_A12 ProTx-III and KB_A12 HsTxI also displayed an increased propensity to self-interact compared to KB_A12 EETI-II in an AC-SINS assay (Table 25)[39] where KB_A12 ProTx-III and KB_A12 HsTxI displayed longer AC-SINS wavelength shifts compared to KB_A12 EETI-II. Therefore, as seen previously with IgG display, there is a relationship between the higher eukaryotic cell display levels of the knotBody and their biophysical properties of propensity to self-interact and aggregate. The knotBody is an example of a bi-specific antibody and therefore this relationship between higher eukaryote cell display level and biophysical properties of the displayed molecule will likely transfer to alternative bi-specific modalities[129].

TABLE 25

AC-SINS scores of purified knotBodies[39].

| KnotBody | AC-SINS score |
|---|---|
| KB_A12 EETI-II | 3 |
| KB_A12 ProTx III | 10 |
| KB_A12 HsTx I | 20 |

In order to improve the biophysical properties of these KnotBodies, three KnotBody mammalian libraries were created by targeted mutagenesis of hydrophobic or positively charged residues in the knottin sequences. Hydrophobic or positively charged residues for targeted mutagenesis on each knottin is highlighted in bold and underlined (see below). These residues were mutated using primers encoding VNS codons (represented as X in the amino acid sequence) or NSG codons (represented as Z in the amino acid sequence). VNS codons (V=A/C/G, N=A/G/CT and S=G/C) encode 16 amino acids (excludes cysteine, tyrosine, tryptophan, phenylalanine and the stop codons) from 23 codon combinations, whilst NSG codons (N=A/G/C/T and S=G/C) encode 7 amino acids (arginine, tryptophan, glycine, threonine, serine, alanine and proline) from 8 codon combinations. NSG codons are used in positions where the wild-type tryptophan residue may be involved in binding contacts to the ion channel.

Wild type ProTx-III knottin sequence, with residues targeted for mutagenesis in bold and under-lined:

(SEQ ID NO: 153)
GCLKFGWKCNPRNDKCCSGLKCGSNHNWCKWHI

ProTx-III sequence in KB A12 ProTx-III Set-A Library:

(SEQ ID NO: 154)
GCXXXXZKCNPRNDKCCSGLKCGSNHNWCKWHI

ProTx-III sequence in KB A12 ProTx-III Set-B Library:

(SEQ ID NO: 155)
GCXXXXZKCNPRNDKCCSGLXCGSNHNWCKZXX

Wild type HsTx1 knottin sequence, with residues targeted for mutagenesis in bold and under-lined:

(SEQ ID NO: 156)
ASCRTPKDCADPCRKETGCPYGKCMNRKCKCNRC

HsTx1 sequence in KB A12 HsTx-I library:

(SEQ ID NO: 157)
ASCRTPKDCADPCXXETGCPYGKCXNRXCKCNRC

The libraries were generated by a two-fragment assembly PCR of KnotBody VL genes. Individual fragments for each library was amplified using primers and templates described in Table 26. The amplified fragments corresponding to each library were assembled using primers pINT BM40 Lead Fwd and pINT CLambda Not Rev. All primer sequences are given in Table 27. Assembled PCR fragments were digested using NheI and NotI restriction enzymes and ligated into pINT17-blasticidin vector encoding D1A12 or D12 VH (the heavy chain used for the KnotBody constructs, described in WO2017/118761). The ligation products were purified using MinElute PCR purification kit (Qiagen, Cat. no. 28004). 3×2.5 μl of the purified ligation mix was electroporated into 3×50 μl of *E. coli* cells (E. cloni 10 G Supreme, Lucigen, Cat. No. 60080-2). Briefly, 50 μl of cells were pulsed using a 0.1 cm cuvette, recovered with 2 ml recovery medium and grown for 1 h at 37° C., 250 rpm and the library seizes were estimated by dilution plating. The library sizes obtained for KB_A12 ProTx-III Set-A, KB_A12 ProTx-III Set-B and KB_A12 HsTx1 libraries were $9\times10^7$, $7\times10^7$ and $2\times10^7$ respectively. In order to create mammalian display libraries, transfection quality DNA were prepared from these library stocks using Macherey Nagel Midi prep kit (Macherey Nagel, Cat. No. 740410.10), following manufactures instructions.

TABLE 26

Primers used for amplifying Fragment 1 and Fragment 2 for the libraries.

| Library | Fragment 1 forward primer | Fragment 1 reverse primer | Fragment 2 forward primer | Fragment 2 reverse primer |
|---|---|---|---|---|
| KB_A12 HsTx1 | pINT BM40 Lead Fwd | HsTx1 Part 1 Rev | HsTx1 Part 2 Fwd | pINT CLambda Not rev |
| KB_A12 ProTx-III Set-A | pINT BM40 Lead Fwd | ProTx-III Part1 Rev | ProTx-III Part 2 Fwd | pINT CLambda Not rev |
| KB_A12 ProTx-III Set-B | pINT BM40 Lead Fwd | ProTx-III setB Part 1 Rev | ProTx-III setB Part 2 fwd | pINT CLambda Not rev |

TABLE 27

Sequences of the primers used.

| Primer Name | Primer Sequence (5'-3') |
|---|---|
| HsTx1 Part 1 Rev | ACAGGGGTCCGCGCAGTCTTTAGGAGTTCG (SEQ ID NO: 158) |
| HsTx1 Part 2 Fwd | CCTAAAGACTGCGCGGACCCCTGTVNSVNSGAGACTGGATGTCCATACGGTAAGTGCVNSAATAGAVNSTGCAAATGTAACCGATGCGCAAACAGT (SEQ ID NO: 159) |
| ProTx-III Part1 Rev | CATCCCCTTCCCGCTGCGTAAATGAGAAG (SEQ ID NO: 160) |
| ProTx-III Part 2 Fwd | CTCATTTACGCAGCGGGAAGGGGATGCVNSVNSVNSVNSNSGAAATGCAACCCAAGAAACGATAAA (SEQ ID NO: 161) |
| ProTx-III setB Part 1 Rev | GAGTCCTGAGCAGCATTTATCGTTTCTTGGGTTGCATTTCSNSNBSNBSNBSNBGCATCCCCTTCCCGCTGCGTAAATGAG (SEQ ID NO: 162) |
| ProTx-III setB Part 2 fwd | CCAAGAAACGATAAATGCTGCTCAGGACTCVNSTGCGGCAGCAACCACAACTGGTGCAAANSGVNSVNSGGCGCAAACAGTGGCGTCAGTGAC (SEQ ID NO: 163) |
| pINT BM40 Lead Fwd | GTTTGCCTGGCCGGGAGGGCTCTGGC (SEQ ID NO: 164) |
| pINT Clambda Not Rev | AGTCACGCTTGGTGCGGCCGC (SEQ ID NO: 165) |

The DNA for each library was electroporated into suspension adapted HEK293F cells using MaxCyte STXG2 (see Example 5). Similarly, wild type KB_A12 ProTx-III and KB_A12 HsTx1 constructs were cloned and electroporated into HEK293F cells as controls. 100 million cells were used each library and 10 million cells were used for each control construct. Two days post transfection, the antibiotic Blasticidin S HCl (LifeTech, Cat. No. R21001) was added at a concentration of 7.5 μg/ml. Cells were seeded at $0.25\times10^6$ cells per ml in Erlenmeyer flasks. To calculate gene integration efficiency, cells were also plated into 10 cm dishes as described in Example 5. The integration efficiency was calculated to be 3%, 2.5% and 2% for the KB_A12 ProTx-III Library Set A, KB_A12 ProTx-III Library Set B, and KB_A12 HsTx1 Library, respectively. Therefore, the library sizes achieved for the 100 million cell transfections were $3\times10^6$, $2.5\times10^6$, and $2\times10^6$, respectively. After 5 days of Blasticidin S HCl (LifeTech, Cat. No. R21001) selection the cells were enriched using anti-Fc MACS beads as described in Example 5. After 14 days of selection the libraries were analysed by flow cytometry for knotbody expression level. As shown in FIG. 55, all three knotbody libraries displayed an improved average expression level compared with the parental knotbodies displayed on HEK293 cells. This provides evidence that knotbody variants have been generated that will possess improved biophysical properties compared with the parental knotbody molecules.

Next, FACS was carried out on the knotbody libraries using the BioRad S3e Cell Sorter. $30\times10^6$ cells of the MACS sorted populations were incubated (as previously) with anti-Human Fc PE (1 μl per $1\times10^6$ cells) (Cambridge Bioscience, Cat. No. 409304). A gate was drawn on a histogram plot for high Fc Expression for the three libraries. This took 8.16% of the gated cells for KB_A12 ProTxIII Set A Library, whilst 0.15% of the control KB_A12 ProTxIII was found in the region. 7.25% of the gated cells for KB_A12 ProTxIII Set B Library was taken, whilst 0.10% of the control was found in this region. 12.6% of the KB_A12 HsTxI Library was taken, whilst 0.03% of the KB_A12 HsTxI control was found in this region. $0.5\times10^6$ cells for each population were taken for genomic DNA extraction. DNA encoding the IgG was amplified by nested PCR using KOD Hot Start DNA polymerase (Merck Millipore) as described in Example 4. PCR products were gel purified and digested with NheI and XhoI, cloned into the pINT3 mammalian expression vector and used to transform *E. coli* DH10B cells.

By following the same methods as described in Examples 4 and 5, where mammalian cell display mutant libraries were created which were then selected on the basis of surface display level, individual knotbody clones will be identified with improved biophysical properties compared with their parental molecules. This example has therefore described the utility of higher eukaryotic mammalian display to improve the biophysical properties of knotbodies or any alternative bi-specific format. The methods described here could also be performed during a knotbody or bi-specific discovery project where multi-parameter FACS can be employed to select both on high display level and specific binding to a target molecule.

REFERENCES

1 Jarasch, A. et al. Developability assessment during the selection of novel therapeutic antibodies. *J Pharm Sci* 104, 1885-1898, doi:10.1002/jps.24430 (2015).
2 Jain, T. et al. Biophysical properties of the clinical-stage antibody landscape. *Proceedings of the National Academy of Sciences of the United States of America* 114, 944-949, doi:10.1073/pnas.1616408114 (2017).
3 Yang, X. et al. Developability studies before initiation of process development: improving manufacturability of monoclonal antibodies. *mAbs* 5, 787-794, doi:10.4161/mabs.25269 (2013).
4 Ratanji, K. D., Derrick, J. P., Dearman, R. J. & Kimber, I. Immunogenicity of therapeutic proteins: influence of aggregation. *J Immunotoxicol* 11, 99-109, doi:10.3109/1547691X.2013.821564 (2014).
5 Moussa, E. M. et al. Immunogenicity of Therapeutic Protein Aggregates. *J Pharm Sci* 105, 417-430, doi:10.1016/j.xphs.2015.11.002 (2016).
6 Buchanan, A. et al. Engineering a therapeutic IgG molecule to address cysteinylation, aggregation and enhance thermal stability and expression. *mAbs* 5, 255-262, doi:10.4161/mabs.23392 (2013).
7 Dobson, C. L. et al. Engineering the surface properties of a human monoclonal antibody prevents self-association and rapid clearance in vivo. *Scientific Reports* 6, 38644, doi:10.1038/srep38644 (2016).
8 Schofield, D. J. et al. Application of phage display to high throughput antibody generation and characterization. *Genome biology* 8, R254, doi:10.1186/gb-2007-8-11-r254 (2007).
9 Jespers, L., Schon, O., Famm, K. & Winter, G. Aggregation-resistant domain antibodies selected on phage by heat denaturation. *Nat Biotechnol* 22, 1161-1165, doi:10.1038/nbt1000 (2004).
10 Fennell, B. J. et al. CDR-restricted engineering of native human scFvs creates highly stable and soluble bifunctional antibodies for subcutaneous delivery. *mAbs* 5, 882-895, doi:10.4161/mabs.26201 (2013).
11 Christ, D., Famm, K. & Winter, G. Repertoires of aggregation-resistant human antibody domains. *Protein engineering, design & selection: PEDS* 20, 413-416, doi:10.1093/protein/gzm037 (2007).
12 Tiller, T. et al. A fully synthetic human Fab antibody library based on fixed VH/VL framework pairings with favorable biophysical properties. *mAbs* 5, 445-470, doi:10.4161/mabs.24218 (2013).
13 Dudgeon, K. et al. General strategy for the generation of human antibody variable domains with increased aggregation resistance. *Proceedings of the National Academy of Sciences of the United States of America* 109, 10879-10884, doi:10.1073/pnas.1202866109 (2012).
14 Bethea, D. et al. Mechanisms of self-association of a human monoclonal antibody CNTO607. *Protein Engineering Design and Selection* 25, 531-538 (2012).
15 Kelly, R. L. et al. High throughput cross-interaction measures for human IgG1 antibodies correlate with clearance rates in mice. *mAbs* 7, 770-777, doi:10.1080/19420862.2015.1043503 (2015).
16 Hötzel, I. et al. A strategy for risk mitigation of antibodies with fast clearance. *mAbs* 4, 753-760, doi:10.4161/mabs.22189 (2012).
17 Pries, A. R., Secomb, T. W. & Gaehtgens, P. The endothelial surface layer. *Pflugers Arch* 440, 653-666, doi:10.1007/s004240000307 (2000).
18 Nieuwdorp, M. et al. The endothelial glycocalyx: a potential barrier between health and vascular disease. *Curr Opin Lipidol* 16, 507-511 (2005).
19 Xu, Y. et al. Addressing polyspecificity of antibodies selected from an in vitro yeast presentation system: a FACS-based, high-throughput selection and analytical tool. *Protein engineering, design & selection: PEDS* 26, 663-670, doi:10.1093/protein/gzt047 (2013).
20 Martin, W. L., West, A. P., Jr., Gan, L. & Bjorkman, P. J. Crystal structure at 2.8 A of an FcRn/heterodimeric Fc complex: mechanism of pH-dependent binding. *Mol Cell* 7, 867-877 (2001).
21 Suzuki, T. et al. Importance of neonatal FcR in regulating the serum half-life of therapeutic proteins containing the Fc domain of human IgG1: a comparative study of the affinity of monoclonal antibodies and Fc-fusion proteins to human neonatal FcR. *Journal of immunology* (Baltimore, Md.: 1950) 184, 1968-1976, doi:10.4049/jimmunol.0903296 (2010).
22 Schoch, A. et al. Charge-mediated influence of the antibody variable domain on FcRn-dependent pharmacokinetics. *Proceedings of the National Academy of Sciences of the United States of America* 112, 5997-6002, doi:10.1073/pnas.1408766112 (2015).
23 Kelly, R. L. et al. Target-independent variable region mediated effects on antibody clearance can be FcRn independent. *mAbs* 8, 1269-1275, doi:10.1080/19420862.2016.1208330 (2016).

24 Boder, E. T. & Wittrup, K. D. Yeast surface display for screening combinatorial polypeptide libraries. *Nat Biotechnol* 15, 553-557, doi:10.1038/nbt0697-553 (1997).

25 Chao, G. et al. Isolating and engineering human antibodies using yeast surface display. *Nat. Protocols* 1, 755-768, (2006).

26 Shusta, E. V., Kieke, M. C., Parke, E., Kranz, D. M. & Wittrup, K. D. Yeast polypeptide fusion surface display levels predict thermal stability and soluble secretion efficiency. *Journal of molecular biology* 292, 949-956, (1999).

27 Kowalski, J. M., Parekh, R. N., Mao, J. & Wittrup, K. D. Protein Folding Stability Can Determine the Efficiency of Escape from Endoplasmic Reticulum Quality Control. *J. Biol. Chem.* 273, 19453-19458 (1998).

28 Kowalski, J. M., Parekh, R. N. & Wittrup, K. D. Secretion Efficiency in *Saccharomyces cerevisiae* of Bovine Pancreatic Trypsin Inhibitor Mutants Lacking Disulfide Bonds Is Correlated with Thermodynamic Stability. *Biochemistry* 37, 1264-1273, doi:10.1021/bi9722397 (1998).

29 Hackel, B. J., Ackerman, M. E., Howland, S. W. & Wittrup, K. D. Stability and CDR Composition Biases Enrich Binder Functionality Landscapes. *Journal of molecular biology* 401, 84-96, (2010).

30 Julian, M. C. et al. Co-evolution of affinity and stability of grafted amyloid-motif domain antibodies. *Protein Eng. Des. Sel.* 28, 339-350, doi:10.1093/protein/gzv050 (2015).

31 Rabia, L. A., Desai, A. A., Jhajj, H. S. & Tessier, P. M. Understanding and overcoming trade-offs between antibody affinity, specificity, stability and solubility. *Biochemical Engineering Journal* 137, 365-374, (2018).

32 Igawa, T., Haraya, K. & Hattori, K. Sweeping antibody as a novel therapeutic antibody modality capable of eliminating soluble antigens from circulation. *Immunol Rev* 270, 132-151, doi:10.1111/imr.12392 (2016).

33 Qin, J. Y. et al. Systematic comparison of constitutive promoters and the doxycycline-inducible promoter. *PloS one* 5, e10611, doi:10.1371/journal.pone.0010611 (2010).

34 Walker, J. M. *The protein protocols handbook.* 3rd edn, (Humana Press, 2009).

35 Janson, J. C. *Protein purification: principles, high resolution methods, and applications.* 3rd edn, (John Wiley & Sons, 2011).

36 Schiel, J. E., Davis, D. L. & Borisov, O. *State-of-the-art and emerging technologies for therapeutic monoclonal antibody characterization.* (American Chemical Society, 2014).

37 Saro, D. et al. in *State-of-the-Art and Emerging Technologies for Therapeutic Monoclonal Antibody Characterization Volume* 2. *Biopharmaceutical Characterization: The NISTmAb Case Study* Vol. 1201 *ACS Symposium Series* Ch. 7, 329-355 (American Chemical Society, 2015).

38 Sun, T. et al. High throughput detection of antibody self-interaction by bio-layer interferometry. *mAbs* 5, 838-841, doi:10.4161/mabs.26186 (2013).

39 Liu, Y. et al. High-throughput screening for developability during early-stage antibody discovery using self-interaction nanoparticle spectroscopy. *mAbs* 6, 483-492, doi:10.4161/mabs.27431 (2014).

40 Geng, S. B., Wittekind, M., Vigil, A. & Tessier, P. M. Measurements of Monoclonal Antibody Self-Association Are Correlated with Complex Biophysical Properties. *Molecular Pharmaceutics* 13, 1636-1645, doi:10.1021/acs.molpharmaceut.6b00071 (2016).

41 Wu, J. et al. Discovery of highly soluble antibodies prior to purification using affinity-capture self-interaction nanoparticle spectroscopy. *Protein engineering, design & selection: PEDS* 28, 403-414, doi:10.1093/protein/gzv045 (2015).

42 Nobbmann, U. et al. Dynamic light scattering as a relative tool for assessing the molecular integrity and stability of monoclonal antibodies. *Biotechnology and Genetic Engineering Reviews* 24, 117-128 (2007).

43 Geng, S. B., Cheung, J. K., Narasimhan, C., Shameem, M. & Tessier, P. M. Improving monoclonal antibody selection and engineering using measurements of colloidal protein interactions. *J Pharm Sci* 103, 3356-3363, doi:10.1002/jps.24130 (2014).

44 Howlett, G. J., Minton, A. P. & Rivas, G. Analytical ultracentrifugation for the study of protein association and assembly. *Curr Opin Chem Biol* 10, 430-436, doi:10.1016/j.cbpa.2006.08.017 (2006).

45 Salinas, B. A. et al. Understanding and modulating opalescence and viscosity in a monoclonal antibody formulation. *J Pharm Sci* 99, 82-93, doi:10.1002/jps.21797 (2010).

46 Gabel, F. et al. Protein dynamics studied by neutron scattering. *Q Rev Biophys* 35, 327-367 (2002).

47 Jacobs, S. A., Wu, S. J., Feng, Y., Bethea, D. & O'Neil, K. T. Cross-interaction chromatography: A rapid method to identify highly soluble monoclonal antibody candidates. *Pharm. Res.* 27, 65-71, doi:10.1007/s11095-009-0007-z (2010).

48 Josic, D., Bal, F. & Schwinn, H. Isolation of plasma proteins from the clotting cascade by heparin affinity chromatography. *J Chromatogr* 632, 1-10 (1993).

49 Fekete, S., Veuthey, J. L., Beck, A. & Guillarme, D. Hydrophobic interaction chromatography for the characterization of monoclonal antibodies and related products. *J Pharm Biomed Anal* 130, 3-18, doi:10.1016/j.jpba.2016.04.004 (2016).

50 Eriksson, K. O. & Belew, M. Hydrophobic interaction chromatography. *Methods Biochem Anal* 54, 165-181 (2011).

51 Bakalova, R. & Ohba, H. Interaction of soybean agglutinin with leukemic T-cells and its use for their in vitro separation from normal lymphocytes by lectin-affinity chromatography. *Biomed Chromatogr* 17, 239-249, doi:10.1002/bmc.218 (2003).

52 Melidoni, A. N., Dyson, M. R., Wormald, S. & McCafferty, J. Selecting antagonistic antibodies that control differentiation through inducible expression in embryonic stem cells. *Proceedings of the National Academy of Sciences of the United States of America* 110, 17802-17807, doi:10.1073/pnas.1312062110 (2013).

53 Xie, J., Zhang, H., Yea, K. & Lerner, R. A. Autocrine signaling based selection of combinatorial antibodies that transdifferentiate human stem cells. *Proceedings of the National Academy of Sciences* 110, 8099-8104, doi:10.1073/pnas.1306263110 (2013).

54 Zhang, H. et al. Selecting Agonists from Single Cells Infected with Combinatorial Antibody Libraries. *Chemistry & Biology* 20, 734-741, doi:10.1016/j.chembiol.2013.04.012 (2013).

55 Igoucheva, O., Alexeev, V. & Yoon, K. Targeted gene correction by small single-stranded oligonucleotides in mammalian cells. *Gene Therapy* 8, 391, doi:10.1038/sj.gt.3301414 (2001).

56 Liang, X., Potter, J., Kumar, S., Ravinder, N. & Chesnut, J. D. Enhanced CRISPR/Cas9-mediated precise genome editing by improved design and delivery of gRNA, Cas9 nuclease, and donor DNA. *J. Biotechnol.* 241, 136-146, (2017).

57 Dyson, M. R. et al. Mapping protein interactions by combining antibody affinity maturation and mass spectrometry. *Analytical biochemistry* 417, 25-35, doi:10.1016/j.ab.2011.05.005 (2011).

58 Gronwald, R. G. et al. Cloning and expression of a cDNA coding for the human platelet-derived growth factor receptor: evidence for more than one receptor class. *Proceedings of the National Academy of Sciences of the United States of America* 85, 3435-3439 (1988).

59 Dux, R., Kindler-Rohrborn, A., Lennartz, K. & Rajewsky, M. F. Calibration of fluorescence intensities to quantify antibody binding surface determinants of cell subpopulations by flow cytometry. *Cytometry* 12, 422-428, doi:10.1002/cyto.990120507 (1991).

60 Brockhoff, G., Hofstaedter, F. & Knuechel, R. Flow cytometric detection and quantitation of the epidermal growth factor receptor in comparison to Scatchard analysis in human bladder carcinoma cell lines. *Cytometry* 17, 75-83, doi:10.1002/cyto.990170110 (1994).

61 Gordon, I. L. Scatchard analysis of fluorescent concanavalin A binding to lymphocytes. *Cytometry* 20, 238-244, doi:10.1002/cyto.990200307 (1995).

62 Sheehan, J. & Marasco, W. A. Phage and Yeast Display. *Microbiol Spectr* 3, AID-0028-2014, doi:10.1128/microbiolspec.AID-0028-2014 (2015).

63 Puck, T. T. The genetics of somatic mammalian cells. *Adv Biol Med Phys* 5, 75-101 (1957).

64 Wurm, F. CHO Quasispecies—Implications for Manufacturing Processes. *Processes* 1, 296-311 (2013).

65 Goh, J. B. & Ng, S. K. Impact of host cell line choice on glycan profile. *Critical Reviews in Biotechnology* 38, 851-867, doi:10.1080/07388551.2017.1416577 (2018).

66 Skerra, A. Alternative non-antibody scaffolds for molecular recognition. *Curr Opin Biotechnol* 18, 295-304, doi:10.1016/j.copbio.2007.04.010 (2007).

67 Gebauer, M. & Skerra, A. Engineered protein scaffolds as next-generation antibody therapeutics. *Curr Opin Chem Biol* 13, 245-255, doi:10.1016/j.cbpa.2009.04.627 (2009).

68 Tiede, C. et al. Adhiron: a stable and versatile peptide display scaffold for molecular recognition applications. *Protein engineering, design & selection: PEDS* 27, 145-155, doi:10.1093/protein/gzu007 (2014).

69 Koide, A., Bailey, C. W., Huang, X. & Koide, S. The fibronectin type III domain as a scaffold for novel binding proteins. *Journal of molecular biology* 284, 1141-1151, doi:10.1006/jmbi.1998.2238 (1998).

70 Nygren, P. A. & Skerra, A. Binding proteins from alternative scaffolds. *J Immunol Methods* 290, 3-28, doi:10.1016/j.jim.2004.04.006 (2004).

71 Chang, H. J. et al. Molecular evolution of cystine-stabilized miniproteins as stable proteinaceous binders. *Structure* 17, 620-631, doi:10.1016/j.str.2009.01.011 (2009).

72 Ward, E. S., Güssow, D., Griffiths, A. D., Jones, P. T. & Winter, G. Binding activities of a repertoire of single immunoglobulin variable domains secreted from *Escherichia coli. Nature* 341, 544, doi:10.1038/341544a0 (1989).

73 McCafferty, J., Griffiths, A. D., Winter, G. & Chiswell, D. J. Phage antibodies: filamentous phage displaying antibody variable domains. *Nature* 348, 552-554, doi:10.1038/348552a0 (1990).

74 Holt, L. J., Herring, C., Jespers, L. S., Woolven, B. P. & Tomlinson, I. M. Domain antibodies: proteins for therapy. *Trends in Biotechnology* 21, 484-490, doi:10.1016/j.tibtech.2003.08.007 (2003).

75 Huston, J. S. et al. Protein engineering of antibody binding sites: recovery of specific activity in an anti-digoxin single-chain Fv analogue produced in *Escherichia coli. Proceedings of the National Academy of Sciences* 85, 5879 (1988).

76 Bird, R. E. et al. Single-chain antigen-binding proteins. *Science* 242, 423-426 (1988).

77 Holliger, P., Prospero, T. & Winter, G. "Diabodies": Small bivalent and bispecific antibody fragments. *Proceedings of the National Academy of Sciences of the United States of America* 90, 6444-6448 (1993).

78 Reiter, Y., Brinkmann, U., Lee, B. & Pastan, I. Engineering antibody Fv fragments for cancer detection and therapy: Bisulfide-stabilized Fv fragments. *Nat. Biotechnol.* 14, 1239, doi:10.1038/nbt1096-1239 (1996).

79 Holliger, P. & Hudson, P. J. Engineered antibody fragments and the rise of single domains. *Nat Biotechnol* 23, 1126-1136, doi:10.1038/nbt1142 (2005).

80 Knappik, A. et al. Fully synthetic human combinatorial antibody libraries (HuCAL) based on modular consensus frameworks and CDRs randomized with trinucleotides. *Journal of molecular biology* 296, 57-86, doi:10.1006/jmbi.1999.3444 (2000).

81 Krebs, B. et al. High-throughput generation and engineering of recombinant human antibodies. *J Immunol Methods* 254, 67-84 (2001).

82 Holliger, P. & Bohlen, H. Engineering antibodies for the clinic. *Cancer Metastasis Rev* 18, 411-419 (1999).

83 Glennie, M. J., McBride, H. M., Worth, A. T. & Stevenson, G. T. Preparation and performance of bispecific F(ab' gamma)2 antibody containing thioether-linked Fab' gamma fragments. *Journal of immunology* (Baltimore, Md.: 1950) 139, 2367-2375 (1987).

84 Repp, R. et al. G-CSF-stimulated PMN in immunotherapy of breast cancer with a bispecific antibody to Fc gamma RI and to HER-2/neu (MDX-210). *J Hematother* 4, 415-421, doi:10.1089/scd.1.1995.4.415 (1995).

85 Suresh, M. R., Cuello, A. C. & Milstein, C. Bispecific monoclonal antibodies from hybrid hybridomas. *Methods in enzymology* 121, 210-228 (1986).

86 Staerz, U. D. & Bevan, M. J. Hybrid hybridoma producing a bispecific monoclonal antibody that can focus effector T-cell activity. *Proceedings of the National Academy of Sciences* 83, 1453 (1986).

87 Merchant, A. M. et al. An efficient route to human bispecific IgG. *Nat. Biotechnol.* 16, 677, doi:10.1038/nbt0798-677 (1998).

88 Von Kreudenstein, T. S. et al. Improving biophysical properties of a bispecific antibody scaffold to aid developability: quality by molecular design. *mAbs* 5, 646-654, doi:10.4161/mabs.25632 (2013).

89 Ghetie, V. et al. Increasing the serum persistence of an IgG fragment by random mutagenesis. *Nat Biotechnol* 15, 637-640, doi:10.1038/nbt0797-637 (1997).

90 Borrok, M. J. et al. An "Fc-Silenced" IgG1 Format With Extended Half-Life Designed for Improved Stability. *J Pharm Sci* 106, 1008-1017, doi:10.1016/j.xphs.2016.12.023 (2017).

91 Schlothauer, T. et al. Analytical FcRn affinity chromatography for functional characterization of monoclonal antibodies. *mAbs* 5, 576-586, doi:10.4161/mabs.24981 (2013).

92 Gossen, M. et al. Transcriptional activation by tetracyclines in mammalian cells. *Science* 268, doi:10.1126/science.7792603 (1995).

93 Sadelain, M., Papapetrou, E. P. & Bushman, F. D. Safe harbours for the integration of new DNA in the human genome. *Nature reviews. Cancer* 12, 51-58, doi:10.1038/nrc3179 (2011).

94 Foote, J. & Winter, G. Antibody framework residues affecting the conformation of the hypervariable loops. *Journal of molecular biology* 224, 487-499 (1992).

95 Haghparast, S. M., Kihara, T. & Miyake, J. Distinct mechanical behavior of HEK293 cells in adherent and suspended states. *PeerJ* 3, e1131, doi:10.7717/peerj.1131 (2015).

96 Rivera, V. M. et al. Regulation of protein secretion through controlled aggregation in the endoplasmic reticulum. *Science* 287, 826-830 (2000).

97 Ferri, N., Corsini, A., Sirtori, C. R. & Ruscica, M. Bococizumab for the treatment of hypercholesterolaemia. *Expert Opin Biol Ther* 17, 237-243, doi:10.1080/14712598.2017.1279602 (2017).

98 Liang, H. et al. Proprotein Convertase Substilisin/Kexin Type 9 Antagonism Reduces Low-Density Lipoprotein Cholesterol in Statin-Treated Hypercholesterolemic Nonhuman Primates. *Journal of Pharmacology and Experimental Therapeutics* 340, 228 (2012).

99 Jones, T. D., Crompton, L. J., Carr, F. J. & Baker, M. P. in *Therapeutic Antibodies: Methods and Protocols* (ed Antony S. Dimitrov) 405-423 (Humana Press, 2009).

100 Bostrom, J., Lee, C. V., Haber, L. & Fuh, G. in *Therapeutic Antibodies: Methods and Protocols* (ed Antony S. Dimitrov) 353-376 (Humana Press, 2009).

101 Dyson, M. R., Shadbolt, S. P., Vincent, K. J., Perera, R. L. & McCafferty, J. Production of soluble mammalian proteins in *Escherichia coli*: identification of protein features that correlate with successful expression. *BMC biotechnology* 4, 32, doi:10.1186/1472-6750-4-32 (2004).

102 Neylon, C. Chemical and biochemical strategies for the randomization of protein encoding DNA sequences: library construction methods for directed evolution. *Nucleic acids research* 32, 1448-1459, doi:10.1093/nar/gkh315 (2004).

103 Fujino, Y. et al. Robust in vitro affinity maturation strategy based on interface-focused high-throughput mutational scanning. *Biochemical and biophysical research communications* 428, 395-400, doi:10.1016/j.bbrc.2012.10.066 (2012).

104 Xin, Y. et al. Anti-neuropilin-1 (MNRP1685A): unexpected pharmacokinetic differences across species, from preclinical models to humans. *Pharm Res* 29, 2512-2521, doi:10.1007/s11095-012-0781-x (2012).

105 Patnaik, A. et al. A Phase Ib study evaluating MNRP1685A, a fully human anti-NRP1 monoclonal antibody, in combination with bevacizumab and paclitaxel in patients with advanced solid tumors. *Cancer Chemother Pharmacol* 73, 951-960, doi:10.1007/s00280-014-2426-8 (2014).

106 Shin, D. S. & Ribas, A. The evolution of checkpoint blockade as a cancer therapy: What's here, what's next? *Curr. Opin. Immunol.* 33, 23-35, doi:10.1016/j.coi.2015.01.006 (2015).

107 Mouquet, H. et al. Polyreactivity increases the apparent affinity of anti-HIV antibodies by heteroligation. *Nature* 467, 591-595, doi:10.1038/nature09385 (2010).

108 Fellouse, F. A. & Sidhu, S. S. in *Making and Using Antibodies: A Practical Handbook* (eds G. C. Howard & M. R. Kaser) Ch. 8, 157-180 (CRC Press, 2007).

109 Peterson, M. L. Mechanisms controlling production of membrane and secreted immunoglobulin during B cell development. *Immunol Res* 37, 33-46 (2007).

110 Peterson, M. L. & Perry, R. P. The regulated production of mu m and mu s mRNA is dependent on the relative efficiencies of mu s poly(A) site usage and the c mu 4-to-M1 splice. *Mol Cell Biol* 9, 726-738 (1989).

111 Yu, B., Wages, J. M. & Larrick, J. W. Antibody-membrane switch (AMS) technology for facile cell line development. *Protein Engineering Design and Selection* 27, 309-315, doi:10.1093/protein/gzu039 (2014).

112 Wang, C. et al. In vitro characterization of the anti-PD-1 antibody nivolumab, BMS-936558, and in vivo toxicology in non-human primates. *Cancer Immunol Res* 2, 846-856, doi:10.1158/2326-6066.CIR-14-0040 (2014).

113 D'Hautcourt, J. L. in *Current Protocols in Cytometry* (John Wiley & Sons, Inc., 2001).

114 Gossen, M. & Bujard, H. Tight control of gene expression in mammalian cells by tetracycline-responsive promoters. *Proc Natl Acad Sci USA* 89, doi:10.1073/pnas.89.12.5547 (1992).

115 Ryan, M. D. & Drew, J. Foot-and-mouth disease virus 2A oligopeptide mediated cleavage of an artificial polyprotein. *The EMBO Journal* 13, 928-933 (1994).

116 Zhou, X., Vink, M., Klaver, B., Berkhout, B. & Das, A. T. Optimization of the Tet-On system for regulated gene expression through viral evolution. *Gene Ther* 13, 1382-1390, doi:10.1038/sj.gt.3302780 (2006).

117 Loew, R., Heinz, N., Hampf, M., Bujard, H. & Gossen, M. Improved Tet-responsive promoters with minimized background expression. *BMC biotechnology* 10, 81, doi:10.1186/1472-6750-10-81 (2010).

118 To, T. L. & Maheshri, N. Noise can induce bimodality in positive transcriptional feedback loops without bistability. *Science* 327, 1142-1145, doi:10.1126/science.1178962 (2010).

119 Mullick, A. et al. The cumate gene-switch: a system for regulated expression in mammalian cells. *BMC biotechnology* 6, 1-18, doi:10.1186/1472-6750-6-43 (2006).

120 Yao, F. et al. Tetracycline repressor, tetR, rather than the tetR-mammalian cell transcription factor fusion derivatives, regulates inducible gene expression in mammalian cells. *Hum Gene Ther* 9, doi:10.1089/hum.1998.9.13-1939 (1998).

121 Wang, Y., O'Malley, B. W., Jr., Tsai, S. Y. & O'Malley, B. W. A regulatory system for use in gene transfer. *Proceedings of the National Academy of Sciences of the United States of America* 91, 8180-8184 (1994).

122 Datta-Mannan, A. et al. The interplay of non-specific binding, target-mediated clearance and FcRn interactions on the pharmacokinetics of humanized antibodies. *mAbs* 7, 1084-1093, doi:10.1080/19420862.2015.1075109 (2015).

123 Sigounas, G., Harindranath, N., Donadel, G. & Notkins, A. L. Half-life of polyreactive antibodies. *J Clin Immunol* 14, 134-140 (1994).

124 Roopenian, D. C. & Akilesh, S. FcRn: the neonatal Fc receptor comes of age. *Nat Rev Immunol* 7, 715-725, doi:10.1038/nri2155 (2007).

125 Eid, J. et al. Real-time DNA sequencing from single polymerase molecules. *Science* 323, 133-138, doi:10.1126/science.1162986 (2009).

126 Giordano, F. et al. De novo yeast genome assemblies from MinION, PacBio and MiSeq platforms. *Scientific Reports* 7, 3935, doi:10.1038/s41598-017-03996-z (2017).

127 Ehrenmann, F., Duroux, P., Giudicelli, V. & Lefranc, M. P. Standardized Sequence and Structure Analysis of Antibody Using IMGT®. 11-31, doi:10.1007/978-3-642-01147-4_2 (2010).
128 Van Blarcom, T. et al. Productive common light chain libraries yield diverse panels of high affinity bispecific antibodies. *mAbs* 10, 256-268, doi:10.1080/19420862.2017.1406570 (2018).
129 Spiess, C., Zhai, Q. & Carter, P. J. Alternative molecular formats and therapeutic applications for bispecific antibodies. *Molecular Immunology* 67, 95-106, (2015).
130 Husain, B. & Ellerman, D. Expanding the Boundaries of Biotherapeutics with Bispecific Antibodies. BioDrugs 32, 441-464, doi:10.1007/s40259-018-0299-9 (2018).
131 Fischer, N. et al. Exploiting light chains for the scalable generation and platform purification of native human bispecific IgG. *Nat Commun* 6, 6113, doi:10.1038/ncomms7113 (2015).
132 Ridgway, J. B. B., Presta, L. G. & Carter, P. 'Knobs-into-holes' engineering of antibody CH3 domains for heavy chain heterodimerization. *Protein Eng. Des. Sel.* 9, 617-621, doi:10.1093/protein/9.7.617 (1996).
133 Wozniak-Knopp, G. et al. Introducing antigen-binding sites in structural loops of immunoglobulin constant domains: Fc fragments with engineered HER2/neu-binding sites and antibody properties. *Protein engineering, design & selection: PEDS* 23, 289-297, doi:10.1093/protein/gzq005 (2010).
134 Traxlmayr, M. W. et al. Directed evolution of Her2/neu-binding IgG1-Fc for improved stability and resistance to aggregation by using yeast surface display. *Protein engineering, design & selection: PEDS* 26, 255-265, doi:10.1093/protein/gzs102 (2013).
135 Mahlangu, J. et al. Emicizumab Prophylaxis in Patients Who Have Hemophilia A without Inhibitors. *N Engl J Med* 379, 811-822, doi:10.1056/NEJMoa1803550 (2018).
136 Sampei, Z. et al. Identification and Multidimensional Optimization of an Asymmetric Bispecific IgG Antibody Mimicking the Function of Factor VIII Cofactor Activity. *PloS one* 8, e57479, doi:10.1371/journal.pone.0057479 (2013).
137 Tabrizi, M. A., Tseng, C. M. & Roskos, L. K. Elimination mechanisms of therapeutic monoclonal antibodies. *Drug Discov Today* 11, 81-88, doi:10.1016/S1359-6446(05)03638-X (2006).
138 Dostalek, M., Gardner, I., Gurbaxani, B. M., Rose, R. H. & Chetty, M. Pharmacokinetics, pharmacodynamics and physiologically-based pharmacokinetic modelling of monoclonal antibodies. *Clin Pharmacokinet* 52, 83-124, doi:10.1007/s40262-012-0027-4 (2013).
139. Sondermann, P. & Szymkowski, D. E. Harnessing Fc receptor biology in the design of therapeutic antibodies. Curr Opin Immunol 40, 78-87 (2016).
140. Park, H. I., Yoon, H. W. & Jung, S. T. The Highly Evolvable Antibody Fc Domain. Trends in Biotechnology 34, 895-908 (2016).
141. Hogarth, P. M. & Pietersz, G. A. Fc receptor-targeted therapies for the treatment of inflammation, cancer and beyond. Nature reviews. Drug discovery 11, 311-331 (2012).
142. Mayes, P. A., Hance, K. W. & Hoos, A. The promise and challenges of immune agonist antibody development in cancer. Nature reviews. Drug discovery 17, 509-527 (2018).
143. Jacobsen, F. W. et al. Engineering an IgG scaffold lacking effector function with optimized developability. J. Biol. Chem. (2016).

What is claimed is:

1. A method of distinguishing or ranking binders according to their solubility and/or resistance to self-association in solution, and/or enriching for binders exhibiting greater solubility and/or greater resistance to self-association in solution, comprising (i) providing a library of mammalian cell clones each containing DNA encoding a binder, (ii) culturing the clones in vitro under conditions for expression of the binders, wherein the binders are presented on the cell surface, (iii) determining surface presentation levels, measured in terms of number of displayed binders per cell, of the binders on the clones, optionally by labelling the binders with an agent incorporating a detectable label, (iv) selecting one or more clones that exhibit higher surface presentation of binders compared with other clones, and (v) identifying binders encoded by the one or more selected clones as having good solubility and/or resistance to self-association in solution, and optionally providing the selected clones for use in one or more further screening steps, wherein the binders are antibodies, and wherein the antibodies comprise transmembrane domains.

2. The method according to claim 1, comprising determining surface presentation levels of the binders on the clones by labelling the binders with an agent incorporating a detectable label, wherein the agent binds to a constant region of the binders, optionally wherein the binders comprise an Fc region and the agent binds to the Fc region.

3. The method according to claim 1, comprising sorting cells into a collected fraction and a discarded fraction according to the level of surface presentation of binders on the cells, whereby cells displaying surface presentation above a pre-determined threshold are sorted into a collected fraction and cells displaying surface presentation below the pre-determined threshold are sorted into a discarded fraction.

4. The method according to claim 3, wherein the discarded fraction comprises cells expressing comparator polypeptides that have a critical concentration of at least 10 mg/ml and wherein the collected fraction comprises cells expressing binders that have a critical concentration at least 1.5-fold higher than the comparator polypeptides in the discarded fraction.

5. The method according to claim 3, wherein sorting is performed by a fluorescence activated cell sorter (FACS).

6. The method according to claim 4, wherein sorting is performed by a FACS.

7. The method according to claim 1, wherein step (ii) comprises culturing the clones of the library as a mixture in one vessel.

8. The method according to claim 1, wherein step (ii) comprises culturing each clone of the library in a separate vessel.

9. The method according to claim 1, wherein the binders are sequence variants of a parent binder.

10. The method according to claim 9, wherein the parent binder has been identified as requiring improvement in solubility or resistance to self-association in solution.

11. The method according to claim 9, wherein the method comprises generating sequence variants of the parent binder and integrating DNA encoding the sequence variants into cellular DNA of mammalian cells to provide the library of cell clones containing DNA encoding the binders, wherein the method comprises analyzing the polypeptide sequence of the parent, identifying one or more amino acid residues that are predicted to promote self-association and/or reduce solubility, and generating mutation at the one or more amino acid residues.

12. The method according to claim 10, wherein the method comprises generating sequence variants of the parent binder and integrating DNA encoding the sequence variants into cellular DNA of mammalian cells to provide the library of cell clones containing DNA encoding the binders, wherein the method comprises analyzing the polypeptide sequence of the parent, identifying one or more amino acid residues that are predicted to promote self-association and/or reduce solubility, and generating mutation at the one or more amino acid residues.

13. The method according to claim 9, wherein the parent binder has a critical concentration of less than 50 mg/ml in phosphate buffered saline solution (PBS) and/or has a solubility limit of less than 50 mg/ml in PBS, and/or wherein the method comprises identifying binders encoded by the one or more selected clones as having a critical concentration and/or a solubility limit at least 1.5-fold higher than that of the parent binder.

14. The method according to claim 10, wherein the parent binder has a critical concentration of less than 50 mg/ml in PBS and/or has a solubility limit of less than 50 mg/ml in PBS, and/or wherein the method comprises identifying binders encoded by the one or more selected clones as having a critical concentration and/or a solubility limit at least 1.5-fold higher than that of the parent binder.

15. The method according to claim 1, comprising simultaneously determining surface presentation levels of the binders and levels of target binding by the binders, and co-selecting clones displaying cognate binders exhibiting higher surface presentation compared with other clones; or simultaneously determining surface presentation levels of the binders and levels of non-specific binding to non-target molecules, and co-selecting clones displaying binders exhibiting higher surface presentation and lower non-specific binding compared with other clones; or simultaneously determining levels of target binding and levels of non-specific binding to non-target molecules by the binders, and co-selecting clones displaying cognate binders exhibiting lower non-specific binding compared with other clones.

16. The method according to claim 1, comprising determining the sequence of the DNA encoding the binder from the one or more selected clones, and providing isolated nucleic acid encoding the binder.

* * * * *

SEQUENCE LISTING

```
<160> NUMBER OF SEQ ID NOS: 368

<210> SEQ ID NO 1
<211> LENGTH: 328
<212> TYPE: DNA
<213> ORGANISM: Artificial Sequence
<220> FEATURE:
<223> OTHER INFORMATION: CMV promoter sequence

<400> SEQUENCE: 1

ttcgtcttca cacgagttta ctccctatca gtgatagaga acgtatgtcg agtttactcc     60

ctatcagtga tagagaacga tgtcgagttt actccctatc agtgatagag aacgtatgtc    120

gagtttactc cctatcagtg atagagaacg tatgtcgagt ttactcccta tcagtgatag    180

agaacgtatg tcgagtttat ccctatcagt gatagagaac gtatgtcgag tttactccct    240

atcagtgata gagaacgtat gtcgaggtag gcgtgtacgg tgggaggcct atataagcag    300

agctcgttta gtgaaccgtc agatcgcc                                       328


<210> SEQ ID NO 2
<211> LENGTH: 123
<212> TYPE: PRT
<213> ORGANISM: Artificial Sequence
<220> FEATURE:
<223> OTHER INFORMATION: Ang2 VH

<400> SEQUENCE: 2

Gln Val Gln Leu Val Glu Ser Gly Gly Gly Val Val Gln Pro Gly Arg
1               5                   10                  15
```

-continued

```
Ser Leu Arg Leu Ser Cys Ala Ala Ser Gly Phe Thr Phe Thr Asn Tyr
            20                  25                  30

Gly Met His Trp Gly Arg Gln Ala Pro Gly Lys Gly Leu Glu Trp Val
        35                  40                  45

Ala Val Ile Ser His Asp Gly Asn Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Ile Asp Phe Trp Ser Gly Leu Asn Trp Phe Asp Pro
            100                 105                 110

Trp Gly Gln Gly Thr Leu Val Thr Val Ser Ser
        115                 120


<210> SEQ ID NO 3
<211> LENGTH: 108
<212> TYPE: PRT
<213> ORGANISM: Artificial Sequence
<220> FEATURE:
<223> OTHER INFORMATION: Ang2 VL

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Cys Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95

Ile Thr Phe Gly Gln Gly Thr Arg Leu Glu Ile Lys
            100                 105


<210> SEQ ID NO 4
<211> LENGTH: 108
<212> TYPE: PRT
<213> ORGANISM: Artificial Sequence
<220> FEATURE:
<223> OTHER INFORMATION: Ang2 VL C49T

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Gly Ser
            20                  25                  30

Tyr Leu Ala Trp Tyr Gln Gln Lys Pro Gly Gln Ala Pro Arg Leu Leu
        35                  40                  45

Ile Thr Gly Ala Ser Ser Trp Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ser Ser Ser Pro
                85                  90                  95
```

-continued

```
Ile Thr Phe Gly Gln Gly Thr Arg Leu Glu Ile Lys
            100                 105


<210> SEQ ID NO 5
<211> LENGTH: 124
<212> TYPE: PRT
<213> ORGANISM: Artificial Sequence
<220> FEATURE:
<223> OTHER INFORMATION: CNT607 VH

<400> SEQUENCE: 5

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Trp Ile Asn Trp Val Arg Gln Ala Pro Gly Lys Gly Leu Glu Trp Val
        35                  40                  45

Ser Gly Ile Ala Tyr Asp Ser Ser Asn Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Gly Ala Phe His Trp Asp Met Gln Pro Asp Tyr Trp
            100                 105                 110

Gly Gln Gly Thr Leu Val Thr Val Ser Ser Ala Ser
        115                 120


<210> SEQ ID NO 6
<211> LENGTH: 122
<212> TYPE: PRT
<213> ORGANISM: Artificial Sequence
<220> FEATURE:
<223> OTHER INFORMATION: CNT607 VH W100A

<400> SEQUENCE: 6

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Trp Ile Asn Trp Val Arg Gln Ala Pro Gly Lys Gly Leu Glu Trp Val
        35                  40                  45

Ser Gly Ile Ala Tyr Asp Ser Ser Asn Thr Leu Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Gly Ala Phe His Ala Asp Met Gln Pro Asp Tyr Trp
            100                 105                 110

Gly Gln Gly Thr Leu Val Thr Val Ser Ser
        115                 120


<210> SEQ ID NO 7
<211> LENGTH: 107
<212> TYPE: PRT
<213> ORGANISM: Artificial Sequence
<220> FEATURE:
<223> OTHER INFORMATION: CNT607 VL
```

<400> SEQUENCE: 7

Ser Tyr Glu Leu Thr Gln Pro Pro Ser Val Ser Val Ala Pro Gly Gln
1               5                   10                  15

Thr Ala Arg Ile Ser Cys Ser Gly Asp Asn Ile Gly Gly Thr Phe Val
            20                  25                  30

Ser Trp Tyr Gln Gln Lys Pro Gly Gln Ala Pro Val Leu Val Ile Tyr
        35                  40                  45

Asp Asp Asn Asp Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gly Thr Trp Asp Met Val Thr Asn Asn
                85                  90                  95

Val Phe Gly Gly Gly Thr Lys Leu Thr Val Leu
            100                 105

<210> SEQ ID NO 8
<211> LENGTH: 128
<212> TYPE: PRT
<213> ORGANISM: Artificial Sequence
<220> FEATURE:
<223> OTHER INFORMATION: MEDI-1912 VH

<400> SEQUENCE: 8

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Trp Phe Gly
            20                  25                  30

Ala Phe Thr Trp Val Arg Gln Ala Pro Gly Gln Gly Leu Glu Trp Met
        35                  40                  45

Gly Gly Ile Ile Pro Ile Phe Gly Leu Thr Asn Leu Ala Gln Asn Phe
    50                  55                  60

Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125

<210> SEQ ID NO 9
<211> LENGTH: 128
<212> TYPE: PRT
<213> ORGANISM: Artificial Sequence
<220> FEATURE:
<223> OTHER INFORMATION: MEDI1912 VH STT

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Thr Gly
            20                  25                  30

Ala Phe Thr Trp Val Arg Gln Ala Pro Gly Gln Gly Leu Glu Trp Met
        35                  40                  45

Gly Gly Ile Ile Pro Ile Phe Gly Thr Thr Asn Leu Ala Gln Asn Phe
    50                  55                  60

```
Gln Gly Arg Val Thr Ile Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Ser Arg Ile Tyr Asp Leu Asn Pro Ser Leu Thr Ala Tyr
            100                 105                 110

Tyr Asp Met Asp Val Trp Gly Gln Gly Thr Met Val Thr Val Ser Ser
        115                 120                 125


<210> SEQ ID NO 10
<211> LENGTH: 110
<212> TYPE: PRT
<213> ORGANISM: Artificial Sequence
<220> FEATURE:
<223> OTHER INFORMATION: MEDI-1912 VL

<400> SEQUENCE: 10

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Trp Val Phe Gly Gly Gly Thr Lys Leu Thr Val Leu
            100                 105                 110


<210> SEQ ID NO 11
<211> LENGTH: 123
<212> TYPE: PRT
<213> ORGANISM: Artificial Sequence
<220> FEATURE:
<223> OTHER INFORMATION: Vesencumab VH

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gln Ile Ser Pro Ala Gly Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Glu Leu Pro Tyr Tyr Arg Met Ser Lys Val Met Asp Val
            100                 105                 110

Trp Gly Gln Gly Thr Leu Val Thr Val Ser Ser
        115                 120
```

-continued

<210> SEQ ID NO 12
<211> LENGTH: 107
<212> TYPE: PRT
<213> ORGANISM: Artificial Sequence
<220> FEATURE:
<223> OTHER INFORMATION: Vesencumab VL

<400> SEQUENCE: 12

Asp Ile Gln Met Thr Gln Ser Pro Ser Ser Leu Ser Ala Ser Val Gly
1 5 10 15

Asp Arg Val Thr Ile Thr Cys Arg Ala Ser Gln Tyr Phe Ser Ser Tyr
20 25 30

Leu Ala Trp Tyr Gln Gln Lys Pro Gly Lys Ala Pro Lys Leu Leu Ile
35 40 45

Tyr Gly Ala Ser Ser Arg Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Leu Gly Ser Pro Pro
85 90 95

Thr Phe Gly Gln Gly Thr Lys Val Glu Ile Lys
100 105

<210> SEQ ID NO 13
<211> LENGTH: 20
<212> TYPE: DNA
<213> ORGANISM: Artificial Sequence
<220> FEATURE:
<223> OTHER INFORMATION: genome specific primer

<400> SEQUENCE: 13
ccggaactct gccctctaac 20

<210> SEQ ID NO 14
<211> LENGTH: 20
<212> TYPE: DNA
<213> ORGANISM: Artificial Sequence
<220> FEATURE:
<223> OTHER INFORMATION: genome specific primer

<400> SEQUENCE: 14
tcctgggata ccccgaagag 20

<210> SEQ ID NO 15
<211> LENGTH: 22
<212> TYPE: DNA
<213> ORGANISM: Artificial Sequence
<220> FEATURE:
<223> OTHER INFORMATION: primer

<400> SEQUENCE: 15
gagggcctgg atcttctttc tc 22

<210> SEQ ID NO 16
<211> LENGTH: 22
<212> TYPE: DNA
<213> ORGANISM: Artificial Sequence
<220> FEATURE:
<223> OTHER INFORMATION: primer

<400> SEQUENCE: 16
gaagtagtcc ttgaccaggc ag 22

<210> SEQ ID NO 17
<211> LENGTH: 20
<212> TYPE: DNA
<213> ORGANISM: Artificial Sequence
<220> FEATURE:
<223> OTHER INFORMATION: VH1 amplified with primer MEDI-1912-F3

<400> SEQUENCE: 17
ccatggccca ggttcagctg 20

<210> SEQ ID NO 18
<211> LENGTH: 54
<212> TYPE: DNA
<213> ORGANISM: Artificial Sequence
<220> FEATURE:
<223> OTHER INFORMATION: VH1 amplified with primer
MEDI1912_W30NNS_F31NNS
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t

<400> SEQUENCE: 18
ctgtcggacc catgtaaagg cgccsnnsnn aaaggtgccg ccgcttgctt tgca 54

<210> SEQ ID NO 19
<211> LENGTH: 24
<212> TYPE: DNA
<213> ORGANISM: Artificial Sequence
<220> FEATURE:
<223> OTHER INFORMATION: VH2 amplified with primer MEDI-1912-F

<400> SEQUENCE: 19
ggcgccttta catgggtccg acag 24

<210> SEQ ID NO 20
<211> LENGTH: 51
<212> TYPE: DNA
<213> ORGANISM: Artificial Sequence
<220> FEATURE:
<223> OTHER INFORMATION: VH2 amplified with primer MEDI-1912_L56NNS
<220> FEATURE:
<221> NAME/KEY: misc_feature
<222> LOCATION: (26)..(27)
<223> OTHER INFORMATION: n is a, c, g, or t

<400> SEQUENCE: 20
ctggaagttc tgggccagat tggtsnngcc gaagataggg atgatgccgc c 51

<210> SEQ ID NO 21
<211> LENGTH: 24
<212> TYPE: DNA
<213> ORGANISM: Artificial Sequence
<220> FEATURE:
<223> OTHER INFORMATION: VH3 amplified with primer MEDI-1912-F2

<400> SEQUENCE: 21
accaatctgg cccagaactt ccag 24

<210> SEQ ID NO 22
<211> LENGTH: 22
<212> TYPE: DNA
<213> ORGANISM: Artificial Sequence
<220> FEATURE:
<223> OTHER INFORMATION: VH3 amplified with primer MEDI-1912-R

<400> SEQUENCE: 22
actcgagacg gtgaccattg tg 22

<210> SEQ ID NO 23
<211> LENGTH: 21
<212> TYPE: DNA
<213> ORGANISM: Artificial Sequence
<220> FEATURE:
<223> OTHER INFORMATION: 7A2-VH-F

<400> SEQUENCE: 23 tttttgcca tggcccaagt g 21

<210> SEQ ID NO 24
<211> LENGTH: 22
<212> TYPE: DNA
<213> ORGANISM: Artificial Sequence
<220> FEATURE:
<223> OTHER INFORMATION: 7A2, 107_A07-VH-R

<400> SEQUENCE: 24
aaaaaaactc gagacggtga cc 22

<210> SEQ ID NO 25
<211> LENGTH: 19
<212> TYPE: DNA
<213> ORGANISM: Artificial Sequence
<220> FEATURE:
<223> OTHER INFORMATION: Bococizumab-VH-F

<400> SEQUENCE: 25 tttttgcca tggcccagg 19

<210> SEQ ID NO 26
<211> LENGTH: 23
<212> TYPE: DNA
<213> ORGANISM: Artificial Sequence
<220> FEATURE:
<223> OTHER INFORMATION: Bococizumab-VH, 7D4-intermediate-R

<400> SEQUENCE: 26
aaaaaaactc gagactgtca cgg 23

<210> SEQ ID NO 27
<211> LENGTH: 24
<212> TYPE: DNA
<213> ORGANISM: Artificial Sequence
<220> FEATURE:
<223> OTHER INFORMATION: Bococizumab, 7D4-intermediate-VL-F

<400> SEQUENCE: 27 tttttgcta gcgacatcca gatg 24

<210> SEQ ID NO 28
<211> LENGTH: 22
<212> TYPE: DNA
<213> ORGANISM: Artificial Sequence
<220> FEATURE:
<223> OTHER INFORMATION: Bococizumab-VL-R

<400> SEQUENCE: 28 tttttgcca tggcccaggt tc 22

<210> SEQ ID NO 29

```
<211> LENGTH: 21
<212> TYPE: DNA
<213> ORGANISM: Artificial Sequence
<220> FEATURE:
<223> OTHER INFORMATION: 7A2-VH-F

<400> SEQUENCE: 29

ttttttgcca tggcccaagt g                                              21

<210> SEQ ID NO 30
<211> LENGTH: 22
<212> TYPE: DNA
<213> ORGANISM: Artificial Sequence
<220> FEATURE:
<223> OTHER INFORMATION: 7A2, 107_A07-VH-R

<400> SEQUENCE: 30

aaaaaaactc gagacggtga cc                                             22

<210> SEQ ID NO 31
<211> LENGTH: 44
<212> TYPE: DNA
<213> ORGANISM: Artificial Sequence
<220> FEATURE:
<223> OTHER INFORMATION: Bococizumab-VL-R-Y53-random
<220> FEATURE:
<221> NAME/KEY: misc_feature
<222> LOCATION: (22)..(23)
<223> OTHER INFORMATION: n is a, c, g, or t

<400> SEQUENCE: 31

ctgggcacgc cggtgtatct snngctggcg ctgtagatca gcag                     44

<210> SEQ ID NO 32
<211> LENGTH: 48
<212> TYPE: DNA
<213> ORGANISM: Artificial Sequence
<220> FEATURE:
<223> OTHER INFORMATION: Bococizumab-VL-R-L94W95-random
<220> FEATURE:
<221> NAME/KEY: misc_feature
<222> LOCATION: (22)..(23)
<223> OTHER INFORMATION: n is a, c, g, or t
<220> FEATURE:
<221> NAME/KEY: misc_feature
<222> LOCATION: (25)..(26)
<223> OTHER INFORMATION: n is a, c, g, or t

<400> SEQUENCE: 32

gtgccctggc caaatgtccg snnsnnagag taccgctgct ggcagtag                 48

<210> SEQ ID NO 33
<211> LENGTH: 24
<212> TYPE: DNA
<213> ORGANISM: Artificial Sequence
<220> FEATURE:
<223> OTHER INFORMATION: Bococizumab-VL-F1

<400> SEQUENCE: 33

ttttttgcta gcgacatcca gatg                                           24

<210> SEQ ID NO 34
<211> LENGTH: 21
<212> TYPE: DNA
<213> ORGANISM: Artificial Sequence
<220> FEATURE:
<223> OTHER INFORMATION: Bococizumab-VL-R1

<400> SEQUENCE: 34
```

gctggcgctg tagatcagca g 21

<210> SEQ ID NO 35
<211> LENGTH: 20
<212> TYPE: DNA
<213> ORGANISM: Artificial Sequence
<220> FEATURE:
<223> OTHER INFORMATION: Bococizumab-VL-F2

<400> SEQUENCE: 35
agatacaccg gcgtgcccag 20

<210> SEQ ID NO 36
<211> LENGTH: 22
<212> TYPE: DNA
<213> ORGANISM: Artificial Sequence
<220> FEATURE:
<223> OTHER INFORMATION: Bococizumab-VL-R2

<400> SEQUENCE: 36
agagtaccgc tgctggcagt ag 22

<210> SEQ ID NO 37
<211> LENGTH: 56
<212> TYPE: DNA
<213> ORGANISM: Artificial Sequence
<220> FEATURE:
<223> OTHER INFORMATION: Bococizumab-VL-R3-extension

<400> SEQUENCE: 37
aaaaaagcgg ccgcggtacg cttgatttcc agcttggtgc cctggccaaa tgtccg 56

<210> SEQ ID NO 38
<211> LENGTH: 24
<212> TYPE: DNA
<213> ORGANISM: Artificial Sequence
<220> FEATURE:
<223> OTHER INFORMATION: Bococizumab-VH-F1

<400> SEQUENCE: 38 tttttgcca tggcccaggt tcag 24

<210> SEQ ID NO 39
<211> LENGTH: 26
<212> TYPE: DNA
<213> ORGANISM: Artificial Sequence
<220> FEATURE:
<223> OTHER INFORMATION: Bococizumab-VH-R1

<400> SEQUENCE: 39
aaaaaaactc gagactgtca cggtgg 26

<210> SEQ ID NO 40
<211> LENGTH: 21
<212> TYPE: DNA
<213> ORGANISM: Artificial Sequence
<220> FEATURE:
<223> OTHER INFORMATION: kappa stuffer F4 primer

<400> SEQUENCE: 40
gtaccgcggc cgcaccttcc g 21

<210> SEQ ID NO 41
<211> LENGTH: 27
<212> TYPE: DNA

<213> ORGANISM: Artificial Sequence
<220> FEATURE:
<223> OTHER INFORMATION: lambda stuffer R3 primer

<400> SEQUENCE: 41
cagccatggc gcctgtggag agaaagg 27

<210> SEQ ID NO 42
<211> LENGTH: 453
<212> TYPE: PRT
<213> ORGANISM: Artificial Sequence
<220> FEATURE:
<223> OTHER INFORMATION: Vesencumab (heavy chain)

<400> SEQUENCE: 42

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gln Ile Ser Pro Ala Gly Gly Tyr Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Glu Leu Pro Tyr Tyr Arg Met Ser Lys Val Met Asp Val
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
```

```
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
            405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450


<210> SEQ ID NO 43
<211> LENGTH: 214
<212> TYPE: PRT
<213> ORGANISM: Artificial Sequence
<220> FEATURE:
<223> OTHER INFORMATION: Vesencumab (light chain)

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Tyr Phe Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Gly Ser Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 44
<211> LENGTH: 440
<212> TYPE: PRT
<213> ORGANISM: Artificial Sequence
<220> FEATURE:
<223> OTHER INFORMATION: Nivolumab (heavy chain)

<400> SEQUENCE: 44

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
```

-continued

```
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 45
<211> LENGTH: 214
<212> TYPE: PRT
<213> ORGANISM: Artificial Sequence
<220> FEATURE:
<223> OTHER INFORMATION: Nivolumab (light chain)

<400> SEQUENCE: 45

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 46
<211> LENGTH: 114
<212> TYPE: PRT
<213> ORGANISM: Artificial Sequence
<220> FEATURE:
<223> OTHER INFORMATION: Briakinumab VH

<400> SEQUENCE: 46

Gln Val Gln Leu Val Glu Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Phe Ile Arg Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser


<210> SEQ ID NO 47
<211> LENGTH: 114
<212> TYPE: PRT
<213> ORGANISM: Artificial Sequence
<220> FEATURE:
<223> OTHER INFORMATION: Briakinumab VL

<400> SEQUENCE: 47

Gln Ser Val Leu Thr Gln Pro Pro Ser Val Ser Gly Ala Pro Gly Gln
1               5                   10                  15

Arg Val Thr Ile Ser Cys Ser Gly Ser Arg Ser Asn Ile Gly Ser Asn
            20                  25                  30

Thr Val Lys Trp Tyr Gln Gln Leu Pro Gly Thr Ala Pro Lys Leu Leu
        35                  40                  45

Ile Tyr Tyr Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

Gln Pro


<210> SEQ ID NO 48
<211> LENGTH: 118
<212> TYPE: PRT
<213> ORGANISM: Artificial Sequence
<220> FEATURE:
<223> OTHER INFORMATION: Ustekinumab VH

<400> SEQUENCE: 48

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
```

```
                85                  90                  95

Ala Arg Arg Arg Pro Gly Gln Gly Tyr Phe Asp Phe Trp Gly Gln Gly
            100                 105                 110

Thr Leu Val Thr Val Ser
        115


<210> SEQ ID NO 49
<211> LENGTH: 110
<212> TYPE: PRT
<213> ORGANISM: Artificial Sequence
<220> FEATURE:
<223> OTHER INFORMATION: Ustekinumab VL

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Ala
            100                 105                 110


<210> SEQ ID NO 50
<211> LENGTH: 11
<212> TYPE: PRT
<213> ORGANISM: Artificial Sequence
<220> FEATURE:
<223> OTHER INFORMATION: Clone 932_01_D10 VH CDR3

<400> SEQUENCE: 50

Asp Ser Arg Pro Pro Tyr Tyr Gly Met Asp Val
1               5                   10


<210> SEQ ID NO 51
<211> LENGTH: 9
<212> TYPE: PRT
<213> ORGANISM: Artificial Sequence
<220> FEATURE:
<223> OTHER INFORMATION: Clone 932_01_D10 VL CDR3

<400> SEQUENCE: 51

Met Gln Ala Leu Gln Thr Pro Pro Thr
1               5


<210> SEQ ID NO 52
<211> LENGTH: 8
<212> TYPE: PRT
<213> ORGANISM: Artificial Sequence
<220> FEATURE:
<223> OTHER INFORMATION: Clone 932_01_C12 VH CDR3

<400> SEQUENCE: 52

Asp Gly Arg Gly Gly Phe Asp Tyr
1               5
```

<210> SEQ ID NO 53
<211> LENGTH: 10
<212> TYPE: PRT
<213> ORGANISM: Artificial Sequence
<220> FEATURE:
<223> OTHER INFORMATION: Clone 932_01_C12 VL CDR3

<400> SEQUENCE: 53

Gln Gln Phe Asn Ser Tyr His Leu Leu Thr
1 5 10

<210> SEQ ID NO 54
<211> LENGTH: 12
<212> TYPE: PRT
<213> ORGANISM: Artificial Sequence
<220> FEATURE:
<223> OTHER INFORMATION: Clone 932_01_A03 VH CDR3

<400> SEQUENCE: 54

Gly Arg Ser Ser Val Ile Asp Tyr Gly Met Asp Val
1 5 10

<210> SEQ ID NO 55
<211> LENGTH: 11
<212> TYPE: PRT
<213> ORGANISM: Artificial Sequence
<220> FEATURE:
<223> OTHER INFORMATION: Clone 932_01_A03 VL CDR3

<400> SEQUENCE: 55

Asn Ser Arg Asp Ser Ser Gly Asn His Val Val
1 5 10

<210> SEQ ID NO 56
<211> LENGTH: 15
<212> TYPE: PRT
<213> ORGANISM: Artificial Sequence
<220> FEATURE:
<223> OTHER INFORMATION: VH CDR3

<400> SEQUENCE: 56

Asp Arg Val Ala Ala Thr His Tyr Tyr Tyr Tyr Gly Met Asp Val
1 5 10 15

<210> SEQ ID NO 57
<211> LENGTH: 9
<212> TYPE: PRT
<213> ORGANISM: Artificial Sequence
<220> FEATURE:
<223> OTHER INFORMATION: VL CDR3

<400> SEQUENCE: 57

Gln Gln Ser Tyr Gly Ser Pro Phe Thr
1 5

<210> SEQ ID NO 58
<211> LENGTH: 10
<212> TYPE: PRT
<213> ORGANISM: Artificial Sequence
<220> FEATURE:
<223> OTHER INFORMATION: VH CDR3

<400> SEQUENCE: 58

Gly Leu Leu Glu Lys Gly Ala Phe Asp Ile
1 5 10

<210> SEQ ID NO 59

<211> LENGTH: 9
<212> TYPE: PRT
<213> ORGANISM: Artificial Sequence
<220> FEATURE:
<223> OTHER INFORMATION: VL CDR3

<400> SEQUENCE: 59

Gln Gln Ser Tyr Ser Thr Pro Gln Thr
1               5

<210> SEQ ID NO 60
<211> LENGTH: 11
<212> TYPE: PRT
<213> ORGANISM: Artificial Sequence
<220> FEATURE:
<223> OTHER INFORMATION: VH CDR3

<400> SEQUENCE: 60

Asp Ser Arg Pro Pro Tyr Tyr Gly Met Asp Val
1               5                   10

<210> SEQ ID NO 61
<211> LENGTH: 10
<212> TYPE: PRT
<213> ORGANISM: Artificial Sequence
<220> FEATURE:
<223> OTHER INFORMATION: VL CDR3

<400> SEQUENCE: 61

Gln Gln Ser Tyr Asn Ser Arg Pro Tyr Thr
1               5                   10

<210> SEQ ID NO 62
<211> LENGTH: 10
<212> TYPE: PRT
<213> ORGANISM: Artificial Sequence
<220> FEATURE:
<223> OTHER INFORMATION: Clone 932_01_A06 VH CDR3

<400> SEQUENCE: 62

Thr Ser Pro Tyr Ser Gly Ser Tyr Asn Asn
1               5                   10

<210> SEQ ID NO 63
<211> LENGTH: 10
<212> TYPE: PRT
<213> ORGANISM: Artificial Sequence
<220> FEATURE:
<223> OTHER INFORMATION: Clone 932_01_A06 VL CDR3

<400> SEQUENCE: 63

Ser Ser Tyr Gly Gly Asn Tyr Lys Tyr Leu
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Clone 932_01_F02 VH CDR3

<400> SEQUENCE: 64

Gly Leu Ser Ser Thr Trp Ala Gly Gly Ala Phe Asp Ile
1               5                   10

<210> SEQ ID NO 65
<211> LENGTH: 11

<212> TYPE: PRT
<213> ORGANISM: Artificial Sequence
<220> FEATURE:
<223> OTHER INFORMATION: Clone 932_01_F02 VL CDR3

<400> SEQUENCE: 65

Asn Ser Arg Asp Ser Ser Gly Asn His Val Val
1               5                   10

<210> SEQ ID NO 66
<211> LENGTH: 12
<212> TYPE: PRT
<213> ORGANISM: Artificial Sequence
<220> FEATURE:
<223> OTHER INFORMATION: VH CDR3

<400> SEQUENCE: 66

Gly Ala His Ser Gly Tyr Asp Ser Asp Phe Asp Tyr
1               5                   10

<210> SEQ ID NO 67
<211> LENGTH: 9
<212> TYPE: PRT
<213> ORGANISM: Artificial Sequence
<220> FEATURE:
<223> OTHER INFORMATION: VL CDR3

<400> SEQUENCE: 67

Gln Gln Tyr Asn Ser Tyr Pro Leu Thr
1               5

<210> SEQ ID NO 68
<211> LENGTH: 11
<212> TYPE: PRT
<213> ORGANISM: Artificial Sequence
<220> FEATURE:
<223> OTHER INFORMATION: Clone 932_01_B01 VH CDR3

<400> SEQUENCE: 68

Val Ser Gly Ser Ser Asn His Ala Phe Asp Ile
1               5                   10

<210> SEQ ID NO 69
<211> LENGTH: 9
<212> TYPE: PRT
<213> ORGANISM: Artificial Sequence
<220> FEATURE:
<223> OTHER INFORMATION: Clone 932_01_B01 VL CDR3

<400> SEQUENCE: 69

His Gln Ser Ser Ser Phe Pro Leu Thr
1               5

<210> SEQ ID NO 70
<211> LENGTH: 13
<212> TYPE: PRT
<213> ORGANISM: Artificial Sequence
<220> FEATURE:
<223> OTHER INFORMATION: Clone 932_01_F01 VH CDR3

<400> SEQUENCE: 70

Asp Thr Ser Ser Arg Tyr Ala Gly Gly Ala Phe Asp Ile
1               5                   10

<210> SEQ ID NO 71
<211> LENGTH: 11
<212> TYPE: PRT

<213> ORGANISM: Artificial Sequence
<220> FEATURE:
<223> OTHER INFORMATION: Clone 932_01_F01 VL CDR3

<400> SEQUENCE: 71

Asn Ser Arg Asp Ser Ser Gly Asn His Val Val
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Clone 932_01_C04 VH CDR3

<400> SEQUENCE: 72

Asp Thr Gly Ser Ser Ala Arg Gly Gly Asp Phe Asp Tyr
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Clone 932_01_C04 VL CDR3

<400> SEQUENCE: 73

Asn Ser Arg Asp Ser Ser Gly Asn His Val Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Clone 931_01_B10 VH CDR3

<400> SEQUENCE: 74

Asp Glu Arg Tyr Tyr Gly Asp Met Asp Val
1               5                   10

<210> SEQ ID NO 75
<211> LENGTH: 9
<212> TYPE: PRT
<213> ORGANISM: Artificial Sequence
<220> FEATURE:
<223> OTHER INFORMATION: Clone 931_01_B10 VL CDR3

<400> SEQUENCE: 75

Met Gln Gly Leu Gln Thr Pro Arg Thr
1               5

<210> SEQ ID NO 76
<211> LENGTH: 13
<212> TYPE: PRT
<213> ORGANISM: Artificial Sequence
<220> FEATURE:
<223> OTHER INFORMATION: Clone 932_01_A01 VH CDR3

<400> SEQUENCE: 76

Asp Tyr Ser Ser Gly Trp Ser Gly Asp Ala Phe Asp Ile
1               5                   10

<210> SEQ ID NO 77
<211> LENGTH: 11
<212> TYPE: PRT
<213> ORGANISM: Artificial Sequence -continued
<220> FEATURE:
<223> OTHER INFORMATION: Clone 930_01_A01 VL CDR3

<400> SEQUENCE: 77

Asn Ser Arg Asp Ser Ser Gly Asn His Val Val
1 5 10

<210> SEQ ID NO 78
<211> LENGTH: 13
<212> TYPE: PRT
<213> ORGANISM: Artificial Sequence
<220> FEATURE:
<223> OTHER INFORMATION: Clone 931_01_B02 VH CDR3

<400> SEQUENCE: 78

Arg Gly Thr Arg Gly Tyr Tyr Tyr Tyr Gly Met Asp Val
1 5 10

<210> SEQ ID NO 79
<211> LENGTH: 10
<212> TYPE: PRT
<213> ORGANISM: Artificial Sequence
<220> FEATURE:
<223> OTHER INFORMATION: Clone 931_01_B02 VL CDR3

<400> SEQUENCE: 79

Gln Gln Ser Tyr Asn Ser Arg Pro Tyr Thr
1 5 10

<210> SEQ ID NO 80
<211> LENGTH: 8
<212> TYPE: PRT
<213> ORGANISM: Artificial Sequence
<220> FEATURE:
<223> OTHER INFORMATION: VH CDR3

<400> SEQUENCE: 80

Thr Asn Asn Gly Phe Ile Asp Tyr
1 5

<210> SEQ ID NO 81
<211> LENGTH: 9
<212> TYPE: PRT
<213> ORGANISM: Artificial Sequence
<220> FEATURE:
<223> OTHER INFORMATION: VL CDR3

<400> SEQUENCE: 81

Ser Gln Ala Ser His Trp Pro Tyr Thr
1 5

<210> SEQ ID NO 82
<211> LENGTH: 9
<212> TYPE: PRT
<213> ORGANISM: Artificial Sequence
<220> FEATURE:
<223> OTHER INFORMATION: VH CDR3

<400> SEQUENCE: 82

Gly Arg Gly Arg Arg Tyr Phe Asp Leu
1 5

<210> SEQ ID NO 83
<211> LENGTH: 9
<212> TYPE: PRT
<213> ORGANISM: Artificial Sequence
<220> FEATURE:

<223> OTHER INFORMATION: VL CDR3

<400> SEQUENCE: 83

Gln Gln Ser Tyr Ser Thr Pro Arg Thr
1 5

<210> SEQ ID NO 84
<211> LENGTH: 12
<212> TYPE: PRT
<213> ORGANISM: Artificial Sequence
<220> FEATURE:
<223> OTHER INFORMATION: Clone 931_01_E03 VH CDR3

<400> SEQUENCE: 84

Asp Gly Asp Glu Gly Glu Leu Gly Ala Phe Asp Ile
1 5 10

<210> SEQ ID NO 85
<211> LENGTH: 9
<212> TYPE: PRT
<213> ORGANISM: Artificial Sequence
<220> FEATURE:
<223> OTHER INFORMATION: Clone 931_01_E03 VL CDR3

<400> SEQUENCE: 85

Gln Gln Ser Tyr Gly Ser Pro Phe Thr
1 5

<210> SEQ ID NO 86
<211> LENGTH: 9
<212> TYPE: PRT
<213> ORGANISM: Artificial Sequence
<220> FEATURE:
<223> OTHER INFORMATION: Clone 930_01_D09 VH CDR3

<400> SEQUENCE: 86

Gly Asp Asn Asn Tyr Tyr Phe Asp Tyr
1 5

<210> SEQ ID NO 87
<211> LENGTH: 9
<212> TYPE: PRT
<213> ORGANISM: Artificial Sequence
<220> FEATURE:
<223> OTHER INFORMATION: Clone 930_01_D09

<400> SEQUENCE: 87

Gln Gln Tyr Tyr Ser Arg Pro Ile Thr
1 5

<210> SEQ ID NO 88
<211> LENGTH: 12
<212> TYPE: PRT
<213> ORGANISM: Artificial Sequence
<220> FEATURE:
<223> OTHER INFORMATION: Clone 930_01_A09 VH CDR3

<400> SEQUENCE: 88

Glu Thr Gly Glu Gly Arg Trp Glu Leu Leu Gly Tyr
1 5 10

<210> SEQ ID NO 89
<211> LENGTH: 9
<212> TYPE: PRT
<213> ORGANISM: Artificial Sequence
<220> FEATURE:
<223> OTHER INFORMATION: Clone 930_01_A09 Clone VL CDR3

<400> SEQUENCE: 89

Met Gln Gly Thr His Trp Pro Arg Thr
1 5

<210> SEQ ID NO 90
<211> LENGTH: 10
<212> TYPE: PRT
<213> ORGANISM: Artificial Sequence
<220> FEATURE:
<223> OTHER INFORMATION: VH CDR3

<400> SEQUENCE: 90

Leu Ser His Thr Ala Pro Leu Val Asp Tyr
1 5 10

<210> SEQ ID NO 91
<211> LENGTH: 9
<212> TYPE: PRT
<213> ORGANISM: Artificial Sequence
<220> FEATURE:
<223> OTHER INFORMATION: VL CDR3

<400> SEQUENCE: 91

Gln Gln Tyr Ser Lys Trp Pro Leu Thr
1 5

<210> SEQ ID NO 92
<211> LENGTH: 13
<212> TYPE: PRT
<213> ORGANISM: Artificial Sequence
<220> FEATURE:
<223> OTHER INFORMATION: Clone 930_01_C02 VH CDR3

<400> SEQUENCE: 92

Ala Ile Ala Pro Arg Arg Tyr Tyr Tyr Gly Met Asp Val
1 5 10

<210> SEQ ID NO 93
<211> LENGTH: 9
<212> TYPE: PRT
<213> ORGANISM: Artificial Sequence
<220> FEATURE:
<223> OTHER INFORMATION: Clone 930_01_C02 VL CDR3

<400> SEQUENCE: 93

Gln Gln Ser Tyr Ser Thr Pro Arg Thr
1 5

<210> SEQ ID NO 94
<211> LENGTH: 13
<212> TYPE: PRT
<213> ORGANISM: Artificial Sequence
<220> FEATURE:
<223> OTHER INFORMATION: Clone 930_01_A12 VH CDR3

<400> SEQUENCE: 94

Ala Ile Ala Pro Arg Arg Tyr Tyr Tyr Gly Met Asp Val
1 5 10

<210> SEQ ID NO 95
<211> LENGTH: 9
<212> TYPE: PRT
<213> ORGANISM: Artificial Sequence
<220> FEATURE:
<223> OTHER INFORMATION: Clone 930_01_A12 VL CDR3

<400> SEQUENCE: 95

Gln Gln Tyr Asn Ser Tyr Pro Leu Thr
1 5

<210> SEQ ID NO 96
<211> LENGTH: 7
<212> TYPE: PRT
<213> ORGANISM: Artificial Sequence
<220> FEATURE:
<223> OTHER INFORMATION: Clone 930_01_A08 VH CDR3

<400> SEQUENCE: 96

Asp Gly Tyr Asn Ser Asp Tyr
1 5

<210> SEQ ID NO 97
<211> LENGTH: 9
<212> TYPE: PRT
<213> ORGANISM: Artificial Sequence
<220> FEATURE:
<223> OTHER INFORMATION: Clone 930_01_A08 VL CDR3

<400> SEQUENCE: 97

Gln Gln Tyr Tyr Ser Lys Pro Leu Thr
1 5

<210> SEQ ID NO 98
<211> LENGTH: 12
<212> TYPE: PRT
<213> ORGANISM: Artificial Sequence
<220> FEATURE:
<223> OTHER INFORMATION: Clone 930_01_C07 VH CDR3

<400> SEQUENCE: 98

Arg Arg Tyr Asn Trp Asp Tyr Asp Tyr Val Asp Val
1 5 10

<210> SEQ ID NO 99
<211> LENGTH: 9
<212> TYPE: PRT
<213> ORGANISM: Artificial Sequence
<220> FEATURE:
<223> OTHER INFORMATION: Clone 930_01_C07 VL CDR3

<400> SEQUENCE: 99

Gln Gln Ser Tyr Ser Thr Pro Arg Thr
1 5

<210> SEQ ID NO 100
<211> LENGTH: 14
<212> TYPE: PRT
<213> ORGANISM: Artificial Sequence
<220> FEATURE:
<223> OTHER INFORMATION: Clone 930_01_A05 VH CDR3

<400> SEQUENCE: 100

Asp Lys Pro Val Gly Ser Ser Gly Trp Tyr Pro Phe Asp Tyr
1 5 10

<210> SEQ ID NO 101
<211> LENGTH: 9
<212> TYPE: PRT
<213> ORGANISM: Artificial Sequence
<220> FEATURE:
<223> OTHER INFORMATION: Clone 930_01_A05 VL CDR3

<400> SEQUENCE: 101

Gln Gln Ser Tyr Ser Thr Pro Tyr Thr
1               5

<210> SEQ ID NO 102
<211> LENGTH: 10
<212> TYPE: PRT
<213> ORGANISM: Artificial Sequence
<220> FEATURE:
<223> OTHER INFORMATION: Clone 930_01_B02 VH CDR3

<400> SEQUENCE: 102

Gln Ile Asn Trp Gly Tyr Tyr Phe Asp Tyr
1               5                   10

<210> SEQ ID NO 103
<211> LENGTH: 9
<212> TYPE: PRT
<213> ORGANISM: Artificial Sequence
<220> FEATURE:
<223> OTHER INFORMATION: Clone 930_01_B02 VL CDR3

<400> SEQUENCE: 103

Met Gln Ala Leu Gln Thr Pro Pro Thr
1               5

<210> SEQ ID NO 104
<211> LENGTH: 18
<212> TYPE: DNA
<213> ORGANISM: Artificial Sequence
<220> FEATURE:
<223> OTHER INFORMATION: CHO-AAVS-Left-F

<400> SEQUENCE: 104
ggtgctcgac tccaccaa                                                    18

<210> SEQ ID NO 105
<211> LENGTH: 21
<212> TYPE: DNA
<213> ORGANISM: Artificial Sequence
<220> FEATURE:
<223> OTHER INFORMATION: CHO-AAVS-Left-R

<400> SEQUENCE: 105
gatggaagtt gccatgaaag a                                                21

<210> SEQ ID NO 106
<211> LENGTH: 22
<212> TYPE: DNA
<213> ORGANISM: Artificial Sequence
<220> FEATURE:
<223> OTHER INFORMATION: CHO-AAVS-Right-F

<400> SEQUENCE: 106
tcttgtattg ccgggatcct tc                                               22

<210> SEQ ID NO 107
<211> LENGTH: 22
<212> TYPE: DNA
<213> ORGANISM: Artificial Sequence
<220> FEATURE:
<223> OTHER INFORMATION: CHO-AAVS-Right-R

<400> SEQUENCE: 107
taactcccag ccctacctac tc                                               22

<210> SEQ ID NO 108
<211> LENGTH: 30
<212> TYPE: DNA
<213> ORGANISM: Artificial Sequence
<220> FEATURE:
<223> OTHER INFORMATION: CHO-AAVS-left-F1-exNcoI

<400> SEQUENCE: 108
ctccacctac cacctcatgg actatatttg 30

<210> SEQ ID NO 109
<211> LENGTH: 36
<212> TYPE: DNA
<213> ORGANISM: Artificial Sequence
<220> FEATURE:
<223> OTHER INFORMATION: CHO-AAVS-left-R1-exNsiI

<400> SEQUENCE: 109
ttttttatgc atcttatgcc agcttttgga tgacgg 36

<210> SEQ ID NO 110
<211> LENGTH: 22
<212> TYPE: DNA
<213> ORGANISM: Artificial Sequence
<220> FEATURE:
<223> OTHER INFORMATION: CHO-AAVS-left-F2-exNheI

<400> SEQUENCE: 110
ctcctctgag tctagccagg cc 22

<210> SEQ ID NO 111
<211> LENGTH: 30
<212> TYPE: DNA
<213> ORGANISM: Artificial Sequence
<220> FEATURE:
<223> OTHER INFORMATION: CHO-AAVS-left-R2-exNcoI

<400> SEQUENCE: 111
caaatatagt ccatgaggtg gtaggtggag 30

<210> SEQ ID NO 112
<211> LENGTH: 38
<212> TYPE: DNA
<213> ORGANISM: Artificial Sequence
<220> FEATURE:
<223> OTHER INFORMATION: CHO-AAVS-left-F3+AsiS1-exDraIII

<400> SEQUENCE: 112
ttttttgcga tcgcgatggc ttacatcccg tgcctttc 38

<210> SEQ ID NO 113
<211> LENGTH: 22
<212> TYPE: DNA
<213> ORGANISM: Artificial Sequence
<220> FEATURE:
<223> OTHER INFORMATION: CHO-AAVS-left-R3-exNheI

<400> SEQUENCE: 113
ggcctggcta gactcagagg ag 22

<210> SEQ ID NO 114
<211> LENGTH: 44
<212> TYPE: DNA
<213> ORGANISM: Artificial Sequence
<220> FEATURE:
<223> OTHER INFORMATION: CHO-AAVS-right-F4-exBstZ171+AscI

<400> SEQUENCE: 114
tatattgtat acggcgcgcc tgtcagggac aagattagtc acag 44

<210> SEQ ID NO 115
<211> LENGTH: 24
<212> TYPE: DNA
<213> ORGANISM: Artificial Sequence
<220> FEATURE:
<223> OTHER INFORMATION: CHO-AAVS-right-R4-ex-BclI

<400> SEQUENCE: 115
gactttggtg ataatgtgag cagc 24

<210> SEQ ID NO 116
<211> LENGTH: 24
<212> TYPE: DNA
<213> ORGANISM: Artificial Sequence
<220> FEATURE:
<223> OTHER INFORMATION: CHO-AAVS-right-F5-ex-BclI

<400> SEQUENCE: 116
gctgctcaca ttatcaccaa agtc 24

<210> SEQ ID NO 117
<211> LENGTH: 35
<212> TYPE: DNA
<213> ORGANISM: Artificial Sequence
<220> FEATURE:
<223> OTHER INFORMATION: CHO-AAVS-right-R5+SbfI

<400> SEQUENCE: 117
tatattcctg caggctcctg caaaggcctg aagag 35

<210> SEQ ID NO 118
<211> LENGTH: 38
<212> TYPE: DNA
<213> ORGANISM: Artificial Sequence
<220> FEATURE:
<223> OTHER INFORMATION: CHO-AAVS-left-R1+NsiI-CRISPR2+3

<400> SEQUENCE: 118
ttttttatgc atcttgatga cggggagata aaagcatc 38

<210> SEQ ID NO 119
<211> LENGTH: 44
<212> TYPE: DNA
<213> ORGANISM: Artificial Sequence
<220> FEATURE:
<223> OTHER INFORMATION: CHO-AAVS-right-F4+BstZ171+AscI

<400> SEQUENCE: 119
tatattgtat acggcgcgcc tgtcagggac aagattagtc acag 44

<210> SEQ ID NO 120
<211> LENGTH: 24
<212> TYPE: DNA
<213> ORGANISM: Artificial Sequence
<220> FEATURE:
<223> OTHER INFORMATION: CHO-AAVS-right-R4-ex-BclI

<400> SEQUENCE: 120
gactttggtg ataatgtgag cagc 24

<210> SEQ ID NO 121
<211> LENGTH: 24

<212> TYPE: DNA
<213> ORGANISM: Artificial Sequence
<220> FEATURE:
<223> OTHER INFORMATION: CHO-AAVS-right-F5-ex-BclI

<400> SEQUENCE: 121
gctgctcaca ttatcaccaa agtc 24

<210> SEQ ID NO 122
<211> LENGTH: 35
<212> TYPE: DNA
<213> ORGANISM: Artificial Sequence
<220> FEATURE:
<223> OTHER INFORMATION: CHO-AAVS-right-R5+SbfI

<400> SEQUENCE: 122
tatattcctg caggctcctg caaaggcctg aagag 35

<210> SEQ ID NO 123
<211> LENGTH: 38
<212> TYPE: DNA
<213> ORGANISM: Artificial Sequence
<220> FEATURE:
<223> OTHER INFORMATION: CHO-AAVS-left-R1+NsiI-CRISPR2+3

<400> SEQUENCE: 123
ttttttatgc atcttgatga cggggagata aaagcatc 38

<210> SEQ ID NO 124
<211> LENGTH: 22
<212> TYPE: DNA
<213> ORGANISM: Artificial Sequence
<220> FEATURE:
<223> OTHER INFORMATION: CRISPR1-R-vector

<400> SEQUENCE: 124
ggaatcatgg gaaataggcc ct 22

<210> SEQ ID NO 125
<211> LENGTH: 22
<212> TYPE: DNA
<213> ORGANISM: Artificial Sequence
<220> FEATURE:
<223> OTHER INFORMATION: CRISPR1-F-vector

<400> SEQUENCE: 125
cgctcacaat tccacacaac at 22

<210> SEQ ID NO 126
<211> LENGTH: 22
<212> TYPE: DNA
<213> ORGANISM: Artificial Sequence
<220> FEATURE:
<223> OTHER INFORMATION: CRISPR-seqF

<400> SEQUENCE: 126
agggcctatt tcccatgatt cc 22

<210> SEQ ID NO 127
<211> LENGTH: 22
<212> TYPE: DNA
<213> ORGANISM: Artificial Sequence
<220> FEATURE:
<223> OTHER INFORMATION: CRISPR-seqR

<400> SEQUENCE: 127

-continued atgttgtgtg gaattgtgag cg 22

<210> SEQ ID NO 128
<211> LENGTH: 18
<212> TYPE: DNA
<213> ORGANISM: Artificial Sequence
<220> FEATURE:
<223> OTHER INFORMATION: TAL target sequence

<400> SEQUENCE: 128
tccccgtcat ccaaaagc 18

<210> SEQ ID NO 129
<211> LENGTH: 18
<212> TYPE: DNA
<213> ORGANISM: Artificial Sequence
<220> FEATURE:
<223> OTHER INFORMATION: TAL target sequence

<400> SEQUENCE: 129
tctgctgtga ctaatctt 18

<210> SEQ ID NO 130
<211> LENGTH: 448
<212> TYPE: DNA
<213> ORGANISM: Artificial Sequence
<220> FEATURE:
<223> OTHER INFORMATION: CRISPR/Cas9 vector

<400> SEQUENCE: 130
agggcctatt tcccatgatt ccttcatatt tgcatatacg atacaaggct gttagagaga 60
taattagaat taatttgact gtaaacacaa agatattagt acaaaatacg tgacgtagaa 120
agtaataatt tcttgggtag tttgcagttt taaaattatg ttttaaaatg gactatcata 180
tgcttaccgt aacttgaaag tatttcgatt tcttggcttt atatatcttg tggaaaggac 240
gaaacaccga tccaaaagct ggcattgtcg ttttagagct agaaatagca agttaaaata 300
aggctagtcc gttatcaact tgaaaaagtg gcaccgagtc ggtgcttttt tctagtatac 360
cgtcgacctc tagctagagc ttggcgtaat catggtcata gctgtttcct gtgtgaaatt 420
gttatccgct cacaattcca cacaacat 448

<210> SEQ ID NO 131
<211> LENGTH: 448
<212> TYPE: DNA
<213> ORGANISM: Artificial Sequence
<220> FEATURE:
<223> OTHER INFORMATION: CRISPR/Cas9 vector

<400> SEQUENCE: 131
agggcctatt tcccatgatt ccttcatatt tgcatatacg atacaaggct gttagagaga 60
taattagaat taatttgact gtaaacacaa agatattagt acaaaatacg tgacgtagaa 120
agtaataatt tcttgggtag tttgcagttt taaaattatg ttttaaaatg gactatcata 180
tgcttaccgt aacttgaaag tatttcgatt tcttggcttt atatatcttg tggaaaggac 240
gaaacaccgt ctccccgtca tccaaaagcg ttttagagct agaaatagca agttaaaata 300
aggctagtcc gttatcaact tgaaaaagtg gcaccgagtc ggtgcttttt tctagtatac 360
cgtcgacctc tagctagagc ttggcgtaat catggtcata gctgtttcct gtgtgaaatt 420
gttatccgct cacaattcca cacaacat 448

-continued

<210> SEQ ID NO 132
<211> LENGTH: 448
<212> TYPE: DNA
<213> ORGANISM: Artificial Sequence
<220> FEATURE:
<223> OTHER INFORMATION: CRISPR/Cas9 vector

<400> SEQUENCE: 132
agggcctatt tcccatgatt ccttcatatt tgcatatacg atacaaggct gttagagaga 60
taattagaat taatttgact gtaaacacaa agatattagt acaaaatacg tgacgtagaa 120
agtaataatt tcttgggtag tttgcagttt taaaattatg ttttaaaatg gactatcata 180
tgcttaccgt aacttgaaag tatttcgatt tcttggcttt atatatcttg tggaaaggac 240
gaaacaccga tgccagcttt tggatgacgg ttttagagct agaaatagca agttaaaata 300
aggctagtcc gttatcaact tgaaaaagtg gcaccgagtc ggtgcttttt tctagtatac 360
cgtcgacctc tagctagagc ttggcgtaat catggtcata gctgtttcct gtgtgaaatt 420
gttatccgct cacaattcca cacaacat 448

<210> SEQ ID NO 133
<211> LENGTH: 37
<212> TYPE: DNA
<213> ORGANISM: Artificial Sequence
<220> FEATURE:
<223> OTHER INFORMATION: primer

<400> SEQUENCE: 133
ctttctctcc acaggcgccc atggccgaag tgcagcc 37

<210> SEQ ID NO 134
<211> LENGTH: 28
<212> TYPE: DNA
<213> ORGANISM: Artificial Sequence
<220> FEATURE:
<223> OTHER INFORMATION: primer

<400> SEQUENCE: 134
ttttttctcg agacggtgac cagggttc 28

<210> SEQ ID NO 135
<211> LENGTH: 28
<212> TYPE: DNA
<213> ORGANISM: Artificial Sequence
<220> FEATURE:
<223> OTHER INFORMATION: primer

<400> SEQUENCE: 135
ttttttgcta gctcctatga gctgactc 28

<210> SEQ ID NO 136
<211> LENGTH: 32
<212> TYPE: DNA
<213> ORGANISM: Artificial Sequence
<220> FEATURE:
<223> OTHER INFORMATION: primer

<400> SEQUENCE: 136
gtcacgcttg gtgcggccgc gggctgacct ag 32

<210> SEQ ID NO 137
<211> LENGTH: 18
<212> TYPE: DNA
<213> ORGANISM: Artificial Sequence
<220> FEATURE:

<223> OTHER INFORMATION: primer

<400> SEQUENCE: 137
ggccgcacca agcgtgac 18

<210> SEQ ID NO 138
<211> LENGTH: 19
<212> TYPE: DNA
<213> ORGANISM: Artificial Sequence
<220> FEATURE:
<223> OTHER INFORMATION: primer

<400> SEQUENCE: 138
ggcgcctgtg gagagaaag 19

<210> SEQ ID NO 139
<211> LENGTH: 28
<212> TYPE: DNA
<213> ORGANISM: Artificial Sequence
<220> FEATURE:
<223> OTHER INFORMATION: primer

<400> SEQUENCE: 139 tttttgcta gctcctatga gctgactc 28

<210> SEQ ID NO 140
<211> LENGTH: 28
<212> TYPE: DNA
<213> ORGANISM: Artificial Sequence
<220> FEATURE:
<223> OTHER INFORMATION: primer

<400> SEQUENCE: 140
ttttttctcg agacggtgac cagggttc 28

<210> SEQ ID NO 141
<211> LENGTH: 899
<212> TYPE: DNA
<213> ORGANISM: Artificial Sequence
<220> FEATURE:
<223> OTHER INFORMATION: Emicizumab VL-CL

<400> SEQUENCE: 141
taataagcta gcagaggaga catccagatg acacagagcc ctagcagcct gtctgccagc 60
gtgggagaca gagtgaccat cacatgcaag gccagccgga acatcgagag acagctggcc 120
tggtatcagc agaagcctgg acaggctcct gagctgctga tctatcaggc cagcagaaaa 180
gaaagcggcg tgcccgatag attcagcggc agcagatacg gcaccgactt caccctgaca 240
atatccagcc tccagcctga ggatatcgcc acctactact gccagcagta cagcgaccct 300
ccactgacat ttggcggagg caccaaggtg gaaatcaagc ggacagcggc cgcccctagc 360
gtgttcatct ttccacctag cgacgagcag ctgaagtctg gcacagcctc tgtcgtgtgc 420
ctgctgaaca acttctaccc cagagaagcc aaggtgcagt ggaaggtgga caacgccctc 480
cagagcggca atagccaaga gagcgtgacc gagcaggaca gcaaggactc tacctacagc 540
ctgagcagca cactgaccct gagcaaggcc gactacgaga agcacaaagt gtacgcctgc 600
gaagtgaccc accagggcct ttctagccct gtgaccaaga gcttcaaccg gggcgaatgt 660
taataatcta gagcctcgac tgtgccttct agttgccagc catctgttgt ttgcccctcc 720
cccgtgcctt ccttgaccct ggaaggtgcc actcccactg tcctttccta ataaaatgag 780
gaaattgcat cgcattgtct gagtaggtgt cattctattc tggggggtgg ggtggggcag 840

```
gacagcaagg gggaggattg ggaagacaat agcaggcatg ctggggaaga tcttaataa     899


<210> SEQ ID NO 142
<211> LENGTH: 1557
<212> TYPE: DNA
<213> ORGANISM: Artificial Sequence
<220> FEATURE:
<223> OTHER INFORMATION: Emicizumab anti-FIXa VH-CH1-CH2-CH3

<400> SEQUENCE: 142

ttattagcca tggcccaggt gcagctggtt gaatctggcg gaggactggt tcagcctggc      60

ggatctctga gactgtcttg tgccgccagc ggcttcacct tcagctacta cgatatccag     120

tgggtccgac aggcccctgg caaaggactt gaatgggtgt ccagcatcag cccctctggc     180

cagtccacct actaccggcg agaagtgaag ggcagattca ccatcagccg ggacaacagc     240

aagaacaccc tgtacctgca gatgaacagc ctgagagccg aggacaccgc cgtgtactac     300

tgcgccagaa gaaccggcag agagtacggc ggaggctggt actttgatta ctggggccag     360

ggcaccctgg tcacagtctc gagcgcctct acaaagggcc ccagcgtttt cccactggct     420

ccctgtagca gaagcaccag cgaatctaca gccgctctgg gctgcctggt caaggactac     480

tttcctgagc ctgtgaccgt gtcctggaac tctggcgctc tgacatctgg cgtgcacacc     540

tttccagccg tgctgcaaag cagcggcctg tacagtctga gcagcgtcgt gacagtgcct     600

agcagctctc tgggcaccca gacctacacc tgtaatgtgg accacaagcc tagcaacacc     660

aaggtggaca agcgcgtgga atctaagtac ggccctcctt gtcctccatg tcctgcacct     720

gagtttctcg gcggaccctc cgtgttcctg tttcctccaa agcctaagga caccctgatg     780

atctccagaa cacccgaagt gacctgcgtg gtggtggacg tttcacaaga ggaccccgag     840

gtgcagttta attggtacgt ggacggcgtg gaagtgcaca acgccaagac caagcctaga     900

gaggaacagt acaacagcac ctacagagtg gtgtccgtgc tgacagtgct gcaccaggat     960

tggctgaacg gcaaagagta caagtgcaag gtgtccaaca agggcctgcc aagcagcatc    1020

gagaaaacca tcagcaaggc caagggccag cctagggaac cccaggttta cacactgcct    1080

ccaagccaga aagagatgac caagaaccag gtgtccctga cctgcctcgt gaagggcttc    1140

taccccttccg atatcgccgt ggaatgggag agcaatggcc agccagagaa caactacaag    1200

accacacctc ctgtgctgga cagcgacggc tcattcttcc tgtacagcaa gctgaccgtg    1260

gacaagagca gatggcaaga gggcaacgtg ttcagctgca gcgtgatgca cgaggccctg    1320

cacaacagat acacccagaa gtccctgtct ctgagccccg aacaaaaact catctcagaa    1380

gaggatctga atgctgtggg ccaggacacg caggaggtca tcgtggtgcc acactccttg    1440

ccctttaagg tggtggtgat ctcagccatc ctggccctgg tggtgctcac catcatctcc    1500

cttatcatcc tcatcatgct ttggcagaag aagccacgtt agtaaaagct tttatta        1557


<210> SEQ ID NO 143
<211> LENGTH: 2152
<212> TYPE: DNA
<213> ORGANISM: Artificial Sequence
<220> FEATURE:
<223> OTHER INFORMATION: Emicizumab anti-FX VH-CH1-CH2-CH3

<400> SEQUENCE: 143

ttattagaat tcaacatgga ctggacctgg agggtcttct gcttgctggc tgtagctcca      60

ggtaaagggc caactggttc cagggctgag gaagggattt tttccagttt agaggactgt     120
```

```
cattctctac tgtgtcctct ccgcaggtgc tcactcccag gttcagctgg tgcagtctgg    180

cagcgagctg aaaaaacctg gcgcctccgt gaaggtgtcc tgcaaggctt ctggctacac    240

ctttaccgac aacaacatgg actgggtccg acaggcccct ggacaaggac ttgagtggat    300

gggcgacatc aacaccagaa gcggcggcag catctacaac gaagagttcc aggacagagt    360

catcatgacc gtggacaaga gcaccgacac cgcctacatg gaactgagca gcctgagaag    420

cgaggacacc gccacctatc actgcgccag aagaaagagc tacggctact acctggacga    480

gtggggcgag ggaacactgg tcacagtgtc tagcgccagc acaaagggcc ctagcgtttt    540

cccactggct ccctgtagca gaagcaccag cgaatctaca gccgctctgg gctgcctcgt    600

gaaggactac tttcctgagc ctgtgaccgt tagctggaac agcggagcac tgacaagcgg    660

cgtgcacaca tttccagccg tgctgcaaag cagcggcctg tactctctga gcagcgtcgt    720

gacagtgcct agcagctctc tgggcaccca gacctacacc tgtaatgtgg accacaagcc    780

tagcaacacc aaggtggaca agcgcgtgga atctaagtac ggccctcctt gtcctccatg    840

tcctgctcca gagtttctcg gcggaccctc cgtgttcctg tttcctccaa agcctaagga    900

caccctgatg atctccagaa cacccgaagt gacctgcgtg gtggtggacg tttcacaaga    960

ggaccccgag gtgcagttca attggtacgt ggacggcgtg gaagtgcaca acgccaagac   1020

caagcctaga gaggaacagt acaacagcac ctacagagtg gtgtccgtgc tgacagtgct   1080

gcaccaggat tggctgaacg gcaaagagta caagtgcaag gtgtccaaca agggcctgcc   1140

aagcagcatc gagaaaacca tcagcaaggc caagggccag cctagggaac cccaggttta   1200

cacactgcct ccaagccaag aggaaatgac caagaaccag gtgtccctga cctgcctggt   1260

caagggcttc taccettccg atatcgccgt ggaatgggag agcaatggcc agccagagaa   1320

caactacaag accacacctc ctgtgctgga cagcgacggc tcattcttcc tgtacagcaa   1380

gctgactgtg gataagagcc ggtggcaaga gggcaacgtg ttcagctgta gcgtgatgca   1440

cgaggccctg cacaaccact acacccaaga gagcctgtct ctgagccctg aacaaaaact   1500

catctcagaa gaggatctga atgctgtggg ccaggacacg caggaggtca tcgtggtgcc   1560

acactccttg ccctttaagg tggtggtgat ctcagccatc ctggccctgg tggtgctcac   1620

catcatctcc cttatcatcc tcatcatgct ttggcagaag aagccacgtt agtaactaag   1680

tcgacatcca gacatgataa gatacattga tgagtttgga caaaccacaa ctagaatgca   1740

gtgaaaaaaa tgctttattt gtgaaatttg tgatgctatt gctttatttg taaccattat   1800

aagctgcaat aaacaagtta acaacaacaa ttgcattcat tttatgtttc aggttcaggg   1860

ggaggtgtgg gaggtttttt aaagcaagta aaacctctac aaatgtggta tggctgatta   1920

tgatcctgca agcctcgtcg tcctggccgg accacgctat ctgtgcaagg tccccggccc   1980

cggacgcgcg ctccatgagc agagcgcccg ccgccgaggc gaagactcgg gcggcgccct   2040

gcccgtccca ccaggtcaac aggcggtaac cggcctcttc atcgggaatg cgcgcgacct   2100

tcagcatcgc cggcatgtcc ccctggcgga cgggaagtat gtatacttat ta           2152
```

<210> SEQ ID NO 144
<211> LENGTH: 389
<212> TYPE: DNA
<213> ORGANISM: Artificial Sequence
<220> FEATURE:
<223> OTHER INFORMATION: Emicizumab anti-FIXa VH

<400> SEQUENCE: 144

```
ttattagcca tggcccaggt gcagctggtt gaatctggcg gaggactggt tcagcctggc     60
```

```
ggatctctga gactgtcttg tgccgccagc ggcttcacct tcagctacta cgatatccag    120

tgggtccgac aggcccctgg caaaggactt gaatgggtgt ccagcatcag cccctctggc    180

cagtccacct actaccggcg agaagtgaag ggcagattca ccatcagccg ggacaacagc    240

aagaacaccc tgtacctgca gatgaacagc ctgagagccg aggacaccgc cgtgtactac    300

tgcgccagaa gaaccggcag agagtacggc ggaggctggt actttgatta ctggggccag    360

ggcaccctgg tcacagtctc gagttatta                                      389
```

<210> SEQ ID NO 145
<211> LENGTH: 353
<212> TYPE: DNA
<213> ORGANISM: Artificial Sequence
<220> FEATURE:
<223> OTHER INFORMATION: Emicizumab VL

<400> SEQUENCE: 145

```
ttattagcta gcgacatcca gatgacacag agccctagca gcctgtctgc cagcgtggga     60

gacagagtga ccatcacatg caaggccagc cggaacatcg agagacagct ggcctggtat    120

cagcagaagc ctggacaggc tcctgagctg ctgatctatc aggccagcag aaaagaaagc    180

ggcgtgcccg atagattcag cggcagcaga tacggcaccg acttcaccct gacaatatcc    240

agcctccagc ctgaggatat cgccacctac tactgccagc agtacagcga ccctccactg    300

acatttggcg gaggcaccaa ggtggaaatc aagcggacag cggccgctta tta           353
```

<210> SEQ ID NO 146
<211> LENGTH: 353
<212> TYPE: DNA
<213> ORGANISM: Artificial Sequence
<220> FEATURE:
<223> OTHER INFORMATION: Emicizumab VL E30Y

<400> SEQUENCE: 146

```
ttattagcta gcgacatcca gatgacacag agccctagca gcctgtctgc cagcgtggga     60

gacagagtga ccatcacatg caaggccagc cggaacatct atagacagct ggcctggtat    120

cagcagaagc ctggacaggc tcctgagctg ctgatctatc aggccagcag aaaatatagc    180

ggcgtgcccg atagattcag cggcagcaga tacggcaccg acttcaccct gacaatatcc    240

agcctccagc ctgaggatat cgccacctac tactgccagc agtacagcga ccctccactg    300

acatttggcg gaggcaccaa ggtggaaatc aagcggacag cggccgctta tta           353
```

<210> SEQ ID NO 147
<211> LENGTH: 353
<212> TYPE: DNA
<213> ORGANISM: Artificial Sequence
<220> FEATURE:
<223> OTHER INFORMATION: Emicizumab VL E30Y E55Y

<400> SEQUENCE: 147

```
ttattagcta gcgacatcca gatgacacag agccctagca gcctgtctgc cagcgtggga     60

gacagagtga ccatcacatg caaggccagc cggaacatct atagacagct ggcctggtat    120

cagcagaagc ctggacaggc tcctgagctg ctgatctatc aggccagcag aaaagaaagc    180

ggcgtgcccg atagattcag cggcagcaga tacggcaccg acttcaccct gacaatatcc    240

agcctccagc ctgaggatat cgccacctac tactgccagc agtacagcga ccctccactg    300

acatttggcg gaggcaccaa ggtggaaatc aagcggacag cggccgctta tta           353
```

<210> SEQ ID NO 148
<211> LENGTH: 353
<212> TYPE: DNA
<213> ORGANISM: Artificial Sequence
<220> FEATURE:
<223> OTHER INFORMATION: Emicizumab VL E30Y E55Y D93S

<400> SEQUENCE: 148
ttattagcta gcgacatcca gatgacacag agccctagca gcctgtctgc cagcgtggga 60
gacagagtga ccatcacatg caaggccagc cggaacatct atagacagct ggcctggtat 120
cagcagaagc ctggacaggc tcctgagctg ctgatctatc aggccagcag aaaatatagc 180
ggcgtgcccg atagattcag cggcagcaga tacggcaccg acttcaccct gacaatatcc 240
agcctccagc ctgaggatat cgccacctac tactgccagc agtacagcag ccctccactg 300
acatttggcg gaggcaccaa ggtggaaatc aagcggacag cggccgctta tta 353

<210> SEQ ID NO 149
<211> LENGTH: 353
<212> TYPE: DNA
<213> ORGANISM: Artificial Sequence
<220> FEATURE:
<223> OTHER INFORMATION: Emicizumab VL E30Y K54R E55Y D93S

<400> SEQUENCE: 149
ttattagcta gcgacatcca gatgacacag agccctagca gcctgtctgc cagcgtggga 60
gacagagtga ccatcacatg caaggccagc cggaacatct atagacagct ggcctggtat 120
cagcagaagc ctggacaggc tcctgagctg ctgatctatc aggccagcag aagatatagc 180
ggcgtgcccg atagattcag cggcagcaga tacggcaccg acttcaccct gacaatatcc 240
agcctccagc ctgaggatat cgccacctac tactgccagc agtacagcag ccctccactg 300
acatttggcg gaggcaccaa ggtggaaatc aagcggacag cggccgctta tta 353

<210> SEQ ID NO 150
<211> LENGTH: 138
<212> TYPE: PRT
<213> ORGANISM: Artificial Sequence
<220> FEATURE:
<223> OTHER INFORMATION: KB_A12 EETI-II

<400> SEQUENCE: 150

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Cys Pro Arg Ile Leu Met Arg Cys Lys Gln
50 55 60

Asp Ser Asp Cys Leu Ala Gly Cys Val Cys Gly Pro Asn Gly Phe Cys
65 70 75 80

Gly Ala Asn Ser Gly Val Ser Asp Arg Phe Ser Ala Ala Lys Ser Gly
85 90 95

Thr Ser Ala Ser Leu Ala Ile Asn Gly Leu Arg Ser Glu Asp Glu Ala
100 105 110

Asp Tyr Tyr Cys Ala Ala Trp Asp Asp Ser Leu Asn Gly Tyr Val Phe
115 120 125

Gly Thr Gly Thr Lys Leu Thr Val Leu Gly 130 135

<210> SEQ ID NO 151
<211> LENGTH: 145
<212> TYPE: PRT
<213> ORGANISM: Artificial Sequence
<220> FEATURE:
<223> OTHER INFORMATION: KB_A12 ProTx-III

<400> SEQUENCE: 151

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Gly Cys Leu Lys Phe Gly Trp Lys Cys Asn
50 55 60

Pro Arg Asn Asp Lys Cys Cys Ser Gly Leu Lys Cys Gly Ser Asn His
65 70 75 80

Asn Trp Cys Lys Trp His Ile Gly Ala Asn Ser Gly Val Ser Asp Arg
85 90 95

Phe Ser Ala Ala Lys Ser Gly Thr Ser Ala Ser Leu Ala Ile Asn Gly
100 105 110

Leu Arg Ser Glu Asp Glu Ala Asp Tyr Tyr Cys Ala Ala Trp Asp Asp
115 120 125

Ser Leu Asn Gly Tyr Val Phe Gly Thr Gly Thr Lys Leu Thr Val Leu
130 135 140

Gly
145

<210> SEQ ID NO 152
<211> LENGTH: 145
<212> TYPE: PRT
<213> ORGANISM: Artificial Sequence
<220> FEATURE:
<223> OTHER INFORMATION: KB_A12 HsTxI

<400> SEQUENCE: 152

Gln Ser Val Leu Thr Gln Pro Pro Ser Val Ser Glu Ala Pro Arg Gln
1 5 10 15

Arg Val Thr Ile Thr Cys Ser Gly Ser Ser Ser Asn Ile Gly Asn Asn
20 25 30

Ala Val Asn Trp Tyr Gln Gln Leu Pro Gly Lys Ala Pro Lys Leu Leu
35 40 45

Ile Tyr Ala Ala Gly Arg Ala Ser Cys Arg Thr Pro Lys Asp Cys Ala
50 55 60

Asp Pro Cys Arg Lys Glu Thr Gly Cys Pro Tyr Gly Lys Cys Met Asn
65 70 75 80

Arg Lys Cys Lys Cys Asn Arg Cys Ala Asn Ser Gly Val Ser Asp Arg
85 90 95

Phe Ser Ala Ala Lys Ser Gly Thr Ser Ala Ser Leu Ala Ile Asn Gly
100 105 110

Leu Arg Ser Glu Asp Glu Ala Asp Tyr Tyr Cys Ala Ala Trp Asp Asp
115 120 125

Ser Leu Asn Gly Tyr Val Phe Gly Thr Gly Thr Lys Leu Thr Val Leu
130 135 140

Gly
145

<210> SEQ ID NO 153
<211> LENGTH: 33
<212> TYPE: PRT
<213> ORGANISM: Artificial Sequence
<220> FEATURE:
<223> OTHER INFORMATION: Wild type ProTx-III knottin sequence

<400> SEQUENCE: 153

Gly Cys Leu Lys Phe Gly Trp Lys Cys Asn Pro Arg Asn Asp Lys Cys
1 5 10 15

Cys Ser Gly Leu Lys Cys Gly Ser Asn His Asn Trp Cys Lys Trp His
20 25 30

Ile

<210> SEQ ID NO 154
<211> LENGTH: 33
<212> TYPE: PRT
<213> ORGANISM: Artificial Sequence
<220> FEATURE:
<223> OTHER INFORMATION: ProTx-III sequence in KB_A12 ProTx-III Set-A Library
<220> FEATURE:
<221> NAME/KEY: MISC_FEATURE
<222> LOCATION: (3)..(6)
<223> OTHER INFORMATION: Xaa can be any naturally occurring amino acid except for Cys, Tyr, Trp, Phe or stop codon.
<220> FEATURE:
<221> NAME/KEY: MISC_FEATURE
<222> LOCATION: (7)..(7)
<223> OTHER INFORMATION: Xaa is one of the following 7 amino acids: Arg, Trp, Gly, Thr, Ser, Ala or Pro

<400> SEQUENCE: 154

Gly Cys Xaa Xaa Xaa Xaa Xaa Lys Cys Asn Pro Arg Asn Asp Lys Cys
1 5 10 15

Cys Ser Gly Leu Lys Cys Gly Ser Asn His Asn Trp Cys Lys Trp His
20 25 30

Ile

<210> SEQ ID NO 155
<211> LENGTH: 33
<212> TYPE: PRT
<213> ORGANISM: Artificial Sequence
<220> FEATURE:
<223> OTHER INFORMATION: ProTx-III sequence in KB_A12 ProTx-III Set-B Library
<220> FEATURE:
<221> NAME/KEY: MISC_FEATURE
<222> LOCATION: (3)..(6)
<223> OTHER INFORMATION: Xaa can be any naturally occurring amino acid except for Cys, Tyr, Trp, Phe or stop codon
<220> FEATURE:
<221> NAME/KEY: MISC_FEATURE
<222> LOCATION: (7)..(7)
<223> OTHER INFORMATION: Xaa is one of the following 7 amino acids: Arg, Trp, Gly, Thr, Ser, Ala or Pro
<220> FEATURE:
<221> NAME/KEY: MISC_FEATURE
<222> LOCATION: (21)..(21)
<223> OTHER INFORMATION: Xaa can be any naturally occurring amino acid except for Cys, Tyr, Trp, Phe or stop codon.
<220> FEATURE:
<221> NAME/KEY: MISC_FEATURE
<222> LOCATION: (31)..(31)
<223> OTHER INFORMATION: Xaa is one of the following 7 amino acids: Arg, Trp, Gly, Thr, Ser, Ala or Pro
<220> FEATURE:

<221> NAME/KEY: MISC_FEATURE
<222> LOCATION: (32)..(33)
<223> OTHER INFORMATION: Xaa can be any naturally occurring amino acid except for Cys, Tyr, Trp, Phe or stop codon.

<400> SEQUENCE: 155

```
Gly Cys Xaa Xaa Xaa Xaa Xaa Lys Cys Asn Pro Arg Asn Asp Lys Cys
1               5                   10                  15

Cys Ser Gly Leu Xaa Cys Gly Ser Asn His Asn Trp Cys Lys Xaa Xaa
            20                  25                  30

Xaa
```

<210> SEQ ID NO 156
<211> LENGTH: 34
<212> TYPE: PRT
<213> ORGANISM: Artificial Sequence
<220> FEATURE:
<223> OTHER INFORMATION: Wild type HsTx1 knottin sequence

<400> SEQUENCE: 156

```
Ala Ser Cys Arg Thr Pro Lys Asp Cys Ala Asp Pro Cys Arg Lys Glu
1               5                   10                  15

Thr Gly Cys Pro Tyr Gly Lys Cys Met Asn Arg Lys Cys Lys Cys Asn
            20                  25                  30

Arg Cys
```

<210> SEQ ID NO 157
<211> LENGTH: 34
<212> TYPE: PRT
<213> ORGANISM: Artificial Sequence
<220> FEATURE:
<223> OTHER INFORMATION: HsTx1 sequence in KB_A12 HsTx-I library
<220> FEATURE:
<221> NAME/KEY: MISC_FEATURE
<222> LOCATION: (14)..(15)
<223> OTHER INFORMATION: Xaa can be any naturally occurring amino acid except for Cys, Tyr, Trp, Phe or stop codon.
<220> FEATURE:
<221> NAME/KEY: MISC_FEATURE
<222> LOCATION: (25)..(25)
<223> OTHER INFORMATION: Xaa can be any naturally occurring amino acid except for Cys, Tyr, Trp, Phe or stop codon.
<220> FEATURE:
<221> NAME/KEY: MISC_FEATURE
<222> LOCATION: (28)..(28)
<223> OTHER INFORMATION: Xaa can be any naturally occurring amino acid except for Cys, Tyr, Trp, Phe or stop codon.

<400> SEQUENCE: 157

```
Ala Ser Cys Arg Thr Pro Lys Asp Cys Ala Asp Pro Cys Xaa Xaa Glu
1               5                   10                  15

Thr Gly Cys Pro Tyr Gly Lys Cys Xaa Asn Arg Xaa Cys Lys Cys Asn
            20                  25                  30

Arg Cys
```

<210> SEQ ID NO 158
<211> LENGTH: 30
<212> TYPE: DNA
<213> ORGANISM: Artificial Sequence
<220> FEATURE:
<223> OTHER INFORMATION: HsTx1 Part 1 Rev

<400> SEQUENCE: 158

```
acaggggtcc gcgcagtctt taggagttcg                                   30
```

```
<210> SEQ ID NO 159
<211> LENGTH: 96
<212> TYPE: DNA
<213> ORGANISM: Artificial Sequence
<220> FEATURE:
<223> OTHER INFORMATION: HsTx1 Part 2 Fwd
<220> FEATURE:
<221> NAME/KEY: misc_feature
<222> LOCATION: (25)..(25)
<223> OTHER INFORMATION: V = A/C/G
<220> FEATURE:
<221> NAME/KEY: misc_feature
<222> LOCATION: (26)..(26)
<223> OTHER INFORMATION: N = A/G/C/T
<220> FEATURE:
<221> NAME/KEY: misc_feature
<222> LOCATION: (27)..(27)
<223> OTHER INFORMATION: S = G/T
<220> FEATURE:
<221> NAME/KEY: misc_feature
<222> LOCATION: (28)..(28)
<223> OTHER INFORMATION: V = A/C/G
<220> FEATURE:
<221> NAME/KEY: misc_feature
<222> LOCATION: (29)..(29)
<223> OTHER INFORMATION: N = A/G/C/T
<220> FEATURE:
<221> NAME/KEY: misc_feature
<222> LOCATION: (30)..(30)
<223> OTHER INFORMATION: S = G/T
<220> FEATURE:
<221> NAME/KEY: misc_feature
<222> LOCATION: (58)..(58)
<223> OTHER INFORMATION: V = A/C/G
<220> FEATURE:
<221> NAME/KEY: misc_feature
<222> LOCATION: (59)..(59)
<223> OTHER INFORMATION: N = A/G/C/T
<220> FEATURE:
<221> NAME/KEY: misc_feature
<222> LOCATION: (60)..(60)
<223> OTHER INFORMATION: S = G/T
<220> FEATURE:
<221> NAME/KEY: misc_feature
<222> LOCATION: (67)..(67)
<223> OTHER INFORMATION: V = A/C/G
<220> FEATURE:
<221> NAME/KEY: misc_feature
<222> LOCATION: (68)..(68)
<223> OTHER INFORMATION: N = A/G/C/T
<220> FEATURE:
<221> NAME/KEY: misc_feature
<222> LOCATION: (69)..(69)
<223> OTHER INFORMATION: S = G/T

<400> SEQUENCE: 159

cctaaagact gcgcggaccc ctgtvnsvns gagactggat gtccatacgg taagtgcvns      60

aatagavnst gcaaatgtaa ccgatgcgca aacagt                               96

<210> SEQ ID NO 160
<211> LENGTH: 29
<212> TYPE: DNA
<213> ORGANISM: Artificial Sequence
<220> FEATURE:
<223> OTHER INFORMATION: ProTx-III Part1 Rev

<400> SEQUENCE: 160

catccccttc ccgctgcgta aatgagaag                                       29

<210> SEQ ID NO 161
<211> LENGTH: 66
<212> TYPE: DNA
<213> ORGANISM: Artificial Sequence
<220> FEATURE:
```

<223> OTHER INFORMATION: ProTx-III Part 2 Fwd
<220> FEATURE:
<221> NAME/KEY: misc_feature
<222> LOCATION: (28)..(28)
<223> OTHER INFORMATION: V = A/C/G
<220> FEATURE:
<221> NAME/KEY: misc_feature
<222> LOCATION: (29)..(29)
<223> OTHER INFORMATION: N = A/G/C/T
<220> FEATURE:
<221> NAME/KEY: misc_feature
<222> LOCATION: (30)..(30)
<223> OTHER INFORMATION: S = G/C
<220> FEATURE:
<221> NAME/KEY: misc_feature
<222> LOCATION: (31)..(31)
<223> OTHER INFORMATION: V = A/C/G
<220> FEATURE:
<221> NAME/KEY: misc_feature
<222> LOCATION: (32)..(32)
<223> OTHER INFORMATION: N = A/G/C/T
<220> FEATURE:
<221> NAME/KEY: misc_feature
<222> LOCATION: (33)..(33)
<223> OTHER INFORMATION: S = G/C
<220> FEATURE:
<221> NAME/KEY: misc_feature
<222> LOCATION: (34)..(34)
<223> OTHER INFORMATION: V = A/C/G
<220> FEATURE:
<221> NAME/KEY: misc_feature
<222> LOCATION: (35)..(35)
<223> OTHER INFORMATION: N = A/G/C/T
<220> FEATURE:
<221> NAME/KEY: misc_feature
<222> LOCATION: (36)..(36)
<223> OTHER INFORMATION: S = G/C
<220> FEATURE:
<221> NAME/KEY: misc_feature
<222> LOCATION: (37)..(37)
<223> OTHER INFORMATION: V = A/C/G
<220> FEATURE:
<221> NAME/KEY: misc_feature
<222> LOCATION: (38)..(38)
<223> OTHER INFORMATION: N = A/G/C/T
<220> FEATURE:
<221> NAME/KEY: misc_feature
<222> LOCATION: (39)..(39)
<223> OTHER INFORMATION: S = G/C
<220> FEATURE:
<221> NAME/KEY: misc_feature
<222> LOCATION: (40)..(40)
<223> OTHER INFORMATION: N = A/G/C/T
<220> FEATURE:
<221> NAME/KEY: misc_feature
<222> LOCATION: (41)..(41)
<223> OTHER INFORMATION: S = G/C

<400> SEQUENCE: 161
ctcatttacg cagcgggaag gggatgcvns vnsvnsvnsn sgaaatgcaa cccaagaaac 60
gataaa 66

<210> SEQ ID NO 162
<211> LENGTH: 81
<212> TYPE: DNA
<213> ORGANISM: Artificial Sequence
<220> FEATURE:
<223> OTHER INFORMATION: ProTx-III setB Part 1 Rev
<220> FEATURE:
<221> NAME/KEY: misc_feature
<222> LOCATION: (41)..(41)
<223> OTHER INFORMATION: S = G/C
<220> FEATURE:
<221> NAME/KEY: misc_feature
<222> LOCATION: (42)..(42)
<223> OTHER INFORMATION: N = A/G/C/T
<220> FEATURE:
<221> NAME/KEY: misc_feature
<222> LOCATION: (43)..(43)
<223> OTHER INFORMATION: S = G/C
<220> FEATURE:
<221> NAME/KEY: misc_feature
<222> LOCATION: (44)..(44)
<223> OTHER INFORMATION: N = A/G/C/T
<220> FEATURE:
<221> NAME/KEY: misc_feature
<222> LOCATION: (45)..(45)
<223> OTHER INFORMATION: B = C, G, or T
<220> FEATURE:
<221> NAME/KEY: misc_feature
<222> LOCATION: (46)..(46)
<223> OTHER INFORMATION: S = G/C
<220> FEATURE:
<221> NAME/KEY: misc_feature
<222> LOCATION: (47)..(47)
<223> OTHER INFORMATION: N = A/G/C/T
<220> FEATURE:
<221> NAME/KEY: misc_feature
<222> LOCATION: (48)..(48)
<223> OTHER INFORMATION: B = C, G, or T
<220> FEATURE:
<221> NAME/KEY: misc_feature
<222> LOCATION: (49)..(49)
<223> OTHER INFORMATION: S = G/C
<220> FEATURE:
<221> NAME/KEY: misc_feature
<222> LOCATION: (50)..(50)
<223> OTHER INFORMATION: N = A/G/C/T
<220> FEATURE:
<221> NAME/KEY: misc_feature
<222> LOCATION: (51)..(51)
<223> OTHER INFORMATION: B = C, G, or T
<220> FEATURE:
<221> NAME/KEY: misc_feature
<222> LOCATION: (52)..(52)
<223> OTHER INFORMATION: S = G/C
<220> FEATURE:
<221> NAME/KEY: misc_feature
<222> LOCATION: (53)..(53)
<223> OTHER INFORMATION: N = A/G/C/T
<220> FEATURE:
<221> NAME/KEY: misc_feature
<222> LOCATION: (54)..(54)
<223> OTHER INFORMATION: B = C, G, or T

<400> SEQUENCE: 162
gagtcctgag cagcatttat cgtttcttgg gttgcatttc snsnbsnbsn bsnbgcatcc 60
ccttcccgct gcgtaaatga g 81

<210> SEQ ID NO 163
<211> LENGTH: 93
<212> TYPE: DNA
<213> ORGANISM: Artificial Sequence
<220> FEATURE:
<223> OTHER INFORMATION: ProTx-III setB Part 2 fwd
<220> FEATURE:
<221> NAME/KEY: misc_feature
<222> LOCATION: (31)..(31)
<223> OTHER INFORMATION: V = A/C/G
<220> FEATURE:
<221> NAME/KEY: misc_feature
<222> LOCATION: (32)..(32)
<223> OTHER INFORMATION: N = A/G/C/T
<220> FEATURE:
<221> NAME/KEY: misc_feature
<222> LOCATION: (33)..(33)
<223> OTHER INFORMATION: S = G/C
<220> FEATURE:
<221> NAME/KEY: misc_feature
<222> LOCATION: (61)..(61)
<223> OTHER INFORMATION: N = A/G/C/T
<220> FEATURE:

<221> NAME/KEY: misc_feature
<222> LOCATION: (62)..(62)
<223> OTHER INFORMATION: S = G/C
<220> FEATURE:
<221> NAME/KEY: misc_feature
<222> LOCATION: (64)..(64)
<223> OTHER INFORMATION: V = A/C/G
<220> FEATURE:
<221> NAME/KEY: misc_feature
<222> LOCATION: (65)..(65)
<223> OTHER INFORMATION: N = A/G/C/T
<220> FEATURE:
<221> NAME/KEY: misc_feature
<222> LOCATION: (66)..(66)
<223> OTHER INFORMATION: S = G/C
<220> FEATURE:
<221> NAME/KEY: misc_feature
<222> LOCATION: (67)..(67)
<223> OTHER INFORMATION: V = A/C/G
<220> FEATURE:
<221> NAME/KEY: misc_feature
<222> LOCATION: (68)..(68)
<223> OTHER INFORMATION: N = A/G/C/T
<220> FEATURE:
<221> NAME/KEY: misc_feature
<222> LOCATION: (69)..(69)
<223> OTHER INFORMATION: S = G/C

<400> SEQUENCE: 163
ccaagaaacg ataaatgctg ctcaggactc vnstgcggca gcaaccacaa ctggtgcaaa 60
nsgvnsvnsg gcgcaaacag tggcgtcagt gac 93

<210> SEQ ID NO 164
<211> LENGTH: 26
<212> TYPE: DNA
<213> ORGANISM: Artificial Sequence
<220> FEATURE:
<223> OTHER INFORMATION: pINT BM40 Lead Fwd

<400> SEQUENCE: 164
gtttgcctgg ccgggagggc tctggc 26

<210> SEQ ID NO 165
<211> LENGTH: 21
<212> TYPE: DNA
<213> ORGANISM: Artificial Sequence
<220> FEATURE:
<223> OTHER INFORMATION: pINT Clambda Not Rev

<400> SEQUENCE: 165
agtcacgctt ggtgcggccg c 21

<210> SEQ ID NO 166
<211> LENGTH: 10380
<212> TYPE: DNA
<213> ORGANISM: Artificial Sequence
<220> FEATURE:
<223> OTHER INFORMATION: pINT17-blasticidin_a

<400> SEQUENCE: 166
gcgatcgctg ctttctctga cctgcattct ctcccctggg cctgtgccgc tttctgtctg 60
cagcttgtgg cctgggtcac ctctacggct ggcccagatc cttccctgcc gcctccttca 120
ggttccgtct tcctccactc cctcttcccc ttgctctctg ctgtgttgct gcccaaggat 180
gctctttccg gagcacttcc ttctcggcgc tgcaccacgt gatgtcctct gagcggatcc 240
tccccgtgtc tgggtcctct ccgggcatct ctcctccctc acccaacccc atgccgtctt 300
cactcgctgg gttccctttt ccttctcctt ctggggcctg tgccatctct cgtttcttag 360

```
gatggccttc tccgacggat gtctcccttg cgtcccgcct cccccttcttg taggcctgca    420
tcatcaccgt ttttctggac aaccccaaag taccccgtct ccctggcttt agccacctct    480
ccatcctctt gctttctttg cctggacacc ccgttctcct gtggattcgg gtcacctctc    540
actcctttca tttgggcagc tcccctaccc cccttacctc tctagtctgt gcaagctctt    600
ccagccccct gtcatggcat cttccagggg tccgagagct cagctagtct tcttcctcca    660
acccgggccc ctatgtccac ttcaggacag catgtttgct gcctccaggg atcctgtgtc    720
cccgagctgg gaccacctta tattcccagg gccggttaat gtggctctgg ttctgggtac    780
ttttatctgt cccctccacc ccacagtggg gcaagatgca tcttctgacc tcttctcttc    840
ctcccacagg gcatggcaaa acctctgagc caggaagaaa gcacactgat tgaaagagca    900
accgctacta tcaacagcat ccccatctcc gaagactatt ctgtggctag tgccgctctg    960
tccagcgacg ggagaatctt caccggtgtg aacgtctacc actttacagg cggaccatgc   1020
gcagagctgg tggtcctggg gactgcagcc gctgcagccg ctggtaatct gacctgtatc   1080
gtggccattg gcaacgaaaa taggggcatc ctgtccccat gcggcaggtg tcggcaggtg   1140
ctgctggatc tgcatcctgg catcaaggca attgtcaaag actctgatgg acagcctacc   1200
gccgtcggta tccgtgaact gctgcctagc ggctatgtct gggagggata atgagcttgg   1260
cttcgaaatg accgaccaag cgacgcccaa cctgccatca cgagatttcg attccaccgc   1320
cgccttctat gaaaggttgg gcttcggaat cgttttccgg gacgccggct ggatgatcct   1380
ccagcgcggg gatctcatgc tggagttctt cgcccacccc aacttgttta ttgcagctta   1440
taatggttac aaataaagca atagcatcac aaatttcaca aataaagcat ttttttcact   1500
gcattctagt tgtggagatc tcgtgaggct ccggtgcccg tcagtgggca gagcgcacat   1560
cgcccacagt ccccgagaag ttggggggag gggtcggcaa ttgaaccggt gcctagagaa   1620
ggtggcgcgg ggtaaactgg gaaagtgatg tcgtgtactg gctccgcctt tttcccgagg   1680
gtgggggaga accgtatata agtgcactag tcgccgtgaa cgttcttttt cgcaacgggt   1740
ttgccgccag aacacaggta agtgccgtgt gtggttcccg cgggcctggc ctctttacgg   1800
gttatggccc ttgcgtgcct tgaattactt ccacctggct gcagtacgtg attcttgatc   1860
ccgagcttcg ggttggaagt gggtgggaga gttcgtggcc ttgcgcttaa ggagcccctt   1920
cgcctcgtgc ttgagttgtg gcctggcctg ggcgctgggg ccgccgcgtg cgaatctggt   1980
ggcaccttcg cgcctgtctc gctgctttcg ataagtctct agccatttaa aatttttgat   2040
gacctgctgc gacgcttttt ttctggcaag atagtcttgt aaatgcgggc caagatcagc   2100
acactggtat ttcggttttt ggggccgcgg gcggcgacgg ggcccgtgcg tcccagcgca   2160
catgttcggc gaggcggggc ctgcgagcgc ggccaccgag aatcggacgg gggtagtctc   2220
aagctgcccg gcctgctctg gtgcctggcc tcgcgccgcc gtgtatcgcc ccgccctggg   2280
cggcaaggct ggcccggtcg gcaccagttg cgtgagcgga aagatggccg cttcccggcc   2340
ctgctgcagg gagcacaaaa tggaggacgc ggcgctcggg agagcgggcg ggtgagtcac   2400
ccacacaaag gaaaagggcc tttccgtcct cagccgtcgc ttcatgtgac tccacggagt   2460
accgggcgcc gtccaggcac ctcgattagt tctccagctt ttggagtacg tcgtctttag   2520
gttgggggga ggggttttat gcgatggagt ttccccacac tgagtgggtg gagactgaag   2580
ttaggccagc ttggcacttg atgtaattct ccttggaatt tgcccttttt gagtttggat   2640
cttggttcat tctcaagcct cagacagtgg ttcaaagttt ttttcttcca tttcaggtgt   2700
```

-continued

```
cgtgaaaact accccctaaaa gccaaaagat ccggagtggc caccatgagg gcctggatct   2760
tctttctcct ttgcctggcc gggagggctc tggcagctag cgacatccag atgacccaga   2820
gcccaagcag cctgagcgcc agcgtgggtg acagagtgac catcacctgt agagccagcg   2880
gtaacatcca caactacctg gcttggtacc agcagaagcc aggtaaggct ccaaagctgc   2940
tgatctacta caccaccacc ctggctgacg gtgtgccaag cagattcagc ggtagcggta   3000
gcggtaccga ctacaccttc accatcagca gcctccagcc agaggacatc gccacctact   3060
actgccagca cttctggagc accccaagga cgttcggcca agggaccaag gtggaaatca   3120
aacgtaccgc ggccgcccct tccgtgttca tcttccctcc ctccgacgag cagctgaagt   3180
ccggcaccgc ctctgtggtg tgcctgctga acaacttcta ccctcgggag gccaaggtgc   3240
agtggaaggt ggacaacgcc ctgcagtccg gcaactccca ggaatccgtc accgagcagg   3300
actccaagga ctctacctac tccctgtcct ccaccctgac cctgtccaag gccgactacg   3360
agaagcacaa gctgtacgcc tgcgaagtga cccaccaggg cctgtcctct cccgtgacca   3420
agtccttcaa ccggggcgag tgctaataag gatccacgac gtgatcagcc tcgactgtgc   3480
cttctagttg ccagccatct gttgtttgcc cctcccccgt gccttccttg accctggaag   3540
gtgccactcc cactgtcctt tcctaataaa atgaggaaat tgcatcgcat tgtctgagta   3600
ggtgtcattc tattctgggg ggtggggtgg ggcaggacag caagggggag gattgggaag   3660
acaatagcag gcatgctggg gacgatcgtc agctggatct agtaatcaat tacggggtca   3720
ttagttcata gcccatatat ggagttccgc gttacataac ttacggtaaa tggcccgcct   3780
ggctgaccgc ccaacgaccc ccgcccattg acgtcaataa tgacgtatgt tcccatagta   3840
acgccaatag ggactttcca ttgacgtcaa tgggtggagt atttacggta aactgcccac   3900
ttggcagtac atcaagtgta tcatatgcca agtacgcccc ctattgacgt caatgacggt   3960
aaatggcccg cctggcatta tgcccagtac atgaccttat gggactttcc tacttggcag   4020
tacatctacg tattagtcat cgctattacc atgctgatgc ggttttggca gtacatcaat   4080
gggcgtggat agcggtttga ctcacgggga tttccaagtc tccaccccat tgacgtcaat   4140
gggagtttgt tttggcacca aaatcaacgg gactttccaa aatgtcgtaa caactccgcc   4200
ccattgacgc aaatgggcgg taggcgtgta cggtgggagg tctatataag cagagctggt   4260
ttagtgaacc gtcagatcag atccatcgat tggccaccat gagttggagc tgtatcatcc   4320
tcttcttggt agcaacagct acaggtaagg ggttaacagt agcaggcttg aggtctggac   4380
atatatatgg gtgacaatga catccacttt gcctttctct ccacaggcgc catggcccag   4440
gtccaactgc aggagagcgg tccaggtctt gtgagaccta gccagaccct gagcctgacc   4500
tgcaccgtgt ctggcagcac cttcagcggc tatggtgtaa actgggtgag acagccacct   4560
ggacgaggtc ttgagtggat tggaatgatt tggggtgatg gaaacacaga ctataattca   4620
gctctcaaat ccagagtgac aatgctggta gacaccagca agaaccagtt cagcctgaga   4680
ctcagcagcg tgacagccgc cgacaccgcg gtctattatt gtgcaagaga gagagattat   4740
aggcttgact actggggtca aggcagcctc gtcacagtct cgagtgcctc caccaagggc   4800
cctagcgtct ttcctctggc cccttcctcc aagtctacct ctggcggcac cgctgctctg   4860
ggctgcctgg tgaaggacta cttccctgag cctgtgaccg tgtcctggaa ctctggcgcc   4920
ctgacctccg gcgtgcatac cttccctgcc gtcctccagt cctccggcct gtactccctg   4980
tcctccgtgg tgaccgtgcc ttcctcctct ctgggcaccc agacctacat ctgcaacgtg   5040
aaccacaagc cttccaacac caaggtggac aagaaggtgg agcctaagtc ctgcgacaag   5100
```

-continued

```
acccacacct gccctccatg tcctgcccct gagctgctgg gcggaccctc cgtgttcctg   5160
ttccctccta agcctaagga caccctgatg atctcccgga cccctgaagt gacctgcgtg   5220
gtggtggacg tgtcccacga agatcctgaa gtgaagttca attggtacgt ggacggcgtg   5280
gaggtgcaca acgccaagac caagcctcgg gaggaacagt acaactccac ctaccgggtg   5340
gtgtctgtgc tgaccgtgct gcaccaggac tggctgaacg gcaaagaata caagtgcaag   5400
gtgtccaaca aggccctgcc tgcccctatc gaaaagacca tctccaaggc taagggccag   5460
ccacgggaac ctcaggtcta cacactgcct cctagccggg acgagctgac caagaaccag   5520
gtgtccctga cctgtctggt gaagggcttc tacccttccg atatcgccgt ggagtgggag   5580
tctaacggcc agcctgagaa caactacaag accacccctc ctgtgctgga ctccgacggc   5640
tccttcttcc tgtactccaa gctgaccgtg gacaagtccc ggtggcagca gggcaacgtg   5700
ttctcctgct ccgtgatgca cgaggccctg cacaaccact acacccagaa gtccctgtcc   5760
ctgtctcctg gcaaggaaca aaaactcatc tcagaagagg atctgaatgc tgtgggccag   5820
gacacgcagg aggtcatcgt ggtgccacac tccttgccct ttaaggtggt ggtgatctca   5880
gccatcctgg ccctggtggt gctcaccatc atctccctta tcatcctcat catgctttgg   5940
cagaagaagc cacgttagta aaagcttgtc acttggaaag taatagtttt tcctgcacgg   6000
gtagtaatca gcctcgactg tgccttctag ttgccagcca tctgttgttt gcccctcccc   6060
cgtgccttcc ttgaccctgg aaggtgccac tcccactgtc ctttcctaat aaaatgagga   6120
aattgcatcg cattgtctga gtaggtgtca ttctattctg gggggtgggg tggggcagga   6180
cagcaagggg gaggattggg aagacaatag caggcatgct ggggatggcc cgggcatgat   6240
aacttcgtat aatgtatgct atacgaagtt atgtatacgg cgcgcccact agggacagga   6300
ttggtgacag aaaagcccca tccttaggcc tcctccttcc tagtctcctg atattgggtc   6360
taacccccac ctcctgttag gcagattcct tatctggtga cacaccccca tttcctggag   6420
ccatctctct ccttgccaga acctctaagg tttgcttacg atggagccag agaggatcct   6480
gggagggaga gcttggcagg gggtgggagg gaagggggg atgcgtgacc tgcccggttc   6540
tcagtggcca ccctgcgcta ccctctccca gaacctgagc tgctctgacg cggctgtctg   6600
gtgcgtttca ctgatcctgg tgctgcagct tccttacact tcccaagagg agaagcagtt   6660
tggaaaaaca aaatcagaat aagttggtcc tgagttctaa ctttggctct tcacctttct   6720
agtccccaat ttatattgtt cctccgtgcg tcagttttac ctgtgagata aggccagtag   6780
ccagccccgt cctggcaggg ctgtggtgag gaggggggtg tccgtgtgga aaactccctt   6840
tgtgagaatg gtgcgtccta ggtgttcacc aggtcgtggc cgcctctact ccctttctct   6900
ttctccatcc ttctttcctt aaagagtccc cagtgctatc tgggacatat tcctccgccc   6960
agagcagggt cccgcttccc taaggccctg ctctgggctt ctgggtttga gtccttggca   7020
agcccaggag aggcgctcag gcttccctgt ccccttcct cgtccaccat ctcatgcccc   7080
tggctctcct gccccttccc tacaggggtt cctggctctg ctctcctgca ggcgatctct   7140
cgatctctcg atttcgatca agacattcct ttaatggtct tttctggaca ccactagggg   7200
tcagaagtag ttcatcaaac tttcttccct ccctaatctc attggttacc ttgggctatc   7260
gaaacttaat taagccacct gacgcgccct gtagcggcgc attaagcgcg gcgggtgtgg   7320
tggttacgcg cagcgtgacc gctacacttg ccagcgccct agcgcccgct cctttcgctt   7380
tcttcccttc ctttctcgcc acgttcgccg gctttccccg tcaagctcta aatcgggggc   7440
```

-continued

```
tccctttagg gttccgattt agtgctttac ggcacctcga ccccaaaaaa cttgattagg   7500
gtgatggttc acgtagtggg ccatcgccct gatagacggt ttttcgccct ttgacgttgg   7560
agtccacgtt ctttaatagt ggactcttgt tccaaactgg aacaacactc aaccctatct   7620
cggtctattc ttttgattta taagggattt tgccgatttc ggcctattgg ttaaaaaatg   7680
agctgattta acaaaaattt aacgcgaatt ttaacaaaat attaacgctt acaatttacg   7740
cgttaagata cattgatgag tttggacaaa ccacaactag ttaattaacc agtcaagtca   7800
gctacttggc gagatcgact tgtctgggtt tcgactacgc tcagaattgc gtcagtcaag   7860
ttcgatctgg tccttgctat tgcacccgtt ctccgattac gagtttcatt taaatcatgt   7920
gagcaaaagg ccagcaaaag gccaggaacc gtaaaaaggc cgcgttgctg gcgtttttcc   7980
ataggctccg cccccctgac gagcatcaca aaaatcgacg ctcaagtcag aggtggcgaa   8040
acccgacagg actataaaga taccaggcgt ttccccctgg aagctccctc gtgcgctctc   8100
ctgttccgac cctgccgctt accggatacc tgtccgcctt tctcccttcg ggaagcgtgg   8160
cgctttctca tagctcacgc tgtaggtatc tcagttcggt gtaggtcgtt cgctccaagc   8220
tgggctgtgt gcacgaaccc cccgttcagc ccgaccgctg cgccttatcc ggtaactatc   8280
gtcttgagtc caacccggta agacacgact tatcgccact ggcagcagcc actggtaaca   8340
ggattagcag agcgaggtat gtaggcggtg ctacagagtt cttgaagtgg tggcctaact   8400
acggctacac tagaagaaca gtatttggta tctgcgctct gctgaagcca gttaccttcg   8460
gaaaaagagt tggtagctct tgatccggca aacaaaccac cgctggtagc ggtggttttt   8520
ttgtttgcaa gcagcagatt acgcgcagaa aaaaaggatc tcaagaagat cctttgatct   8580
tttctacggg gtctgacgct cagtggaacg aaaactcacg ttaagggatt ttggtcatga   8640
gattatcaaa aaggatcttc acctagatcc ttttaaatta aaaatgaagt tttaaatcaa   8700
tctaaagtat atatgagtaa acttggtctg acagttacca atgcttaatc agtgaggcac   8760
ctatctcagc gatctgtcta tttcgttcat ccatagttgc atttaaattt ccgaactctc   8820
caaggccctc gtcggaaaat cttcaaacct ttcgtccgat ccatcttgca ggctacctct   8880
cgaacgaact atcgcaagtc tcttggccgg ccttgcgcct tggctattgc ttggcagcgc   8940
ctatcgccag gtattactcc aatcccgaat atccgagatc gggatcaccc gagagaagtt   9000
caacctacat cctcaatccc gatctatccg agatccgagg aatatcgaaa tcggggcgcg   9060
cctggtgtac cgagaacgat cctctcagtg cgagtctcga cgatccatat cgttgcttgg   9120
cagtcagcca gtcggaatcc agcttgggac ccaggaagtc caatcgtcag atattgtact   9180
caagcctggt cacggcagcg taccgatctg tttaaaccta gatattgata gtctgatcgg   9240
tcaacgtata atcgagtcct agcttttgca aacatctatc aagagacagg atcagcagga   9300
ggctttcgca tgattgaaca agatggattg cacgcaggtt ctccggcggc ttgggtggag   9360
aggctattcg gctatgactg ggcacaacag acaatcggct gctctgatgc cgccgtgttc   9420
cggctgtcag cgcaggggcg tccggttctt tttgtcaaga ccgacctgtc cggtgccctg   9480
aatgaactgc aagacgaggc agcgcggcta tcgtggctgg cgacgacggg cgttccttgc   9540
gcggctgtgc tcgacgttgt cactgaagcg ggaagggact ggctgctatt gggcgaagtg   9600
ccggggcagg atctcctgtc atctcacctt gctcctgccg agaaagtatc catcatggct   9660
gatgcaatgc ggcggctgca tacgcttgat ccggctacct gcccattcga ccaccaagcg   9720
aaacatcgca tcgagcgagc acgtactcgg atggaagccg gtcttgtcga tcaggatgat   9780
ctggacgaag agcatcaggg gctcgcgcca gccgaactgt tcgccaggct caaggcgtct   9840
```

-continued

```
atgcccgacg gcgaggatct cgtcgtgacc cacggcgatg cctgcttgcc gaatatcatg   9900

gtggaaaatg gccgcttttc tggattcatc gactgtggcc gtctgggtgt ggcggaccgc   9960

tatcaggaca tagcgttggc tacccgtgat attgctgaag agcttggcgg cgaatgggct  10020

gaccgcttcc ttgtgcttta cggtatcgcc gcgcccgatt cgcagcgcat cgccttctat  10080

cgccttcttg acgagttctt ctgaccgatt ctaggtgcat tggcgcagaa aaaaatgcct  10140

gatgcgacgc tgcgcgtctt atactcccac atatgccaga ttcagcaacg gatacggctt  10200

ccccaacttg cccacttcca tacgtgtcct ccttaccaga aatttatcct taaggtcgtt  10260

taaactcgac tctggctcta tcgaatctcc gtcgtttcga gcttacgcga acagccgtgg  10320

cgctcatttg ctcgtcgggc atcgaatctc gtcagctatc gtcagcttac ctttttggca  10380
```

<210> SEQ ID NO 167
<211> LENGTH: 132
<212> TYPE: PRT
<213> ORGANISM: Artificial Sequence
<220> FEATURE:
<223> OTHER INFORMATION: Blasticidin resistance amino acid

<400> SEQUENCE: 167

```
Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
            20                  25                  30

Ser Ala Ala Leu Ser Ser Asp Gly Arg Ile Phe Thr Gly Val Asn Val
        35                  40                  45

Tyr His Phe Thr Gly Gly Pro Cys Ala Glu Leu Val Val Leu Gly Thr
    50                  55                  60

Ala Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
    130
```

<210> SEQ ID NO 168
<211> LENGTH: 18
<212> TYPE: PRT
<213> ORGANISM: Artificial Sequence
<220> FEATURE:
<223> OTHER INFORMATION: BM40 leader

<400> SEQUENCE: 168

```
Met Arg Ala Trp Ile Phe Phe Leu Leu Cys Leu Ala Gly Arg Ala Leu
1               5                   10                  15

Ala Ala
```

<210> SEQ ID NO 169
<211> LENGTH: 110
<212> TYPE: PRT
<213> ORGANISM: Artificial Sequence
<220> FEATURE:
<223> OTHER INFORMATION: Humanised D1.3 VL

<400> SEQUENCE: 169

Ser Asp Ile Gln Met Thr Gln Ser Pro Ser Ser Leu Ser Ala Ser Val
1 5 10 15

Gly Asp Arg Val Thr Ile Thr Cys Arg Ala Ser Gly Asn Ile His Asn
20 25 30

Tyr Leu Ala Trp Tyr Gln Gln Lys Pro Gly Lys Ala Pro Lys Leu Leu
35 40 45

Ile Tyr Tyr Thr Thr Thr Leu Ala Asp Gly Val Pro Ser Arg Phe Ser
50 55 60

Gly Ser Gly Ser Gly Thr Asp Tyr Thr Phe Thr Ile Ser Ser Leu Gln
65 70 75 80

Pro Glu Asp Ile Ala Thr Tyr Tyr Cys Gln His Phe Trp Ser Thr Pro
85 90 95

Arg Thr Phe Gly Gln Gly Thr Lys Val Glu Ile Lys Arg Thr
100 105 110

<210> SEQ ID NO 170
<211> LENGTH: 102
<212> TYPE: PRT
<213> ORGANISM: Artificial Sequence
<220> FEATURE:
<223> OTHER INFORMATION: Humanised C kappa

<400> SEQUENCE: 170

Pro Ser Val Phe Ile Phe Pro Pro Ser Asp Glu Gln Leu Lys Ser Gly
1 5 10 15

Thr Ala Ser Val Val Cys Leu Leu Asn Asn Phe Tyr Pro Arg Glu Ala
20 25 30

Lys Val Gln Trp Lys Val Asp Asn Ala Leu Gln Ser Gly Asn Ser Gln
35 40 45

Glu Ser Val Thr Glu Gln Asp Ser Lys Asp Ser Thr Tyr Ser Leu Ser
50 55 60

Ser Thr Leu Thr Leu Ser Lys Ala Asp Tyr Glu Lys His Lys Leu Tyr
65 70 75 80

Ala Cys Glu Val Thr His Gln Gly Leu Ser Ser Pro Val Thr Lys Ser
85 90 95

Phe Asn Arg Gly Glu Cys
100

<210> SEQ ID NO 171
<211> LENGTH: 15
<212> TYPE: PRT
<213> ORGANISM: Artificial Sequence
<220> FEATURE:
<223> OTHER INFORMATION: Mouse VH leader with intron

<400> SEQUENCE: 171

Met Ser Trp Ser Cys Ile Ile Leu Phe Leu Val Ala Thr Ala Thr
1 5 10 15

<210> SEQ ID NO 172
<211> LENGTH: 116
<212> TYPE: PRT
<213> ORGANISM: Artificial Sequence
<220> FEATURE:
<223> OTHER INFORMATION: Humanised D1.3 VH

<400> SEQUENCE: 172

Met Ala Gln Val Gln Leu Gln Glu Ser Gly Pro Gly Leu Val Arg Pro
1 5 10 15

Ser Gln Thr Leu Ser Leu Thr Cys Thr Val Ser Gly Ser Thr Phe Ser
20 25 30

Gly Tyr Gly Val Asn Trp Val Arg Gln Pro Pro Gly Arg Gly Leu Glu
35 40 45

Trp Ile Gly Met Ile Trp Gly Asp Gly Asn Thr Asp Tyr Asn Ser Ala
50 55 60

Leu Lys Ser Arg Val Thr Met Leu Val Asp Thr Ser Lys Asn Gln Phe
65 70 75 80

Ser Leu Arg Leu Ser Ser Val Thr Ala Ala Asp Thr Ala Val Tyr Tyr
85 90 95

Cys Ala Arg Glu Arg Asp Tyr Arg Leu Asp Tyr Trp Gly Gln Gly Ser
100 105 110

Leu Val Thr Val
115

<210> SEQ ID NO 173
<211> LENGTH: 332
<212> TYPE: PRT
<213> ORGANISM: Artificial Sequence
<220> FEATURE:
<223> OTHER INFORMATION: Optimised human IgG1 CH1-CH3

<400> SEQUENCE: 173

Ser Ser Ala Ser Thr Lys Gly Pro Ser Val Phe Pro Leu Ala Pro Ser
1 5 10 15

Ser Lys Ser Thr Ser Gly Gly Thr Ala Ala Leu Gly Cys Leu Val Lys
20 25 30

Asp Tyr Phe Pro Glu Pro Val Thr Val Ser Trp Asn Ser Gly Ala Leu
35 40 45

Thr Ser Gly Val His Thr Phe Pro Ala Val Leu Gln Ser Ser Gly Leu
50 55 60

Tyr Ser Leu Ser Ser Val Val Thr Val Pro Ser Ser Ser Leu Gly Thr
65 70 75 80

Gln Thr Tyr Ile Cys Asn Val Asn His Lys Pro Ser Asn Thr Lys Val
85 90 95

Asp Lys Lys Val Glu Pro Lys Ser Cys Asp Lys Thr His Thr Cys Pro
100 105 110

Pro Cys Pro Ala Pro Glu Leu Leu Gly Gly Pro Ser Val Phe Leu Phe
115 120 125

Pro Pro Lys Pro Lys Asp Thr Leu Met Ile Ser Arg Thr Pro Glu Val
130 135 140

Thr Cys Val Val Val Asp Val Ser His Glu Asp Pro Glu Val Lys Phe
145 150 155 160

Asn Trp Tyr Val Asp Gly Val Glu Val His Asn Ala Lys Thr Lys Pro
165 170 175

Arg Glu Glu Gln Tyr Asn Ser Thr Tyr Arg Val Val Ser Val Leu Thr
180 185 190

Val Leu His Gln Asp Trp Leu Asn Gly Lys Glu Tyr Lys Cys Lys Val
195 200 205

Ser Asn Lys Ala Leu Pro Ala Pro Ile Glu Lys Thr Ile Ser Lys Ala
210 215 220

Lys Gly Gln Pro Arg Glu Pro Gln Val Tyr Thr Leu Pro Pro Ser Arg
225 230 235 240

Asp Glu Leu Thr Lys Asn Gln Val Ser Leu Thr Cys Leu Val Lys Gly
245 250 255

```
Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330


<210> SEQ ID NO 174
<211> LENGTH: 10
<212> TYPE: PRT
<213> ORGANISM: Artificial Sequence
<220> FEATURE:
<223> OTHER INFORMATION: MYC epitope

<400> SEQUENCE: 174

Glu Gln Lys Leu Ile Ser Glu Glu Asp Leu
1               5                   10


<210> SEQ ID NO 175
<211> LENGTH: 50
<212> TYPE: PRT
<213> ORGANISM: Artificial Sequence
<220> FEATURE:
<223> OTHER INFORMATION: PDGFR anchor

<400> SEQUENCE: 175

Asn Ala Val Gly Gln Asp Thr Gln Glu Val Ile Val Val Pro His Ser
1               5                   10                  15

Leu Pro Phe Lys Val Val Val Ile Ser Ala Ile Leu Ala Leu Val Val
            20                  25                  30

Leu Thr Ile Ile Ser Leu Ile Ile Leu Ile Met Leu Trp Gln Lys Lys
        35                  40                  45

Pro Arg
    50


<210> SEQ ID NO 176
<211> LENGTH: 264
<212> TYPE: PRT
<213> ORGANISM: Artificial Sequence
<220> FEATURE:
<223> OTHER INFORMATION: Kanamycin resistance amino acid

<400> SEQUENCE: 176

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95
```

-continued

```
Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Ser Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 177
<211> LENGTH: 392
<212> TYPE: DNA
<213> ORGANISM: Artificial Sequence
<220> FEATURE:
<223> OTHER INFORMATION: MEDI 1912

<400> SEQUENCE: 177

```
ccatggccca ggttcagctg gttcagtctg gcgccgaagt gaagaaacct ggcagcagcg     60

tgaaggtgtc ctgcaaagca agcggcggca ccttttggtt cggcgccttt acatgggtcc    120

gacaggctcc aggacagggc cttgaatgga tgggcggcat catccctatc ttcggcctga    180

ccaatctggc ccagaacttc cagggcagag tgaccatcac agccgacgag agcaccagca    240

ccgtgtacat ggaactgagc agcctgagaa gcgaggacac cgccgtgtac tactgtgcca    300

gaagcagccg gatctacgat ctgaacccta gcctgaccgc ctactacgac atggatgtgt    360

ggggccaggg cacaatggtc accgtctcga gt                                  392
```

<210> SEQ ID NO 178
<211> LENGTH: 129
<212> TYPE: PRT
<213> ORGANISM: Artificial Sequence
<220> FEATURE:
<223> OTHER INFORMATION: VH MEDI 1912

<400> SEQUENCE: 178

```
Met Ala Gln Val Gln Leu Val Gln Ser Gly Ala Glu Val Lys Lys Pro
1               5                   10                  15

Gly Ser Ser Val Lys Val Ser Cys Lys Ala Ser Gly Gly Thr Phe Trp
            20                  25                  30

Phe Gly Ala Phe Thr Trp Val Arg Gln Ala Pro Gly Gln Gly Leu Glu
        35                  40                  45

Trp Met Gly Gly Ile Ile Pro Ile Phe Gly Leu Thr Asn Leu Ala Gln
    50                  55                  60
```

-continued

```
Asn Phe Gln Gly Arg Val Thr Ile Thr Ala Asp Glu Ser Thr Ser Thr
65                  70                  75                  80

Val Tyr Met Glu Leu Ser Ser Leu Arg Ser Glu Asp Thr Ala Val Tyr
                85                  90                  95

Tyr Cys Ala Arg Ser Ser Arg Ile Tyr Asp Leu Asn Pro Ser Leu Thr
            100                 105                 110

Ala Tyr Tyr Asp Met Asp Val Gly Gln Gly Thr Met Val Thr Val Ser
        115                 120                 125

Ser


<210> SEQ ID NO 179
<211> LENGTH: 8
<212> TYPE: PRT
<213> ORGANISM: Artificial Sequence
<220> FEATURE:
<223> OTHER INFORMATION: MEDI 1912 CDR1

<400> SEQUENCE: 179

Gly Gly Thr Phe Trp Phe Gly Ala
1               5


<210> SEQ ID NO 180
<211> LENGTH: 8
<212> TYPE: PRT
<213> ORGANISM: Artificial Sequence
<220> FEATURE:
<223> OTHER INFORMATION: MEDI 1912 CDR2

<400> SEQUENCE: 180

Ile Ile Pro Ile Phe Gly Leu Thr
1               5


<210> SEQ ID NO 181
<211> LENGTH: 21
<212> TYPE: PRT
<213> ORGANISM: Artificial Sequence
<220> FEATURE:
<223> OTHER INFORMATION: MEDI 1912 CDR3

<400> SEQUENCE: 181

Ala Arg Ser Ser Arg Ile Tyr Asp Leu Asn Pro Ser Leu Thr Ala Tyr
1               5                   10                  15

Tyr Asp Met Asp Val
            20


<210> SEQ ID NO 182
<211> LENGTH: 225
<212> TYPE: PRT
<213> ORGANISM: Artificial Sequence
<220> FEATURE:
<223> OTHER INFORMATION: 5A10 (mouse)

<400> SEQUENCE: 182

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
```

65 70 75 80

Met Gln Leu Ser Ser Leu Thr Ser Glu Asp Ser Ala Val Tyr Tyr Cys
85 90 95

Ala Arg Glu Arg Pro Leu Tyr Ala Met Asp Tyr Trp Gly Gln Gly Thr
100 105 110

Ser Val Thr Val Ser Ser Asp Ile Val Met Thr Gln Ser His Lys Phe
115 120 125

Met Ser Thr Ser Val Gly Asp Arg Val Ser Ile Thr Cys Lys Ala Ser
130 135 140

Gln Asp Val Ser Thr Ala Val Ala Trp Tyr Gln Gln Lys Pro Gly Gln
145 150 155 160

Ser Pro Lys Leu Leu Ile Tyr Ser Ala Ser Tyr Arg Tyr Thr Gly Val
165 170 175

Pro Asp Arg Phe Thr Gly Ser Gly Ser Gly Thr Asp Phe Thr Phe Thr
180 185 190

Ile Ser Ser Val Gln Ala Glu Asp Leu Ala Val Tyr Tyr Cys Gln Gln
195 200 205

Arg Tyr Ser Thr Pro Arg Thr Phe Gly Gly Gly Thr Lys Leu Glu Ile
210 215 220

Lys
225

<210> SEQ ID NO 183
<211> LENGTH: 225
<212> TYPE: PRT
<213> ORGANISM: Artificial Sequence
<220> FEATURE:
<223> OTHER INFORMATION: 5A10-i

<400> SEQUENCE: 183

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Tyr Met His Trp Val Arg Gln Ala Pro Gly Gln Gly Leu Glu Trp Met
35 40 45

Gly Glu Ile Asn Pro Ser Gly Gly Arg Thr Asn Tyr Asn Glu Lys Phe
50 55 60

Lys Ser Arg Val Thr Met Thr Arg Asp Thr Ser Thr Ser Thr Val Tyr
65 70 75 80

Met Glu Leu Ser Ser Leu Arg Ser Glu Asp Thr Ala Val Tyr Tyr Cys
85 90 95

Ala Arg Glu Arg Pro Leu Tyr Ala Met Asp Tyr Trp Gly Gln Gly Thr
100 105 110

Thr Val Thr Val Ser Ser Asp Ile Gln Met Thr Gln Ser Pro Ser Ser
115 120 125

Leu Ser Ala Ser Val Gly Asp Arg Val Thr Ile Thr Cys Lys Ala Ser
130 135 140

Gln Asp Val Ser Thr Ala Val Ala Trp Tyr Gln Gln Lys Pro Gly Lys
145 150 155 160

Ala Pro Lys Leu Leu Ile Tyr Ser Ala Ser Tyr Arg Tyr Thr Gly Val
165 170 175

Pro Ser Arg Phe Ser Gly Ser Gly Ser Gly Thr Asp Phe Thr Phe Thr
180 185 190

Ile Ser Ser Leu Gln Pro Glu Asp Ile Ala Thr Tyr Tyr Cys Gln Gln

```
        195                 200                 205

Arg Tyr Ser Thr Pro Arg Thr Phe Gly Gln Gly Thr Lys Leu Glu Ile
    210                 215                 220

Lys
225


<210> SEQ ID NO 184
<211> LENGTH: 225
<212> TYPE: PRT
<213> ORGANISM: Artificial Sequence
<220> FEATURE:
<223> OTHER INFORMATION: Boccocizumab

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
            100                 105                 110

Thr Val Thr Val Ser Ser Asp Ile Gln Met Thr Gln Ser Pro Ser Ser
        115                 120                 125

Leu Ser Ala Ser Val Gly Asp Arg Val Thr Ile Thr Cys Arg Ala Ser
    130                 135                 140

Gln Gly Ile Ser Ser Ala Leu Ala Trp Tyr Gln Gln Lys Pro Gly Lys
145                 150                 155                 160

Ala Pro Lys Leu Leu Ile Tyr Ser Ala Ser Tyr Arg Tyr Thr Gly Val
                165                 170                 175

Pro Ser Arg Phe Ser Gly Ser Gly Ser Gly Thr Asp Phe Thr Phe Thr
            180                 185                 190

Ile Ser Ser Leu Gln Pro Glu Asp Ile Ala Thr Tyr Tyr Cys Gln Gln
        195                 200                 205

Arg Tyr Ser Leu Trp Arg Thr Phe Gly Gln Gly Thr Lys Leu Glu Ile
    210                 215                 220

Lys
225


<210> SEQ ID NO 185
<211> LENGTH: 90
<212> TYPE: PRT
<213> ORGANISM: Artificial Sequence
<220> FEATURE:
<223> OTHER INFORMATION: Bococizumab VH (query 1)

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

-continued

```
Tyr Met His Trp Val Arg Gln Ala Pro Gly Gln Gly Leu Glu Trp Met
        35                  40                  45

Gly Glu Ile Ser Pro Phe Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp
                85                  90


<210> SEQ ID NO 186
<211> LENGTH: 90
<212> TYPE: PRT
<213> ORGANISM: Artificial Sequence
<220> FEATURE:
<223> OTHER INFORMATION: IGHV1-46*01

<400> SEQUENCE: 186

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp
                85                  90


<210> SEQ ID NO 187
<211> LENGTH: 90
<212> TYPE: PRT
<213> ORGANISM: Artificial Sequence
<220> FEATURE:
<223> OTHER INFORMATION: IGHV1-46*03

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp
                85                  90


<210> SEQ ID NO 188
<211> LENGTH: 90
<212> TYPE: PRT
<213> ORGANISM: Artificial Sequence
<220> FEATURE:
<223> OTHER INFORMATION: IGHV1-46*02

<400> SEQUENCE: 188

Gln Val Gln Leu Val Gln Ser Gly Ala Glu Val Lys Lys Pro Gly Ala
```

```
1               5                   10                  15

Ser Val Lys Val Ser Cys Lys Ala Ser Gly Tyr Thr Phe Asn Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp
                85                  90
```

<210> SEQ ID NO 189
<211> LENGTH: 90
<212> TYPE: PRT
<213> ORGANISM: Artificial Sequence
<220> FEATURE:
<223> OTHER INFORMATION: IGHV1-2*02

<400> SEQUENCE: 189

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp
                85                  90
```

<210> SEQ ID NO 190
<211> LENGTH: 90
<212> TYPE: PRT
<213> ORGANISM: Artificial Sequence
<220> FEATURE:
<223> OTHER INFORMATION: IGHV1-2*05

<400> SEQUENCE: 190

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp
                85                  90
```

<210> SEQ ID NO 191
<211> LENGTH: 90
<212> TYPE: PRT
<213> ORGANISM: Artificial Sequence
<220> FEATURE:

<223> OTHER INFORMATION: IGHV1-2*01

<400> SEQUENCE: 191

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Arg Ile Asn Pro Asn Ser Gly Gly Thr Asn Tyr Ala Gln Lys Phe
50 55 60

Gln Gly Arg Val Thr Ser Thr Arg Asp Thr Ser Ile Ser Thr Ala Tyr
65 70 75 80

Met Glu Leu Ser Arg Leu Arg Ser Asp Asp
85 90

<210> SEQ ID NO 192
<211> LENGTH: 90
<212> TYPE: PRT
<213> ORGANISM: Artificial Sequence
<220> FEATURE:
<223> OTHER INFORMATION: IGHV1-2*04

<400> SEQUENCE: 192

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Gly Tyr
20 25 30

Tyr Met His Trp Val Arg Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Trp Val Thr Met Thr Arg Asp Thr Ser Ile Ser Thr Ala Tyr
65 70 75 80

Met Glu Leu Ser Arg Leu Arg Ser Asp Asp
85 90

<210> SEQ ID NO 193
<211> LENGTH: 90
<212> TYPE: PRT
<213> ORGANISM: Artificial Sequence
<220> FEATURE:
<223> OTHER INFORMATION: IGHV1-2*03
<220> FEATURE:
<221> NAME/KEY: misc_feature
<222> LOCATION: (38)..(38)
<223> OTHER INFORMATION: Xaa can be any naturally occurring amino acid

<400> SEQUENCE: 193

Gln Val Gln Leu Val Gln Ser Gly Ala Glu Val Lys Lys Leu Gly Ala
1 5 10 15

Ser Val Lys Val Ser Cys Lys Ala Ser Gly Tyr Thr Phe Thr Gly Tyr
20 25 30

Tyr Met His Trp Val Xaa Gln Ala Pro Gly Gln Gly Leu Glu Trp Met
35 40 45

Gly Trp Ile Asn Pro Asn Ser Gly Gly Thr Asn Tyr Ala Gln Lys Phe
50 55 60

Gln Gly Arg Val Thr Met Thr Arg Asp Thr Ser Ile Ser Thr Ala Tyr
65 70 75 80

```
Met Glu Leu Ser Arg Leu Arg Ser Asp Asp
                85                  90


<210> SEQ ID NO 194
<211> LENGTH: 90
<212> TYPE: PRT
<213> ORGANISM: Artificial Sequence
<220> FEATURE:
<223> OTHER INFORMATION: IGHV1-3*01

<400> SEQUENCE: 194

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Arg Leu Glu Trp Met
        35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp
                85                  90


<210> SEQ ID NO 195
<211> LENGTH: 90
<212> TYPE: PRT
<213> ORGANISM: Artificial Sequence
<220> FEATURE:
<223> OTHER INFORMATION: IGHV1-18*01

<400> SEQUENCE: 195

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp
                85                  90


<210> SEQ ID NO 196
<211> LENGTH: 90
<212> TYPE: PRT
<213> ORGANISM: Artificial Sequence
<220> FEATURE:
<223> OTHER INFORMATION: IGHV1-18*04

<400> SEQUENCE: 196

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
```

50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp
85 90

<210> SEQ ID NO 197
<211> LENGTH: 90
<212> TYPE: PRT
<213> ORGANISM: Artificial Sequence
<220> FEATURE:
<223> OTHER INFORMATION: IGHV1-18*03

<400> SEQUENCE: 197

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp
85 90

<210> SEQ ID NO 198
<211> LENGTH: 90
<212> TYPE: PRT
<213> ORGANISM: Artificial Sequence
<220> FEATURE:
<223> OTHER INFORMATION: IGHV1-45*01

<400> SEQUENCE: 198

Gln Met Gln Leu Val Gln Ser Gly Ala Glu Val Lys Lys Thr Gly Ser
1 5 10 15

Ser Val Lys Val Ser Cys Lys Ala Ser Gly Tyr Thr Phe Thr Tyr Arg
20 25 30

Tyr Leu His Trp Val Arg Gln Ala Pro Gly Gln Ala Leu Glu Trp Met
35 40 45

Gly Trp Ile Thr Pro Phe Asn Gly Asn Thr Asn Tyr Ala Gln Lys Phe
50 55 60

Gln Asp Arg Val Thr Ile Thr Arg Asp Arg Ser Met Ser Thr Ala Tyr
65 70 75 80

Met Glu Leu Ser Ser Leu Arg Ser Glu Asp
85 90

<210> SEQ ID NO 199
<211> LENGTH: 90
<212> TYPE: PRT
<213> ORGANISM: Artificial Sequence
<220> FEATURE:
<223> OTHER INFORMATION: IGHV1-45*02

<400> SEQUENCE: 199

Gln Met Gln Leu Val Gln Ser Gly Ala Glu Val Lys Lys Thr Gly Ser
1 5 10 15

Ser Val Lys Val Ser Cys Lys Ala Ser Gly Tyr Thr Phe Thr Tyr Arg
20 25 30

```
Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp
                85                  90
```

<210> SEQ ID NO 200
<211> LENGTH: 90
<212> TYPE: PRT
<213> ORGANISM: Artificial Sequence
<220> FEATURE:
<223> OTHER INFORMATION: IGHV1-8*01

<400> SEQUENCE: 200

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp
                85                  90
```

<210> SEQ ID NO 201
<211> LENGTH: 375
<212> TYPE: DNA
<213> ORGANISM: Artificial Sequence
<220> FEATURE:
<223> OTHER INFORMATION: Bococizumab VH variant

<400> SEQUENCE: 201

```
tttttgcca tggcccaggt tcagctggtt cagtctggcg ccgaagtgaa gaaacctggc     60

gcctctgtga aggtgtcctg caaggccagc ggctacacct ttaccagcta cgctatgcac    120

tgggtccgac aggcccctgg acaaggactt gagtggatgg gcgagatcag cccattcggc    180

ggcaggacca actacaacga gaagttcaag agccgcgtga ccatgaccag agacaccagc    240

acctccaccg tgtacatgga actgagcagc ctgagaagcg aggacaccgc cgtgtactac    300

tgtgccagag agaggccact gtacgcctct gatctttggg gccagggcac caccgtgaca    360

gtctcgagtt ttttt                                                     375
```

<210> SEQ ID NO 202
<211> LENGTH: 375
<212> TYPE: DNA
<213> ORGANISM: Artificial Sequence
<220> FEATURE:
<223> OTHER INFORMATION: Bococizumab VH variant

<400> SEQUENCE: 202

```
tttttgcca tggcccaggt tcagctggtt cagtctggcg ccgaagtgaa gaaacctggc     60

gcctctgtga aggtgtcctg caaggccagc ggctacacct ttaccagcta cgatatgcac    120
```

-continued

```
tgggtccgac aggcccctgg acaaggactt gagtggatgg gcgagatcag cccattcggc    180

ggcaggacca actacaacga gaagttcaag agccgcgtga ccatgaccag agacaccagc    240

acctccaccg tgtacatgga actgagcagc ctgagaagcg aggacaccgc cgtgtactac    300

tgtgccagag agaggccact gtacgcctct gatctttggg gccagggcac caccgtgaca    360

gtctcgagtt ttttt                                                     375
```

<210> SEQ ID NO 203
<211> LENGTH: 375
<212> TYPE: DNA
<213> ORGANISM: Artificial Sequence
<220> FEATURE:
<223> OTHER INFORMATION: Bococizumab VH variant

<400> SEQUENCE: 203

```
tttttgcca tggcccaggt tcagctggtt cagtctggcg ccgaagtgaa gaaacctggc     60

gcctctgtga aggtgtcctg caaggccagc ggctacacct ttaccagcta ctacatgcac    120

tgggtccgac aggcccctgg acaaggactt gagtggatgg gcgagatcaa cccatctggc    180

ggcagcacca actacaacga gaagttcaag agccgcgtga ccatgaccag agacaccagc    240

acctccaccg tgtacatgga actgagcagc ctgagaagcg aggacaccgc cgtgtactac    300

tgtgccagag agaggccact gtacgcctct gatctttggg gccagggcac caccgtgaca    360

gtctcgagtt ttttt                                                     375
```

<210> SEQ ID NO 204
<211> LENGTH: 375
<212> TYPE: DNA
<213> ORGANISM: Artificial Sequence
<220> FEATURE:
<223> OTHER INFORMATION: Bococizumab VH variant

<400> SEQUENCE: 204

```
tttttgcca tggcccaggt tcagctggtt cagtctggcg ccgaagtgaa gaaacctggc     60

gcctctgtga aggtgtcctg caaggccagc ggctacacct ttaccagcta cgctatgcac    120

tgggtccgac aggcccctgg acaaggactt gagtggatgg gcgagatcaa cccatctggc    180

ggcagcacca actacaacga gaagttcaag agccgcgtga ccatgaccag agacaccagc    240

acctccaccg tgtacatgga actgagcagc ctgagaagcg aggacaccgc cgtgtactac    300

tgtgccagag agaggccact gtacgcctct gatctttggg gccagggcac caccgtgaca    360

gtctcgagtt ttttt                                                     375
```

<210> SEQ ID NO 205
<211> LENGTH: 375
<212> TYPE: DNA
<213> ORGANISM: Artificial Sequence
<220> FEATURE:
<223> OTHER INFORMATION: Bococizumab VH variant

<400> SEQUENCE: 205

```
tttttgcca tggcccaggt tcagctggtt cagtctggcg ccgaagtgaa gaaacctggc     60

gcctctgtga aggtgtcctg caaggccagc ggctacacct ttaccagcta cgatatgcac    120

tgggtccgac aggcccctgg acaaggactt gagtggatgg gcgagatcaa cccatctggc    180

ggcagcacca actacaacga gaagttcaag agccgcgtga ccatgaccag agacaccagc    240

acctccaccg tgtacatgga actgagcagc ctgagaagcg aggacaccgc cgtgtactac    300

tgtgccagag agaggccact gtacgcctct gatctttggg gccagggcac caccgtgaca    360
```

gtctcgagtt ttttt 375

<210> SEQ ID NO 206
<211> LENGTH: 375
<212> TYPE: DNA
<213> ORGANISM: Artificial Sequence
<220> FEATURE:
<223> OTHER INFORMATION: Bococizumab VH variant

<400> SEQUENCE: 206 tttttgcca tggcccaggt tcagctggtt cagtctggcg ccgaagtgaa gaaacctggc 60
gcctctgtga aggtgtcctg caaggccagc ggctacacct ttaccagcta ctacatgcac 120
tgggtccgac aggcccctgg acaaggactt gagtggatgg gcgagatcag cccattcggc 180
ggcaggacca actacaacga gaagttcaag agccgcgtga ccatgaccag agacaccagc 240
acctccaccg tgtacatgga actgagcagc ctgagaagcg aggacaccgc cgtgtactac 300
tgtgccagag agaggccact gtacgcctct gatctttggg gccagggcac caccgtgaca 360
gtctcgagtt ttttt 375

<210> SEQ ID NO 207
<211> LENGTH: 353
<212> TYPE: DNA
<213> ORGANISM: Artificial Sequence
<220> FEATURE:
<223> OTHER INFORMATION: Bococizumab VH variant

<400> SEQUENCE: 207 tttttgcta gcgacatcca gatgacacag agccctagca gcctgtctgc cagcgtggga 60
gacagagtga ccatcacctg tagagccagc cagggcatct cttctgccct ggcatggtat 120
cagcagaagc ctggcaaggc ccctaagctg ctgatctaca gcgccagcta aagatacacc 180
ggcgtgccca gcagattttc tggcagcggc tctggcaccg acttcacctt caccataagc 240
agcctgcagc ctgaggatat cgccacctac tactgccagc agcggtactc ttagtaacgg 300
acatttggcc agggcaccaa gctggaaatc aagcgtaccg cggccgcttt ttt 353

<210> SEQ ID NO 208
<211> LENGTH: 8
<212> TYPE: PRT
<213> ORGANISM: Artificial Sequence
<220> FEATURE:
<223> OTHER INFORMATION: VH CDR1 Bococizumab clones 884 01 A01-04, A06,
A-8-12, B02-B03, B05, B07-C03, C05-D06, D08, D10-E02, E04-E-06,
E08-F04, F06-F10, F12-G07, G09-H07, Bococizuma

<400> SEQUENCE: 208

Gly Tyr Thr Phe Thr Ser Tyr Tyr
1 5

<210> SEQ ID NO 209
<211> LENGTH: 8
<212> TYPE: PRT
<213> ORGANISM: Artificial Sequence
<220> FEATURE:
<223> OTHER INFORMATION: VH CDR1 Bococizumab clones 884 01 A05

<400> SEQUENCE: 209

Gly Tyr Thr Phe Thr Ser Tyr Ser
1 5

<210> SEQ ID NO 210

<211> LENGTH: 8
<212> TYPE: PRT
<213> ORGANISM: Artificial Sequence
<220> FEATURE:
<223> OTHER INFORMATION: VH CDR1 Bococizumab clones 884 01 A07, B01, B06, C04, D09, F11

<400> SEQUENCE: 210

Gly Tyr Thr Phe Thr Ser Tyr Asp
1 5

<210> SEQ ID NO 211
<211> LENGTH: 8
<212> TYPE: PRT
<213> ORGANISM: Artificial Sequence
<220> FEATURE:
<223> OTHER INFORMATION: VH CDR1 Bococizumab clones 884 01 B04, E03, F05, G08

<400> SEQUENCE: 211

Gly Tyr Thr Phe Thr Ser Tyr Ala
1 5

<210> SEQ ID NO 212
<211> LENGTH: 8
<212> TYPE: PRT
<213> ORGANISM: Artificial Sequence
<220> FEATURE:
<223> OTHER INFORMATION: VH CDR1 Bococizumab clones 5A10i

<400> SEQUENCE: 212

Gly Tyr Thr Phe Thr Ser Tyr Trp
1 5

<210> SEQ ID NO 213
<211> LENGTH: 11
<212> TYPE: PRT
<213> ORGANISM: Artificial Sequence
<220> FEATURE:
<223> OTHER INFORMATION: VH CDR2 Bococizumab clones 884 01 A01-04, A06, A-8-12, B02-B05, B07-C03, C05-D06, D08, D10-E02, E04-E06, E08-H07

<400> SEQUENCE: 213

Ile Asn Pro Ser Gly Gly Ser Thr Asn Tyr Asn
1 5 10

<210> SEQ ID NO 214
<211> LENGTH: 11
<212> TYPE: PRT
<213> ORGANISM: Artificial Sequence
<220> FEATURE:
<223> OTHER INFORMATION: VH CDR2 Bococizumab clones 884 01 A05

<400> SEQUENCE: 214

Ile Asn Pro Ser Gly Gly Arg Thr Asn Tyr Asn
1 5 10

<210> SEQ ID NO 215
<211> LENGTH: 11
<212> TYPE: PRT
<213> ORGANISM: Artificial Sequence
<220> FEATURE:
<223> OTHER INFORMATION: VH CDR2 Bococizumab clones B01, B06, C04, D09, E03, Bococizuma b

<400> SEQUENCE: 215

Ile Ser Pro Phe Gly Gly Arg Thr Asn Tyr Asn
1 5 10

<210> SEQ ID NO 216
<211> LENGTH: 11
<212> TYPE: PRT
<213> ORGANISM: Artificial Sequence
<220> FEATURE:
<223> OTHER INFORMATION: VH CDR2 Bococizumab clones 5A10i

<400> SEQUENCE: 216

Ile Asn Pro Ser Asn Gly Arg Thr Asn Tyr Asn
1 5 10

<210> SEQ ID NO 217
<211> LENGTH: 5
<212> TYPE: PRT
<213> ORGANISM: Artificial Sequence
<220> FEATURE:
<223> OTHER INFORMATION: VL CDR2 Bococizumab clones 884-01-A01, A12. B06, C08, C11, D06, F04, F07, F12, G09, G10, H03, H04, H06,

<400> SEQUENCE: 217

Ser Leu Arg Tyr Thr
1 5

<210> SEQ ID NO 218
<211> LENGTH: 5
<212> TYPE: PRT
<213> ORGANISM: Artificial Sequence
<220> FEATURE:
<223> OTHER INFORMATION: VL CDR2 Bococizumab clones 884-01-A02, A08, B08, E03, E10, F08, G03, G05, H02,

<400> SEQUENCE: 218

Ser Glu Arg Tyr Thr
1 5

<210> SEQ ID NO 219
<211> LENGTH: 5
<212> TYPE: PRT
<213> ORGANISM: Artificial Sequence
<220> FEATURE:
<223> OTHER INFORMATION: VL CDR2 Bococizumab clones 884-01-A03, A05, B01, D03, G02,

<400> SEQUENCE: 219

Ser Gln Arg Tyr Thr
1 5

<210> SEQ ID NO 220
<211> LENGTH: 5
<212> TYPE: PRT
<213> ORGANISM: Artificial Sequence
<220> FEATURE:
<223> OTHER INFORMATION: VL CDR2 Bococizumab clones 884-01-A04, B11, C01, C03, D01, G06,

<400> SEQUENCE: 220

Ser Ser Arg Tyr Thr
1 5

<210> SEQ ID NO 221
<211> LENGTH: 5
<212> TYPE: PRT
<213> ORGANISM: Artificial Sequence
<220> FEATURE:
<223> OTHER INFORMATION: VL CDR2 Bococizumab clones 884-01-A06, B05, B07, B12, D05, D07, F03, H01,H05,

<400> SEQUENCE: 221

Ser Ala Arg Tyr Thr
1 5

<210> SEQ ID NO 222
<211> LENGTH: 5
<212> TYPE: PRT
<213> ORGANISM: Artificial Sequence
<220> FEATURE:
<223> OTHER INFORMATION: VL CDR2 Bococizumab clones 884-01-A07, c09, H07

<400> SEQUENCE: 222

Ser Pro Arg Tyr Thr
1 5

<210> SEQ ID NO 223
<211> LENGTH: 5
<212> TYPE: PRT
<213> ORGANISM: Artificial Sequence
<220> FEATURE:
<223> OTHER INFORMATION: VL CDR2 Bococizumab clones 884-01-A09, B03, C02, C04, D09-D11 E02,

<400> SEQUENCE: 223

Ser Asp Arg Tyr Thr
1 5

<210> SEQ ID NO 224
<211> LENGTH: 5
<212> TYPE: PRT
<213> ORGANISM: Artificial Sequence
<220> FEATURE:
<223> OTHER INFORMATION: VL CDR2 Bococizumab clones 884-01-A11, B04, C10, D02, D08, E01, E04, F09, F11,

<400> SEQUENCE: 224

Ser Thr Arg Tyr Thr
1 5

<210> SEQ ID NO 225
<211> LENGTH: 5
<212> TYPE: PRT
<213> ORGANISM: Artificial Sequence
<220> FEATURE:
<223> OTHER INFORMATION: VL CDR2 Bococizumab clones 884-01-B02, B10, C05, C07, D04, D12, E12, G08,

<400> SEQUENCE: 225

Ser Met Arg Tyr Thr
1 5

<210> SEQ ID NO 226
<211> LENGTH: 5
<212> TYPE: PRT
<213> ORGANISM: Artificial Sequence
<220> FEATURE:
<223> OTHER INFORMATION: VL CDR2 Bococizumab clones 884-01-B09, C06, E05, E06, E09, F10, G04, G07, G11, G12,

<400> SEQUENCE: 226

Ser Val Arg Tyr Thr
1 5

<210> SEQ ID NO 227
<211> LENGTH: 5
<212> TYPE: PRT
<213> ORGANISM: Artificial Sequence
<220> FEATURE:
<223> OTHER INFORMATION: VL CDR2 Bococizumab clones 884-01-E08, F06

<400> SEQUENCE: 227

Ser Asn Arg Tyr Thr
1 5

<210> SEQ ID NO 228
<211> LENGTH: 5
<212> TYPE: PRT
<213> ORGANISM: Artificial Sequence
<220> FEATURE:
<223> OTHER INFORMATION: VL CDR2 Bococizumab clones 884-01-F01

<400> SEQUENCE: 228

Ser Tyr Leu Glu Ser
1 5

<210> SEQ ID NO 229
<211> LENGTH: 5
<212> TYPE: PRT
<213> ORGANISM: Artificial Sequence
<220> FEATURE:
<223> OTHER INFORMATION: VL CDR2 Bococizumab clones 884-01-F02, F05,
Bococizuma b, 5A10i

<400> SEQUENCE: 229

Ser Tyr Arg Tyr Thr
1 5

<210> SEQ ID NO 230
<211> LENGTH: 5
<212> TYPE: PRT
<213> ORGANISM: Artificial Sequence
<220> FEATURE:
<223> OTHER INFORMATION: VL CDR2 Bococizumab clones 884-01-G01

<400> SEQUENCE: 230

Ser His Arg Tyr Thr
1 5

<210> SEQ ID NO 231
<211> LENGTH: 9
<212> TYPE: PRT
<213> ORGANISM: Artificial Sequence
<220> FEATURE:
<223> OTHER INFORMATION: VL CDR3 Bococizumab clones 884-01-A01

<400> SEQUENCE: 231

Gln Gln Arg Tyr Ser Leu Gln Arg Thr
1 5

<210> SEQ ID NO 232
<211> LENGTH: 9
<212> TYPE: PRT
<213> ORGANISM: Artificial Sequence
<220> FEATURE:
<223> OTHER INFORMATION: VL CDR3 Bococizumab clones 884-01-A02,

<400> SEQUENCE: 232

Gln Gln Arg Tyr Ser Pro Trp Arg Thr
1 5

<210> SEQ ID NO 233
<211> LENGTH: 9
<212> TYPE: PRT
<213> ORGANISM: Artificial Sequence
<220> FEATURE:
<223> OTHER INFORMATION: VL CDR3 Bococizumab clones 884-01-A03, F05,

<400> SEQUENCE: 233

Gln Gln Arg Tyr Ser Asn Ser Arg Thr
1               5

<210> SEQ ID NO 234
<211> LENGTH: 9
<212> TYPE: PRT
<213> ORGANISM: Artificial Sequence
<220> FEATURE:
<223> OTHER INFORMATION: VL CDR3 Bococizumab clones 884-01-A04, B12,

<400> SEQUENCE: 234

Gln Gln Arg Tyr Ser Leu Lys Arg Thr
1               5

<210> SEQ ID NO 235
<211> LENGTH: 9
<212> TYPE: PRT
<213> ORGANISM: Artificial Sequence
<220> FEATURE:
<223> OTHER INFORMATION: VL CDR3 Bococizumab clones 884-01-A05,

<400> SEQUENCE: 235

Gln Gln Arg Tyr Ser Ser Pro Arg Thr
1               5

<210> SEQ ID NO 236
<211> LENGTH: 9
<212> TYPE: PRT
<213> ORGANISM: Artificial Sequence
<220> FEATURE:
<223> OTHER INFORMATION: VL CDR3 Bococizumab clones 884-01-A06, B05,

<400> SEQUENCE: 236

Gln Gln Arg Tyr Ser Asn Asn Arg Thr
1               5

<210> SEQ ID NO 237
<211> LENGTH: 9
<212> TYPE: PRT
<213> ORGANISM: Artificial Sequence
<220> FEATURE:
<223> OTHER INFORMATION: VL CDR3 Bococizumab clones 884-01-A07,

<400> SEQUENCE: 237

Gln Gln Arg Tyr Ser Ser Gly Arg Thr
1               5

<210> SEQ ID NO 238
<211> LENGTH: 9
<212> TYPE: PRT
<213> ORGANISM: Artificial Sequence
<220> FEATURE:
<223> OTHER INFORMATION: VL CDR3 Bococizumab clones 884-01-A08, A11,

<400> SEQUENCE: 238

Gln Gln Arg Tyr Ser Leu Ala Arg Thr
1               5

<210> SEQ ID NO 239
<211> LENGTH: 9
<212> TYPE: PRT
<213> ORGANISM: Artificial Sequence
<220> FEATURE:

<223> OTHER INFORMATION: VL CDR3 Bococizumab clones 884-01-A09, B09,

<400> SEQUENCE: 239

Gln Gln Arg Tyr Ser Thr Leu Arg Thr
1 5

<210> SEQ ID NO 240
<211> LENGTH: 9
<212> TYPE: PRT
<213> ORGANISM: Artificial Sequence
<220> FEATURE:
<223> OTHER INFORMATION: VL CDR3 Bococizumab clones 884-01-A11

<400> SEQUENCE: 240

Gln Gln Arg Tyr Ser Leu Ala Arg Thr
1 5

<210> SEQ ID NO 241
<211> LENGTH: 9
<212> TYPE: PRT
<213> ORGANISM: Artificial Sequence
<220> FEATURE:
<223> OTHER INFORMATION: VL CDR3 Bococizumab clones 884-01-A12,

<400> SEQUENCE: 241

Gln Gln Arg Tyr Ser Ser Leu Arg Thr
1 5

<210> SEQ ID NO 242
<211> LENGTH: 9
<212> TYPE: PRT
<213> ORGANISM: Artificial Sequence
<220> FEATURE:
<223> OTHER INFORMATION: VL CDR3 Bococizumab clones 884-01-B01,

<400> SEQUENCE: 242

Gln Gln Arg Tyr Ser Thr His Arg Thr
1 5

<210> SEQ ID NO 243
<211> LENGTH: 9
<212> TYPE: PRT
<213> ORGANISM: Artificial Sequence
<220> FEATURE:
<223> OTHER INFORMATION: VL CDR3 Bococizumab clones 884-01-B02, D04

<400> SEQUENCE: 243

Gln Gln Arg Tyr Ser Phe Ala Arg Thr
1 5

<210> SEQ ID NO 244
<211> LENGTH: 9
<212> TYPE: PRT
<213> ORGANISM: Artificial Sequence
<220> FEATURE:
<223> OTHER INFORMATION: VL CDR3 Bococizumab clones 884-01-B03

<400> SEQUENCE: 244

Gln Gln Arg Tyr Ser Ile Arg Arg Thr
1 5

<210> SEQ ID NO 245
<211> LENGTH: 9
<212> TYPE: PRT
<213> ORGANISM: Artificial Sequence
<220> FEATURE:
<223> OTHER INFORMATION: VL CDR3 Bococizumab clones 884-01-B04

<400> SEQUENCE: 245

Gln Gln Arg Tyr Ser Val Cys Arg Thr
1 5

<210> SEQ ID NO 246
<211> LENGTH: 9
<212> TYPE: PRT
<213> ORGANISM: Artificial Sequence
<220> FEATURE:
<223> OTHER INFORMATION: VL CDR3 Bococizumab clones 884-01-B06

<400> SEQUENCE: 246

Gln Gln Arg Tyr Ser Trp Ala Arg Thr
1 5

<210> SEQ ID NO 247
<211> LENGTH: 9
<212> TYPE: PRT
<213> ORGANISM: Artificial Sequence
<220> FEATURE:
<223> OTHER INFORMATION: VL CDR3 Bococizumab clones 884-01-B07

<400> SEQUENCE: 247

Gln Gln Arg Tyr Ser Thr Thr Arg Thr
1 5

<210> SEQ ID NO 248
<211> LENGTH: 9
<212> TYPE: PRT
<213> ORGANISM: Artificial Sequence
<220> FEATURE:
<223> OTHER INFORMATION: VL CDR3 Bococizumab clones 884-01-B08

<400> SEQUENCE: 248

Gln Gln Arg Tyr Ser Gln Met Arg Thr
1 5

<210> SEQ ID NO 249
<211> LENGTH: 9
<212> TYPE: PRT
<213> ORGANISM: Artificial Sequence
<220> FEATURE:
<223> OTHER INFORMATION: VL CDR3 Bococizumab clones 884-01-B10

<400> SEQUENCE: 249

Gln Gln Arg Tyr Ser Ala Asp Arg Thr
1 5

<210> SEQ ID NO 250
<211> LENGTH: 9
<212> TYPE: PRT
<213> ORGANISM: Artificial Sequence
<220> FEATURE:
<223> OTHER INFORMATION: VL CDR3 Bococizumab clones 884-01-B11

<400> SEQUENCE: 250

Gln Gln Arg Tyr Ser Phe Asn Arg Thr
1 5

<210> SEQ ID NO 251
<211> LENGTH: 9
<212> TYPE: PRT
<213> ORGANISM: Artificial Sequence
<220> FEATURE:
<223> OTHER INFORMATION: VL CDR3 Bococizumab clones 884-01-C01

<400> SEQUENCE: 251

Gln Gln Arg Tyr Ser Tyr Asp Arg Thr
1 5

<210> SEQ ID NO 252
<211> LENGTH: 9
<212> TYPE: PRT
<213> ORGANISM: Artificial Sequence
<220> FEATURE:
<223> OTHER INFORMATION: VL CDR3 Bococizumab clones 884-01-C02

<400> SEQUENCE: 252

Gln Gln Arg Tyr Ser Ser Gln Arg Thr
1 5

<210> SEQ ID NO 253
<211> LENGTH: 9
<212> TYPE: PRT
<213> ORGANISM: Artificial Sequence
<220> FEATURE:
<223> OTHER INFORMATION: VL CDR3 Bococizumab clones 884-01-C03

<400> SEQUENCE: 253

Gln Gln Arg Tyr Ser Tyr Val Arg Thr
1 5

<210> SEQ ID NO 254
<211> LENGTH: 9
<212> TYPE: PRT
<213> ORGANISM: Artificial Sequence
<220> FEATURE:
<223> OTHER INFORMATION: VL CDR3 Bococizumab clones 884-01-C04

<400> SEQUENCE: 254

Gln Gln Arg Tyr Ser Leu Tyr Arg Thr
1 5

<210> SEQ ID NO 255
<211> LENGTH: 9
<212> TYPE: PRT
<213> ORGANISM: Artificial Sequence
<220> FEATURE:
<223> OTHER INFORMATION: VL CDR3 Bococizumab clones 884-01-C05

<400> SEQUENCE: 255

Gln Gln Arg Tyr Ser Ala Asp Arg Thr
1 5

<210> SEQ ID NO 256
<211> LENGTH: 9
<212> TYPE: PRT
<213> ORGANISM: Artificial Sequence
<220> FEATURE:
<223> OTHER INFORMATION: VL CDR3 Bococizumab clones 884-01-C06

<400> SEQUENCE: 256

Gln Gln Arg Tyr Ser Ser Met Arg Thr
1 5

<210> SEQ ID NO 257
<211> LENGTH: 9
<212> TYPE: PRT
<213> ORGANISM: Artificial Sequence
<220> FEATURE:
<223> OTHER INFORMATION: VL CDR3 Bococizumab clones 884-01-C07

<400> SEQUENCE: 257

Gln Gln Arg Tyr Ser Tyr Tyr Arg Thr
1 5

<210> SEQ ID NO 258
<211> LENGTH: 9
<212> TYPE: PRT
<213> ORGANISM: Artificial Sequence
<220> FEATURE:
<223> OTHER INFORMATION: VL CDR3 Bococizumab clones 884-01-C08

<400> SEQUENCE: 258

Gln Gln Arg Tyr Ser Leu Ile Arg Thr
1 5

<210> SEQ ID NO 259
<211> LENGTH: 9
<212> TYPE: PRT
<213> ORGANISM: Artificial Sequence
<220> FEATURE:
<223> OTHER INFORMATION: VL CDR3 Bococizumab clones 884-01-C09

<400> SEQUENCE: 259

Gln Gln Arg Tyr Ser Glu Arg Arg Thr
1 5

<210> SEQ ID NO 260
<211> LENGTH: 5
<212> TYPE: PRT
<213> ORGANISM: Artificial Sequence
<220> FEATURE:
<223> OTHER INFORMATION: VL CDR3 Bococizumab clones 884-01-C10

<400> SEQUENCE: 260

Gln Gln Arg Tyr Ser
1 5

<210> SEQ ID NO 261
<211> LENGTH: 9
<212> TYPE: PRT
<213> ORGANISM: Artificial Sequence
<220> FEATURE:
<223> OTHER INFORMATION: VL CDR3 Bococizumab clones 884-01-C11

<400> SEQUENCE: 261

Gln Gln Arg Tyr Ser Gln Met Arg Thr
1 5

<210> SEQ ID NO 262
<211> LENGTH: 9
<212> TYPE: PRT
<213> ORGANISM: Artificial Sequence
<220> FEATURE:
<223> OTHER INFORMATION: VL CDR3 Bococizumab clones 884-01-D01

<400> SEQUENCE: 262

Gln Gln Arg Tyr Ser Val Asn Arg Thr
1 5

<210> SEQ ID NO 263
<211> LENGTH: 9
<212> TYPE: PRT
<213> ORGANISM: Artificial Sequence
<220> FEATURE:
<223> OTHER INFORMATION: VL CDR3 Bococizumab clones 884-01-D02

<400> SEQUENCE: 263

Gln Gln Arg Tyr Ser Phe Phe Arg Thr
1 5

<210> SEQ ID NO 264
<211> LENGTH: 9
<212> TYPE: PRT
<213> ORGANISM: Artificial Sequence
<220> FEATURE:
<223> OTHER INFORMATION: VL CDR3 Bococizumab clones 884-01-D03

<400> SEQUENCE: 264

Gln Gln Arg Tyr Ser Asn Val Arg Thr
1 5

<210> SEQ ID NO 265
<211> LENGTH: 9
<212> TYPE: PRT
<213> ORGANISM: Artificial Sequence
<220> FEATURE:
<223> OTHER INFORMATION: VL CDR3 Bococizumab clones 884-01-D05

<400> SEQUENCE: 265

Gln Gln Arg Tyr Ser Ala Val Arg Thr
1 5

<210> SEQ ID NO 266
<211> LENGTH: 9
<212> TYPE: PRT
<213> ORGANISM: Artificial Sequence
<220> FEATURE:
<223> OTHER INFORMATION: VL CDR3 Bococizumab clones 884-01-D06

<400> SEQUENCE: 266

Gln Gln Arg Tyr Ser Asp Pro Arg Thr
1 5

<210> SEQ ID NO 267
<211> LENGTH: 9
<212> TYPE: PRT
<213> ORGANISM: Artificial Sequence
<220> FEATURE:
<223> OTHER INFORMATION: VL CDR3 Bococizumab clones 884-01-D07

<400> SEQUENCE: 267

Gln Gln Arg Tyr Ser Met Thr Arg Thr
1 5

<210> SEQ ID NO 268
<211> LENGTH: 9
<212> TYPE: PRT
<213> ORGANISM: Artificial Sequence
<220> FEATURE:
<223> OTHER INFORMATION: VL CDR3 Bococizumab clones 884-01-D08

<400> SEQUENCE: 268

Gln Gln Arg Tyr Ser Ile Ser Arg Thr
1 5

<210> SEQ ID NO 269
<211> LENGTH: 9
<212> TYPE: PRT
<213> ORGANISM: Artificial Sequence
<220> FEATURE:
<223> OTHER INFORMATION: VL CDR3 Bococizumab clones 884-01-D09

<400> SEQUENCE: 269

Gln Gln Arg Tyr Ser Leu Tyr Arg Thr 1 5

<210> SEQ ID NO 270
<211> LENGTH: 9
<212> TYPE: PRT
<213> ORGANISM: Artificial Sequence
<220> FEATURE:
<223> OTHER INFORMATION: VL CDR3 Bococizumab clones 884-01-D10

<400> SEQUENCE: 270

Gln Gln Arg Tyr Ser Asn Met Arg Thr
1 5

<210> SEQ ID NO 271
<211> LENGTH: 9
<212> TYPE: PRT
<213> ORGANISM: Artificial Sequence
<220> FEATURE:
<223> OTHER INFORMATION: VL CDR3 Bococizumab clones 884-01-D11

<400> SEQUENCE: 271

Gln Gln Arg Tyr Ser Gln Met Arg Thr
1 5

<210> SEQ ID NO 272
<211> LENGTH: 9
<212> TYPE: PRT
<213> ORGANISM: Artificial Sequence
<220> FEATURE:
<223> OTHER INFORMATION: VL CDR3 Bococizumab clones 884-01-D12

<400> SEQUENCE: 272

Gln Gln Arg Tyr Ser Ala Asp Arg Thr
1 5

<210> SEQ ID NO 273
<211> LENGTH: 9
<212> TYPE: PRT
<213> ORGANISM: Artificial Sequence
<220> FEATURE:
<223> OTHER INFORMATION: VL CDR3 Bococizumab clones 884-01-E01

<400> SEQUENCE: 273

Gln Gln Arg Tyr Ser Thr Ile Arg Thr
1 5

<210> SEQ ID NO 274
<211> LENGTH: 9
<212> TYPE: PRT
<213> ORGANISM: Artificial Sequence
<220> FEATURE:
<223> OTHER INFORMATION: VL CDR3 Bococizumab clones 884-01-E02

<400> SEQUENCE: 274

Gln Gln Arg Tyr Ser Cys Ala Arg Thr
1 5

<210> SEQ ID NO 275
<211> LENGTH: 9
<212> TYPE: PRT
<213> ORGANISM: Artificial Sequence
<220> FEATURE:
<223> OTHER INFORMATION: VL CDR3 Bococizumab clones 884-01-E03

<400> SEQUENCE: 275

Gln Gln Arg Tyr Ser Asn His Arg Thr
1 5

<210> SEQ ID NO 276
<211> LENGTH: 9
<212> TYPE: PRT
<213> ORGANISM: Artificial Sequence
<220> FEATURE:
<223> OTHER INFORMATION: VL CDR3 Bococizumab clones 884-01-E04

<400> SEQUENCE: 276

Gln Gln Arg Tyr Ser Ala Lys Arg Thr
1 5

<210> SEQ ID NO 277
<211> LENGTH: 9
<212> TYPE: PRT
<213> ORGANISM: Artificial Sequence
<220> FEATURE:
<223> OTHER INFORMATION: VL CDR3 Bococizumab clones 884-01-E05

<400> SEQUENCE: 277

Gln Gln Arg Tyr Ser His Arg Arg Thr
1 5

<210> SEQ ID NO 278
<211> LENGTH: 9
<212> TYPE: PRT
<213> ORGANISM: Artificial Sequence
<220> FEATURE:
<223> OTHER INFORMATION: VL CDR3 Bococizumab clones 884-01-E06

<400> SEQUENCE: 278

Gln Gln Arg Tyr Ser Cys Thr Arg Thr
1 5

<210> SEQ ID NO 279
<211> LENGTH: 9
<212> TYPE: PRT
<213> ORGANISM: Artificial Sequence
<220> FEATURE:
<223> OTHER INFORMATION: VL CDR3 Bococizumab clones 884-01-E08

<400> SEQUENCE: 279

Gln Gln Arg Tyr Ser Tyr Met Arg Thr
1 5

<210> SEQ ID NO 280
<211> LENGTH: 9
<212> TYPE: PRT
<213> ORGANISM: Artificial Sequence
<220> FEATURE:
<223> OTHER INFORMATION: VL CDR3 Bococizumab clones 884-01-E09

<400> SEQUENCE: 280

Gln Gln Arg Tyr Ser His Phe Arg Thr
1 5

<210> SEQ ID NO 281
<211> LENGTH: 9
<212> TYPE: PRT
<213> ORGANISM: Artificial Sequence
<220> FEATURE:
<223> OTHER INFORMATION: VL CDR3 Bococizumab clones 884-01-E10

<400> SEQUENCE: 281

Gln Gln Arg Tyr Ser Ser Ala Arg Thr
1 5

<210> SEQ ID NO 282
<211> LENGTH: 9
<212> TYPE: PRT
<213> ORGANISM: Artificial Sequence
<220> FEATURE:
<223> OTHER INFORMATION: VL CDR3 Bococizumab clones 884-01-E12

<400> SEQUENCE: 282

Gln Gln Arg Tyr Ser Asn Arg Arg Thr
1 5

<210> SEQ ID NO 283
<211> LENGTH: 9
<212> TYPE: PRT
<213> ORGANISM: Artificial Sequence
<220> FEATURE:
<223> OTHER INFORMATION: VL CDR3 Bococizumab clones 884-01-F01

<400> SEQUENCE: 283

Gln His Ser Arg Asp Leu Pro Leu Thr
1 5

<210> SEQ ID NO 284
<211> LENGTH: 9
<212> TYPE: PRT
<213> ORGANISM: Artificial Sequence
<220> FEATURE:
<223> OTHER INFORMATION: VL CDR3 Bococizumab clones 884-01-F02

<400> SEQUENCE: 284

Gln Gln Arg Tyr Ser Thr Gly Arg Thr
1 5

<210> SEQ ID NO 285
<211> LENGTH: 9
<212> TYPE: PRT
<213> ORGANISM: Artificial Sequence
<220> FEATURE:
<223> OTHER INFORMATION: VL CDR3 Bococizumab clones 884-01-F03

<400> SEQUENCE: 285

Gln Gln Arg Tyr Ser Asp Thr Arg Thr
1 5

<210> SEQ ID NO 286
<211> LENGTH: 9
<212> TYPE: PRT
<213> ORGANISM: Artificial Sequence
<220> FEATURE:
<223> OTHER INFORMATION: VL CDR3 Bococizumab clones 884-01-F04

<400> SEQUENCE: 286

Gln Gln Arg Tyr Ser Glu Thr Arg Thr
1 5

<210> SEQ ID NO 287
<211> LENGTH: 9
<212> TYPE: PRT
<213> ORGANISM: Artificial Sequence
<220> FEATURE:
<223> OTHER INFORMATION: VL CDR3 Bococizumab clones 884-01-F06

<400> SEQUENCE: 287

Gln Gln Arg Tyr Ser Asn Ser Arg Thr
1 5

<210> SEQ ID NO 288
<211> LENGTH: 9
<212> TYPE: PRT
<213> ORGANISM: Artificial Sequence
<220> FEATURE:
<223> OTHER INFORMATION: VL CDR3 Bococizumab clones 884-01-F06

<400> SEQUENCE: 288

Gln Gln Arg Tyr Ser Pro Pro Arg Thr
1 5

<210> SEQ ID NO 289
<211> LENGTH: 9
<212> TYPE: PRT
<213> ORGANISM: Artificial Sequence
<220> FEATURE:
<223> OTHER INFORMATION: VL CDR3 Bococizumab clones 884-01-F07

<400> SEQUENCE: 289

Gln Gln Arg Tyr Ser Ser Ala Arg Thr
1 5

<210> SEQ ID NO 290
<211> LENGTH: 9
<212> TYPE: PRT
<213> ORGANISM: Artificial Sequence
<220> FEATURE:
<223> OTHER INFORMATION: VL CDR3 Bococizumab clones 884-01-F08

<400> SEQUENCE: 290

Gln Gln Arg Tyr Ser Leu Glu Arg Thr
1 5

<210> SEQ ID NO 291
<211> LENGTH: 9
<212> TYPE: PRT
<213> ORGANISM: Artificial Sequence
<220> FEATURE:
<223> OTHER INFORMATION: VL CDR3 Bococizumab clones 884-01-F09

<400> SEQUENCE: 291

Gln Gln Arg Tyr Ser His Ser Arg Thr
1 5

<210> SEQ ID NO 292
<211> LENGTH: 9
<212> TYPE: PRT
<213> ORGANISM: Artificial Sequence
<220> FEATURE:
<223> OTHER INFORMATION: VL CDR3 Bococizumab clones 884-01-F10

<400> SEQUENCE: 292

Gln Gln Arg Tyr Ser Val Ala Arg Thr
1 5

<210> SEQ ID NO 293
<211> LENGTH: 9
<212> TYPE: PRT
<213> ORGANISM: Artificial Sequence
<220> FEATURE:
<223> OTHER INFORMATION: VL CDR3 Bococizumab clones 884-01-F11

<400> SEQUENCE: 293

Gln Gln Arg Tyr Ser Leu Thr Arg Thr
1 5

<210> SEQ ID NO 294

-continued

<211> LENGTH: 9
<212> TYPE: PRT
<213> ORGANISM: Artificial Sequence
<220> FEATURE:
<223> OTHER INFORMATION: VL CDR3 Bococizumab clones 884-01-F12

<400> SEQUENCE: 294

Gln Gln Arg Tyr Ser His Pro Arg Thr
1               5

<210> SEQ ID NO 295
<211> LENGTH: 9
<212> TYPE: PRT
<213> ORGANISM: Artificial Sequence
<220> FEATURE:
<223> OTHER INFORMATION: VL CDR3 Bococizumab clones 884-01-G01

<400> SEQUENCE: 295

Gln Gln Arg Tyr Ser Asp Thr Arg Thr
1               5

<210> SEQ ID NO 296
<211> LENGTH: 9
<212> TYPE: PRT
<213> ORGANISM: Artificial Sequence
<220> FEATURE:
<223> OTHER INFORMATION: VL CDR3 Bococizumab clones 884-01-G02

<400> SEQUENCE: 296

Gln Gln Arg Tyr Ser Asn Met Arg Thr
1               5

<210> SEQ ID NO 297
<211> LENGTH: 9
<212> TYPE: PRT
<213> ORGANISM: Artificial Sequence
<220> FEATURE:
<223> OTHER INFORMATION: VL CDR3 Bococizumab clones 884-01-G03

<400> SEQUENCE: 297

Gln Gln Arg Tyr Ser Ser Lys Arg Thr
1               5

<210> SEQ ID NO 298
<211> LENGTH: 9
<212> TYPE: PRT
<213> ORGANISM: Artificial Sequence
<220> FEATURE:
<223> OTHER INFORMATION: VL CDR3 Bococizumab clones 884-01-G04

<400> SEQUENCE: 298

Gln Gln Arg Tyr Ser His Phe Arg Thr
1               5

<210> SEQ ID NO 299
<211> LENGTH: 9
<212> TYPE: PRT
<213> ORGANISM: Artificial Sequence
<220> FEATURE:
<223> OTHER INFORMATION: VL CDR3 Bococizumab clones 884-01-G05

<400> SEQUENCE: 299

Gln Gln Arg Tyr Ser Pro Pro Arg Thr
1               5

<210> SEQ ID NO 300
<211> LENGTH: 9

<212> TYPE: PRT
<213> ORGANISM: Artificial Sequence
<220> FEATURE:
<223> OTHER INFORMATION: VL CDR3 Bococizumab clones 884-01-G06

<400> SEQUENCE: 300

Gln Gln Arg Tyr Ser Glu Ser Arg Thr
1               5

<210> SEQ ID NO 301
<211> LENGTH: 9
<212> TYPE: PRT
<213> ORGANISM: Artificial Sequence
<220> FEATURE:
<223> OTHER INFORMATION: VL CDR3 Bococizumab clones 884-01-G07

<400> SEQUENCE: 301

Gln Gln Arg Tyr Ser Val Tyr Arg Thr
1               5

<210> SEQ ID NO 302
<211> LENGTH: 9
<212> TYPE: PRT
<213> ORGANISM: Artificial Sequence
<220> FEATURE:
<223> OTHER INFORMATION: VL CDR3 Bococizumab clones 884-01-G08

<400> SEQUENCE: 302

Gln Gln Arg Tyr Ser Cys Ile Arg Thr
1               5

<210> SEQ ID NO 303
<211> LENGTH: 9
<212> TYPE: PRT
<213> ORGANISM: Artificial Sequence
<220> FEATURE:
<223> OTHER INFORMATION: VL CDR3 Bococizumab clones 884-01-G09

<400> SEQUENCE: 303

Gln Gln Arg Tyr Ser Ala Thr Arg Thr
1               5

<210> SEQ ID NO 304
<211> LENGTH: 9
<212> TYPE: PRT
<213> ORGANISM: Artificial Sequence
<220> FEATURE:
<223> OTHER INFORMATION: VL CDR3 Bococizumab clones 884-01-G10

<400> SEQUENCE: 304

Gln Gln Arg Tyr Ser Ala Thr Arg Thr
1               5

<210> SEQ ID NO 305
<211> LENGTH: 9
<212> TYPE: PRT
<213> ORGANISM: Artificial Sequence
<220> FEATURE:
<223> OTHER INFORMATION: VL CDR3 Bococizumab clones 884-01-G11

<400> SEQUENCE: 305

Gln Gln Arg Tyr Ser Asp Cys Arg Thr
1               5

<210> SEQ ID NO 306
<211> LENGTH: 9
<212> TYPE: PRT

<213> ORGANISM: Artificial Sequence
<220> FEATURE:
<223> OTHER INFORMATION: VL CDR3 Bococizumab clones 884-01-G12

<400> SEQUENCE: 306

Gln Gln Arg Tyr Ser Met Ala Arg Thr
1               5

<210> SEQ ID NO 307
<211> LENGTH: 9
<212> TYPE: PRT
<213> ORGANISM: Artificial Sequence
<220> FEATURE:
<223> OTHER INFORMATION: VL CDR3 Bococizumab clones 884-01-H01

<400> SEQUENCE: 307

Gln Gln Arg Tyr Ser Gly Glu Arg Thr
1               5

<210> SEQ ID NO 308
<211> LENGTH: 9
<212> TYPE: PRT
<213> ORGANISM: Artificial Sequence
<220> FEATURE:
<223> OTHER INFORMATION: VL CDR3 Bococizumab clones 884-01-H02

<400> SEQUENCE: 308

Gln Gln Arg Tyr Ser Ile Arg Arg Thr
1               5

<210> SEQ ID NO 309
<211> LENGTH: 9
<212> TYPE: PRT
<213> ORGANISM: Artificial Sequence
<220> FEATURE:
<223> OTHER INFORMATION: VL CDR3 Bococizumab clones 884-01-H03

<400> SEQUENCE: 309

Gln Gln Arg Tyr Ser Leu Met Arg Thr
1               5

<210> SEQ ID NO 310
<211> LENGTH: 9
<212> TYPE: PRT
<213> ORGANISM: Artificial Sequence
<220> FEATURE:
<223> OTHER INFORMATION: VL CDR3 Bococizumab clones 884-01-H04

<400> SEQUENCE: 310

Gln Gln Arg Tyr Ser Leu Asp Arg Thr
1               5

<210> SEQ ID NO 311
<211> LENGTH: 9
<212> TYPE: PRT
<213> ORGANISM: Artificial Sequence
<220> FEATURE:
<223> OTHER INFORMATION: VL CDR3 Bococizumab clones 884-01-H05

<400> SEQUENCE: 311

Gln Gln Arg Tyr Ser Tyr Val Arg Thr
1               5

<210> SEQ ID NO 312
<211> LENGTH: 9
<212> TYPE: PRT
<213> ORGANISM: Artificial Sequence
<220> FEATURE:
<223> OTHER INFORMATION: VL CDR3 Bococizumab clones 884-01-H06

<400> SEQUENCE: 312

Gln Gln Arg Tyr Ser Ser Ala Arg Thr
1 5

<210> SEQ ID NO 313
<211> LENGTH: 9
<212> TYPE: PRT
<213> ORGANISM: Artificial Sequence
<220> FEATURE:
<223> OTHER INFORMATION: VL CDR3 Bococizumab clones 884-01-H07

<400> SEQUENCE: 313

Gln Gln Arg Tyr Ser Leu Asn Arg Thr
1 5

<210> SEQ ID NO 314
<211> LENGTH: 9
<212> TYPE: PRT
<213> ORGANISM: Artificial Sequence
<220> FEATURE:
<223> OTHER INFORMATION: VL CDR3 Bococizumab clones Bococizuma b

<400> SEQUENCE: 314

Gln Gln Arg Tyr Ser Leu Trp Arg Thr
1 5

<210> SEQ ID NO 315
<211> LENGTH: 9
<212> TYPE: PRT
<213> ORGANISM: Artificial Sequence
<220> FEATURE:
<223> OTHER INFORMATION: VL CDR3 Bococizumab clones 5A10i

<400> SEQUENCE: 315

Gln Gln Arg Tyr Ser Thr Pro Arg Thr
1 5

<210> SEQ ID NO 316
<211> LENGTH: 224
<212> TYPE: DNA
<213> ORGANISM: Artificial Sequence
<220> FEATURE:
<223> OTHER INFORMATION: Splice acceptor

<400> SEQUENCE: 316
aagtccctaa gcttgtctcc gggtaaatga gtgccacggc cggcaagccc ccgctcaagt 60
ccctaagctt gtctccaggt aaatgagtgc cacggccggc aagcccccgc tcaagtccct 120
aagcttgtct ccgggtaagt gagtgccacg gccggcaagc ccccgctcaa gtccctaagc 180
ttgtctccag gtaagtgagt gccacggccg gcaagccccc gctc 224

<210> SEQ ID NO 317
<211> LENGTH: 3640
<212> TYPE: DNA
<213> ORGANISM: Artificial Sequence
<220> FEATURE:
<223> OTHER INFORMATION: pINT17-J30

<400> SEQUENCE: 317
agtctcgagt gcctccacca agggccctag cgtctttcct ctggcccctt cctccaagtc 60
tacctctggc ggcaccgctg ctctgggctg cctggtgaag gactacttcc ctgagcctgt 120

-continued

```
gaccgtgtcc tggaactctg gcgccctgac ctccggcgtg catacctttcc ctgccgtcct    180
ccagtcctcc ggcctgtact ccctgtcctc cgtggtgacc gtgccttcct cctctctggg    240
cacccagacc tacatctgca acgtgaacca caagccttcc aacaccaagg tggacaagaa    300
ggtggagcct aagtcctgcg acaagaccca cacctgccct ccatgtcctg cccctgagct    360
gctgggcgga ccctccgtgt tcctgttccc tcctaagcct aaggacaccc tgatgatctc    420
ccggacccct gaagtgacct gcgtggtggt ggacgtgtcc cacgaagatc ctgaagtgaa    480
gttcaattgg tacgtggacg gcgtggaggt gcacaacgcc aagaccaagc ctcgggagga    540
acagtacaac tccacctacc gggtggtgtc tgtgctgacc gtgctgcacc aggactggct    600
gaacggcaaa gaatacaagt gcaaggtgtc caacaaggcc ctgcctgccc ctatcgaaaa    660
gaccatctcc aaggctaagg gccagccacg ggaacctcag gtctacacac tgcctcctag    720
ccgggacgag ctgaccaaga accaggtgtc cctgacctgt ctggtgaagg gcttctaccc    780
ttccgatatc gccgtggagt gggagtctaa cggccagcct gagaacaact acaagaccac    840
ccctcctgtg ctggactccg acggctcctt cttcctgtac tccaagctga ccgtggacaa    900
gtcccggtgg cagcagggca acgtgttctc ctgctccgtg atgcacgagg ccctgcacaa    960
ccactacacc cagaagtccc tgtccctaag cttgtctcca ggtaagtgag tgccacggcc   1020
ggcaagcccc cgctccccag gctctcgggg tcgcgcgagg atgcttggca cgtaccccgt   1080
ctacatactt cccgggcacc cagcatggaa ataaagcacc cagcgctgcc ctgggcccct   1140
gcgagactgt gatggttctt tccgtgggtc aggccgagtc tgaggcctga gtggcatgag   1200
ggaggcagag cgggttccac tgtccccaca ctggcccagg ctgtgcaggt gtgcctgggc   1260
cgcctagggt ggggctcagc caggggctgc cctcggcagg gtgggggatt tgccagcgtg   1320
gccctccctc cagcagcagc tgccctgggc tgggccacgg gaagccctag gagcccctgg   1380
ggacagacac acagcccctg cctctgtagg agactgtcct gtcctgtgag cgccctgtcc   1440
tccgacctcc atgcccactc gggggcatgc ctagtccatg tgcgtaggga caggccctcc   1500
ctcacccatc tacccccacg gcactaaccc ctggctgccc tgcccagcct cgcacccgca   1560
tggggacaca accgactccg ggacatgca ctctcgggcc ctgtggaggg actggtccag   1620
atgcccacac acacactcag cccagacccg ttcaacaaac cccgcgctga ggttggccgg   1680
ccacacggcc accacacaca cacgtgcacg cctcacacac ggagcctcac ccgggcgaac   1740
cgcacagcac ccagaccaga gcaaggtcct cgcacacgtg aacactcctc agacacaggc   1800
ccccacgagc cccacgcggc acctcaaggc ccacgagccg ctcggcagct tctccacatg   1860
ctgacctgct cagacaaacc cagccctcct ctcacaaggt gcccctgcag ccgccacaca   1920
cacacaggcc cccacacaca ggggaacaca cgccacgtcg cgtccctggc actggcccac   1980
ttcccaatgc cgcccttccc tgcagctgag gtcacatgag gtgtgggctt caccatcctc   2040
ctgccctctg ggcctcaggg agggacacag gagatgggga gcgggtcctg ctgagggcca   2100
ggtcgctatc tagggctggg tgtctggctg agtcccgggg ccaaagctgg tgcccagggc   2160
aggcagctgt ggggagctga cctcaggaca ctgctggccc atcccggccg ggccctacat   2220
cctgggtcct gccacagagg gaatcacccc cagaggcccg agcccagcag gacacagtat   2280
tgaccaccca cttcctgtcc agagctgcaa ctggaggaga gctgtgcgga ggcgcaggac   2340
ggggagctgg acgggctgtg gaccaccatc accatcttca tcacactctt cctgctaagc   2400
gtgtgctaca gtgccaccat caccttcttc aaggttaaat aataatagct tacgacgtga   2460
tcagcctcga ctgtgccttc tagttgccag ccatctgttg tttgcccctc ccccgtgcct   2520
```

-continued tccttgaccc tggaaggtgc cactcccact gtcctttcct aataaaatga ggaaattgca 2580
tcgcattgtc tgagtaggtg tcattctatt ctggggggtg gggtggggca ggacagcaag 2640
ggggaggatt gggaagacaa tagcaggcat gctggggaat tctggcccgg gcatgataac 2700
gtgacagaaa agccccatcc ttaggcctcc tccttcctag tctcctgata ttgggtctaa 2760
cccccacctc ctgttaggca gattccttat ctggtgacac acccccattt cctggagcca 2820
tctctctcct tgccagaacc tctaaggttt gcttacgatg gagccagaga ggatcctggg 2880
agggagagct tggcaggggg tgggagggaa ggggggggatg cgtgacctgc ccggttctca 2940
gtggccaccc tgcgctaccc tctcccagaa cctgagctgc tctgacgcgg ctgtctggtg 3000
cgtttcactg atcctggtgc tgcagcttcc ttacacttcc caagaggaga agcagtttgg 3060
aaaaacaaaa tcagaataag ttggtcctga gttctaactt tggctcttca cctttctagt 3120
ccccaattta tattgttcct ccgtgcgtca gttttacctg tgagataagg ccagtagcca 3180
gccccgtcct ggcagggctg tggtgaggag gggggtgtcc gtgtggaaaa ctccctttgt 3240
gagaatggtg cgtcctaggt gttcaccagg tcgtggccgc ctctactccc tttctctttc 3300
tccatccttc tttccttaaa gagtccccag tgctatctgg gacatattcc tccgcccaga 3360
gcagggtccc gcttccctaa ggccctgctc tgggcttctg ggtttgagtc cttggcaagc 3420
ccaggagagg cgctcaggct tccctgtccc ccttcctcgt ccaccatctc atgcccctgg 3480
ctctcctgcc ccttccctac aggggttcct ggctctgctc tcctgcaggc gatctctcga 3540
tctctcgatt tcgatcaaga cattccttta atggtctttt ctggacacca ctaggggtca 3600
gaagtagttc atcaaacttt cttccctccc taatctcatt 3640

<210> SEQ ID NO 318
<211> LENGTH: 334
<212> TYPE: PRT
<213> ORGANISM: Artificial Sequence
<220> FEATURE:
<223> OTHER INFORMATION: IgG1 CH1-3

<400> SEQUENCE: 318

Ser Ser Ala Ser Thr Lys Gly Pro Ser Val Phe Pro Leu Ala Pro Ser
1 5 10 15

Ser Lys Ser Thr Ser Gly Gly Thr Ala Ala Leu Gly Cys Leu Val Lys
20 25 30

Asp Tyr Phe Pro Glu Pro Val Thr Val Ser Trp Asn Ser Gly Ala Leu
35 40 45

Thr Ser Gly Val His Thr Phe Pro Ala Val Leu Gln Ser Ser Gly Leu
50 55 60

Tyr Ser Leu Ser Ser Val Val Thr Val Pro Ser Ser Ser Leu Gly Thr
65 70 75 80

Gln Thr Tyr Ile Cys Asn Val Asn His Lys Pro Ser Asn Thr Lys Val
85 90 95

Asp Lys Lys Val Glu Pro Lys Ser Cys Asp Lys Thr His Thr Cys Pro
100 105 110

Pro Cys Pro Ala Pro Glu Leu Leu Gly Gly Pro Ser Val Phe Leu Phe
115 120 125

Pro Pro Lys Pro Lys Asp Thr Leu Met Ile Ser Arg Thr Pro Glu Val
130 135 140

Thr Cys Val Val Val Asp Val Ser His Glu Asp Pro Glu Val Lys Phe
145 150 155 160

-continued

```
Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Asp Glu Leu Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285

Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Leu Ser Pro Gly Lys
                325                 330
```

<210> SEQ ID NO 319
<211> LENGTH: 45
<212> TYPE: PRT
<213> ORGANISM: Artificial Sequence
<220> FEATURE:
<223> OTHER INFORMATION: M1 exon

<400> SEQUENCE: 319

```
Leu Gln Leu Glu Glu Ser Cys Ala Glu Ala Gln Asp Gly Glu Leu Asp
1               5                   10                  15

Gly Leu Trp Thr Thr Ile Thr Ile Phe Ile Thr Leu Phe Leu Leu Ser
            20                  25                  30

Val Cys Tyr Ser Ala Thr Ile Thr Phe Phe Lys Val Lys
        35                  40                  45
```

<210> SEQ ID NO 320
<211> LENGTH: 7680
<212> TYPE: DNA
<213> ORGANISM: Artificial Sequence
<220> FEATURE:
<223> OTHER INFORMATION: pINT18-Tet1

<400> SEQUENCE: 320

```
gcgatcgctg ctttctctga cctgcattct ctcccctggg cctgtgccgc tttctgtctg      60

cagcttgtgg cctgggtcac ctctacggct ggcccagatc cttccctgcc gcctccttca     120

ggttccgtct tcctccactc cctcttcccc ttgctctctg ctgtgttgct gcccaaggat     180

gctctttccg gagcacttcc ttctcggcgc tgcaccacgt gatgtcctct gagcggatcc     240

tccccgtgtc tgggtcctct ccgggcatct ctcctccctc acccaacccc atgccgtctt     300

cactcgctgg gttccctttt ccttctcctt ctggggcctg tgccatctct cgtttcttag     360

gatggccttc tccgacggat gtctcccttg cgtcccgcct ccccttcttg taggcctgca     420

tcatcaccgt tttctggac aaccccaaag taccccgtct ccctggcttt agccacctct     480

ccatcctctt gctttctttg cctggacacc ccgttctcct gtggattcgg gtcacctctc     540
```

```
actcctttca tttgggcagc tcccctaccc cccttacctc tctagtctgt gcaagctctt    600
ccagccccct gtcatggcat cttccagggg tccgagagct cagctagtct tcttcctcca    660
acccgggccc ctatgtccac ttcaggacag catgtttgct gcctccaggg atcctgtgtc    720
cccgagctgg gaccacctta tattcccagg gccggttaat gtggctctgg ttctgggtac    780
ttttatctgt cccctccacc ccacagtggg gcaagatgca tcttctgacc tcttctcttc    840
ctcccacagg gcatggcaaa acctctgagc caggaagaaa gcacactgat tgaaagagca    900
accgctacta tcaacagcat ccccatctcc gaagactatt ctgtggctag tgccgctctg    960
tccagcgacg ggagaatctt caccggtgtg aacgtctacc actttacagg cggaccatgc   1020
gcagagctgg tggtcctggg gactgcagcc gctgcagccg ctggtaatct gacctgtatc   1080
gtggccattg gcaacgaaaa taggggcatc ctgtccccat gcggcaggtg tcggcaggtg   1140
ctgctggatc tgcatcctgg catcaaggca attgtcaaag actctgatgg acagcctacc   1200
gccgtcggta tccgtgaact gctgcctagc ggctatgtct gggagggata atgagcttgg   1260
cttcgaaaca cacagatcta cacggtacca gcttacgacg tgatcagcct cgactgtgcc   1320
ttctagttgc cagccatctg ttgtttgccc ctcccccgtg ccttccttga ccctggaagg   1380
tgccactccc actgtccttt cctaataaaa tgaggaaatt gcatcgcatt gtctgagtag   1440
gtgtcattct attctggggg gtggggtggg gcaggacagc aagggggagg attgggaaga   1500
caatagcagg catgctgggg acgatcgtca gctggatcta gtaatcaatt acggggtcat   1560
tagttcatag cccatatatg gagttccgcg ttacataact tacggtaaat ggcccgcctg   1620
gctgaccgcc caacgacccc cgcccattga cgtcaataat gacgtatgtt cccatagtaa   1680
cgccaatagg gactttccat tgacgtcaat gggtggagta tttacggtaa actgcccact   1740
tggcagtaca tcaagtgtat catatgccaa gtacgccccc tattgacgtc aatgacggta   1800
aatggcccgc ctggcattat gcccagtaca tgaccttatg ggactttcct acttggcagt   1860
acatctacgt attagtcatc gctattacca tgctgatgcg gttttggcag tacatcaatg   1920
ggcgtggata gcggtttgac tcacggggat ttccaagtct ccaccccatt gacgtcaatg   1980
ggagtttgtt ttggcaccaa aatcaacggg actttccaaa atgtcgtaac aactccgccc   2040
cattgacgca aatgggcggt aggcgtgtac ggtgggaggt ctatataagc agagctggtt   2100
tagtgaaccg tcagatcaga tccatcgatc taggaattca ccatgccaaa gagacccaga   2160
ccctctagat tagataaaag taaagtgatt aacagcgcat tagagctgct taatgaggtc   2220
ggaatcgaag gtttaacaac ccgtaaactc gcccagaagc tgggtgtaga gcagcctaca   2280
ctgtattggc atgtaaaaaa taagcgggct ttgctcgacg ccttagccat tgagatgtta   2340
gataggcacc atactcactt ttgcccttta aaaggggaaa gctggcaaga tttttttacgc   2400
aataacgcta aaagttttag atgtgcttta ctaagtcatc gcaatggagc aaaagtacat   2460
tcagatacac ggcctacaga aaaacagtat gaaactctcg aaaatcaatt agccttttta   2520
tgccaacaag gtttttcact agagaacgcg ttatatgcac tcagcgctgt ggggcatttt   2580
actttaggtt gcgtattgga agatcaagag catcaagtcg ctaaagaaga aagggaaaca   2640
cctactactg atagtatgcc gccattatta cgacaagcta tcgaattatt tgatcaccaa   2700
ggtgcagagc cagccttctt attcggcctt gaattgatca tatgcggatt agaaaaacaa   2760
cttaaatgtg aaagtgggtc cgcgtacagc cgcgcgcgta cgaaaaacaa ttacgggtct   2820
accatcgagg gcctgctcga tctcccggac gacgacgccc ccgaagaggc ggggctggcg   2880
```

gctccgcgcc tgtcctttct ccccgcggga cacacgcgca gactgtcgac ggccccccg 2940
accgatgtca gcctggggga cgagctccac ttagacggcg aggacgtggc gatggcgcat 3000
gccgacgcgc tagacgattt cgatctggac atgttggggg acggggattc cccgggtccg 3060
ggatttaccc cccacgactc cgccccctac ggcgctctgg atatggccga cttcgagttt 3120
gagcagatgt ttaccgatgc ccttggaatt gacgagtacg gtgggtaggg ggcgcgagga 3180
tccagacatg ataagataca ttgatgagtt tggacaaacc acaactagaa tgcagtgaaa 3240
aaaatgcttt atttgtgaaa tttgtgatgc tattgcttta tttgtaacca ttataagctg 3300
caataaacaa gttaacaaca acaattgcat tcattttatg tttcaggttc agggggaggt 3360
gtgggaggtt ttttaaagca agtaaaacct ctacaaatgt ggtatggctg attatgatcc 3420
tgcaagcctc gtcgtcctgg ccggaccacg ctatctgtgc aaggtccccg gccccggacg 3480
cgcgctccat gagcagagcg cccgccgccg aggcgaagac tcgggcggcg ccctgcccgt 3540
cccaccaggt caacaggcgg taaccggcct cttcatcggg aatgcgcgcg accttcagca 3600
tcgccggcat gtcccctgg cggacgggaa gtatccagct cgaccatgct tggcgagatt 3660
ttcaggagct aaggtagctt cgtcttcaca cgagtttact ccctatcagt gatagagaac 3720
gtatgtcgag tttactccct atcagtgata gagaacgatg tcgagtttac tccctatcag 3780
tgatagagaa cgtatgtcga gtttactccc tatcagtgat agagaacgta tgtcgagttt 3840
actccctatc agtgatagag aacgtatgtc gagtttatcc ctatcagtga tagagaacgt 3900
atgtcgagtt tactccctat cagtgataga gaacgtatgt cgaggtaggc gtgtacggtg 3960
ggaggcctat ataagcagag ctcgtttagt gaaccgtcag atcgcctgga ttcgaatgag 4020
ggcctggatc ttctttctcc tttgcctggc cgggagggct ctggcagcta gcgagattgt 4080
cctgacccag agccccgcaa cactgtccct gtcccccgga gaaagagcaa ccctgtcctg 4140
tagagcatca aaaggtgtgt ctaccagtgg gtacagctat ctgcactggt accagcagaa 4200
gcccggacag gcccctaggc tgctgatcta cctggcttct tatctggaga gtggagtgcc 4260
agcacggttc tcaggttccg gcagcggaac agactttacc ctgacaattt ccagcctgga 4320
gccagaagac ttcgccgtgt actattgcca gcattccaga gatctgcccc tgacttttgg 4380
cggagggacc aaggtcgaaa tcaaaaggac tgcggccgca accgtggctg ccccttccgt 4440
gttcatcttc cctccctccg acgagcagct gaagtccggc accgcctctg tggtgtgcct 4500
gctgaacaac ttctaccctc gggaggccaa ggtgcagtgg aaggtggaca acgccctgca 4560
gtccggcaac tcccaggaat ccgtcaccga gcaggactcc aaggactcta cctactccct 4620
gtcctccacc ctgaccctgt ccaaggccga ctacgagaag cacaagctgt acgcctgcga 4680
agtgacccac cagggcctgt cctctcccgt gaccaagtcc ttcaaccggg gcgagtgctc 4740
tagacgagca aagagaggca gcggcgcgac caactttagc ctgctgaaac aggcgggcga 4800
tgtggaagaa aacccaggac ccgagctcat gagttggagc tgtatcatcc tcttcttggt 4860
agcaacagct acaggtaagg ggttaacagt agcaggcttg aggtctggac atatatatgg 4920
gtgacaatga catccacttt gcctttctct ccacaggcgc catggcccag gtgcagctgg 4980
tgcagagcgg cgtggaagtg aaaaagcctg gggcatccgt gaaggtctcc tgtaaagcaa 5040
gcgggtacac attcaccaac tactatatgt actgggtgag acaggcacca ggacagggac 5100
tggagtggat gggcggaatc aacccttcta atgggggtac aaacttcaac gaaaagttta 5160
aaaacagggt cactctgacc acagattcca gcactaccac agcctatatg gagctgaagt 5220
ccctccagtt cgacgatacc gccgtgtact attgcgctag gcgggactac aggttcgata 5280
tgggctttga ctattggggg cagggaacta ccgtcacagt ctcgagtgcc tccaccaagg 5340
gccctagcgt ctttcctctg gccccttcct ccaagtctac ctctggcggc accgctgctc 5400
tgggctgcct ggtgaaggac tacttccctg agcctgtgac cgtgtcctgg aactctggcg 5460
ccctgacctc cggcgtgcat accttccctg ccgtcctcca gtcctccggc ctgtactccc 5520
tgtcctccgt ggtgaccgtg ccttcctcct ctctgggcac ccagacctac atctgcaacg 5580
tgaaccacaa gccttccaac accaaggtgg acaagaaggt ggagcctaag tcctgcgaca 5640
agacccacac ctgccctcca tgtcctgccc ctgagctgct gggcggaccc tccgtgttcc 5700
tgttccctcc taagcctaag gacaccctga tgatctcccg gacccctgaa gtgacctgcg 5760
tggtggtgga cgtgtcccac gaagatcctg aagtgaagtt caattggtac gtggacggcg 5820
tggaggtgca caacgccaag accaagcctc gggaggaaca gtacaactcc acctaccggg 5880
tggtgtctgt gctgaccgtg ctgcaccagg actggctgaa cggcaaagaa tacaagtgca 5940
aggtgtccaa caaggccctg cctgccccta tcgaaaagac catctccaag gctaagggcc 6000
agccacggga acctcaggtc tacacactgc ctcctagccg ggacgagctg accaagaacc 6060
aggtgtccct gacctgtctg gtgaagggct tctacccttc cgatatcgcc gtggagtggg 6120
agtctaacgg ccagcctgag aacaactaca agaccacccc tcctgtgctg gactccgacg 6180
gctccttctt cctgtactcc aagctgaccg tggacaagtc ccggtggcag cagggcaacg 6240
tgttctcctg ctccgtgatg cacgaggccc tgcacaacca ctacacccag aagtccctgt 6300
ccctgtctcc tggcaaggaa caaaaactca tctcagaaga ggatctgaat gctgtgggcc 6360
aggacacgca ggaggtcatc gtggtgccac actccttgcc ctttaaggtg gtggtgatct 6420
cagccatcct ggccctggtg gtgctcacca tcatctccct tatcatcctc atcatgcttt 6480
ggcagaagaa gccacgttag taaaagcttg tcacttggaa agtaatagtt tttcctgcac 6540
gggtagtaat cagcctcgac tgtgccttct agttgccagc catctgttgt ttgcccctcc 6600
cccgtgcctt ccttgaccct ggaaggtgcc actcccactg tcctttccta ataaaatgag 6660
gaaattgcat cgcattgtct gagtaggtgt cattctattc tggggggtgg ggtggggcag 6720
gacagcaagg gggaggattg ggaagacaat agcaggcatg ctggggatgg cccgggcatg 6780
ataacttcgt ataatgtatg ctatacgaag ttatgtatac ggcgcgccca ctagggacag 6840
gattggtgac agaaaagccc catccttagg cctcctcctt cctagtctcc tgatattggg 6900
tctaaccccc acctcctgtt aggcagattc cttatctggt gacacacccc catttcctgg 6960
agccatctct ctccttgcca gaacctctaa ggtttgctta cgatggagcc agagaggatc 7020
ctgggaggga gagcttggca gggggtggga gggaaggggg ggatgcgtga cctgcccggt 7080
tctcagtggc caccctgcgc taccctctcc cagaacctga gctgctctga cgcggctgtc 7140
tggtgcgttt cactgatcct ggtgctgcag cttccttaca cttcccaaga ggagaagcag 7200
tttggaaaaa caaaatcaga ataagttggt cctgagttct aactttggct cttcaccttt 7260
ctagtcccca atttatattg ttcctccgtg cgtcagtttt acctgtgaga taaggccagt 7320
agccagcccc gtcctggcag ggctgtggtg aggagggggg tgtccgtgtg gaaaactccc 7380
tttgtgagaa tggtgcgtcc taggtgttca ccaggtcgtg gccgcctcta ctccctttct 7440
ctttctccat ccttctttcc ttaaagagtc cccagtgcta tctgggacat attcctccgc 7500
ccagagcagg gtcccgcttc cctaaggccc tgctctgggc ttctgggttt gagtccttgg 7560
caagcccagg agaggcgctc aggcttccct gtccccttc ctcgtccacc atctcatgcc 7620

```
cctggctctc ctgccccttc cctacagggg ttcctggctc tgctctcctg caggcgatct   7680


<210> SEQ ID NO 321
<211> LENGTH: 132
<212> TYPE: PRT
<213> ORGANISM: Artificial Sequence
<220> FEATURE:
<223> OTHER INFORMATION: Blasticin resistance amino acid

<400> SEQUENCE: 321

Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
            20                  25                  30

Ser Ala Ala Leu Ser Ser Asp Gly Arg Ile Phe Thr Gly Val Asn Val
        35                  40                  45

Tyr His Phe Thr Gly Gly Pro Cys Ala Glu Leu Val Val Leu Gly Thr
    50                  55                  60

Ala Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95

Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
    130


<210> SEQ ID NO 322
<211> LENGTH: 335
<212> TYPE: PRT
<213> ORGANISM: Artificial Sequence
<220> FEATURE:
<223> OTHER INFORMATION: Reverse Tet activator (rTA)

<400> SEQUENCE: 322

Pro Ser Arg Leu Asp Lys Ser Lys Val Ile Asn Ser Ala Leu Glu Leu
1               5                   10                  15

Leu Asn Glu Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Ala Ile Glu Met Leu Asp Arg His His
    50                  55                  60

Thr His Phe Cys Pro Leu Lys Gly Glu Ser Trp Gln Asp Phe Leu Arg
65                  70                  75                  80

Asn Asn Ala Lys Ser Phe Arg Cys Ala Leu Leu Ser His Arg Asn Gly
                85                  90                  95

Ala Lys Val His Ser Asp Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Asp Gln Glu His Gln Val Ala Lys Glu Glu Arg Glu Thr
145                 150                 155                 160
```

-continued

```
Pro Thr Thr Asp Ser Met Pro Pro Leu Leu Arg Gln Ala Ile Glu Leu
                165                 170                 175

Phe Asp His Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Ser Ala
        195                 200                 205

Tyr Ser Arg Ala Arg Thr Lys Asn Asn Tyr Gly Ser Thr Ile Glu Gly
    210                 215                 220

Leu Leu Asp Leu Pro Asp Asp Asp Ala Pro Glu Glu Ala Gly Leu Ala
225                 230                 235                 240

Ala Pro Arg Leu Ser Phe Leu Pro Ala Gly His Thr Arg Arg Leu Ser
                245                 250                 255

Thr Ala Pro Pro Thr Asp Val Ser Leu Gly Asp Glu Leu His Leu Asp
            260                 265                 270

Gly Glu Asp Val Ala Met Ala His Ala Asp Ala Leu Asp Asp Phe Asp
        275                 280                 285

Leu Asp Met Leu Gly Asp Gly Asp Ser Pro Gly Pro Gly Phe Thr Pro
    290                 295                 300

His Asp Ser Ala Pro Tyr Gly Ala Leu Asp Met Ala Asp Phe Glu Phe
305                 310                 315                 320

Glu Gln Met Phe Thr Asp Ala Leu Gly Ile Asp Glu Tyr Gly Gly
                325                 330                 335


<210> SEQ ID NO 323
<211> LENGTH: 17
<212> TYPE: PRT
<213> ORGANISM: Artificial Sequence
<220> FEATURE:
<223> OTHER INFORMATION: BM40 leader

<400> SEQUENCE: 323

Met Arg Ala Trp Ile Phe Phe Leu Leu Cys Leu Ala Gly Arg Ala Leu
1               5                   10                  15

Ala


<210> SEQ ID NO 324
<211> LENGTH: 111
<212> TYPE: PRT
<213> ORGANISM: Artificial Sequence
<220> FEATURE:
<223> OTHER INFORMATION: Anti-PD1 MK3475 VL

<400> SEQUENCE: 324

Leu Ala Arg Leu Ser Pro Arg Ala Pro Gln His Cys Pro Cys Pro Pro
1               5                   10                  15

Glu Lys Glu Gln Pro Cys Pro Val Glu His Gln Lys Val Cys Leu Pro
            20                  25                  30

Val Gly Thr Ala Ile Cys Thr Gly Thr Ser Arg Ser Pro Asp Arg Pro
        35                  40                  45

Leu Gly Cys Ser Thr Trp Leu Leu Ile Trp Arg Val Glu Cys Gln His
    50                  55                  60

Gly Ser Gln Val Pro Ala Ala Glu Gln Thr Leu Pro Gln Phe Pro Ala
65                  70                  75                  80

Trp Ser Gln Lys Thr Ser Pro Cys Thr Ile Ala Ser Ile Pro Glu Ile
                85                  90                  95

Cys Pro Leu Leu Ala Glu Gly Pro Arg Ser Lys Ser Lys Gly Leu
            100                 105                 110
```

<210> SEQ ID NO 325
<211> LENGTH: 106
<212> TYPE: PRT
<213> ORGANISM: Artificial Sequence
<220> FEATURE:
<223> OTHER INFORMATION: Human C kappa

<400> SEQUENCE: 325

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Leu Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 326
<211> LENGTH: 20
<212> TYPE: PRT
<213> ORGANISM: Artificial Sequence
<220> FEATURE:
<223> OTHER INFORMATION: P2A peptide

<400> SEQUENCE: 326

```
Gly Ser Gly Ala Thr Asn Phe Ser Leu Leu Lys Gln Ala Gly Asp Val
1               5                   10                  15

Glu Glu Asn Pro
            20
```

<210> SEQ ID NO 327
<211> LENGTH: 15
<212> TYPE: PRT
<213> ORGANISM: Artificial Sequence
<220> FEATURE:
<223> OTHER INFORMATION: Mouse leader with intron

<400> SEQUENCE: 327

```
Met Ser Trp Ser Cys Ile Ile Leu Phe Leu Val Ala Thr Ala Thr
1               5                   10                  15
```

<210> SEQ ID NO 328
<211> LENGTH: 120
<212> TYPE: PRT
<213> ORGANISM: Artificial Sequence
<220> FEATURE:
<223> OTHER INFORMATION: Anti-PD1 MK3475 VH

<400> SEQUENCE: 328

```
Met Ala Gln Val Gln Leu Val Gln Ser Gly Val Glu Val Lys Lys Pro
1               5                   10                  15

Gly Ala Ser Val Lys Val Ser Cys Lys Ala Ser Gly Tyr Thr Phe Thr
            20                  25                  30

Asn Tyr Tyr Met Tyr Trp Val Arg Gln Ala Pro Gly Gln Gly Leu Glu
        35                  40                  45
```

-continued

```
Trp Met Gly Gly Ile Asn Pro Ser Asn Gly Gly Thr Asn Phe Asn Glu
    50                  55                  60

Lys Phe Lys Asn Arg Val Thr Leu Thr Thr Asp Ser Ser Thr Thr Thr
65                  70                  75                  80

Ala Tyr Met Glu Leu Lys Ser Leu Gln Phe Asp Asp Thr Ala Val Tyr
                85                  90                  95

Tyr Cys Ala Arg Arg Asp Tyr Arg Phe Asp Met Gly Phe Asp Tyr Trp
            100                 105                 110

Gly Gln Gly Thr Thr Val Thr Val
        115                 120


<210> SEQ ID NO 329
<211> LENGTH: 332
<212> TYPE: PRT
<213> ORGANISM: Artificial Sequence
<220> FEATURE:
<223> OTHER INFORMATION: Optimised human IgG1 CHI-CH3

<400> SEQUENCE: 329

Ser Ser Ala Ser Thr Lys Gly Pro Ser Val Phe Pro Leu Ala Pro Ser
1               5                   10                  15

Ser Lys Ser Thr Ser Gly Gly Thr Ala Ala Leu Gly Cys Leu Val Lys
            20                  25                  30

Asp Tyr Phe Pro Glu Pro Val Thr Val Ser Trp Asn Ser Gly Ala Leu
        35                  40                  45

Thr Ser Gly Val His Thr Phe Pro Ala Val Leu Gln Ser Ser Gly Leu
    50                  55                  60

Tyr Ser Leu Ser Ser Val Val Thr Val Pro Ser Ser Ser Leu Gly Thr
65                  70                  75                  80

Gln Thr Tyr Ile Cys Asn Val Asn His Lys Pro Ser Asn Thr Lys Val
                85                  90                  95

Asp Lys Lys Val Glu Pro Lys Ser Cys Asp Lys Thr His Thr Cys Pro
            100                 105                 110

Pro Cys Pro Ala Pro Glu Leu Leu Gly Gly Pro Ser Val Phe Leu Phe
        115                 120                 125

Pro Pro Lys Pro Lys Asp Thr Leu Met Ile Ser Arg Thr Pro Glu Val
    130                 135                 140

Thr Cys Val Val Val Asp Val Ser His Glu Asp Pro Glu Val Lys Phe
145                 150                 155                 160

Asn Trp Tyr Val Asp Gly Val Glu Val His Asn Ala Lys Thr Lys Pro
                165                 170                 175

Arg Glu Glu Gln Tyr Asn Ser Thr Tyr Arg Val Val Ser Val Leu Thr
            180                 185                 190

Val Leu His Gln Asp Trp Leu Asn Gly Lys Glu Tyr Lys Cys Lys Val
        195                 200                 205

Ser Asn Lys Ala Leu Pro Ala Pro Ile Glu Lys Thr Ile Ser Lys Ala
    210                 215                 220

Lys Gly Gln Pro Arg Glu Pro Gln Val Tyr Thr Leu Pro Pro Ser Arg
225                 230                 235                 240

Asp Glu Leu Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
            260                 265                 270

Glu Asn Asn Tyr Lys Thr Thr Pro Pro Val Leu Asp Ser Asp Gly Ser
        275                 280                 285
```

-continued

```
Phe Phe Leu Tyr Ser Lys Leu Thr Val Asp Lys Ser Arg Trp Gln Gln
    290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys
                325                 330


<210> SEQ ID NO 330
<211> LENGTH: 23
<212> TYPE: PRT
<213> ORGANISM: Artificial Sequence
<220> FEATURE:
<223> OTHER INFORMATION: Hinge

<400> SEQUENCE: 330

Glu Pro Lys Ser Cys Asp Lys Thr His Thr Cys Pro Pro Cys Pro Ala
1               5                   10                  15

Pro Glu Leu Leu Gly Gly Pro
            20


<210> SEQ ID NO 331
<211> LENGTH: 10
<212> TYPE: PRT
<213> ORGANISM: Artificial Sequence
<220> FEATURE:
<223> OTHER INFORMATION: MYC epitope

<400> SEQUENCE: 331

Glu Gln Lys Leu Ile Ser Glu Glu Asp Leu
1               5                   10


<210> SEQ ID NO 332
<211> LENGTH: 50
<212> TYPE: PRT
<213> ORGANISM: Artificial Sequence
<220> FEATURE:
<223> OTHER INFORMATION: PDGVR anchor

<400> SEQUENCE: 332

Asn Ala Val Gly Gln Asp Thr Gln Glu Val Ile Val Val Pro His Ser
1               5                   10                  15

Leu Pro Phe Lys Val Val Val Ile Ser Ala Ile Leu Ala Leu Val Val
            20                  25                  30

Leu Thr Ile Ile Ser Leu Ile Ile Leu Ile Met Leu Trp Gln Lys Lys
        35                  40                  45

Pro Arg
    50


<210> SEQ ID NO 333
<211> LENGTH: 6280
<212> TYPE: DNA
<213> ORGANISM: Artificial Sequence
<220> FEATURE:
<223> OTHER INFORMATION: pINT-TetD1.3

<400> SEQUENCE: 333

ggagatcttc cccagcatgc ctgctattgt cttcccaatc ctcccccttg ctgtcctgcc      60

ccaccccacc ccccagaata gaatgacacc tactcagaca atgcgatgca atttcctcat     120

tttattagga aaggacagtg ggagtggcac cttccagggt caaggaaggc acgggggagg     180

ggcaaacaac agatggctgg caactagaag gcacagtcga ggctctagat tattagcact     240

cgccccggtt gaaggacttg gtcacgggag aggacaggcc ctggtgggtc acttcgcagg     300
```

-continued

```
cgtacagctt gtgcttctcg tagtcggcct tggacagggt cagggtggag gacagggagt    360
aggtagagtc cttggagtcc tgctcggtga cggattcctg ggagttgccg gactgcaggg    420
cgttgtccac cttccactgc accttggcct cccgagggta gaagttgttc agcaggcaca    480
ccacagaggc ggtgccggac ttcagctgct cgtcggaggg agggaagatg aacacggaag    540
gggcggccgc ggtacgtttg atttccacct tggtcccttg gccgaacgtc cttggggtgc    600
tccagaagtg ctggcagtag taggtggcga tgtcctctgg ctggaggctg ctgatggtga    660
aggtgtagtc ggtaccgcta ccgctaccgc tgaatctgct tggcacaccg tcagccaggg    720
tggtggtgta gtagatcagc agctttggag ccttacctgg cttctgctgg taccaagcca    780
ggtagttgtg gatgttaccg ctggctctac aggtgatggt cactctgtca cccacgctgg    840
cgctcaggct gcttgggctc tgggtcatct ggatgtctcc tctgctagct gaaaatatac    900
agcaaacatc agtacaacat aaatatctgt gtatgaaaat cacctttaat cttgctagac    960
atgaagaaag aatatgcaat acatttttaa aattaggatt ttaaaatcaa gccaaaaatc   1020
acctattgca gagtccccaa tgaaagaaat tacagattga aagaatatct ccgcctaggt   1080
ttgtggaaat attctcacct ggaacccaga gcagcagaaa cccaatgagt tgtgatggca   1140
acatggtggc cactccggat ctgatctgcg atctgacggt tcactaaacg agctctgctt   1200
atataggcct cccaccgtac acgccacctc gacatactcg tgtttactcc ctatcagtga   1260
tagagaacgt atgaagagtt tactccctat cagtgataga gaacgtatgc agactttact   1320
ccctatcagt gatagagaac gtataaggag tttactccct atcagtgata gagaacgtat   1380
gaccagttta ctccctatca gtgatagaga acgtatctac agtttactcc ctatcagtga   1440
tagagaacgt atatccagtt tactccctat cagtgataga gaacgtatta gctttaggcg   1500
tgtacggtgg gcgcctataa aagcagagct cgtttagtga accgtcagat cgcctggagc   1560
aattccacaa cacttttgtc ttataccaac tttccgtacc acttcctacc ctcgtaaaag   1620
atcagatcca tcgattggcc accatgagtt ggagctgtat catcctcttc ttggtagcaa   1680
cagctacagg taaggggtta acagtagcag gcttgaggtc tggacatata tatgggtgac   1740
aatgacatcc actttgcctt tctctccaca ggcgccatgg cccaggtcca actgcaggag   1800
agcggtccag gtcttgtgag acctagccag accctgagcc tgacctgcac cgtgtctggc   1860
agcaccttca gcggctatgg tgtaaactgg gtgagacagc cacctggacg aggtcttgag   1920
tggattggaa tgatttgggg tgatggaaac acagactata attcagctct caaatccaga   1980
gtgacaatgc tggtagacac cagcaagaac cagttcagcc tgagactcag cagcgtgaca   2040
gccgccgaca ccgcggtcta ttattgtgca agagagagag attataggct tgactactgg   2100
ggtcaaggca gcctcgtcac agtctcgagt gcctccacca agggccctag cgtctttcct   2160
ctggcccctt cctccaagtc tacctctggc ggcaccgctg ctctgggctg cctggtgaag   2220
gactacttcc ctgagcctgt gaccgtgtcc tggaactctg gcgccctgac ctccggcgtg   2280
cataccttcc ctgccgtcct ccagtcctcc ggcctgtact ccctgtcctc cgtggtgacc   2340
gtgccttcct cctctctggg cacccagacc tacatctgca acgtgaacca caagccttcc   2400
aacaccaagg tggacaagaa ggtggagcct aagtcctgcg acaagaccca cacctgccct   2460
ccatgtcctg cccctgagct gctgggcgga ccctccgtgt tcctgttccc tcctaagcct   2520
aaggacaccc tgatgatctc ccggacccct gaagtgacct gcgtggtggt ggacgtgtcc   2580
cacgaagatc ctgaagtgaa gttcaattgg tacgtggacg gcgtggaggt gcacaacgcc   2640
```

aagaccaagc ctcgggagga acagtacaac tccacctacc gggtggtgtc tgtgctgacc 2700
gtgctgcacc aggactggct gaacggcaaa gaatacaagt gcaaggtgtc caacaaggcc 2760
ctgcctgccc ctatcgaaaa gaccatctcc aaggctaagg gccagccacg ggaacctcag 2820
gtctacacac tgcctcctag ccgggacgag ctgaccaaga accaggtgtc cctgacctgt 2880
ctggtgaagg gcttctaccc ttccgatatc gccgtggagt gggagtctaa cggccagcct 2940
gagaacaact acaagaccac ccctcctgtg ctggactccg acggctcctt cttcctgtac 3000
tccaagctga ccgtggacaa gtcccggtgg cagcagggca acgtgttctc ctgctccgtg 3060
atgcacgagg ccctgcacaa ccactacacc cagaagtccc tgtccctgtc tcctggcaag 3120
gaacaaaaac tcatctcaga agaggatctg aatgctgtgg gccaggacac gcaggaggtc 3180
atcgtggtgc cacactcctt gccctttaag gtggtggtga tctcagccat cctggccctg 3240
gtggtgctca ccatcatctc ccttatcatc ctcatcatgc tttggcagaa gaagccacgt 3300
tagtaaaagc ttgtcacttg gaaagtaata gtttttcctg cacgggtagt aatcagcctc 3360
gactgtgcct tctagttgcc agccatctgt tgtttgcccc tcccccgtgc cttccttgac 3420
cctggaaggt gccactccca ctgtcctttc ctaataaaat gaggaaattg catcgcattg 3480
tctgagtagg tgtcattcta ttctgggggg tggggtgggg caggacagca agggggagga 3540
ttgggaagac aatagcaggc atgctgggga tggcccgggc atgataactt cgtataatgt 3600
atgctatacg aagttatgta gagtaattca tacaaaagga ctcgcccctg ccttggggaa 3660
tcccagggac cgtcgttaaa ctcccactaa cgtagaaccc agagatcgct gcgttcccgc 3720
cccctcaccc gcccgctctc gtcatcactg aggtggagaa gagcatgcgt gaggctccgg 3780
tgcccgtcag tgggcagagc gcacatcgcc cacagtcccc gagaagttgg ggggaggggt 3840
cggcaattga accggtgcct agagaaggtg gcgcggggta aactgggaaa gtgatgtcgt 3900
gtactggctc cgcctttttc ccgagggtgg gggagaaccg tatataagtg cagtagtcgc 3960
cgtgaacgtt ctttttcgca acgggtttgc cgccagaaca caggtaagtg ccgtgtgtgg 4020
ttcccgcggg cctggcctct ttacgggtta tggcccttgc gtgccttgaa ttacttccac 4080
gcccctggct gcagtacgtg attcttgatc ccgagcttcg ggttggaagt gggtgggaga 4140
gttcgaggcc ttgcgcttaa ggagcccctt cgcctcgtgc ttgagttgag gcctggcttg 4200
ggcgctgggg ccgccgcgtg cgaatctggt ggcaccttcg cgcctgtctc gctgctttcg 4260
ataagtctct agccatttaa aatttttgat gacctgctgc gacgcttttt ttctggcaag 4320
atagtcttgt aaatgcgggc catgatctgc acactggtat ttcggttttt ggggccgcgg 4380
gcggcgacgg ggcccgtgcg tcccagcgca catgttcggc gaggcggggc ctgcgagcgc 4440
ggccaccgag aatcggacgg gggtagtctc aagctggccg gcctgctctg gtgcctggcc 4500
tcgcgccgcc gtgtatcgcc ccgccctggg cggcaaggct ggcccggtcg gcaccagttg 4560
cgtgagcgga aagatggccg cttcccggcc ctgctgcagg gagctcaaaa tggaggacgc 4620
ggcgctcggg agagcgggcg ggtgagtcac ccacacaaag gaaaagggcc tttccgtcct 4680
cagccgtcgc ttcatgtgac tccacggagt accgggcgcc gtccaggcac ctcgattagt 4740
tcacgagctt ttggagtacg tcgtctttag gttgggggga ggggttttat gcgatggagt 4800
ttccccacac tgagtgggtg gagactgaag ttaggccagc ttggcacttg atgtaattct 4860
ccttggaatt tgcccttttt gagtttggat cttggttcat tctcaagcct cagacagtgg 4920
ttcaaagttt ttttcttcca tttcaggtgt cgtgagagct cgtttagtga accgtcagat 4980
cgcctggaga cgccatccac gctgttttga cctccataga agacaccggg accgatccag 5040

```
cctccgcggc cccgaattca ccatgtctag actggacaag agcaaagtca taaactctgc   5100

tctggaatta ctcaatggag tcggtatcga aggcctgacg acaaggaaac tcgctcaaaa   5160

gctgggagtt gagcagccta ccctgtactg gcacgtgaag aacaagcggg ccctgctcga   5220

tgccctgcca atcgagatgc tggacaggca tcatacccac tcctgccccc tggaaggcga   5280

gtcatggcaa gactttctgc ggaacaacgc caagtcatac cgctgtgctc tcctctcaca   5340

tcgcgacggg gctaaagtgc atctcggcac ccgcccaaca gagaaacagt acgaaaccct   5400

ggaaaatcag ctcgcgttcc tgtgtcagca aggcttctcc ctggagaacg cactgtacgc   5460

tctgtccgcc gtgggccact ttacactggg ctgcgtattg gaggaacagg agcatcaagt   5520

agcaaaagag gaaagagaga cacctaccac cgattctatg cccccacttc tgaaacaagc   5580

aattgagctg ttcgaccggc agggagccga acctgccttc cttttcggcc tggaactaat   5640

catatgtggc ctggagaaac agctaaagtg cgaaagcggc gggccgaccg acgcccttga   5700

cgattttgac ttagacatgc tcccagccga tgcccttgac gactttgacc ttgatatgct   5760

gcctgctgac gctcttgacg attttgacct tgacatgctc cccgggtaac taagtaagga   5820

tccagacatg ataagataca ttgatgagtt tggacaaacc acaactagaa tgcagtgaaa   5880

aaaatgcttt atttgtgaaa tttgtgatgc tattgcttta tttgtaacca ttataagctg   5940

caataaacaa gttaacaaca acaattgcat tcattttatg tttcaggttc agggggaggt   6000

gtgggaggtt ttttaaagca agtaaaacct ctacaaatgt ggtatggctg attatgatcc   6060

tgcaagcctc gtcgtcctgg ccggaccacg ctatctgtgc aaggtccccg gccccggacg   6120

cgcgctccat gagcagagcg cccgccgccg aggcgaagac tcgggcggcg ccctgcccgt   6180

cccaccaggt caacaggcgg taaccggcct cttcatcggg aatgcgcgcg accttcagca   6240

tcgccggcat gtccccctgg cggacgggaa gtatgtatac                        6280
```

<210> SEQ ID NO 334
<211> LENGTH: 103
<212> TYPE: PRT
<213> ORGANISM: Artificial Sequence
<220> FEATURE:
<223> OTHER INFORMATION: Human c kappa (reverse strand)

<400> SEQUENCE: 334

```
Ala Pro Ser Val Phe Ile Phe Pro Pro Ser Asp Glu Gln Leu Lys Ser
1               5                   10                  15

Gly Thr Ala Ser Val Val Cys Leu Leu Asn Asn Phe Tyr Pro Arg Glu
            20                  25                  30

Ala Lys Val Gln Trp Lys Val Asp Asn Ala Leu Gln Ser Gly Asn Ser
        35                  40                  45

Gln Glu Ser Val Thr Glu Gln Asp Ser Lys Asp Ser Thr Tyr Ser Leu
    50                  55                  60

Ser Ser Thr Leu Thr Leu Ser Lys Ala Asp Tyr Glu Lys His Lys Leu
65                  70                  75                  80

Tyr Ala Cys Glu Val Thr His Gln Gly Leu Ser Ser Pro Val Thr Lys
                85                  90                  95

Ser Phe Asn Arg Gly Glu Cys
            100
```

<210> SEQ ID NO 335
<211> LENGTH: 109
<212> TYPE: PRT
<213> ORGANISM: Artificial Sequence

<220> FEATURE:
<223> OTHER INFORMATION: D1.3 VL

<400> SEQUENCE: 335

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Tyr
            20                  25                  30

Leu Ala Trp Tyr Gln Gln Lys Pro Gly Lys Ala Pro Lys Leu Leu Ile
        35                  40                  45

Tyr Tyr Thr Thr Thr Leu Ala Asp Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln His Phe Trp Ser Thr Pro Arg
                85                  90                  95

Thr Phe Gly Gln Gly Thr Lys Val Glu Ile Lys Arg Thr
            100                 105

<210> SEQ ID NO 336
<211> LENGTH: 4
<212> TYPE: PRT
<213> ORGANISM: Artificial Sequence
<220> FEATURE:
<223> OTHER INFORMATION: Lead (reverse)

<400> SEQUENCE: 336

Ala Ser Arg Gly
1

<210> SEQ ID NO 337
<211> LENGTH: 15
<212> TYPE: PRT
<213> ORGANISM: Artificial Sequence
<220> FEATURE:
<223> OTHER INFORMATION: LEADER I (reverse)

<400> SEQUENCE: 337

Met Leu Pro Ser Gln Leu Ile Gly Phe Leu Leu Leu Trp Val Pro
1               5                   10                  15

<210> SEQ ID NO 338
<211> LENGTH: 15
<212> TYPE: PRT
<213> ORGANISM: Artificial Sequence
<220> FEATURE:
<223> OTHER INFORMATION: Leader

<400> SEQUENCE: 338

Met Ser Trp Ser Cys Ile Ile Leu Phe Leu Val Ala Thr Ala Thr
1               5                   10                  15

<210> SEQ ID NO 339
<211> LENGTH: 4
<212> TYPE: PRT
<213> ORGANISM: Artificial Sequence
<220> FEATURE:
<223> OTHER INFORMATION: Leader

<400> SEQUENCE: 339

Gly Ala Met Ala
1

<210> SEQ ID NO 340
<211> LENGTH: 115
<212> TYPE: PRT
<213> ORGANISM: Artificial Sequence
<220> FEATURE:
<223> OTHER INFORMATION: D1.3 VH

<400> SEQUENCE: 340

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser
        115
```

<210> SEQ ID NO 341
<211> LENGTH: 331
<212> TYPE: PRT
<213> ORGANISM: Artificial Sequence
<220> FEATURE:
<223> OTHER INFORMATION: IgG1 CH1-3

<400> SEQUENCE: 341

```
Ser Ala Ser Thr Lys Gly Pro Ser Val Phe Pro Leu Ala Pro Ser Ser
1               5                   10                  15

Lys Ser Thr Ser Gly Gly Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Ile Cys Asn Val Asn His Lys Pro Ser Asn Thr Lys Val Asp
                85                  90                  95

Lys Lys Val Glu Pro Lys Ser Cys Asp Lys Thr His Thr Cys Pro Pro
            100                 105                 110

Cys Pro Ala Pro Glu Leu Leu Gly Gly Pro Ser Val Phe Leu Phe Pro
        115                 120                 125

Pro Lys Pro Lys Asp Thr Leu Met Ile Ser Arg Thr Pro Glu Val Thr
    130                 135                 140

Cys Val Val Val Asp Val Ser His Glu Asp Pro Glu Val Lys Phe Asn
145                 150                 155                 160

Trp Tyr Val Asp Gly Val Glu Val His Asn Ala Lys Thr Lys Pro Arg
                165                 170                 175

Glu Glu Gln Tyr Asn Ser Thr Tyr Arg Val Val Ser Val Leu Thr Val
            180                 185                 190
```

```
Leu His Gln Asp Trp Leu Asn Gly Lys Glu Tyr Lys Cys Lys Val Ser
        195                 200                 205

Asn Lys Ala Leu Pro Ala Pro Ile Glu Lys Thr Ile Ser Lys Ala Lys
    210                 215                 220

Gly Gln Pro Arg Glu Pro Gln Val Tyr Thr Leu Pro Pro Ser Arg Asp
225                 230                 235                 240

Glu Leu Thr Lys Asn Gln Val Ser Leu Thr Cys Leu Val Lys Gly Phe
                245                 250                 255

Tyr Pro Ser Asp Ile Ala Val Glu Trp Glu Ser Asn Gly Gln Pro Glu
            260                 265                 270

Asn Asn Tyr Lys Thr Thr Pro Pro Val Leu Asp Ser Asp Gly Ser Phe
        275                 280                 285

Phe Leu Tyr Ser Lys Leu Thr Val Asp Lys Ser Arg Trp Gln Gln Gly
    290                 295                 300

Asn Val Phe Ser Cys Ser Val Met His Glu Ala Leu His Asn His Tyr
305                 310                 315                 320

Thr Gln Lys Ser Leu Ser Leu Ser Pro Gly Lys
                325                 330


<210> SEQ ID NO 342
<211> LENGTH: 23
<212> TYPE: PRT
<213> ORGANISM: Artificial Sequence
<220> FEATURE:
<223> OTHER INFORMATION: hinge

<400> SEQUENCE: 342

Glu Pro Lys Ser Cys Asp Lys Thr His Thr Cys Pro Pro Cys Pro Ala
1               5                   10                  15

Pro Glu Leu Leu Gly Gly Pro
            20


<210> SEQ ID NO 343
<211> LENGTH: 10
<212> TYPE: PRT
<213> ORGANISM: Artificial Sequence
<220> FEATURE:
<223> OTHER INFORMATION: MYC-epitope

<400> SEQUENCE: 343

Glu Gln Lys Leu Ile Ser Glu Glu Asp Leu
1               5                   10


<210> SEQ ID NO 344
<211> LENGTH: 50
<212> TYPE: PRT
<213> ORGANISM: Artificial Sequence
<220> FEATURE:
<223> OTHER INFORMATION: PDGFR anchor

<400> SEQUENCE: 344

Asn Ala Val Gly Gln Asp Thr Gln Glu Val Ile Val Val Pro His Ser
1               5                   10                  15

Leu Pro Phe Lys Val Val Val Ile Ser Ala Ile Leu Ala Leu Val Val
            20                  25                  30

Leu Thr Ile Ile Ser Leu Ile Ile Leu Ile Met Leu Trp Gln Lys Lys
        35                  40                  45

Pro Arg
    50
```

<210> SEQ ID NO 345
<211> LENGTH: 248
<212> TYPE: PRT
<213> ORGANISM: Artificial Sequence
<220> FEATURE:
<223> OTHER INFORMATION: TET-ON 3G

<400> SEQUENCE: 345

```
Met Ser Arg Leu Asp Lys Ser Lys Val Ile Asn Ser Ala Leu Glu Leu
1               5                   10                  15

Leu Asn Gly Val Gly Ile Glu Gly Leu Thr Thr Arg Lys Leu Ala Gln
            20                  25                  30

Lys Leu Gly Val Glu Gln Pro Thr Leu Tyr Trp His Val Lys Asn Lys
        35                  40                  45

Arg Ala Leu Leu Asp Ala Leu Pro Ile Glu Met Leu Asp Arg His His
    50                  55                  60

Thr His Ser Cys Pro Leu Glu Gly Glu Ser Trp Gln Asp Phe Leu Arg
65                  70                  75                  80

Asn Asn Ala Lys Ser Tyr Arg Cys Ala Leu Leu Ser His Arg Asp Gly
                85                  90                  95

Ala Lys Val His Leu Gly Thr Arg Pro Thr Glu Lys Gln Tyr Glu Thr
            100                 105                 110

Leu Glu Asn Gln Leu Ala Phe Leu Cys Gln Gln Gly Phe Ser Leu Glu
        115                 120                 125

Asn Ala Leu Tyr Ala Leu Ser Ala Val Gly His Phe Thr Leu Gly Cys
    130                 135                 140

Val Leu Glu Glu Gln Glu His Gln Val Ala Lys Glu Glu Arg Glu Thr
145                 150                 155                 160

Pro Thr Thr Asp Ser Met Pro Pro Leu Leu Lys Gln Ala Ile Glu Leu
                165                 170                 175

Phe Asp Arg Gln Gly Ala Glu Pro Ala Phe Leu Phe Gly Leu Glu Leu
            180                 185                 190

Ile Ile Cys Gly Leu Glu Lys Gln Leu Lys Cys Glu Ser Gly Gly Pro
        195                 200                 205

Thr Asp Ala Leu Asp Asp Phe Asp Leu Asp Met Leu Pro Ala Asp Ala
    210                 215                 220

Leu Asp Asp Phe Asp Leu Asp Met Leu Pro Ala Asp Ala Leu Asp Asp
225                 230                 235                 240

Phe Asp Leu Asp Met Leu Pro Gly
                245
```

<210> SEQ ID NO 346
<211> LENGTH: 99
<212> TYPE: DNA
<213> ORGANISM: Homo sapiens

<400> SEQUENCE: 346

```
cagggccggt taatgtggct ctggttctgg gtacttttat ctgtcccctc caccccacag     60

tggggccact agggacagga ttggtgacag aaaagcccc                            99
```

<210> SEQ ID NO 347
<211> LENGTH: 89
<212> TYPE: DNA
<213> ORGANISM: Artificial Sequence
<220> FEATURE:
<223> OTHER INFORMATION: CHO AAVS intron

<400> SEQUENCE: 347
cgggatcctt ctggattcgg gatgctttta tctccccgtc atccaaaagc tggcattgtc 60
agggacaaga ttagtcacag cagagcccc 89

<210> SEQ ID NO 348
<211> LENGTH: 960
<212> TYPE: DNA
<213> ORGANISM: Artificial Sequence
<220> FEATURE:
<223> OTHER INFORMATION: pINT17-BSD-CHO-D1.3 range 1-960

<400> SEQUENCE: 348
gcgatcgcga tggcttacat cccgtgcctt tccaggctgg tggctgccct ggctgtgccg 60
caggcttcca gggcccagct ctgacttgac gccccccccc caatccccca ctccctcctc 120
tgagtctagc caggcccagg cccttcagtg tcacttcttt tggggggtcc accttgttcc 180
ctaccccact tcctgtgacc cgtgctgtcc gctgtggcct caggagggtc ctttgcccct 240
ccaaggcagt gtacccottt gttcccctgg agaagaggcg ctccaccgtc tgttgggccc 300
catcccataa ccttcctccc ctccccatgt cctattaatt caattctcgg ctcatcccct 360
tttggtgatc ttgccaccca cccccacccc ccataggttt ctcctcaact ctctctctct 420
ctctctctct ctctctctct ctctctctct ctctctctct ctgtctctct ctctctgtgt 480
ccacattgat ttgcctttct ggaaacttct aagcattcgg tcttccaagc cctatttctc 540
tctcctctgg ttttgttttt gttgttgttt tttgtttttt cccctgtgta gcccaggcca 600
acctcaaata caggtcctgt gtctctgacc ccctcatttg tgggattaca ggcatgccca 660
ctccacctac cacctcatgg actatatttg ggcagcatcc tgctttaaaa actatgccct 720
gtctcttaga tttccaccct gtcaccttct agaacctacc ccaccaggac cctgggcgac 780
tcagacactg tgattatctt tttccagtga tctgtgcccc gagagtgagg accatcttgt 840
attgccggga tccttctgga ttcgggatgc ttttatctcc ccgtcatcca aaagctggca 900
taagatgcat cttctgacct cttctcttcc tcccacaggg catggcaaaa cctctgagcc 960

<210> SEQ ID NO 349
<211> LENGTH: 6
<212> TYPE: PRT
<213> ORGANISM: Artificial Sequence
<220> FEATURE:
<223> OTHER INFORMATION: Blasticidin

<400> SEQUENCE: 349

Met Ala Lys Pro Leu Ser
1 5

<210> SEQ ID NO 350
<211> LENGTH: 1040
<212> TYPE: DNA
<213> ORGANISM: Artificial Sequence
<220> FEATURE:
<223> OTHER INFORMATION: pINT17-BSD-CHO-D1.3 range 6321-7360

<400> SEQUENCE: 350
gggcatgata acttcgtata atgtatgcta tacgaagtta tgtatacggc gcgcctgtca 60
gggacaagat tagtcacagc agagccccca tccccgttct tcttcctcct ggccacagtg 120
ttggttcact ttcagtcttt catggcaact tccatctcct gggttgtcgt cctcttgcta 180
ggatgctcgt ggaggtgggg aataaaggtt cagtgtttca ctcatccagg cagaggaaaa 240
acagaatccg tctgtcctgg gctgggctgt cttttagaca gagtgcttgc ctagagtgca 300

```
ggaagcctca ggttccaacc ccaataccac agaaatcagg tgcttggaaa gtagaggcag    360

gagggttgga attcagtgtc accttcatct acacagtgac tttgaggcca tcttgatagc    420

ccacatgaga cccagttgca aaatcttgac caaacaaaaa aagtccgtgc tgactttttg    480

tgtcagtctg cttcttgtgt cttgtatctt gagtgtcttt tctcggtgcg ccttagtttt    540

tttacctgta gaatgggacc agtggtcacc cctgtcccca gagggactct atggtgagag    600

gcgtcctgtg gaaaacttcc tttatggggc cggcgtgagc tgtgtgggac atcgtcctct    660

atatatagca gggtcctgtt ttcccgaggc cacactcagg gtgtcagcgt ctttgaccag    720

tccaggagat cagctcaggc tgctcacatt atcaccaaag tccctggccc tcccaagagt    780

tccctcccaa ctgcatcccc ttcctctgca tctgctggag gtccctagag catcctctct    840

gacaggaacc tgtgacctca ggcctgacgt gtcagccttc caggtgggac tctcctcccg    900

ccatgcagac accttggtga cctgactctt caggcctttg caggagcctg caggcgatct    960

ctcgatctct cgatttcgat caagacattc ctttaatggt cttttctgga caccactagg   1020

ggtcagaagt agttcatcaa                                               1040
```

<210> SEQ ID NO 351
<211> LENGTH: 408
<212> TYPE: DNA
<213> ORGANISM: Artificial Sequence
<220> FEATURE:
<223> OTHER INFORMATION: anti-PD1 337_1_C08 VH

<400> SEQUENCE: 351

```
gcctttctct ccacaggcgc catggccgaa gtgcagctgg tgcagtctgg agctgaggtg     60

aagaggcctg gggcctcagt gacagtttcc tgcaaggctt ccggttacac ctttaccaac    120

cacggtatca gctgggtgcg acaggcccct ggacaaggcc ttgagtggat gggatggaac    180

agcccttaca atggaaacac aaactatgca cagaggttcc agggcagagt caccatgacc    240

acagacacat ccacgaacac agcctacatg gagctgagga ccctgacatc tgacgacacg    300

gccatgtatt actgtgccag agatagggat tactatgatg cggggagcta ctggggccag    360

ggaaccctgg tcaccgtctc gagtgccagc accaagggcc ccagcgtg                 408
```

<210> SEQ ID NO 352
<211> LENGTH: 127
<212> TYPE: PRT
<213> ORGANISM: Artificial Sequence
<220> FEATURE:
<223> OTHER INFORMATION: anti-PD1 337_1_C08 VH

<400> SEQUENCE: 352

```
Glu Val Gln Leu Val Gln Ser Gly Ala Glu Val Lys Arg Pro Gly Ala
1               5                   10                  15

Ser Val Thr Val Ser Cys Lys Ala Ser Gly Tyr Thr Phe Thr Asn His
            20                  25                  30

Gly Ile Ser Trp Val Arg Gln Ala Pro Gly Gln Gly Leu Glu Trp Met
        35                  40                  45

Gly Trp Asn Ser Pro Tyr Asn Gly Asn Thr Asn Tyr Ala Gln Arg Phe
    50                  55                  60

Gln Gly Arg Val Thr Met Thr Thr Asp Thr Ser Thr Asn Thr Ala Tyr
65                  70                  75                  80

Met Glu Leu Arg Thr Leu Thr Ser Asp Asp Thr Ala Met Tyr Tyr Cys
                85                  90                  95

Ala Arg Asp Arg Asp Tyr Tyr Asp Ala Gly Ser Tyr Trp Gly Gln Gly
```

-continued

```
            100                 105                 110

Thr Leu Val Thr Val Ser Ser Ala Ser Thr Lys Gly Pro Ser Val
        115                 120                 125


<210> SEQ ID NO 353
<211> LENGTH: 345
<212> TYPE: DNA
<213> ORGANISM: Artificial Sequence
<220> FEATURE:
<223> OTHER INFORMATION: anti-PD1 337_1_C08 VL

<400> SEQUENCE: 353

gctagctcct atgagctgac tcagccaccc tcggtgtcag tatccccagg acagacggcc     60

aggatcacct gctctggaga ttcattgcca aagcaatatg cttattggta ccagcaaaag    120

ccaggccagg cccctgtatt agtgatatat aaagacagcg agaggccctc agggatccct    180

gagcgattct ctggctccgg ctcagggaca acagtcacat tgaccatcag tggagtccag    240

gcagaagacg aggctgacta ttattgtcaa tcagcagaca gtgataatgc ttttgtcttt    300

ggaagaggga ccaagctgac cgtcctaggt cagcccgcgg ccgct                    345


<210> SEQ ID NO 354
<211> LENGTH: 7390
<212> TYPE: DNA
<213> ORGANISM: Artificial Sequence
<220> FEATURE:
<223> OTHER INFORMATION: pINT17-Bi-CMV-Emicizumab

<400> SEQUENCE: 354

gagatcttcc ccagcatgcc tgctattgtc ttcccaatcc tcccccttgc tgtcctgccc     60

caccccaccc cccagaatag aatgacacct actcagacaa tgcgatgcaa tttcctcatt    120

ttattaggaa aggacagtgg gagtggcacc ttccagggtc aaggaaggca cgggggaggg    180

gcaaacaaca gatggctggc aactagaagg cacagtcgag gctctagatt attaacattc    240

gccccggttg aagctcttgg tcacagggct agaaaggccc tggtgggtca cttcgcaggc    300

gtacactttg tgcttctcgt agtcggcctt gctcagggtc agtgtgctgc tcaggctgta    360

ggtagagtcc ttgctgtcct gctcggtcac gctctcttgg ctattgccgc tctggagggc    420

gttgtccacc ttccactgca ccttggcttc tctggggtag aagttgttca gcaggcacac    480

gacagaggct gtgccagact tcagctgctc gtcgctaggt ggaaagatga acacgctagg    540

ggcggccgct gtccgcttga tttccacctt ggtgcctccg ccaaatgtca gtggagggtc    600

gctgtactgc tggcagtagt aggtggcgat atcctcaggc tggaggctgg atattgtcag    660

ggtgaagtcg gtgccgtatc tgctgccgct gaatctatcg ggcacgccgc tttcttttct    720

gctggcctga tagatcagca gctcaggagc ctgtccaggc ttctgctgat accaggccag    780

ctgtctctcg atgttccggc tggccttgca tgtgatggtc actctgtctc ccacgctggc    840

agacaggctg ctagggctct gtgtcatctg gatgtctcct ctgctagctg aaaatataca    900

gcaaacatca gtacaacata aatatctgtg tatgaaaatc acctttaatc ttgctagaca    960

tgaagaaaga atatgcaata catttttaaa attaggattt taaaatcaag ccaaaaatca   1020

cctattgcag agtccccaat gaaagaaatt acagattgaa agaatatctc cgcctaggtt   1080

tgtggaaata ttctcacctg gaacccagag cagcagaaac ccaatgagtt gtgatggcaa   1140

catggtggcc actccggatc tgatctgacg gttcactaaa ccagctctgc ttatatagac   1200

ctcccaccgt acacgcctac cgcccatttg ggatctagta atcaattacg gggtcattag   1260
```

-continued

```
ttcatagccc atatatggag ttccgcgtta cataacttac ggtaaatggc ccgcctggct   1320
gaccgcccaa cgacccccgc ccattgacgt caataatgac gtatgttccc atagtaacgc   1380
caatagggac tttccattga cgtcaatggg tggagtattt acggtaaact gcccacttgg   1440
cagtacatca agtgtatcat atgccaagta cgccccctat tgacgtcaat gacggtaaat   1500
ggcccgcctg gcattatgcc cagtacatga ccttatggga ctttcctact tggcagtaca   1560
tctacgtatt agtcatcgct attaccatgc tgatgcggtt ttggcagtac atcaatgggc   1620
gtggatagcg gtttgactca cggggatttc caagtctcca ccccattgac gtcaatggga   1680
gtttgttttg gcaccaaaat caacgggact ttccaaaatg tcgtaacaac tccgccccat   1740
tgacgcaaat gggcggtagg cgtgtacggt gggaggtcta tataagcaga gctggtttag   1800
tgaaccgtca gatcagatcc atcgattggc caccatgagt tggagctgta tcatcctctt   1860
cttggtagca acagctacag gtaaggggtt aacagtagca ggcttgaggt ctggacatat   1920
atatgggtga caatgacatc cactttgcct ttctctccac aggcgccatg gcccaggtgc   1980
agctggttga atctggcgga ggactggttc agcctggcgg atctctgaga ctgtcttgtg   2040
ccgccagcgg cttcaccttc agctactacg atatccagtg ggtccgacag gccccctggca   2100
aaggacttga atgggtgtcc agcatcagcc cctctggcca gtccacctac taccggcgag   2160
aagtgaaggg cagattcacc atcagccggg acaacagcaa gaacaccctg tacctgcaga   2220
tgaacagcct gagagccgag gacaccgccg tgtactactg cgccagaaga accggcagag   2280
agtacggcgg aggctggtac tttgattact ggggccaggg caccctggtc acagtctcga   2340
gcgcctctac aaagggcccc agcgttttcc cactggctcc ctgtagcaga agcaccagcg   2400
aatctacagc cgctctgggc tgcctggtca aggactactt tcctgagcct gtgaccgtgt   2460
cctggaactc tggcgctctg acatctggcg tgcacacctt tccagccgtg ctgcaaagca   2520
gcggcctgta cagtctgagc agcgtcgtga cagtgcctag cagctctctg ggcacccaga   2580
cctacacctg taatgtggac cacaagccta gcaacaccaa ggtggacaag cgcgtggaat   2640
ctaagtacgg ccctccttgt cctccatgtc ctgcacctga gtttctcggc ggaccctccg   2700
tgttcctgtt tcctccaaag cctaaggaca ccctgatgat ctccagaaca cccgaagtga   2760
cctgcgtggt ggtggacgtt tcacaagagg accccgaggt gcagtttaat tggtacgtgg   2820
acggcgtgga agtgcacaac gccaagacca agcctagaga ggaacagtac aacagcacct   2880
acagagtggt gtccgtgctg acagtgctgc accaggattg gctgaacggc aaagagtaca   2940
agtgcaaggt gtccaacaag ggcctgccaa gcagcatcga gaaaaccatc agcaaggcca   3000
agggccagcc tagggaaccc caggtttaca cactgcctcc aagccagaaa gagatgacca   3060
agaaccaggt gtccctgacc tgcctcgtga agggcttcta cccttccgat atcgccgtgg   3120
aatgggagag caatggccag ccagagaaca actacaagac cacacctcct gtgctggaca   3180
gcgacggctc attcttcctg tacagcaagc tgaccgtgga caagagcaga tggcaagagg   3240
gcaacgtgtt cagctgcagc gtgatgcacg aggccctgca caacagatac acccagaagt   3300
ccctgtctct gagccccgaa caaaaactca tctcagaaga ggatctgaat gctgtgggcc   3360
aggacacgca ggaggtcatc gtggtgccac actccttgcc ctttaaggtg gtggtgatct   3420
cagccatcct ggccctggtg gtgctcacca tcatctccct tatcatcctc atcatgcttt   3480
ggcagaagaa gccacgttag taaaagcttg tcacttggaa agtaatagtt tttcctgcac   3540
gggtagtaat cagcctcgac tgtgccttct agttgccagc catctgttgt ttgcccctcc   3600
cccgtgcctt ccttgaccct ggaaggtgcc actcccactg tcctttccta ataaaatgag   3660
```

```
gaaattgcat cgcattgtct gagtaggtgt cattctattc tggggggtgg ggtggggcag   3720
gacagcaagg gggaggattg ggaagacaat agcaggcatg ctggggatgg cccgggcatg   3780
ataacttcgt ataatgtatg ctatacgaag ttatgtagag taattcatac aaaaggactc   3840
gcccctgcct tggggaatcc cagggaccgt cgttaaactc ccactaacgt agaacccaga   3900
gatcgctgcg ttcccgcccc ctcacccgcc cgctctcgtc atcactgagg tggagaagag   3960
catgcgtgag gctccggtgc ccgtcagtgg gcagagcgca catcgcccac agtccccgag   4020
aagttggggg gaggggtcgg caattgaacc ggtgcctaga gaaggtggcg cggggtaaac   4080
tgggaaagtg atgtcgtgta ctggctccgc ctttttcccg agggtggggg agaaccgtat   4140
ataagtgcag tagtcgccgt gaacgttctt tttcgcaacg ggtttgccgc cagaacacag   4200
gtaagtgccg tgtgtggttc ccgcgggcct ggcctcttta cgggttatgg cccttgcgtg   4260
ccttgaatta cttccacgcc cctggctgca gtacgtgatt cttgatcccg agcttcgggt   4320
tggaagtggg tgggagagtt cgaggccttg cgcttaagga gccccttcgc ctcgtgcttg   4380
agttgaggcc tggcttgggc gctggggccg ccgcgtgcga atctggtggc accttcgcgc   4440
ctgtctcgct gctttcgata agtctctagc catttaaaat ttttgatgac ctgctgcgac   4500
gctttttttc tggcaagata gtcttgtaaa tgcgggccat gatctgcaca ctggtatttc   4560
ggtttttggg gccgcgggcg gcgacggggc ccgtgcgtcc cagcgcacat gttcggcgag   4620
gcggggcctg cgagcgcggc caccgagaat cggacggggg tagtctcaag ctggccggcc   4680
tgctctggtg cctggcctcg cgccgccgtg tatcgccccg ccctgggcgg caaggctggc   4740
ccggtcggca ccagttgcgt gagcggaaag atggccgctt cccggccctg ctgcagggag   4800
ctcaaaatgg aggacgcggc gctcgggaga gcgggcgggt gagtcaccca cacaaaggaa   4860
aagggccttt ccgtcctcag ccgtcgcttc atgtgactcc acggagtacc gggcgccgtc   4920
caggcacctc gattagttca cgagcttttg gagtacgtcg tctttaggtt ggggggaggg   4980
gttttatgcg atggagtttc cccacactga gtgggtggag actgaagtta ggccagcttg   5040
gcacttgatg taattctcct tggaatttgc cctttttgag tttggatctt ggttcattct   5100
caagcctcag acagtggttc aaagtttttt tcttccattt caggtgtcgt gagagctcgt   5160
ttagtgaacc gtcagatcgc ctggagacgc catccacgct gttttgacct ccatagaaga   5220
caccgggacc gatccagcct ccgcggcccc gaattcaaca tggactggac ctggagggtc   5280
ttctgcttgc tggctgtagc tccaggtaaa gggccaactg gttccagggc tgaggaaggg   5340
attttttcca gtttagagga ctgtcattct ctactgtgtc ctctccgcag gtgctcactc   5400
ccaggttcag ctggtgcagt ctggcagcga gctgaaaaaa cctggcgcct ccgtgaaggt   5460
gtcctgcaag gcttctggct acacctttac cgacaacaac atggactggg tccgacaggc   5520
ccctggacaa ggacttgagt ggatgggcga catcaacacc agaagcggcg gcagcatcta   5580
caacgaagag ttccaggaca gagtcatcat gaccgtggac aagagcaccg acaccgccta   5640
catggaactg agcagcctga gaagcgagga caccgccacc tatcactgcg ccagaagaaa   5700
gagctacggc tactacctgg acgagtgggg cgagggaaca ctggtcacag tgtctagcgc   5760
cagcacaaag ggccctagcg ttttcccact ggctccctgt agcagaagca ccagcgaatc   5820
tacagccgct ctgggctgcc tcgtgaagga ctactttcct gagcctgtga ccgttagctg   5880
gaacagcgga gcactgacaa gcggcgtgca cacatttcca gccgtgctgc aaagcagcgg   5940
cctgtactct ctgagcagcg tcgtgacagt gcctagcagc tctctgggca cccagaccta   6000
```

-continued

```
cacctgtaat gtggaccaca agcctagcaa caccaaggtg gacaagcgcg tggaatctaa   6060
gtacggccct ccttgtcctc catgtcctgc tccagagttt ctcggcggac cctccgtgtt   6120
cctgtttcct ccaaagccta aggacaccct gatgatctcc agaacacccg aagtgacctg   6180
cgtggtggtg gacgtttcac aagaggaccc cgaggtgcag ttcaattggt acgtggacgg   6240
cgtggaagtg cacaacgcca agaccaagcc tagagaggaa cagtacaaca gcacctacag   6300
agtggtgtcc gtgctgacag tgctgcacca ggattggctg aacggcaaag agtacaagtg   6360
caaggtgtcc aacaagggcc tgccaagcag catcgagaaa accatcagca aggccaaggg   6420
ccagcctagg gaaccccagg tttacacact gcctccaagc caagaggaaa tgaccaagaa   6480
ccaggtgtcc ctgacctgcc tggtcaaggg cttctaccct tccgatatcg ccgtggaatg   6540
ggagagcaat ggccagccag agaacaacta caagaccaca cctcctgtgc tggacagcga   6600
cggctcattc ttcctgtaca gcaagctgac tgtggataag agccggtggc aagagggcaa   6660
cgtgttcagc tgtagcgtga tgcacgaggc cctgcacaac cactacaccc aagagagcct   6720
gtctctgagc cctgaacaaa aactcatctc agaagaggat ctgaatgctg tgggccagga   6780
cacgcaggag gtcatcgtgg tgccacactc cttgcccttt aaggtggtgg tgatctcagc   6840
catcctggcc ctggtggtgc tcaccatcat ctcccttatc atcctcatca tgctttggca   6900
gaagaagcca cgttagtaac taagtcgaca tccagacatg ataagataca ttgatgagtt   6960
tggacaaacc acaactagaa tgcagtgaaa aaaatgcttt atttgtgaaa tttgtgatgc   7020
tattgcttta tttgtaacca ttataagctg caataaacaa gttaacaaca acaattgcat   7080
tcattttatg tttcaggttc agggggaggt gtgggaggtt ttttaaagca agtaaaacct   7140
ctacaaatgt ggtatggctg attatgatcc tgcaagcctc gtcgtcctgg ccggaccacg   7200
ctatctgtgc aaggtccccg gccccggacg cgcgctccat gagcagagcg cccgccgccg   7260
aggcgaagac tcgggcggcg ccctgcccgt cccaccaggt caacaggcgg taaccggcct   7320
cttcatcggg aatgcgcgcg accttcagca tcgccggcat gtccccctgg cggacgggaa   7380
gtatgtatac                                                          7390
```

```
<210> SEQ ID NO 355
<211> LENGTH: 104
<212> TYPE: PRT
<213> ORGANISM: Artificial Sequence
<220> FEATURE:
<223> OTHER INFORMATION: Human C kappa (reverse)

<400> SEQUENCE: 355

Ala Ala Pro Ser Val Phe Ile Phe Pro Pro Ser Asp Glu Gln Leu Lys
1               5                   10                  15

Ser Gly Thr Ala Ser Val Val Cys Leu Leu Asn Asn Phe Tyr Pro Arg
            20                  25                  30

Glu Ala Lys Val Gln Trp Lys Val Asp Asn Ala Leu Gln Ser Gly Asn
        35                  40                  45

Ser Gln Glu Ser Val Thr Glu Gln Asp Ser Lys Asp Ser Thr Tyr Ser
    50                  55                  60

Leu Ser Ser Thr Leu Thr Leu Ser Lys Ala Asp Tyr Glu Lys His Lys
65                  70                  75                  80

Val Tyr Ala Cys Glu Val Thr His Gln Gly Leu Ser Ser Pro Val Thr
                85                  90                  95

Lys Ser Phe Asn Arg Gly Glu Cys
            100
```

<210> SEQ ID NO 356
<211> LENGTH: 112
<212> TYPE: PRT
<213> ORGANISM: Artificial Sequence
<220> FEATURE:
<223> OTHER INFORMATION: Emicizumab (reverse)

<400> SEQUENCE: 356

```
Arg Gly Asp Ile Gln Met Thr Gln Ser Pro Ser Ser Leu Ser Ala Ser
1               5                   10                  15

Val Gly Asp Arg Val Thr Ile Thr Cys Lys Ala Ser Arg Asn Ile Glu
            20                  25                  30

Arg Gln Leu Ala Trp Tyr Gln Gln Lys Pro Gly Gln Ala Pro Glu Leu
        35                  40                  45

Leu Ile Tyr Gln Ala Ser Arg Lys Glu Ser Gly Val Pro Asp Arg Phe
    50                  55                  60

Ser Gly Ser Arg Tyr Gly Thr Asp Phe Thr Leu Thr Ile Ser Ser Leu
65                  70                  75                  80

Gln Pro Glu Asp Ile Ala Thr Tyr Tyr Cys Gln Gln Tyr Ser Asp Pro
                85                  90                  95

Pro Leu Thr Phe Gly Gly Gly Thr Lys Val Glu Ile Lys Arg Thr Ala
            100                 105                 110
```

<210> SEQ ID NO 357
<211> LENGTH: 15
<212> TYPE: PRT
<213> ORGANISM: Artificial Sequence
<220> FEATURE:
<223> OTHER INFORMATION: Leader I (reverse)

<400> SEQUENCE: 357

```
Met Leu Pro Ser Gln Leu Ile Gly Phe Leu Leu Leu Trp Val Pro
1               5                   10                  15
```

<210> SEQ ID NO 358
<211> LENGTH: 15
<212> TYPE: PRT
<213> ORGANISM: Artificial Sequence
<220> FEATURE:
<223> OTHER INFORMATION: Leader

<400> SEQUENCE: 358

```
Met Ser Trp Ser Cys Ile Ile Leu Phe Leu Val Ala Thr Ala Thr
1               5                   10                  15
```

<210> SEQ ID NO 359
<211> LENGTH: 122
<212> TYPE: PRT
<213> ORGANISM: Artificial Sequence
<220> FEATURE:
<223> OTHER INFORMATION: Emicizumab anti-FIXa VH

<400> SEQUENCE: 359

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Tyr
            20                  25                  30

Asp Ile Gln Trp Val Arg Gln Ala Pro Gly Lys Gly Leu Glu Trp Val
        35                  40                  45

Ser Ser Ile Ser Pro Ser Gly Gln Ser Thr Tyr Tyr Arg Arg Glu Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Thr Gly Arg Glu Tyr Gly Gly Gly Trp Tyr Phe Asp Tyr
            100                 105                 110

Trp Gly Gln Gly Thr Leu Val Thr Val Ser
        115                 120


<210> SEQ ID NO 360
<211> LENGTH: 326
<212> TYPE: PRT
<213> ORGANISM: Artificial Sequence
<220> FEATURE:
<223> OTHER INFORMATION: Emicizumab anti-FIXa CH1-3

<400> SEQUENCE: 360

Ser Ala Ser Thr Lys Gly Pro Ser Val Phe Pro Leu Ala Pro Cys Ser
1               5                   10                  15

Arg Ser Thr Ser Glu Ser Thr Ala Ala Leu Gly Cys Leu Val Lys Asp
            20                  25                  30

Tyr Phe Pro Glu Pro Val Thr Val Ser Trp Asn Ser Gly Ala Leu Thr
        35                  40                  45

Ser Gly Val His Thr Phe Pro Ala Val Leu Gln Ser Ser Gly Leu Tyr
    50                  55                  60

Ser Leu Ser Ser Val Val Thr Val Pro Ser Ser Ser Leu Gly Thr Gln
65                  70                  75                  80

Thr Tyr Thr Cys Asn Val Asp His Lys Pro Ser Asn Thr Lys Val Asp
                85                  90                  95

Lys Arg Val Glu Ser Lys Tyr Gly Pro Pro Cys Pro Pro Cys Pro Ala
            100                 105                 110

Pro Glu Phe Leu Gly Gly Pro Ser Val Phe Leu Phe Pro Pro Lys Pro
        115                 120                 125

Lys Asp Thr Leu Met Ile Ser Arg Thr Pro Glu Val Thr Cys Val Val
    130                 135                 140

Val Asp Val Ser Gln Glu Asp Pro Glu Val Gln Phe Asn Trp Tyr Val
145                 150                 155                 160

Asp Gly Val Glu Val His Asn Ala Lys Thr Lys Pro Arg Glu Glu Gln
                165                 170                 175

Tyr Asn Ser Thr Tyr Arg Val Val Ser Val Leu Thr Val Leu His Gln
            180                 185                 190

Asp Trp Leu Asn Gly Lys Glu Tyr Lys Cys Lys Val Ser Asn Lys Gly
        195                 200                 205

Leu Pro Ser Ser Ile Glu Lys Thr Ile Ser Lys Ala Lys Gly Gln Pro
    210                 215                 220

Arg Glu Pro Gln Val Tyr Thr Leu Pro Pro Ser Gln Lys Glu Met Thr
225                 230                 235                 240

Lys Asn Gln Val Ser Leu Thr Cys Leu Val Lys Gly Phe Tyr Pro Ser
                245                 250                 255

Asp Ile Ala Val Glu Trp Glu Ser Asn Gly Gln Pro Glu Asn Asn Tyr
            260                 265                 270

Lys Thr Thr Pro Pro Val Leu Asp Ser Asp Gly Ser Phe Phe Leu Tyr
        275                 280                 285

Ser Lys Leu Thr Val Asp Lys Ser Arg Trp Gln Glu Gly Asn Val Phe
    290                 295                 300
```

```
Ser Cys Ser Val Met His Glu Ala Leu His Asn Arg Tyr Thr Gln Lys
305                 310                 315                 320

Ser Leu Ser Leu Ser Pro
                325


<210> SEQ ID NO 361
<211> LENGTH: 16
<212> TYPE: PRT
<213> ORGANISM: Artificial Sequence
<220> FEATURE:
<223> OTHER INFORMATION: SIGPP-Part 1

<400> SEQUENCE: 361

Met Asp Trp Thr Trp Arg Val Phe Cys Leu Leu Ala Val Ala Pro Gly
1               5                   10                  15


<210> SEQ ID NO 362
<211> LENGTH: 119
<212> TYPE: PRT
<213> ORGANISM: Artificial Sequence
<220> FEATURE:
<223> OTHER INFORMATION: VH2-ANTI-FX-ACE910

<400> SEQUENCE: 362

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asp Asn
            20                  25                  30

Asn Met Asp Trp Val Arg Gln Ala Pro Gly Gln Gly Leu Glu Trp Met
        35                  40                  45

Gly Asp Ile Asn Thr Arg Ser Gly Gly Ser Ile Tyr Asn Glu Glu Phe
    50                  55                  60

Gln Asp Arg Val Ile Met Thr Val Asp Lys Ser Thr Asp Thr Ala Tyr
65                  70                  75                  80

Met Glu Leu Ser Ser Leu Arg Ser Glu Asp Thr Ala Thr Tyr His Cys
                85                  90                  95

Ala Arg Arg Lys Ser Tyr Gly Tyr Tyr Leu Asp Glu Trp Gly Glu Gly
            100                 105                 110

Thr Leu Val Thr Val Ser Ser
        115


<210> SEQ ID NO 363
<211> LENGTH: 325
<212> TYPE: PRT
<213> ORGANISM: Artificial Sequence
<220> FEATURE:
<223> OTHER INFORMATION: CH1-3 IgG4

<400> SEQUENCE: 363

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
```

```
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
            165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Glu Ser
305                 310                 315                 320

Leu Ser Leu Ser Pro
                325


<210> SEQ ID NO 364
<211> LENGTH: 110
<212> TYPE: PRT
<213> ORGANISM: Artificial Sequence
<220> FEATURE:
<223> OTHER INFORMATION: Emicizumab

<400> SEQUENCE: 364

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Glu Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Ala
            100                 105                 110
```

-continued

<210> SEQ ID NO 365
<211> LENGTH: 110
<212> TYPE: PRT
<213> ORGANISM: Artificial Sequence
<220> FEATURE:
<223> OTHER INFORMATION: E30Y

<400> SEQUENCE: 365

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Tyr Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Glu Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Ala
            100                 105                 110
```

<210> SEQ ID NO 366
<211> LENGTH: 110
<212> TYPE: PRT
<213> ORGANISM: Artificial Sequence
<220> FEATURE:
<223> OTHER INFORMATION: E30Y_E55Y

<400> SEQUENCE: 366

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Tyr Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Lys Tyr Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Asp Pro Pro Leu
                85                  90                  95

Thr Phe Gly Gly Gly Thr Lys Val Glu Ile Lys Arg Thr Ala
            100                 105                 110
```

<210> SEQ ID NO 367
<211> LENGTH: 110
<212> TYPE: PRT
<213> ORGANISM: Artificial Sequence
<220> FEATURE:
<223> OTHER INFORMATION: E30Y-E557_D93s

<400> SEQUENCE: 367

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Tyr Arg Gln
            20                  25                  30

Leu Ala Trp Tyr Gln Gln Lys Pro Gly Gln Ala Pro Glu Leu Leu Ile
        35                  40                  45
```

-continued

```
Tyr Gln Ala Ser Arg Lys Tyr Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys Arg Thr Ala
            100                 105                 110


<210> SEQ ID NO 368
<211> LENGTH: 110
<212> TYPE: PRT
<213> ORGANISM: Artificial Sequence
<220> FEATURE:
<223> OTHER INFORMATION: E30Y_K54R_E55Y_D93S

<400> SEQUENCE: 368

Asp Ile Gln Met Thr Gln Ser Pro Ser Ser Leu Ser Ala Ser Val Gly
1               5                   10                  15

Asp Arg Val Thr Ile Thr Cys Lys Ala Ser Arg Asn Ile Tyr Arg Gln
            20                  25                  30

Leu Ala Trp Tyr Gln Gln Lys Pro Gly Gln Ala Pro Glu Leu Leu Ile
        35                  40                  45

Tyr Gln Ala Ser Arg Arg Tyr Ser Gly Val Pro Asp Arg Phe Ser Gly
    50                  55                  60

Ser Arg Tyr Gly Thr Asp Phe Thr Leu Thr Ile Ser Ser Leu Gln Pro
65                  70                  75                  80

Glu Asp Ile Ala Thr Tyr Tyr Cys Gln Gln Tyr Ser Ser Pro Pro Leu
                85                  90                  95

Thr Phe Gly Gly Gly Thr Lys Val Glu Ile Lys Arg Thr Ala
            100                 105                 110
```